(12) United States Patent
Park et al.

(10) Patent No.: US 11,515,484 B2
(45) Date of Patent: Nov. 29, 2022

(54) HETEROCYCLIC COMPOUND AND ORGANIC LIGHT EMITTING ELEMENT COMPRISING SAME

(71) Applicant: LT MATERIALS CO., LTD., Yongin (KR)

(72) Inventors: Geon-Yu Park, Osan-si (KR); Young-Seok No, Osan-si (KR); Seung-Gyu Yang, Osan-si (KR); Ju-Hyon Cha, Osan-si (KR); Dong-Jun Kim, Yongin-si (KR); Dae-Hyuk Choi, Yongin-si (KR); Joo-Dong Lee, Seongnam-si (KR)

(73) Assignee: LT MATERIALS CO., LTD., Yongin (KR)

( * ) Notice: Subject to any disclaimer, the term of this patent is extended or adjusted under 35 U.S.C. 154(b) by 320 days.

(21) Appl. No.: 16/647,422

(22) PCT Filed: Sep. 17, 2018

(86) PCT No.: PCT/KR2018/010936
§ 371 (c)(1),
(2) Date: Mar. 13, 2020

(87) PCT Pub. No.: WO2019/054833
PCT Pub. Date: Mar. 21, 2019

(65) Prior Publication Data
US 2020/0266355 A1    Aug. 20, 2020

(30) Foreign Application Priority Data
Sep. 15, 2017    (KR) .................. 10-2017-0118675

(51) Int. Cl.
  *H01L 29/08*    (2006.01)
  *H01L 51/00*    (2006.01)
  (Continued)

(52) U.S. Cl.
  CPC ........ *H01L 51/0067* (2013.01); *C07D 209/86* (2013.01); *C07D 405/10* (2013.01);
  (Continued)

(58) Field of Classification Search
  CPC ............. H01L 51/0067; H01L 51/0072; H01L 51/0073; H01L 51/0074; H01L 51/5072;
  (Continued)

(56) References Cited

U.S. PATENT DOCUMENTS 4,356,429 A   10/1982   Tang
6,229,012 B1   5/2001   Hu et al.
(Continued)

FOREIGN PATENT DOCUMENTS

EP   3 107 131 A1    12/2016
JP   2001-257076 A   9/2001
(Continued)

OTHER PUBLICATIONS

International Search Report (PCT/ISA/210) issued in PCT/KR2018/010936, dated Dec. 26, 2018.
(Continued)

*Primary Examiner* — Phuc T Dang
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

17 Claims, 3 Drawing Sheets

(51) Int. Cl.
*C07D 209/86* (2006.01)
*C07D 405/10* (2006.01)
*C07D 405/14* (2006.01)
*C07D 409/14* (2006.01)
*H01L 51/50* (2006.01)
*H01L 51/56* (2006.01)

(52) U.S. Cl.
CPC ......... *C07D 405/14* (2013.01); *C07D 409/14* (2013.01); *H01L 51/0072* (2013.01); *H01L 51/0073* (2013.01); *H01L 51/0074* (2013.01); *H01L 51/001* (2013.01); *H01L 51/5004* (2013.01); *H01L 51/5012* (2013.01); *H01L 51/5072* (2013.01); *H01L 51/5092* (2013.01); *H01L 51/5096* (2013.01); *H01L 51/56* (2013.01); *H01L 2251/552* (2013.01); *H01L 2251/558* (2013.01)

(58) Field of Classification Search
CPC ............ H01L 51/5092; H01L 51/5096; C07D 209/86; C07D 405/10; C07D 405/14
USPC .......................................................... 257/40
See application file for complete search history.

(56) References Cited

U.S. PATENT DOCUMENTS

| | | | |
|---|---|---|---|
| 9,136,480 B2* | 9/2015 | Kim | H01L 51/0067 |
| 9,431,614 B2* | 8/2016 | Seo | H01L 51/006 |
| 2007/0178333 A1* | 8/2007 | Igarashi | H01L 51/0077 428/917 |
| 2012/0223276 A1 | 9/2012 | Parham et al. | |
| 2014/0209871 A1* | 7/2014 | Park | H01L 51/0061 548/425 |
| 2015/0207082 A1 | 7/2015 | Dyatkin et al. | |
| 2015/0259347 A1* | 9/2015 | Park | C07F 9/6561 257/40 |
| 2015/0318487 A1 | 11/2015 | Ito et al. | |
| 2015/0336937 A1 | 11/2015 | Lee et al. | |
| 2016/0149157 A1* | 5/2016 | Cho | H01L 51/0058 257/40 |
| 2016/0197285 A1 | 7/2016 | Zeng et al. | |
| 2016/0248023 A1 | 8/2016 | Parham et al. | |
| 2016/0293851 A1 | 10/2016 | Park et al. | |
| 2017/0213968 A1 | 7/2017 | Park et al. | |
| 2017/0263871 A1* | 9/2017 | Wang | H05B 33/14 |
| 2018/0037546 A1 | 2/2018 | Sugino et al. | |
| 2019/0252613 A1 | 8/2019 | Song et al. | |
| 2019/0386226 A1 | 12/2019 | Parham et al. | |
| 2020/0119285 A1 | 4/2020 | No et al. | |
| 2020/0144511 A1 | 5/2020 | Bae et al. | |

FOREIGN PATENT DOCUMENTS

| | | |
|---|---|---|
| JP | 2016-128432 A | 7/2016 |
| JP | 2016-149473 A | 8/2016 |
| JP | 2016-534988 A | 11/2016 |
| JP | 2017-107992 A | 6/2017 |
| JP | 2020-514385 A | 5/2020 |
| KR | 10-2012-0104246 A | 9/2012 |
| KR | 10-2015-0031396 A | 3/2015 |
| KR | 10-2015-0074603 A | 7/2015 |
| KR | 10-2015-0088176 A | 7/2015 |
| KR | 10-2015-0126756 A | 11/2015 |
| KR | 10-2015-0134248 A | 12/2015 |
| KR | 10-2016-0011522 A | 2/2016 |
| KR | 10-2017-0102000 A | 9/2017 |
| KR | 10-1857632 B1 | 5/2018 |
| WO | WO 2016/108596 A3 | 7/2016 |
| WO | WO 2018/174682 A1 | 9/2018 |
| WO | WO 2018/216921 A2 | 11/2018 |
| WO | WO 2019/007866 A1 | 1/2019 |

OTHER PUBLICATIONS

Kuwabara et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials", Advanced Materials, vol. 6, No. 9, 1996, pp. 677-679.
Office Action issued in Korean Patent Application No. 10-2017-0118675, dated May 27, 2019.
Office Action issued in Taiwanese Patent Application No. 107132676, dated Dec. 17, 2019.
Office Action issued in Taiwanese Patent Application No. 107132676, dated Jul. 2, 2019.
Written Opinion (PCT/ISA/237) issued in PCT/KR2018/010936, dated Dec. 26, 2018.

* cited by examiner

【FIG. 1】
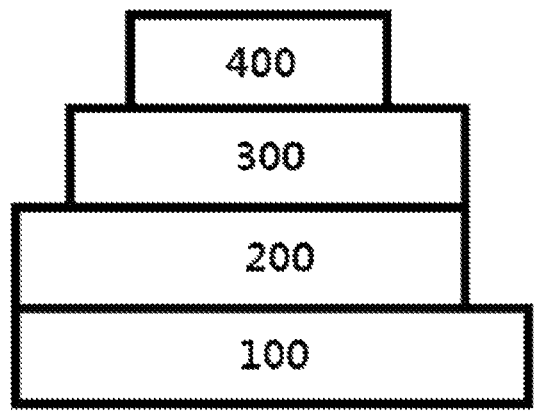
【FIG. 2】
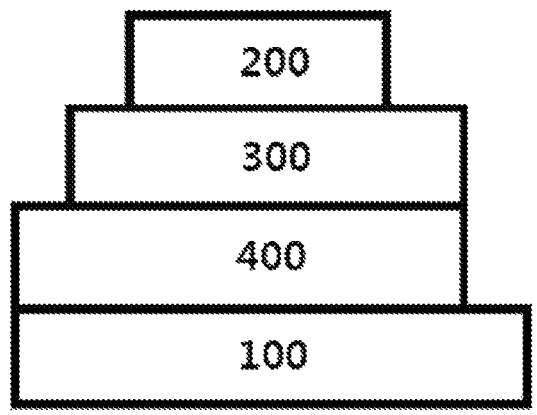

[FIG. 3]
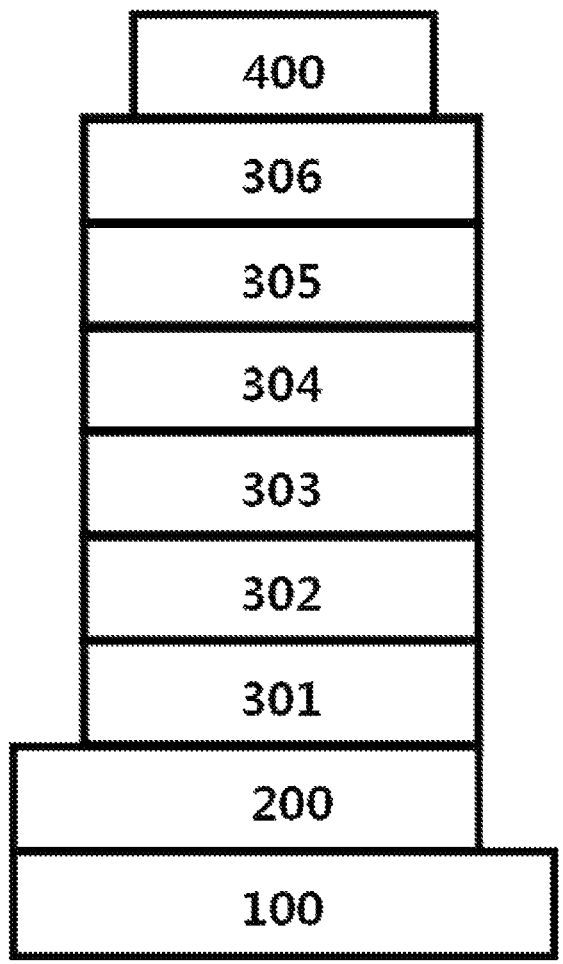

[FIG. 4]

| Compound | Structural Formula | HOMO | LUMO |
|---|---|---|---|
| 1-25 | | | |
| Ref. 1 | | | |
| Ref. 4 | | | |

HETEROCYCLIC COMPOUND AND ORGANIC LIGHT EMITTING ELEMENT COMPRISING SAME

TECHNICAL FIELD

This application claims priority to and the benefits of Korean Patent Application No. 10-2017-0118675, filed with the Korean Intellectual Property Office on Sep. 15, 2017, the entire contents of which are incorporated herein by reference.

The present specification relates to a heterocyclic compound and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film. Development of an organic thin film material has been continuously required for enhancing performance, lifetime or efficiency of an organic light emitting device.

DISCLOSURE

Technical Problem

The present disclosure is directed to providing a heterocyclic compound and an organic light emitting device comprising the same.

Technical Solution

One embodiment of the present application provides a heterocyclic compound represented by the following Chemical Formula 1.

[Chemical Formula 1]

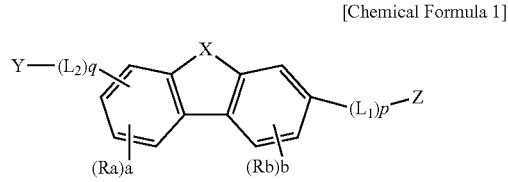

In Chemical Formula 1,
X is O or S,
Y is a hole transferring group or a substituted or unsubstituted aryl group,
Z is an electron transferring group,
L1 and L2 are the same as or different from each other, and each independently a direct bond; a substituted or unsubstituted arylene group; or a substituted or unsubstituted heteroarylene group, p and q are each an integer of 0 to 3, and when p is 2 or greater, L1s are the same as or different from each other, and when q is 2 or greater, L2s are the same as or different from each other, and Ra and Rb are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, a and b are each an integer of 1 to 3, and when a is 2 or greater, Ras are the same as or different from each other, and when b is 2 or greater, Rbs are the same as or different from each other.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Advantageous Effects

The compound described in the present specification can be used as an organic material layer material of an organic light emitting device. The compound is capable of performing a role of a hole injection material, a hole transfer material, a light emitting material, an electron transfer material, an electron injection material and the like in the organic light emitting device. Particularly, the compound can be used as a light emitting layer material of the organic light emitting device. For example, the compound can be used alone as a light emitting material, or can be used as a host material of a light emitting layer. Particularly, Chemical Formula 1 has a structure with better electron stability by having a number 3 carbon position of a dibenzofuran or dibenzothiophene structure substituted with an electron transferring group, and having benzene not substituted with the electron transferring group in the dibenzofuran or dibenzothiophene structure substituted with a hole transferring group, and as a result, a device lifetime can be enhanced.

DESCRIPTION OF DRAWINGS

FIG. 1 to FIG. 3 are diagrams each schematically illustrating a lamination structure of an organic light emitting device according to one embodiment of the present application. FIG. 4 shows the structural formula, and HOMO and LUMO orbitals for certain compounds.

REFERENCE NUMERAL

100: Substrate
200: Anode

300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

BEST MODE FOR DISCLOSURE

Hereinafter, the present application will be described in detail.

The term "substituted" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group comprises linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group comprises linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenyl-vinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group comprises linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group comprises monocyclic or multicyclic having 3 to 60 carbon atoms, and may be further substituted with other substituents. Herein, the multicyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group comprises O, S, Se, N or Si as a heteroatom, comprises monocyclic or multicyclic having 2 to 60 carbon atoms, and may be further substituted with other substituents. Herein, the multicyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group comprises monocyclic or multicyclic having 6 to 60 carbon atoms, and may be further substituted with other substituents. Herein, the multicyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group comprises a spiro group. The number of carbon atoms of the aryl group may be from 6 to 60, specifically from 6 to 40 and more specifically from 6 to 25. Specific examples of the aryl group may comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the fluorenyl group may be substituted, and adjacent substituents may bond to each other to form a ring.

When the fluorenyl group is substituted,

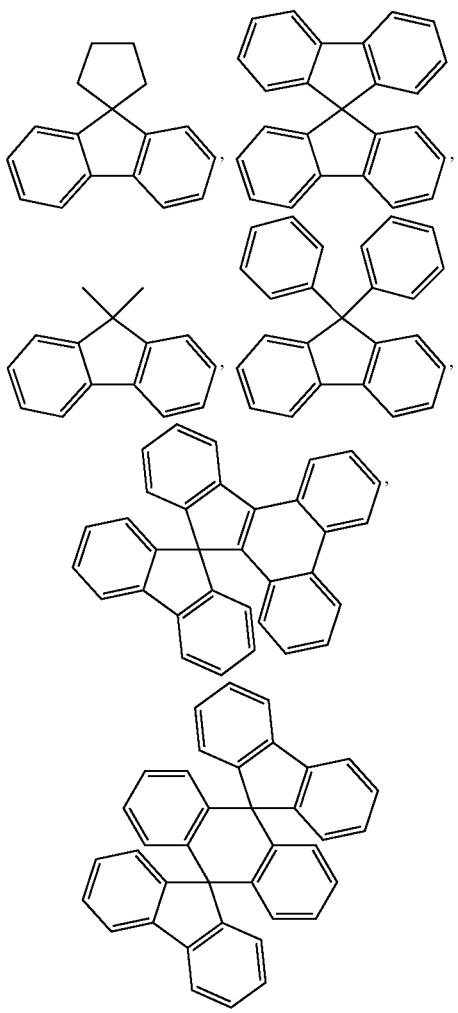

and the like may be included. However, the structure is not limited thereto.

In the present specification, the heteroaryl group comprises O, S, Se, N or Si as a heteroatom, comprises monocyclic or multicyclic having 2 to 60 carbon atoms, and may be further substituted with other substituents. Herein, the multicyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydrodibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; —$NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for each being a divalent. In addition, the heteroarylene group means the heteroaryl group having two bonding sites, that is, a divalent group. Descriptions on the heteroaryl group provided above may be applied thereto except for each being a divalent.

In the present specification, the phosphine oxide group may specifically be substituted with an aryl group, and the examples described above may be used as the aryl group. Examples of the phosphine oxide group may comprise a diphenylphosphine oxide group, a dinaphthylphosphine oxide group and the like, but are not limited thereto.

In the present specification, the silyl group is a substituent comprising Si, having the Si atom directly linked as a radical, and is represented by —$SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

Structures illustrated as the cycloalkyl group, the cycloheteroalkyl group, the aryl group and the heteroaryl group described above may be used as the aliphatic or aromatic hydrocarbon ring or heteroring that adjacent groups may form except for those that are not monovalent.

In the present specification, an electron transferring group means a functional group having a greater electron transferring property than a hole transferring property, and may be referred to as an N-type functional group.

In the present specification, a hole transferring group means a functional group having a greater hole transferring property than an electron transferring property, and may be referred to as a P-type functional group.

One embodiment of the present application provides a compound represented by Chemical Formula 1.

In one embodiment of the present application, Chemical Formula 1 may be represented by the following Chemical Formula 2.

[Chemical Formula 2]

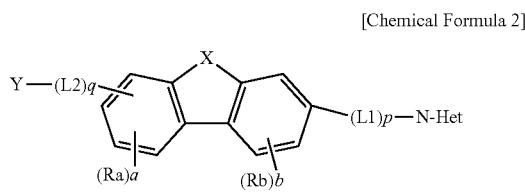

In Chemical Formula 2, N-Het is a substituted or unsubstituted monocyclic or polycyclic heteroaryl group comprising one or more Ns, and the remaining substituents have the same definitions as in Chemical Formula 1.

In one embodiment of the present application, N-Het of Chemical Formula 2 is a substituted or unsubstituted monocyclic heteroaryl group comprising one or more Ns.

In one embodiment of the present application, N-Het of Chemical Formula 2 is a substituted or unsubstituted dicyclic or higher polycyclic heteroaryl group comprising one or more Ns.

In one embodiment of the present application, N-Het of Chemical Formula 2 is a substituted or unsubstituted monocyclic or polycyclic heteroaryl group comprising two or more Ns.

In one embodiment of the present application, N-Het of Chemical Formula 2 is a dicyclic or higher polycyclic heteroaryl group comprising two or more Ns.

In one embodiment of the present application, N-Het of Chemical Formula 2 is a monocyclic heteroaryl group comprising three Ns.

In one embodiment of the present application, N-Het of Chemical Formula 2 forms a carbon-carbon bond with L1.

In one embodiment of the present application, N-Het of Chemical Formula 2 has N that forms the ring having a sp2 bond with neighboring C.

In one embodiment of the present application, Y is a substituted or unsubstituted dibenzofuran group; a substituted or unsubstituted dibenzothiophene group; a substituted or unsubstituted carbazole group; a substituted or unsubstituted group having a monocyclic or polycyclic ring fused to carbazole; a substituted or unsubstituted silyl group; or a substituted or unsubstituted aryl group.

In one embodiment of the present application, Chemical Formula 1 may be represented by one of the following Chemical Formula 3 to 5.

[Chemical Formula 3]

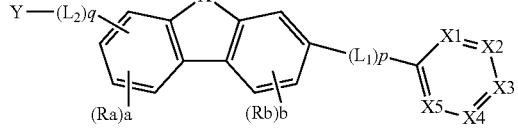

[Chemical Formula 4]

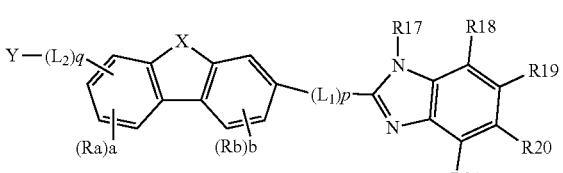

[Chemical Formula 5]

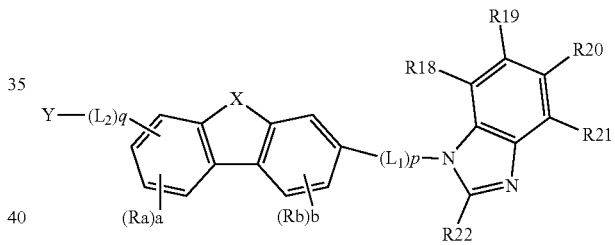

In Chemical Formula 3 to 5,

X1 is CR11 or N, X2 is CR12 or N, X3 is CR13 or N. X4 is CR14 or N, and X5 is CR15 or N.

R11 to R15 and R17 to R22 are the same as or different from each other, and each independently selected from die group consisting of hydrogen; deuterium; halogen; a cyano group; a substituted or unsubstituted alkyl group; a substituted or unsubstituted alkenyl group; a substituted or =substituted alkynyl group: a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; a substituted or unsubstituted silyl group; and a substituted or unsubstituted amine group, or two or more groups adjacent to each other bond to each other to form a substituted or unsubstituted aliphatic or aromatic hydrocarbon ring or heteroring, and one of the remaining substituents have the same definitions as in Chemical Formula 1.

In one embodiment of the present application, Chemical Formula 1 may be represented by one of the following Chemical Formula 6 to 8.

[Chemical Formula 6]

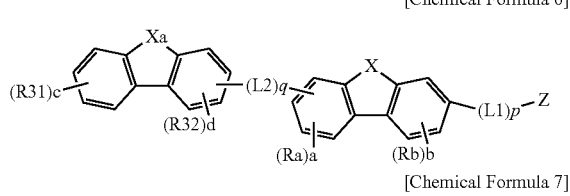

[Chemical Formula 7]

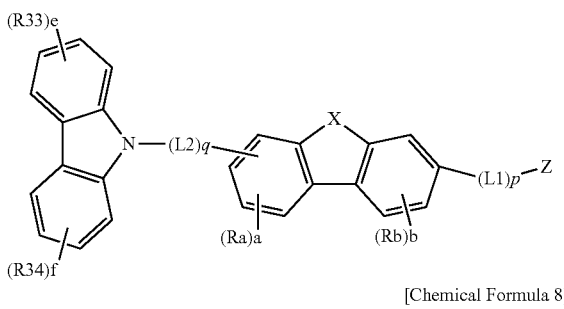

[Chemical Formula 8]

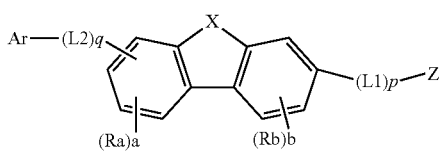

In Chemical Formula 6 to 8,

Xa is S, O, CRcRd or NRe,

R31 to R34, Re, Rd and Re are the same as or different from each other, and each independently selected from the, group consisting of hydrogen; deuterium; halogen; a cyano, group;

a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group: a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, c, e and f are each an integer of 0 to 4, d is an integer of 0 to 3, and when c is 2 or greater, R34s are the same as or different from each other, when d is 2 or greater, R32s are the same as or different from each other, when e is 2 or greater, R33s are the same as or different from each other, and when f is 2 or greater, R34s are the same as or different from each other, Ar is a substituted or unsubstituted aryl group; or a substituted or unsubstituted silvi group, and the remaining substituents have the same definitions as in Chemical Formula 1.

In one embodiment of the present application, X is S, and Chemical Formula 1 may represented by one of Chemical Formula 6 to 8.

In one embodiment of the present application, X is Chemical Formula 1 is represented by one of Chemical Formula 6 to 8, and L2 of Chemical Formula 7 is a direct bond.

In one embodiment of the present application, X is O, and Chemical Formula 1 may be represented by Chemical Formula 6 or Chemical Formula 8.

In one embodiment of the present application,

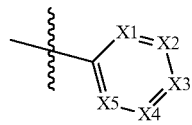

may be represented by one of the following Chemical Formula 9 to 11. Herein,

is a site linked to L1.

[Chemical Formula 9]

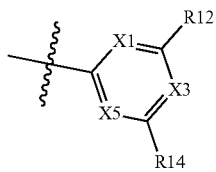

[Chemical Formula 10]

[Chemical Formula 11]

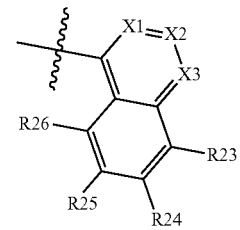

In Chemical Formula 9, one or more of X1, X3 and X5 are N, and the rest have the same definitions as in Chemical Formula 3, in Chemical Formula 10, one of more of X1, X2 and X5 are N, and the rest have the same definitions as in Chemical Formula 3, in Chemical Formula 11, one or more of X1 to X3 are N, and the rest have the same definitions as in Chemical Formula 3, R12, R14 and R23 to R26 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

In one embodiment of the present application, Chemical Formula 9 may be selected from among the following structural formula.

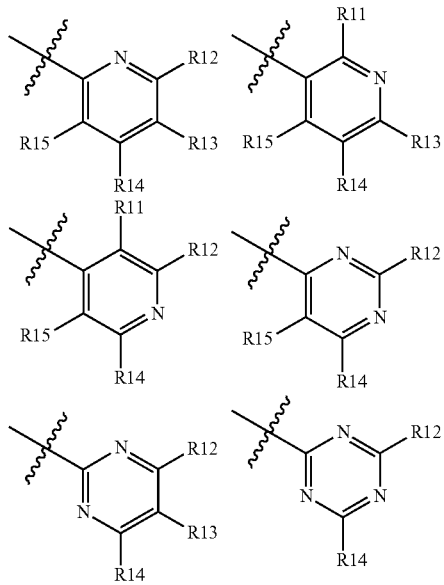

In one embodiment of the present application, Chemical Formula 10 may be represented by the following Chemical Formula 12.

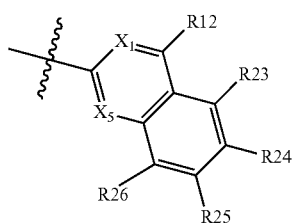

[Chemical Formula 12]

Substituents of Chemical Formula 12 have the same definitions as in Chemical Formula 10.

In one embodiment of the present application, Chemical Formula 11 may be represented by the following Chemical Formula 13.

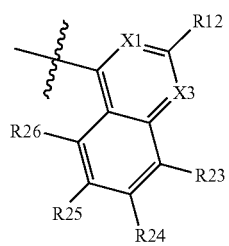

[Chemical Formula 13]

Substituents of Chemical Formula 13 have the same definitions as in Chemical Formula 11.

In one embodiment of the present application, Chemical Formula 10 may be represented by the following Chemical Formula 14.

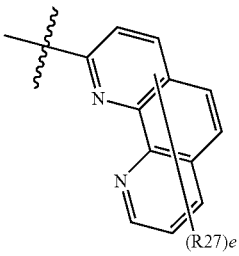

[Chemical Formula 14]

In Chemical Formula 14, R27s are the same as or different from each other, and selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, e is an integer of 0 to 7, and when e is 2 or greater, R27s are the same as or different from each other.

In one embodiment of the present application, Chemical Formula 1 may be represented by the following Chemical Formula 15.

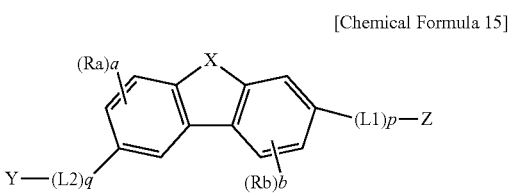

[Chemical Formula 15]

In Chemical Formula 15, substituents have the same definitions as in Chemical Formula 1.

In one embodiment of the present application. Chemical Formula 1 may be represented by one of the following Chemical Formula 16 to 18.

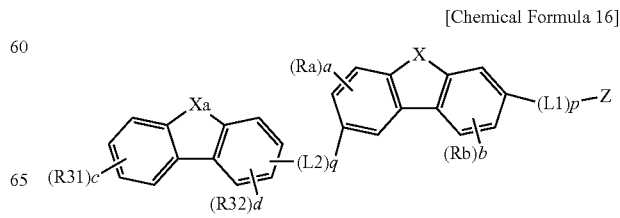

[Chemical Formula 16]

[Chemical Formula 17]

[Chemical Formula 18]

In Chemical Formula 16 to 18, substituents have the same definitions as n Chemical Formula 6 to 8.

In one embodiment of the present application, Chemical Formula 1 may be represented by the following Chemical Formula 19.

[Chemical Formula 19]

In Chemical Formula 19, substituents have the same definitions as in Chemical Formula 1.

In one embodiment of the present application, Chemical Formula 1 may be represented one of the following Chemical Formula 20 to 22.

[Chemical Formula 20]

[Chemical Formula 21]

[Chemical Formula 22]

In Chemical Formula 20 to 22, substituents have the same definitions as in Chemical Formula 6 to 8.

In one embodiment of the present application, (herein, is a site linked to L2.) may be represented by the following Chemical Formula 23 when R31 bonds to adjacent groups to form a ring.

[Chemical Formula 23]

In Chemical Formula 23,

R32 and d have the same definitions as in Chemical Formula 6,

Xc is O, S, NR or CR'R",

R1 to R4, R, R', R" and R36 are the same as or different from each other, and selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, h is an integer of 0 to 2, and when h is 2 or greater, R36s are the same as or different from each other.

In another embodiment. Chemical Formula 23 may be selected from among the following structural formula.
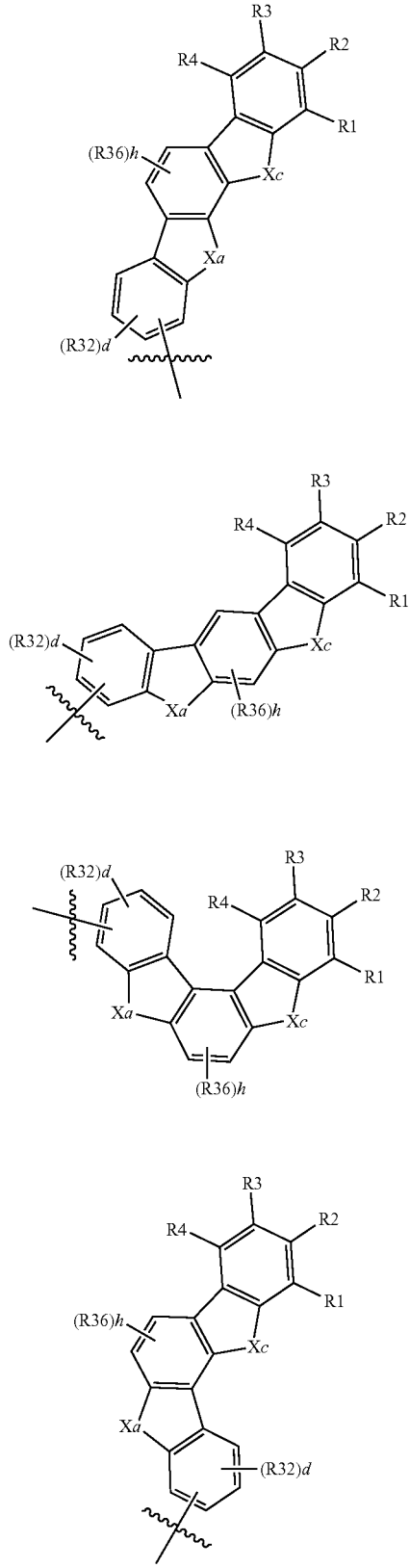
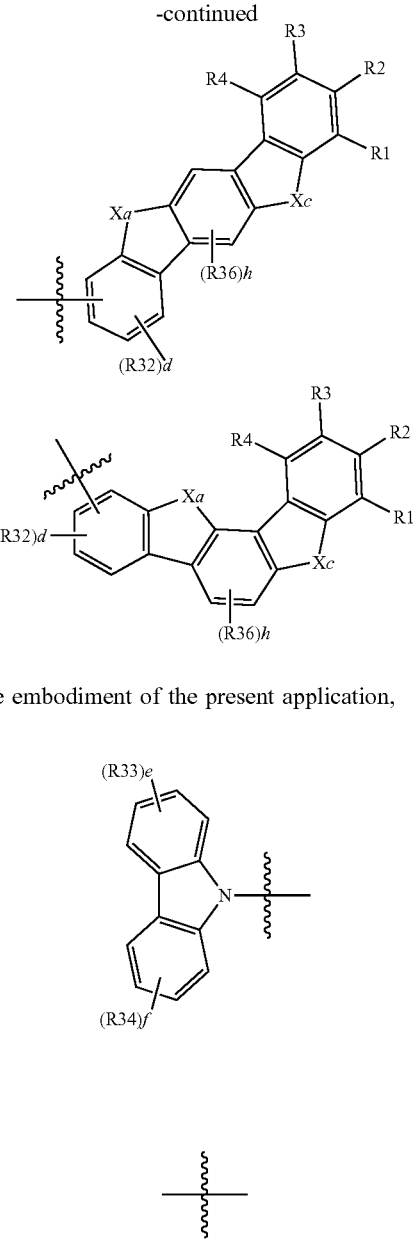
In one embodiment of the present application,
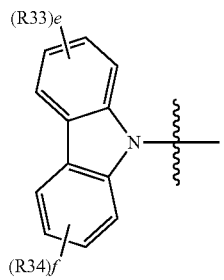
(herein,
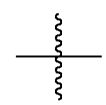
is a site linked to L2.) may be represented by the following Chemical Formula 24 when R33 or R34 bonds to adjacent groups to form a ring.
[Chemical Formula 24]
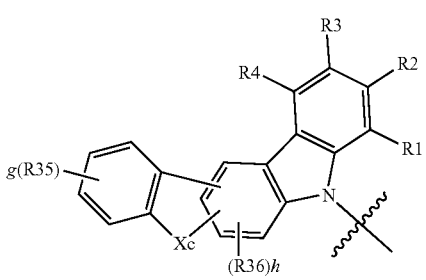

In Chemical Formula 24,

Xc is O, S, NR or CR'R",

R1 to R4, R, R', R", R35 and R36 are the same as or different from each other, and selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring, g is an integer of 0 to 4, and when g is 2 or greater, R35s are the same as or different from each other, h is an integer of 0 to 2, and when h is 2 or greater, R36s are the same as or different from each other.

In another embodiment, Chemical Formula 24 may be selected from among the following structural formula.

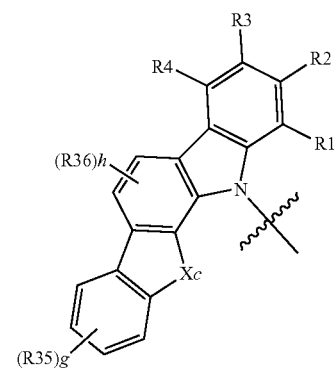

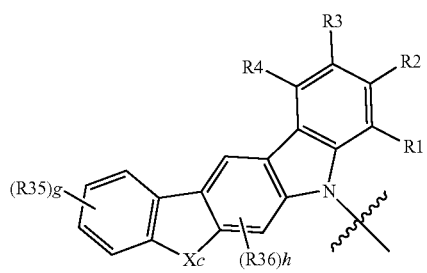

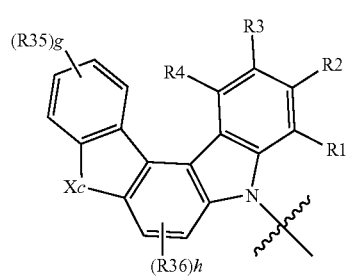

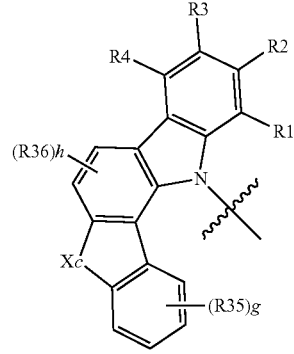

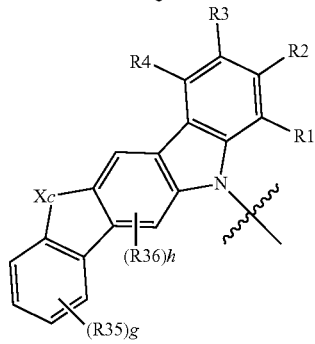

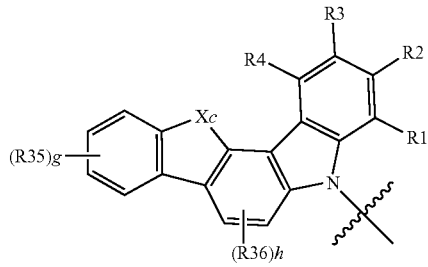

In another embodiment, L1 and L2 are the same as or different from each other, and each independently a direct bond; an arylene group; or a heteroarylene group.

In another embodiment, L1 and L2 are the same as or different from each other, and each independently a direct bond; a phenylene group; a naphthalene group; a biphenylylene group; or a divalent pyridine group.

In another embodiment, Ra and Rb are hydrogen; or deuterium.

In another embodiment, Ra and Rb are hydrogen.

In another embodiment, R1 to R4 and R31 to R34 are the same as or different from each other, and each independently hydrogen; deuterium; an aryl group unsubstituted or substituted with an alkyl group, an aryl group or a heteroaryl group; or a heteroaryl group unsubstituted or substituted with an aryl group or a heteroaryl group.

In another embodiment, R1 to R4 and R31 to R34 are the same as or different from each other, and each independently hydrogen; deuterium; an aryl group; a heteroaryl group; or a heteroaryl group substituted with an aryl group.

In another embodiment, R1 to R4 and R31 to R34 are the same as or different from each other, and each independently hydrogen; deuterium; a phenyl group; a dibenzofuran group; a dibenzothiophene group; a carbazole group; or a carbazole group substituted with phenyl.

In another embodiment, R1 to R4 and R31 to R34 are the same as or different from each other, and each independently hydrogen; deuterium; a phenyl group; a dibenzofuran group; or a carbazole group substituted with phenyl.

In another embodiment, R1 to R4 and R31 to R34 are the same as or different from each other, and each independently hydrogen; or a phenyl group.

In another embodiment, R18 to R21 are the same as or different from each other, and each independently hydrogen; deuterium; an aryl group; or a heteroaryl group.

In another embodiment, R18 to R21 are the same as or different from each other, and each independently hydrogen; or deuterium.

In another embodiment, R18 to R21 are hydrogen.

In another embodiment, R17 and R22 are the same as or different from each other, and each independently hydrogen; deuterium; an aryl group; or a heteroaryl group.

In another embodiment, R17 and R22 are the same as or different from each other, and each independently an aryl group; or a heteroaryl group.

In another embodiment, R17 and R22 are the same as or different from each other, and each independently an aryl group.

In another embodiment, R17 and R22 are a phenyl group.

In another embodiment, R11 to R15 are the same as or different from each other, and each independently hydrogen; deuterium; a substituted or unsubstituted aryl group; or a substituted or unsubstituted heteroaryl group.

In another embodiment, R11 to R15 are the same as or different from each other, and each independently hydrogen; deuterium; or an aryl group unsubstituted or substituted with an alkyl group.

In another embodiment, R11 to R15 are the same as or different from each other, and each independently hydrogen; a phenyl group; a biphenylyl group; a naphthyl group; or a dimethylfluorenyl group.

In another embodiment, R12 and R14 are the same as or different from each other, and each independently an aryl group unsubstituted or substituted with one or more substituents selected from the group consisting of an alkyl group, an aryl group or a triphenylsilyl group; or a heteroaryl group unsubstituted or substituted with an aryl group.

In another embodiment, R12 and R14 are the same as or different from each other, and each independently a phenyl group unsubstituted or substituted with a phenyl group, a triphenylsilyl group or a triphenylene group; a biphenyl group unsubstituted or substituted with a phenyl group or a triphenylene group; a dimethylfluorene group; a diphenylfluorene group; a triphenylene group; a dibenzofuran group; a dibenzothiophene group; a carbazole group unsubstituted or substituted with a phenyl group.

In another embodiment, R23 to R26 are the same as or different from each other, and each independently hydrogen; deuterium; an aryl group; or a heteroaryl group.

In another embodiment, R23 to R26 are the same as or different from each other, and each independently hydrogen; deuterium; or an aryl group.

In another embodiment, R23 to R26 are the same as or different from each other, and each independently hydrogen; or an aryl group.

In another embodiment, R23 to R26 are the same as or different from each other, and each independently hydrogen; or a phenyl group.

In another embodiment, R27 is hydrogen; deuterium; an aryl group; or a heteroaryl group.

In another embodiment, R27 is hydrogen; deuterium; or an aryl group.

In another embodiment, R27 is hydrogen; or an aryl group.

In another embodiment, R27 is hydrogen; or a phenyl group.

In another embodiment, Xc is O or S.

In another embodiment, Xc is NR, and R is an aryl group.

In another embodiment, Xc is NR, and R is a phenyl group.

In another embodiment, Xc is CR'R", and R' and R" are an alkyl group.

In another embodiment, Xc is CR'R", and R' and R" are a methyl group.

In one embodiment of the present application, Rc, Rd and Re are an alkyl group; or an aryl group.

In another embodiment, Rc, Rd and Re are a methyl group; or a phenyl group.

In another embodiment, R35 and R36 are the same as or different from each other, and each independently hydrogen; deuterium; an aryl group; or a heteroaryl group.

In another embodiment, R35 and R36 are the same as or different from each other, and each independently hydrogen; deuterium; or an aryl group.

In another embodiment, R35 and R36 are the same as or different from each other, and each independently hydrogen; or a phenyl group.

In another embodiment, R35 and R36 are the same as or different from each other, and each independently hydrogen; or deuterium.

In another embodiment, R35 and R36 are hydrogen.

In one embodiment, Ar is an aryl group unsubstituted or substituted with an alkyl group, an aryl group or a heteroaryl group; or a silyl group substituted with a phenyl group.

In another embodiment, Ar is a phenyl group; a biphenylyl group; a triphenylene group; a phenanthrenyl group; a fluorene group unsubstituted or substituted with a methyl group or a phenyl group; a silyl group substituted with a phenyl group; or a spirobifluorene group.

According to one embodiment of the present application, Chemical Formula 1 may be represented by any one of the following compounds, but is not limited thereto.

21
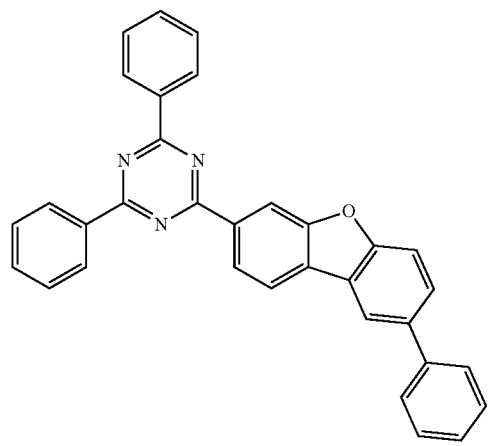
1-1
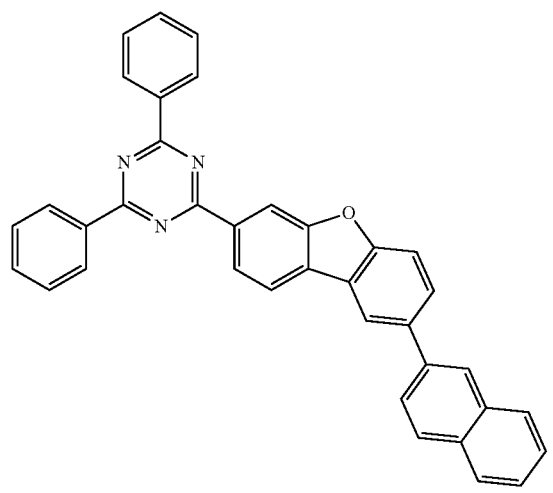
1-3
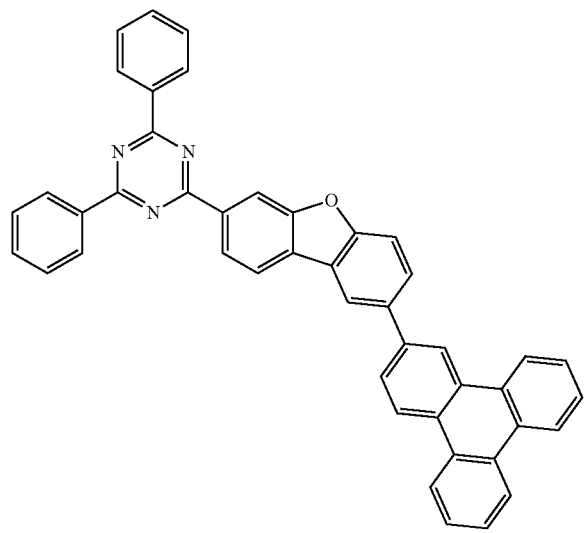
1-5
22
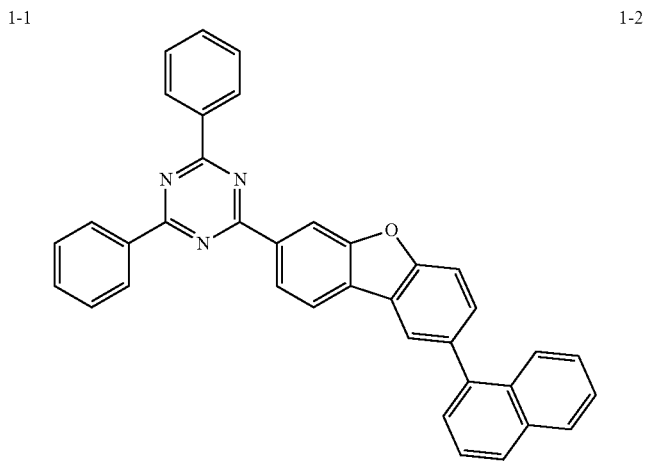
1-2
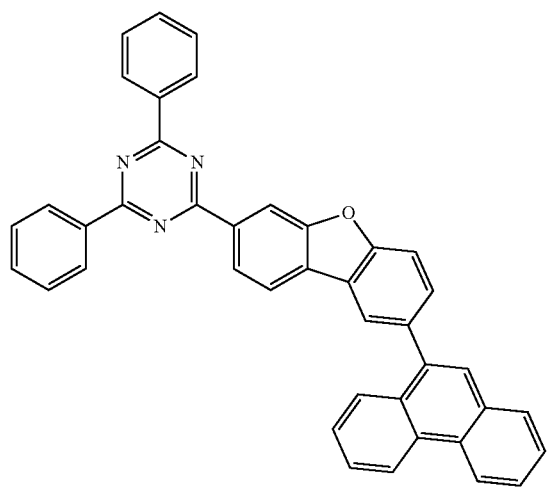
1-4
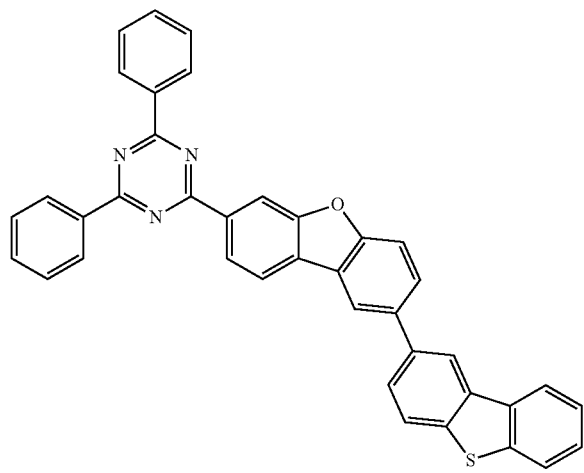
1-6

-continued
1-7
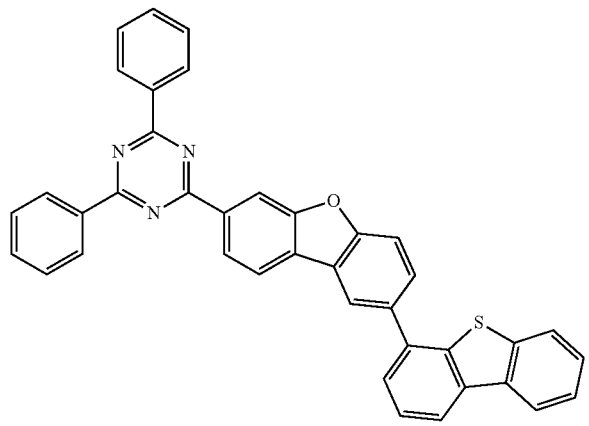
1-8
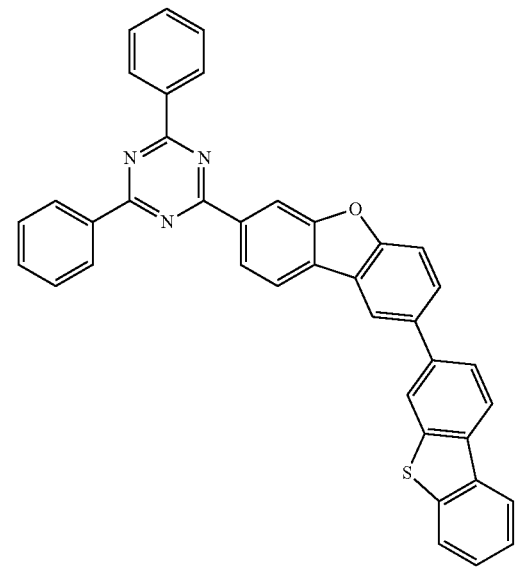
1-9
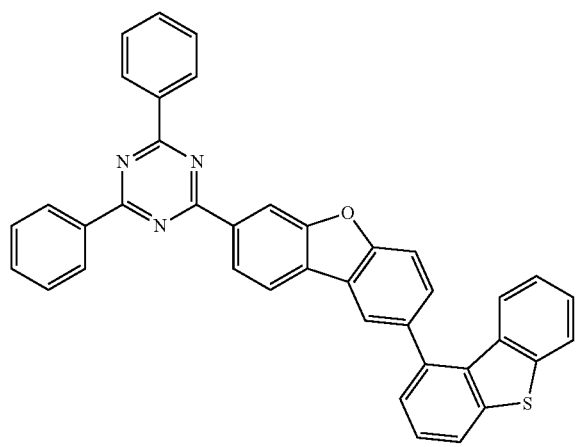
1-10
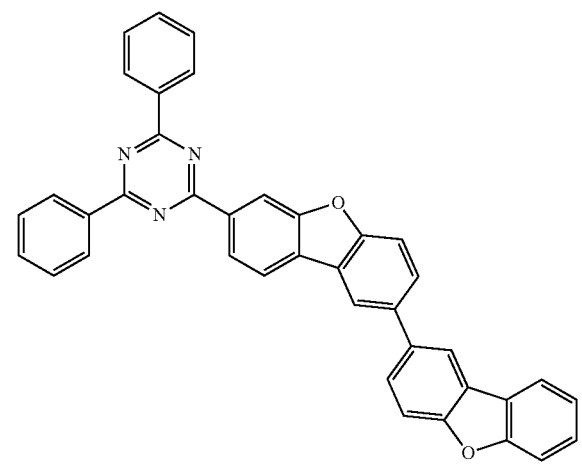
1-11
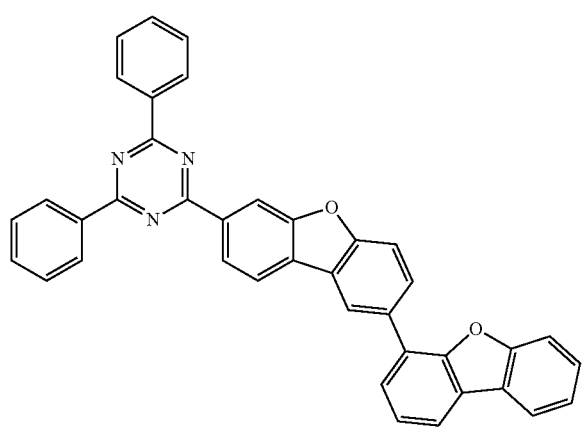
1-12
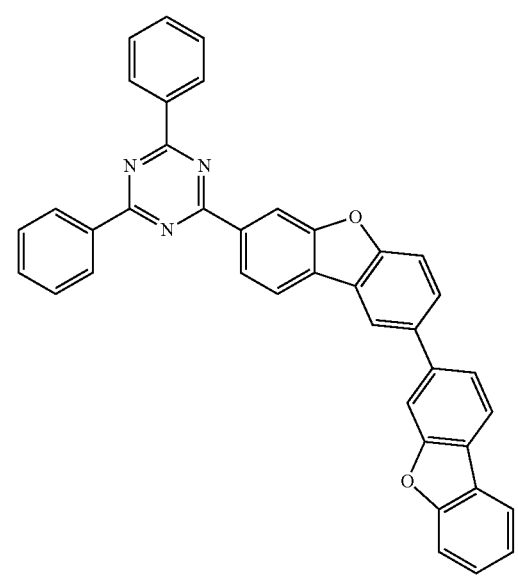

-continued
1-13
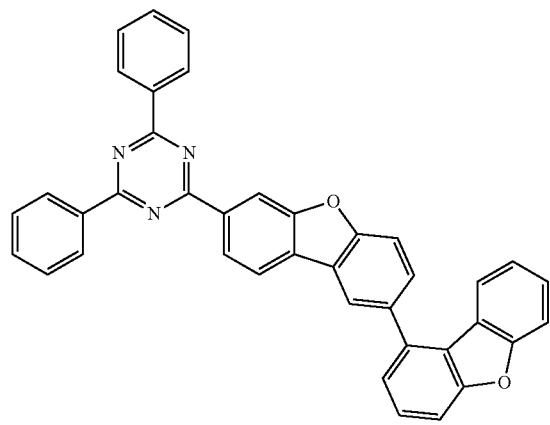
1-14
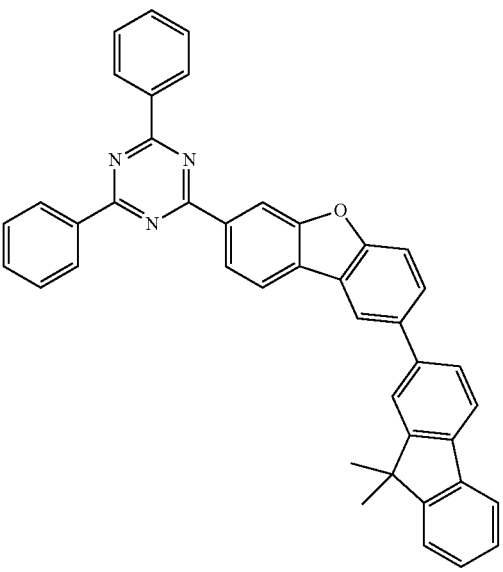
1-15
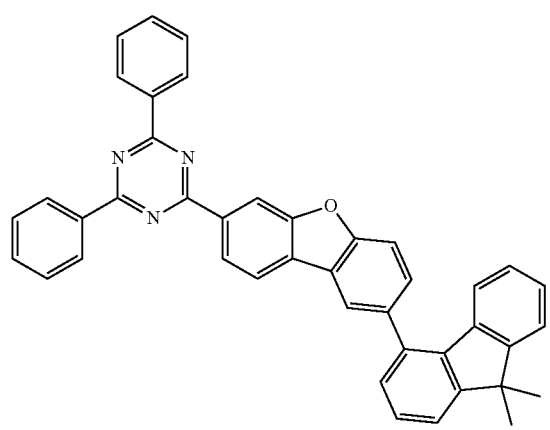
1-16
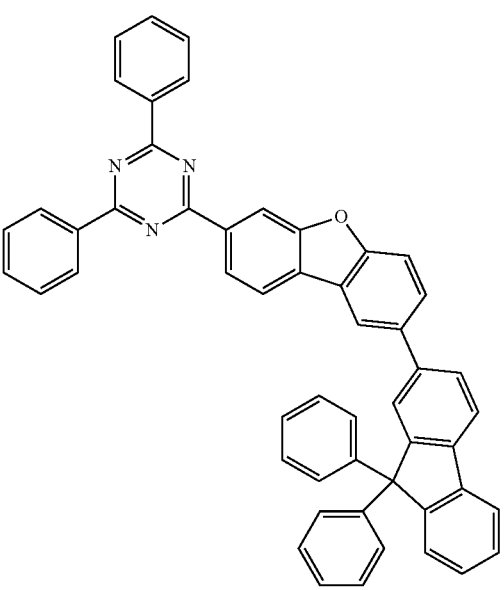

-continued
1-17
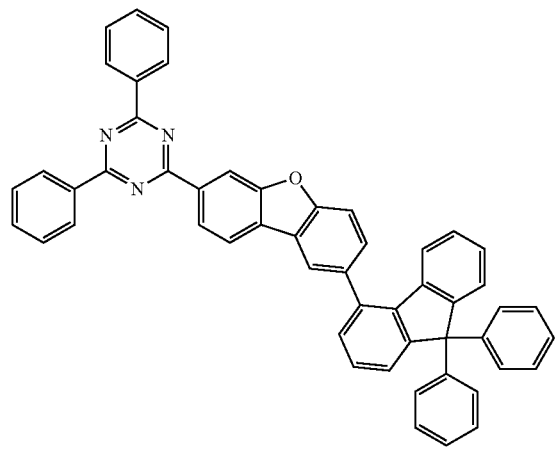
1-18
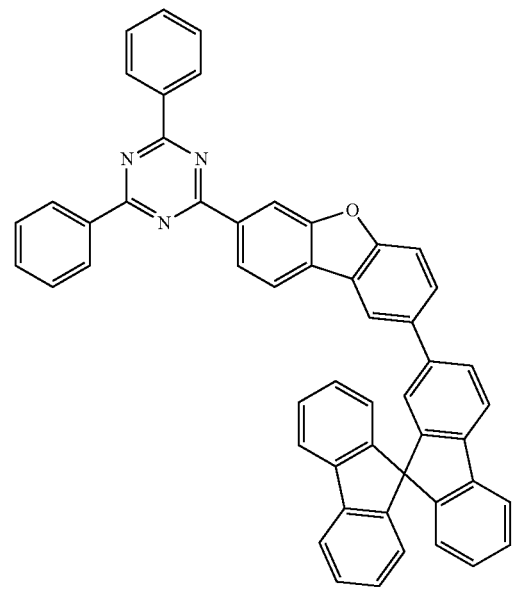
1-19
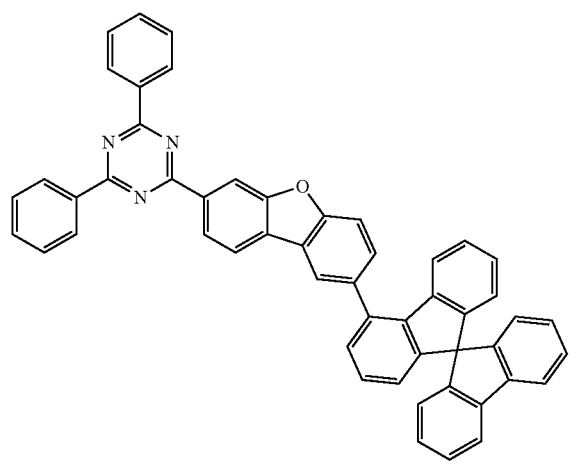
1-20
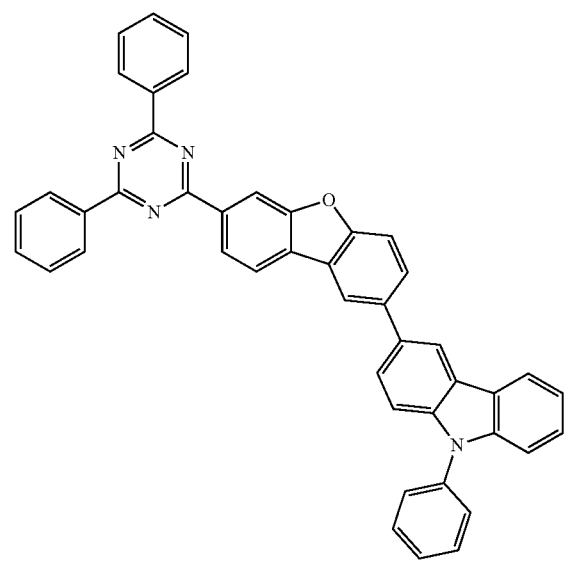

-continued
1-21
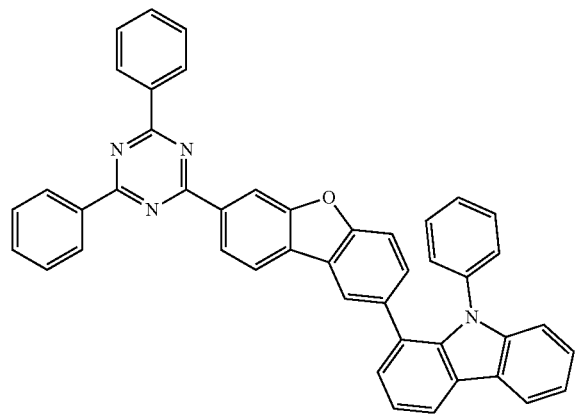
1-22
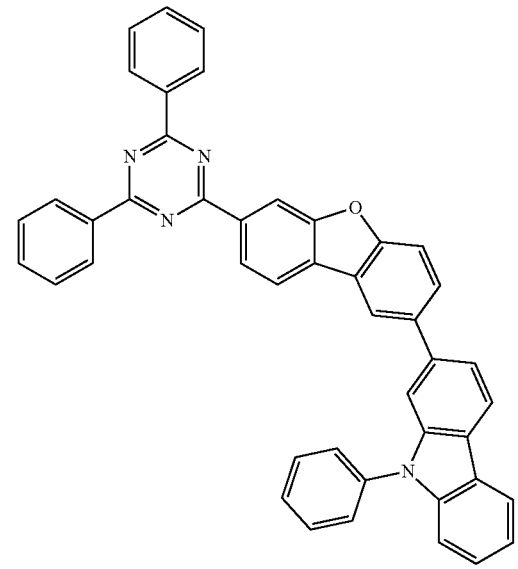
1-23
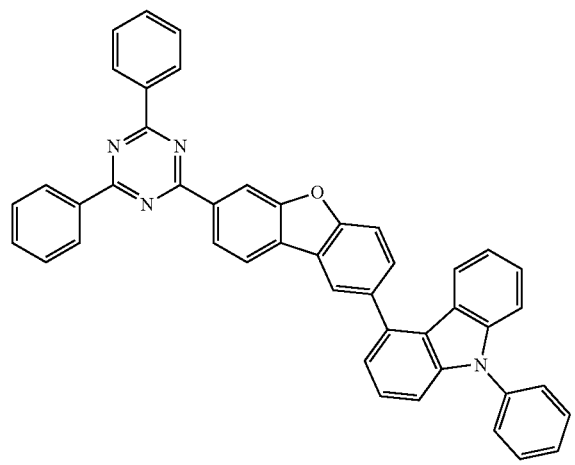
1-24
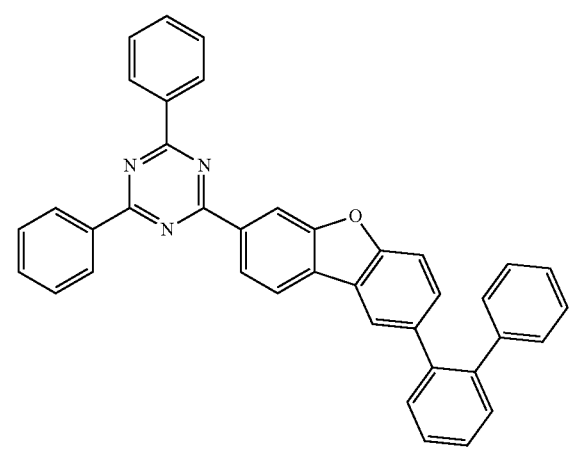
1-25
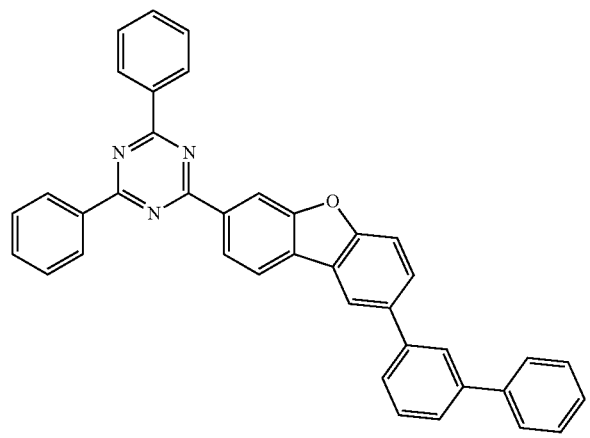
1-26
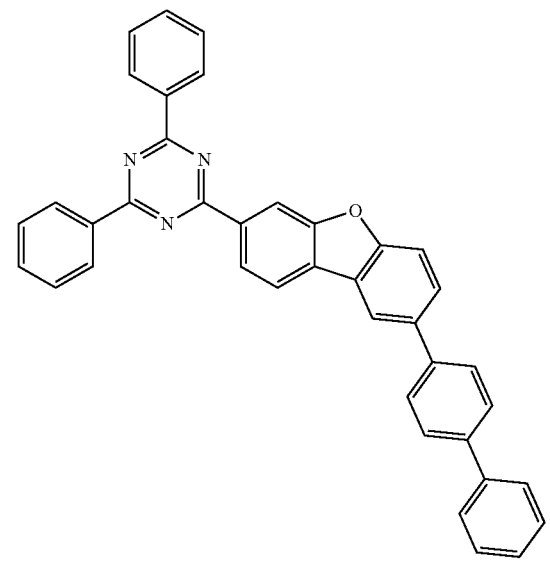

-continued
1-27
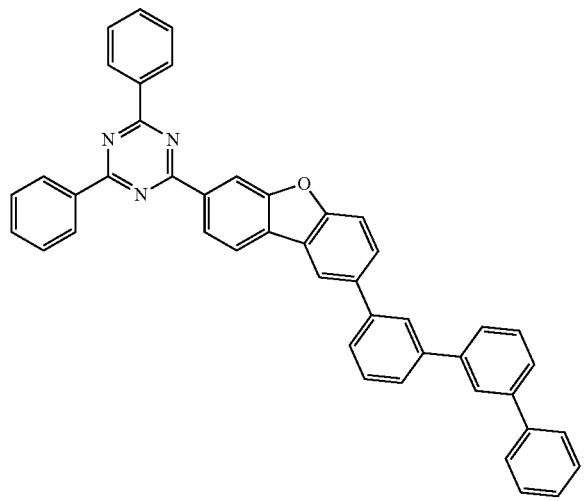
1-28
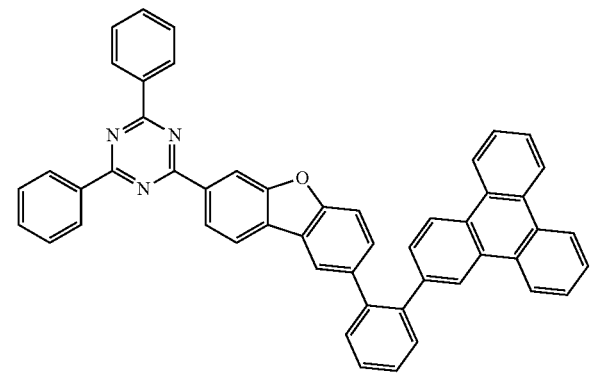
1-29
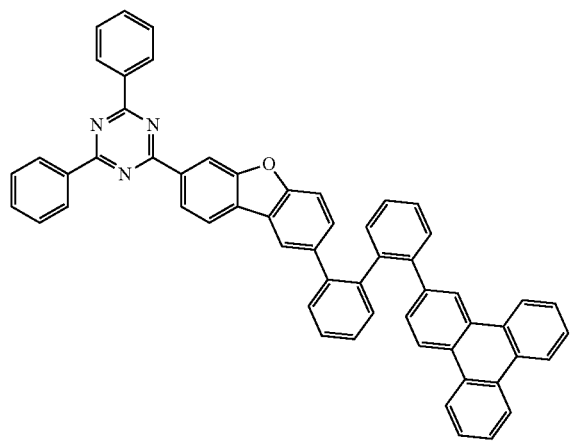
1-30
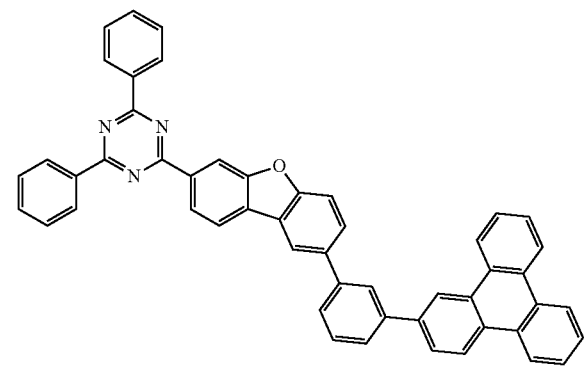
1-31
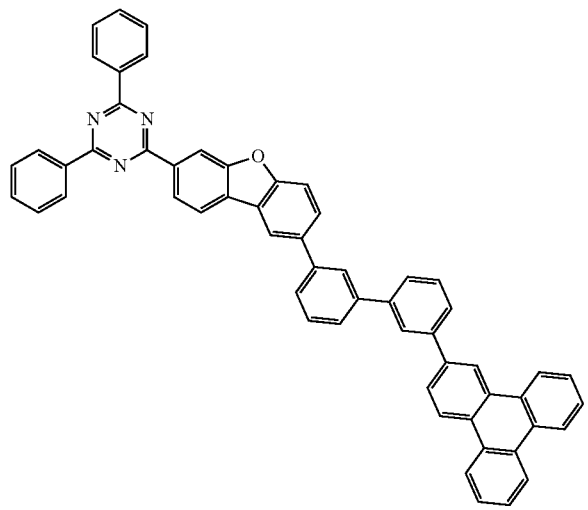
1-32
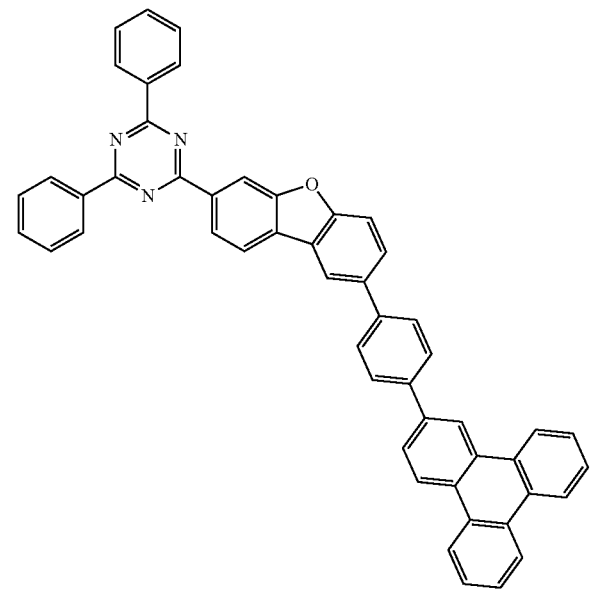

-continued
1-33
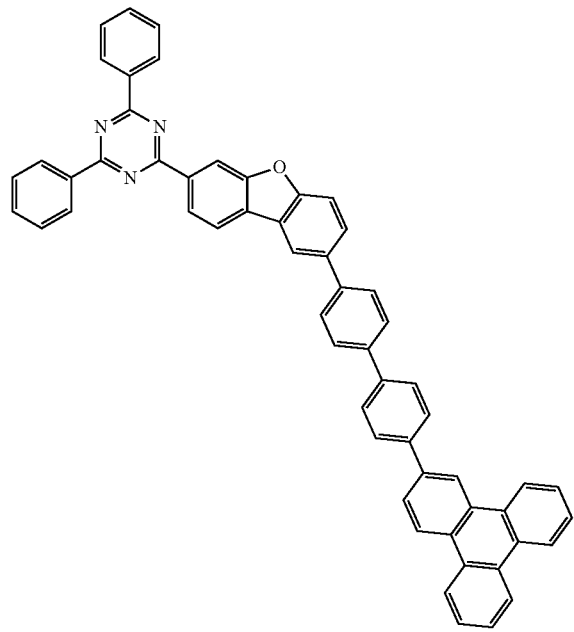
1-34
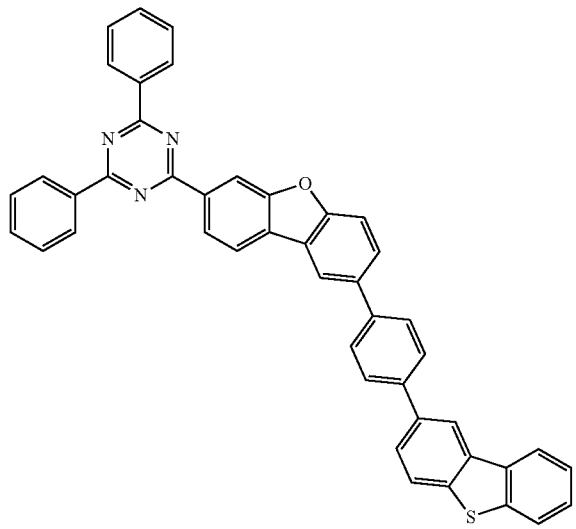
1-35
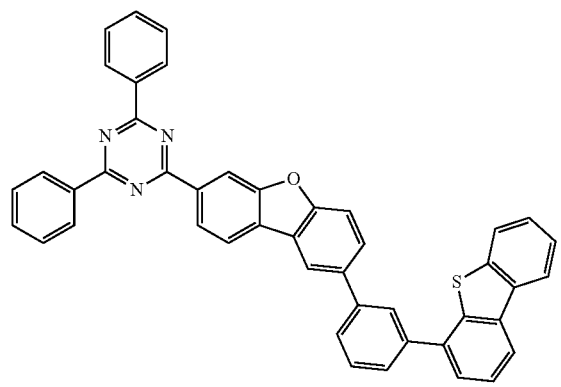
1-36
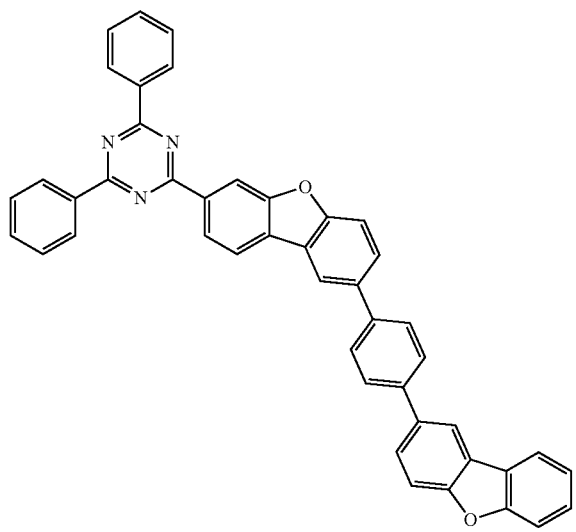
1-37
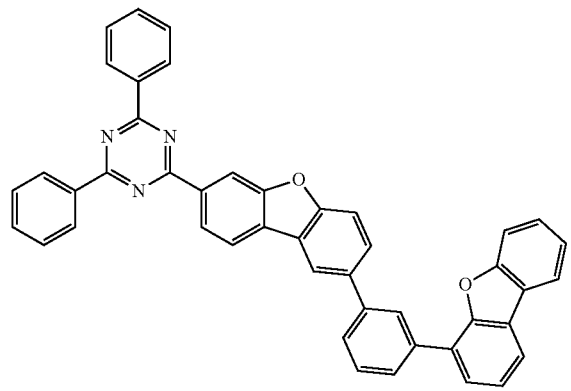
1-38
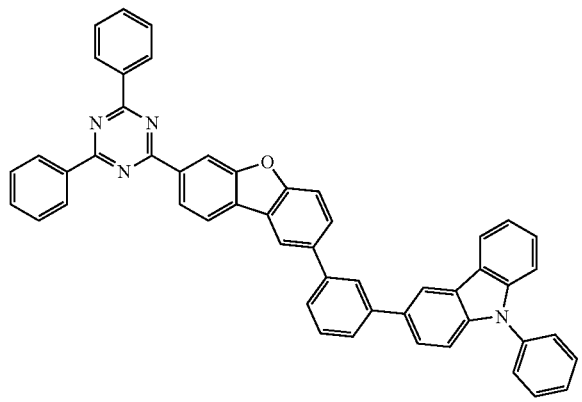

-continued
1-39 1-40
1-41 1-42
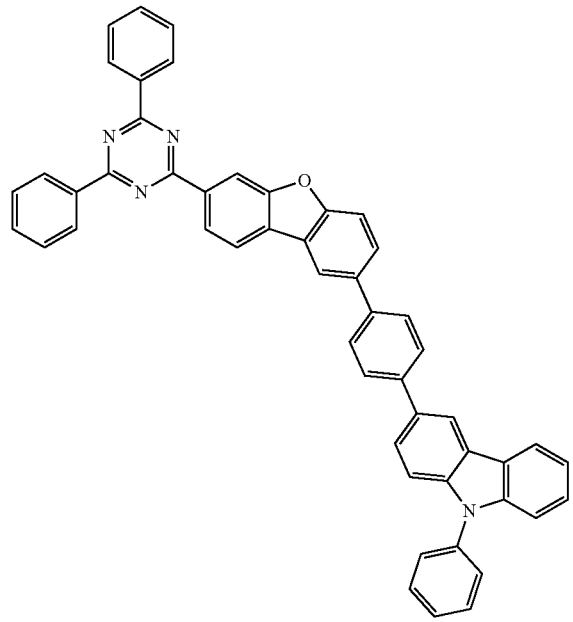

1-43
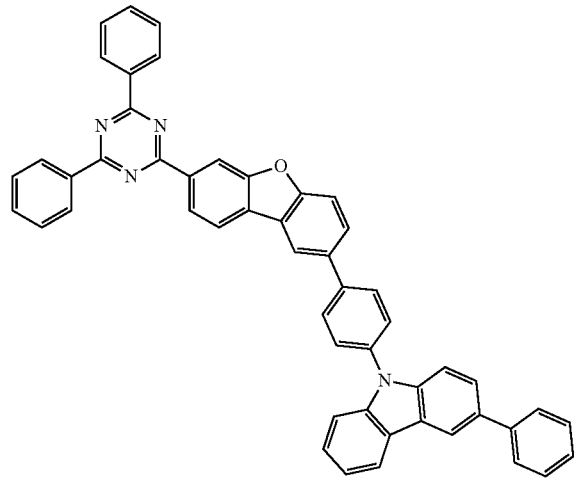
1-44
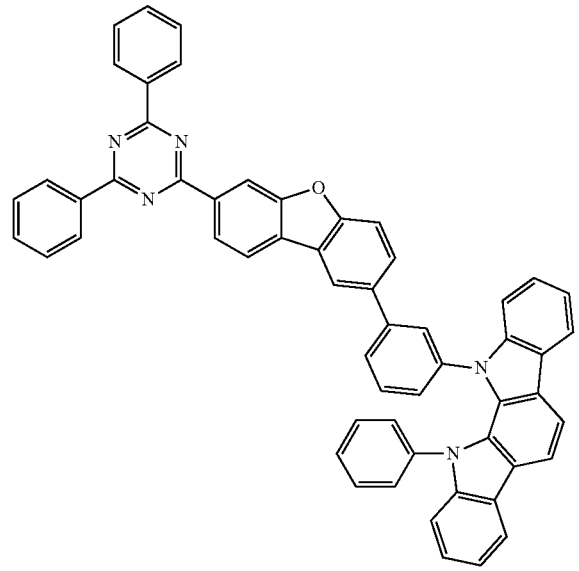
1-45
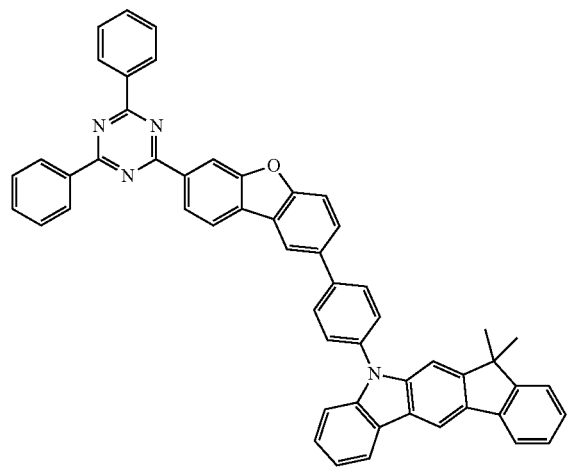
1-46
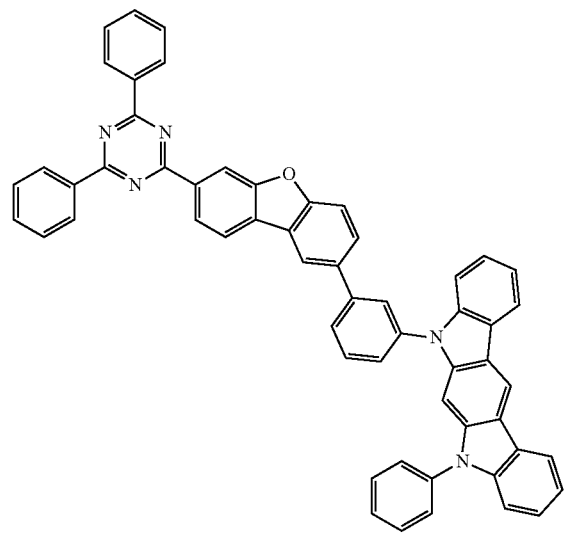

-continued
1-47
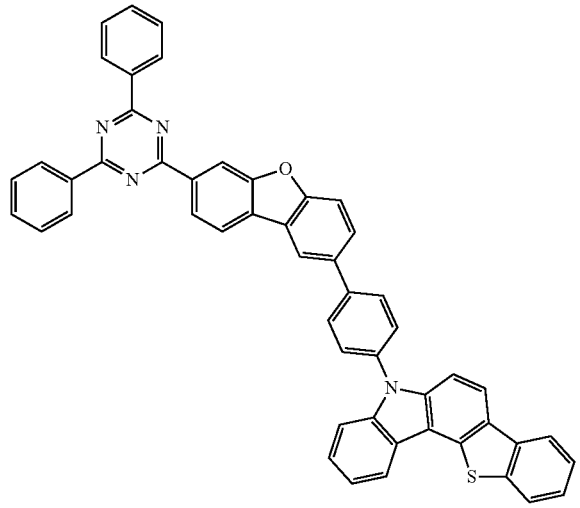
1-48
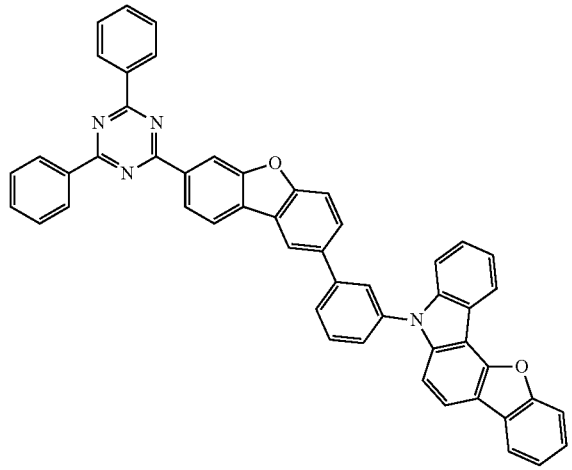
1-49
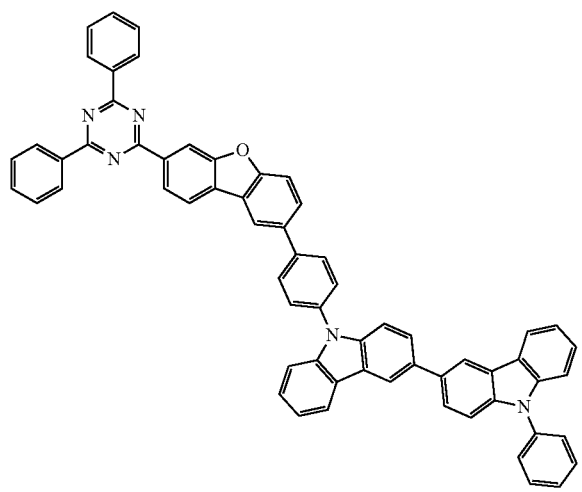
1-50
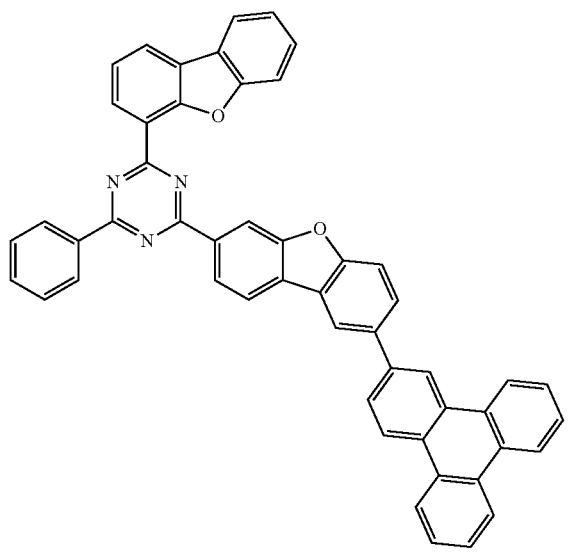
1-51
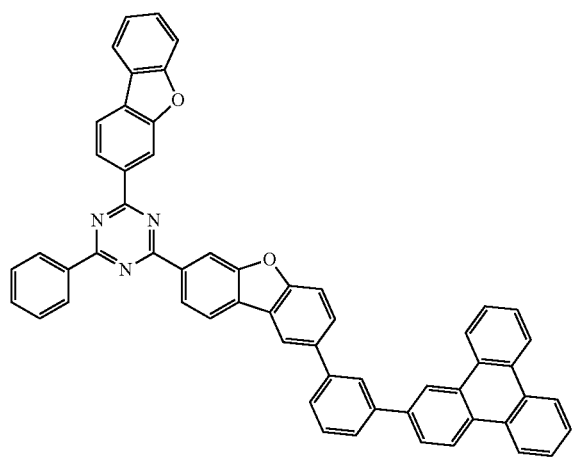
1-52
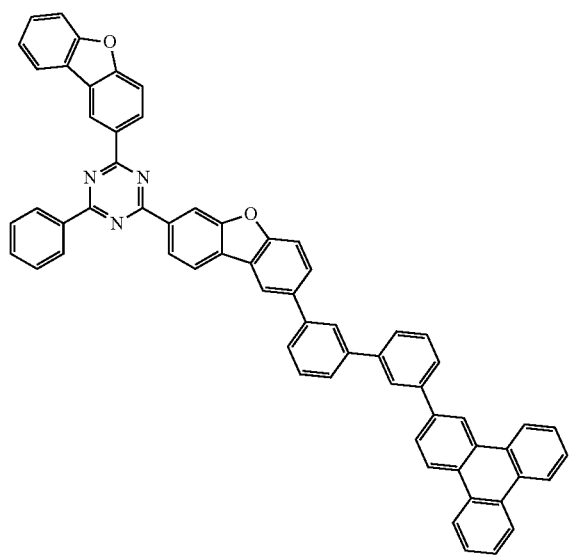

1-53
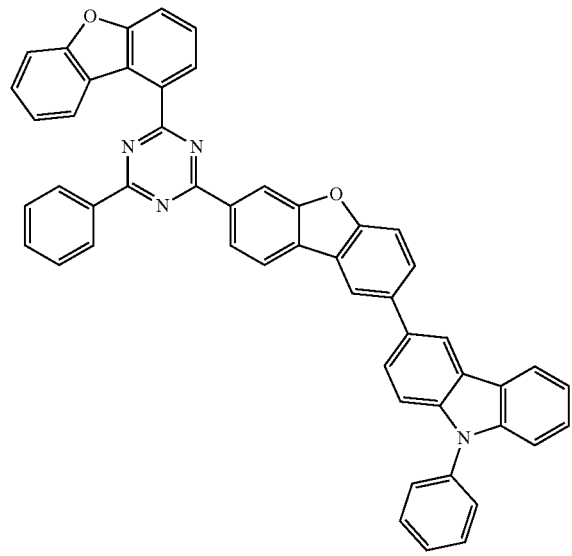
1-54
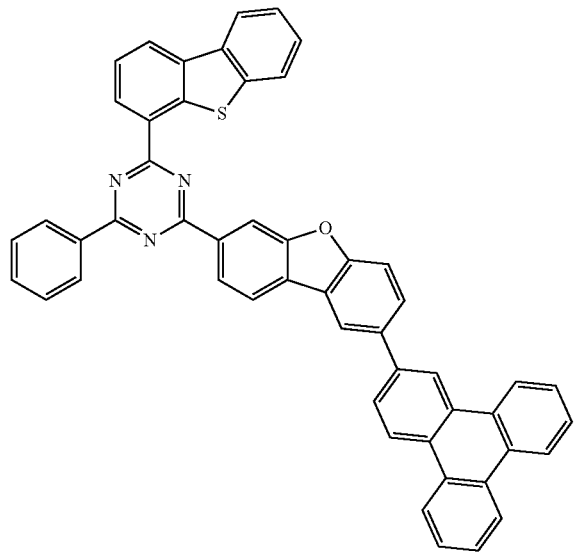
1-55
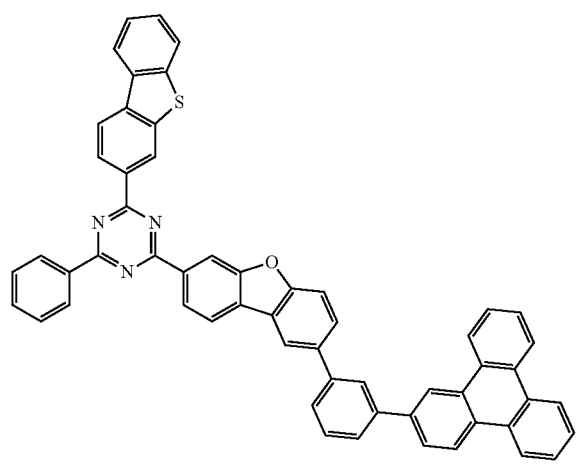
1-56
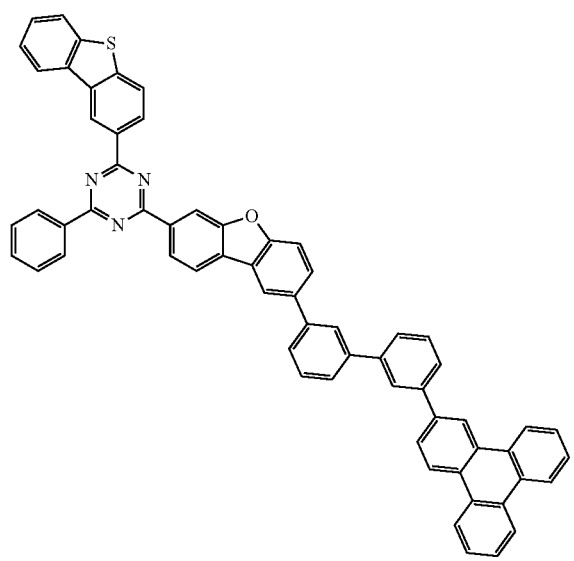

1-57
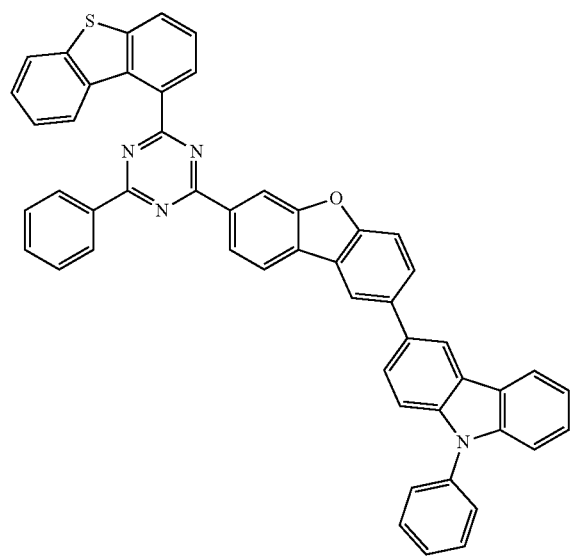
1-58
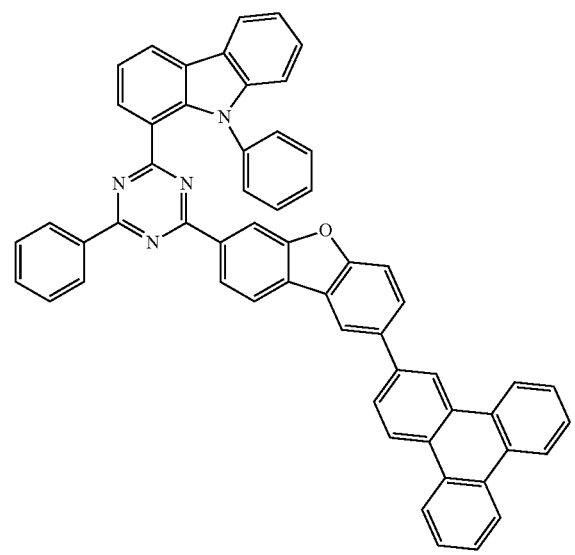
1-59
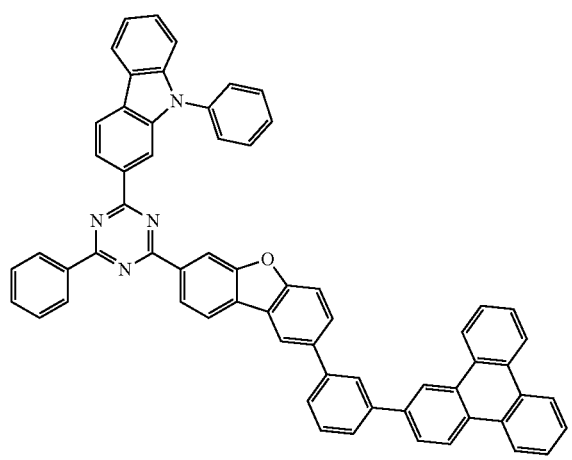
1-60
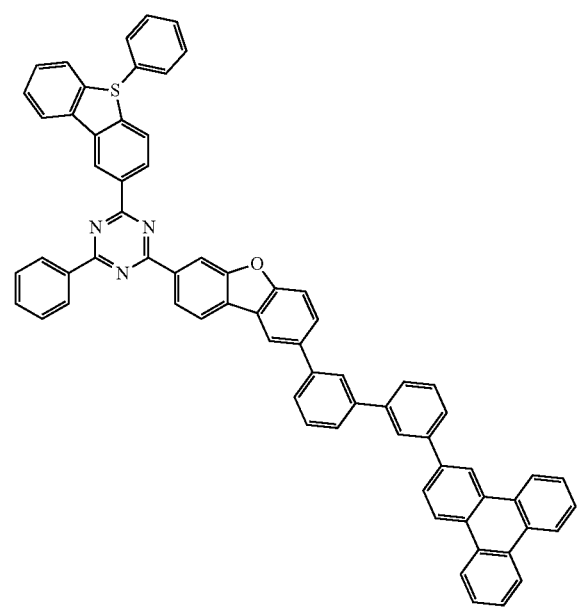

1-61
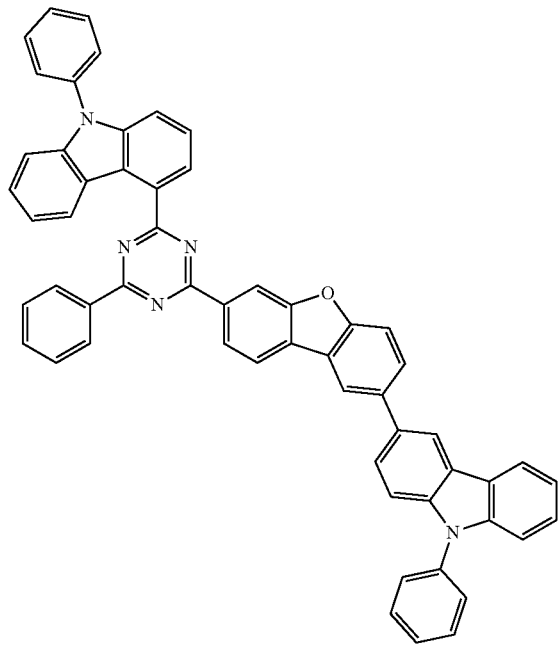
1-62
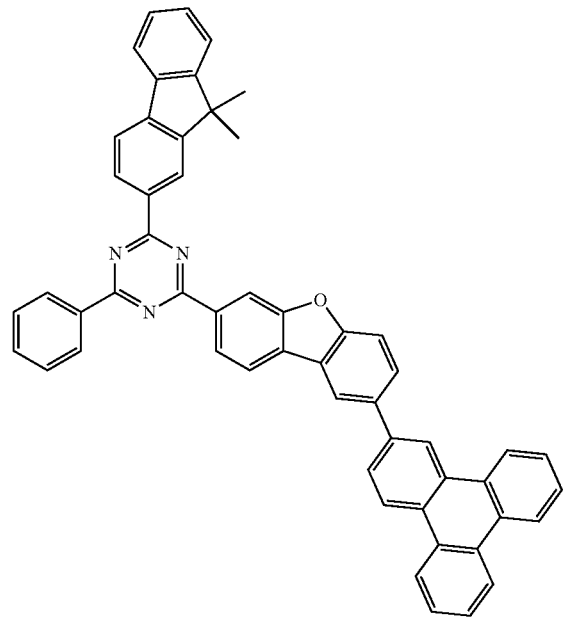
1-63
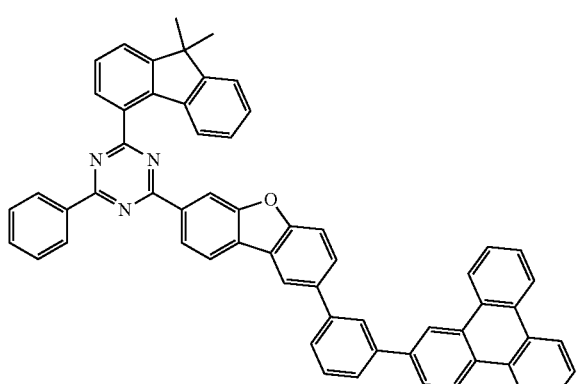
1-64
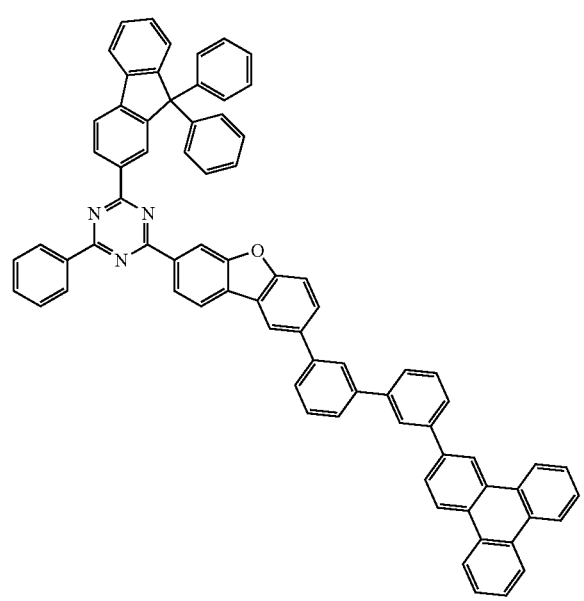

1-65
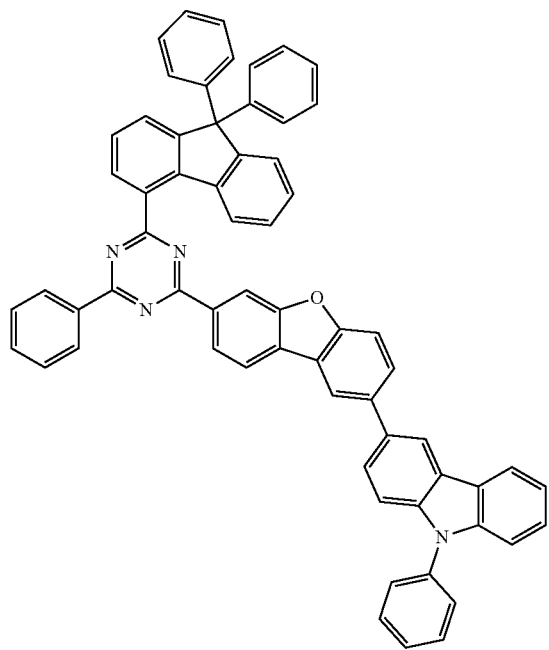
1-66
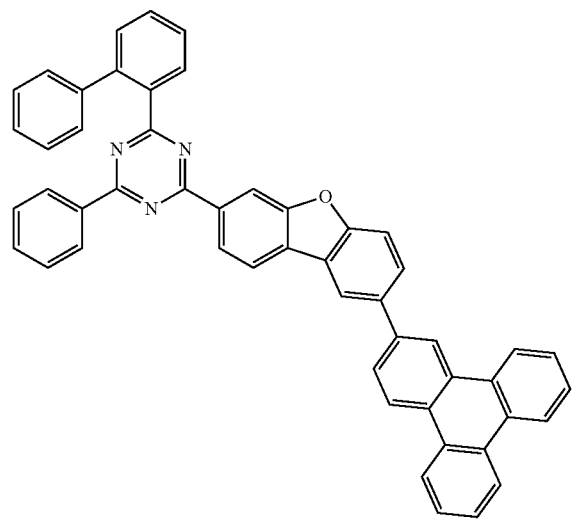
1-67
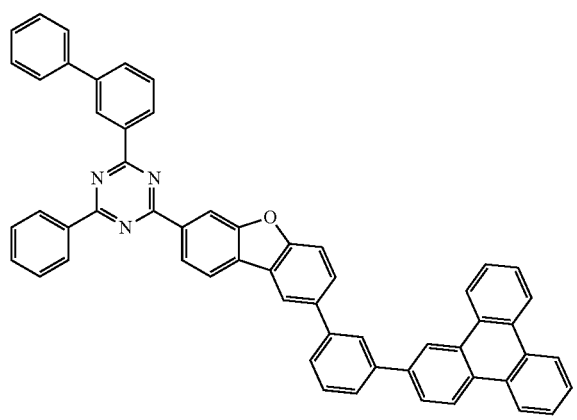
1-68
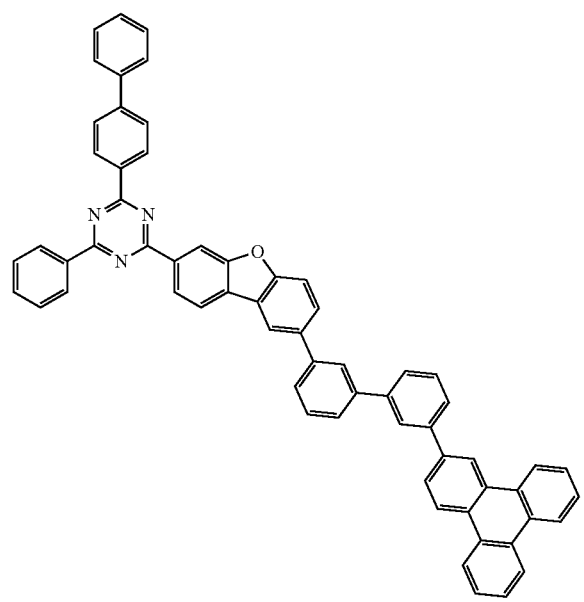

1-69
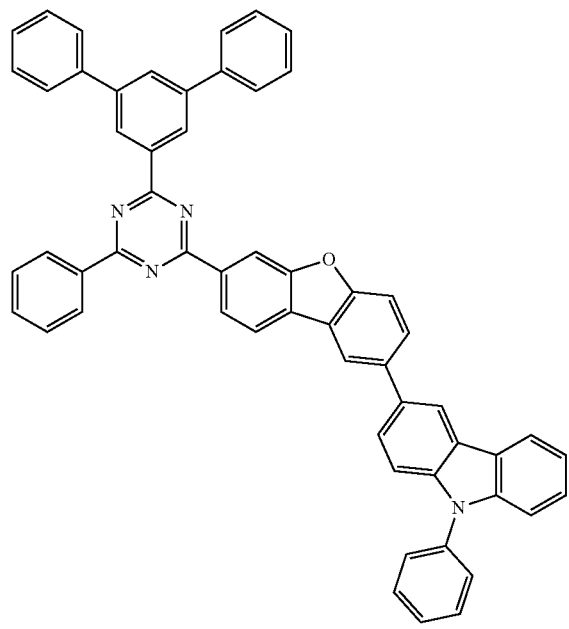
1-70
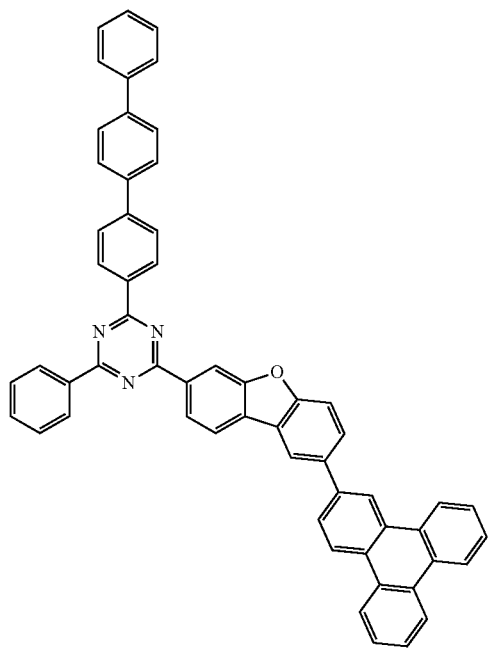
1-71
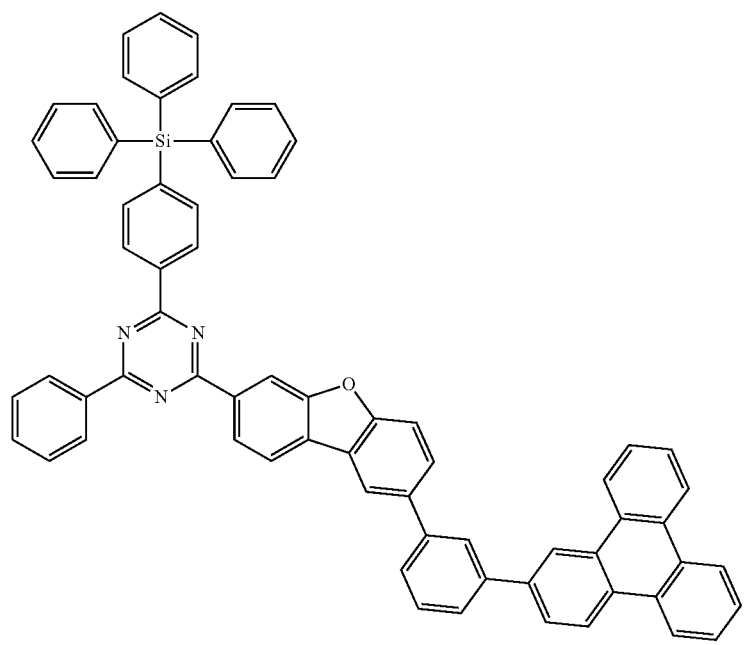

-continued
1-72
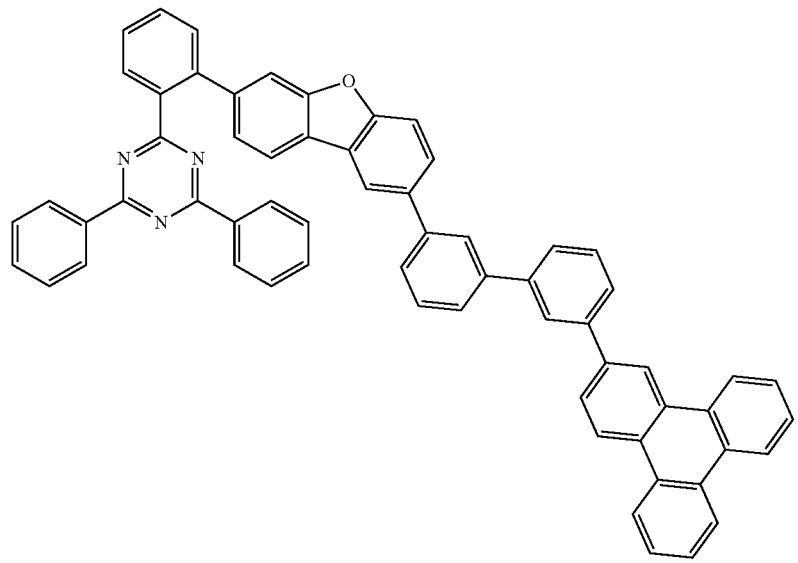
1-73
1-74
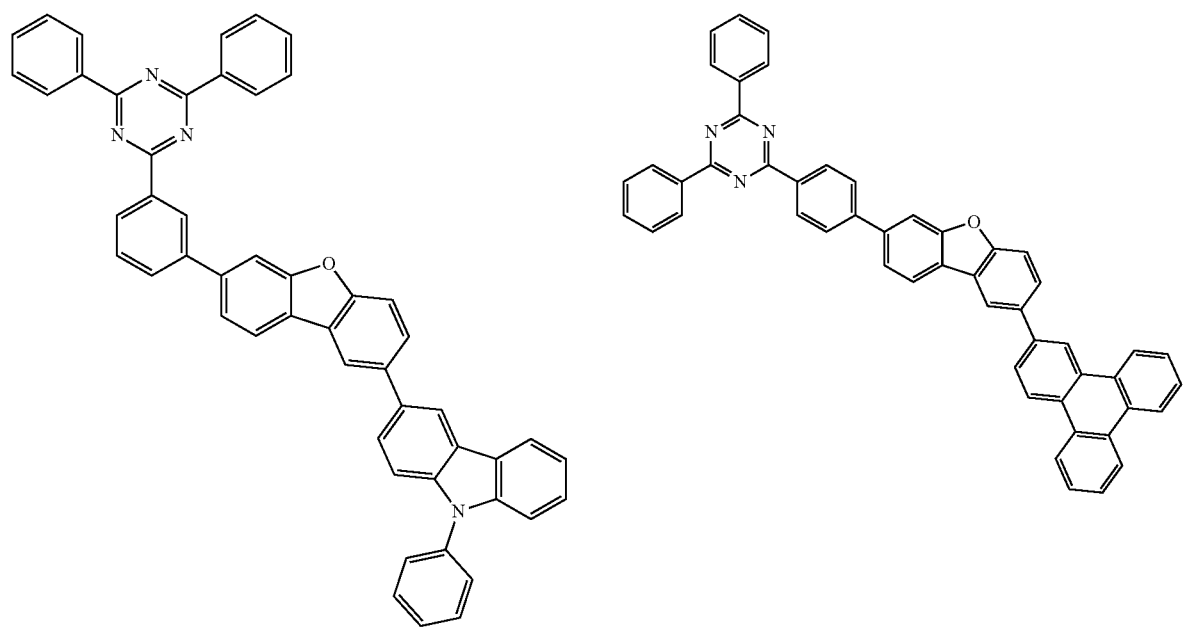

-continued
1-75
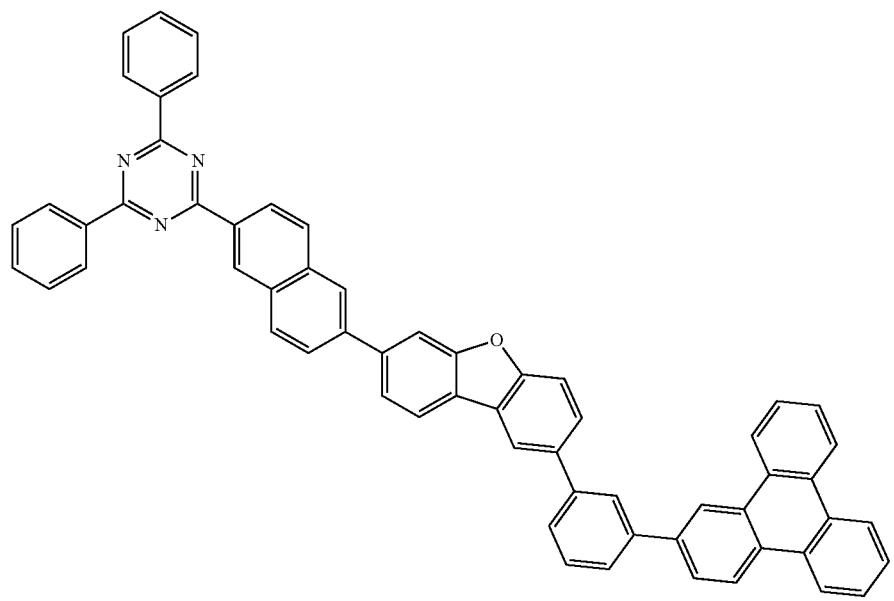
1-76
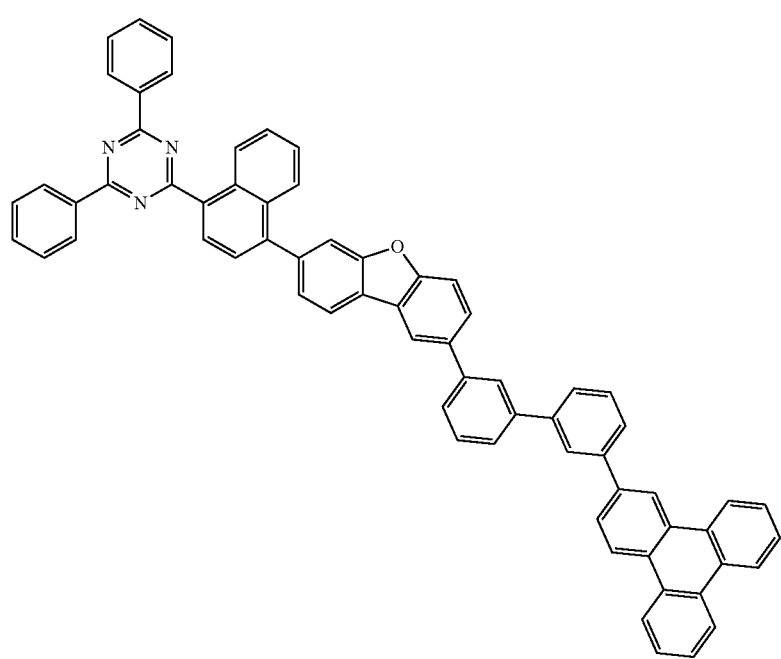

-continued
1-77
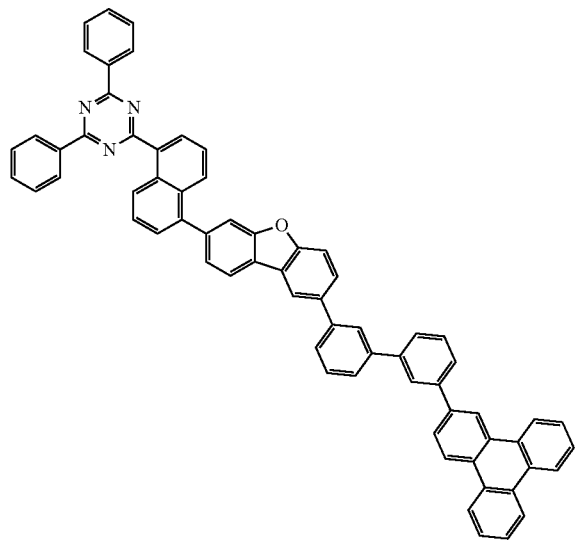
1-78
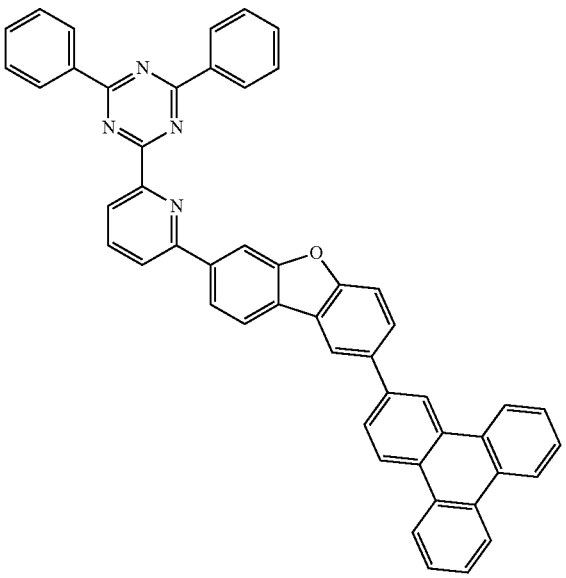
1-79
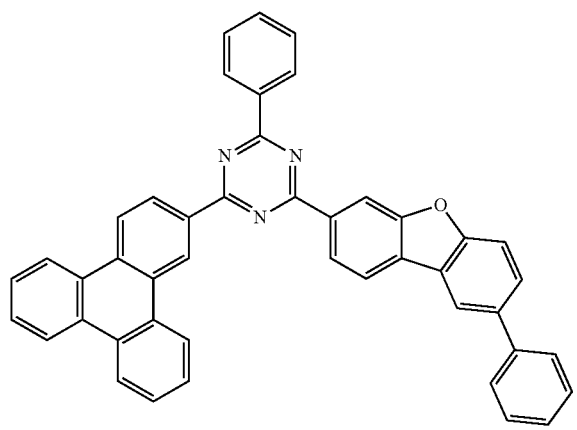
1-80
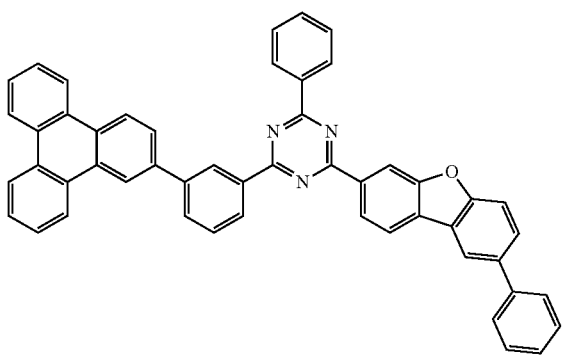
1-81
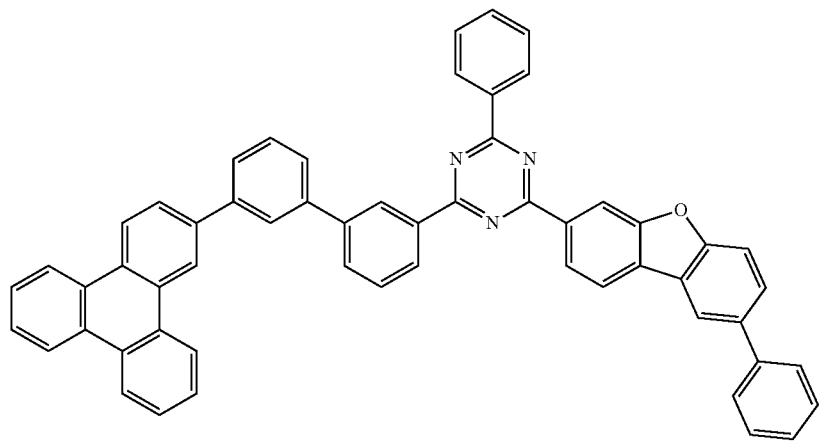

-continued
1-82
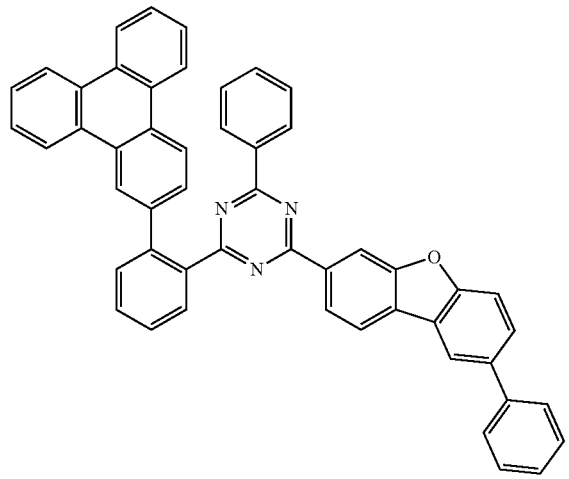
1-83
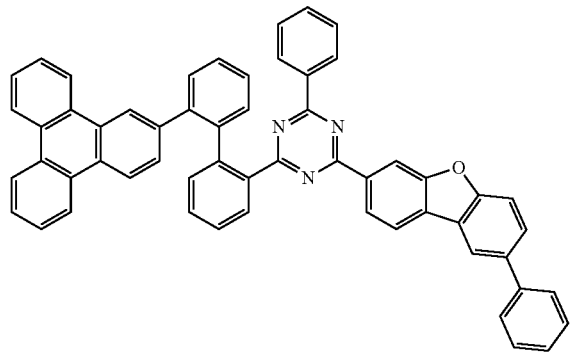
1-84
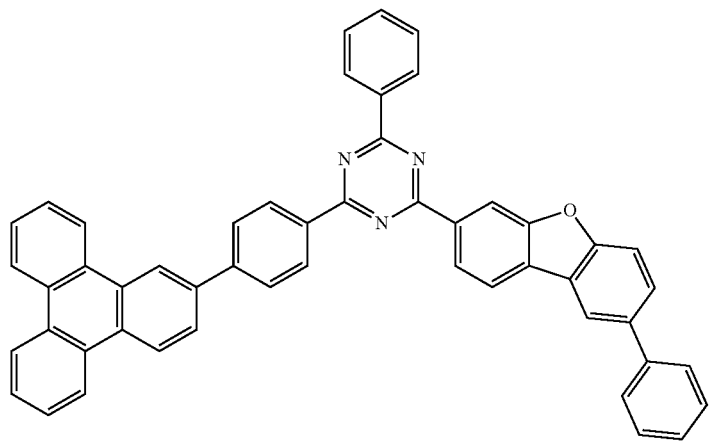
1-85
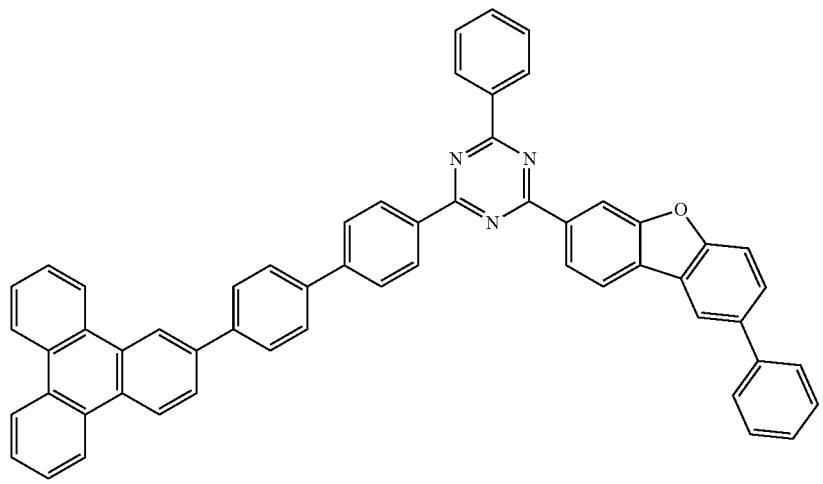

-continued
1-86
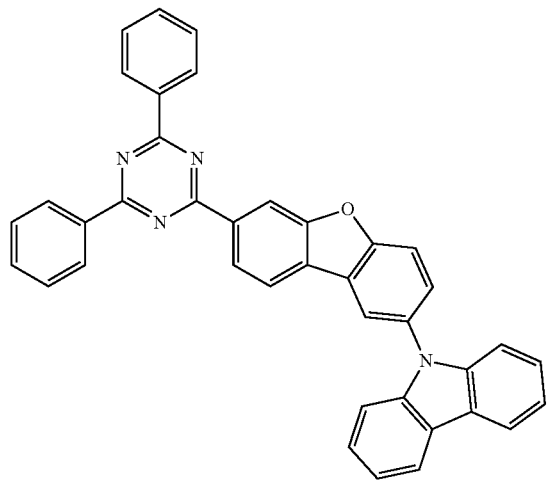
1-87
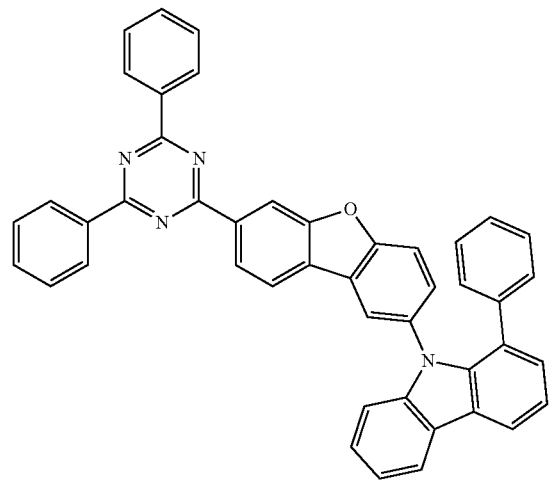
1-88
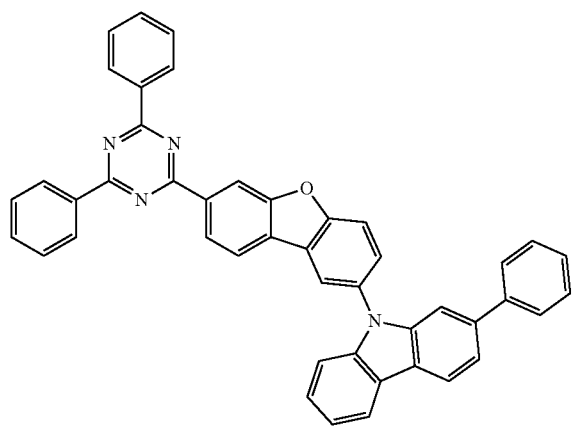
1-89
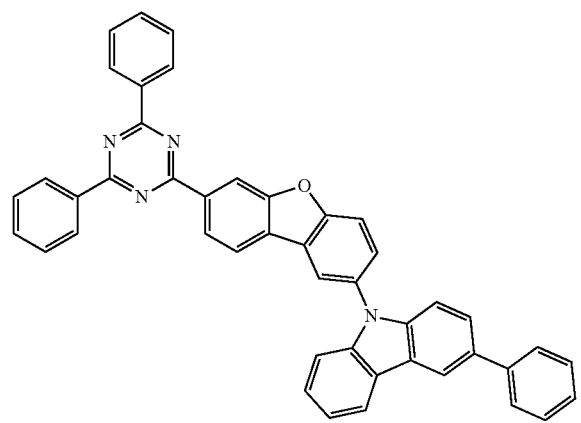
1-90
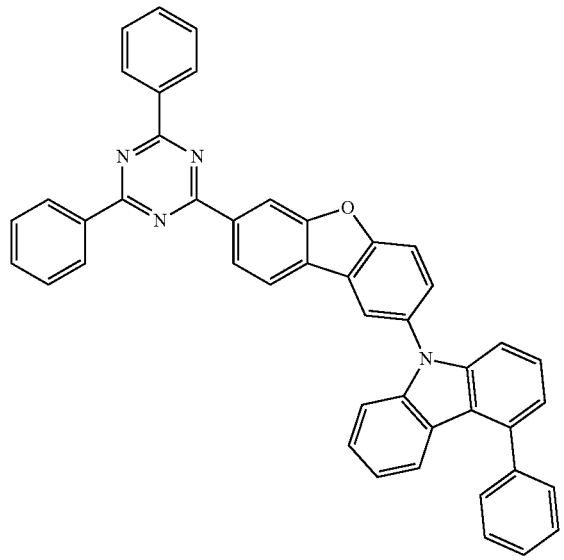
1-91
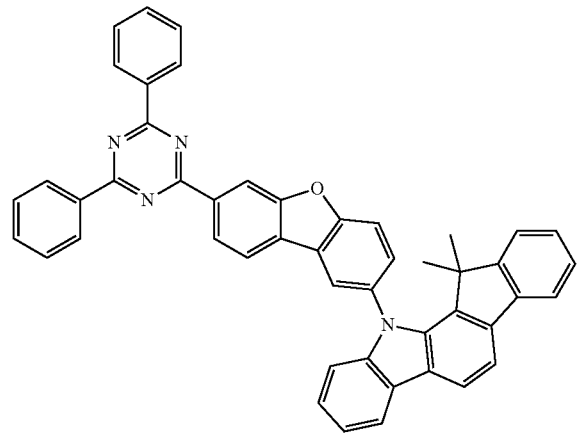

-continued
1-92
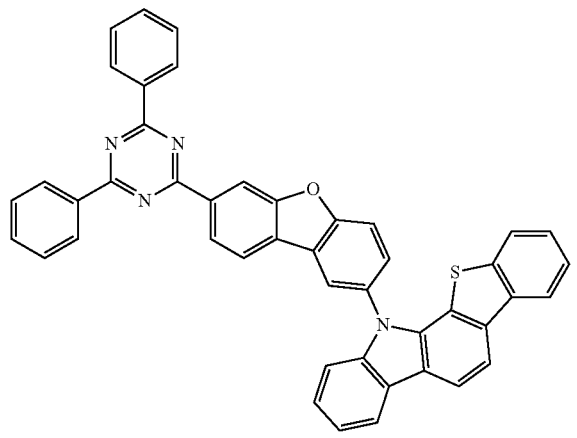
1-93
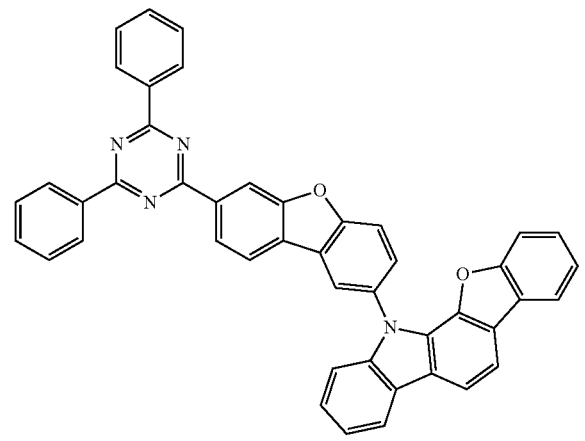
1-94
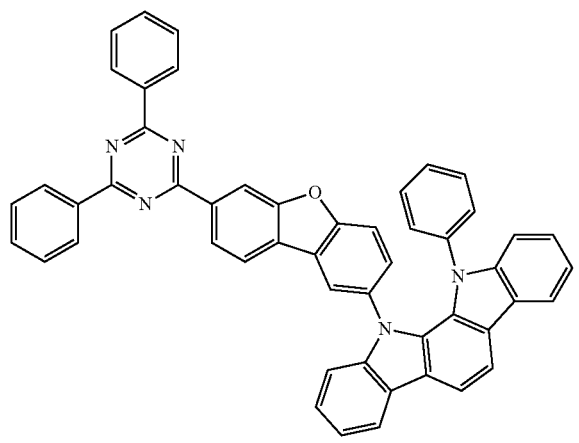
1-95
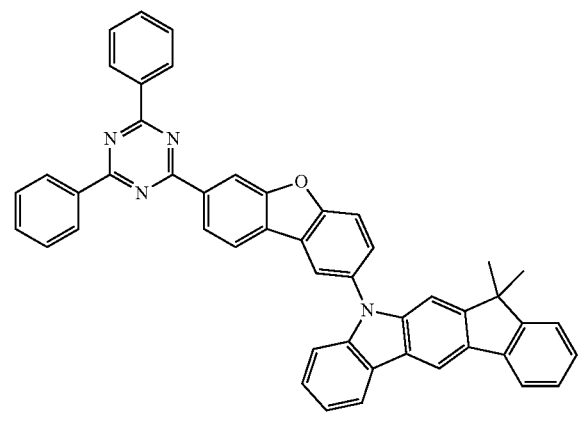
1-96
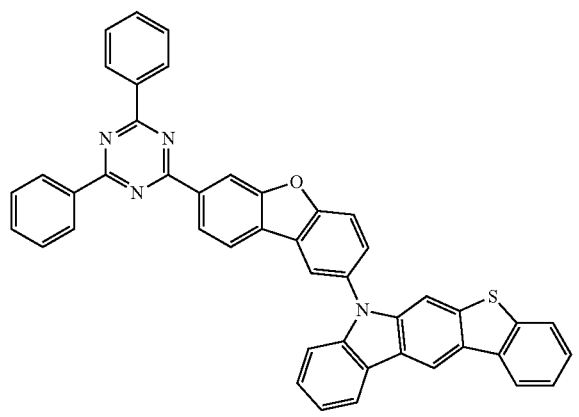
1-97
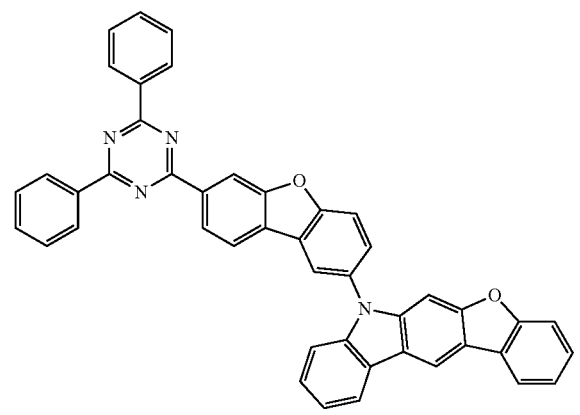

1-98
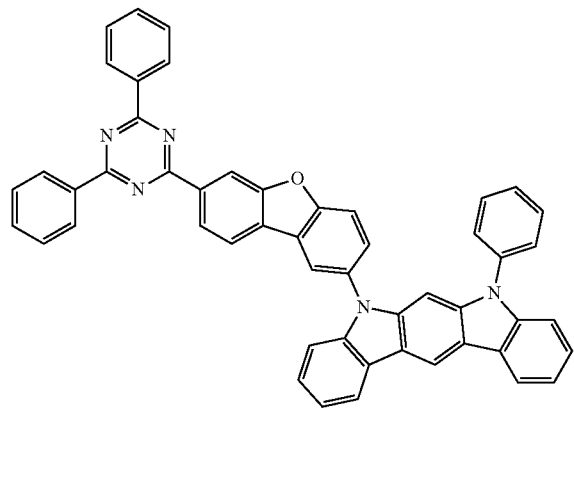
1-99
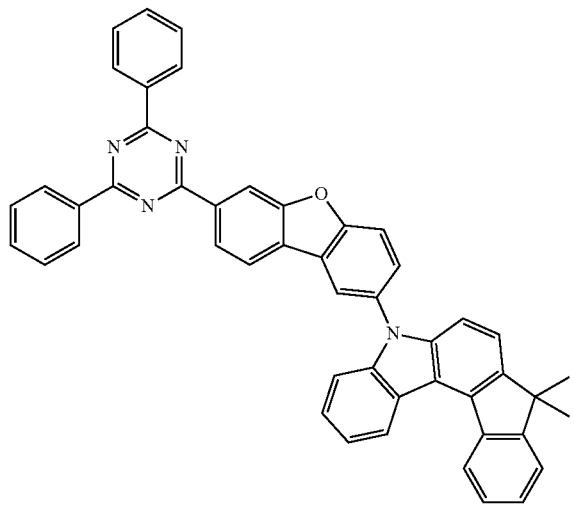
1-100
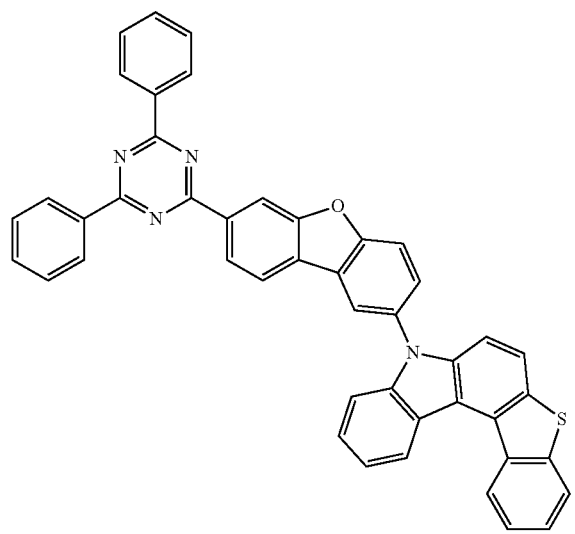
2-1
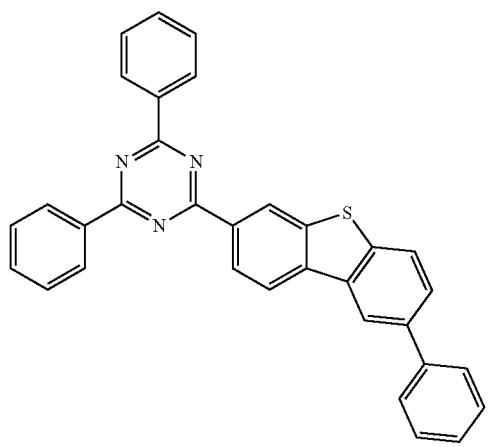
2-2
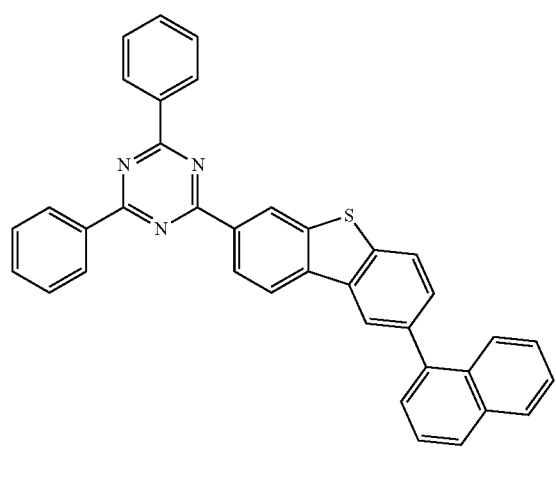
2-3
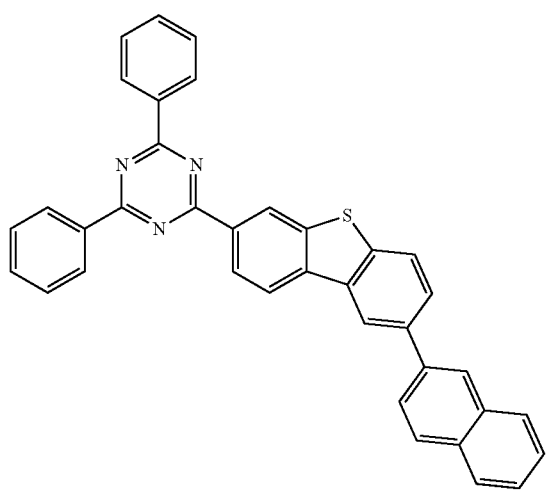

-continued
2-4
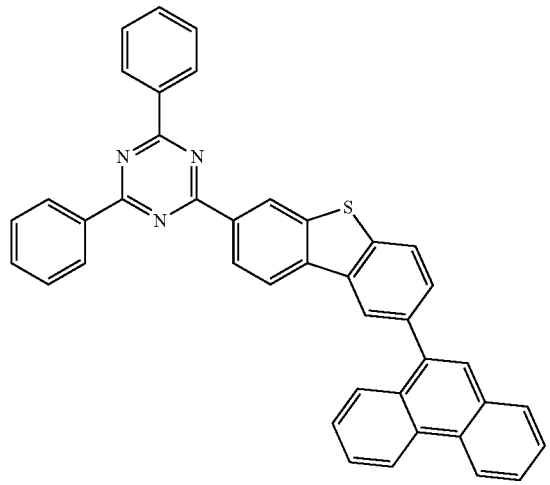
2-5
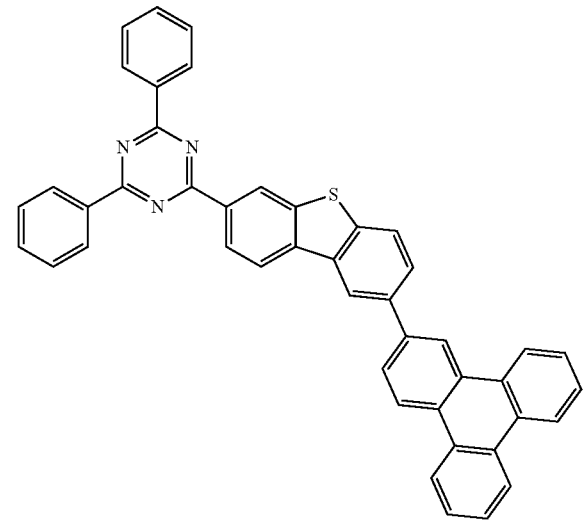
2-6
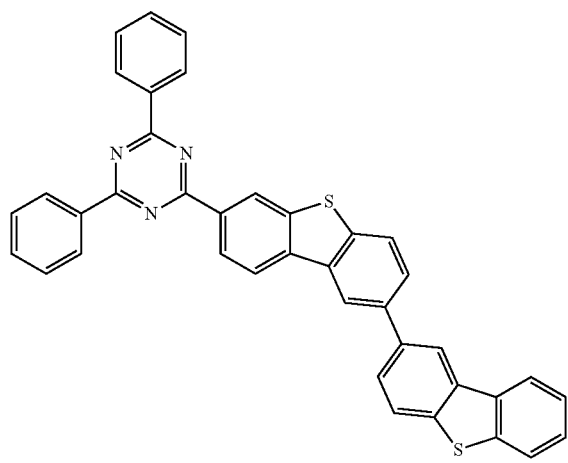
2-7
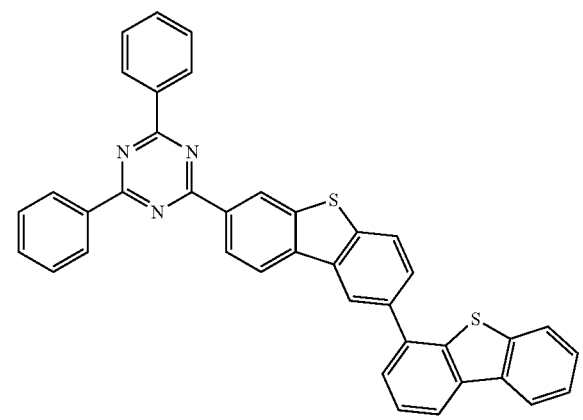
2-8
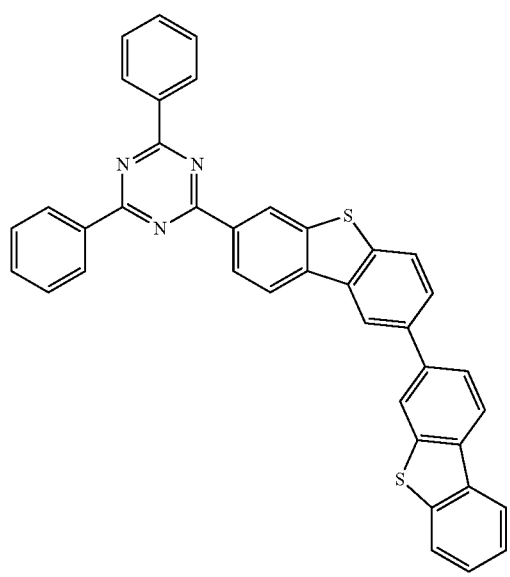
2-9
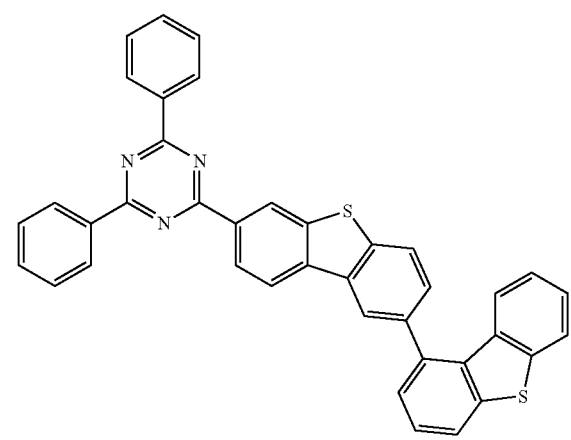

-continued
2-10
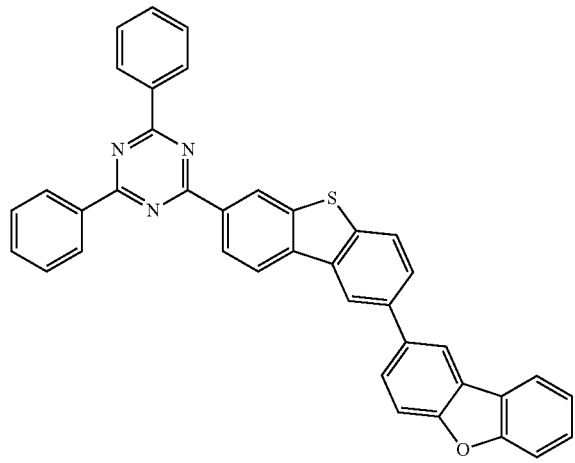
2-11
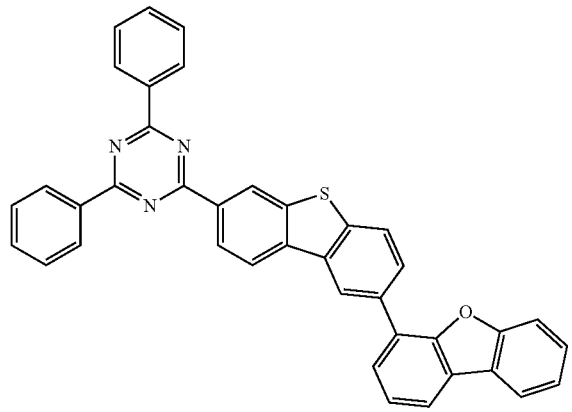
2-12
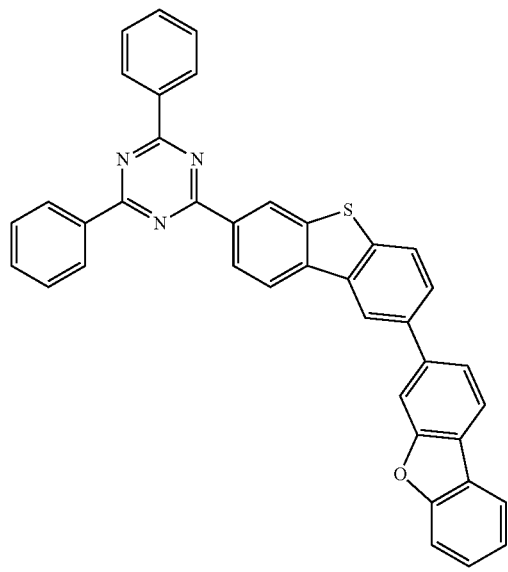
2-13
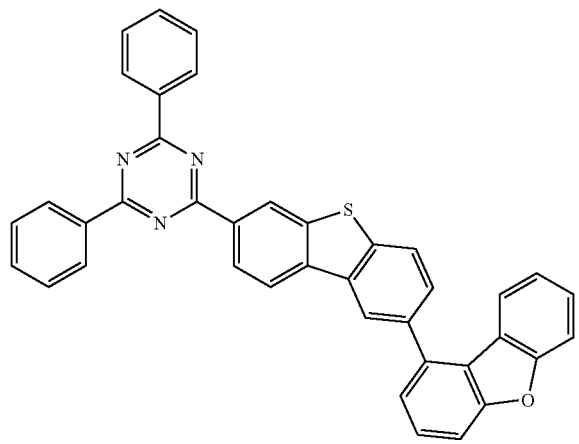
2-14
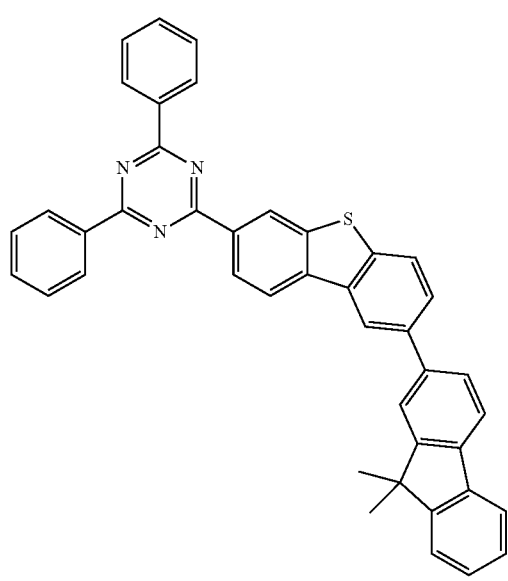
2-15
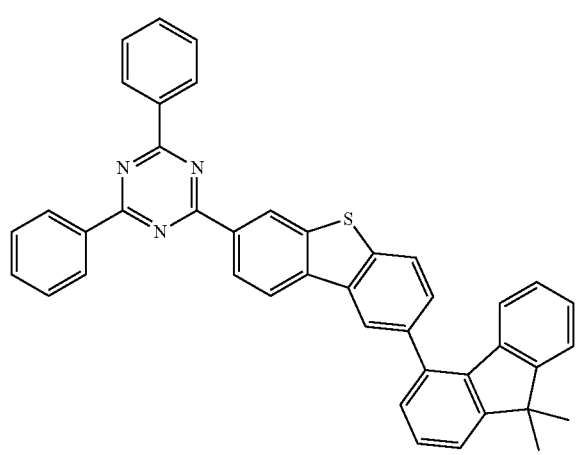

2-16
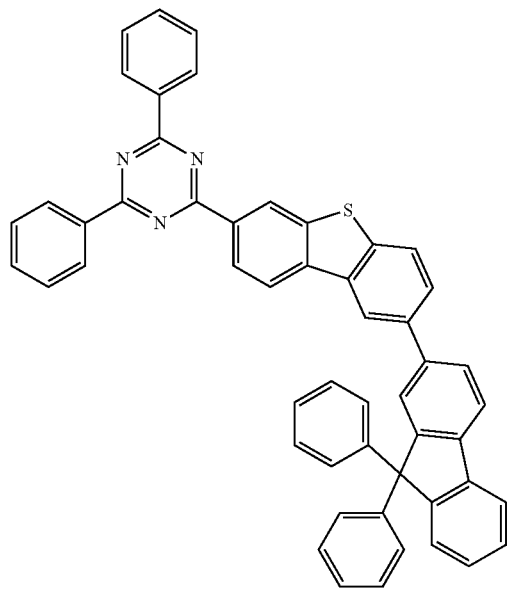
2-17
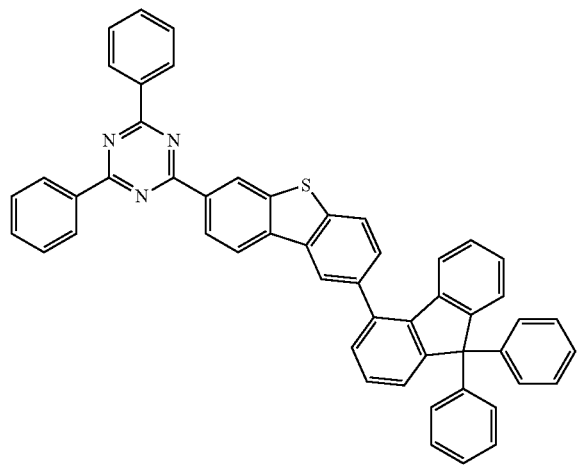
2-18
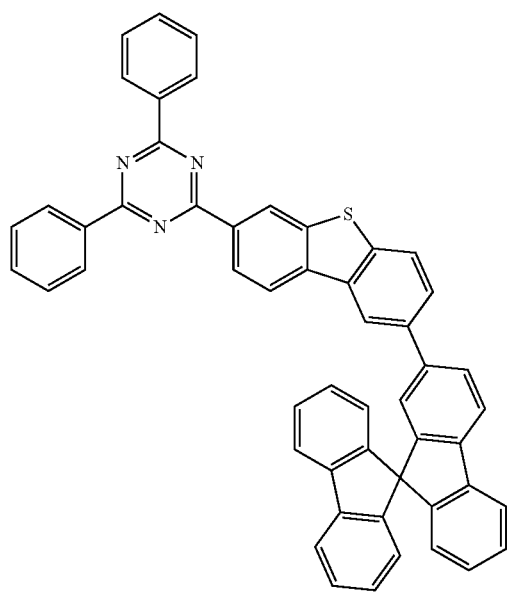
2-19
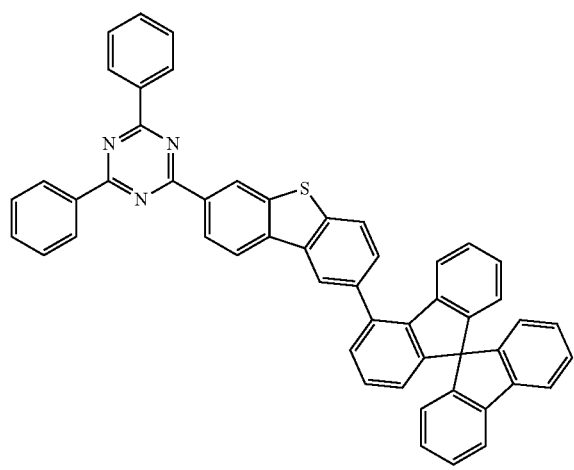

-continued
2-20
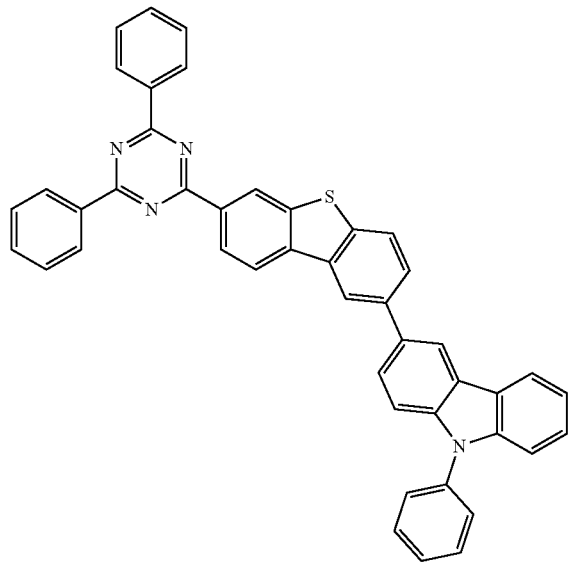
2-21
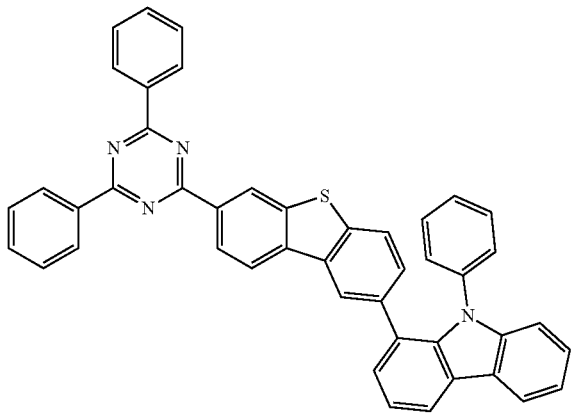
2-22
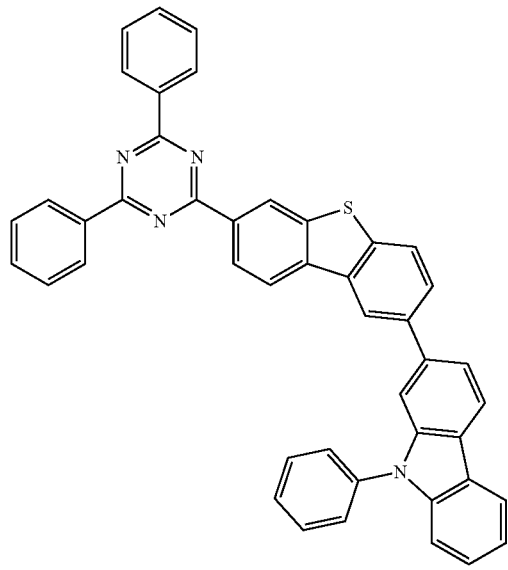
2-23
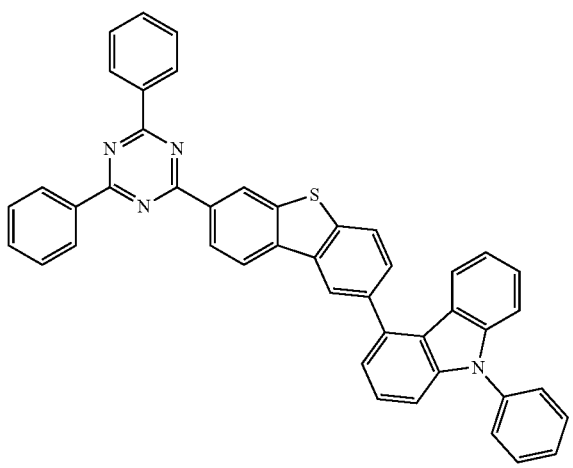
2-24
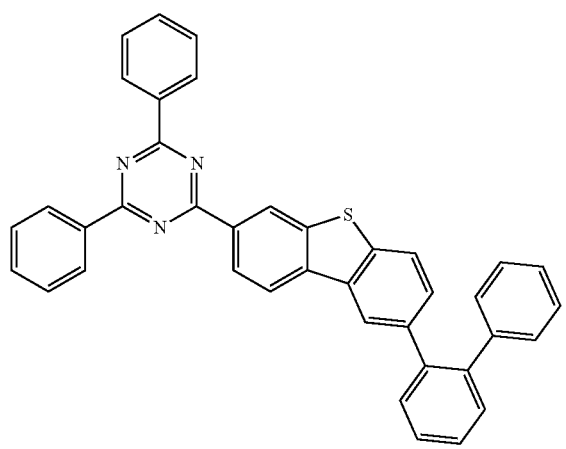
2-25
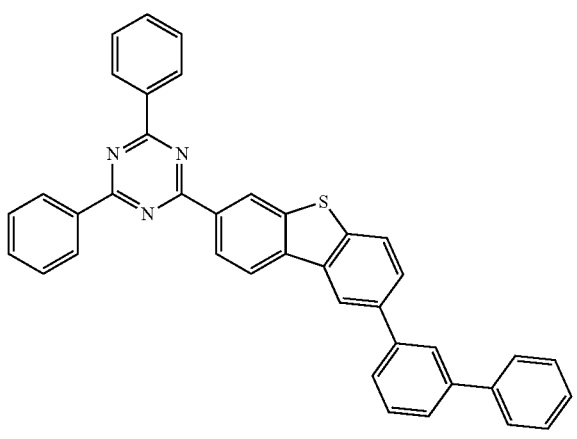

2-26
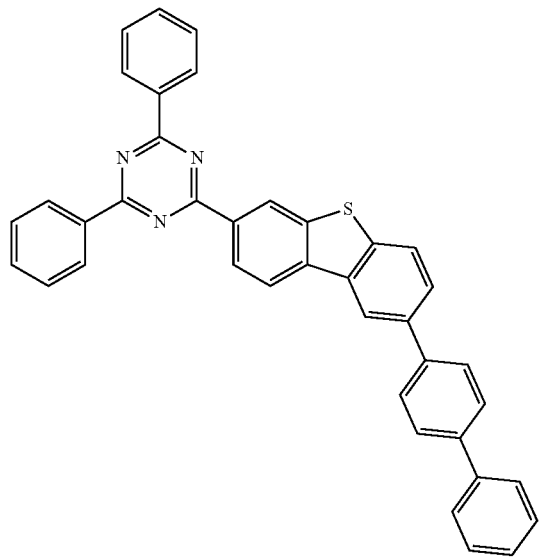
2-27
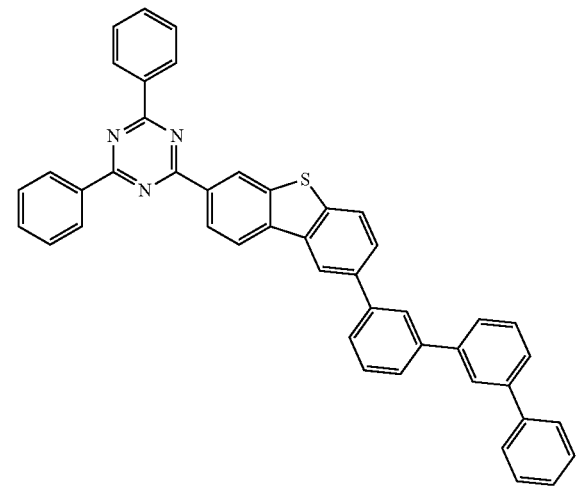
2-28
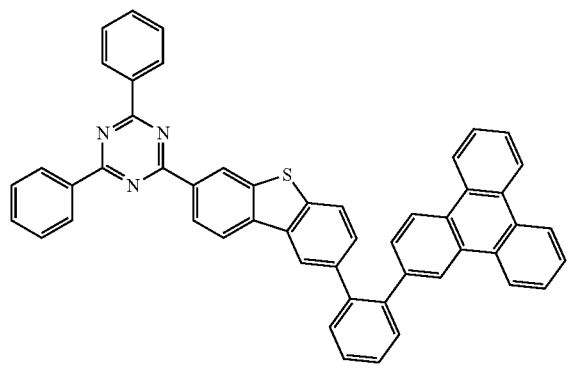
2-29
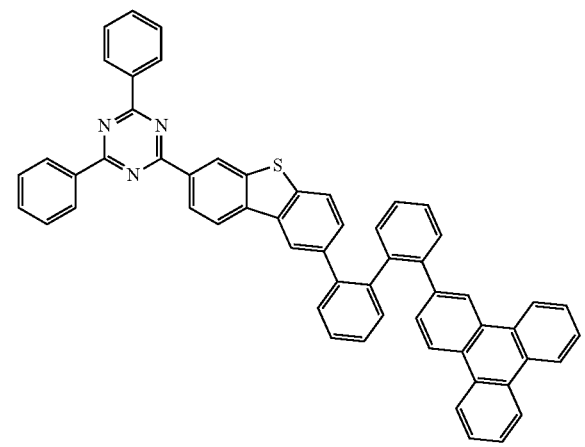
2-30
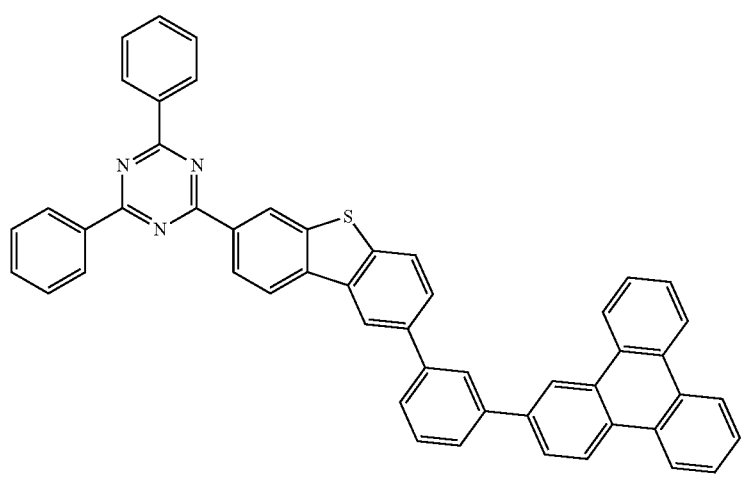

2-31
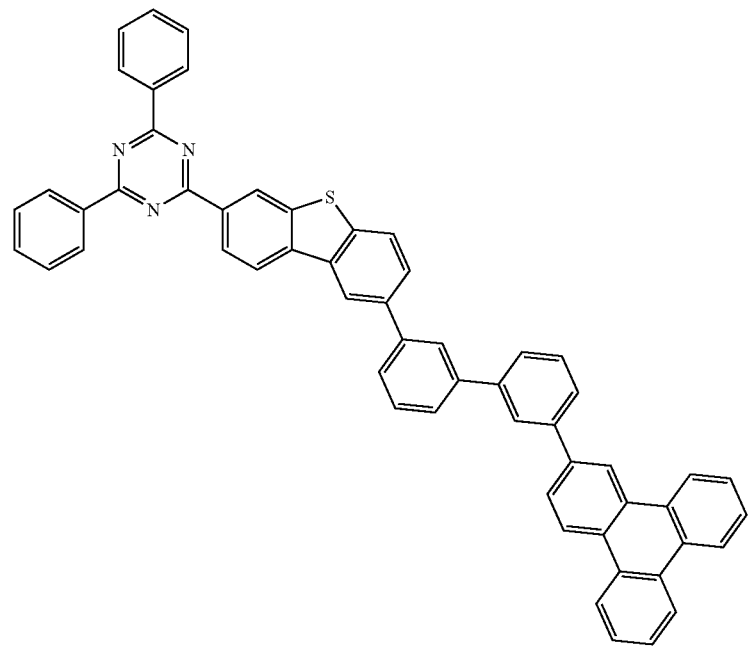
2-32
2-33
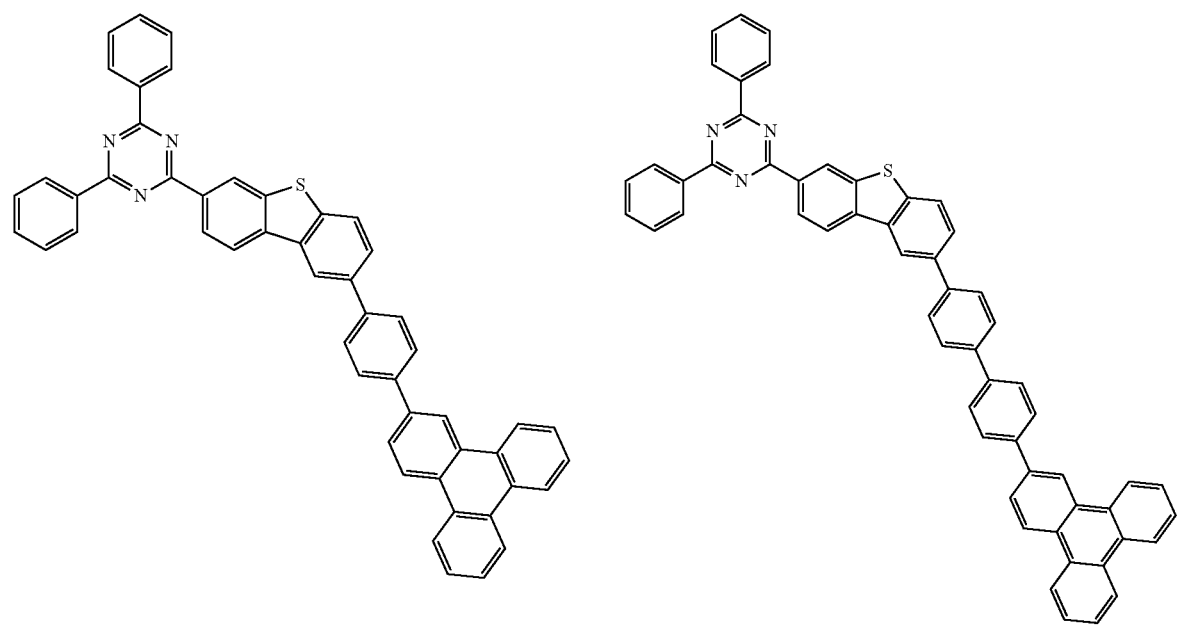

-continued
2-34
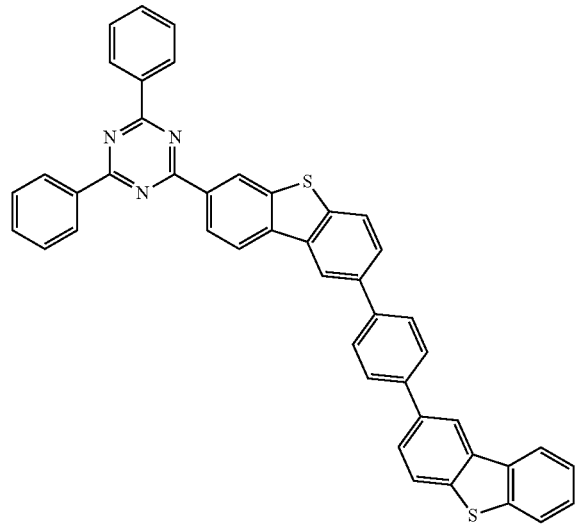
2-35
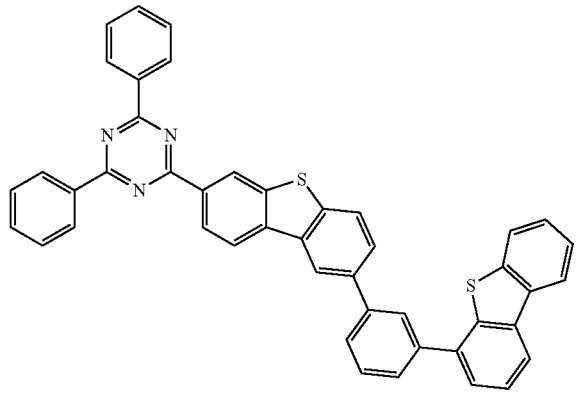
2-36
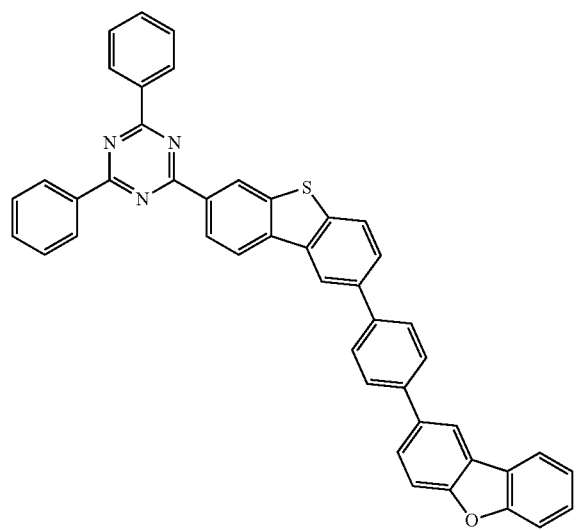
2-37
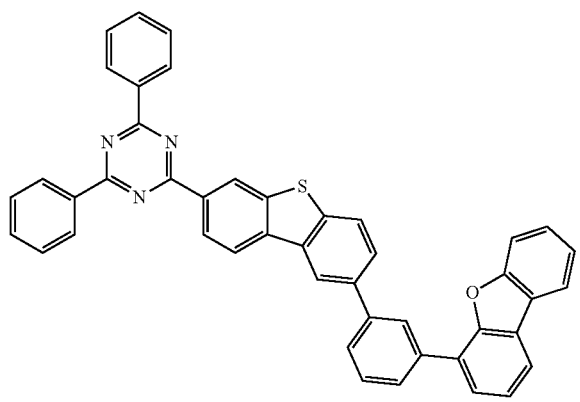

-continued
2-38
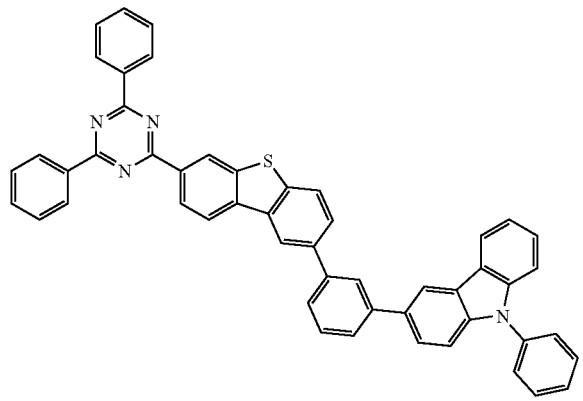
2-39
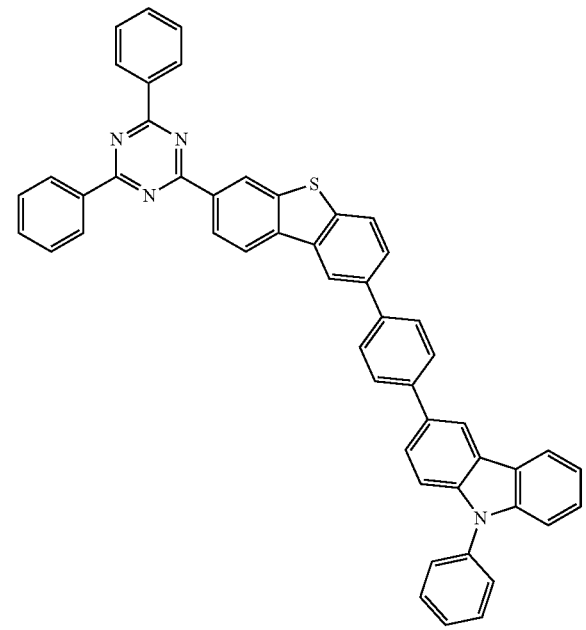
2-40
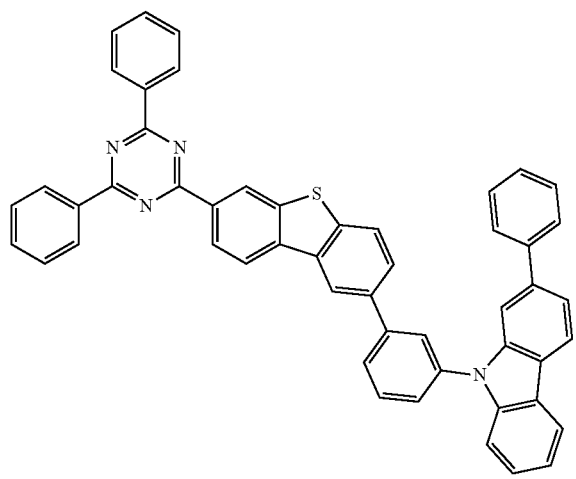
2-41
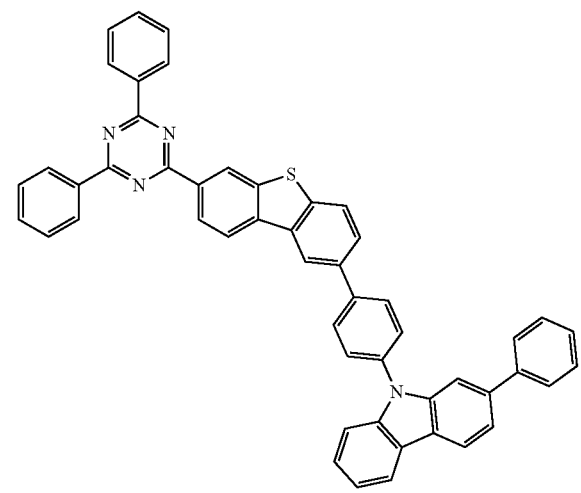
2-42
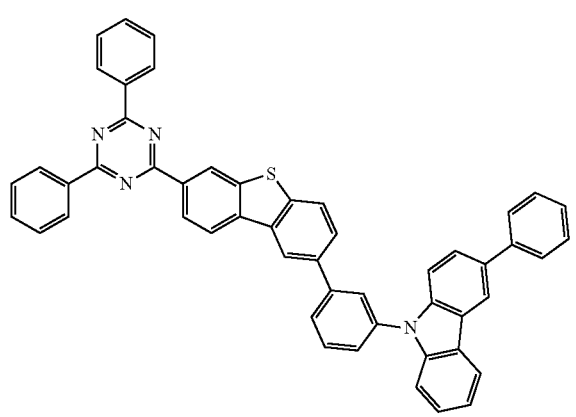
2-43
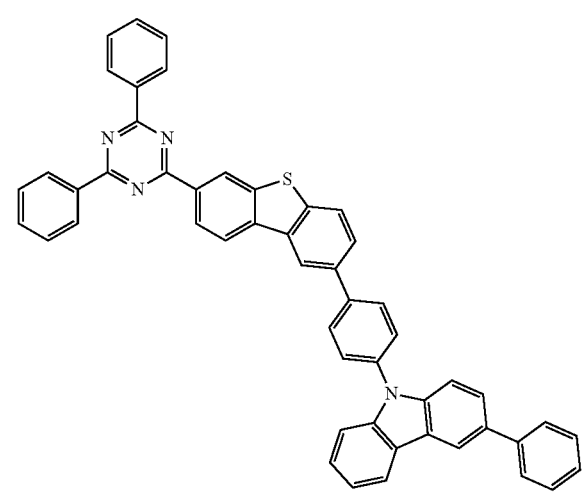

-continued
2-44
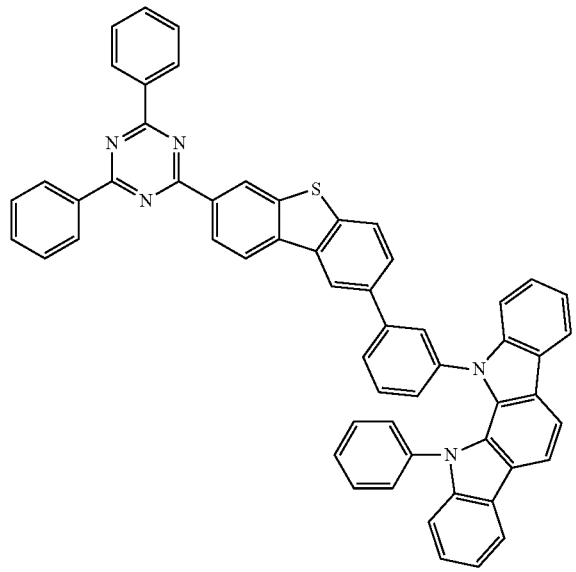
2-45
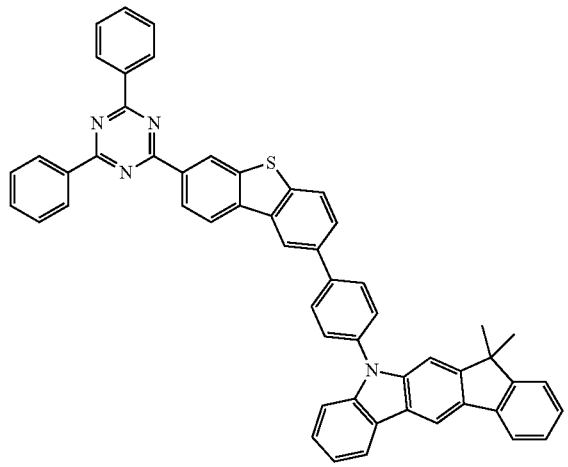
2-46
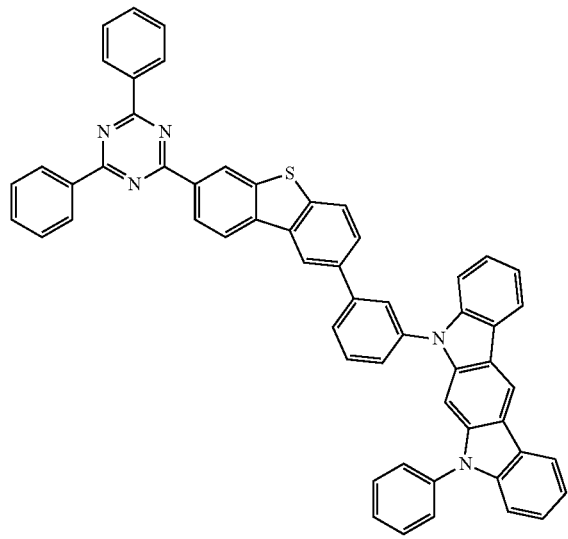
2-47
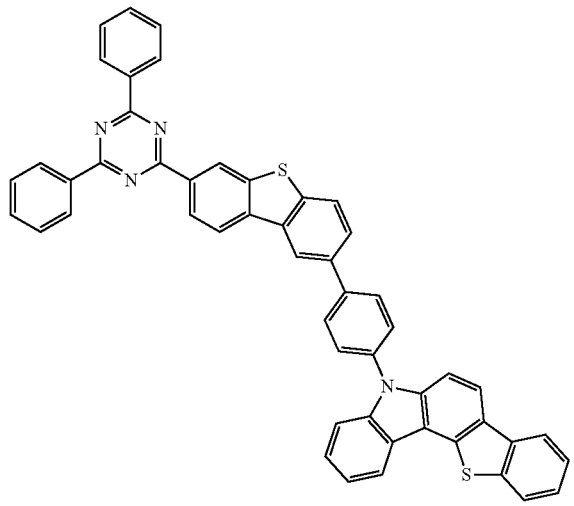
2-48
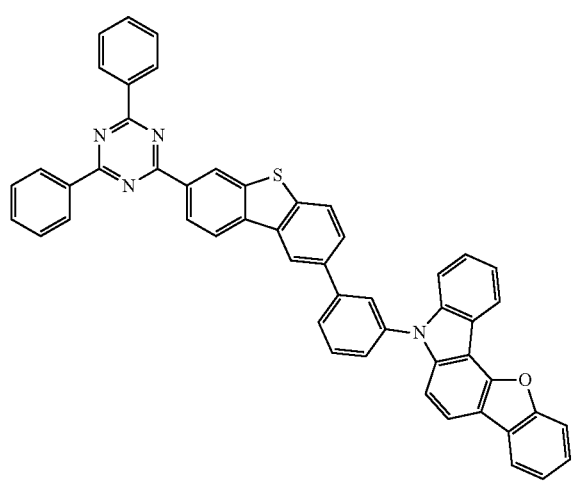
2-49
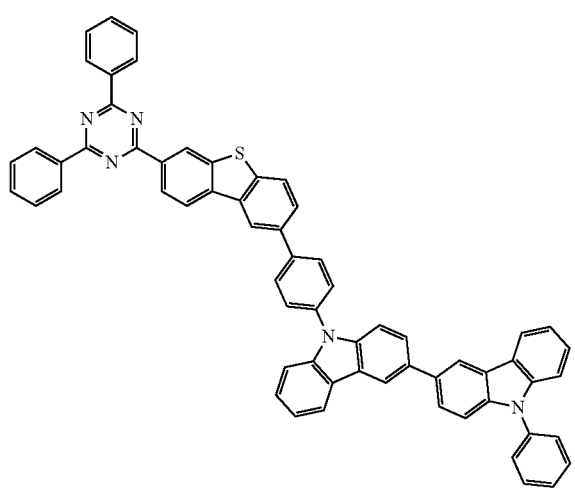

2-50
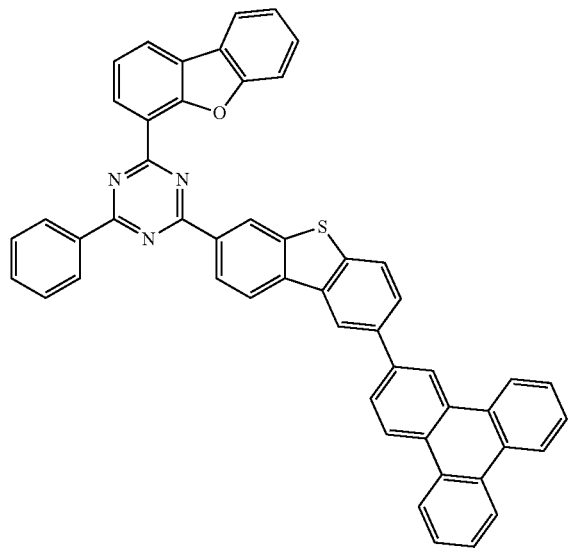
2-51
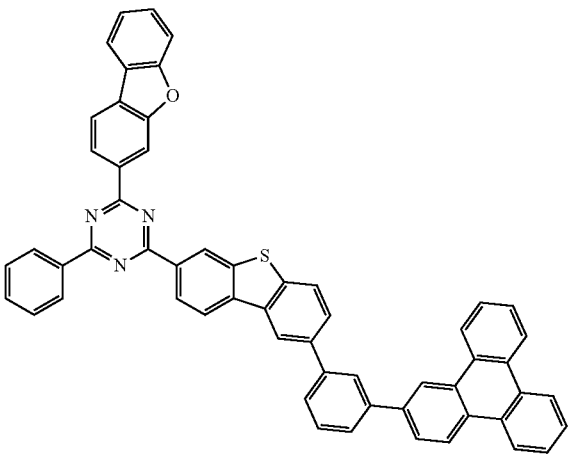
2-52
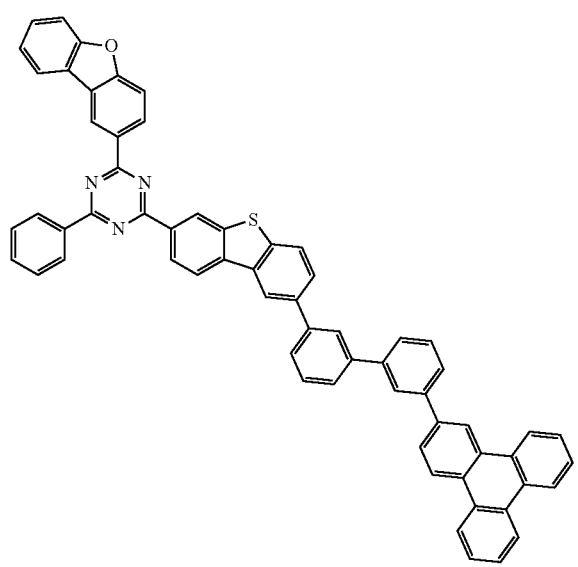
2-53
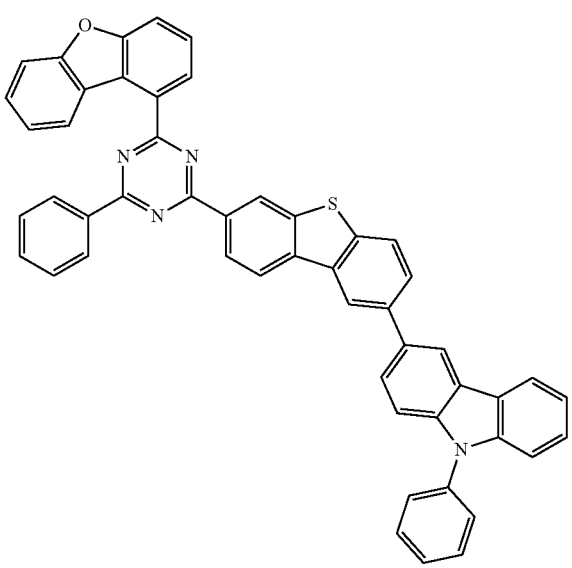

2-54
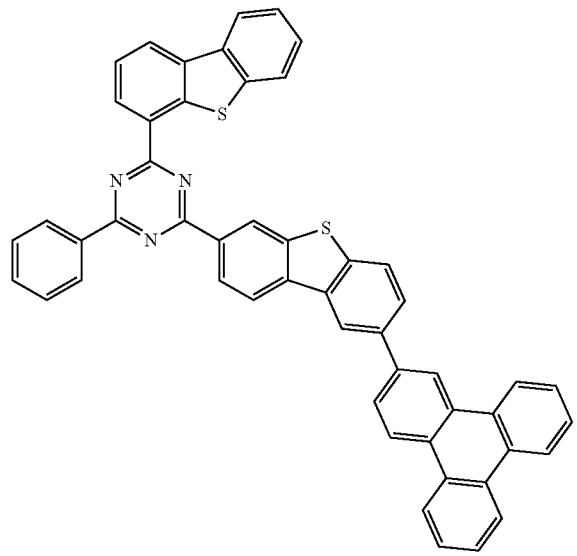
2-55
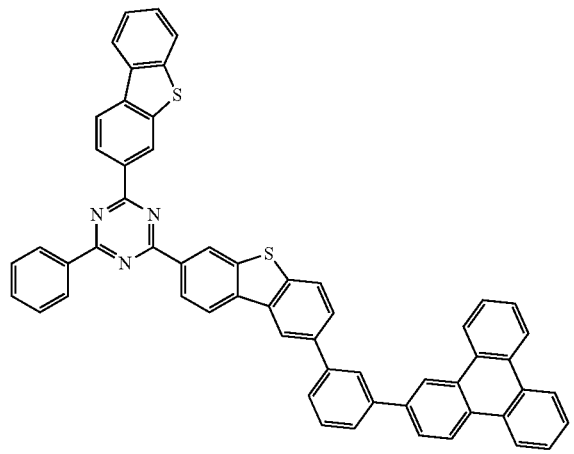
2-56
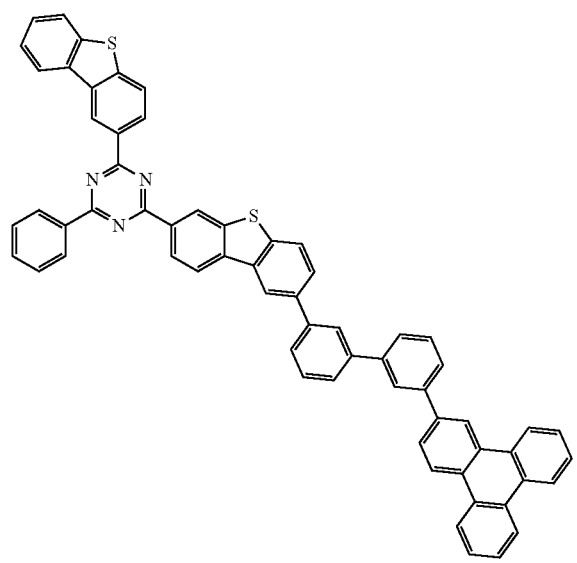
2-57
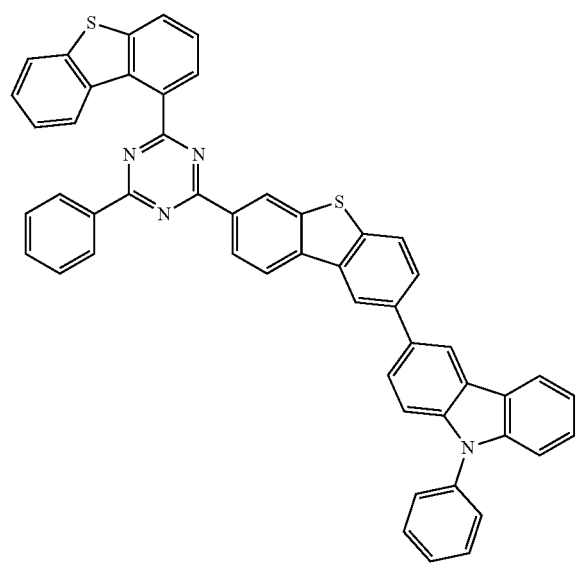

2-58
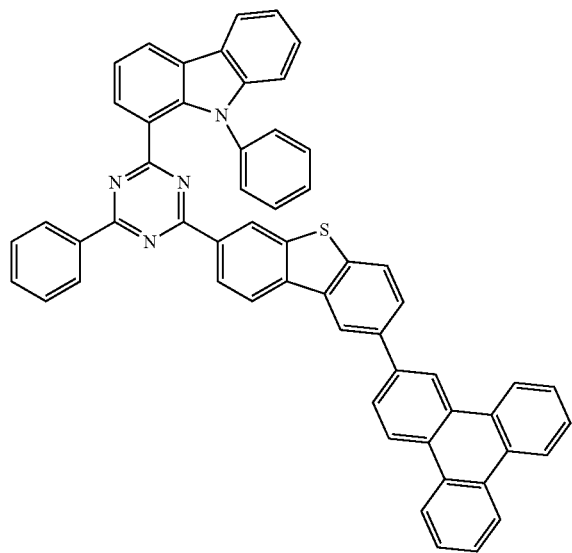
2-59
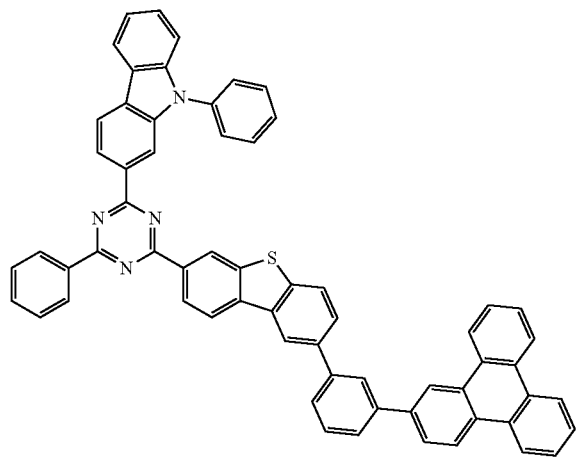
2-60
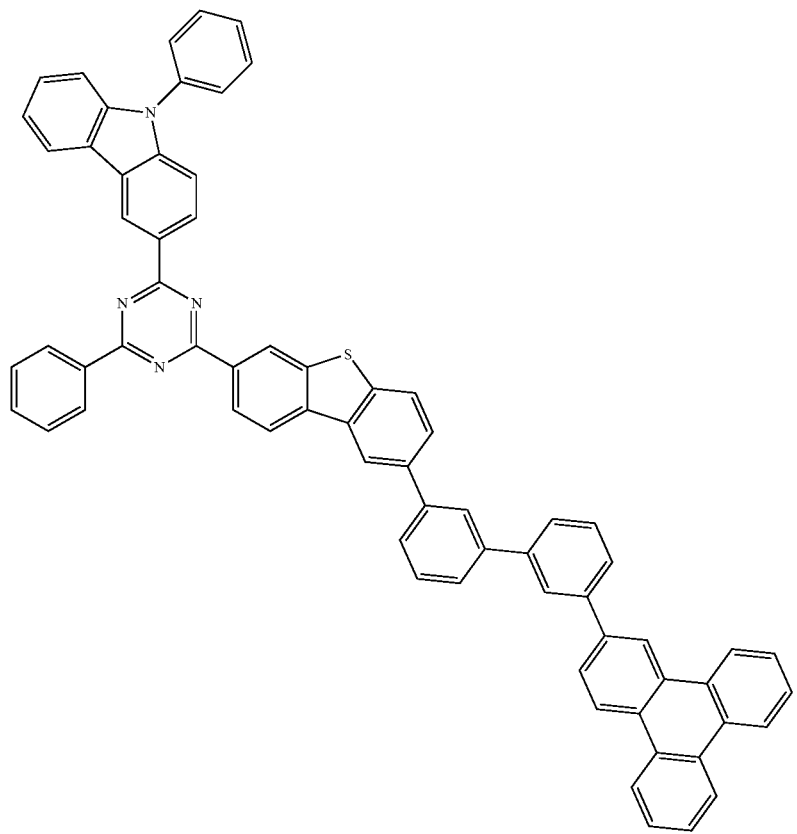

-continued
2-61
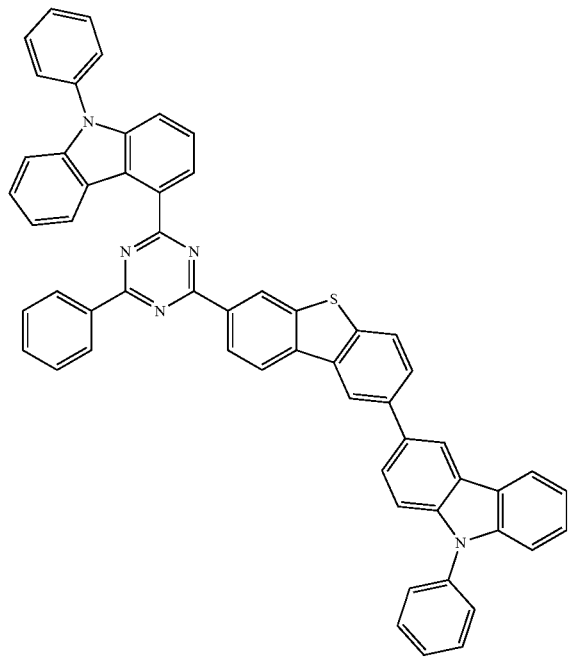
2-62
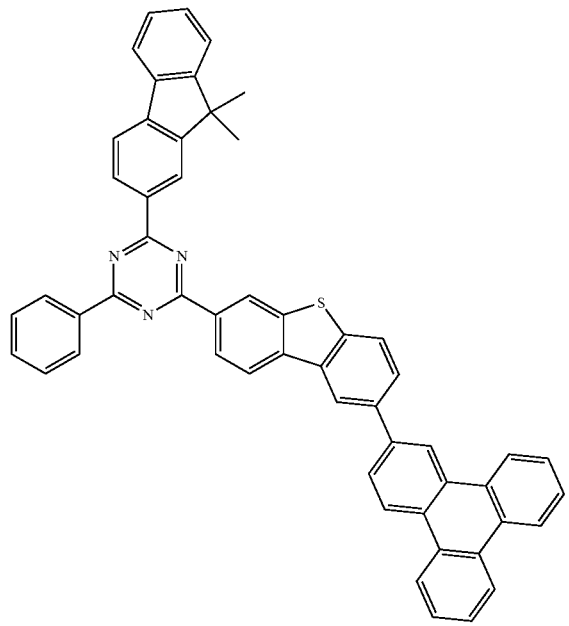
2-63
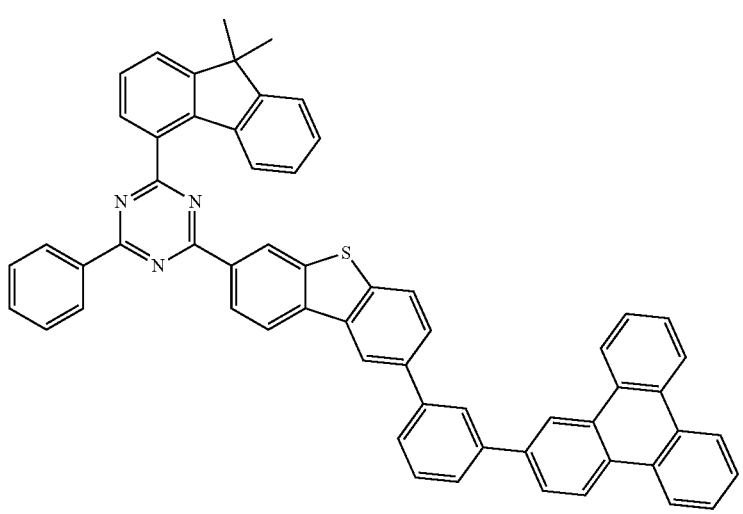

2-64
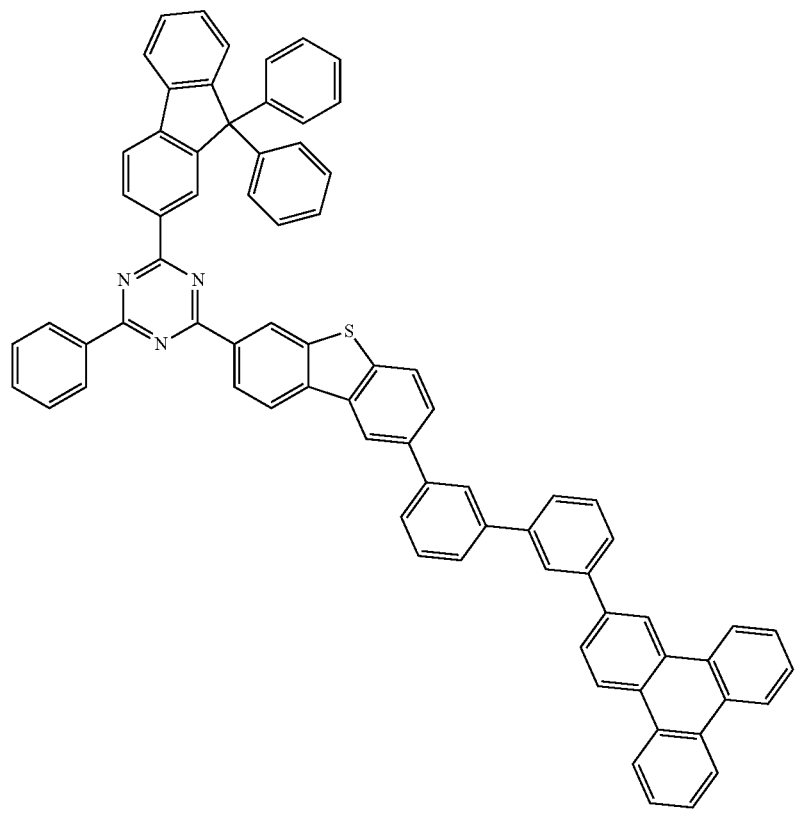
2-65 2-66
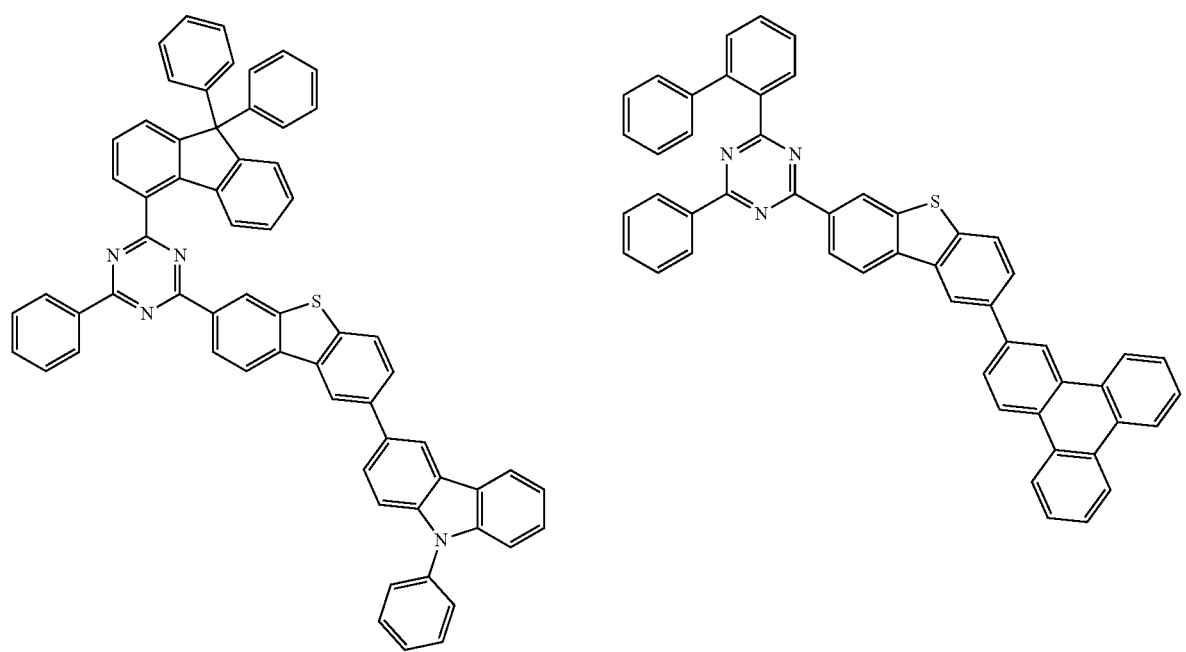

2-67
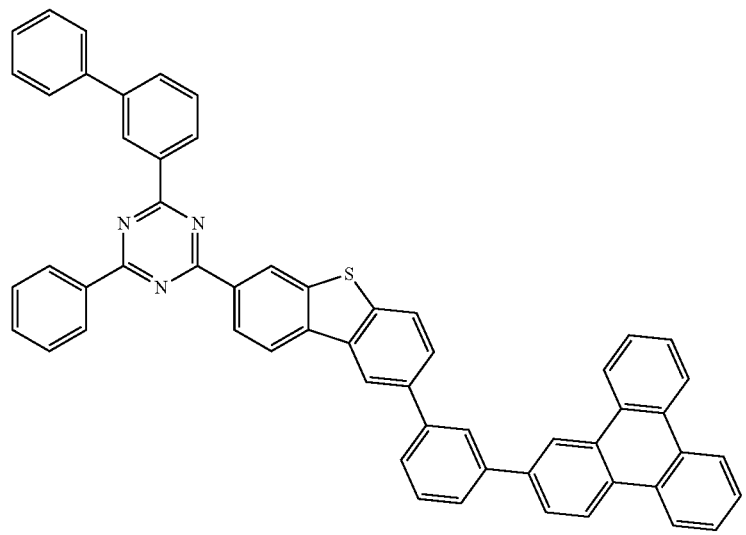
2-68
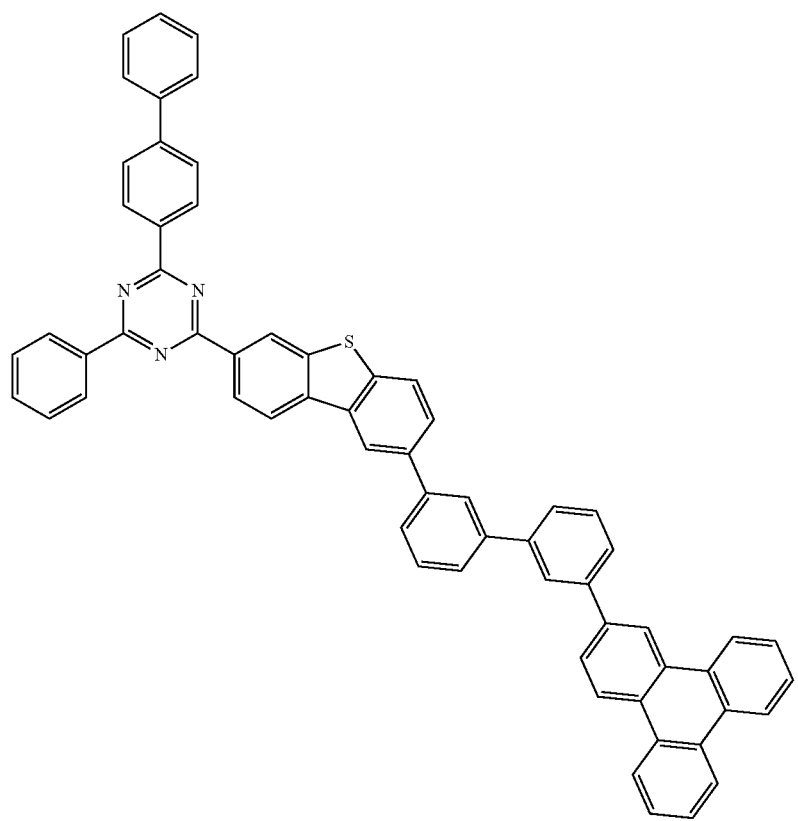

2-69
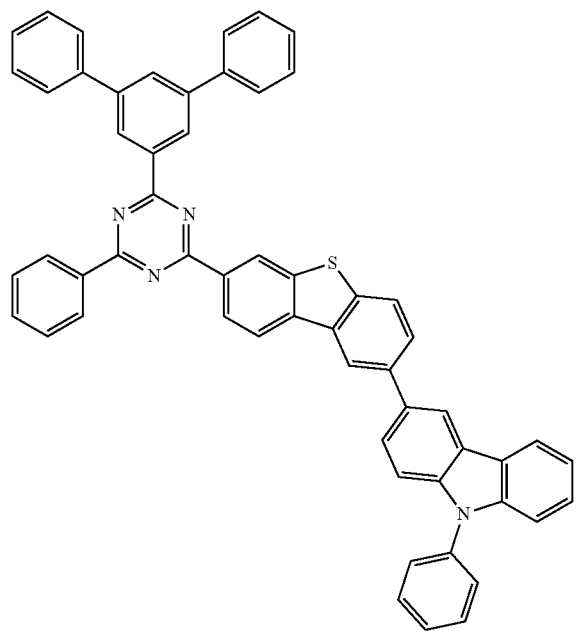
2-70
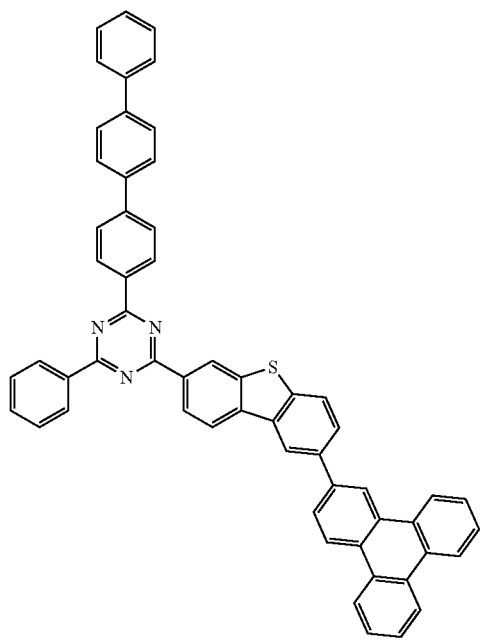
2-71
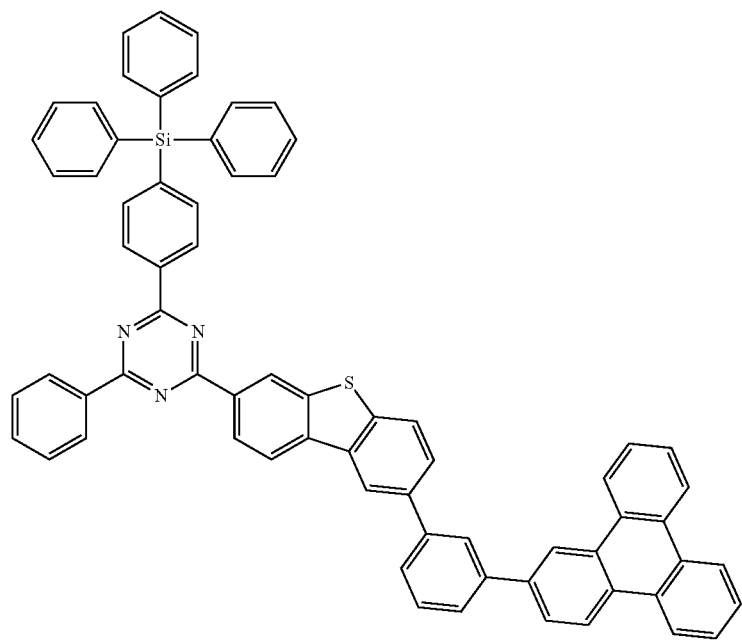

-continued
2-72
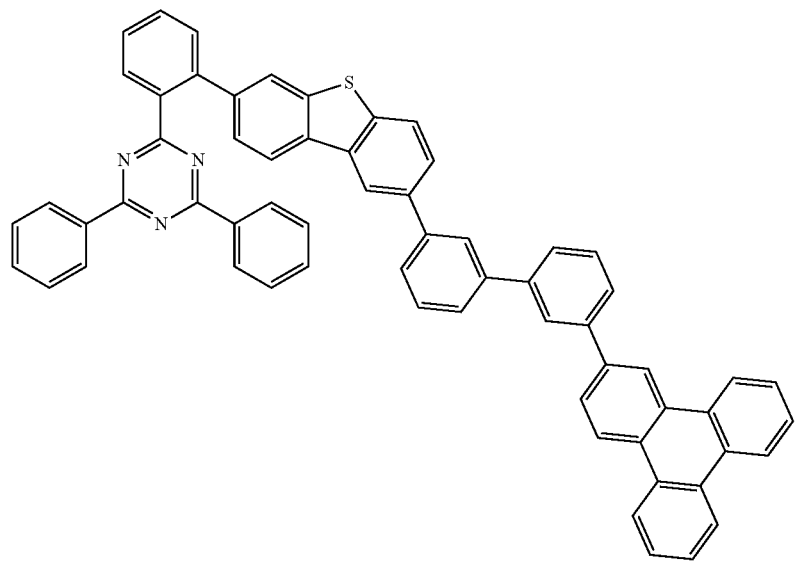
2-73
2-74
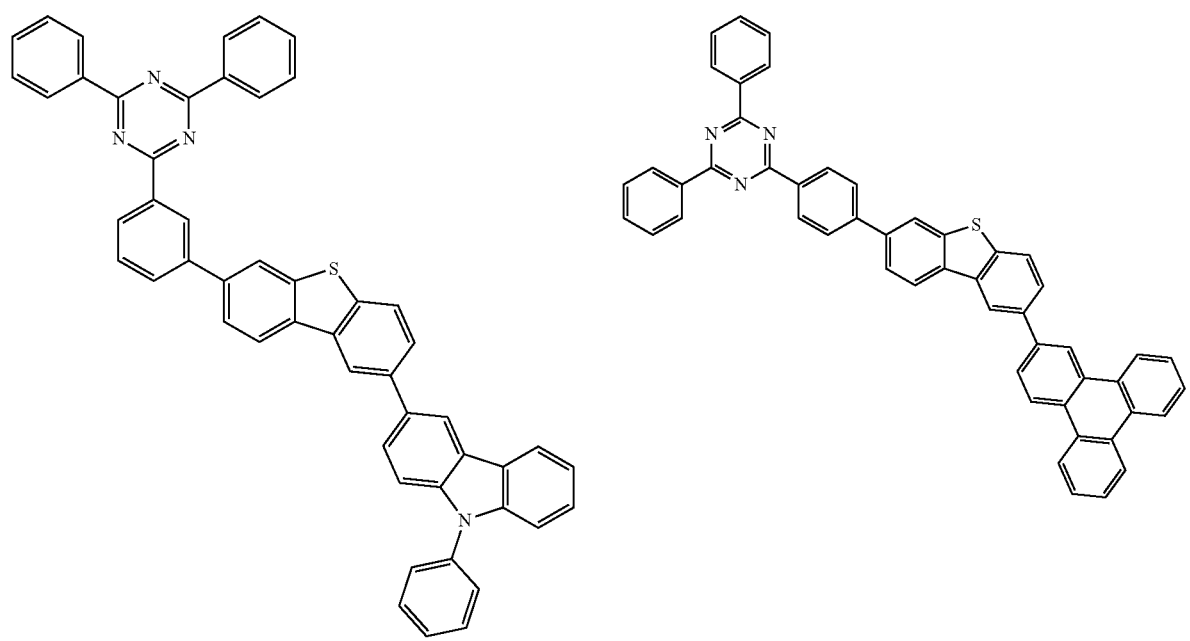

2-75
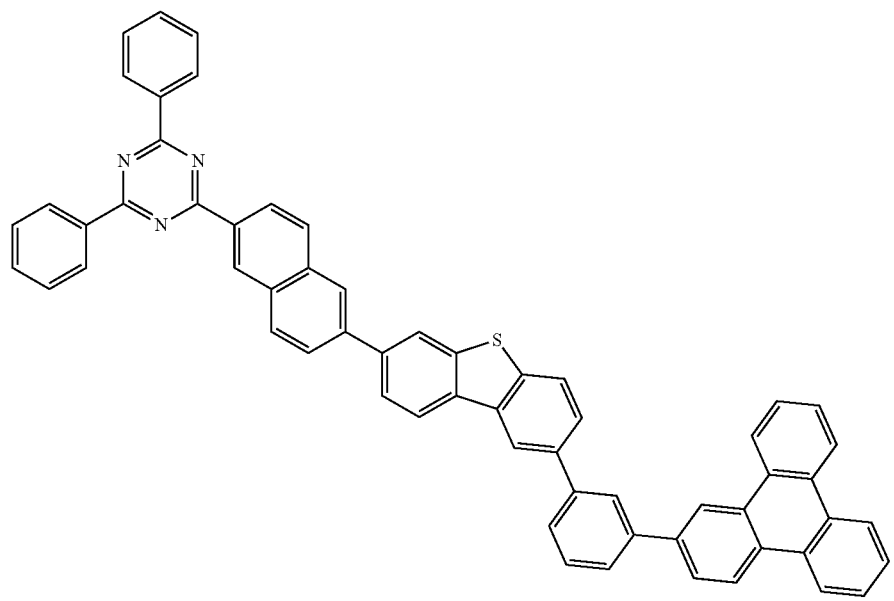
2-76
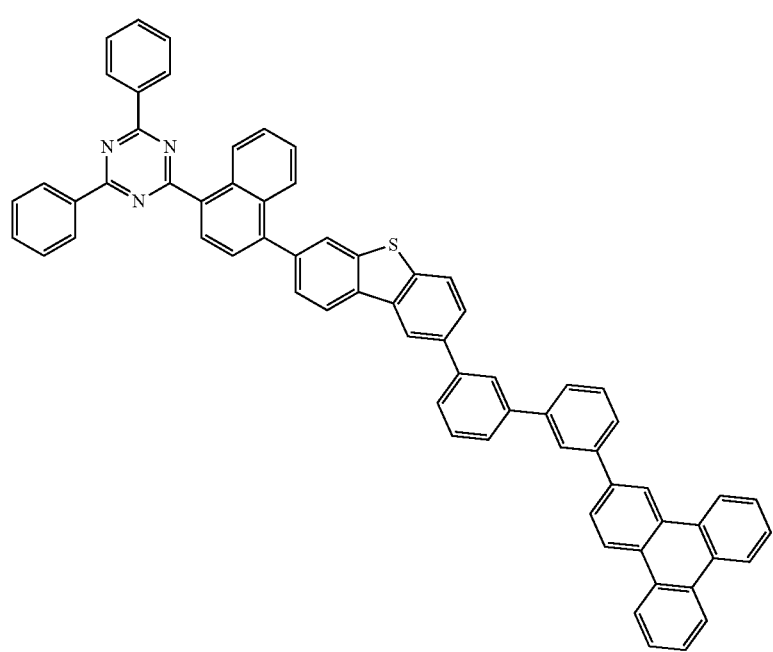

-continued
2-77
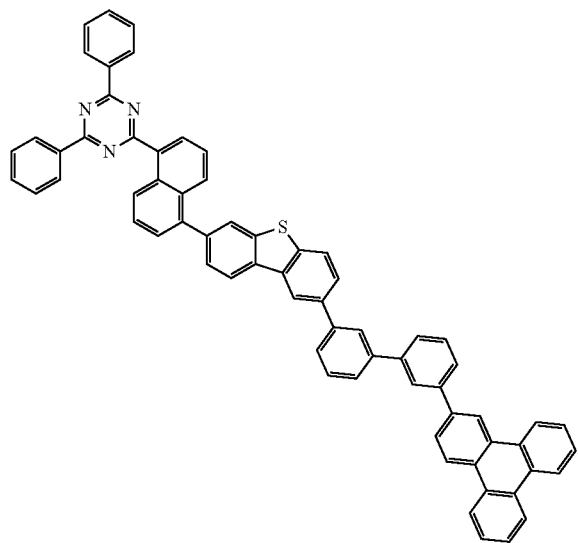
2-78
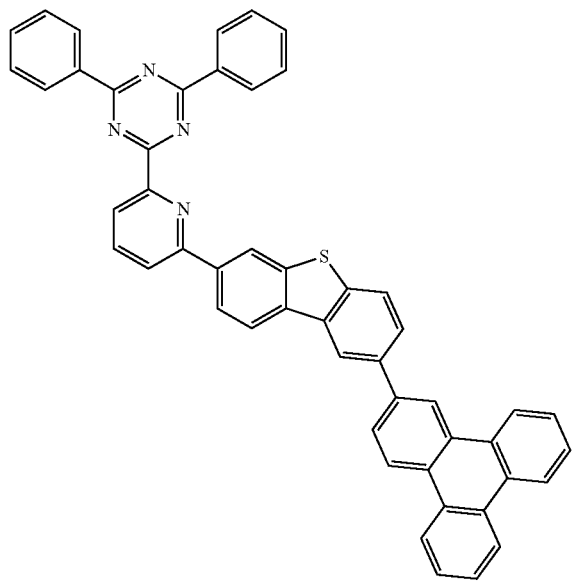
2-79
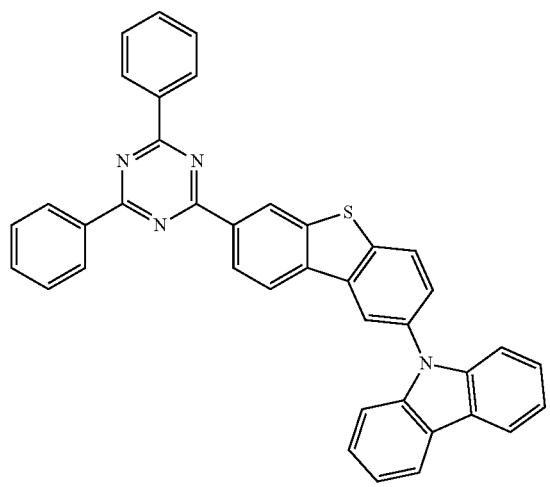
2-80
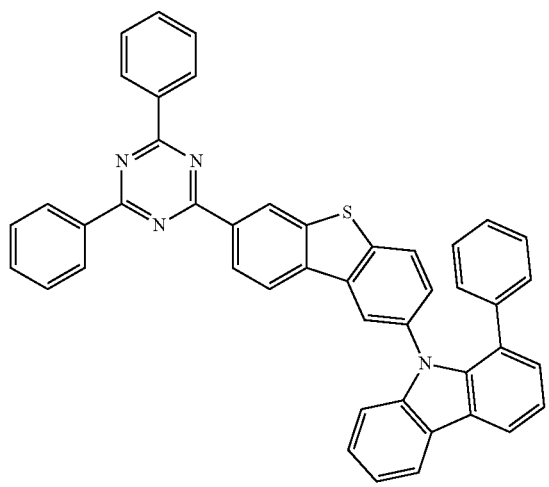
2-81
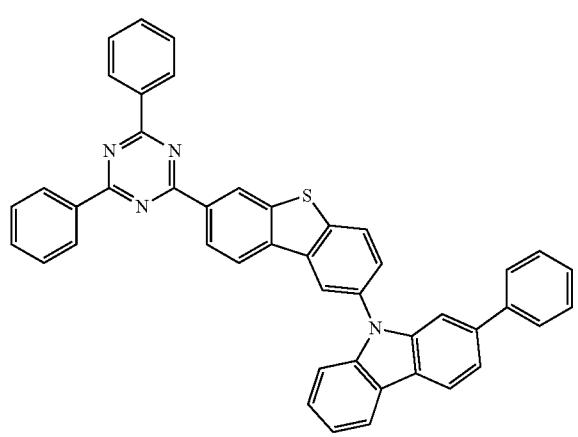
2-82
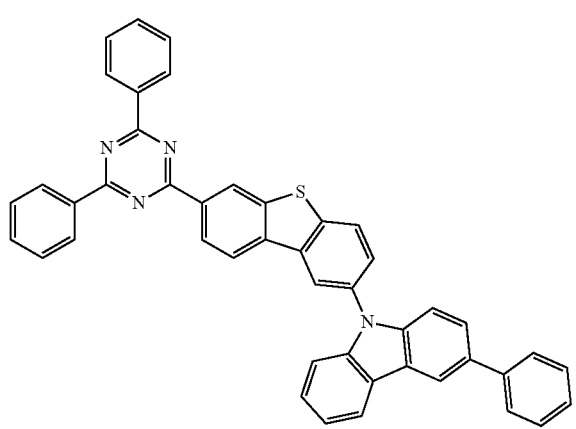

-continued
2-83
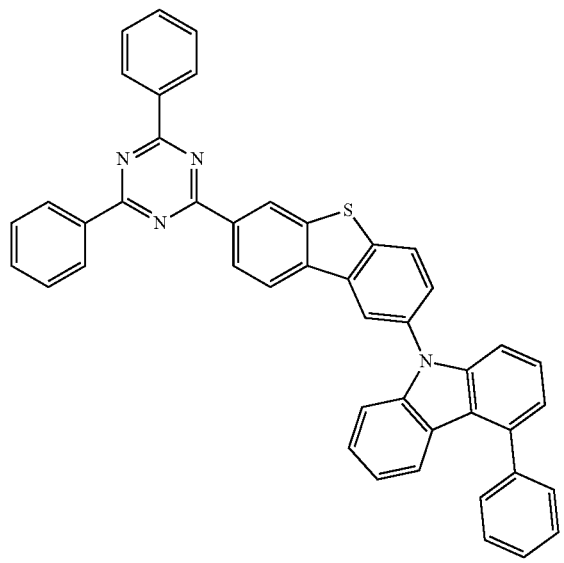
2-84
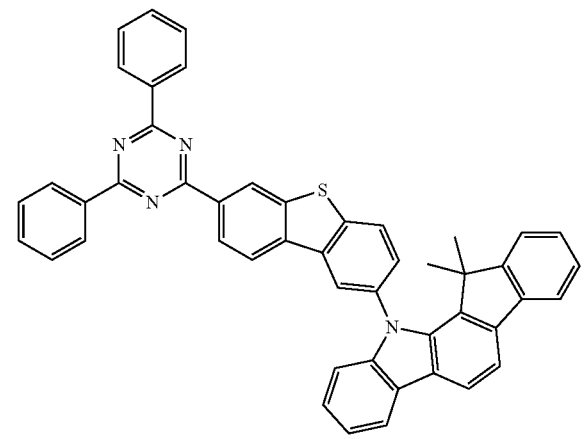
2-85
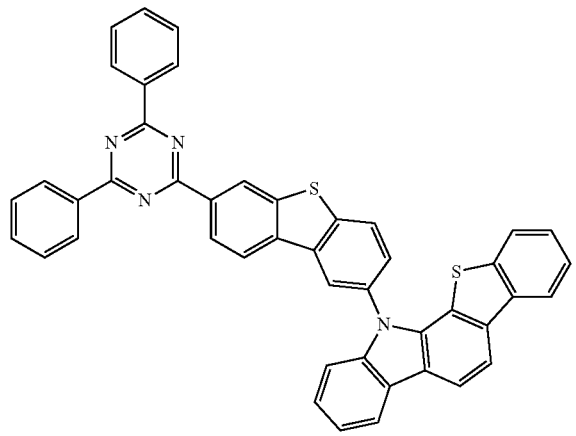
2-86
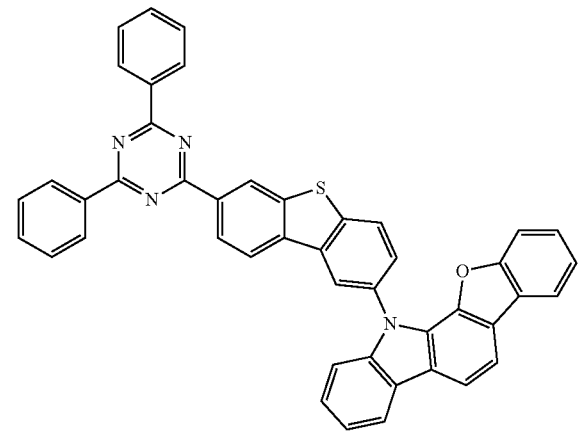
2-87
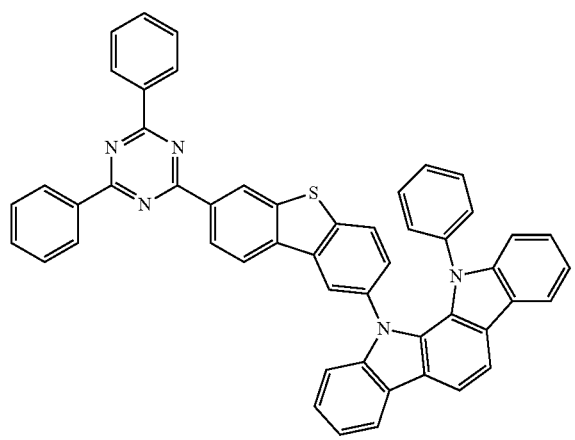
2-88
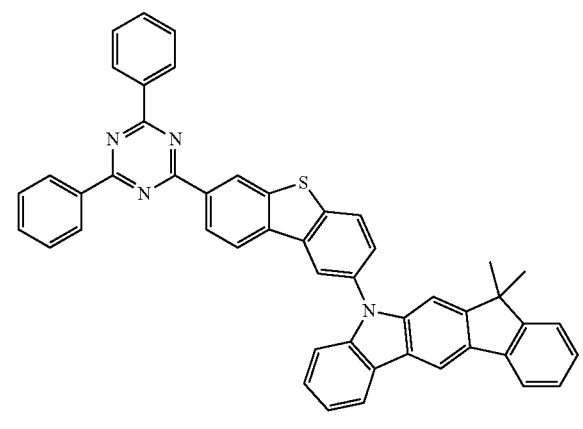

-continued
2-89
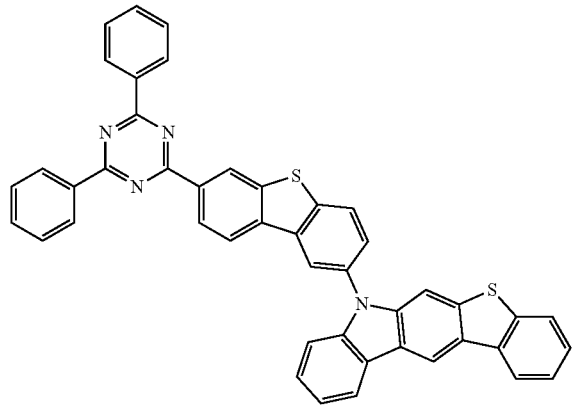
2-90
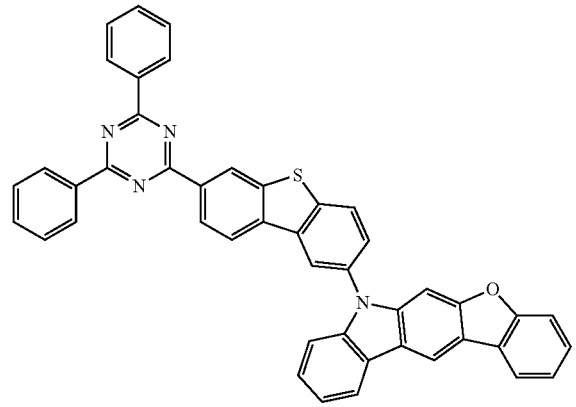
2-91
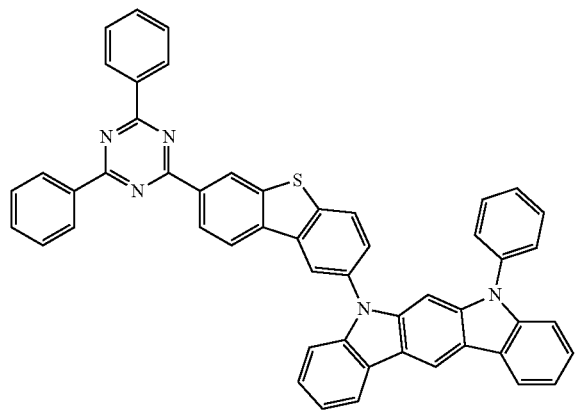
2-92
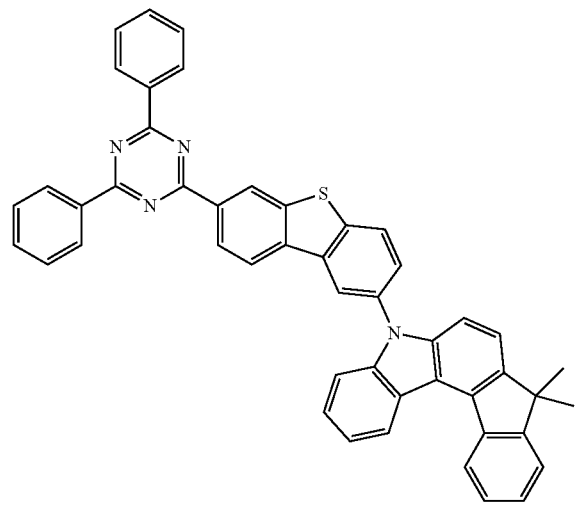
2-93
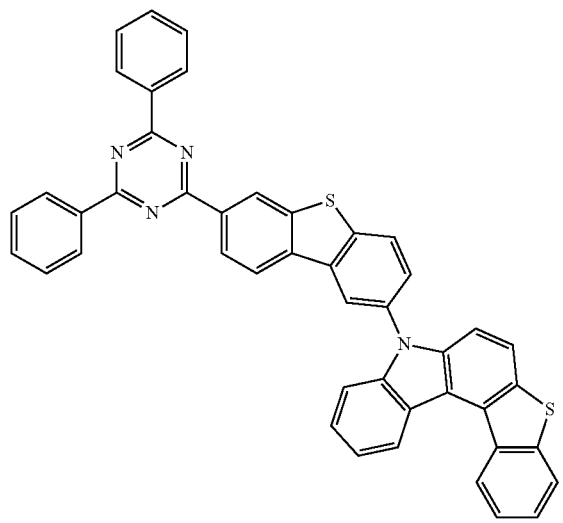
2-94
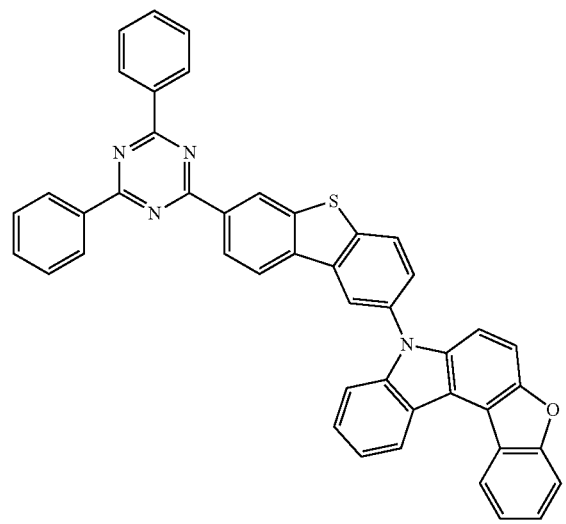

2-95
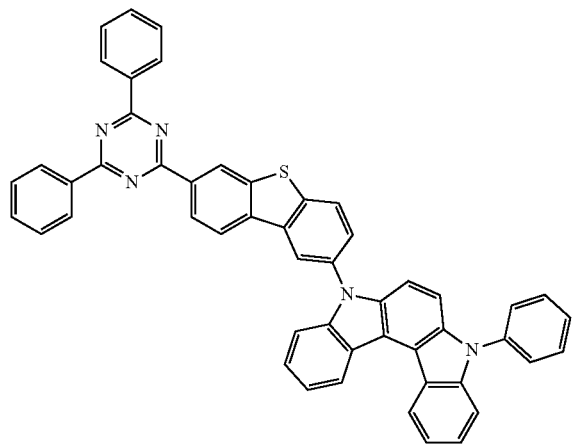
2-96
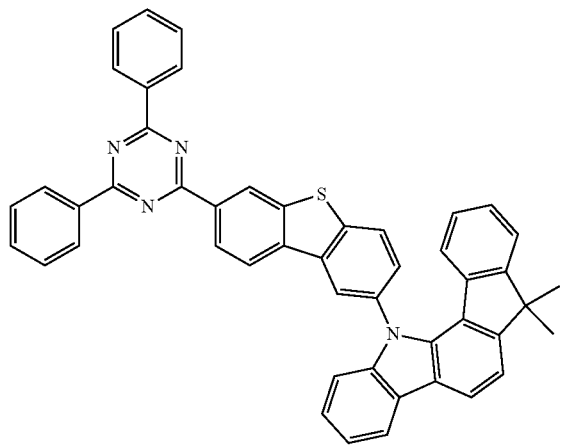
2-97
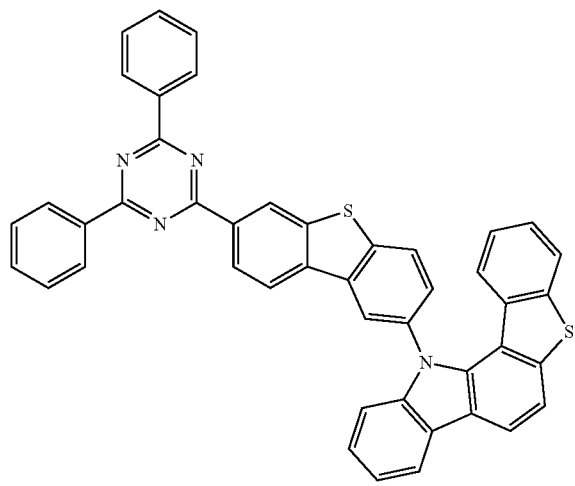
2-98
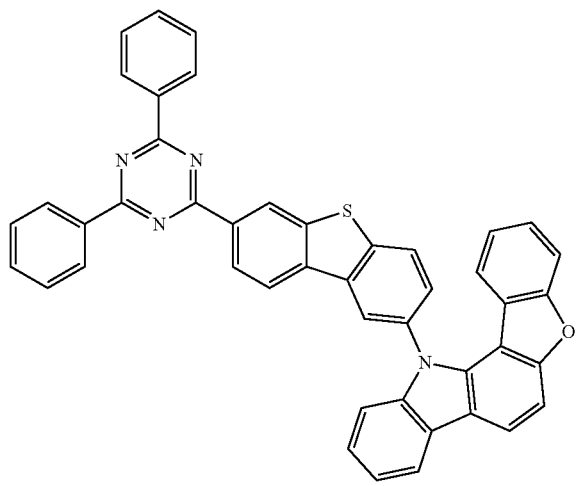
2-99
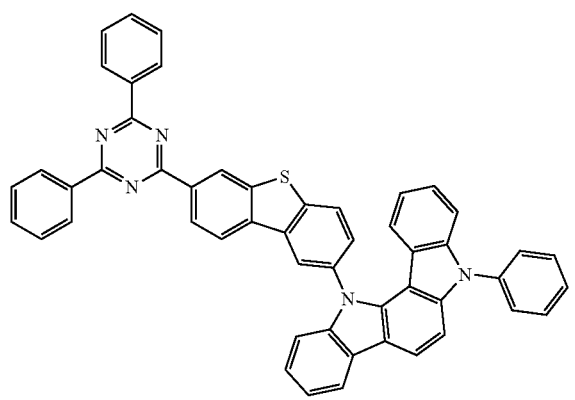
2-100
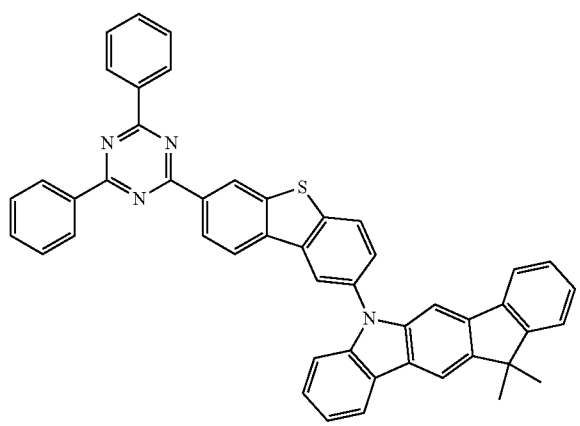

-continued
2-101
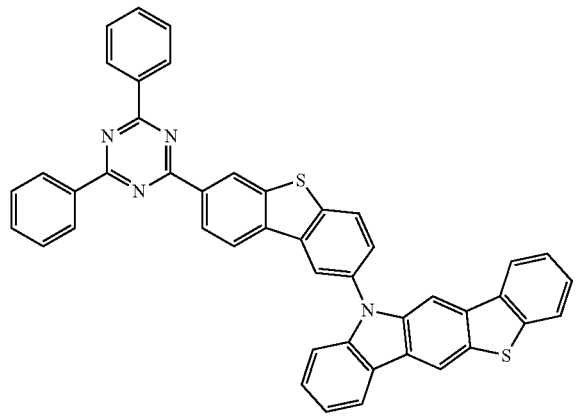
2-102
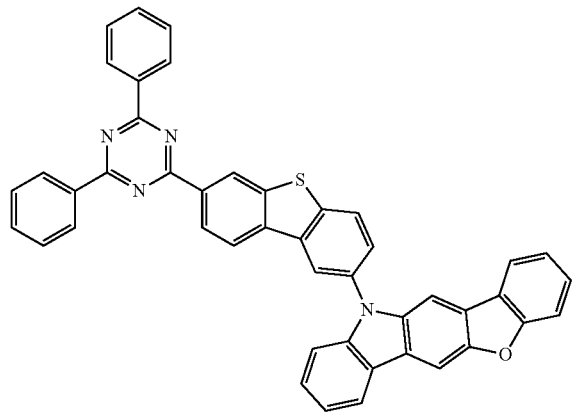
2-103
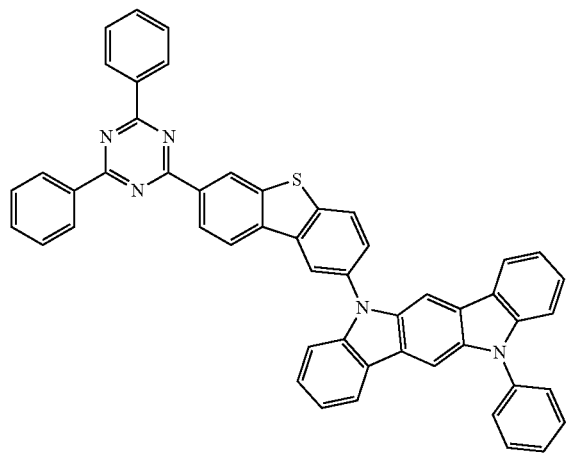
2-104
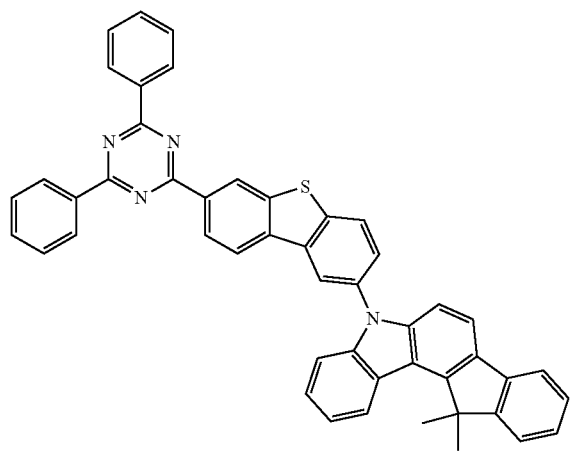
2-105
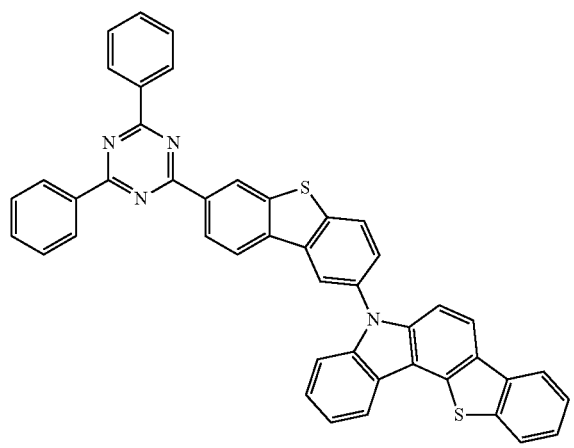
2-106
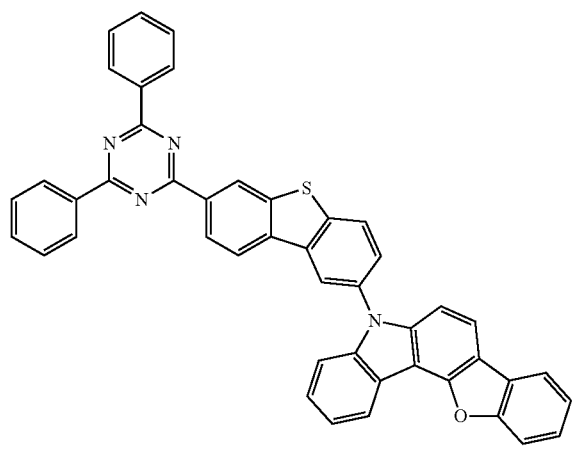

2-107
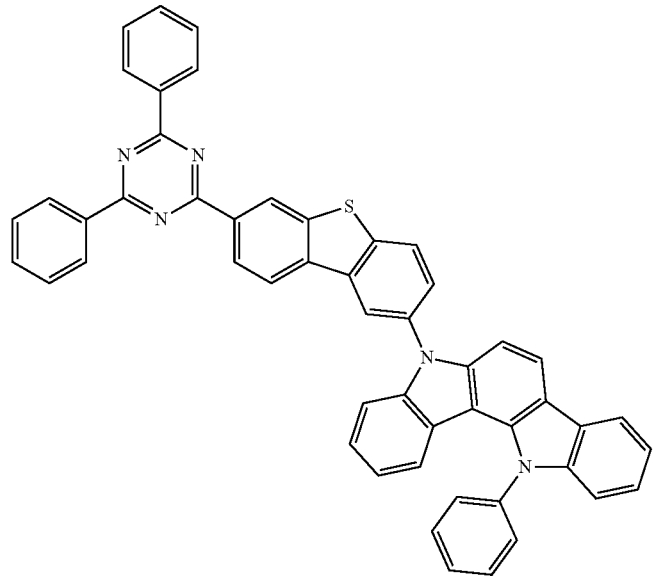
2-108
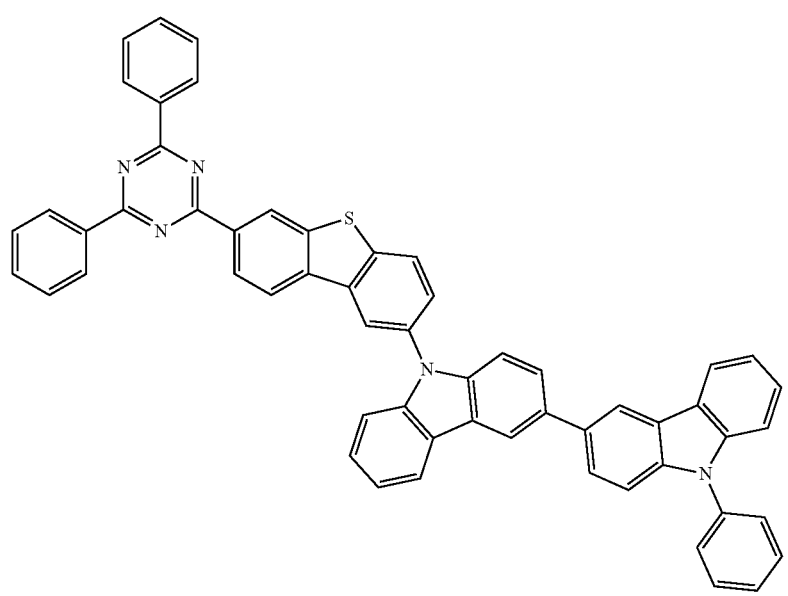
2-109 2-110
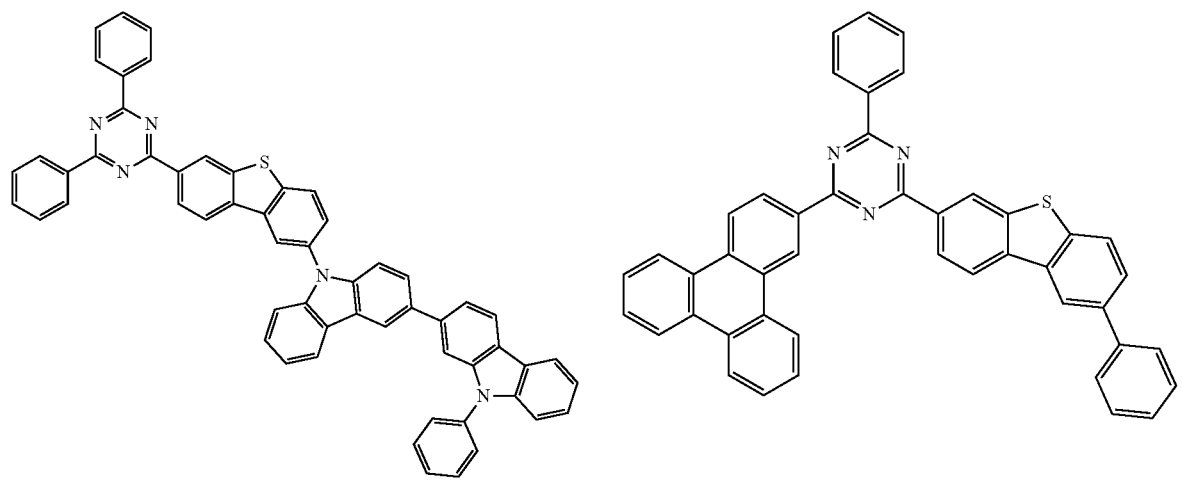

113                                                         114
-continued
2-111
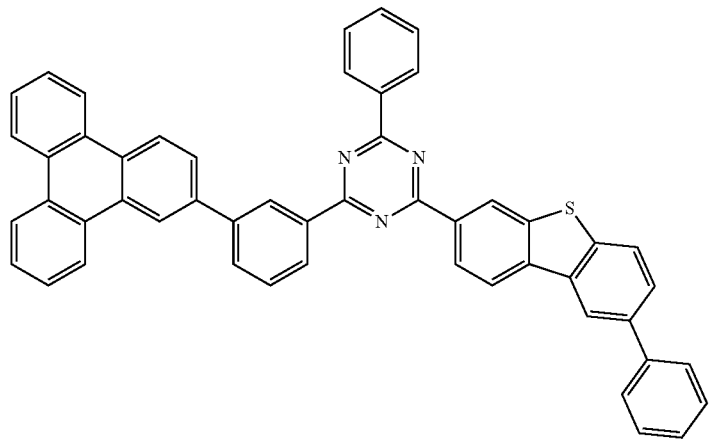
2-112
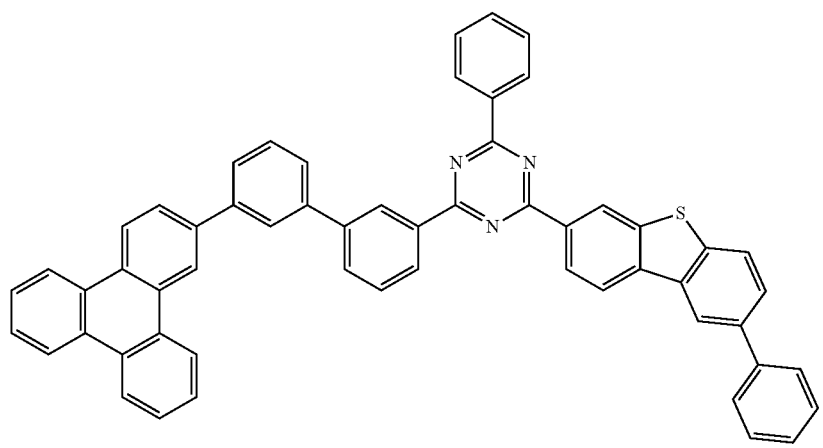
2-113
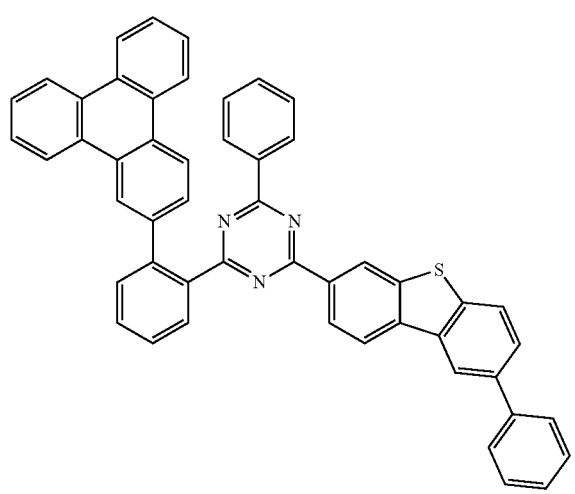
2-114
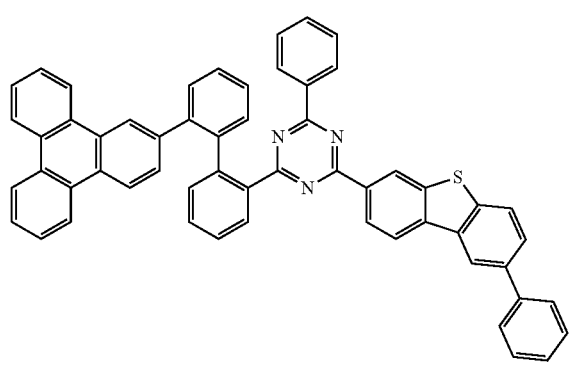

2-115
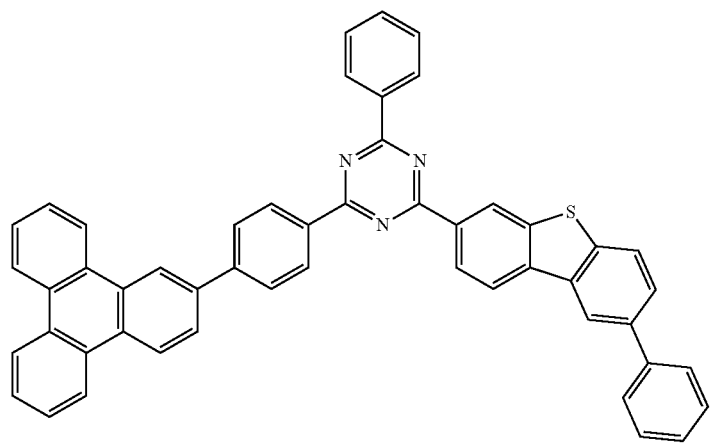
2-116
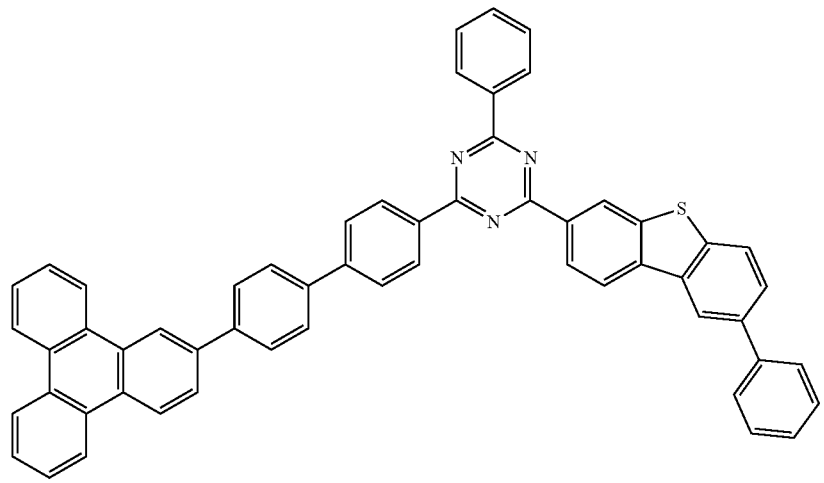
2-117
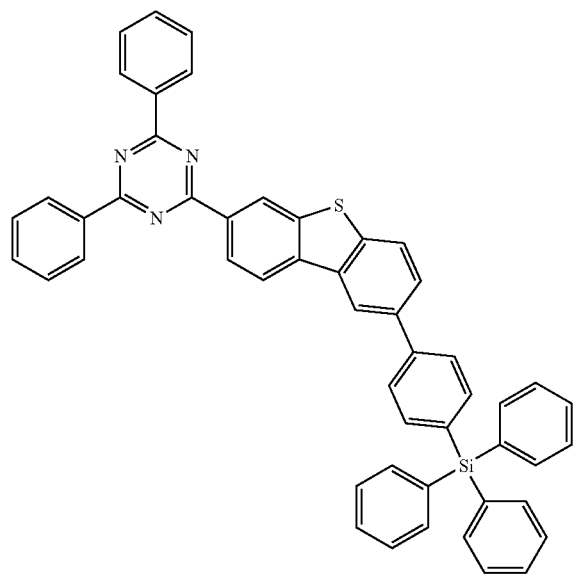
2-118
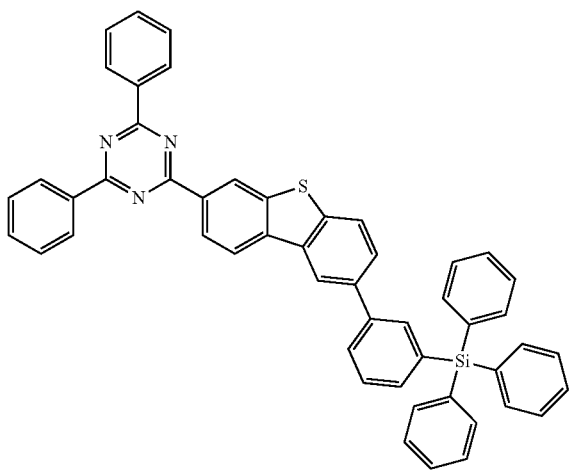

2-119
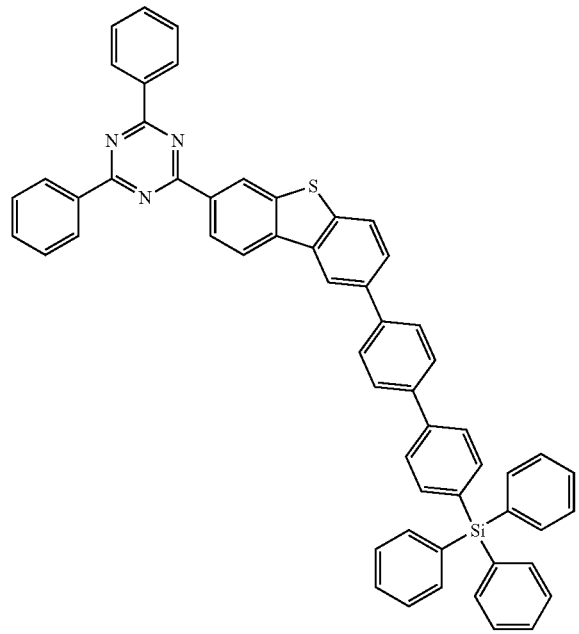
2-120
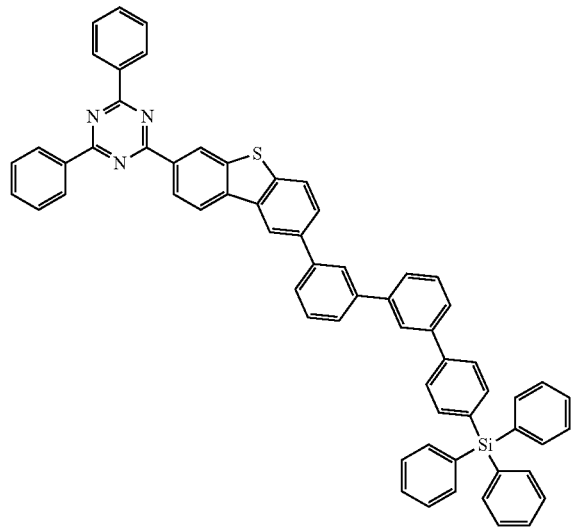
4-1
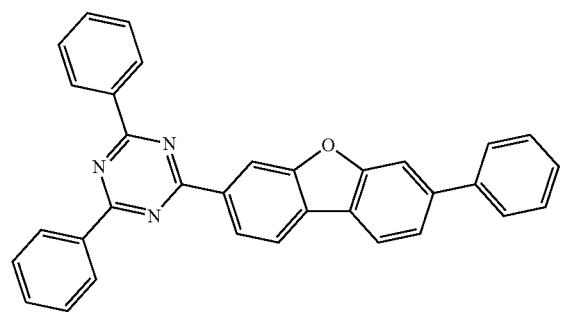
4-2
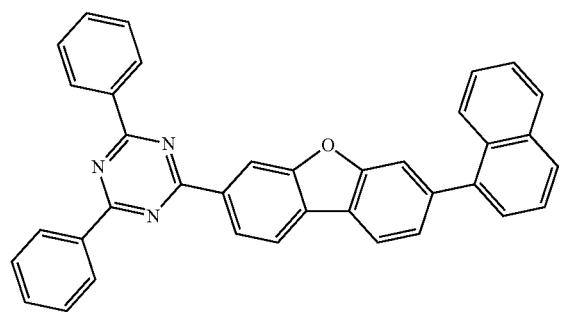
4-3
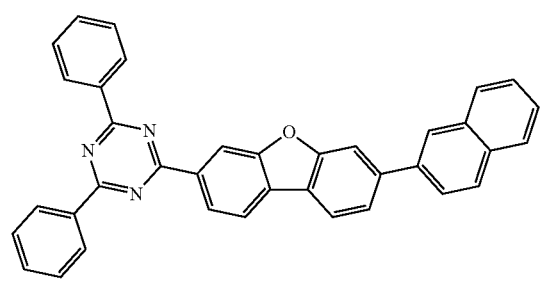
4-4
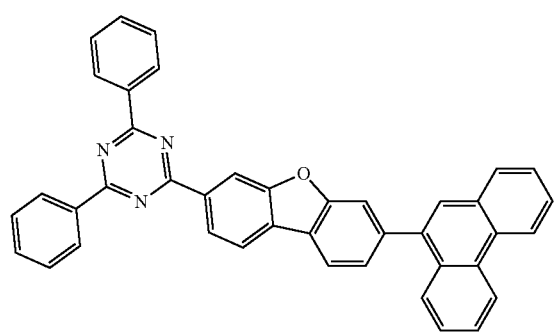

-continued
| 4-5 | 4-6 |
|---|---|
| 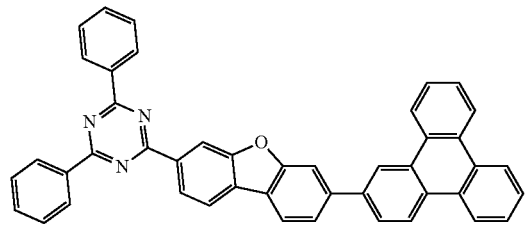 | 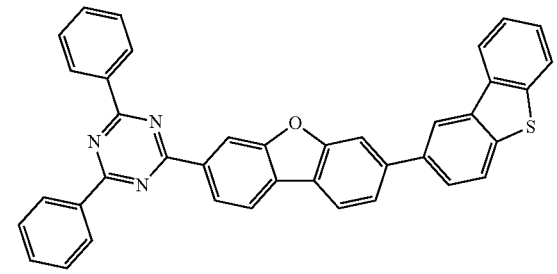 |
| 4-7 | 4-8 |
| 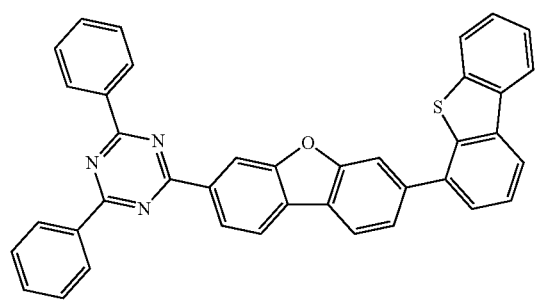 | 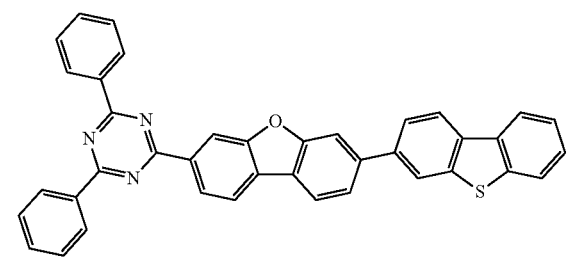 |
| 4-9 | 4-10 |
| 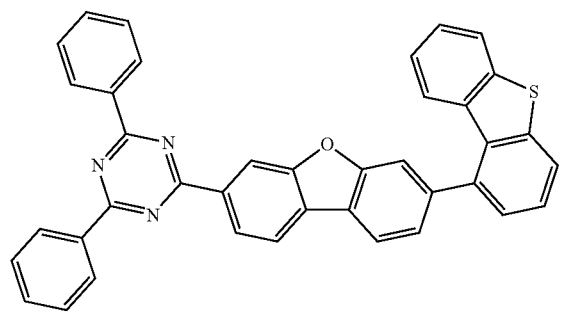 | 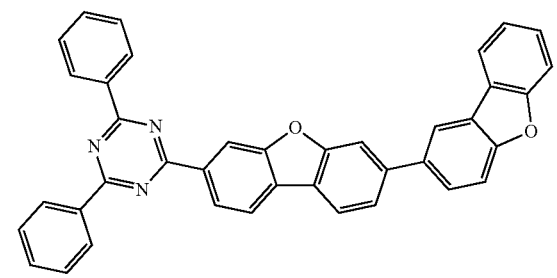 |
| 4-11 | 4-12 |
| 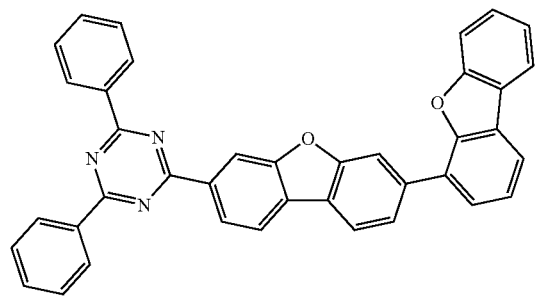 | 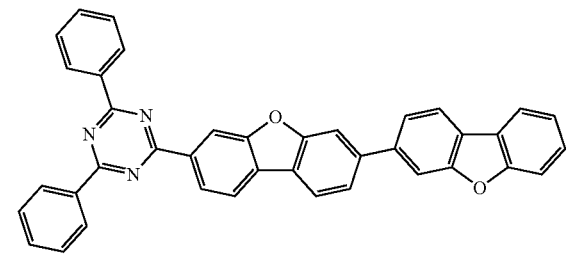 |
| 4-13 | 4-14 |
| 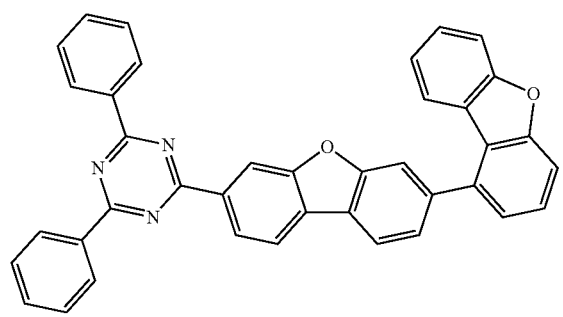 | 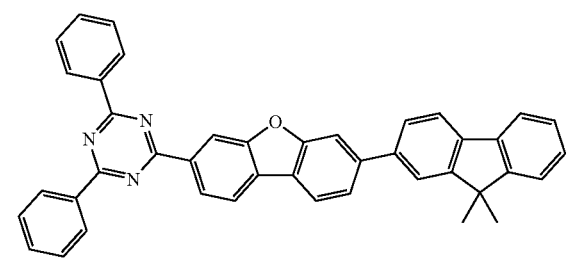 |

-continued
4-15
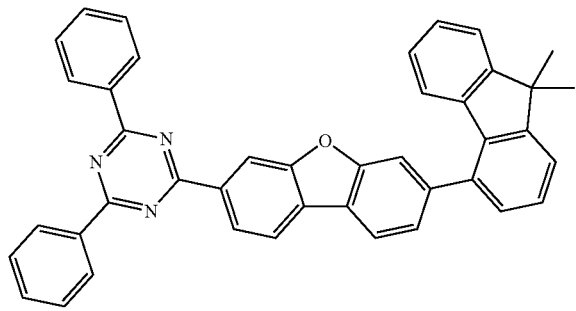
4-16
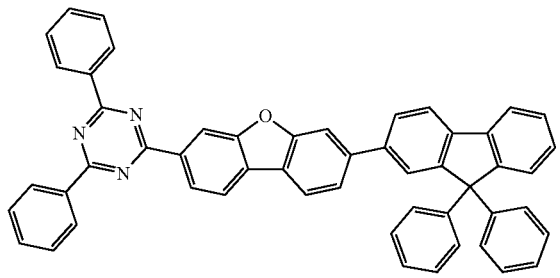
4-17
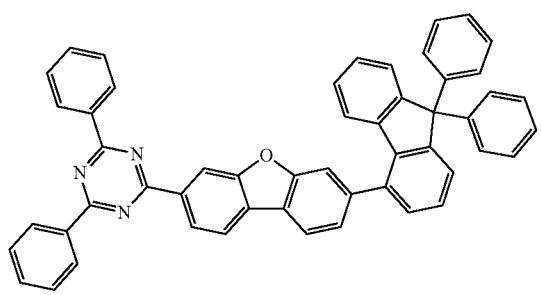
4-18
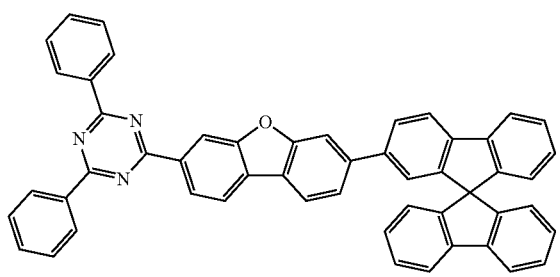
4-19
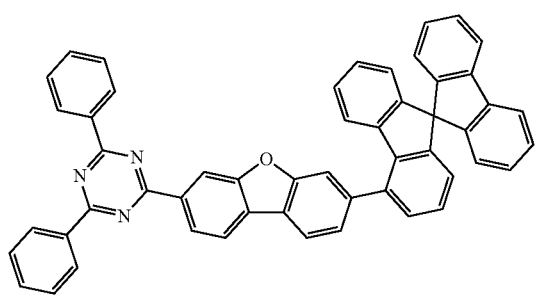
4-20
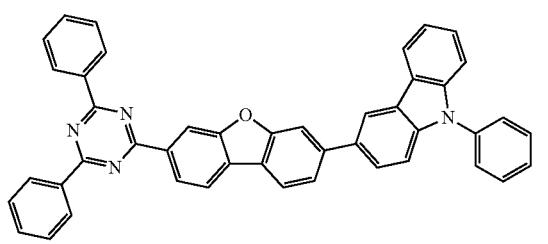
4-21
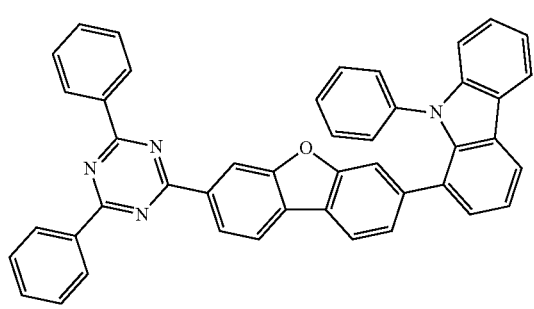
4-22
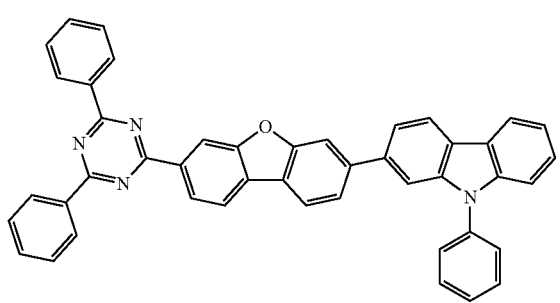
4-23
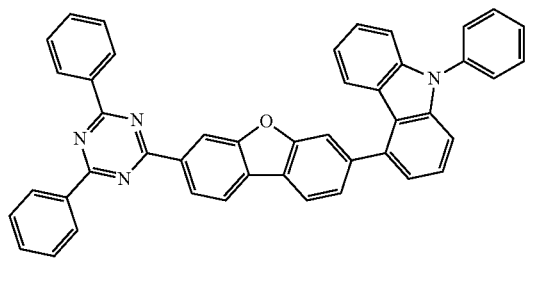
4-24
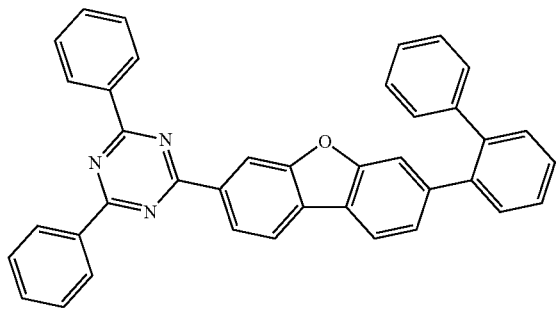

-continued
4-25
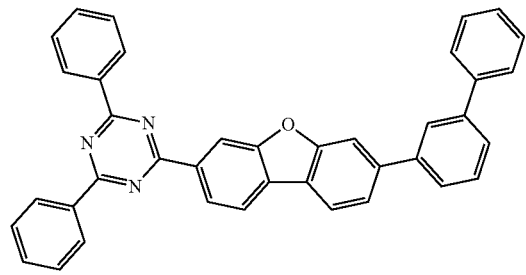
4-26
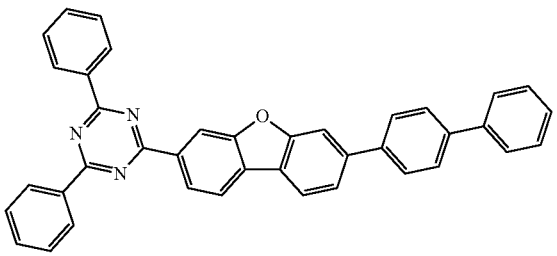
4-27
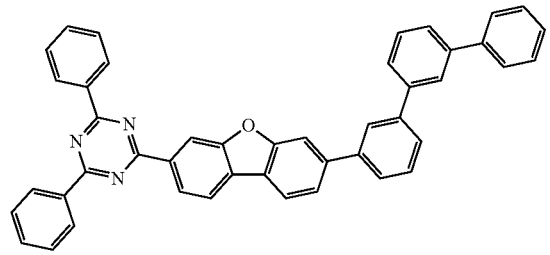
4-28
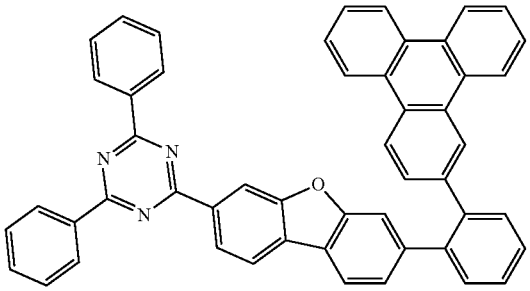
4-29
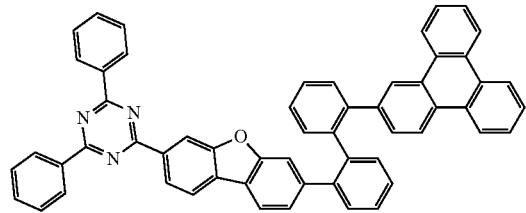
4-30
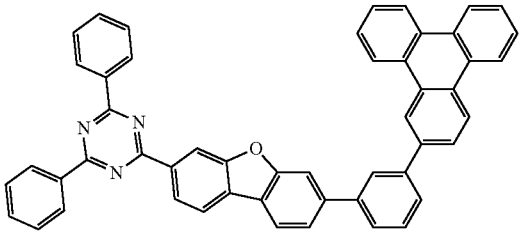
4-31
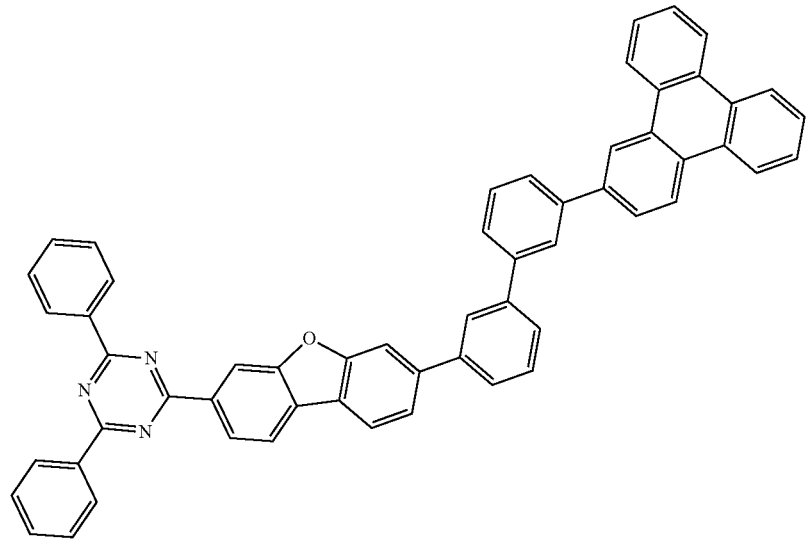

-continued
4-32
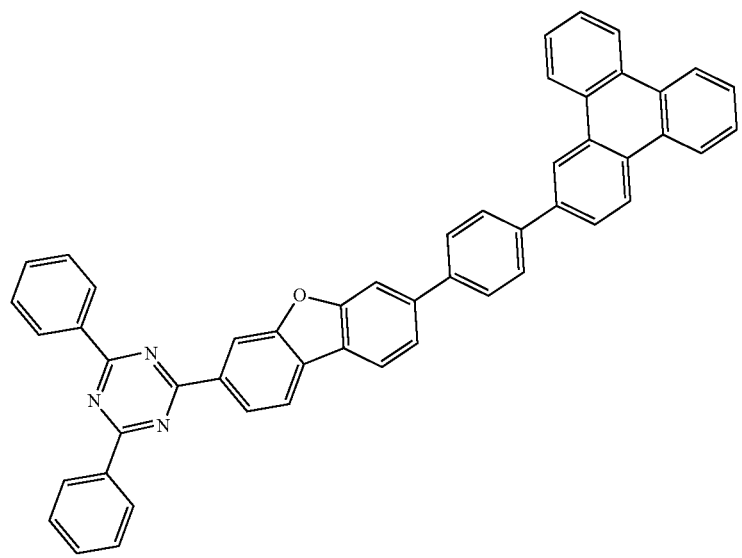
4-33
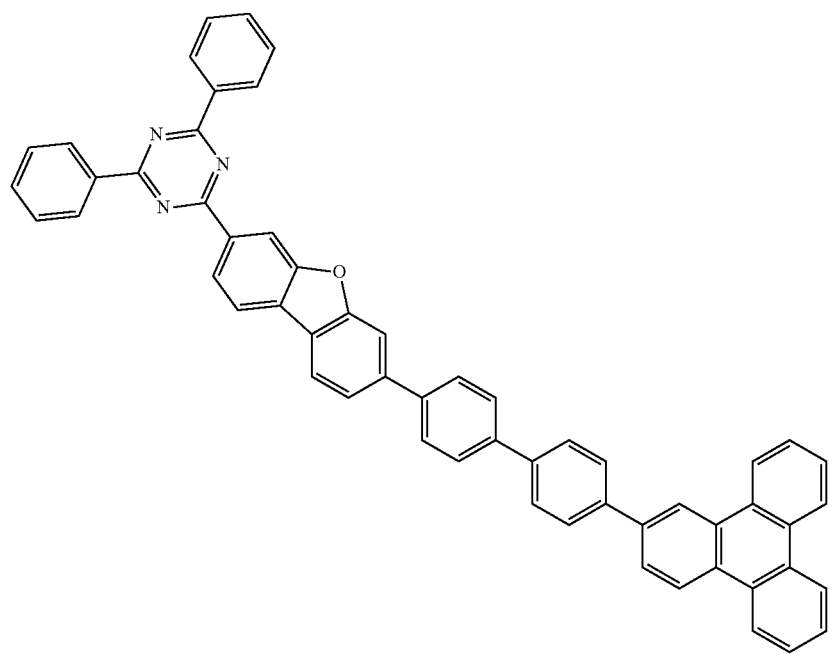
4-34
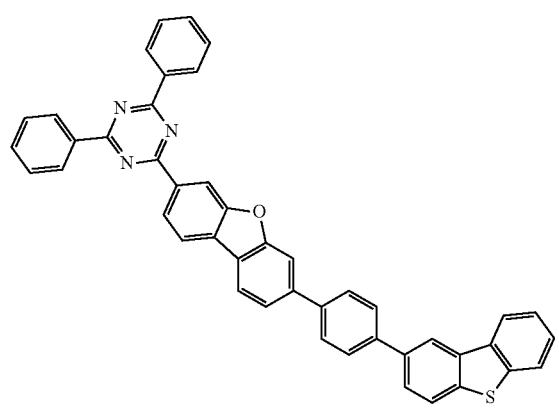
4-35
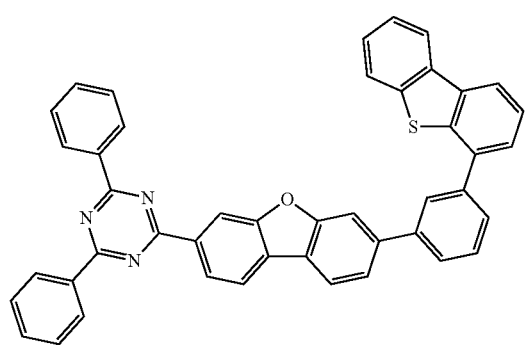

-continued
4-36
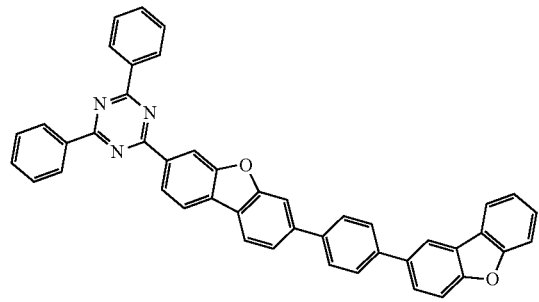
4-37
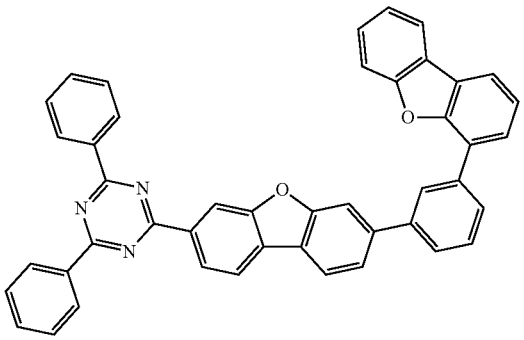
4-38
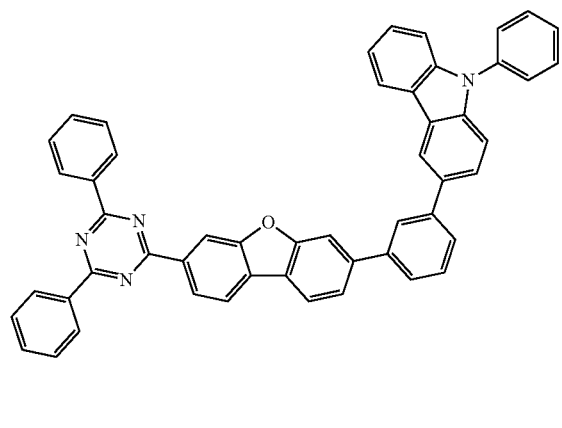
4-39
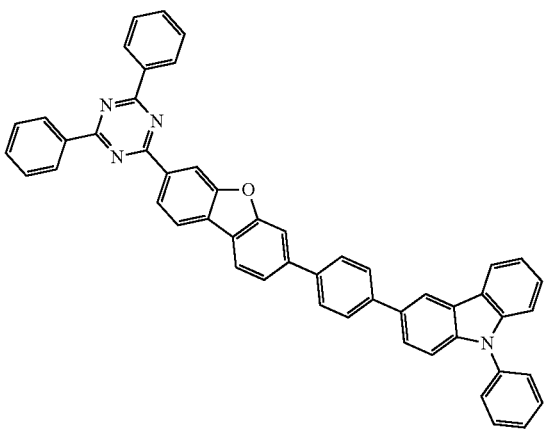
4-40
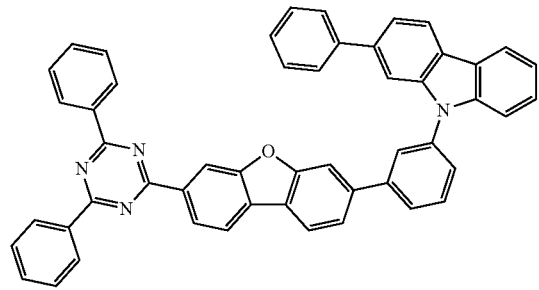
4-41
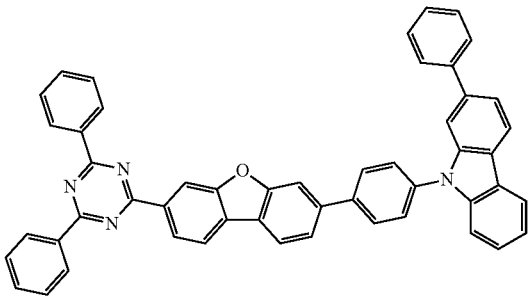
4-42
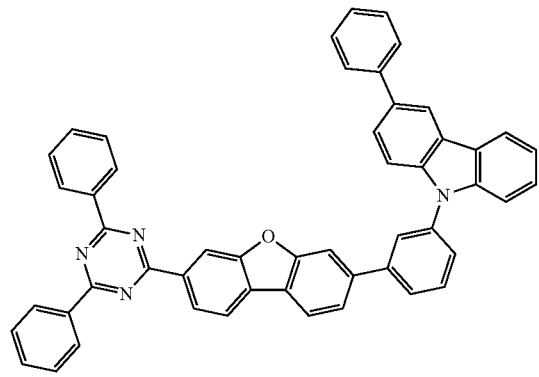
4-43
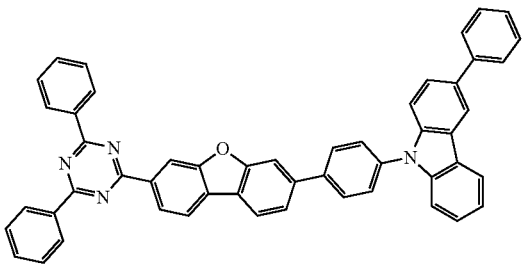

4-44
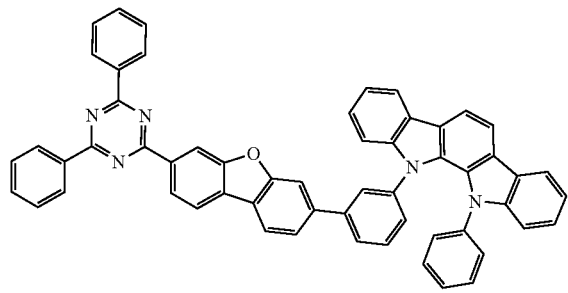
4-45
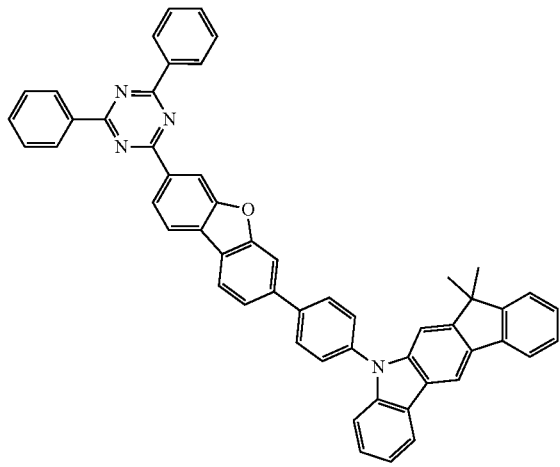
4-46
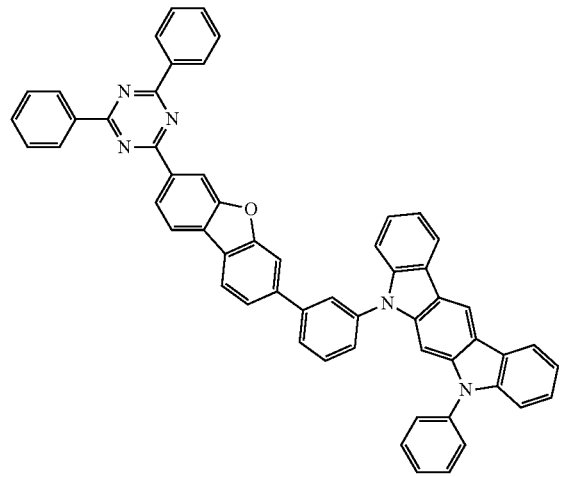
4-47
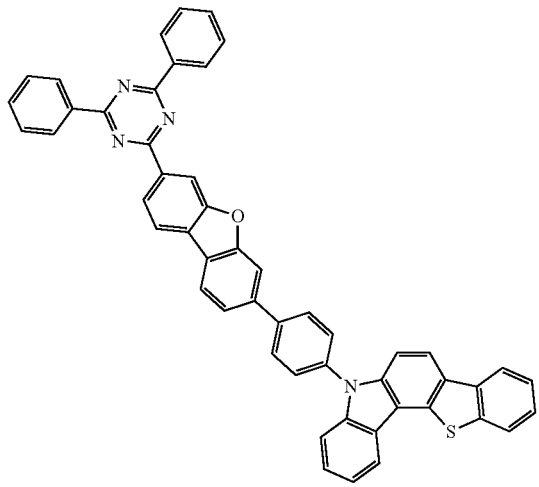
4-48
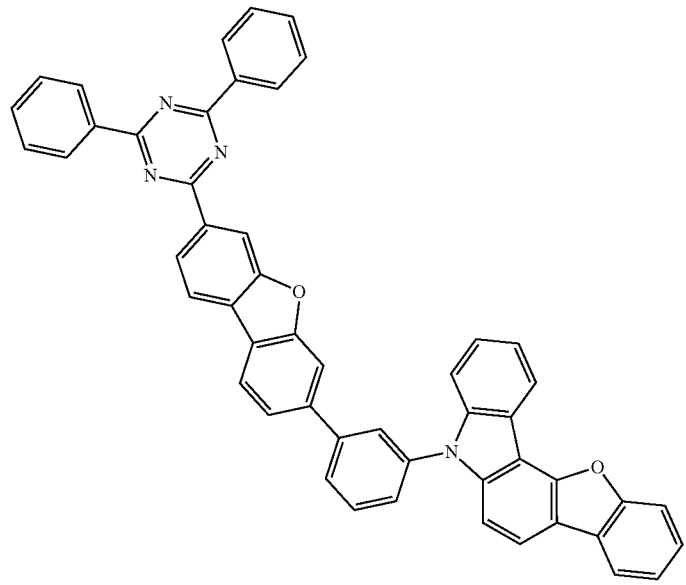

4-49
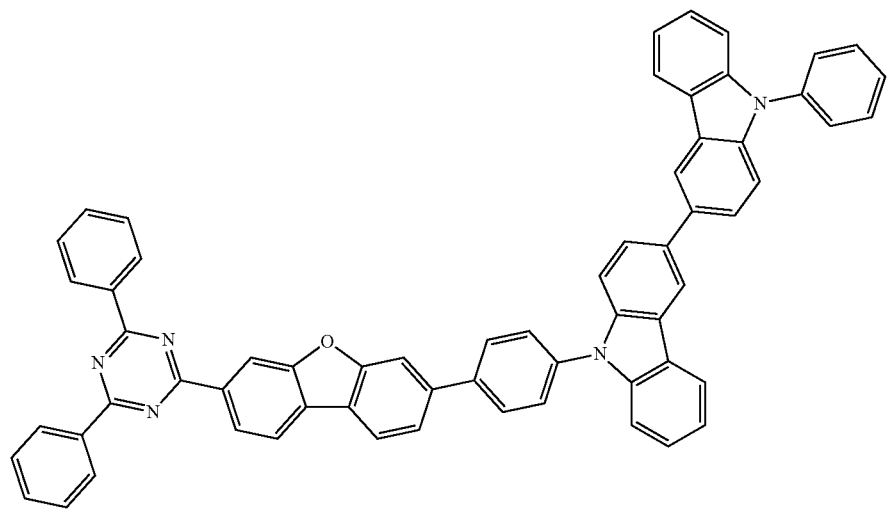
4-50
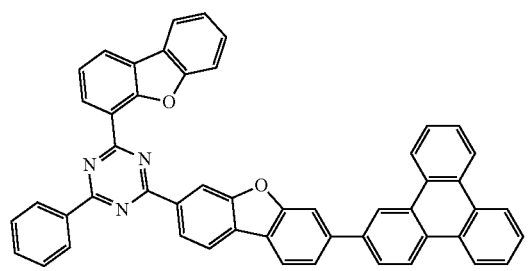
4-51
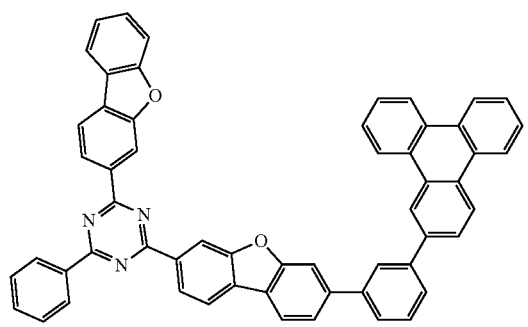
4-52
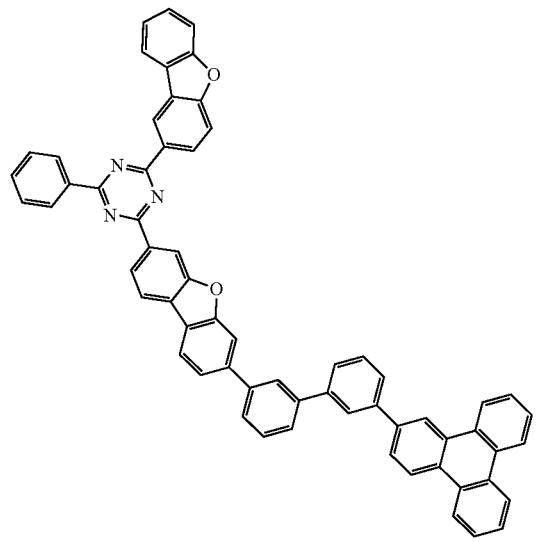
4-53
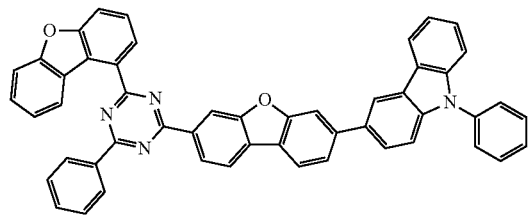

-continued
4-54
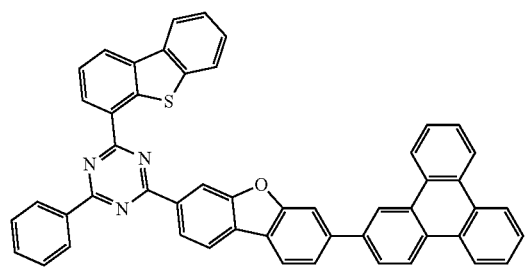
4-55
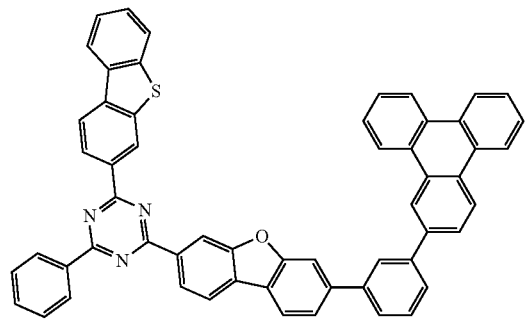
4-56
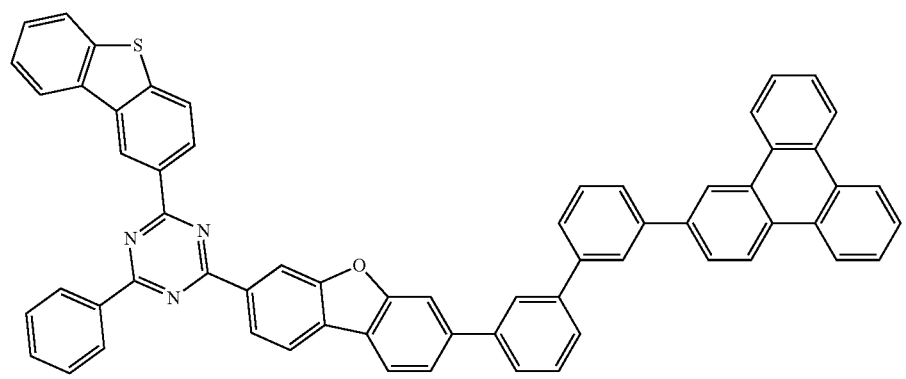
4-57
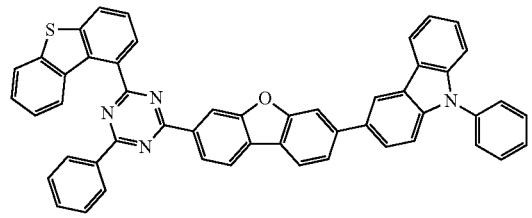
4-58
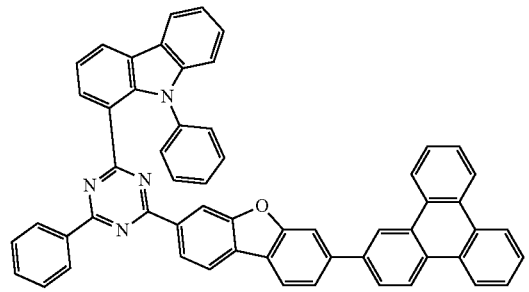
4-59
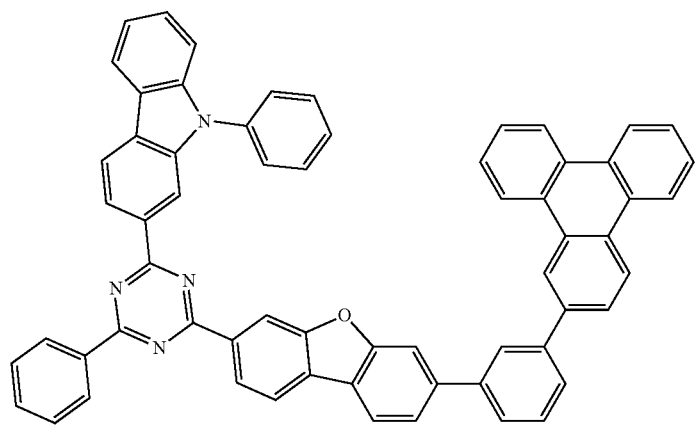

-continued
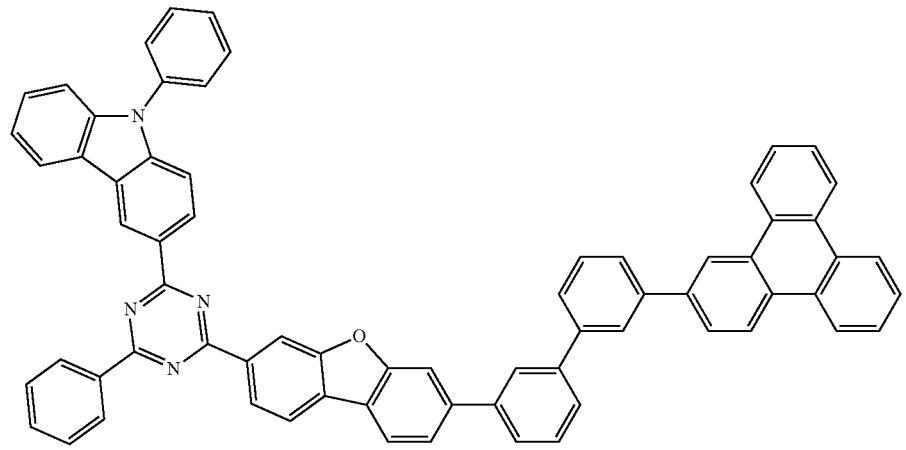
4-60
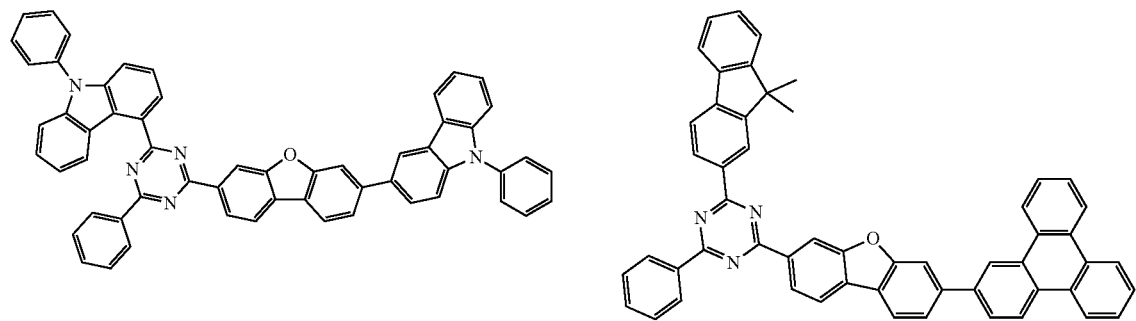
4-61
4-62
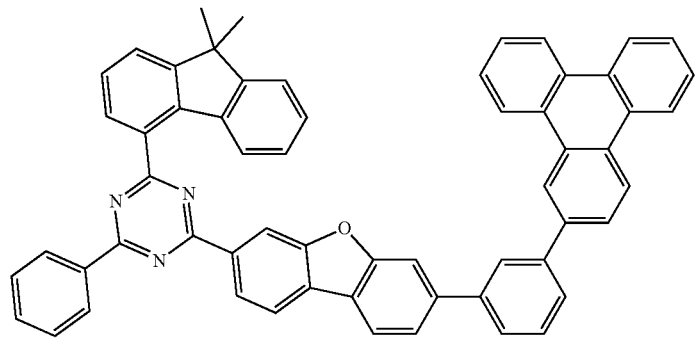
4-63
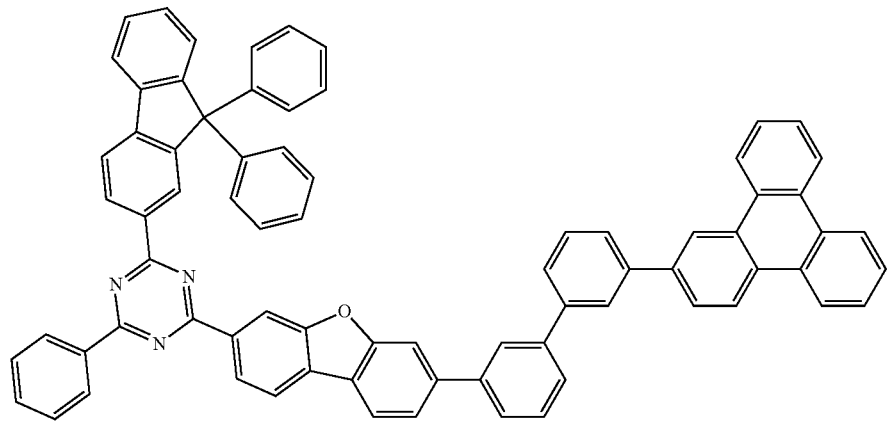
4-64

-continued
4-65
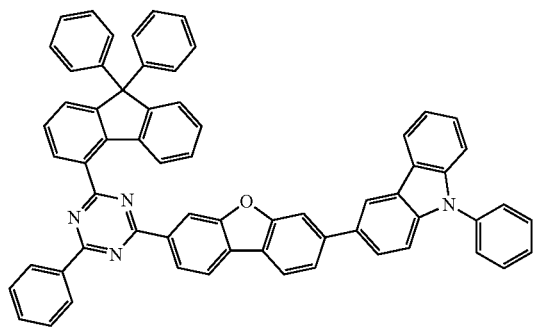
4-66
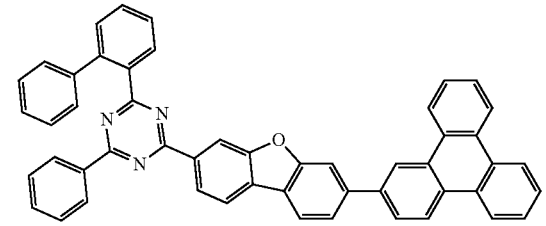
4-67
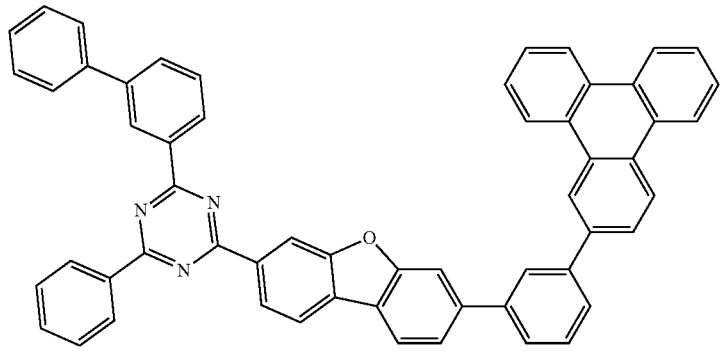
4-68
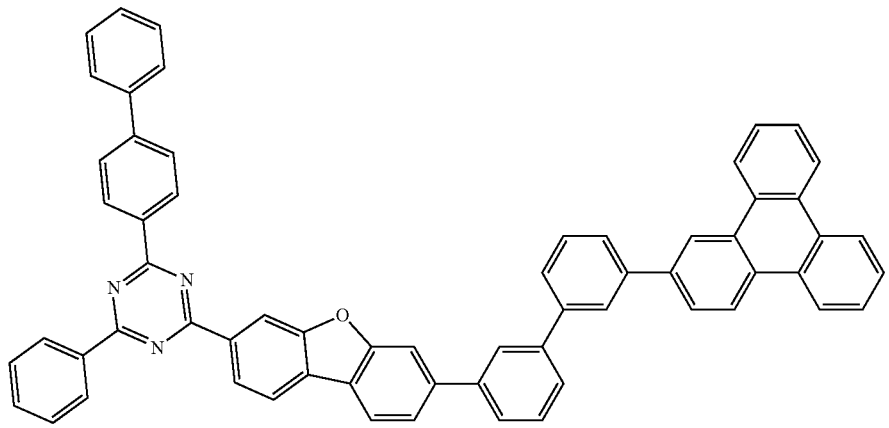
4-69
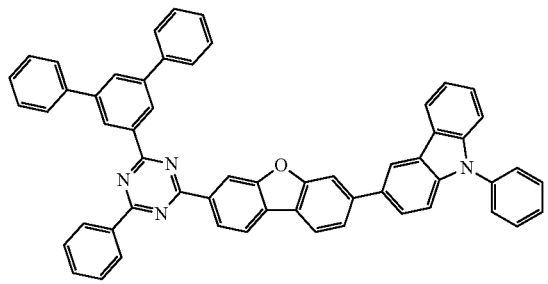
4-70
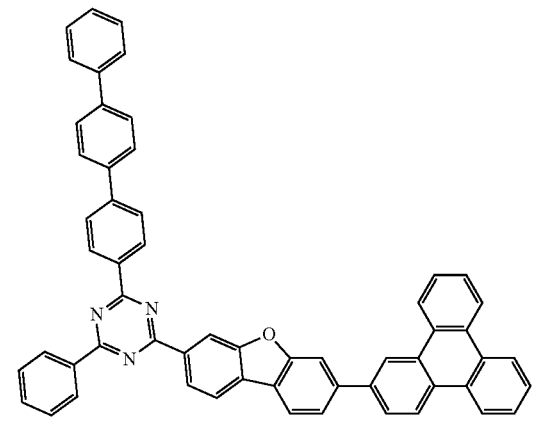

4-71
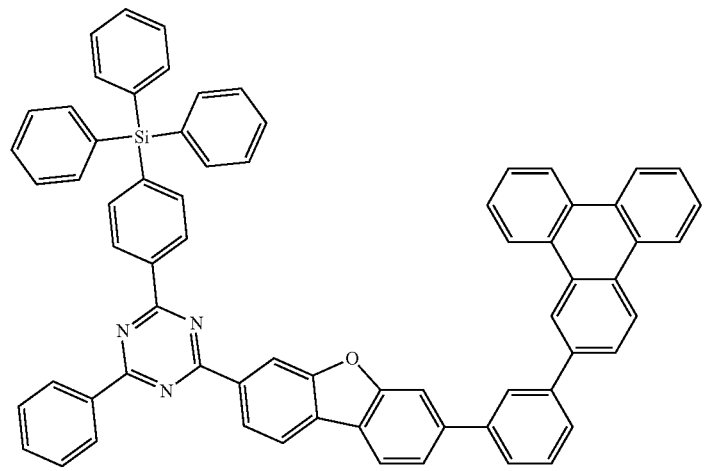
4-72
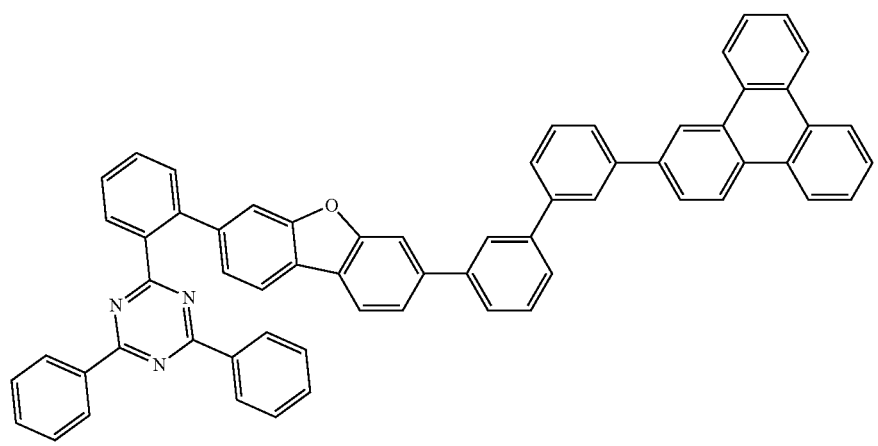
4-73
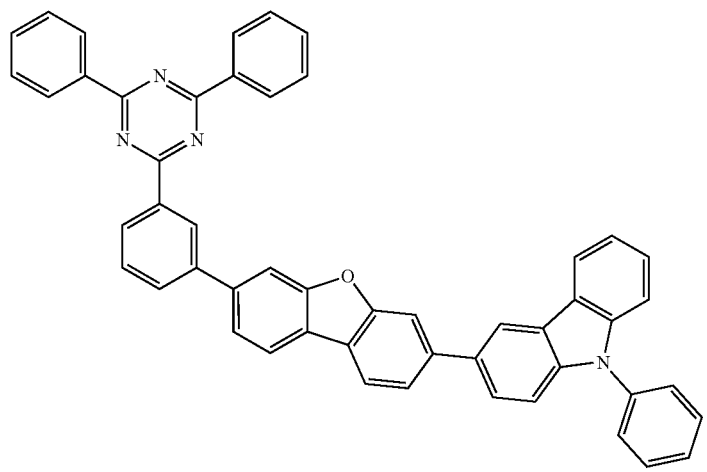

4-74
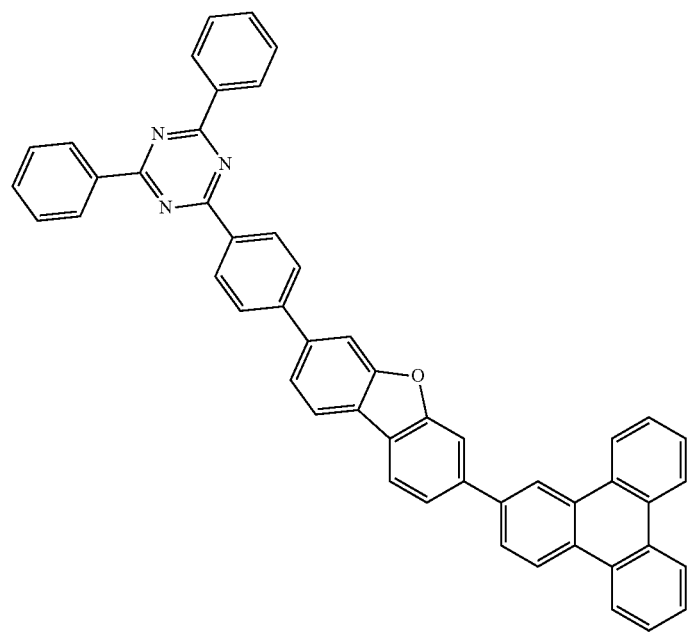
4-75
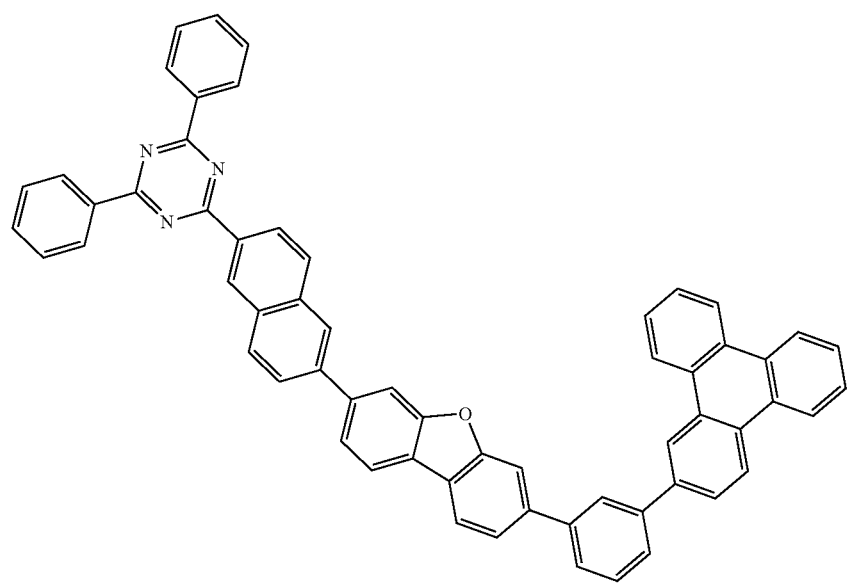

4-76
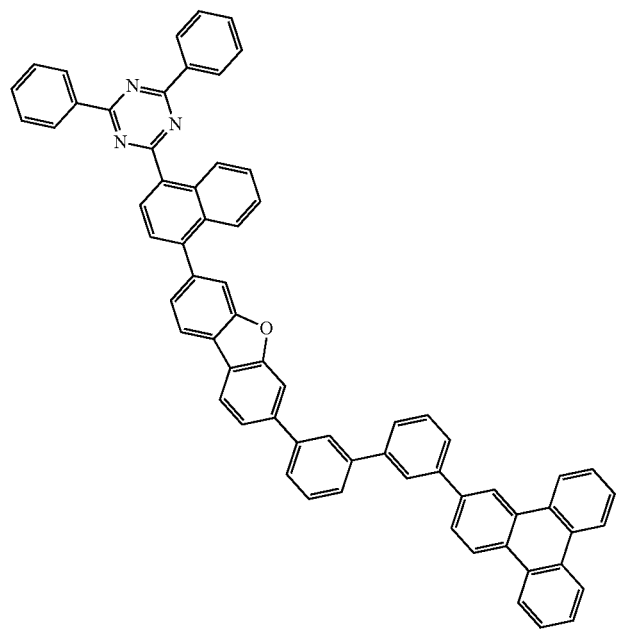
4-77
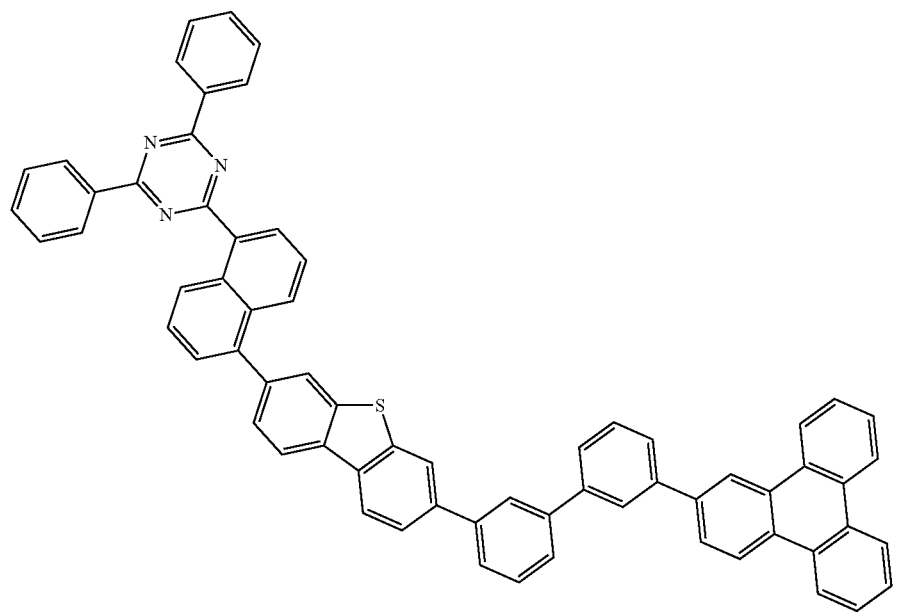
4-78
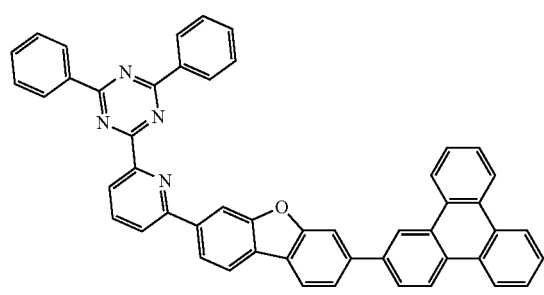
4-79
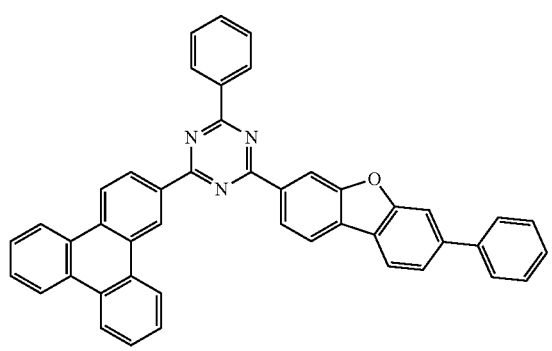

4-80
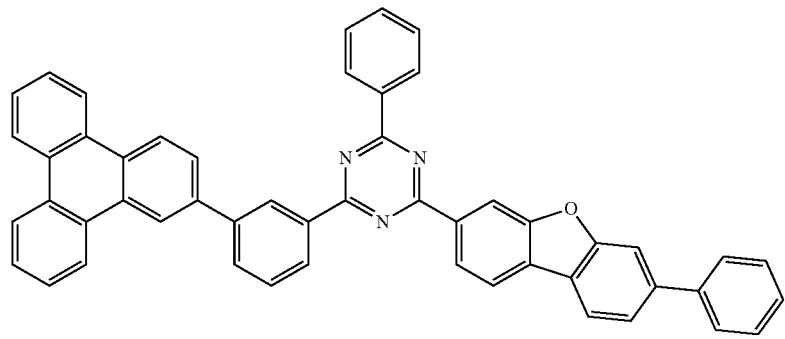
4-81
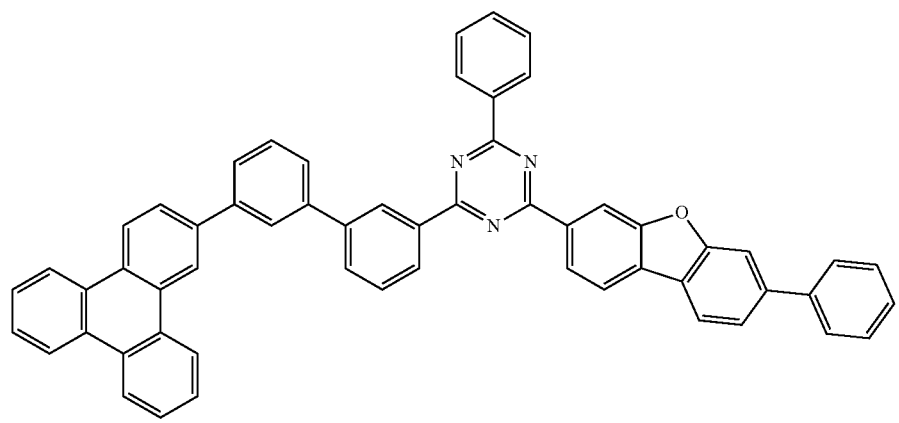
4-82
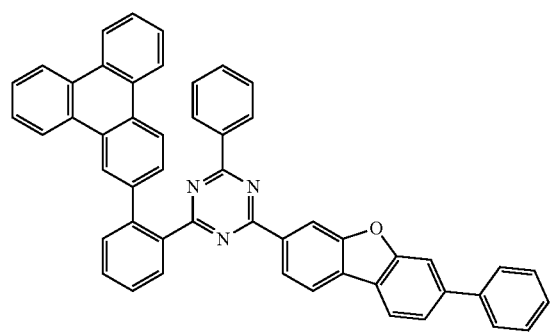
4-83
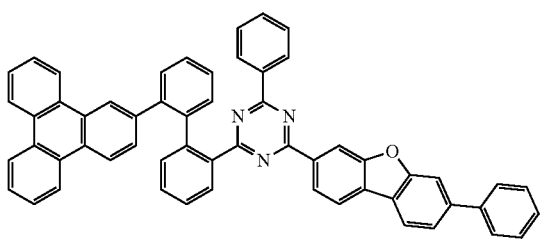
4-84
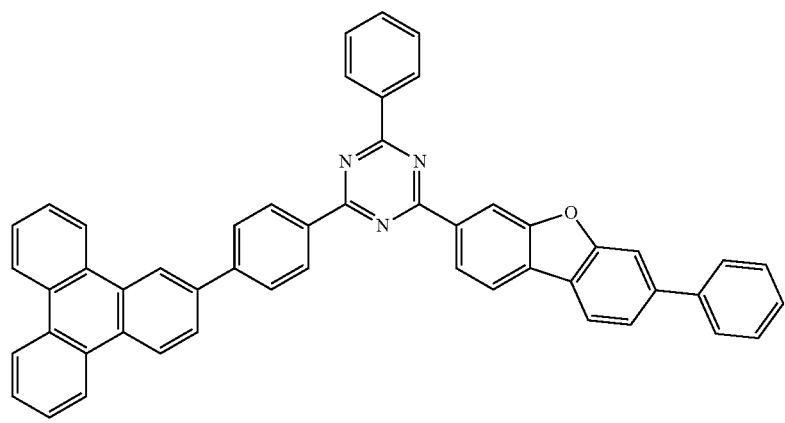

4-85
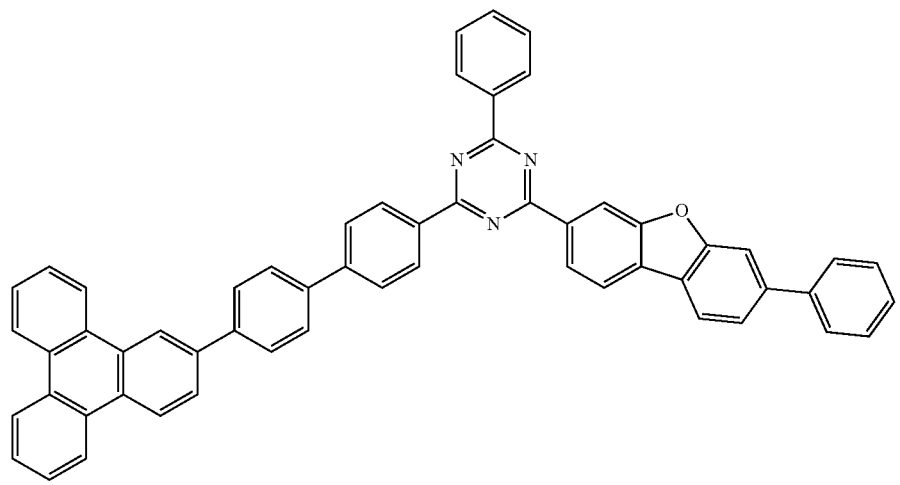
4-86
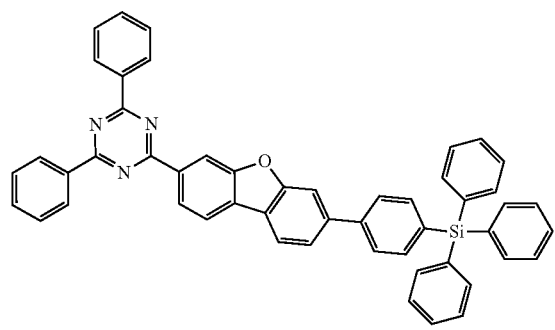
4-87
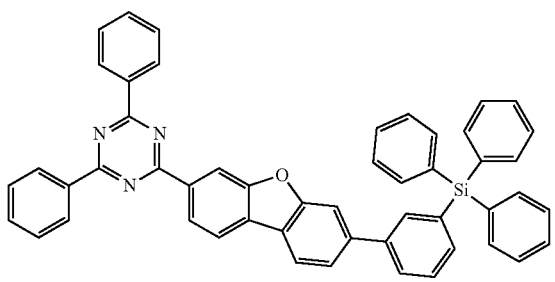
4-88
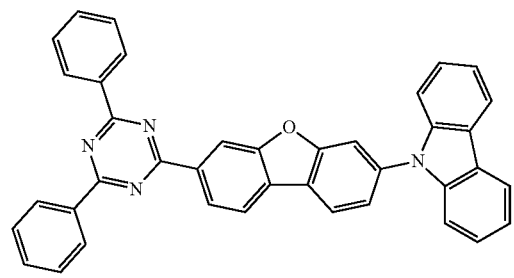
4-89
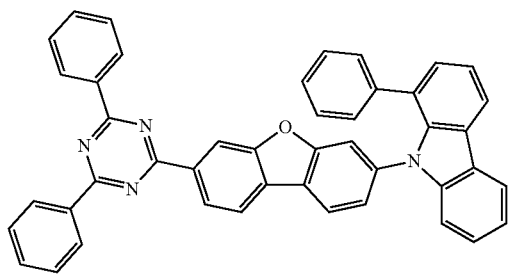
4-90
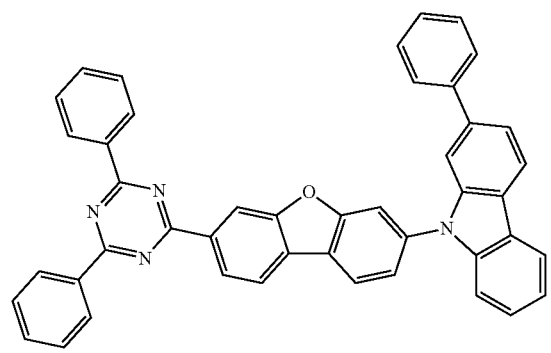
4-91
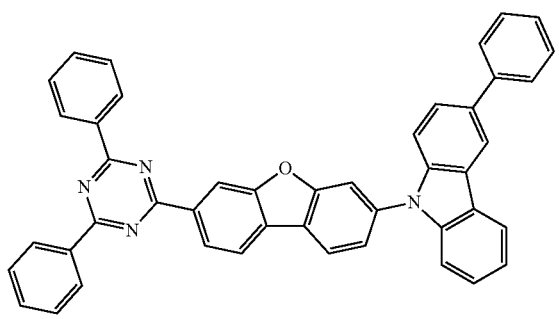

-continued
4-92
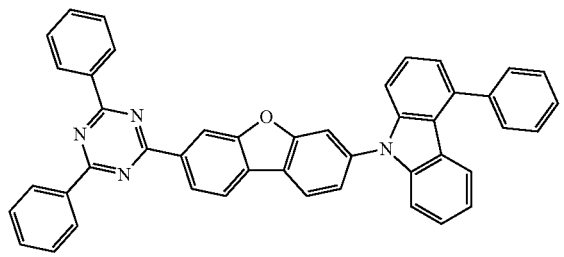
4-93
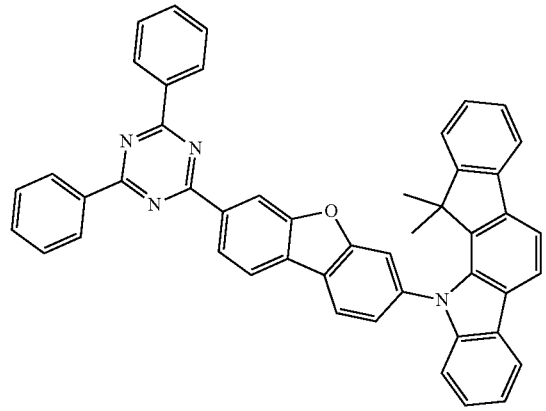
4-94
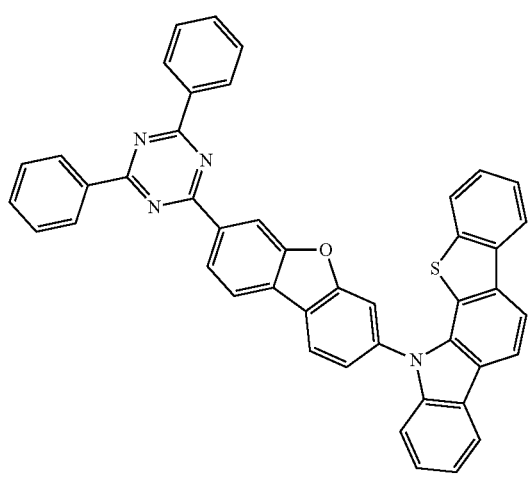
4-95
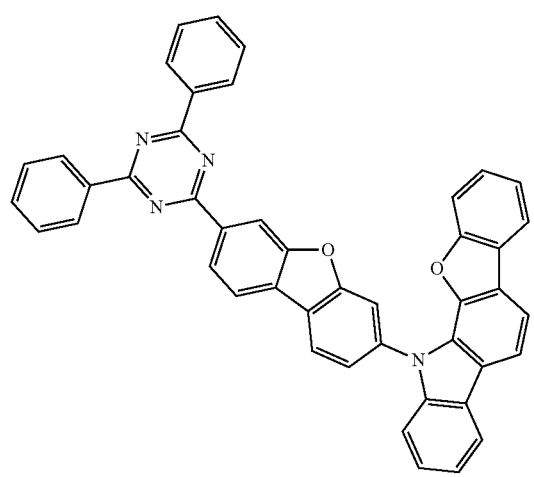
4-96
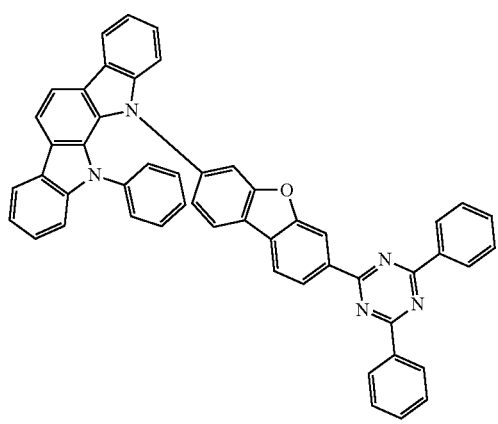
4-97
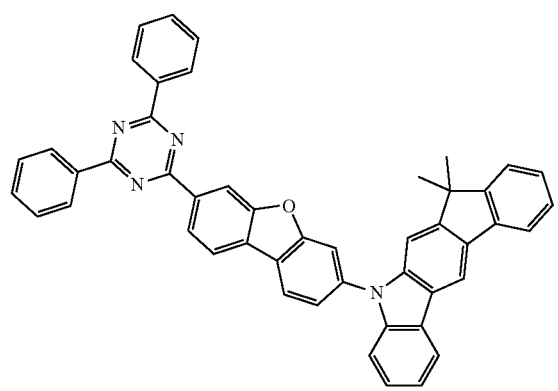

-continued
4-98
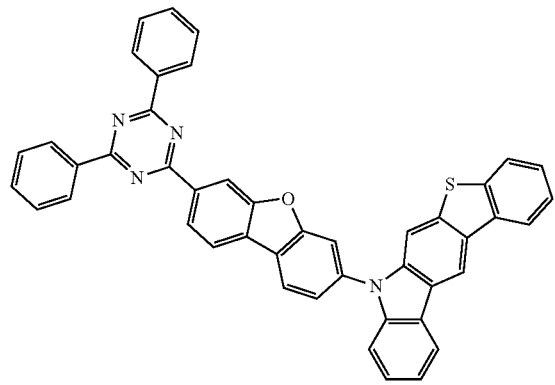
4-99
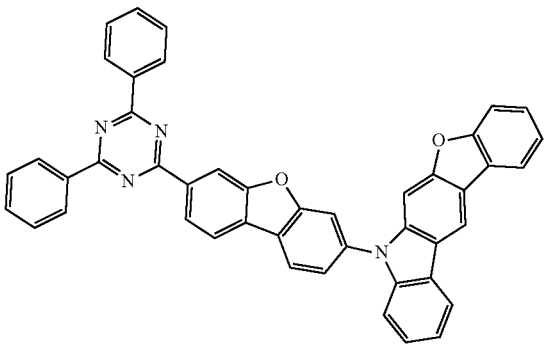
4-100
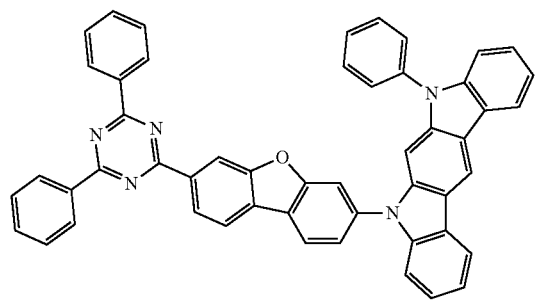
4-101
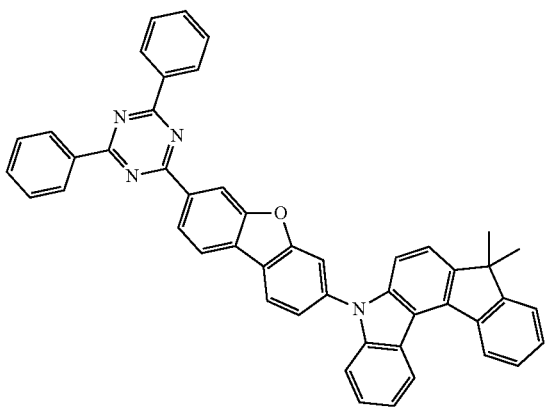
4-102
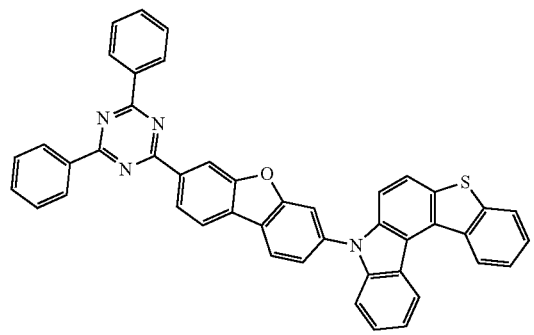
4-103
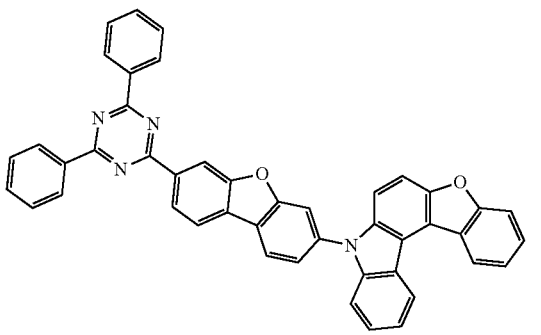
4-104
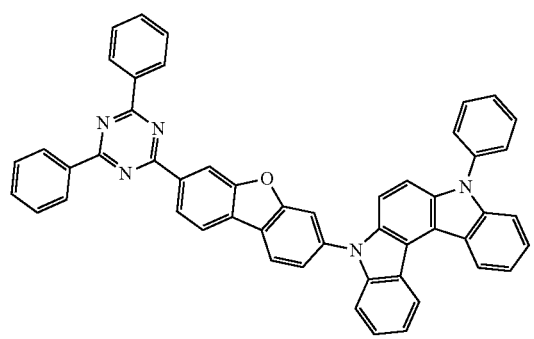
4-105
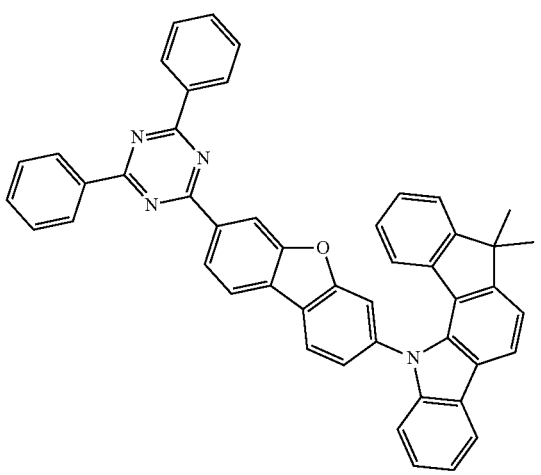

4-106
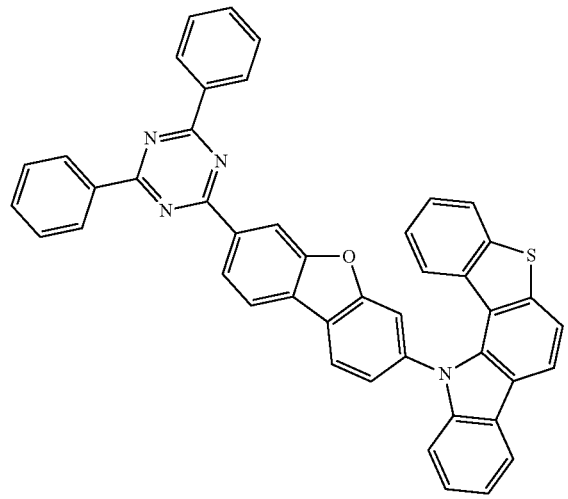
4-107
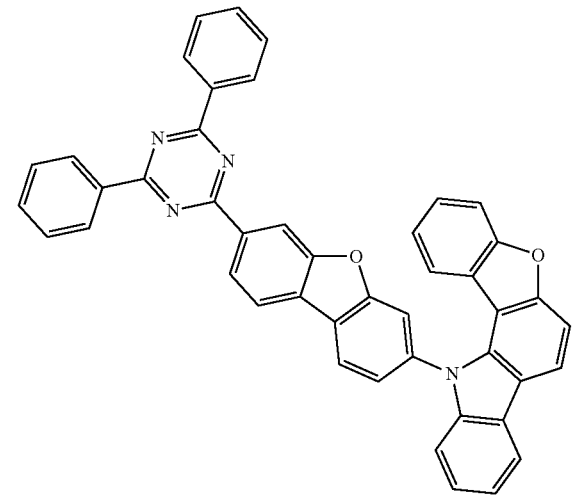
4-108
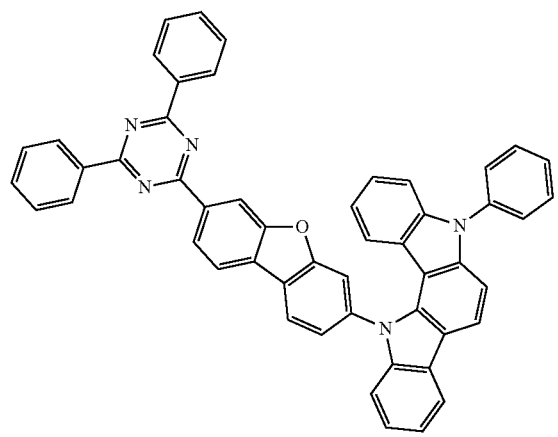
4-109
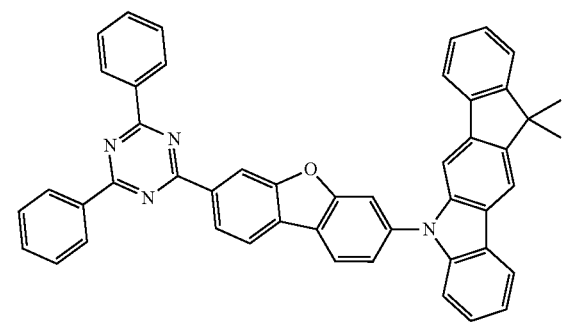
4-110
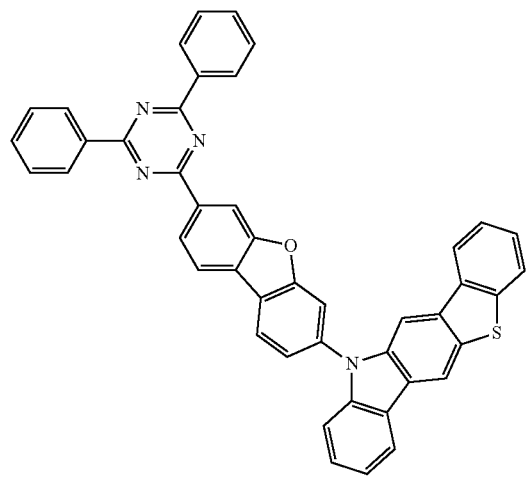
4-111
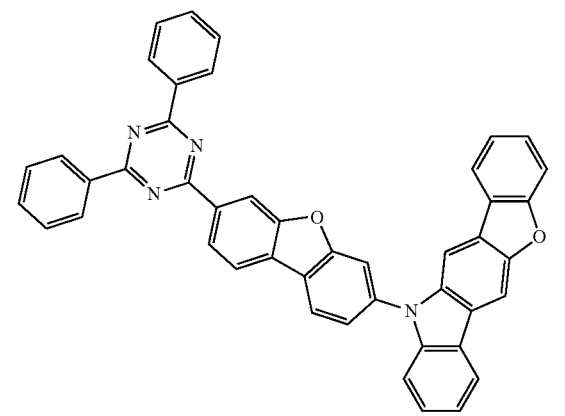

-continued
4-112
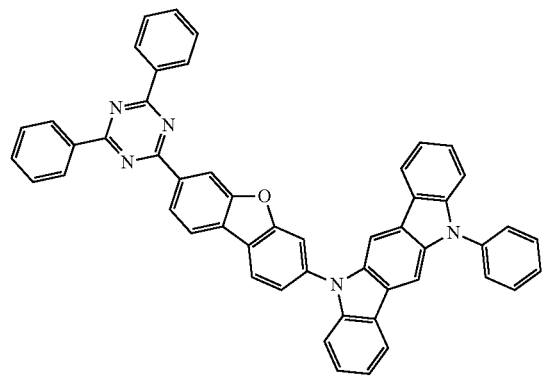
4-113
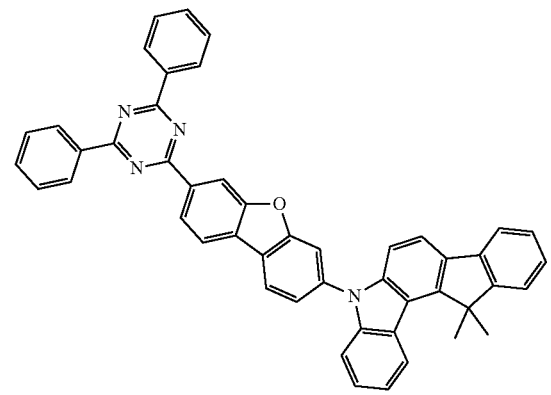
4-114
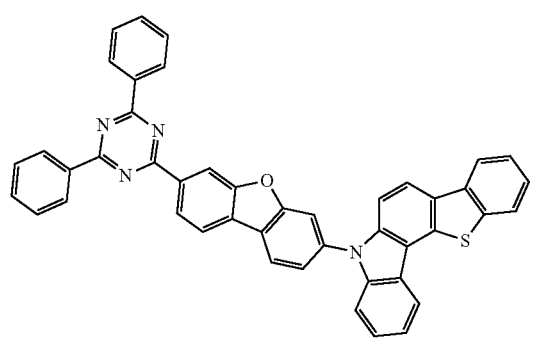
4-115
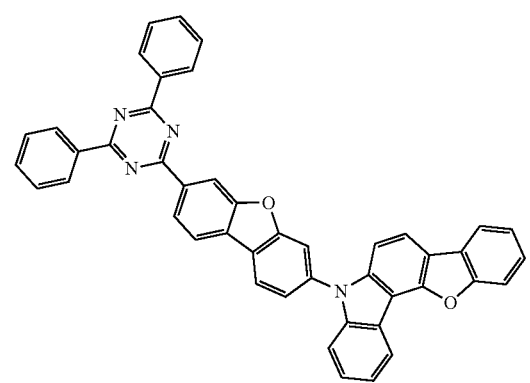
4-116
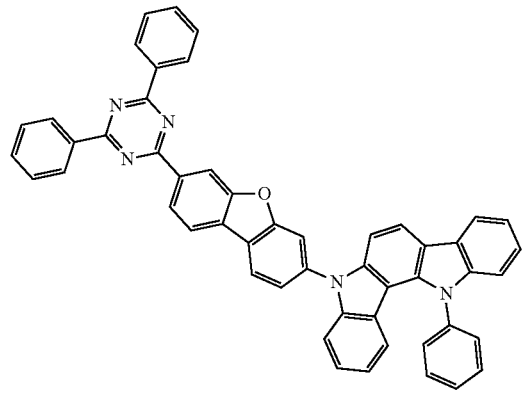
4-117
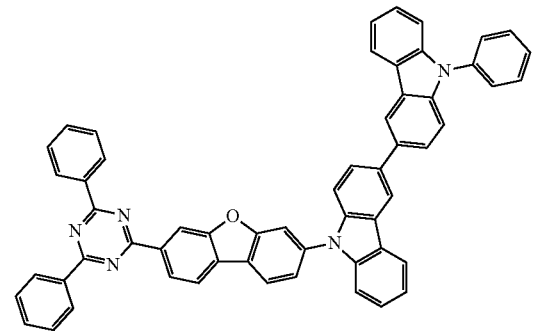
4-118
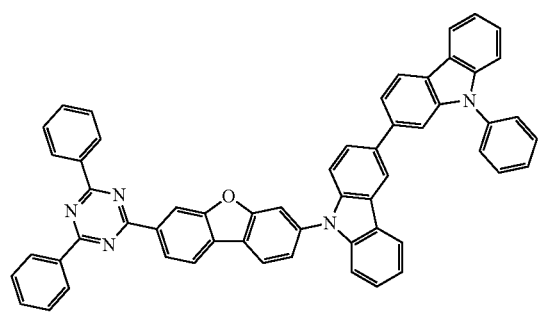
4-119
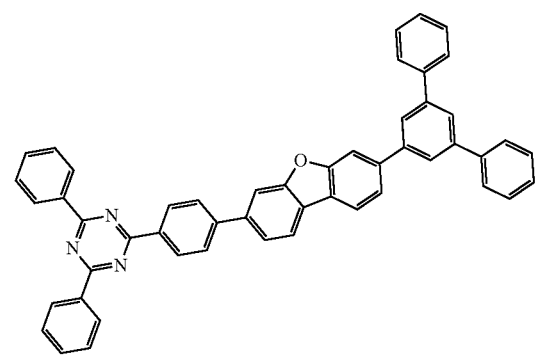

-continued
4-120
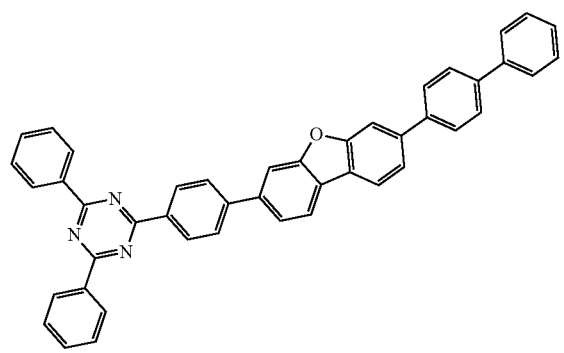
4-121
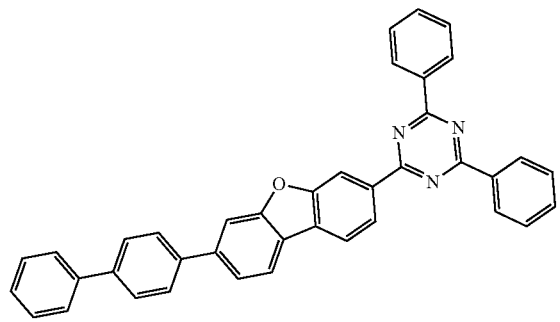
4-122
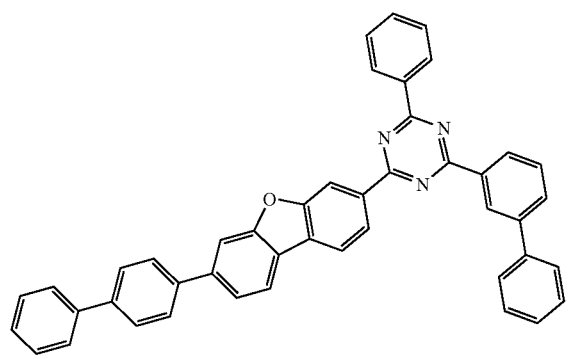
4-123
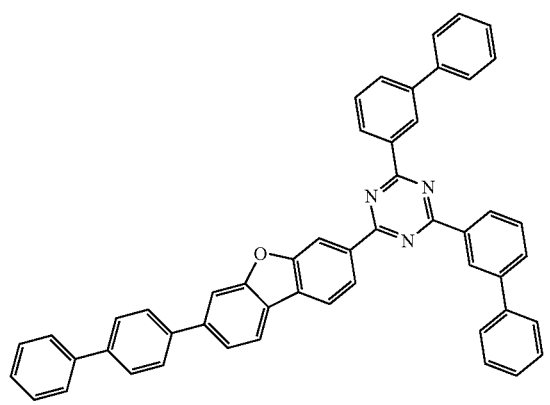
4-124
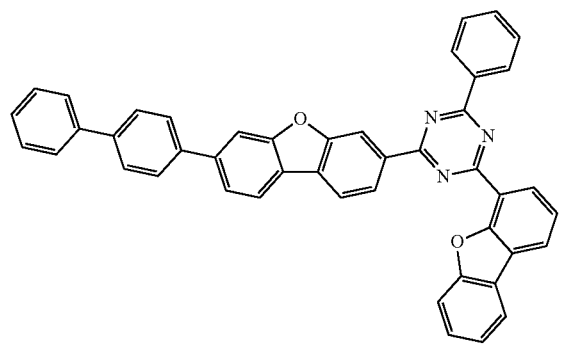
4-125
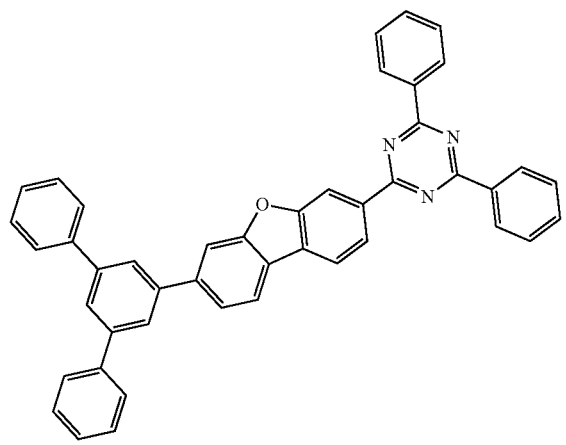
4-126
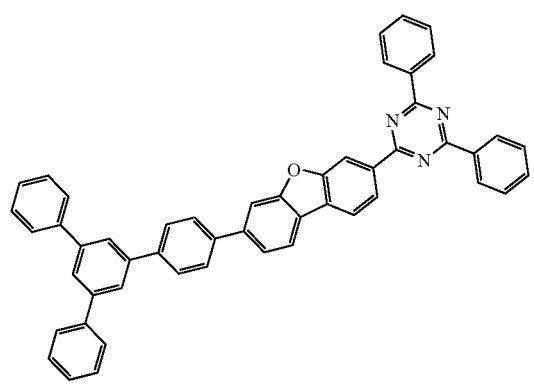
4-127
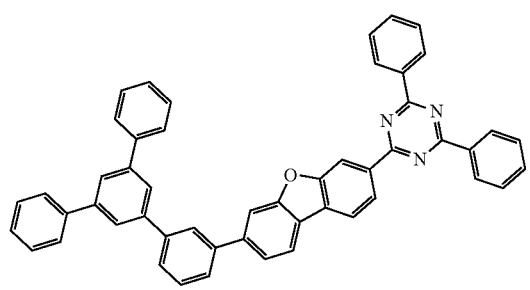

-continued
4-128
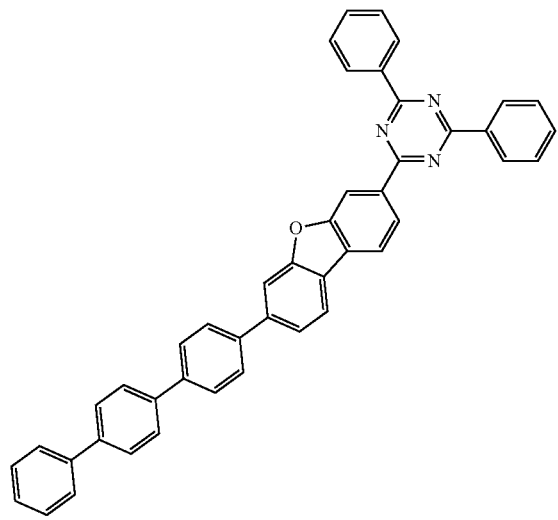
4-129
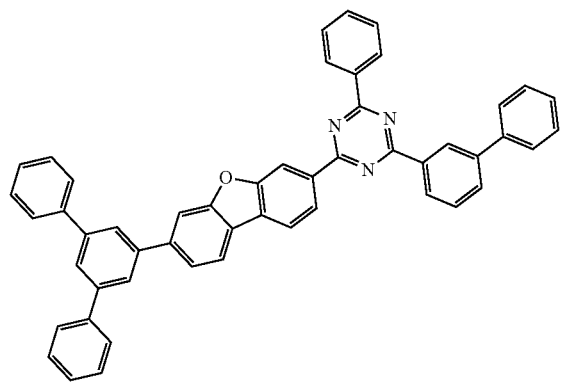
4-130
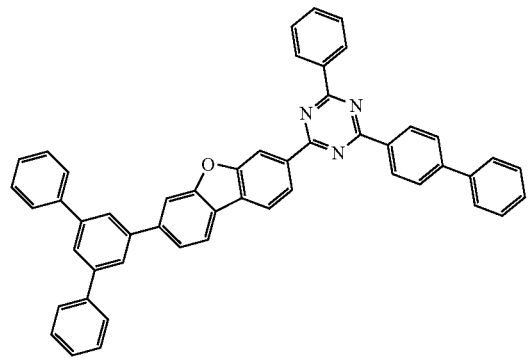
4-131
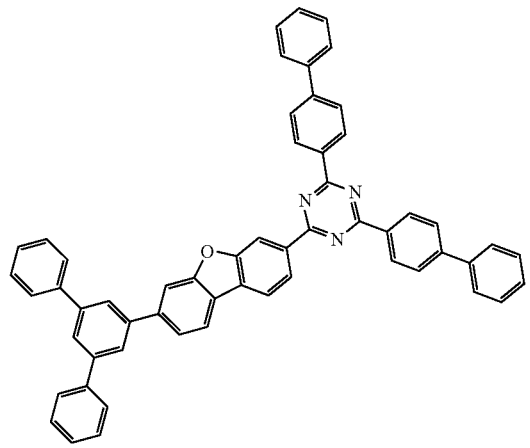
4-132
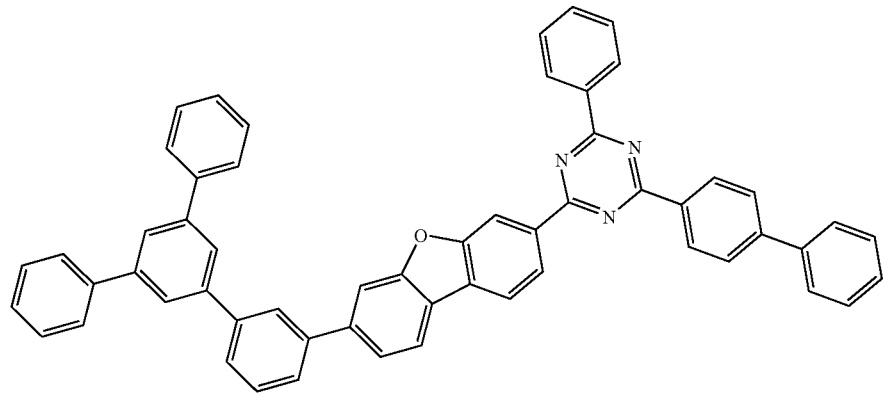

-continued
4-133
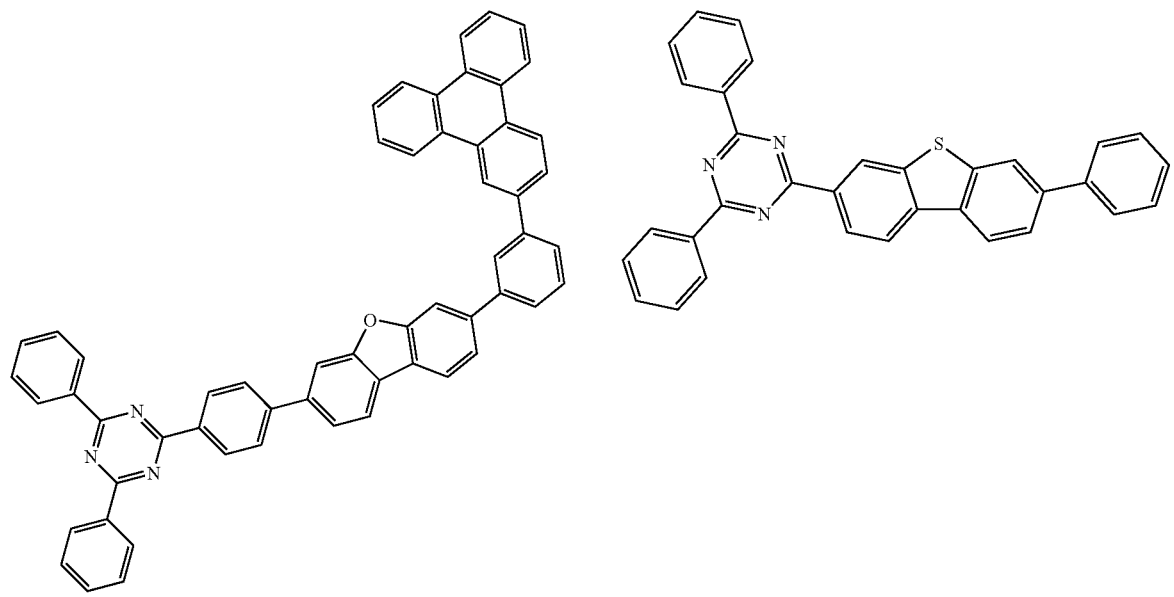
5-1
5-2 5-3
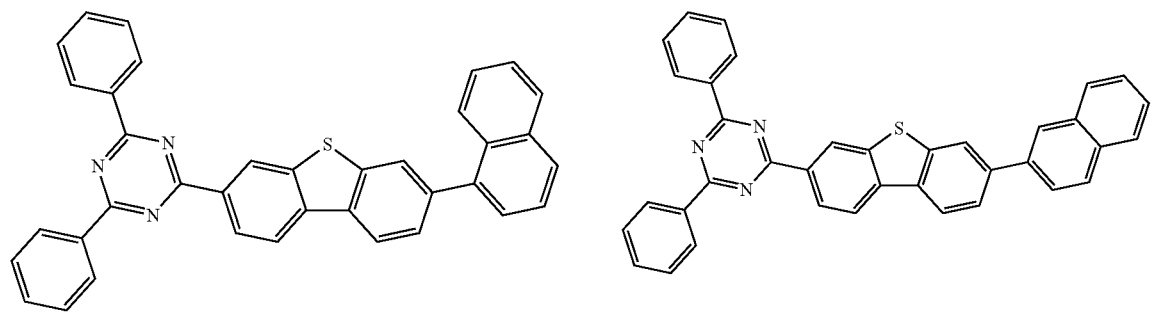
5-4 5-5
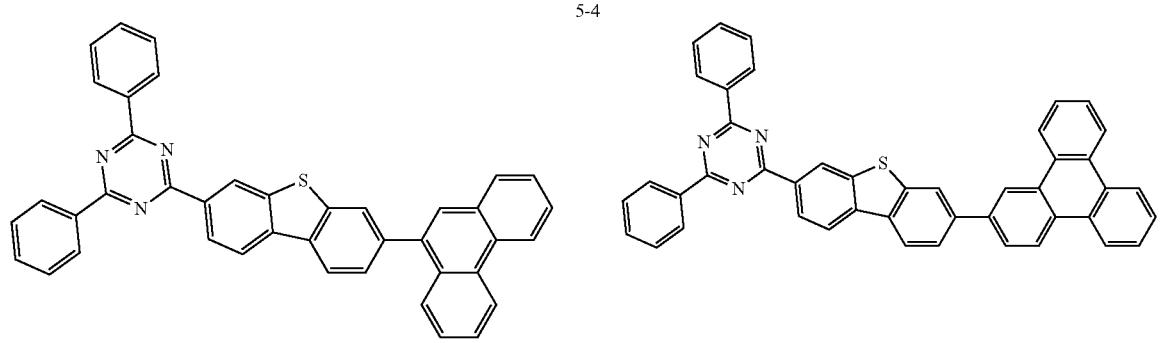
5-6 5-7
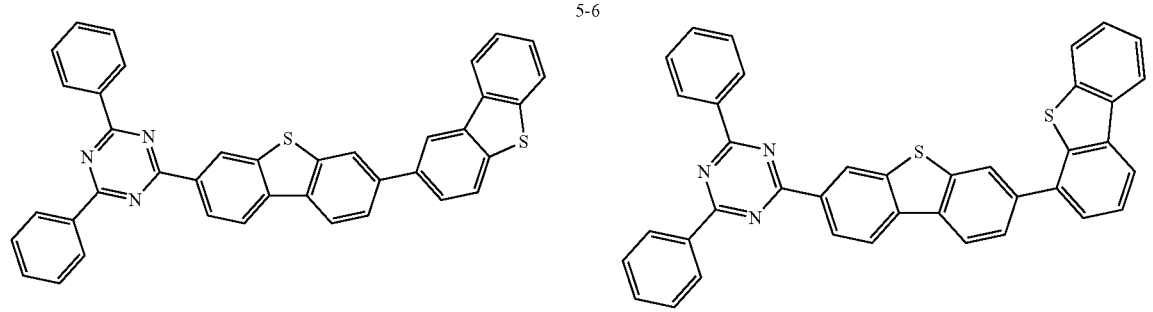

-continued
5-8
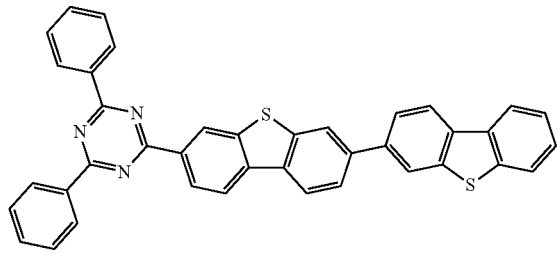
5-9
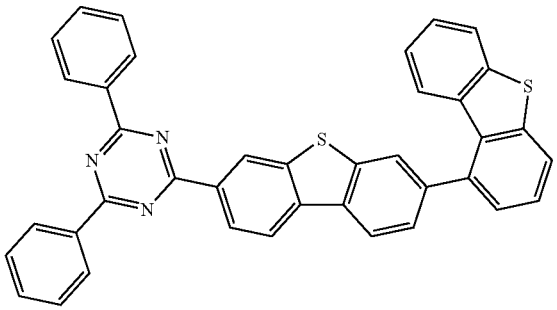
5-10
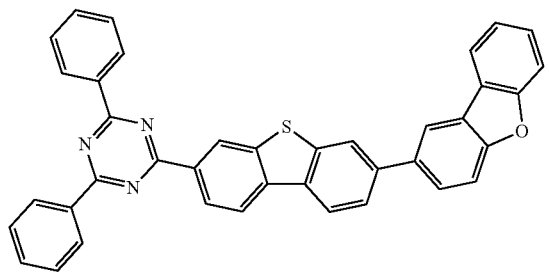
5-11
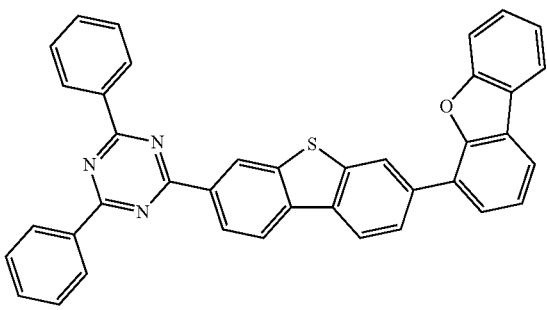
5-12
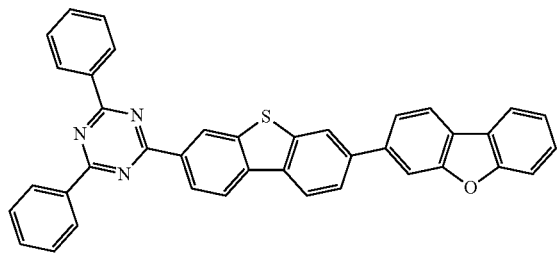
5-13
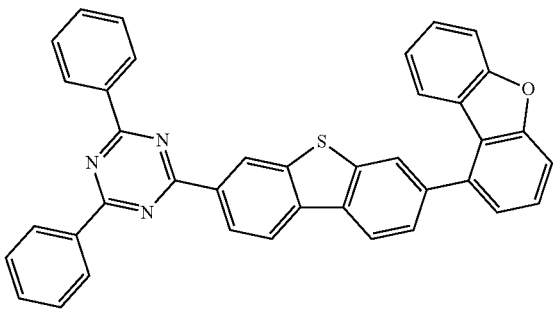
5-14
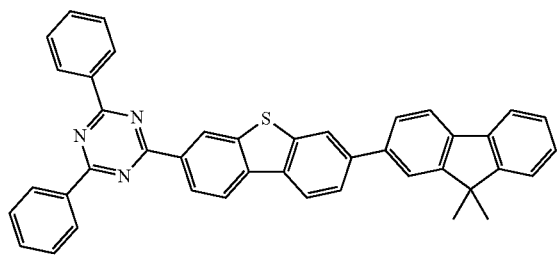
5-15
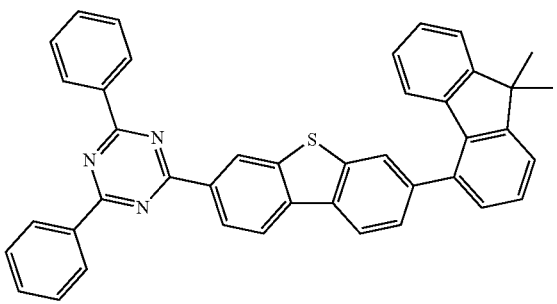
5-16
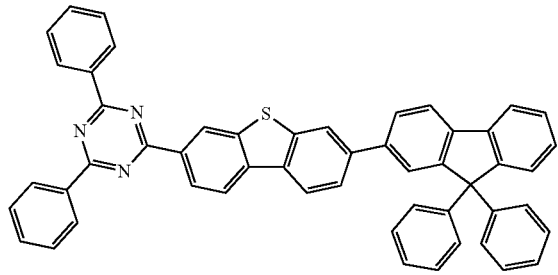
5-17
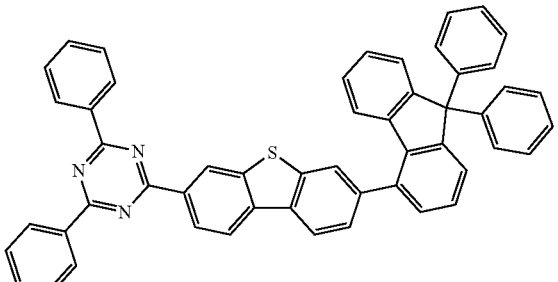

-continued
5-18
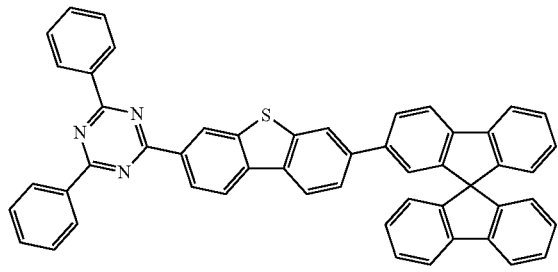
5-19
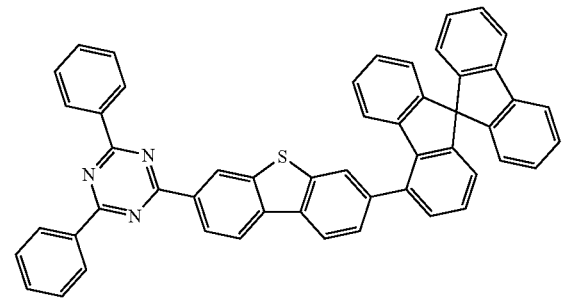
5-20
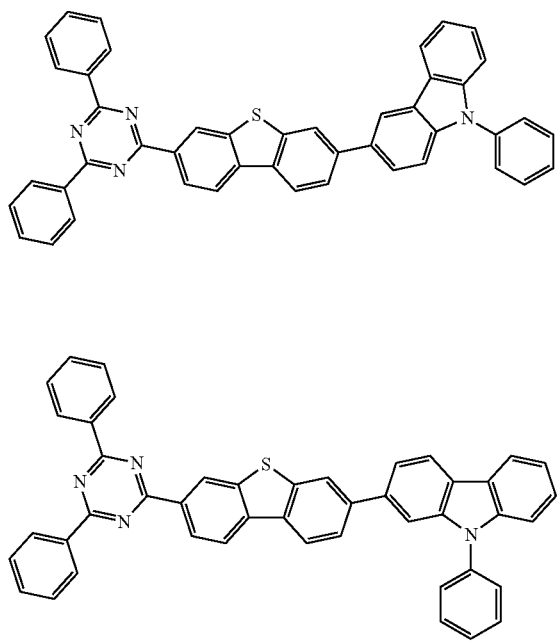
5-21
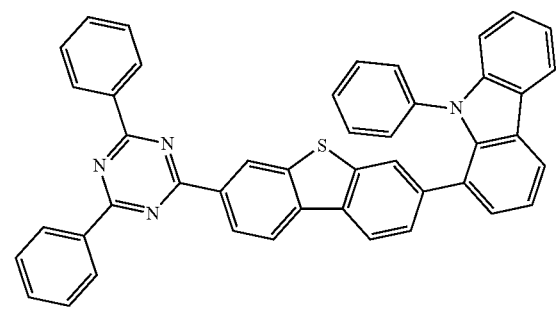
5-23
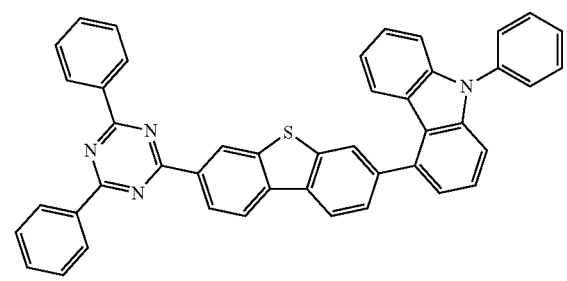
5-24
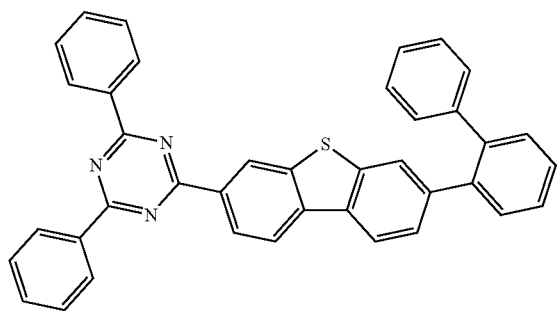
5-25
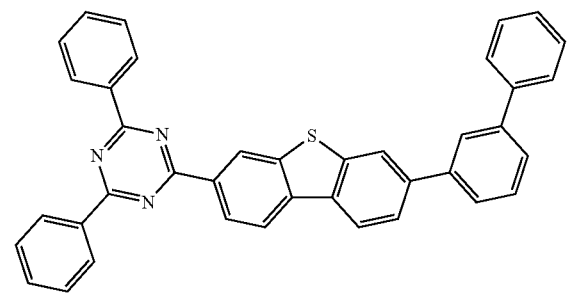
5-26
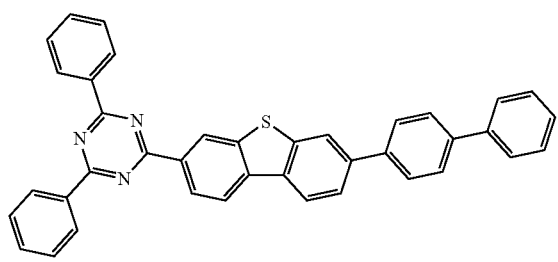
5-27
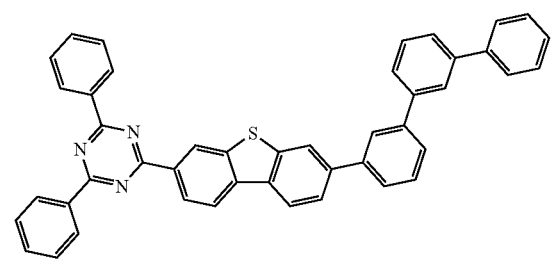

-continued
5-28
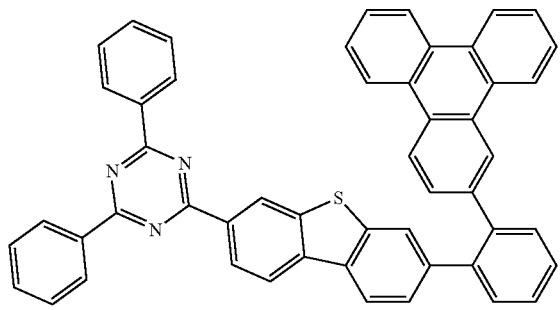
5-29
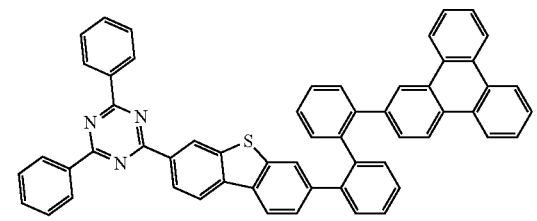
5-30
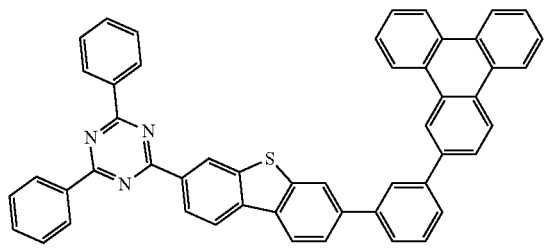
5-31
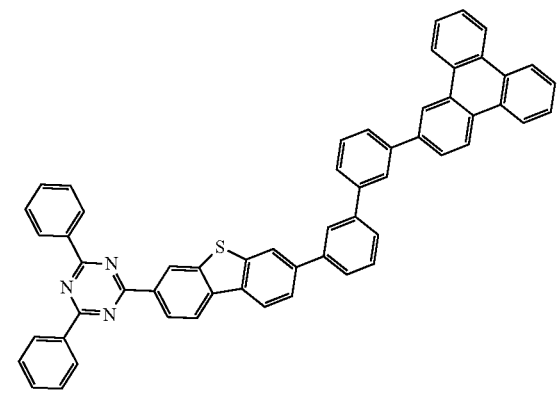
5-32
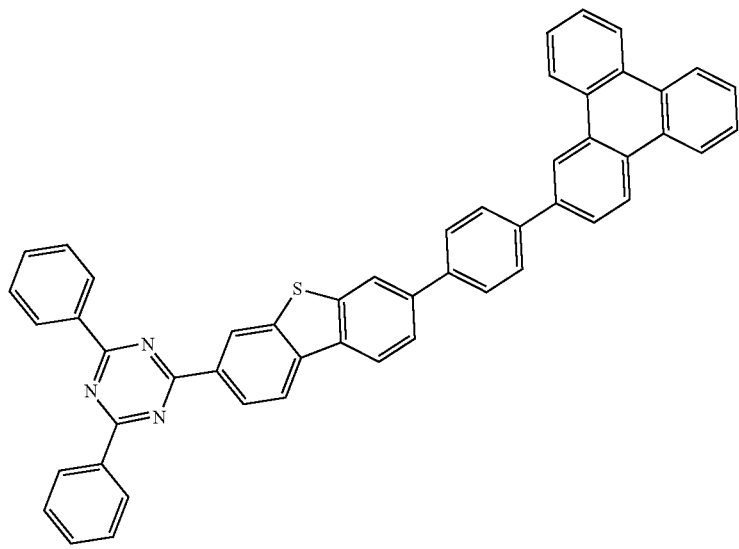

5-33
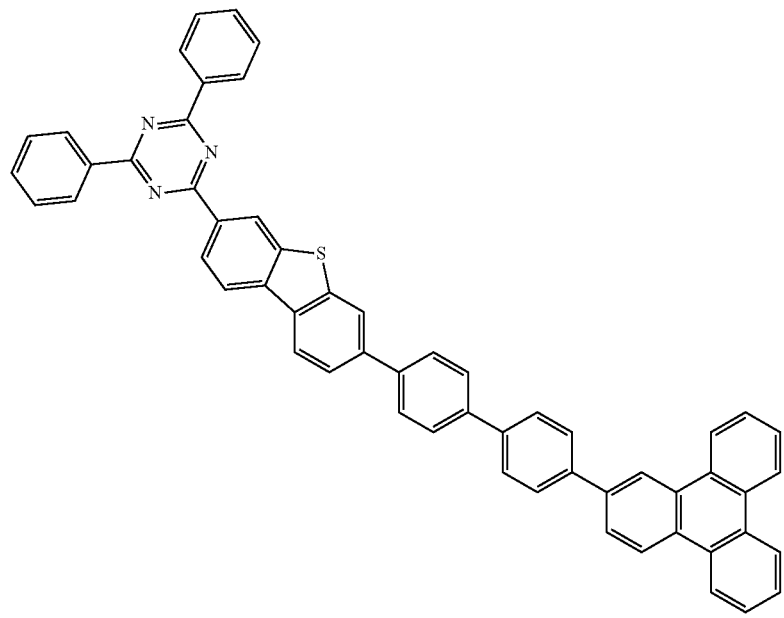
5-34
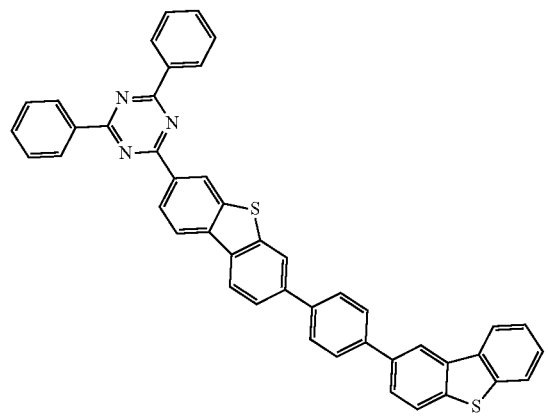
5-35
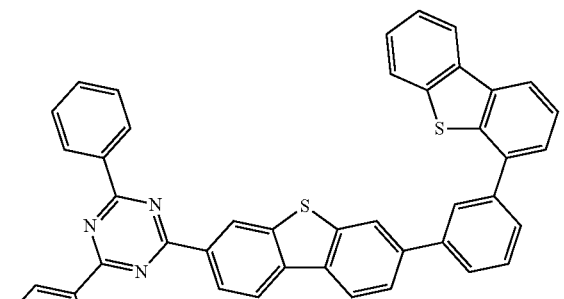
5-36
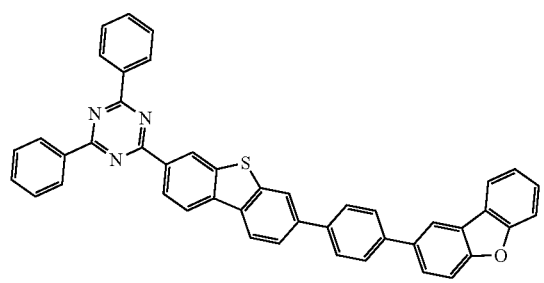
5-37
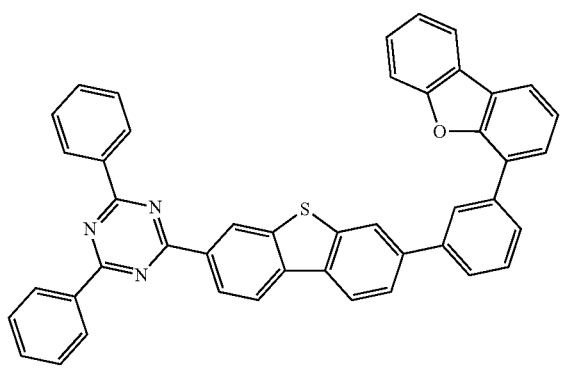

-continued
5-38
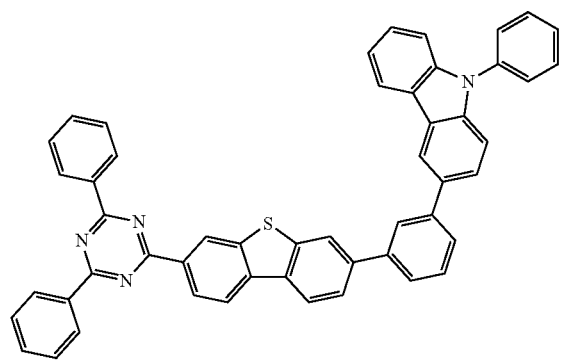
5-39
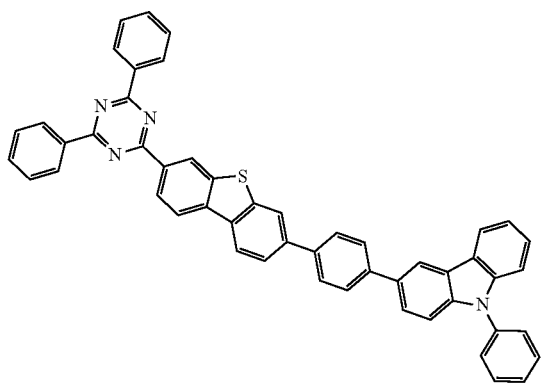
5-40
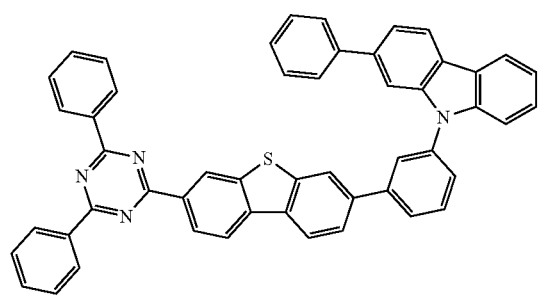
5-41
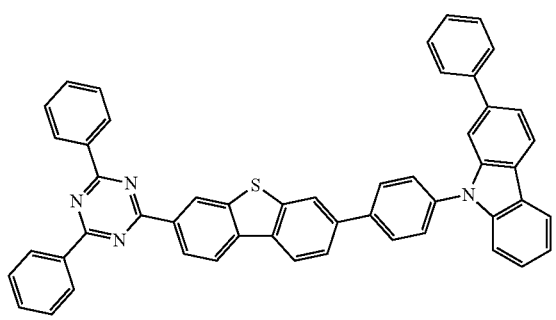
5-42
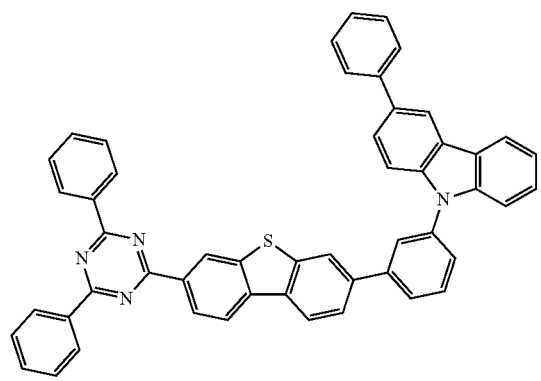
5-43
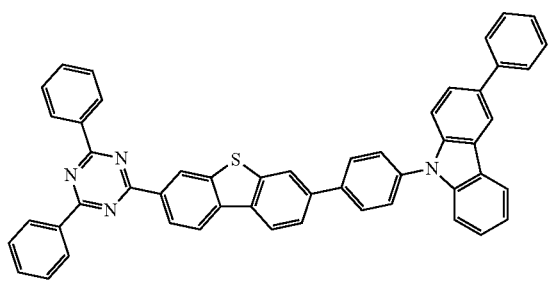
5-44
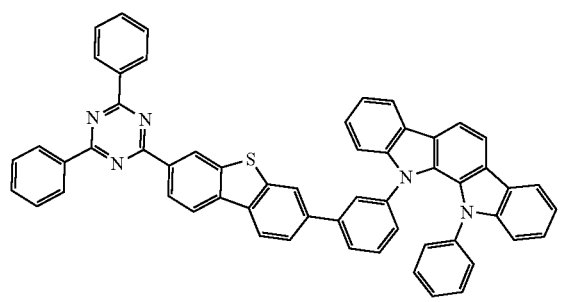
5-45
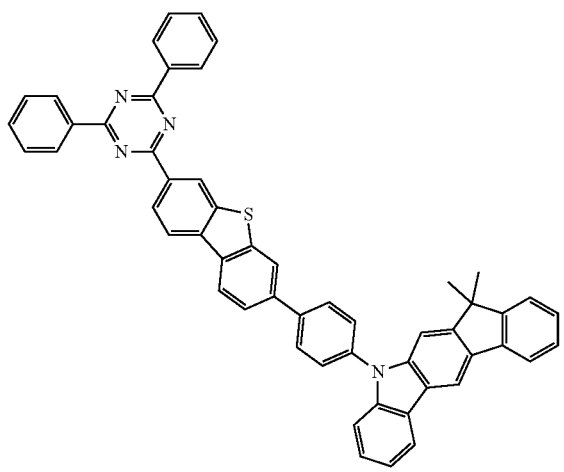

-continued
5-46
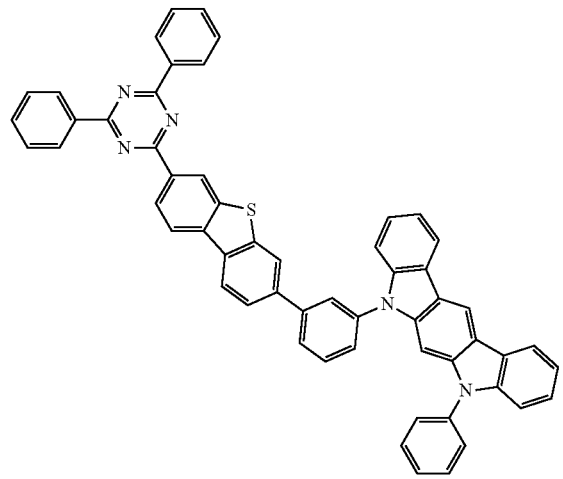
5-47
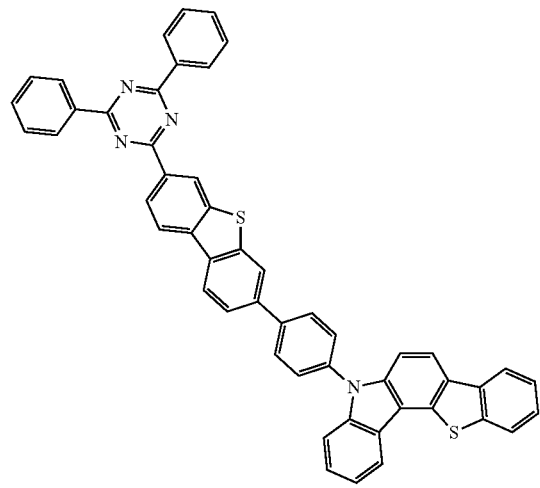
5-48
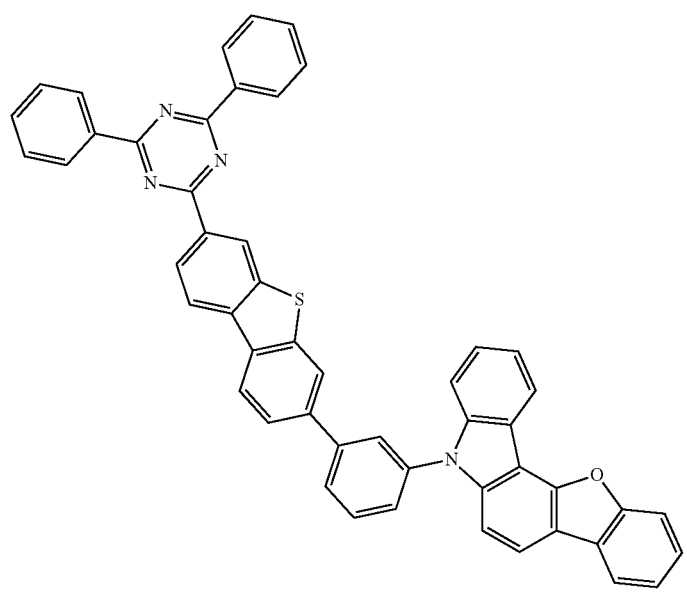
5-49
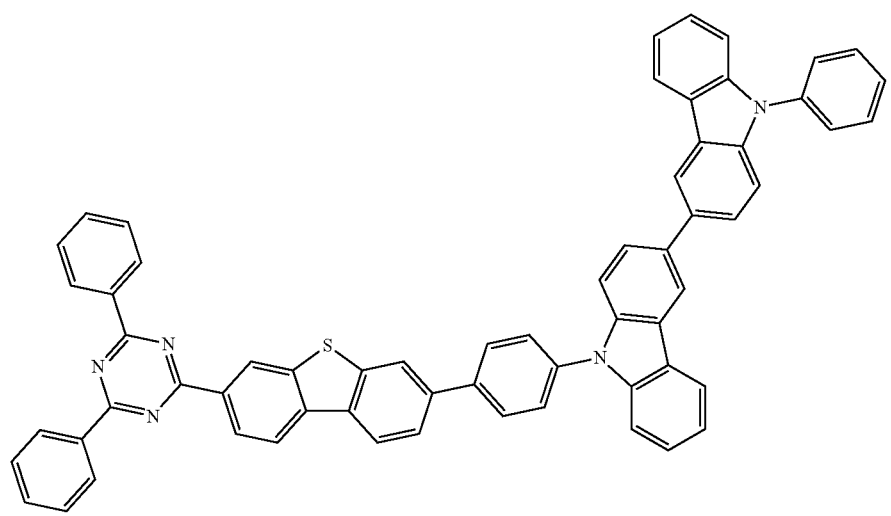

-continued
5-50
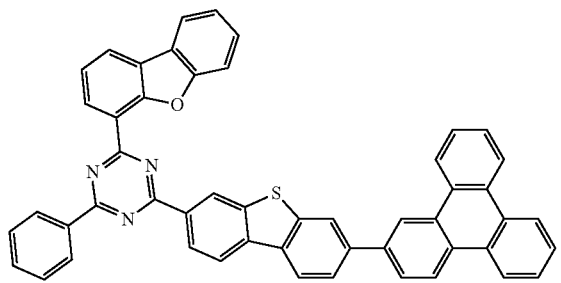
5-51
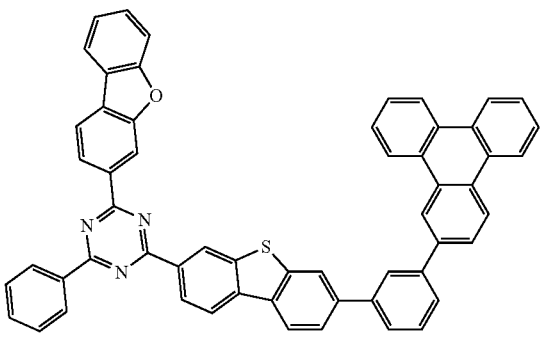
5-52
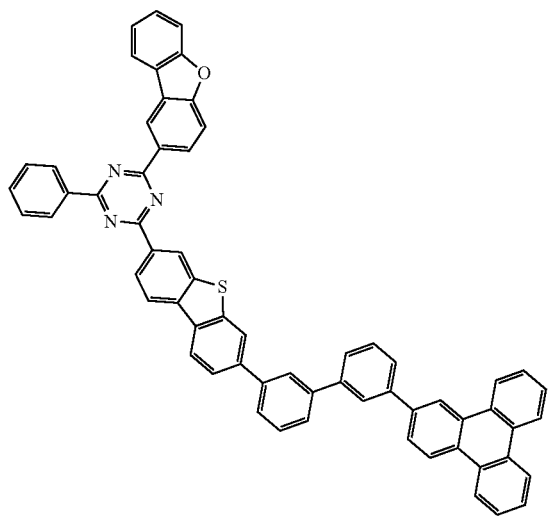
5-53
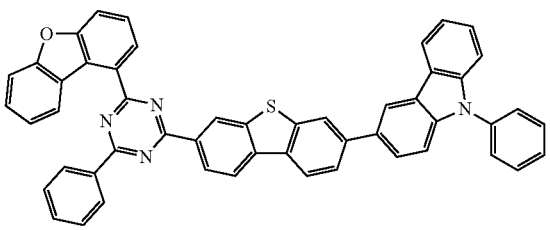
5-54
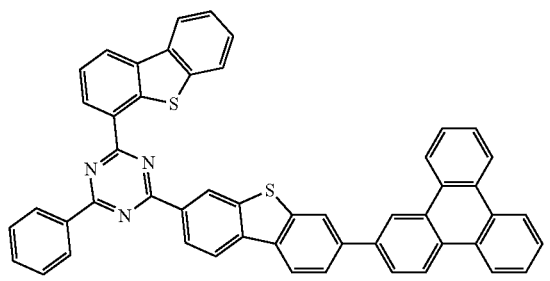
5-55
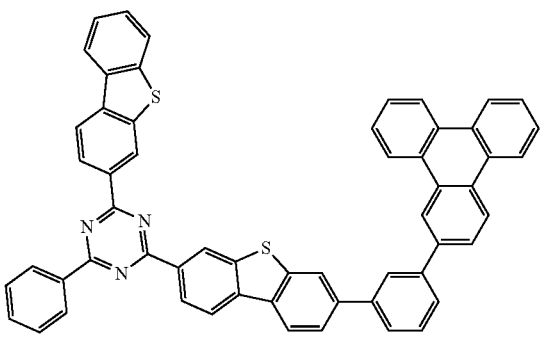
5-56
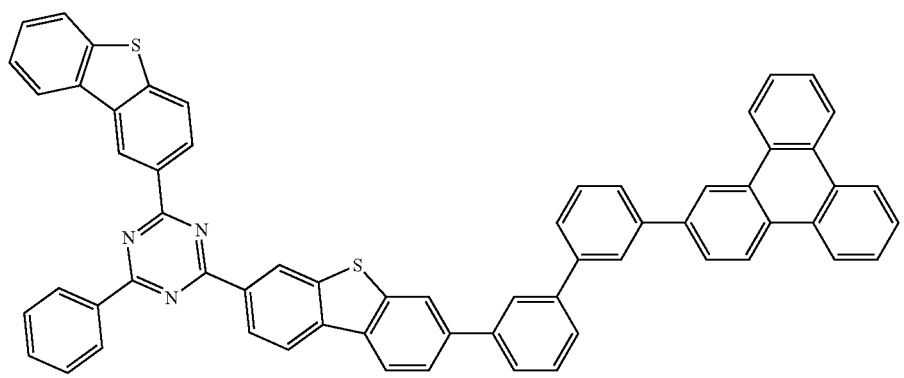

-continued
5-57
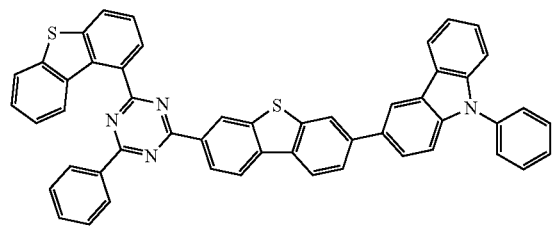
5-58
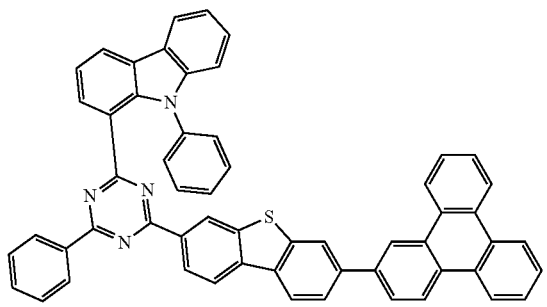
5-59
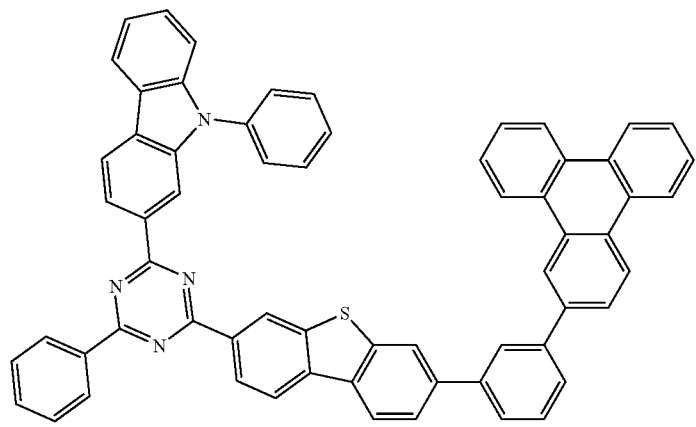
5-60
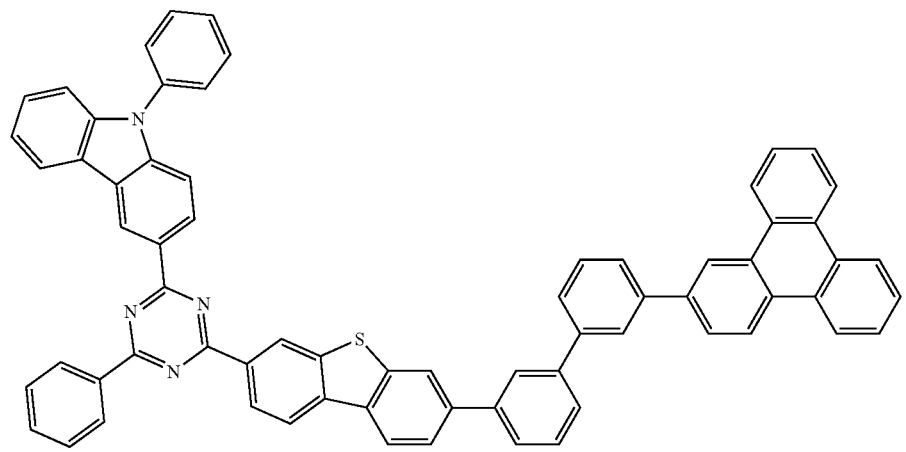
5-61
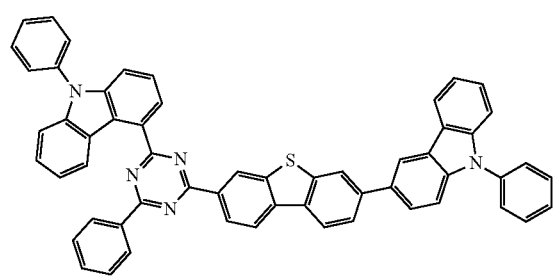
5-62
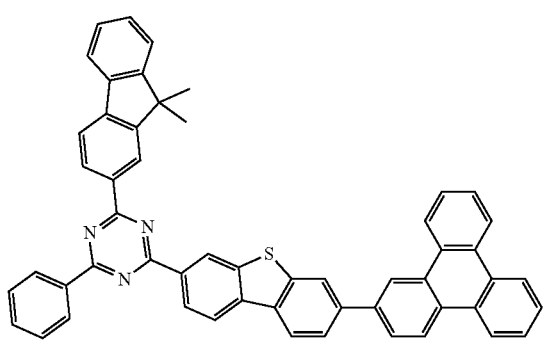

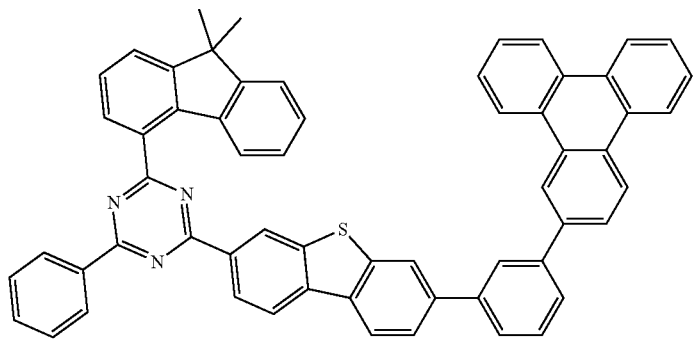
5-63
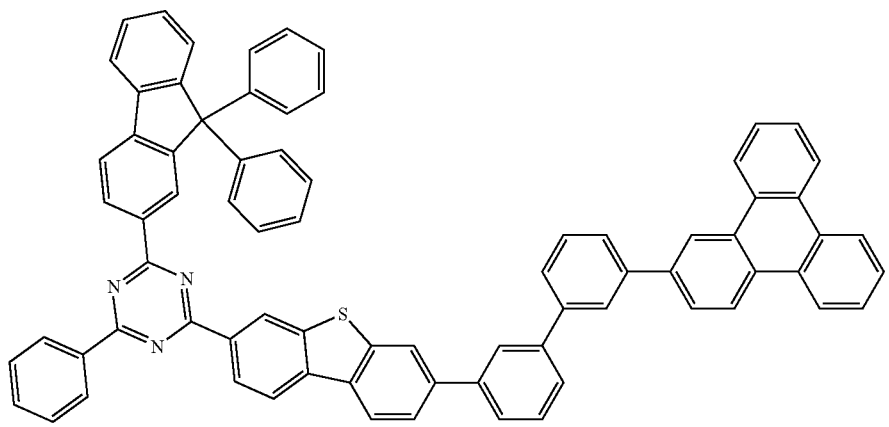
5-64
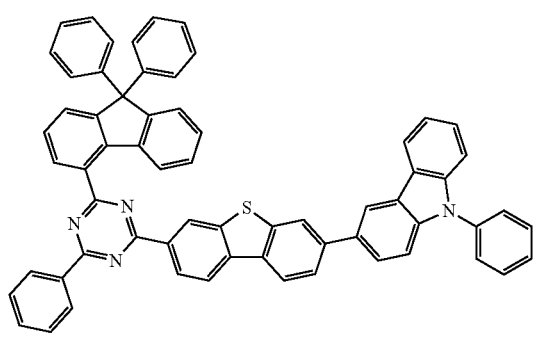
5-65
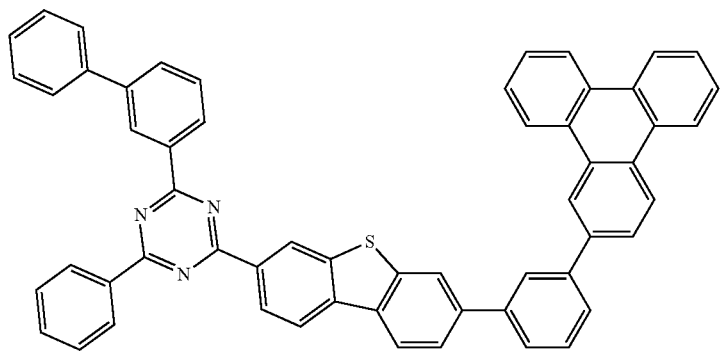
5-66
5-67

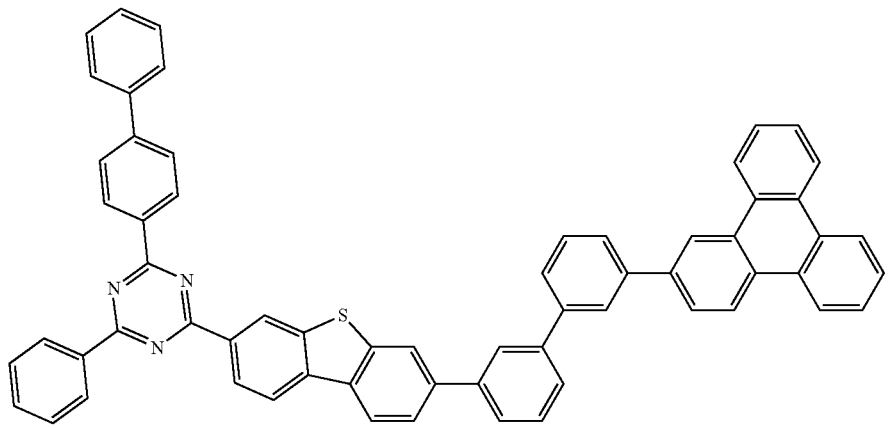
5-68
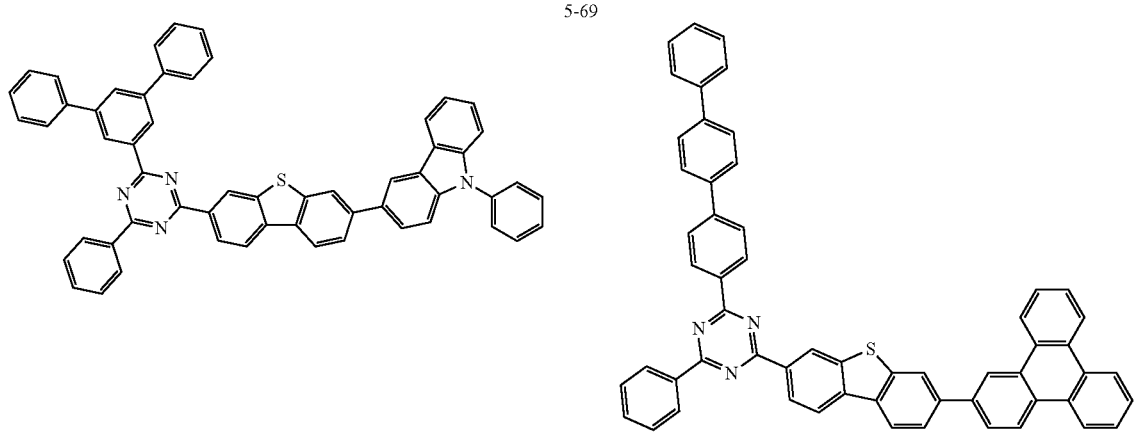
5-69
5-70
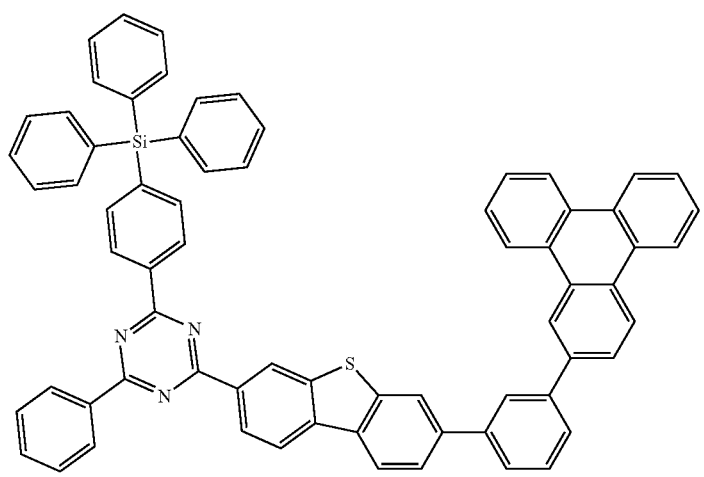
5-71

5-72
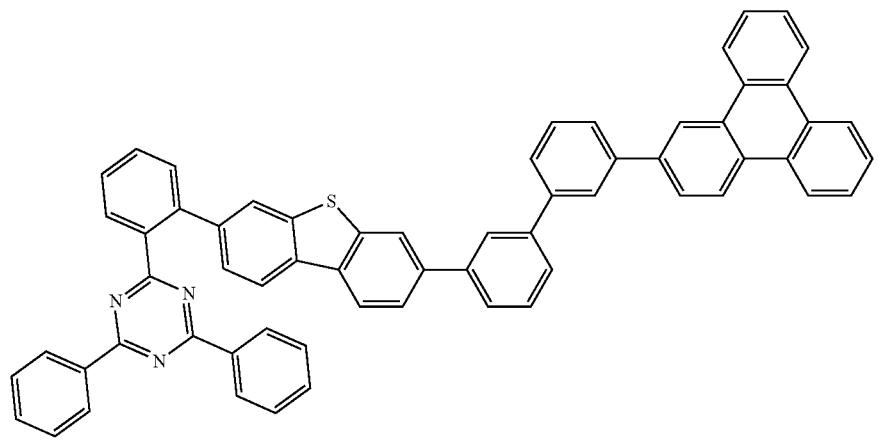
5-73
5-74
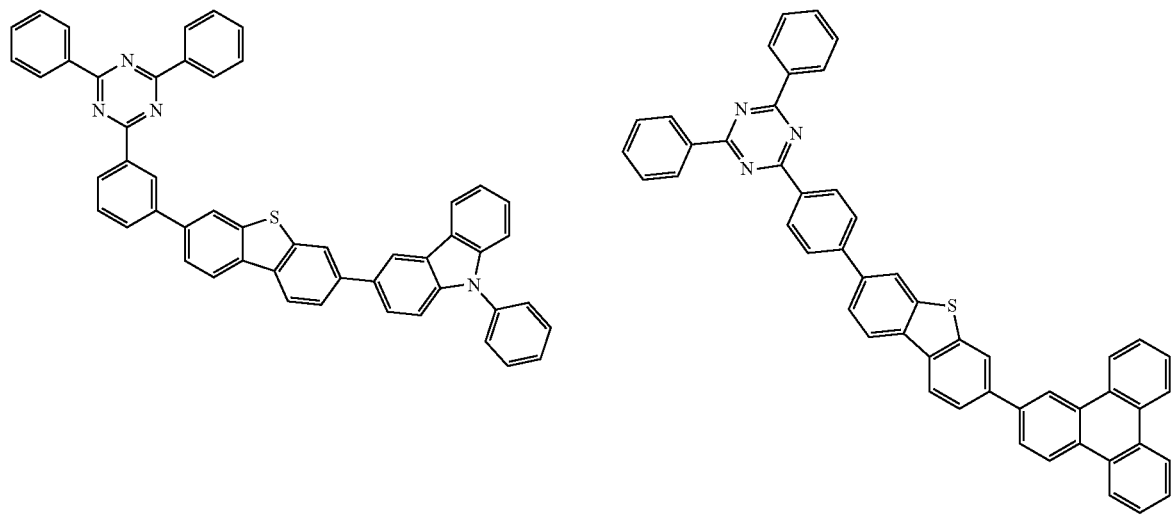
5-75
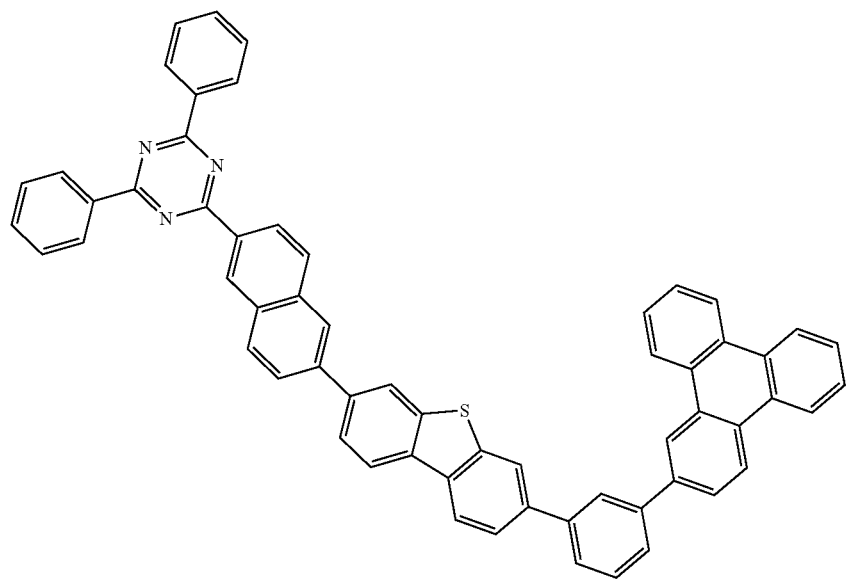

5-76
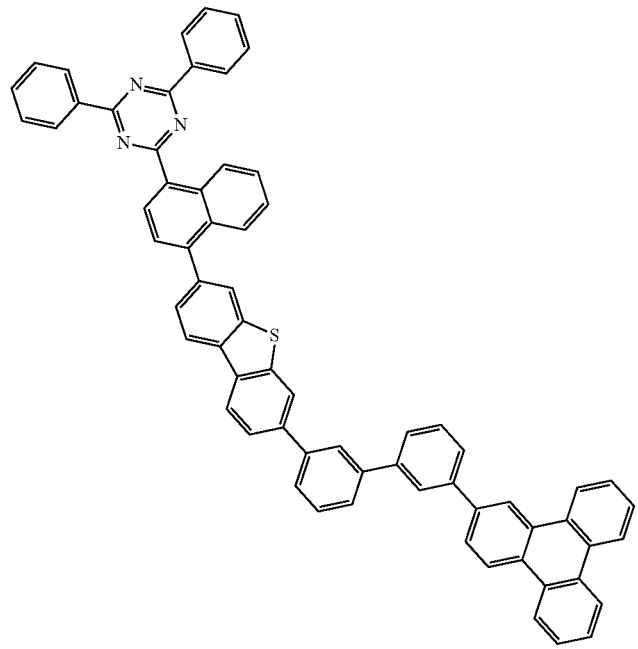
5-77
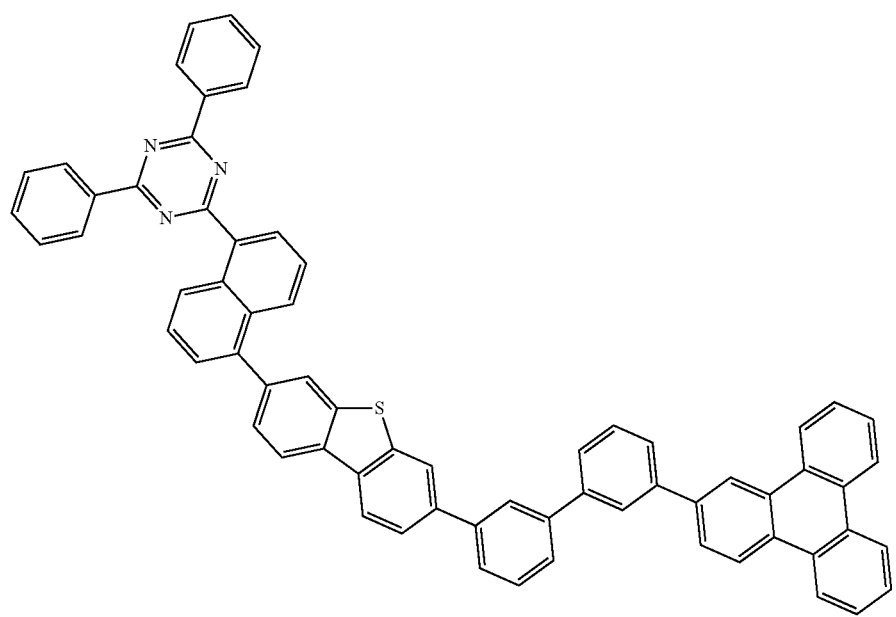
5-78
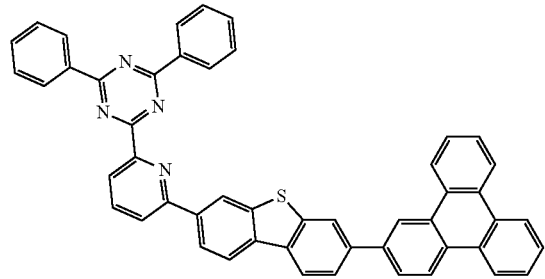
5-79
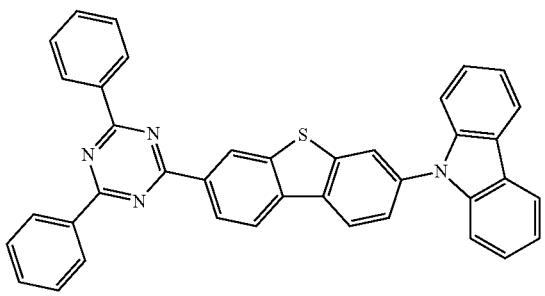

-continued
5-80
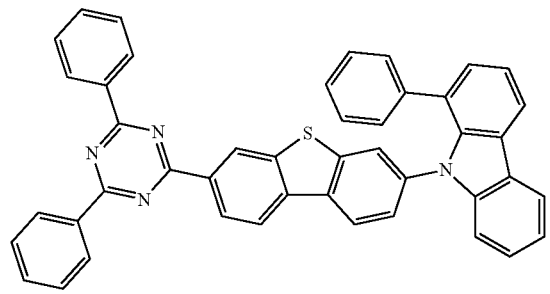
5-81
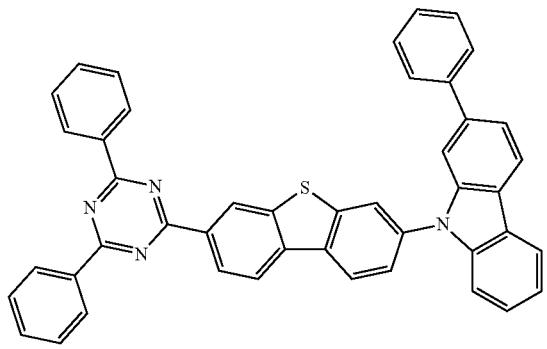
5-82
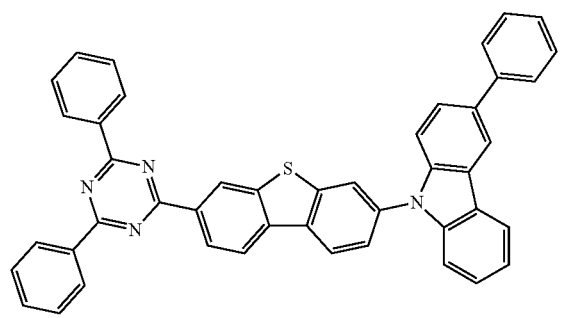
5-83
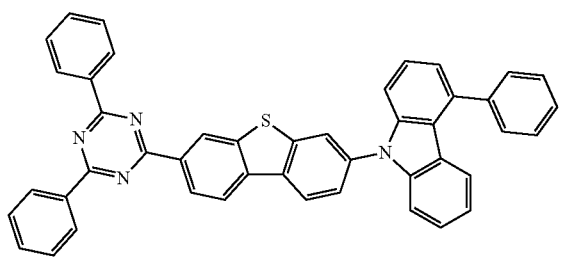
5-84
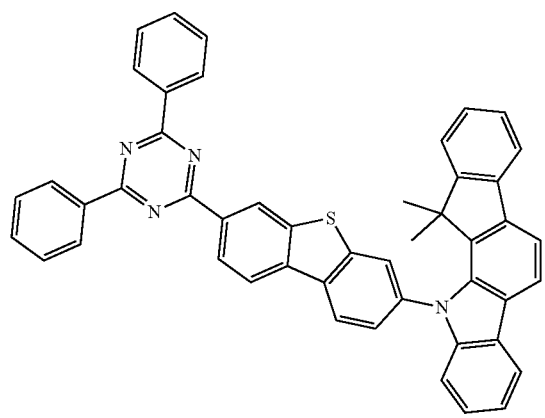
5-85
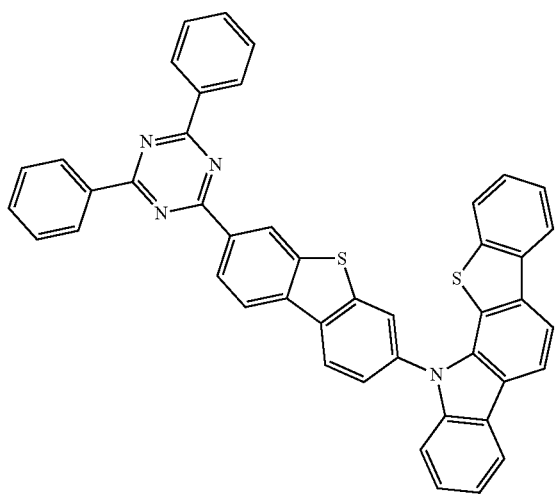

-continued
5-86
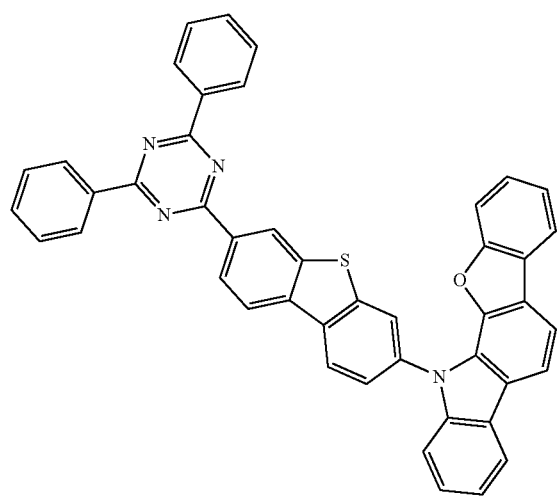
5-87
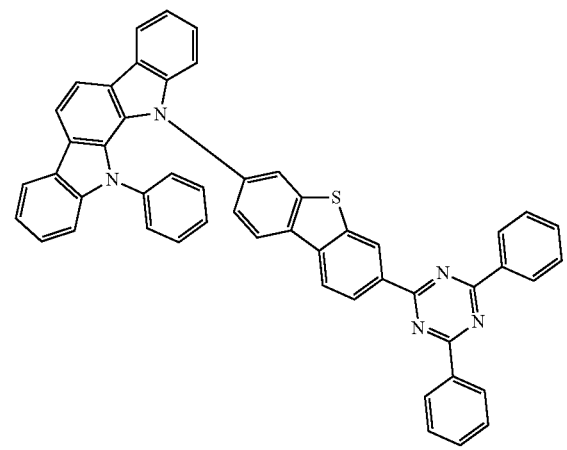
5-88
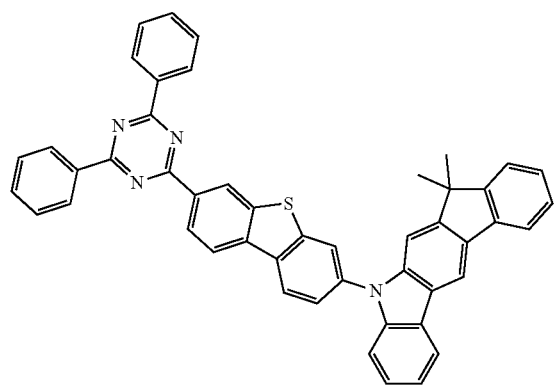
5-89
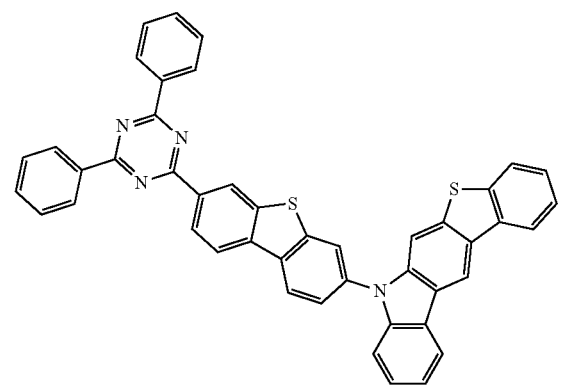
5-90
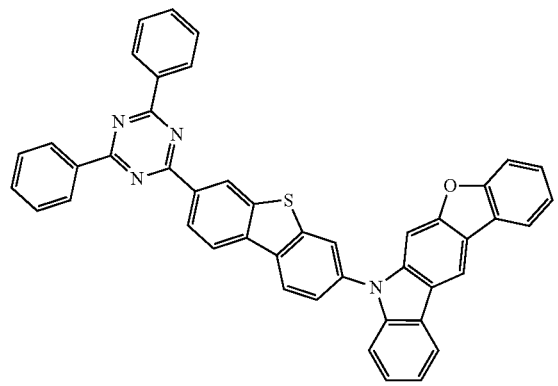
5-91
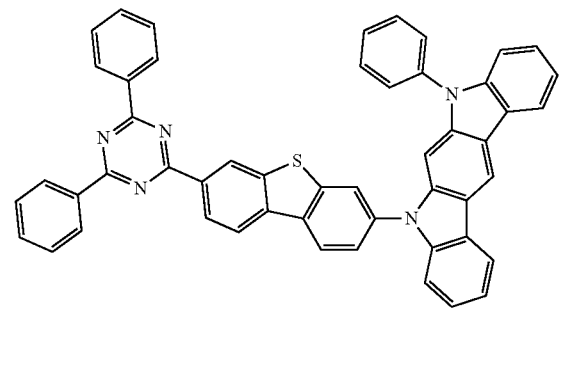

-continued
5-92
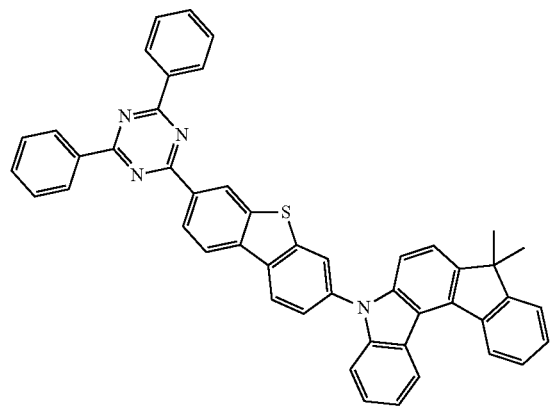
5-93
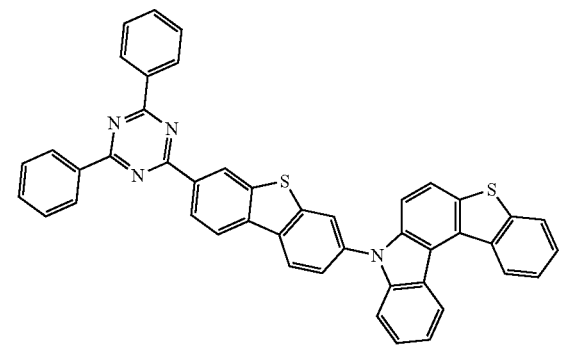
5-94
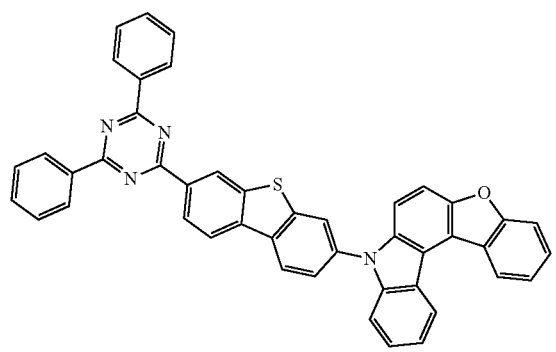
5-95
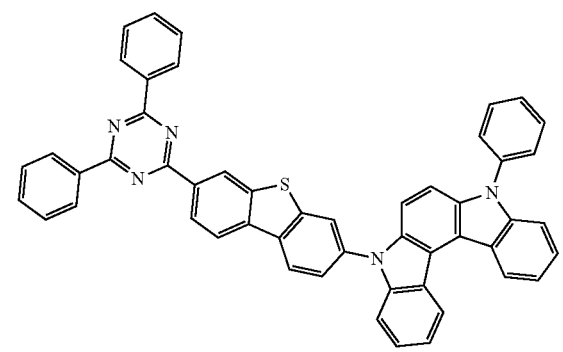
5-96
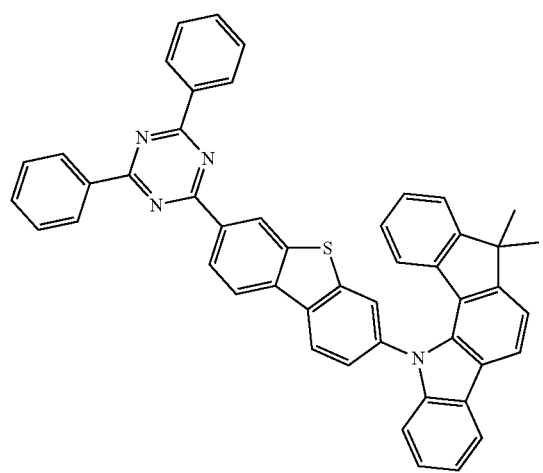
5-97
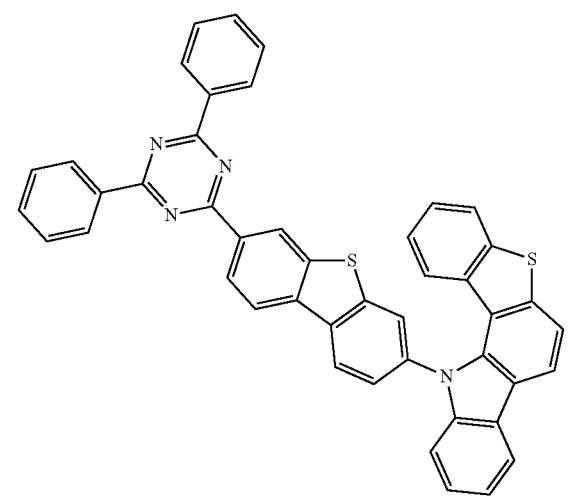

-continued
5-98
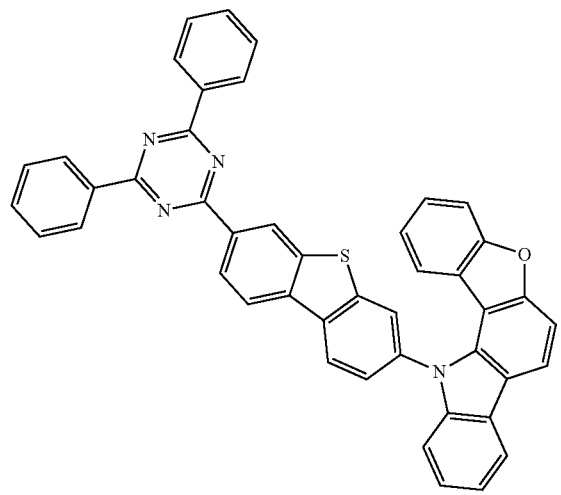
5-99
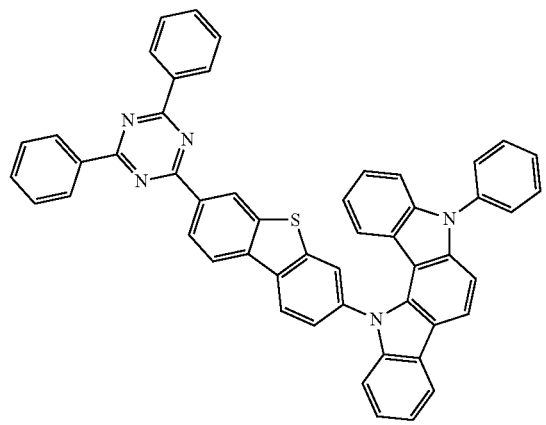
5-100
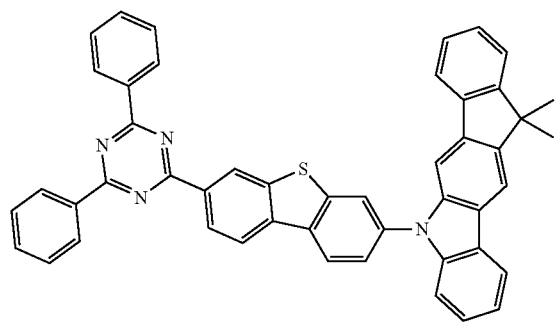
5-101
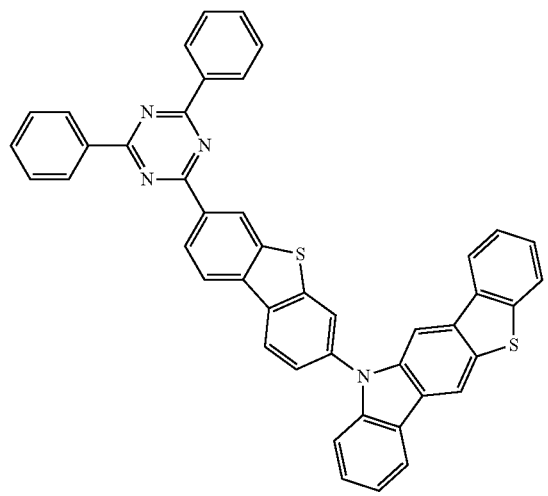
5-102
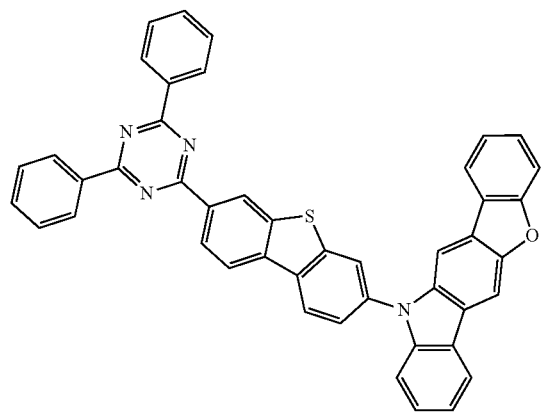
5-103
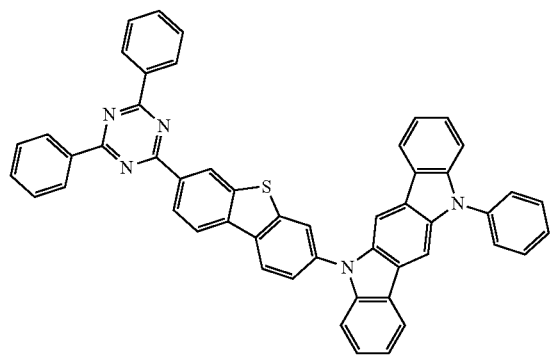

-continued
5-104
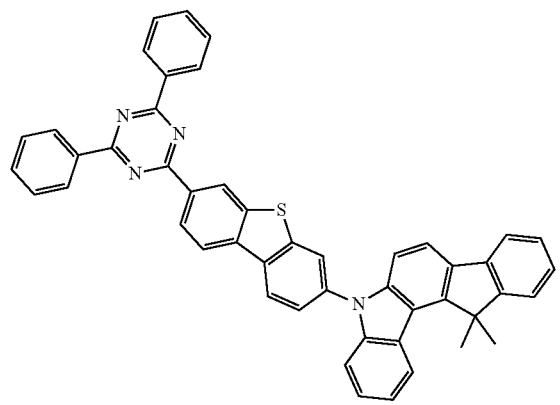
5-105
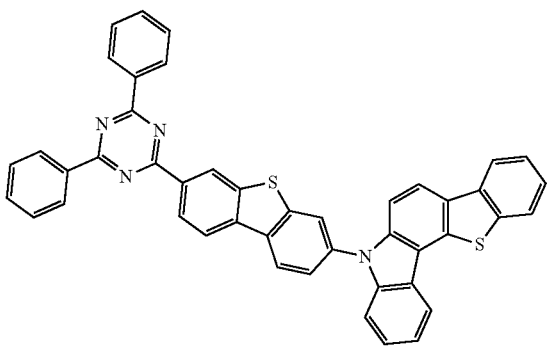
5-106
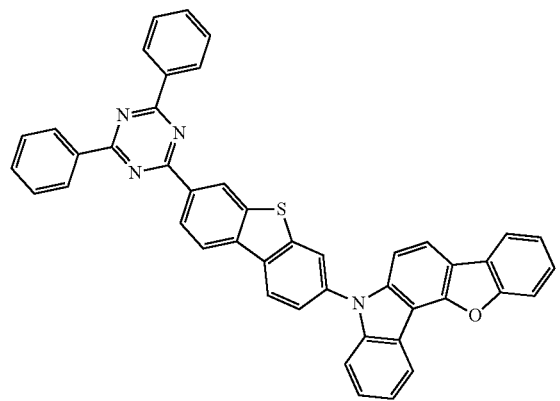
5-107
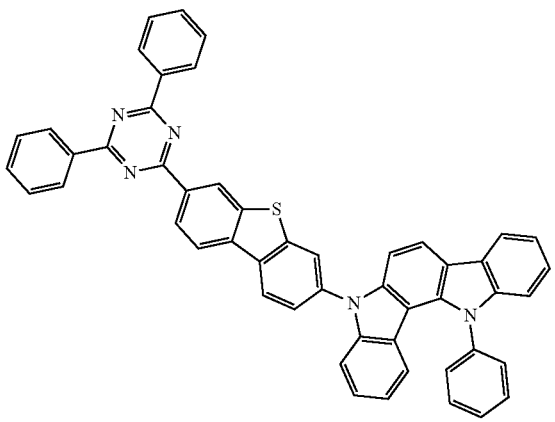
5-108
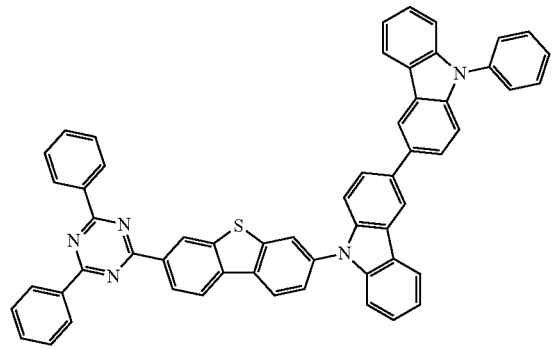
5-109
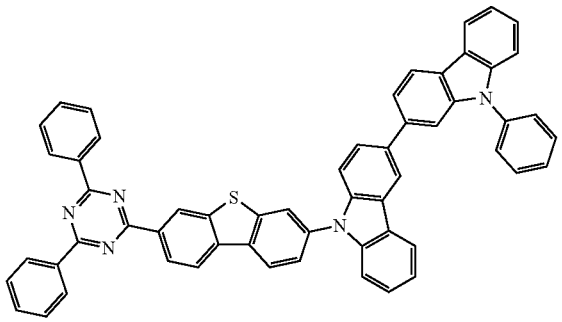

5-110
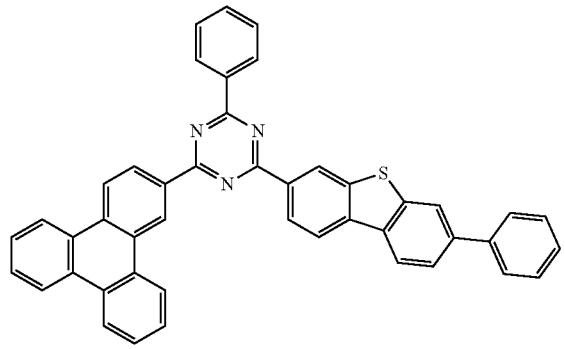
5-111
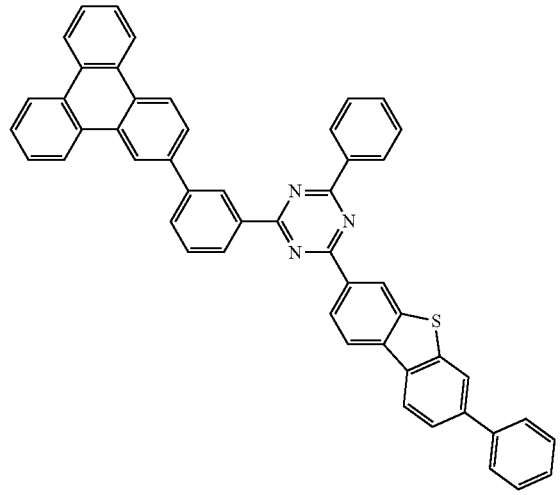
5-112
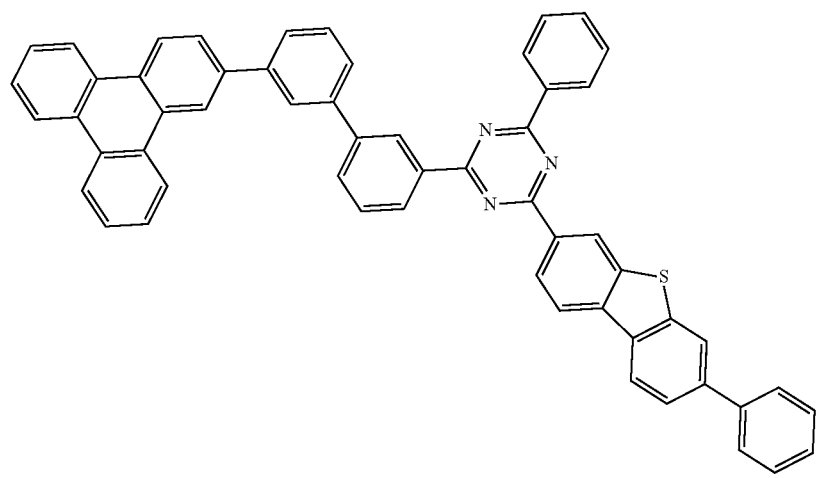
5-113
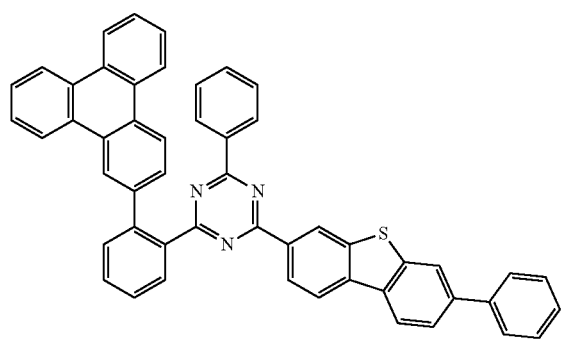
5-114
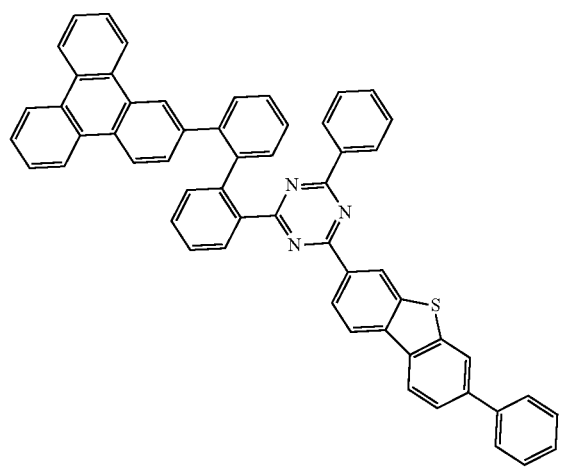

5-115

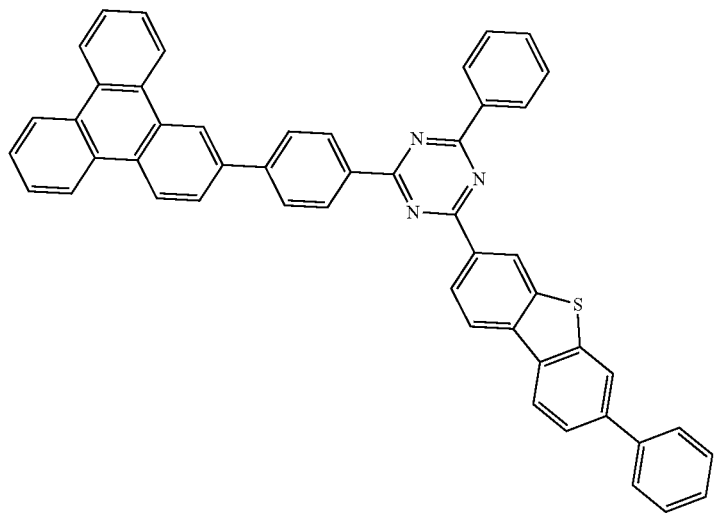

5-116

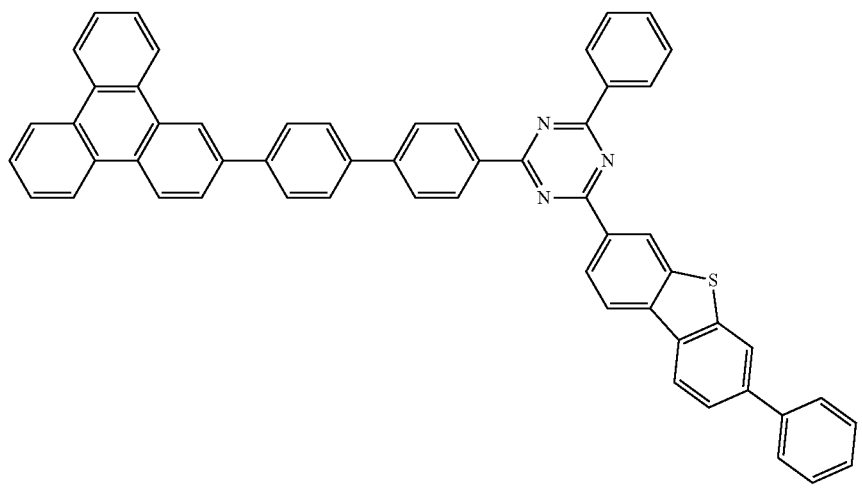

5-117

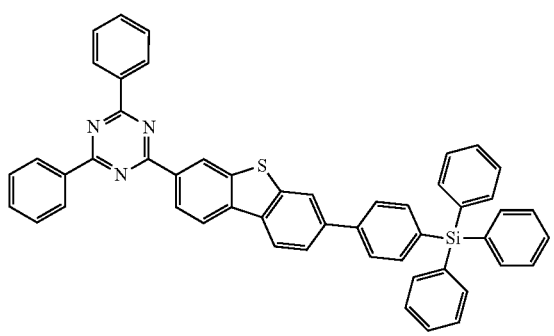

5-118

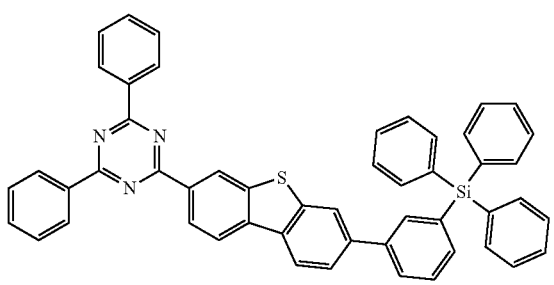

The compound of Chemical Formula 1 described above may be prepared based on preparation examples to describe later.

By introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound according to Chemical Formula 1.

In one embodiment of the present application, the first electrode may be an anode, and the second electrode may be a cathode.

In another embodiment, the first electrode may be a cathode, and the second electrode may be an anode.

In one embodiment of the present application, the organic light emitting device may be a blue organic light emitting device, and the heterocyclic compound according to Chemical Formula 1 may be used as a material of the blue organic light emitting device.

In one embodiment of the present application, the organic light emitting device may be a green organic light emitting device, and the heterocyclic compound according to Chemical Formula 1 may be used as a material of the green organic light emitting device.

In one embodiment of the present application, the organic light emitting device may be a red organic light emitting device, and the heterocyclic compound according to Chemical Formula 1 may be used as a material of the red organic light emitting device.

Specific descriptions on the heterocyclic compound represented by Chemical Formula 1 are the same as the descriptions provided above.

The organic light emitting device according to one embodiment of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device according to one embodiment of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise less numbers of organic material layers.

In the organic light emitting device according to one embodiment of the present disclosure, the organic material layer may comprise a light emitting layer, and the light emitting layer may comprise the heterocyclic compound.

In another organic light emitting device, the organic material layer comprises a light emitting layer, the light emitting layer comprises a host material, and the host material may comprise the heterocyclic compound.

As another embodiment, the organic material layer comprising the heterocyclic compound comprises the heterocyclic compound represented by Chemical Formula 1 as a host, and may be used together with an iridium-based dopant.

In the organic light emitting device according to one embodiment of the present disclosure, the organic material layer comprises an electron injection layer or an electron transfer layer, and the electron transfer layer or the electron injection layer may comprise the heterocyclic compound.

In another organic light emitting device, the organic material layer comprises an electron blocking layer or a hole blocking layer, and the electron blocking layer or the hole blocking layer may comprise the heterocyclic compound.

The organic light emitting device according to one embodiment of the present disclosure may further comprise one, two or more layers selected from the group consisting of a light emitting layer, a hole injection layer, a hole transfer layer, an electron injection layer, an electron transfer layer, an electron blocking layer and a hole blocking layer.

According to another embodiment, when the heterocyclic compound of Chemical Formula 1 is included in the light emitting layer, this light emitting layer may further comprise a compound of the following Chemical Formula 25.

[Chemical Formula 25]

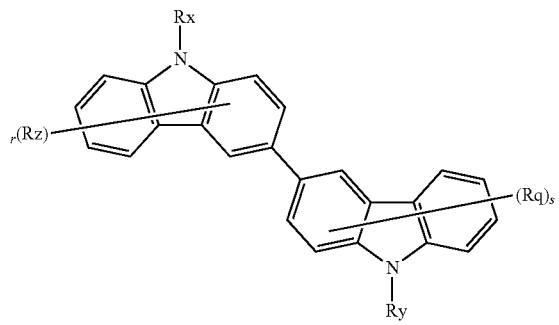

In Chemical Formula 25,

Rz and Rq are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring, R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, Rx and Ry are the same as or different from each other, and each independently a substituted or unsubstituted aryl group; or a substituted or unsubstituted heteroaryl group, and r and s are an integer of 0 to 7.

When comprising the compound of Chemical Formula 1 and the compound of Chemical Formula 25 at the same time in an organic material layer of an organic light emitting device, more superior efficiency and lifetime effects are obtained. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with lifetime enhancement.

In the organic light emitting device according to one embodiment of the present application, Rz and Rq of Chemical Formula 25 may be hydrogen.

In the organic light emitting device according to one embodiment of the present application, Rx and Ry of Chemical Formula 25 are the same as or different from each other, and may be each independently a substituted or unsubstituted aryl group.

In the organic light emitting device according to another embodiment of the present application, Rx and Ry of Chemical Formula 25 are the same as or different from each other, and may be each independently a substituted or unsubstituted C6 to C60 aryl group.

In the organic light emitting device according to another embodiment of the present application, Rx and Ry of Chemical Formula 25 are the same as or different from each other, and may be each independently a substituted or unsubstituted C6 to C40 aryl group.

In the organic light emitting device according to another embodiment of the present application, Rx and Ry of Chemical Formula 25 are the same as or different from each other, and may be each independently a C6 to C40 aryl group unsubstituted or substituted with one or more substituents selected from the group consisting of a C1 to C40 alkyl group, a C6 to C40 aryl group, —CN and —SiRR'R".

In the organic light emitting device according to another embodiment of the present application, Rx and Ry of Chemical Formula 25 are the same as or different from each other, and may be each independently a phenyl group unsubstituted or substituted with a phenyl group, —CN or —SiRR'R"; a biphenyl group unsubstituted or substituted with a phenyl group; a naphthyl group; a fluorene group unsubstituted or substituted with a methyl group or a phenyl group; a spirobifluorene group; or a triphenylene group.

In the organic light emitting device according to one embodiment of the present application, R, R' and R" of Chemical Formula 25 may be a phenyl group.

In the organic light emitting device according to one embodiment of the present application, Chemical Formula 25 may be represented by any one of the following heterocyclic compounds.

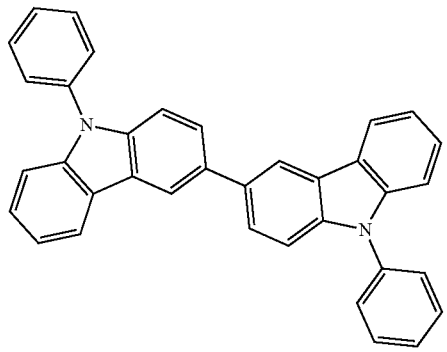

3-1

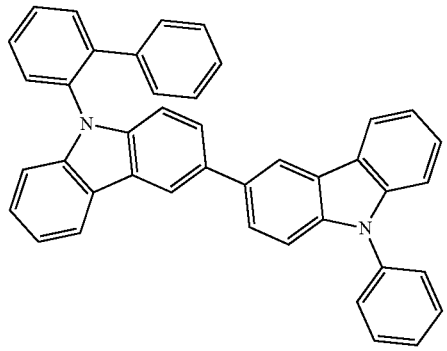

3-2

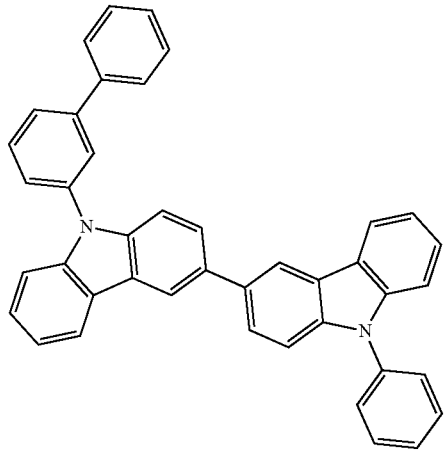

3-3

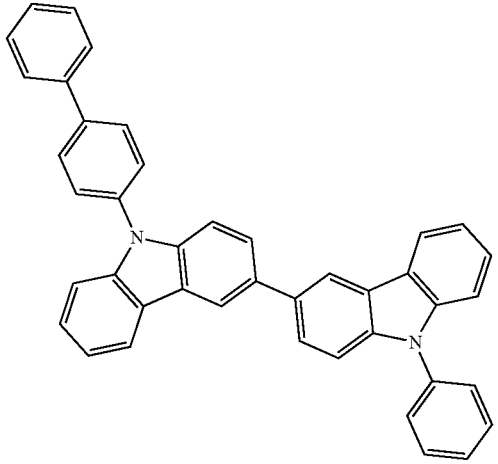

3-4

-continued
3-5
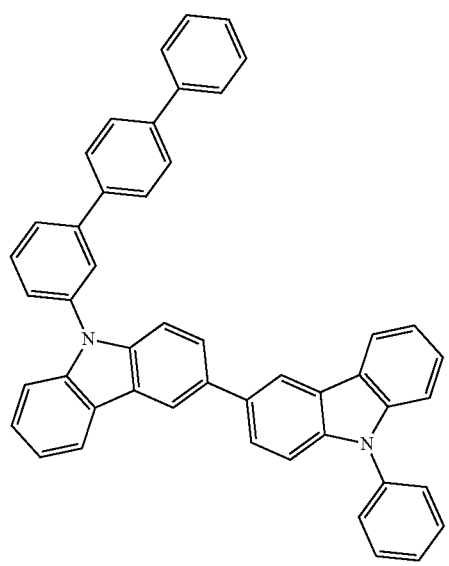
3-6
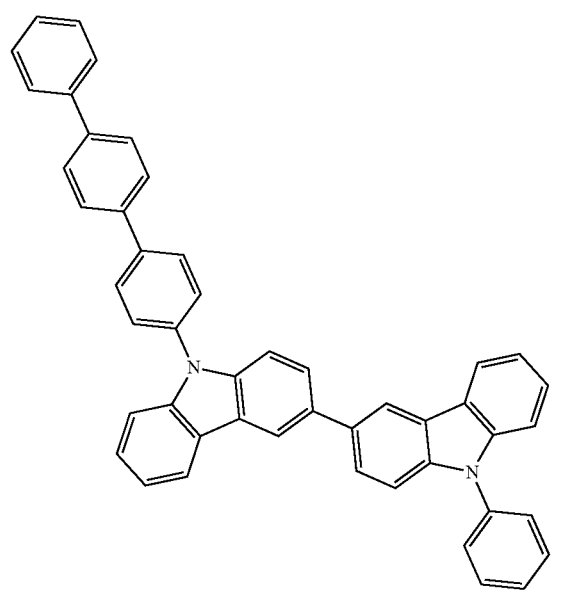
3-7
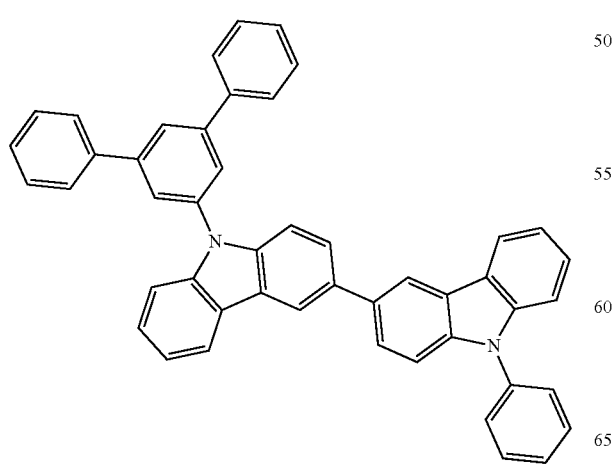
-continued
3-8
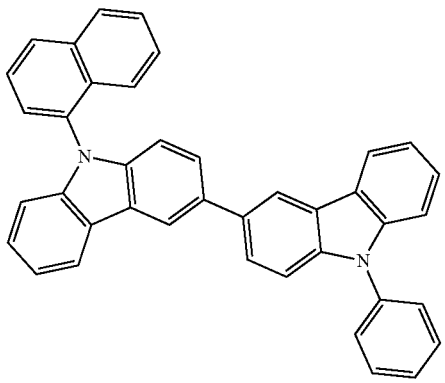
3-9
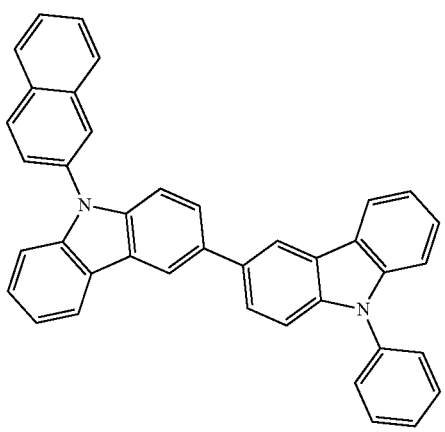
3-10
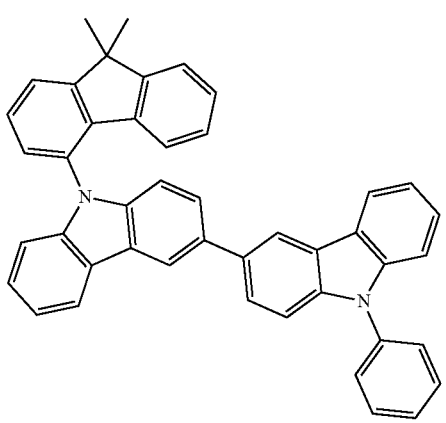

3-11
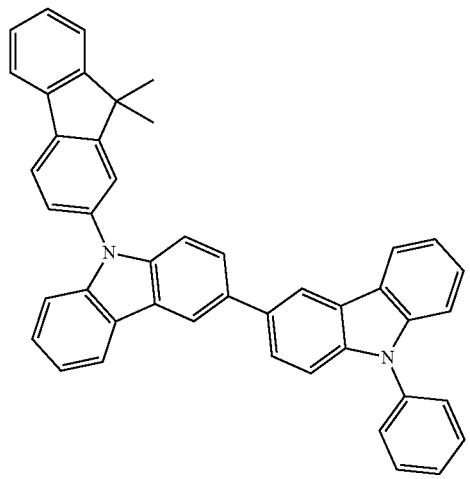
3-12
3-13
3-14
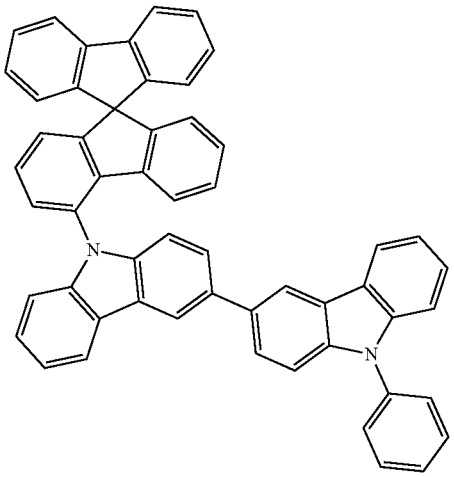
3-15
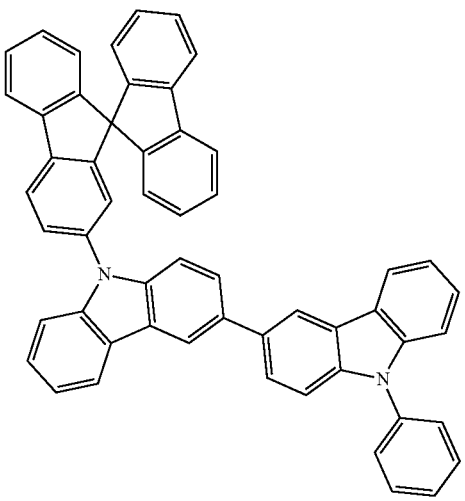
3-16
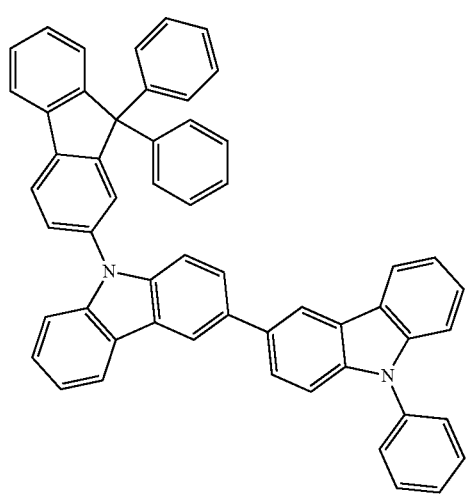
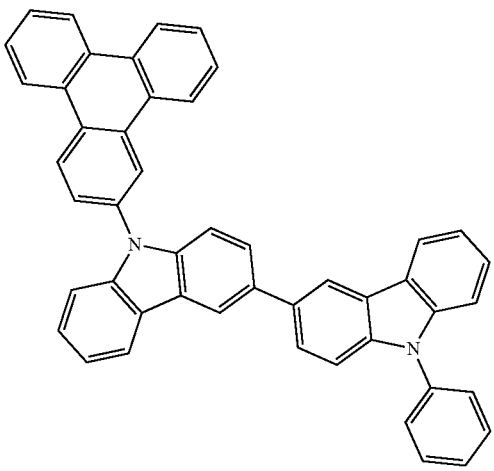

3-17
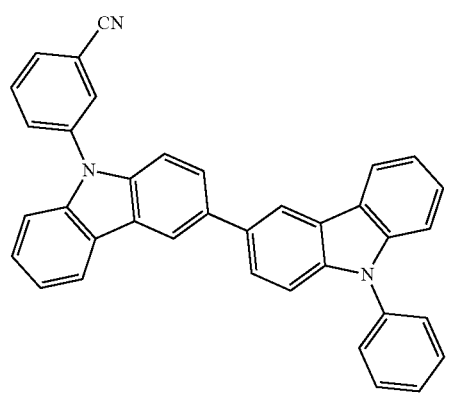
3-18
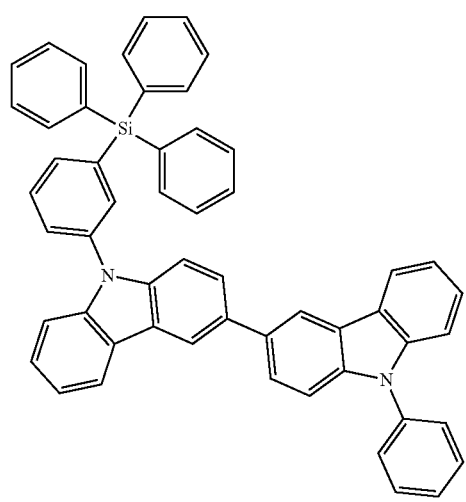
3-19
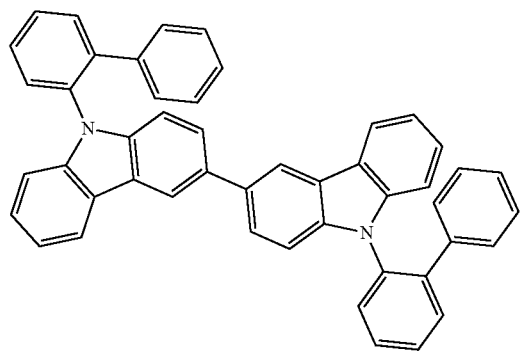
3-20
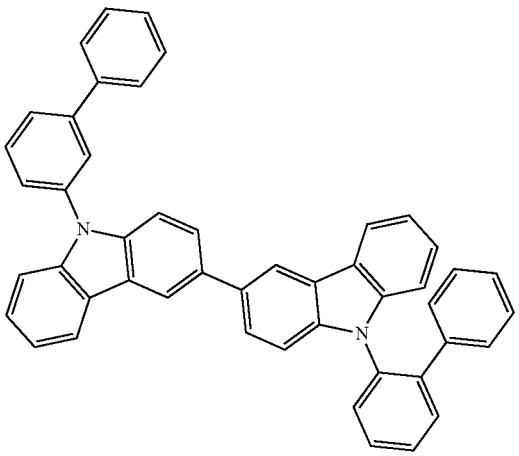
3-21
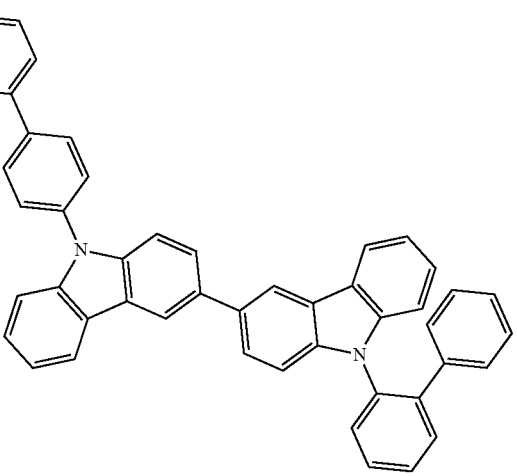
3-22
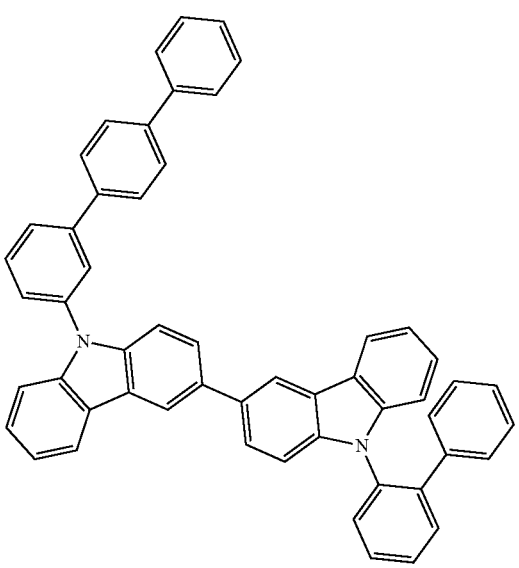

3-23
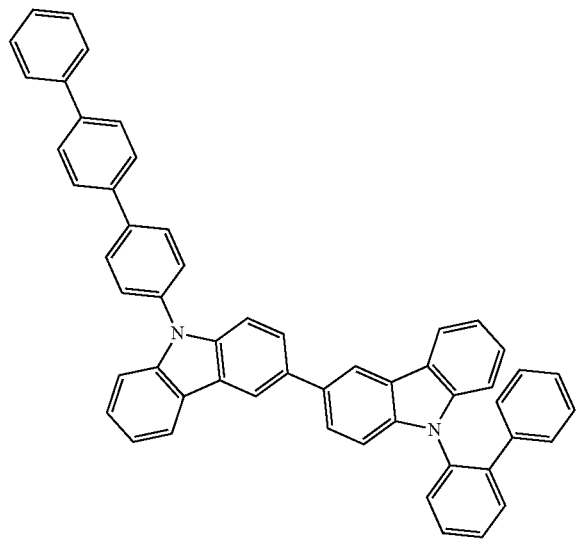
3-24
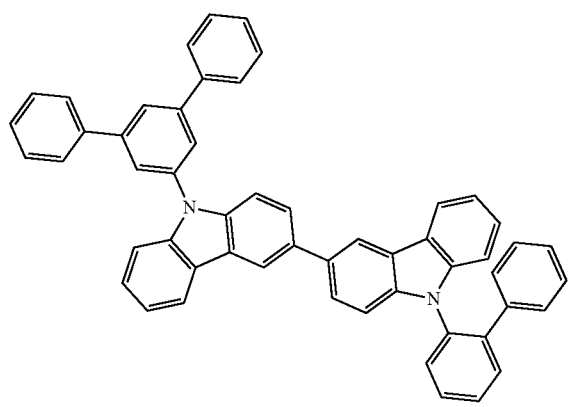
3-25
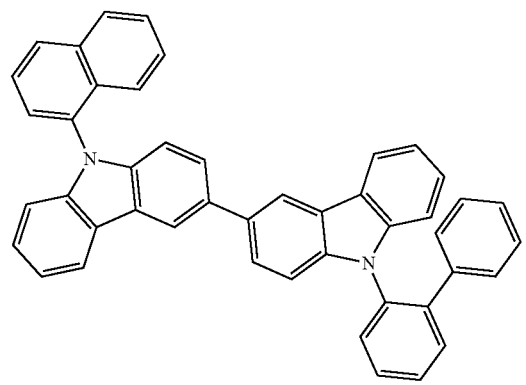
3-26
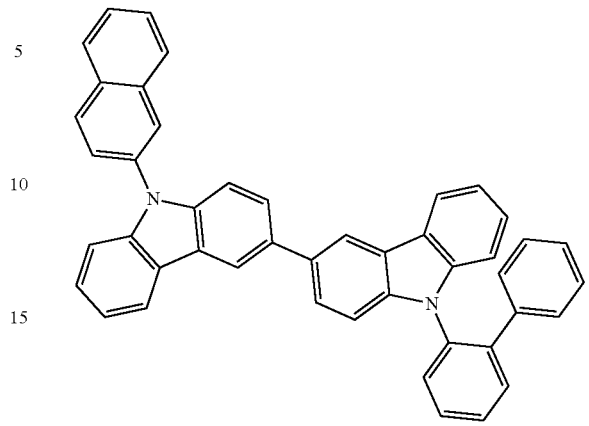
3-27
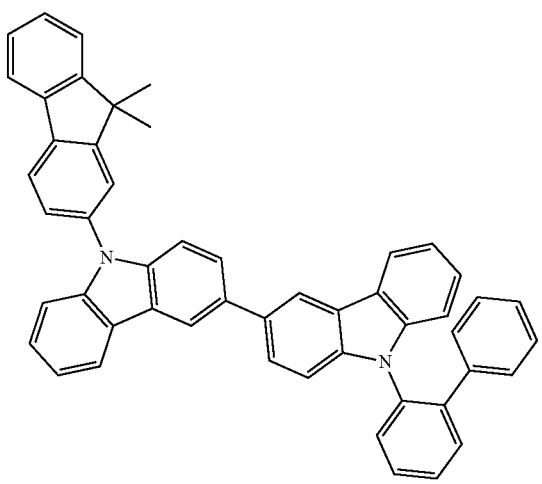
3-28
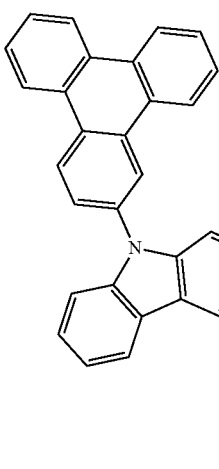

3-29
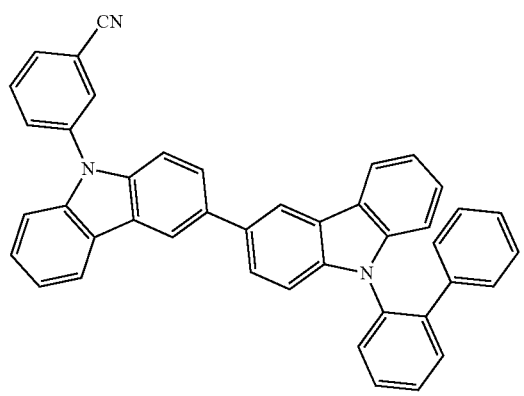
3-32
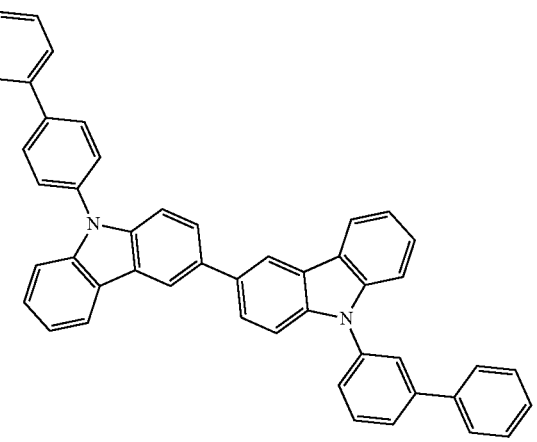
3-30
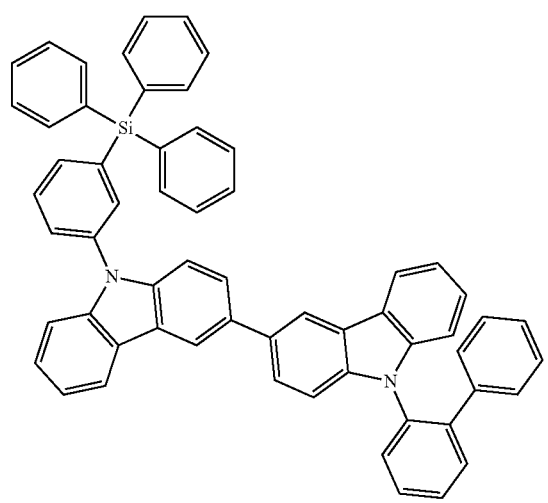
3-33
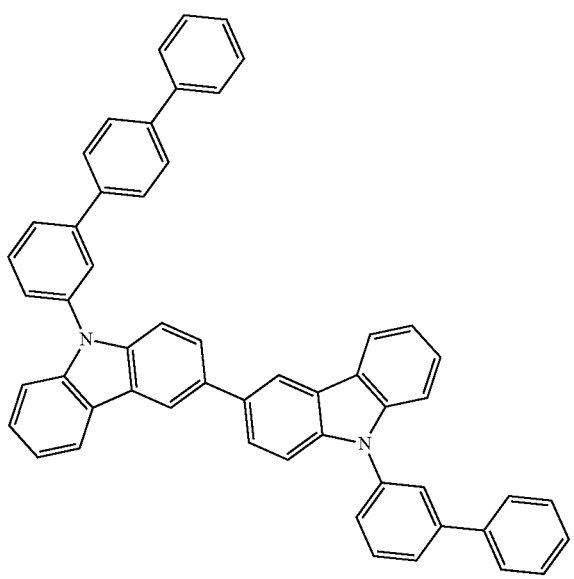
3-31
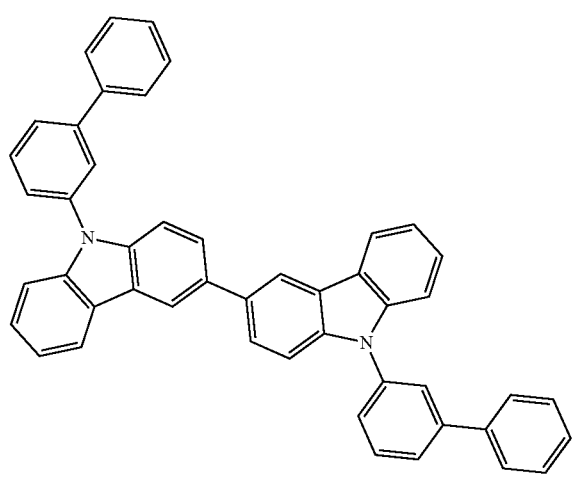
3-34
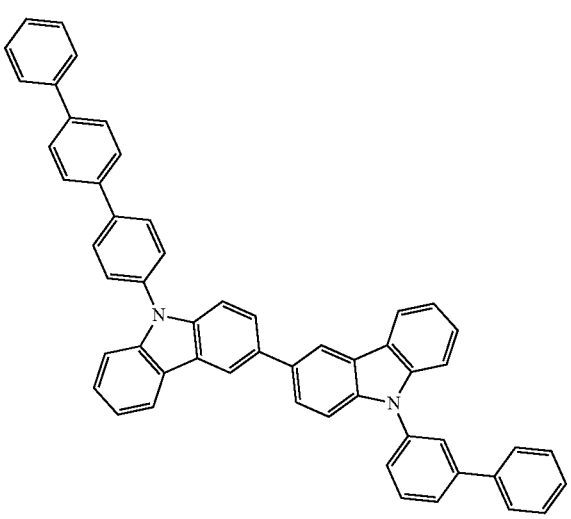

3-35
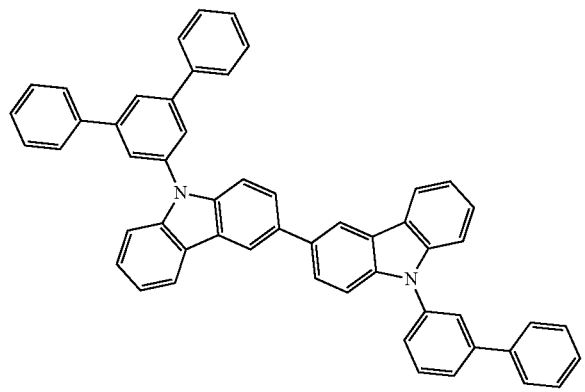
3-36
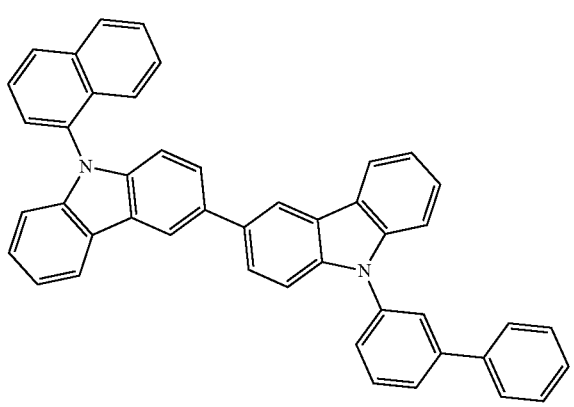
3-37
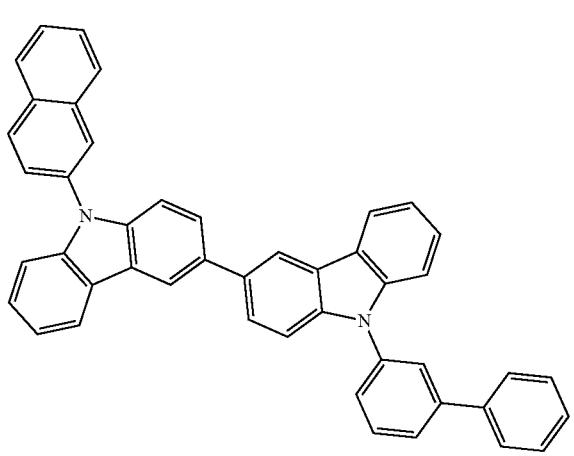
3-38
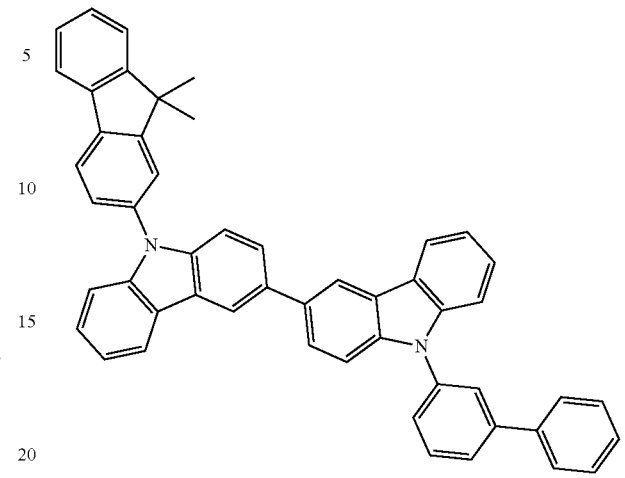
3-39
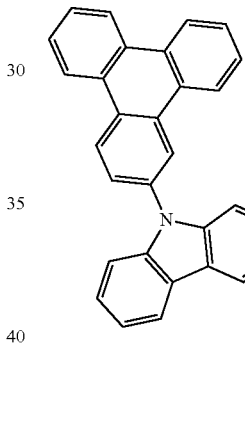
3-40
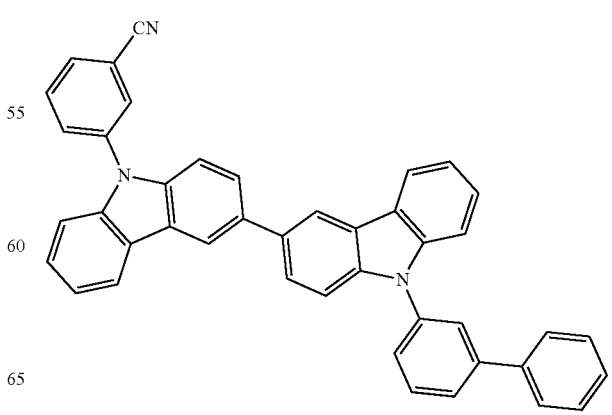

3-41
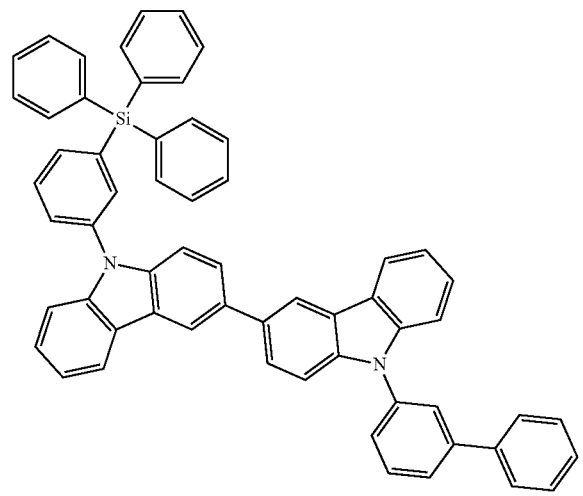
3-42
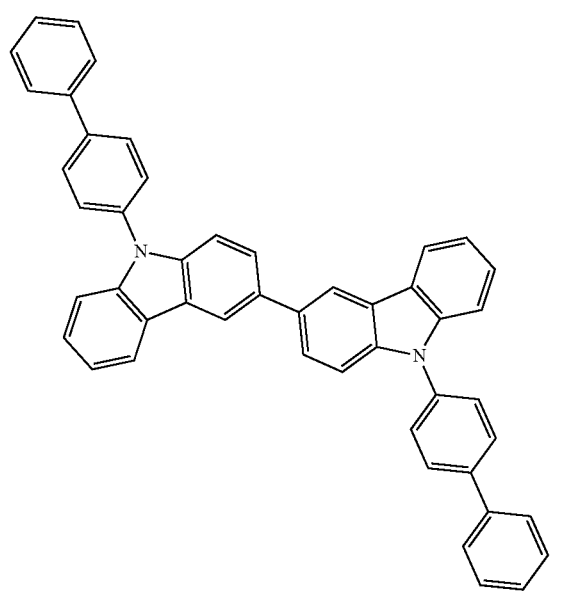
3-43
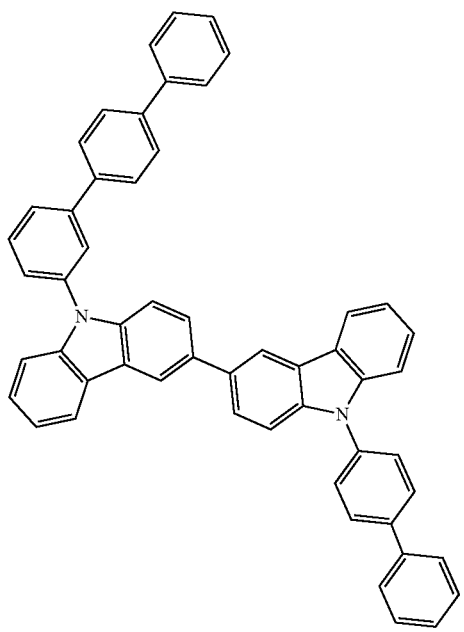
3-44
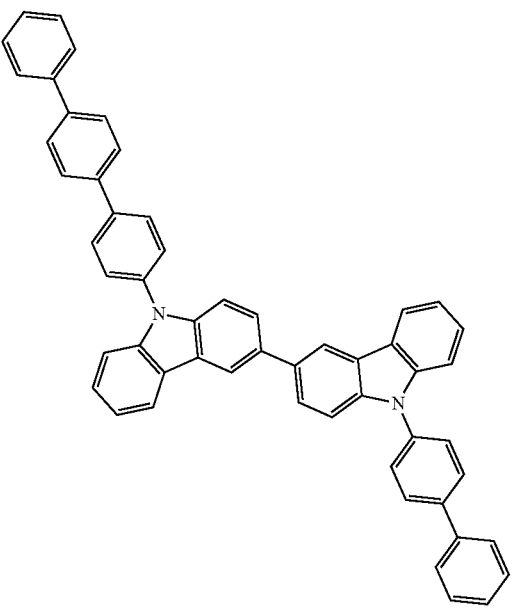

3-45
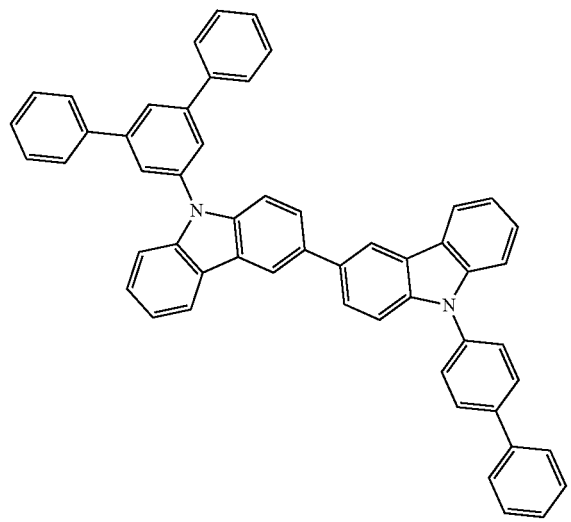
3-46
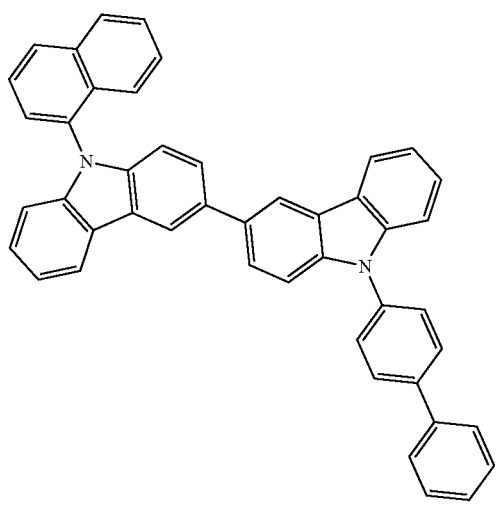
3-47
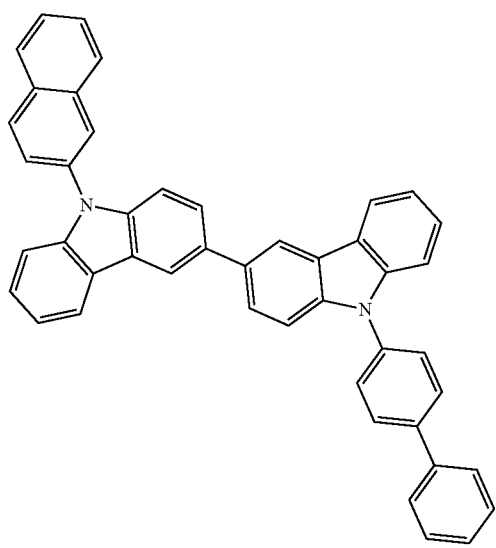
3-48
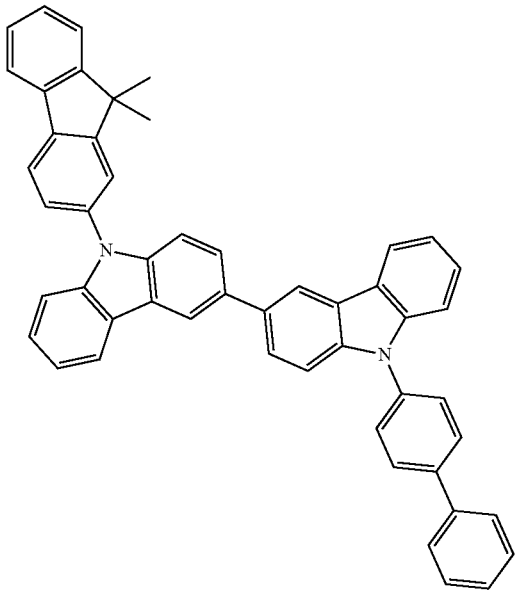
3-49
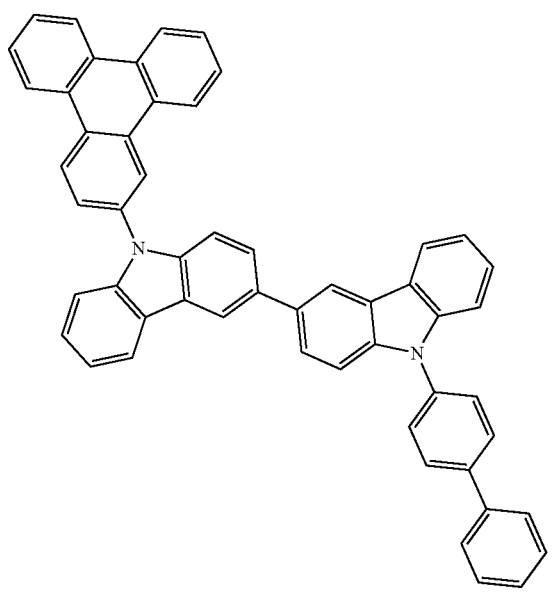

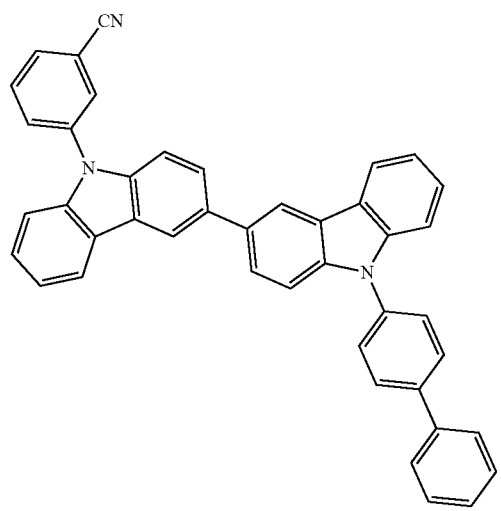
3-50
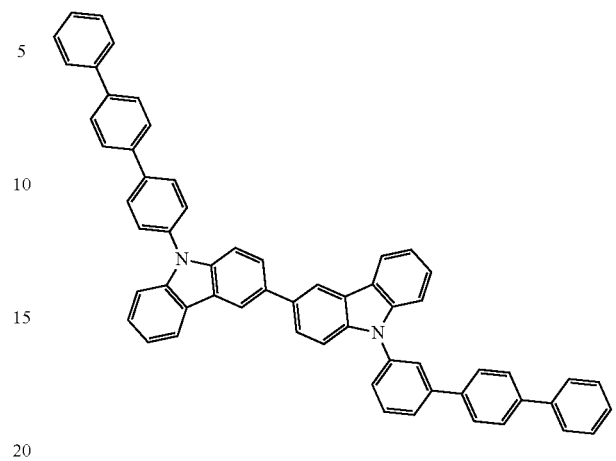
3-53
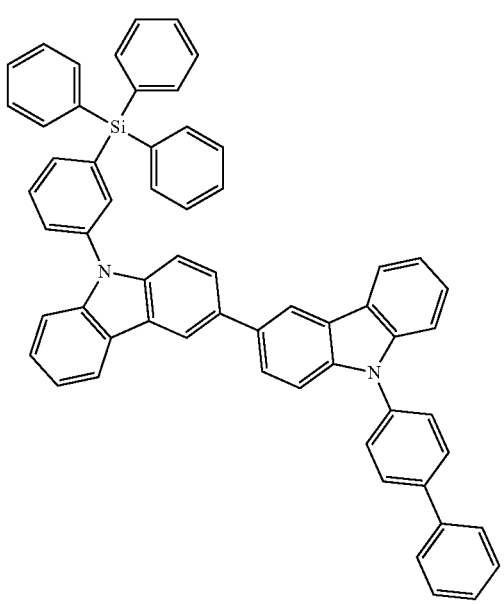
3-51
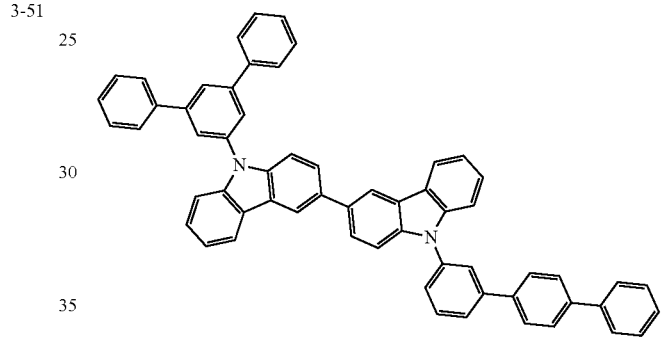
3-54
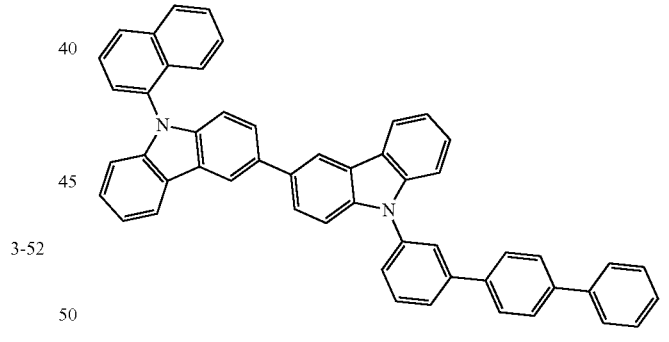
3-55
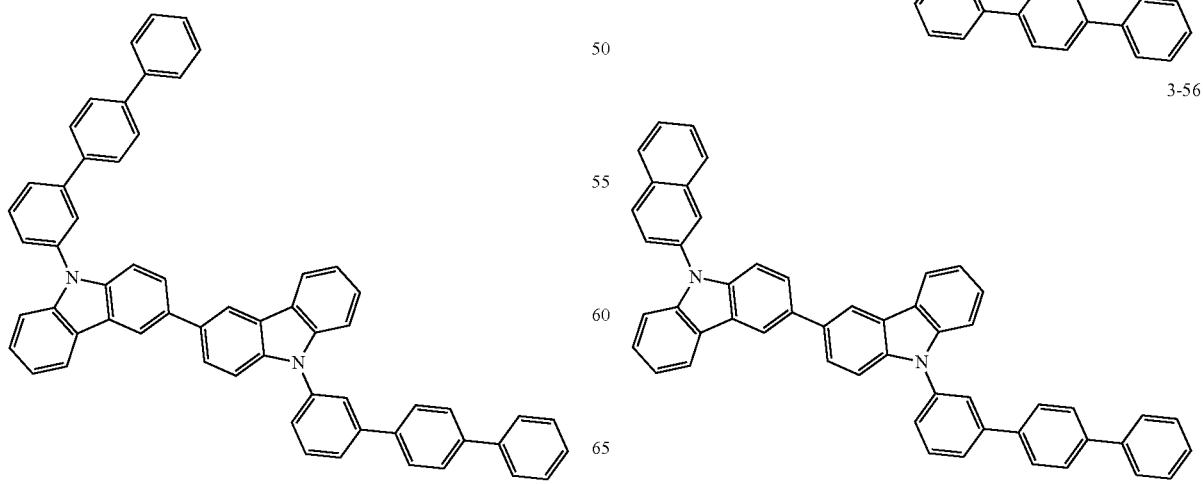
3-52
3-56

-continued
3-57
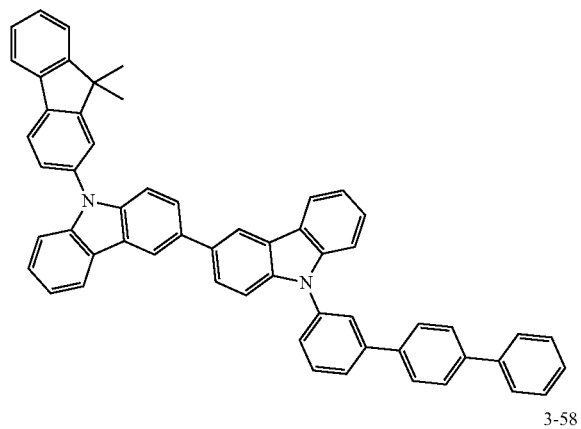
3-58
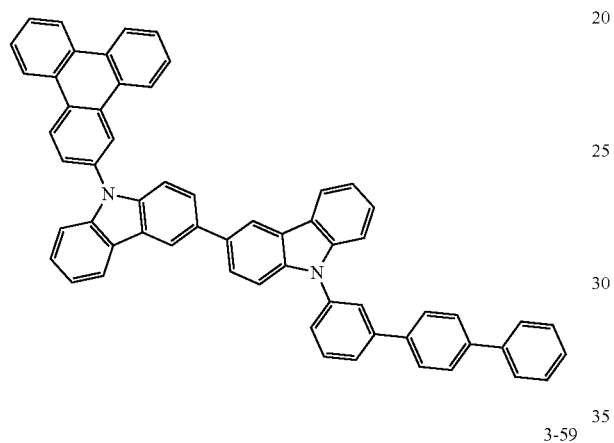
3-59
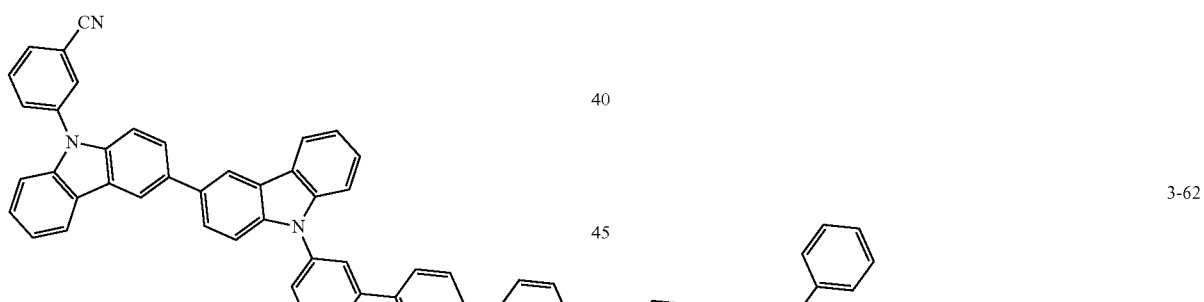
3-60
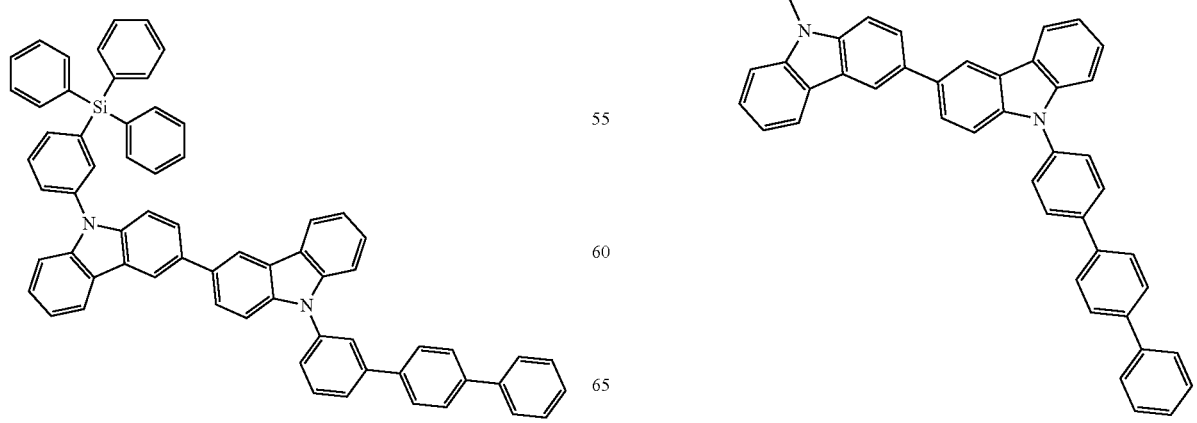
-continued
3-61
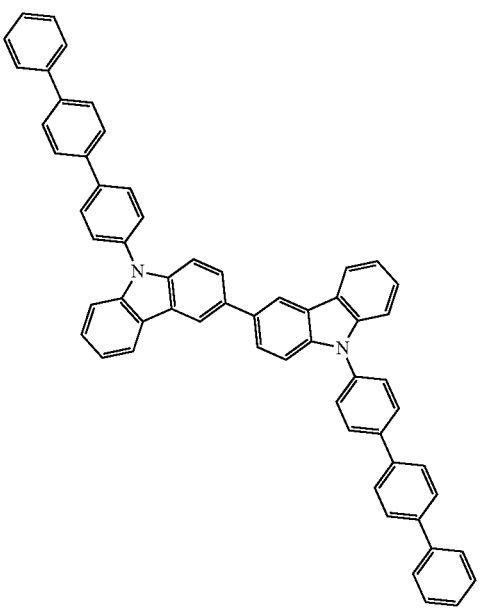
3-62

3-63
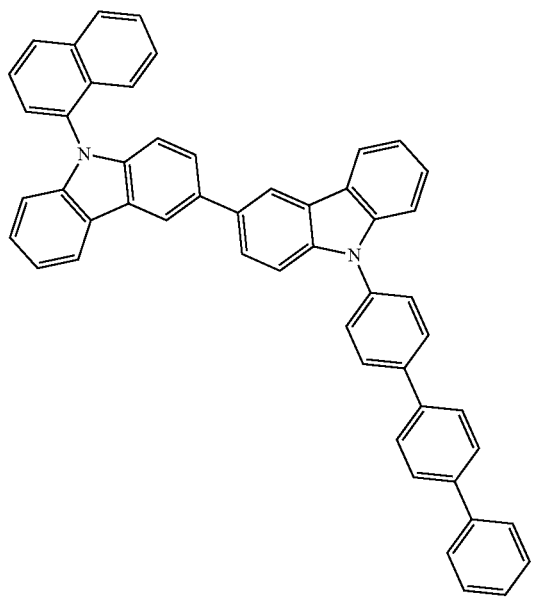
3-64
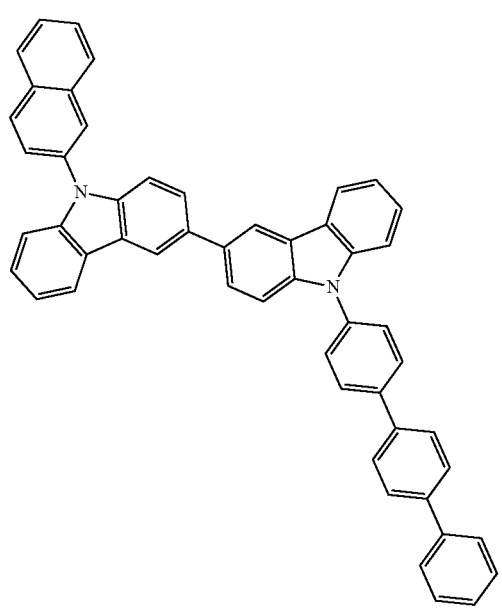
3-65
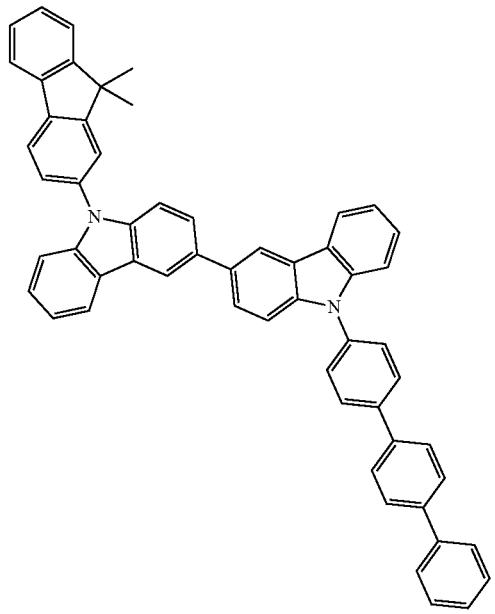
3-66
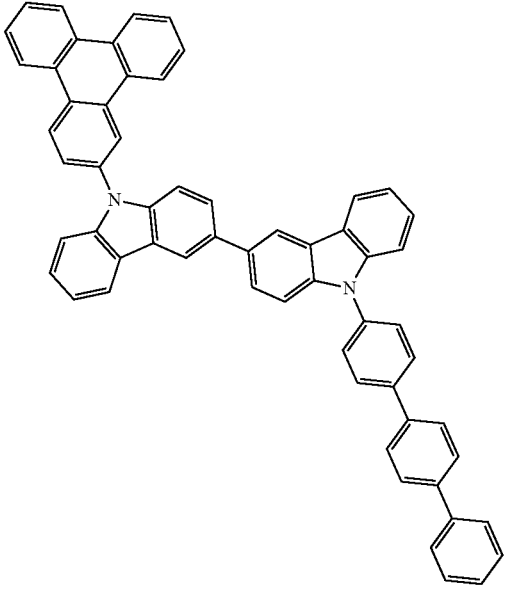

3-67
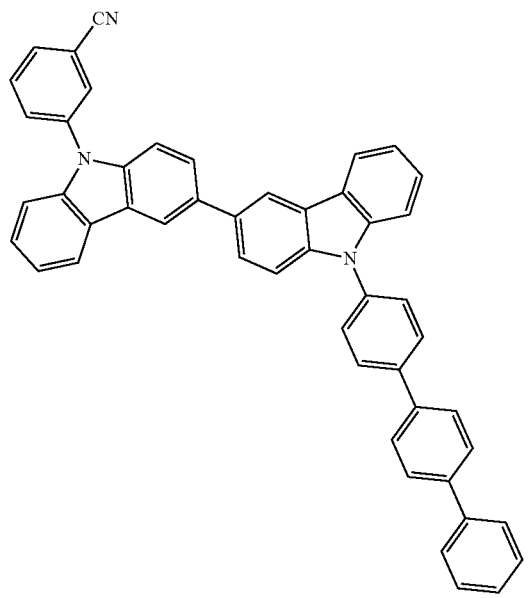
3-69
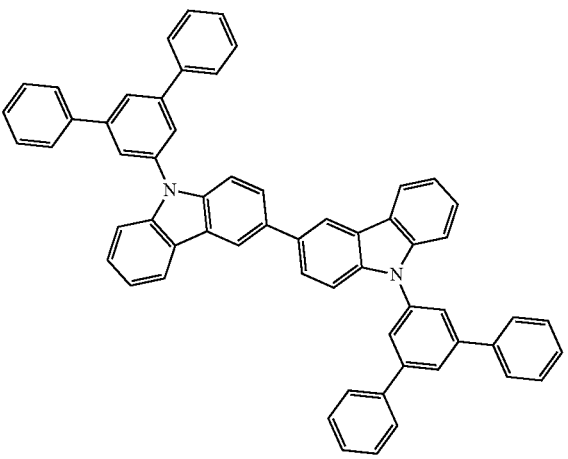
3-70
3-68
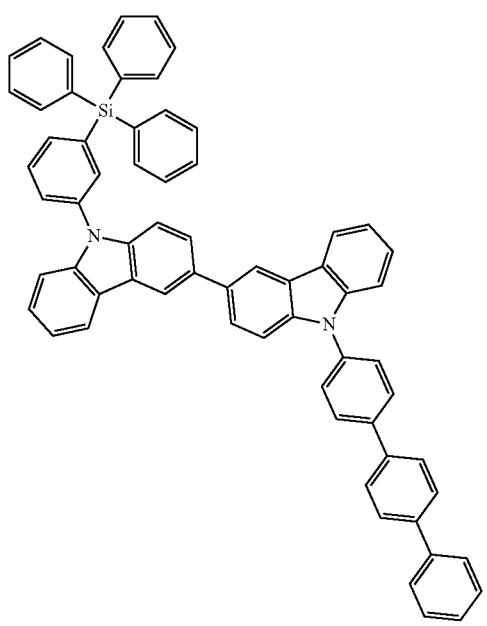
3-71

-continued 3-72

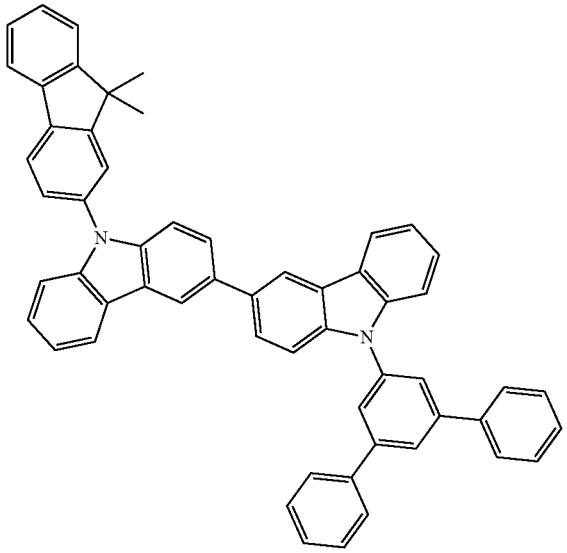

In the organic light emitting device of the present disclosure, the heterocyclic compound represented by Chemical Formula 1: the compound represented by Chemical Formula 25 may have a weight ratio of 1:10 to 10:1, 1:8 to 8:1, 1:5 to 5:1, or 1:2 to 2:1, however, the weight ratio is not limited thereto.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

The organic material layer comprising the compound of Chemical Formula 1 may further comprise other materials as necessary.

In the organic light emitting device according to one embodiment of the present application, materials other than the compound of Chemical Formula 1 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrene-sulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involved in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Mode for Disclosure

Hereinafter, the present specification will be described in more detail with reference to examples, however, these are for illustrative purposes only, and the scope of the present application is not limited thereto.

EXAMPLE

<Preparation Example 1> Preparation of Compound 1-5

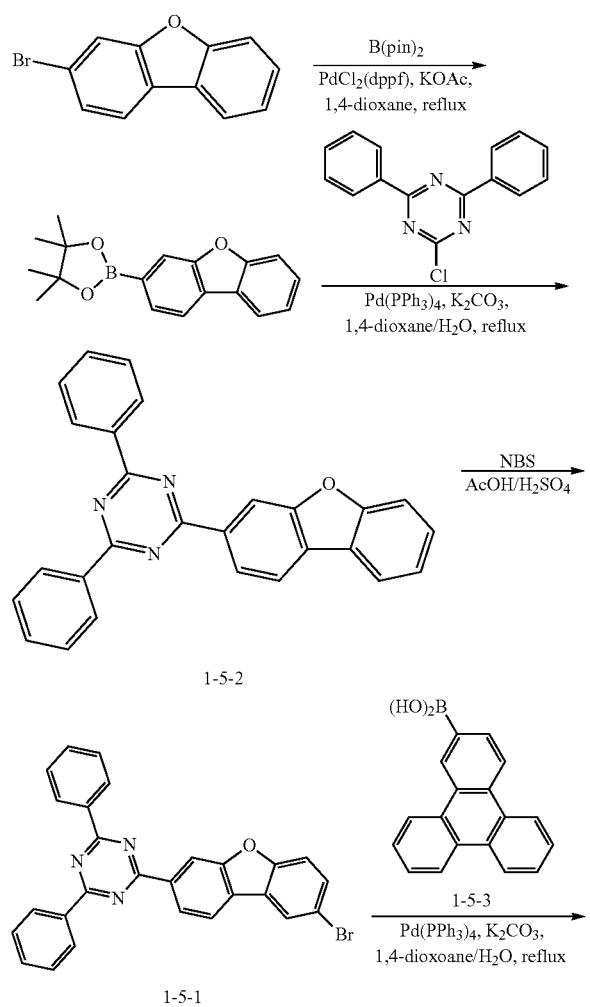

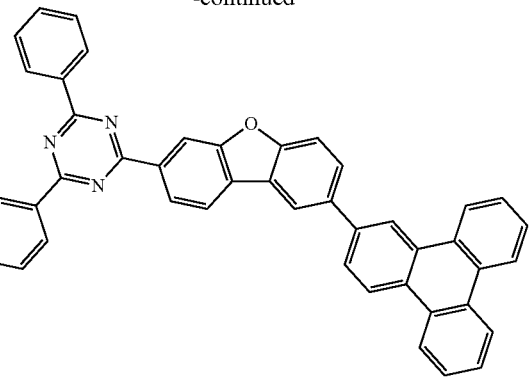

1-5

1) Preparation of Compound 1-5-3

After dissolving 3-bromodibenzo[b,d]furan (31.3 g, 126.7 mM), bis(pinacolato)diboron (190.0 g, 190.0 mM), $PdCl_2$(dppf) (4.6 g, 6.3 mM) and KOAc (37.3 g, 380.1 mM) in 1,4-dioxane (300 mL), the result was refluxed for 24 hours. After the reaction was completed, distilled water and dichloromethane (DCM) were introduced thereto at room temperature (25° C.) for extraction, and after drying the organic layer with $MgSO_4$, the solvent was removed using a rotary evaporator. The reaction material was purified using column chromatography (DCM:Hex=1:3) and recrystallized with methanol to obtain target Compound 1-5-3 (37 g, quant.).

2) Preparation of Compound 1-5-2

After dissolving Compound 1-5-3 (28 g, 95.2 mM), 2-chloro-4,6-diphenyl-1,3,5-triazine (30.6 g, 114.2 mM), $Pd(PPh_3)_4$ (5.5 g, 4.7 mM) and $K_2CO_3$ (26.3 g, 190.3 mM) in 1,4-dioxane/$H_2O$ (300 mL/60 mL), the result was refluxed for 24 hours. After the reaction was completed, distilled water and DCM were introduced thereto at room temperature for extraction, and after drying the organic layer with $MgSO_4$, the solvent was removed using a rotary evaporator. The reaction material was purified using column chromatography (DCM:Hex=1:3) and recrystallized with methanol to obtain target Compound 1-5-2 (35 g, 92%).

3) Preparation of Compound 1-5-1

$H_2SO_4$ (700 mL) was added dropwise to Compound 1-5-2 (35.1 g, 87.9 mM), NBS (18.8 g, 105.4 mM) and AcOH (700 mL), and the result was stirred for 4 hours at room temperature. After the reaction was completed, distilled water and DCM were introduced thereto at room temperature for extraction, and after drying the organic layer with $MgSO_4$, the solvent was removed using a rotary evaporator. The reaction material was purified using column chromatography (DCM:Hex=1:3) and recrystallized with methanol to obtain target Compound 1-5-1 (36 g, 85%).

4) Preparation of Compound 1-5

After dissolving Compound 1-5-1 (4 g, 8.4 mM), triphenylen-2-ylboronic acid (2.7 g, 10.0 mM), $Pd(PPh_3)_4$ (483 mg, 0.42 mM) and $K_2CO_3$ (2.3 g, 16.7 mM) in 1,4-dioxane/$H_2O$ (100 mL/20 mL), the result was refluxed for 24 hours. After the reaction was completed, distilled water and DCM were introduced thereto at room temperature for extraction, and after drying the organic layer with $MgSO_4$, the solvent was removed using a rotary evaporator. The reaction material was purified using column chromatography (DCM:Hex=1:3) and recrystallized with methanol to obtain target Compound 1-5 (4 g, 76%).

<Preparation Example 2> Preparation of Compound 1-51
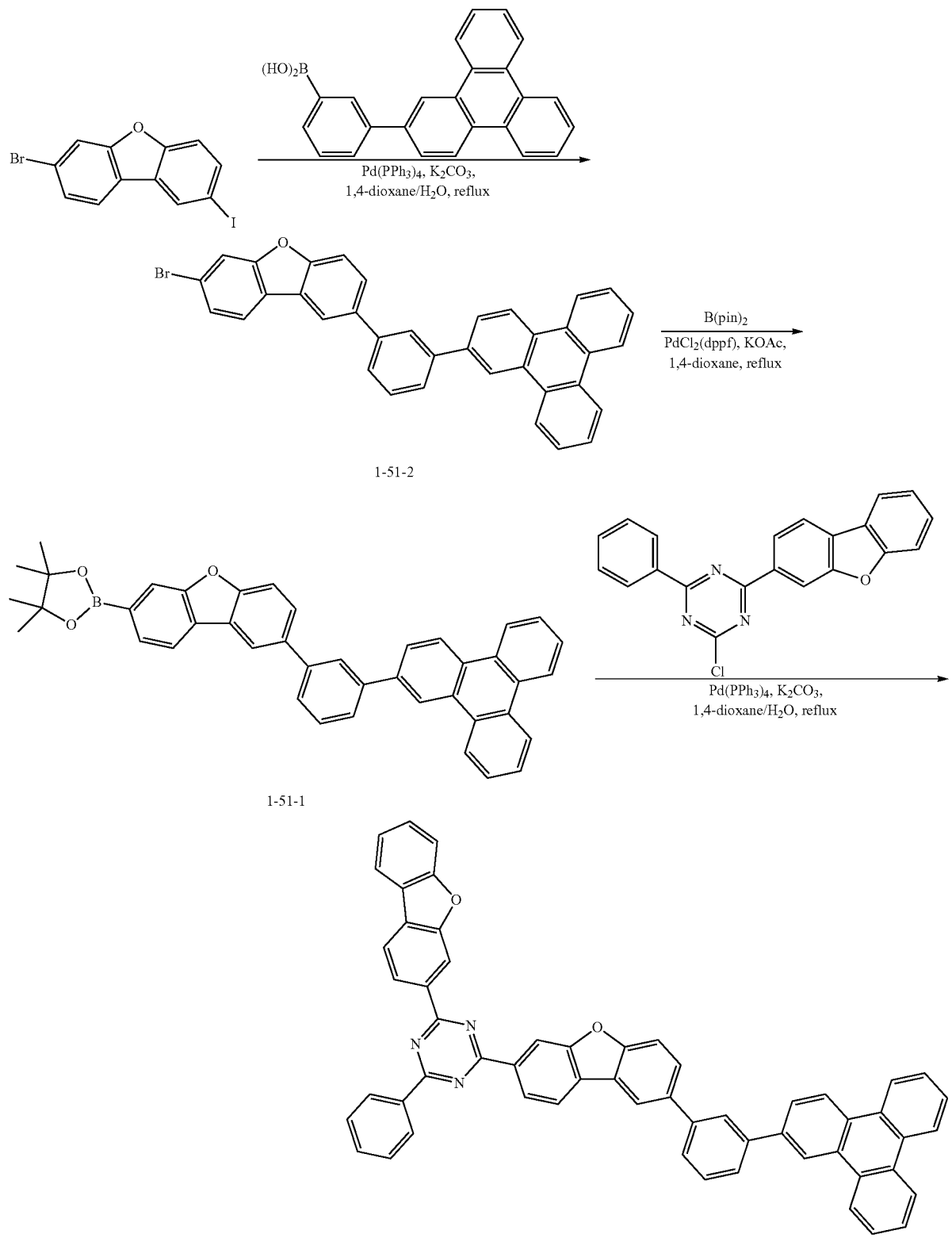

1) Preparation of Compound 1-51-2

After dissolving 3-bromo-8-iododibenzo[b,d]furan (5.0 g, 13.4 mM), (3-(triphenylen-2-yl)phenyl)boronic acid (4.7 g, 13.4 mM), Pd(PPh)$_4$ (774 mg, 0.67 mM) and K$_2$CO$_3$ (3.7 g, 26.8 mM) in 1,4-dioxane/H$_2$O (100 mL/20 mL), the result was refluxed for 24 hours. After the reaction was completed, distilled water and DCM were introduced thereto at room temperature for extraction, and after drying the organic layer with MgSO$_4$, the solvent was removed using a rotary evaporator. The reaction material was purified using column chromatography (DCM:Hex=1:3) and recrystallized with methanol to obtain target Compound 1-51-2 (5.9 g, 80%).

2) Preparation of Compound 1-51-1

After dissolving Compound 1-51-2 (5.9 g, 10.2 mM), bis(pinacolato)diboron (3.9 g, 15.2 mM), PdCl$_2$(dppf) (373 mg, 0.51 mM) and KOAc (3.0 g, 30.6 mM) in 1,4-dioxane (100 mL), the result was refluxed for 24 hours. After the reaction was completed, distilled water and DCM were introduced thereto at room temperature for extraction, and after drying the organic layer with MgSO$_4$, the solvent was removed using a rotary evaporator. The reaction material was purified using column chromatography (DCM:Hex=1:3) and recrystallized with methanol to obtain target Compound 1-51-1 (6.1 g, quant.).

3) Preparation of Compound 1-51

After dissolving Compound 1-51-1 (6.1 g, 10.2 mM), 2-chloro-4-(dibenzo[b,d]furan-3-yl)-6-phenyl-1,3,5-triazine (3.6 g, 10.2 mM), Pd(PPh)$_4$ (589 mg, 0.51 mM) and K$_2$CO$_3$ (2.8 g, 20.4 mM) in 1,4-dioxane/H$_2$O (100 mL/20 mL), the result was refluxed for 24 hours. After the reaction was completed, distilled water and DCM were introduced thereto at room temperature for extraction, and after drying the organic layer with MgSO$_4$, the solvent was removed using a rotary evaporator. The reaction material was purified using column chromatography (DCM:Hex=1:3) and recrystallized with methanol to obtain Compound 1-51 (6.5 g, 80%).

Target Compound A was synthesized in the same manner as in Preparation Example 1 except that Intermediate A of the following Table 1 was used instead of triphenylen-2-ylboronic acid.

TABLE 1

| Compound Number | Intermediate A | Target Compound A | Total Yield |
|---|---|---|---|
| 1-1 | (HO)$_2$B–phenyl | [structure] | 57% |
| 1-3 | (HO)$_2$B–naphthyl | [structure] | 54% |

TABLE 1-continued
| Compound Number | Intermediate A | Target Compound A | Total Yield |
|---|---|---|---|
| 1-6 | 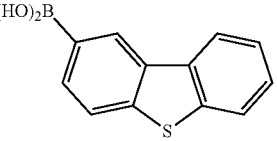 | 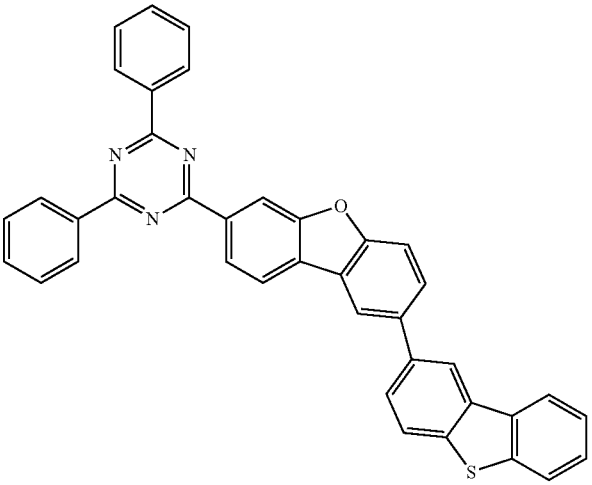 | 51% |
| 1-10 | 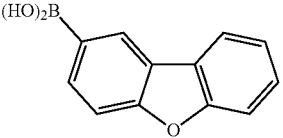 | 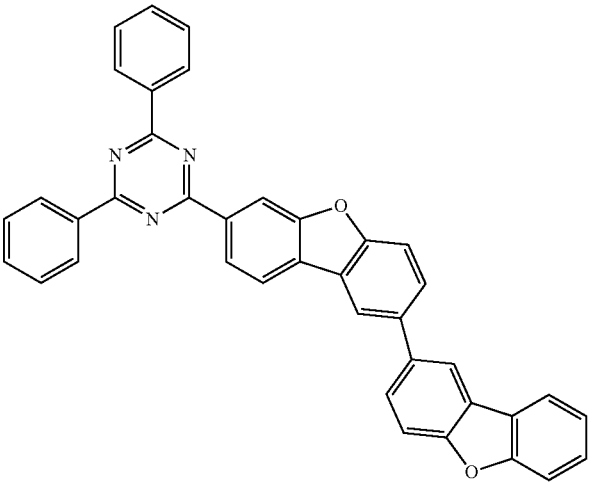 [SMILES: c1ccc(-c2nc(-c3ccccc3)nc(-c3ccc4c(c3)oc3ccc(-c5ccc6sc7ccccc7c6c5)cc34)n2)cc1] | 53% |
| 1-15 | 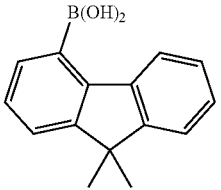 [SMILES: CC1(C)c2ccccc2-c2c(B(O)O)cccc21] | 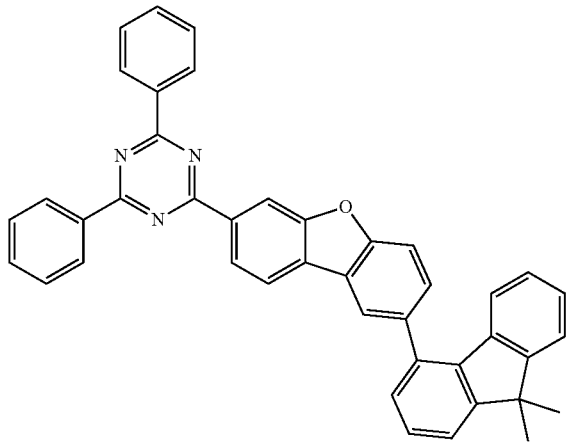 [SMILES: CC1(C)c2ccccc2-c2c(-c3ccc4oc5cc(-c6nc(-c7ccccc7)nc(-c7ccccc7)n6)ccc5c4c3)cccc21] | 50% |

TABLE 1-continued

| Compound Number | Intermediate A | Target Compound A | Total Yield |
|---|---|---|---|
| 1-20 | | | 52% |
| 1-26 | | | 51% |

TABLE 1-continued
| Compound Number | Intermediate A | Target Compound A | Total Yield |
|---|---|---|---|
| 1-29 | 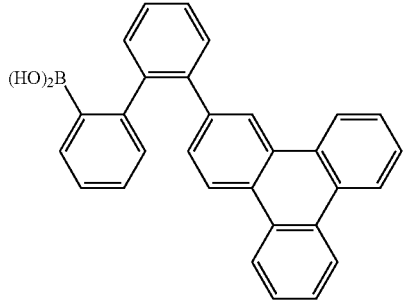 [SMILES: OB(O)c1ccccc1-c1ccccc1-c1ccc2c3ccccc3c3ccccc3c2c1] | 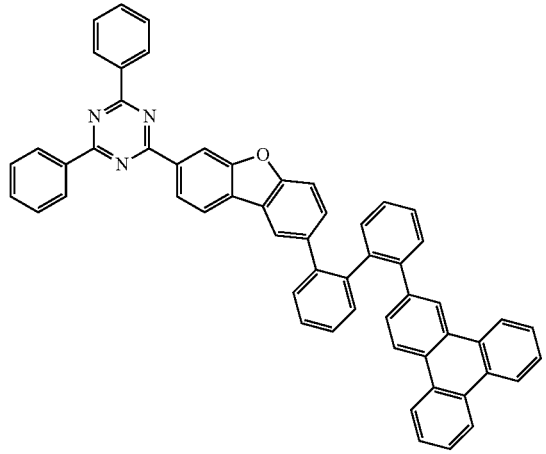 [SMILES: c1ccc(-c2nc(-c3ccccc3)nc(-c3ccc4c(c3)oc3ccc(-c5ccccc5-c5ccccc5-c5ccc6c7ccccc7c7ccccc7c6c5)cc34)n2)cc1] | 58% |
| 1-30 | 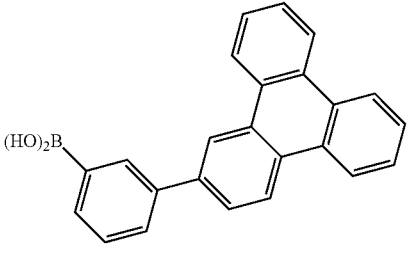 [SMILES: OB(O)c1cccc(-c2ccc3c4ccccc4c4ccccc4c3c2)c1] | 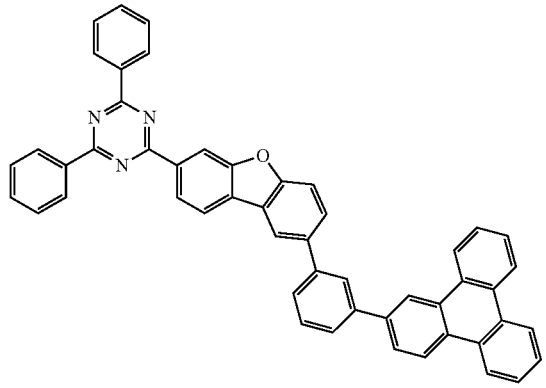 [SMILES: c1ccc(-c2nc(-c3ccccc3)nc(-c3ccc4c(c3)oc3ccc(-c5cccc(-c6ccc7c8ccccc8c8ccccc8c7c6)c5)cc34)n2)cc1] | 53% |
| 1-31 | 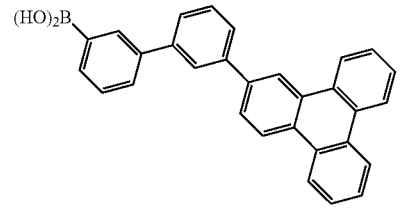 [SMILES: OB(O)c1cccc(-c2cccc(-c3ccc4c5ccccc5c5ccccc5c4c3)c2)c1] | 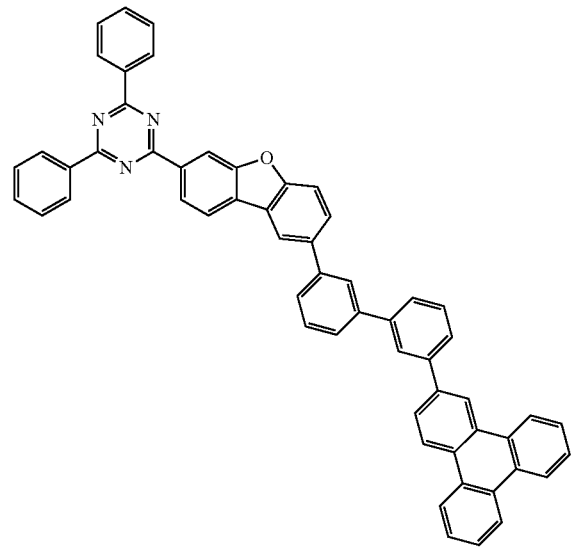 [SMILES: c1ccc(-c2nc(-c3ccccc3)nc(-c3ccc4c(c3)oc3ccc(-c5cccc(-c6cccc(-c7ccc8c9ccccc9c9ccccc9c8c7)c6)c5)cc34)n2)cc1] | 50% |

TABLE 1-continued

| Compound Number | Intermediate A | Target Compound A | Total Yield |
|---|---|---|---|
| 1-42 | | | 55% |

Target Compound A was synthesized in the same manner as in Preparation Example 2 except that Intermediate A of the following Table 2 was used instead of 2-chloro-4-(dibenzo[b,d]furan-3-yl)-6-phenyl-1,3,5-triazine, and Intermediate B of the following Table 2 was used instead of (3-(triphenylen-2-yl)phenyl)boronic acid.

TABLE 2

| Compound Number | Intermediate A | Intermediate B | Target Compound A | Yield |
|---|---|---|---|---|
| 1-50 | | | | 51% |
| 1-55 | | | | 52% |

TABLE 2-continued
| Compound Number | Intermediate A | Intermediate B | Target Compound A | Yield |
|---|---|---|---|---|
| 1-59 | 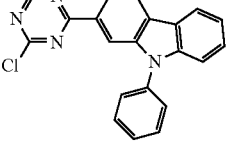 | 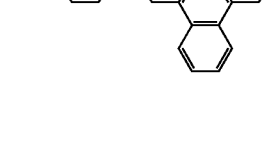 | 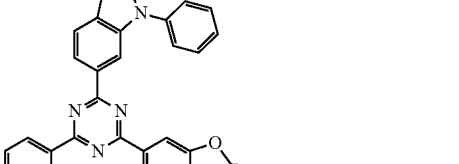 | 53% |
| 1-63 |  |  |  | 55% |
| 1-68 |  |  |  | 56% |

TABLE 2-continued

| Compound Number | Intermediate A | Intermediate B | Target Compound A | Yield |
|---|---|---|---|---|
| 1-74 | | | | 54% |

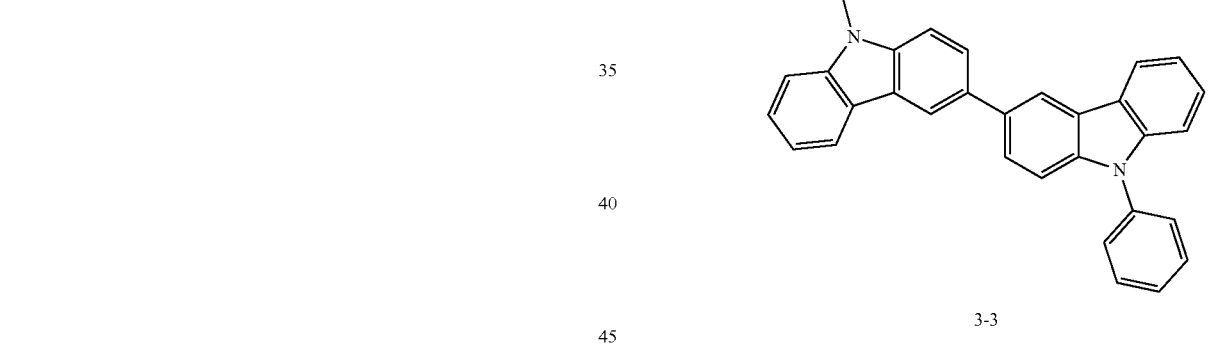

Compounds 2-1 to 2-116 were synthesized in the same manner as in Preparation Example 1 and Preparation Example 2 except that 3-bromodibenzo[b,d]thiophene was used instead of 3-bromodibenzo[b,d]furan.

<Preparation Example 3> Synthesis of Compound 3-3

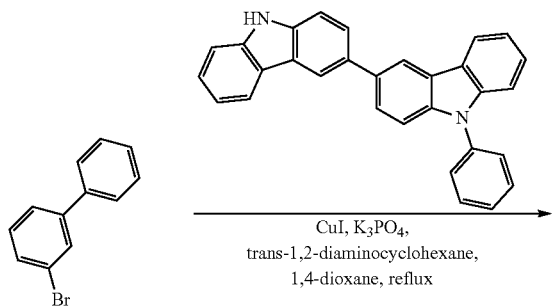

1) Preparation of Compound 3-3

After dissolving 3-bromo-1,1'-biphenyl (3.7 g, 15.8 mM), 9-phenyl-9H,9'H-3,3'-bicarbazole (6.5 g, 15.8 mM), CuI (3.0 g, 15.8 mM), trans-1,2-diaminocyclohexane (1.9 mL, 15.8 mM) and $K_3PO_4$ (3.3 g, 31.6 mM) in 1,4-oxane (100 mL), the result was refluxed for 24 hours. After the reaction was completed, distilled water and DCM were introduced thereto at room temperature for extraction, and after drying the organic layer with $MgSO_4$, the solvent was removed using a rotary evaporator. The reaction material was purified using column chromatography (DCM:Hex=1:3) and recrystallized with methanol to obtain target Compound 3-3 (7.5 g, 85%).

Target Compound A was synthesized in the same manner as in Preparation Example 3 except that Intermediate A of the following Table 3 was used instead of 3-bromo-1,1'-biphenyl, and Intermediate B of the following Table 3 was used instead of 9-phenyl-9H,9'H-3,3'-bicarbazole.

TABLE 3

| Compound Number | Intermediate A | Intermediate B | Target Compound A | Total Yield |
|---|---|---|---|---|
| 3-4 | | | | 83% |
| 3-7 | | | | 84% |
| 3-31 | | | | 81% |
| 3-32 | | | | 80% |

TABLE 3-continued
| Compound Number | Intermediate A | IntermediateB | Target Compound A | Total Yield |
|---|---|---|---|---|
| 3-42 | 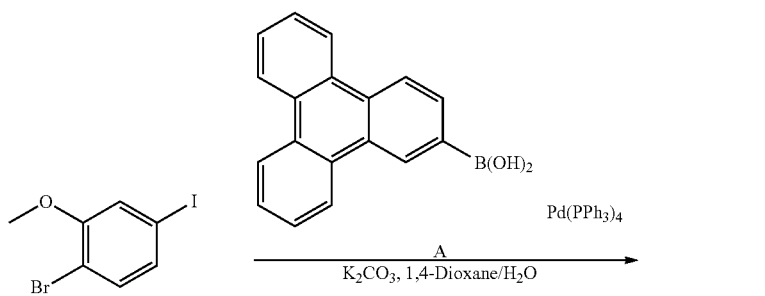 | | | 82% |
<Preparation Example 4> Preparation of Compound 4-5
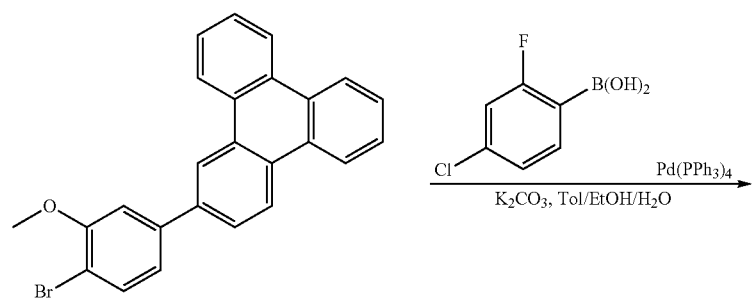
4-5-5

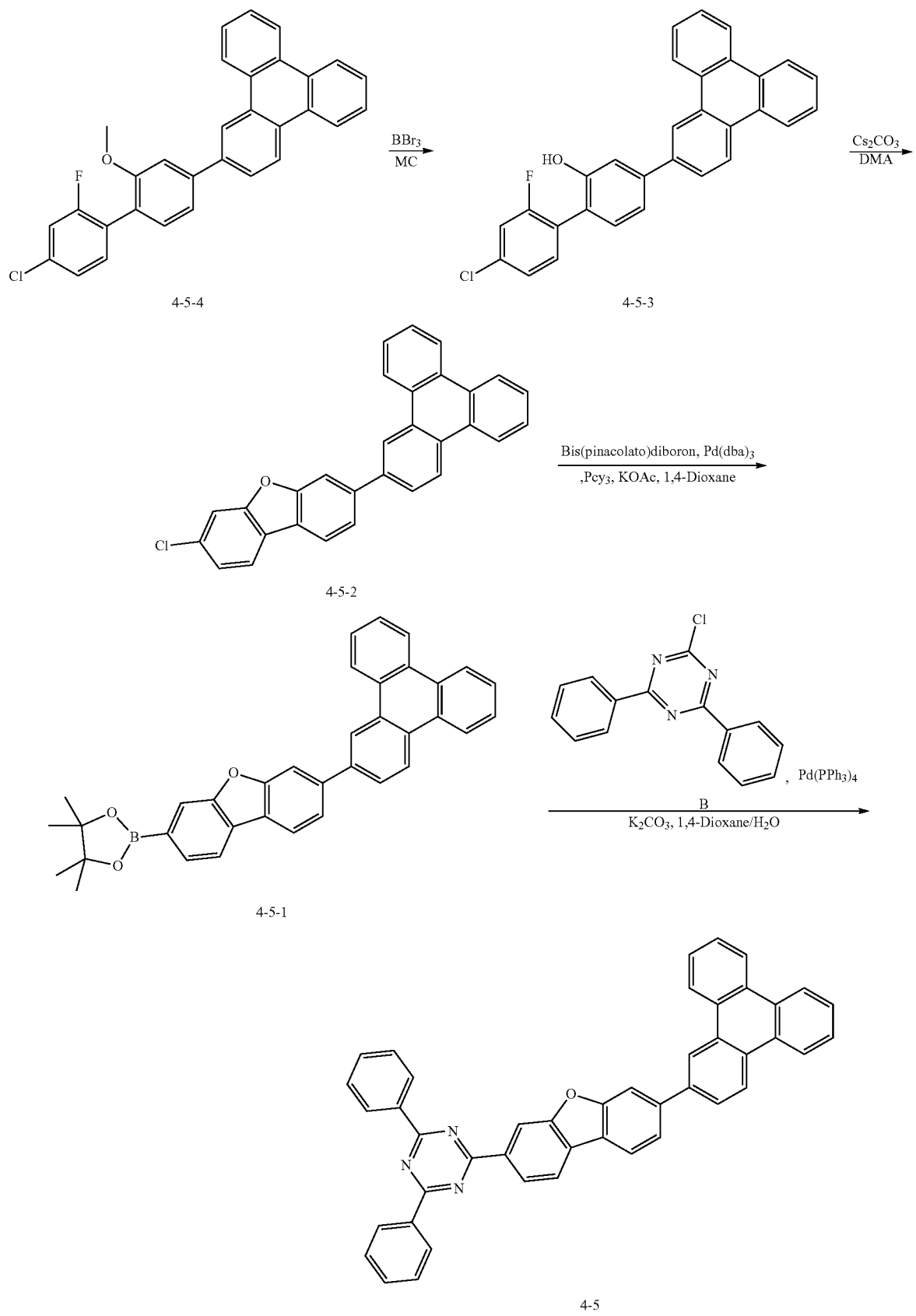

1) Preparation of Compound 4-5-5

In a one neck round bottom flask (one neck r.b.f), a mixture of 1-bromo-4-iodo-2-methoxybenzene (50 g, 159.7 mmol), triphenylen-2-ylboronic acid (43.4 g, 159.7 mmol), tetrakis(triphenylphosphine)palladium(0) (9.2 g, 7.89 mmol), potassium carbonate (44.1 g, 319 mmol) and 1,4-dioxane/water (500 ml/100 ml) was refluxed at 110° C. The result was extracted with dichloromethane and dried with MgSO$_4$. The result was silica gel filtered and then concentrated to obtain Compound 4-5-5. (48 g, 72%)

2) Preparation of Compound 4-5-4

In a one neck round bottom flask (one neck r.b.f), a mixture of 2-(4-bromo-3-methoxyphenyl)triphenylene (48 g, 116 mmol), (4-chloro-2-fluorophenyl)boronic acid (20.2 g, 116 mmol), tetrakis(triphenylphosphine)palladium(0) (6.7 g, 5.8 mmol), potassium carbonate (32 g, 232 mmol) and toluene/ethanol/water (500 ml/100 ml/100 ml) was refluxed at 110° C. The result was extracted with dichloromethane and dried with MgSO$_4$. The result was silica gel filtered and then concentrated to obtain Compound 4-5-4. (46 g, 85%)

3) Preparation of Compound 4-5-3

In a one neck round bottom flask (one neck r.b.f), a mixture of 2-(4'-chloro-2'-fluoro-2-methoxy-[1,1'-biphenyl]-4-yl)triphenylene (46 g, 99.3 mmol) and MC (400 ml) was cooled to 0° C., BBr$_3$ (50 g, 198 mmol) was added dropwise thereto, the temperature was raised to room temperature, and the result was stirred for 1 hour. The reaction was terminated with distilled water, and the result was extracted with dichloromethane and dried with MgSO$_4$. The result was column purified with MC:HX=1:1 to obtain Compound 4-5-3. (39 g, 87%)

4) Preparation of Compound 4-5-2

In a one neck round bottom flask (one neck r.b.f), a dimethylacetamide (400 ml) mixture of 4'-chloro-2'-fluoro-4-(triphenylen-2-yl)-[1,1'-biphenyl]-2-ol (39 g, 86.8 mmol) and Cs$_2$CO$_3$ (56 g, 73 mmol) was stirred at 120° C. The result was cooled, then filtered, and, after removing the solvent of the filtrate, column purified with HX:MC=4:1 to obtain Compound 4-5-2. (35 g, 94%)

5) Preparation of Compound 4-5-1

In a one neck round bottom flask (one neck r.b.f), a 1,4-dioxane (100 ml) mixture of 3-chloro-7-(triphenylen-2-yl)dibenzo[b,d]furan (10 g, 23.3 mmol), bis(pinacolato)diboron (11.8 g, 46.6 mmol), Pcy$_3$ (1 g, 1.16 mmol), potassium acetate (6.8 g, 69 mmol) and Pd$_2$(dba)$_3$ (1 g, 1.16 mmol) was refluxed at 140° C. After cooling the result, the filtered filtrate was concentrated and column purified with HX:MC=3:1 to obtain Compound 4-5-1. (9.8 g, 81%)

6) Preparation of Compound 4-5

In a one neck round bottom flask (one neck r.b.f), a mixture of 4,4,5,5-tetramethyl-2-(7-(triphenylen-2-yl)dibenzo[b,d]furan-3-yl)-1,3,2-dioxaborolane (9.8 g, 18.8 mmol), 2-chloro-4,6-diphenyl-1,3,5-triazine (5 g, 18.8 mmol), tetrakis(triphenylphosphine)palladium(0) (2.1 g, 1.88 mmol), potassium carbonate (5.19 g, 37.6 mmol) and 1,4-dioxane/water (100 ml/25 ml) was refluxed for 4 hours at 120° C. The result was filtered at 120° C. and washed with 1,4-dioxane, distilled water and MeOH to obtain Compound 4-5. (10.2 g, 87%)

Target Compound A was synthesized in the same manner as in Preparation Example 4 except that Intermediates A and B of the following Table 4 were used instead of triphenylen-2-ylboronic acid and 2-chloro-4,6-diphenyl-1,3,5-triazine, respectively.

TABLE 4

| Compound Number | Intermediate A | Intermediate B | Target Compound A | Yield |
|---|---|---|---|---|
| 4-1 | 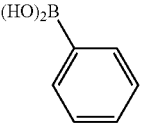 | 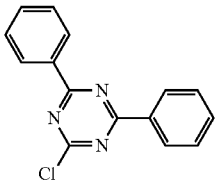 [SMILES: Clc1nc(-c2ccccc2)nc(-c2ccccc2)n1] | 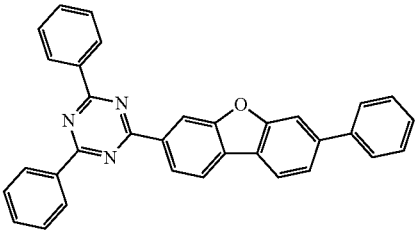 [SMILES: c1ccc(-c2ccc3c(c2)oc2cc(-c4nc(-c5ccccc5)nc(-c5ccccc5)n4)ccc23)cc1] | 43% |
| 4-3 | 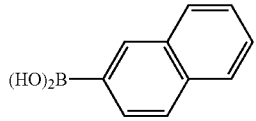 [SMILES: OB(O)c1ccc2ccccc2c1] | 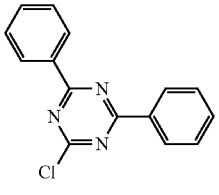 [SMILES: Clc1nc(-c2ccccc2)nc(-c2ccccc2)n1] | 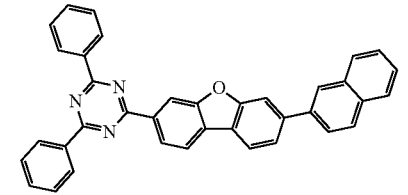 [SMILES: c1ccc(-c2nc(-c3ccccc3)nc(-c3ccc4c(c3)oc3cc(-c5ccc6ccccc6c5)ccc34)n2)cc1] | 55% |
| 4-6 | 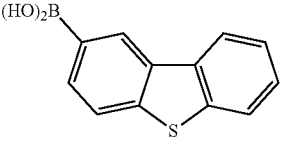 | 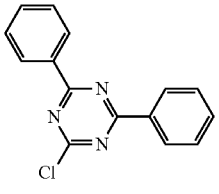 [SMILES: Clc1nc(-c2ccccc2)nc(-c2ccccc2)n1] | 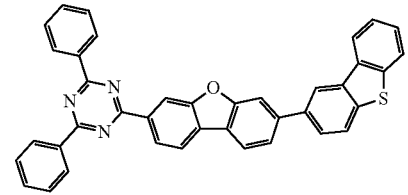 [SMILES: c1ccc(-c2nc(-c3ccccc3)nc(-c3ccc4c(c3)oc3cc(-c5ccc6sc7ccccc7c6c5)ccc34)n2)cc1] | 32% |

TABLE 4-continued
| Compound Number | Intermediate A | Intermediate B | Target Compound A | Yield |
|---|---|---|---|---|
| 4-10 | 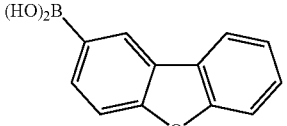 | 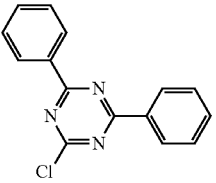 [SMILES: Clc1nc(-c2ccccc2)nc(-c2ccccc2)n1] | 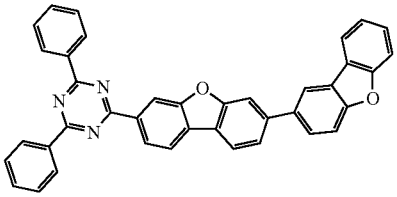 [SMILES: c1ccc(-c2nc(-c3ccccc3)nc(-c3ccc4c(c3)oc3cc(-c5ccc6oc7ccccc7c6c5)ccc34)n2)cc1] | 42% |
| 4-15 | 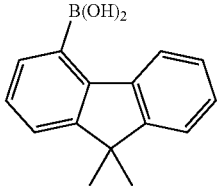 [SMILES: CC1(C)c2ccccc2-c2c(B(O)O)cccc21] | 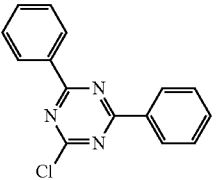 | 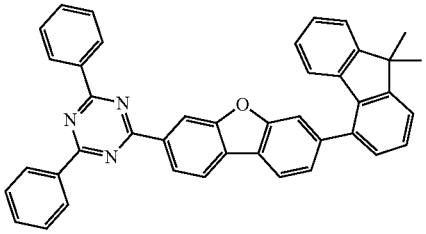 [SMILES: CC1(C)c2ccccc2-c2c(-c3ccc4c(c3)oc3cc(-c5nc(-c6ccccc6)nc(-c6ccccc6)n5)ccc34)cccc21] | 52% |
| 4-20 | 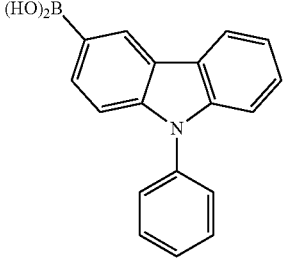 [SMILES: OB(O)c1ccc2c(c1)c1ccccc1n2-c1ccccc1] | 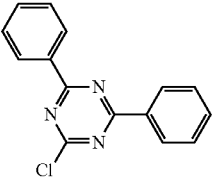 [SMILES: Clc1nc(-c2ccccc2)nc(-c2ccccc2)n1] | 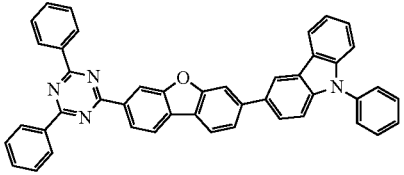 [SMILES: c1ccc(-c2nc(-c3ccccc3)nc(-c3ccc4c(c3)oc3cc(-c5ccc6c(c5)c5ccccc5n6-c5ccccc5)ccc34)n2)cc1] | 39% |
| 4-26 | 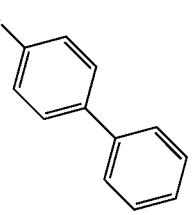 | 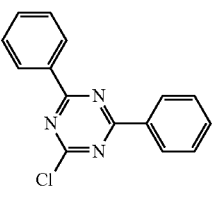 [SMILES: Clc1nc(-c2ccccc2)nc(-c2ccccc2)n1] | 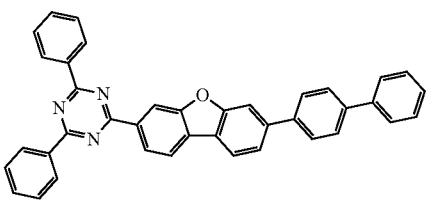 [SMILES: c1ccc(-c2ccc(-c3ccc4c(c3)oc3cc(-c5nc(-c6ccccc6)nc(-c6ccccc6)n5)ccc34)cc2)cc1] | 47% |
| 4-29 | 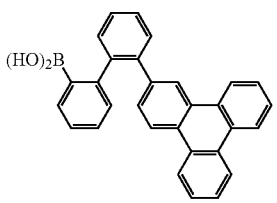 [SMILES: OB(O)c1ccccc1-c1ccccc1-c1ccc2c3ccccc3c3ccccc3c2c1] | 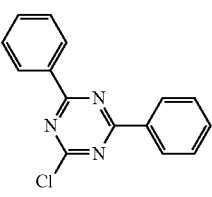 [SMILES: Clc1nc(-c2ccccc2)nc(-c2ccccc2)n1] | 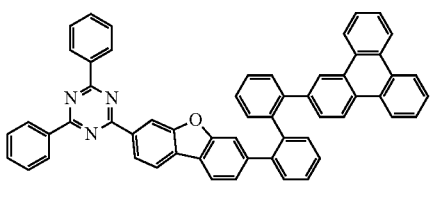 [SMILES: c1ccc(-c2nc(-c3ccccc3)nc(-c3ccc4c(c3)oc3cc(-c5ccccc5-c5ccccc5-c5ccc6c7ccccc7c7ccccc7c6c5)ccc34)n2)cc1] | 35% |
| 4-30 | 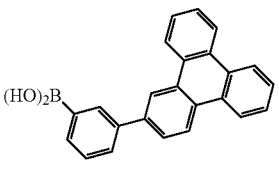 [SMILES: OB(O)c1cccc(-c2ccc3c4ccccc4c4ccccc4c3c2)c1] | 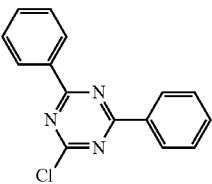 [SMILES: Clc1nc(-c2ccccc2)nc(-c2ccccc2)n1] | 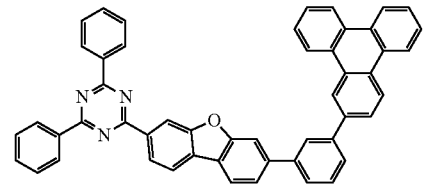 [SMILES: c1ccc(-c2nc(-c3ccccc3)nc(-c3ccc4c(c3)oc3cc(-c5cccc(-c6ccc7c8ccccc8c8ccccc8c7c6)c5)ccc34)n2)cc1] | 48% |
| 4-31 | 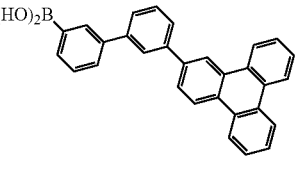 | 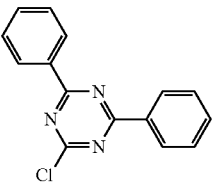 [SMILES: Clc1nc(-c2ccccc2)nc(-c2ccccc2)n1] | 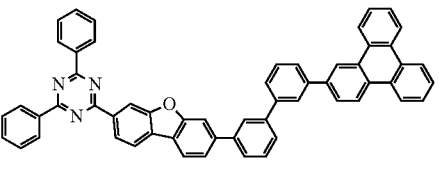 [SMILES: c1ccc(-c2nc(-c3ccccc3)nc(-c3ccc4c(c3)oc3cc(-c5cccc(-c6cccc(-c7ccc8c9ccccc9c9ccccc9c8c7)c6)c5)ccc34)n2)cc1] | 49% |

TABLE 4-continued
| Compound Number | Intermediate A | Intermediate B | Target Compound A | Yield |
|---|---|---|---|---|
| 4-42 | 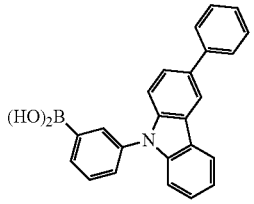 [SMILES: OB(O)c1cccc(-n2c3ccccc3c3cc(-c4ccccc4)ccc32)c1] | 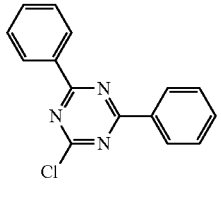 [SMILES: Clc1nc(-c2ccccc2)nc(-c2ccccc2)n1] | 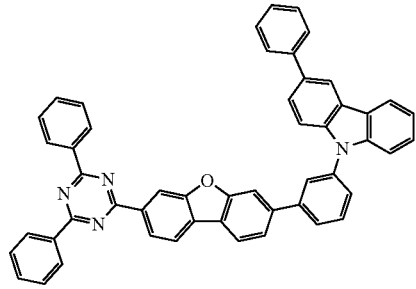 [SMILES: c1ccc(-c2ccc3c(c2)c2ccccc2n3-c2cccc(-c3ccc4c(c3)oc3cc(-c5nc(-c6ccccc6)nc(-c6ccccc6)n5)ccc34)c2)cc1] | 41% |
| 4-50 | 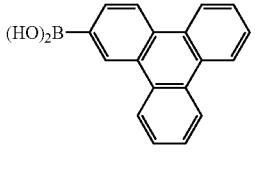 [SMILES: OB(O)c1ccc2c3ccccc3c3ccccc3c2c1] | 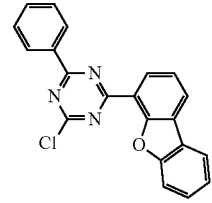 [SMILES: Clc1nc(-c2ccccc2)nc(-c2cccc3c2oc2ccccc23)n1] | 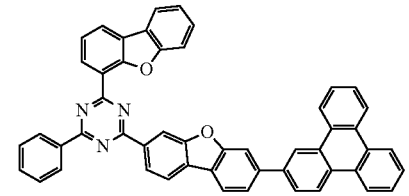 [SMILES: c1ccc(-c2nc(-c3ccc4c(c3)oc3cc(-c5ccc6c7ccccc7c7ccccc7c6c5)ccc34)nc(-c3cccc4c3oc3ccccc34)n2)cc1] | 53% |
| 4-55 | 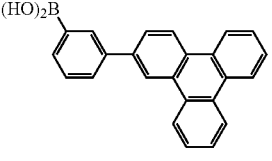 [SMILES: OB(O)c1cccc(-c2ccc3c4ccccc4c4ccccc4c3c2)c1] | 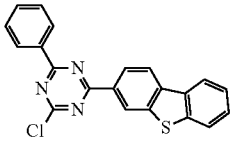 [SMILES: Clc1nc(-c2ccccc2)nc(-c2ccc3c(c2)sc2ccccc23)n1] | 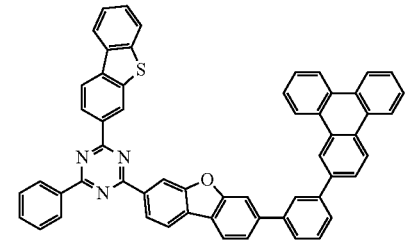 [SMILES: c1ccc(-c2nc(-c3ccc4c(c3)oc3cc(-c5cccc(-c6ccc7c8ccccc8c8ccccc8c7c6)c5)ccc34)nc(-c3ccc4c(c3)sc3ccccc34)n2)cc1] | 51% |
| 4-59 | 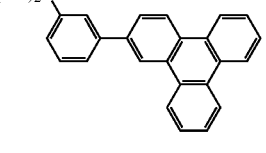 | 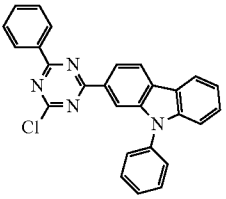 [SMILES: Clc1nc(-c2ccccc2)nc(-c2ccc3c4ccccc4n(-c4ccccc4)c3c2)n1] | 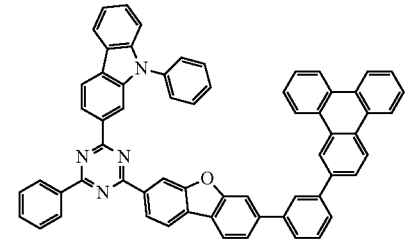 [SMILES: c1ccc(-c2nc(-c3ccc4c(c3)oc3cc(-c5cccc(-c6ccc7c8ccccc8c8ccccc8c7c6)c5)ccc34)nc(-c3ccc4c5ccccc5n(-c5ccccc5)c4c3)n2)cc1] | 42% |
| 4-63 | 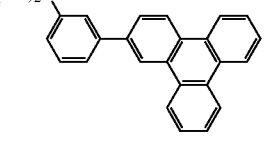 | 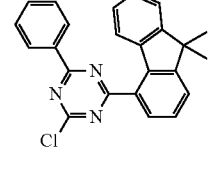 | 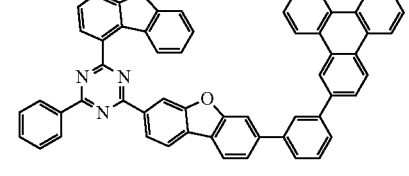 | 47% |
| 4-68 | 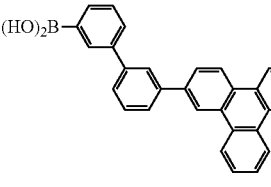 | 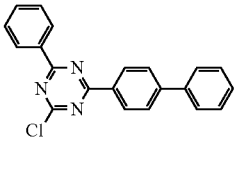 [SMILES: Clc1nc(-c2ccccc2)nc(-c2ccc(-c3ccccc3)cc2)n1] | 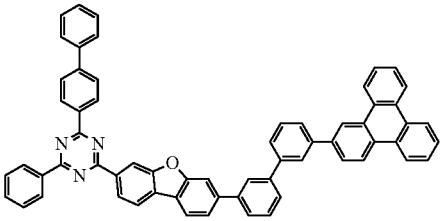 [SMILES: c1ccc(-c2ccc(-c3nc(-c4ccccc4)nc(-c4ccc5c(c4)oc4cc(-c6cccc(-c7cccc(-c8ccc9c%10ccccc%10c%10ccccc%10c9c8)c7)c6)ccc45)n3)cc2)cc1] | 50% |

TABLE 4-continued
| Compound Number | Intermediate A | Intermediate B | Target Compound A | Yield |
|---|---|---|---|---|
| 4-74 | (HO)₂B-[triphenylene] | [triazine-phenyl-Br] | [target structure] | 49% |
<Preparation Example 5> Preparation of Compound 5-5
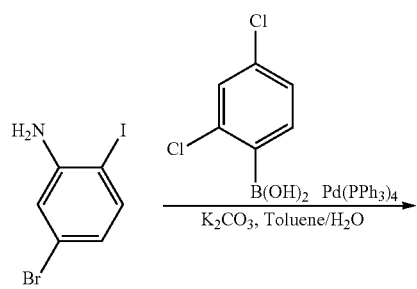
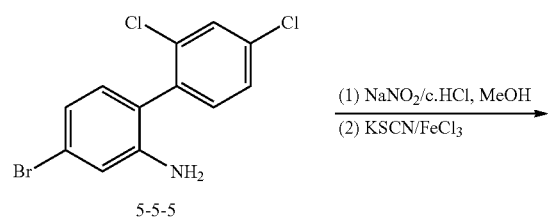
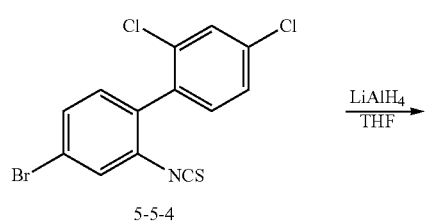
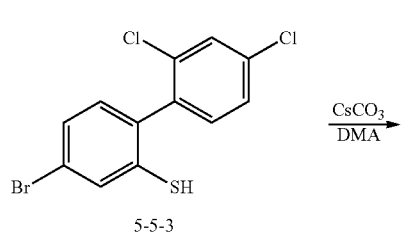
-continued
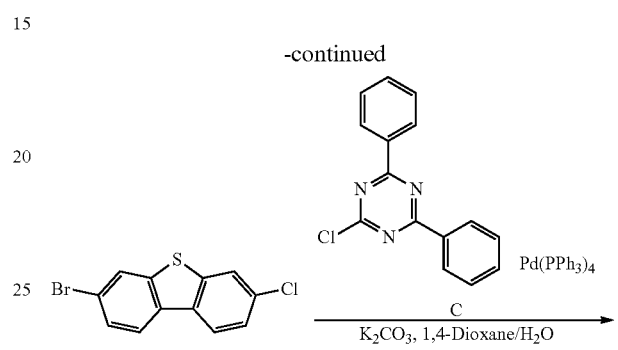
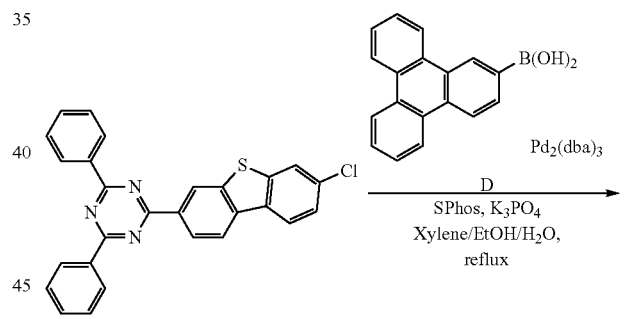
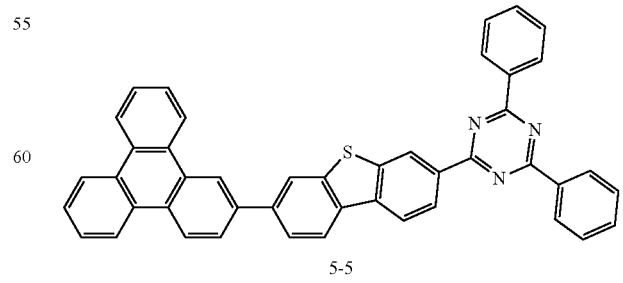
5-5

1) Preparation of Compound 5-5-5

In a one neck round bottom flask (one neck r.b.f), a mixture of 5-bromo-2-iodoaniline (30 g, 100 mmol), (2,4-dichlorophenyl)boronic acid (19.2 g, 100 mmol), tetrakis (triphenylphosphine)palladium(0) (5.7 g, 5 mmol), potassium carbonate (27.6 g, 200 mmol) and toluene/water (300 ml/60 ml) was refluxed at 110° C. The result was extracted with dichloromethane, dried with $MgSO_4$, and column purified to obtain Compound 5-5-5. (25 g, 67%)

2) Preparation of Compound 5-5-4

In a one neck round bottom flask (one neck r.b.f), MeOH (300 ml) of 4-bromo-2',4'-dichloro-[1,1'-biphenyl]-2-amine (25 g, 78.8 mmol) was cooled to 0° C., and c.HCl was added dropwise thereto. $NaNO_2$ (5.2 g, 78.8 mmol) was introduced thereto, and the result was stirred for 10 minutes. KSCN (22.9 g, 236 mmol) and $FeCl_3$ (12.7 g, 78.8 mmol) were introduced thereto, and the temperature was raised to room temperature. After the reaction was terminated, the result was neutralized with 2 M NaOH, extracted with dichloromethane, and dried with $MgSO_4$. The result was column purified to obtain Compound 5-5-4. (20 g, 70%)

3) Preparation of Compound 5-5-3

In a one neck round bottom flask (one neck r.b.f), a THF (200 ml) solution of 4-bromo-2',4'-dichloro-2-isothiocyanato-1,1'-biphenyl (20 g, 55.6 mmol) was cooled to 0° C., and $LiAlH_4$ (1 M in THF (61 ml), 61 mmol) was slowly added dropwise thereto. The reaction was terminated with distilled water, the result was extracted with 2 M HCl and ethyl acetate, and dried with $MgSO_4$ to obtain Compound 5-5-3. (14 g, 75%)

4) Preparation of Compound 5-5-2

In a one neck round bottom flask (one neck r.b.f), a dimethylacetamide (140 ml) mixture of 4-bromo-2',4'-dichloro-[1,1'-biphenyl]-2-thiol (14 g, 41.9 mmol) and $Cs_2CO_3$ (27 g, 83 mmol) was stirred at 140° C. The result was cooled, then filtered, and, after removing the solvent of the filtrate, column purified to obtain Compound 5-5-2. (10.8 g, 87%)

5) Preparation of Compound 5-5-1

In a one neck round bottom flask (one neck r.b.f), a mixture of 3-bromo-7-chlorodibenzo[b,d]thiophene (10.8 g, 36.2 mmol), 2-chloro-4,6-diphenyl-1,3,5-triazine (9.7 g, 36.2 mmol), tetrakis(triphenylphosphine)palladium(0) (2 g, 1.81 mmol), potassium carbonate (10 g, 72.4 mmol) and 1,4-dioxane/water (100 ml/25 ml) was refluxed for 6 hours at 120° C. The result was filtered at 120° C., and then washed with 1,4-dioxane, distilled water and MeOH to obtain Compound 5-5-1. (13.5 g, 83%)

6) Preparation of Compound 5-5

In a one neck round bottom flask (one neck r.b.f), a xylene/EtOH/$H_2O$ (100 ml/20 ml/20 ml) mixture of 2-(7-chlorodibenzo[b,d]thiophen-3-yl)-4,6-diphenyl-1,3,5-triazine (13.5 g 30 mmol), triphenylen-2-ylboronic acid (8.1 g, 30 mmol), $Pd_2(dba)_3$ (1.39 g, 1.52 mmol), Sphos (1.23 g, 3 mmol) and $K_3PO_4$ (12.9 g, 60.8 mmol) was stirred at 160° C. The reaction solution was filtered while hot at 130° C., and washed with 100° C. 1,4-dioxane, $H_2O$ and MeOH. (15.3 g, 79%)

Target Compound A was synthesized in the same manner as in Preparation Example 5 except that Intermediates A and B of the following Table 5 were used instead of 2-chloro-4,6-diphenyl-1,3,5-triazine and triphenylen-2-ylboronic acid, respectively.

TABLE 5

| Compound Number | Intermediate A | Intermediate B | Target Compound A | Yield |
| --- | --- | --- | --- | --- |
| 5-20 | | | | 39% |
| 5-31 | | | | 49% |

Synthesis identification results of the compounds prepared above are as described in the following [Table 6] and [Table 7].

TABLE 6

| Compound Number | $^1$H NMR (CDCl$_3$, 200 Mz) |
|---|---|
| 1-1 | δ = 8.36(4H, m), 8.03(1H, d), 7.88~7.76(7H, m), 7.50~7.41(9H, m) |
| 1-3 | δ = 8.36(4H, m), 8.09~7.99(4H, m), 7.88~7.76(5H, m), 7.63~7.50(9H, m), 7.38(1H, d) |
| 1-5 | δ = 9.27(1H, s), 8.79(1H, d), 8.37~8.30(8H, m), 8.03(1H, d), 7.88~7.64(9H, m), 7.52~7.50(7H, m) |
| 1-6 | δ = 8.45(1H, d), 8.36(4H, m), 8.12(2H, m), 8.03~7.76(8H, m), 7.56~7.49(8H, m) |
| 1-10 | δ = 8.36(4H, m), 8.03~7.98(2H, m), 7.88~7.76(8H, m), 7.96~7.79(8H, m), 7.69(1H, d), 7.60~7.41(12H, m) |
| 1-15 | δ = 8.95(1H, d), 8.50(1H, d), 8.36(4H, m), 8.20(1H, m), 8.09(1H, m), 7.88~7.69(8H, m), 7.61~7.50(10H, d), 7.39(1H, t) |
| 1-20 | δ = 9.60(1H, d), 9.27(1H, s), 8.37~8.30(7H, m), 7.88~7.50(22H, m) |
| 1-26 | δ = 8.36(4H, m), 8.03(1H, d), 7.83~7.79(7H, m), 7.50~7.41(9H, d), 7.25(4H, d) |
| 1-29 | δ = 9.27(1H, s), 8.79(1H, d), 8.37~8.30(8H, m), 7.94~7.50(25H, m) |
| 1-30 | δ = 9.27(1H, d), 8.79(1H, d), 8.37~8.30(8H, m), 8.03(1H, d), 7.94~7.61(13H, m), 7.52~7.50(7H, m) |
| 1-31 | δ = 9.27(1H, s), 8.79(1H, d), 8.37~8.30(8H, m), 8.03(1H, d), 7.94~7.50(24H, m) |
| 1-42 | δ = 8.55(1H, d), 8.36(4H, m), 8.21(1H, s), 8.03~7.68(13H, m), 7.60(1H, m), 7.50~7.35(11H, m), 7.16(1H, t) |
| 1-50 | δ = 9.27(1H, s), 8.79(1H, d), 8.37~8.30(6H, m), 8.08(1H, d), 7.98~7.50(22H, m), 7.39~7.31(2H, m) |
| 1-55 | δ = 9.27(1H, s), 8.79(1H, d), 8.37~8.30(6H, m), 7.98~7.50(23H, m), 7.39~7.31(2H, m) |
| 1-59 | δ = 9.27(1H, s), 8.79(1H, d), 8.55(1H, d), 8.45~8.30(7H, m), 7.98~7.50(23H, m) |
| 1-63 | δ = 9.27(1H, s), 8.79(1H, d), 8.37~8.30(6H, d), 8.03(1H, d), 7.94~7.47(23H, m), 7.28(1H, t), 1.69(6H, s) |
| 1-68 | δ = 9.27(1H, s), 8.79(1H, d), 8.37~8.30(6H, m), 8.03~7.41(29H, m), 7.25(1H, s) |
| 1-74 | δ = 9.27(1H, s), 8.79(1H, d), 8.37~8.30(8H, m), 8.03~7.96(3H, m), 7.88~7.64(9H, m), 7.52~7.50(7H, m), 7.25(2H, d) |
| 2-5 | δ = 9.27(1H, s), 8.79(1H, d), 8.37~8.20(10H, m), 8.12(2H, m), 7.99~7.94(2H, m), 7.70~7.64(4H, m), 7.52~7.50(7H, m) |
| 2-20 | δ = 8.36~8.12(11H, m), 7.99~7.89(3H, m), 7.62~7.50(13H, m), 7.20(1H, m) |
| 2-31 | δ = 9.27(1H, s), 8.79(1H, d), 8.37~8.20(10H, m), 8.12(2H, m), 7.99~7.94(4H, m), 7.73~7.50(17H, m) |
| 3-3 | δ = 8.55(1H, d), 8.30(1H, d), 8.21-8.13(3H, m), 7.99~7.89(4H, m), 7.77~7.35(17H, m), 7.20~7.16(2H, m) |
| 3-4 | δ = 8.55(1H, d), 8.30(1H, d), 8.19~8.13(2H, m), 7.99~7.89(8H, m), 7.77~7.75(3H, m), 7.62~7.35(11H, m), 7.20~7.16(2H, m) |
| 3-7 | δ = 8.55(1H, d), 8.31-8.30(3H, m), 8.19~8.13(2H, m), 7.99~7.89(5H, m), 7.77~7.75(5H, m), 7.62~7.35(14H, m), 7.20~7.16(2H, m) |
| 3-31 | δ = 8.55(1H, d), 8.30(1H, d), 8.21~8.13(4H, m), 7.99~7.89(4H, m), 7.77~7.35(20H, m), 7.20~7.16(2H, m) |
| 3-32 | δ = 8.55(1H, d), 8.30(1H, d), 8.21~8.13(3H, m), 7.99~7.89(8H, m), 7.77~7.35(17H, m), 7.20~7.16(2H, m) |
| 4-1 | δ = 8.28(4H, d), 7.95(2H,d), 7.75(2H,d), 7.64(2H, s), 7.52~7.41(11H, m) |
| 4-3 | δ = 8.28(4H, d), 8.00~7.92(5H, m), 7.75~7.73(3H, m), 7.64~7.41(11H, m) |
| 4-5 | δ = 9.15(1H, s), 8.93(2H, d), 8.28(4H, d), 8.12~8.04(3H, m), 7.95~7.75(8H, m), 7.64(2H, s), 7.51~7.41(8H, m) |
| 4-6 | δ = 8.45(1H, d), 8.28(4H, d), 8.00~7.95(5H, m), 7.86(1H, d), 7.75(2H, d), 7.64(2H, s), 7.52~7.41(8H, m) |

TABLE 6-continued

| Compound Number | $^1$H NMR (CDCl$_3$, 200 Mz) |
|---|---|
| 4-10 | δ = 8.28(4H, d), 7.95~7.89(3H, m), 7.81-7.64 (8H, m), 7.51-7.32(8H, m) |
| 4-15 | 8.28 (4H, d), 7.95(2H, d), 7.87(1H, d), 7.75(2H, d), 7.64~7.63(3H, m), 7.55~7.28(1H, m), 1.72(6H, s) |
| 4-20 | δ = 8.28(4H, d), 8.18~8.12(2H, m), 8.00~7.95(3H, m), 7.77~7.75(3H, m), 7.65~7.41 (15H, m) |
| 4-26 | δ = 8.28(4H, d), 7.95(2H, d), 7.75(2H, d), 7.64(2H, s), 7.52~7.41(11H, m), 7.25 (4H, s) |
| 4-29 | δ = 9.15(1H, s), 8.93(2H, d), 8.28(4H, d), 8.12(3H, m), 8.04(1H, d), 7.95~~7.75(11H, m), 7.64(2H, s), 7.51~7.41(10H, m) |
| 4-30 | δ = 9.15 (1H, s), 8.93(2H, d), 8.28(4H, d), 8.18~8.04(4H, m), 7.95~7.41(20H, m) |
| 4-31 | δ = 9.15 (1H, s), 8.93(2H, d), 8.28(4H, d), 8.18~8.12(3H, m), 8.04(1H, d), 7.95~7.40(24H, m) |
| 4-42 | δ = 8.55 (1H, d), 8.28(4H, d), 8.09(1H, s), 7.95~7.87(4H, m), 7.77~7.69(6H, m), 7.52~7.33(16H, m) |
| 4-50 | δ = 9.15(1H, s), 8.93(2H, d), 8.28(2H, d), 8.12~7.64(18H, m), 7.51~7.38 (6H, m) |
| 4-55 | δ = 9.15(1H, s), 8.93(2H, d), 8.45(1H, d), 8.28(2H, d), 8.18~7.41(27H, m) |
| 4-59 | δ = 9.15(1H, s), 8.93(2H, d), 8.55(1H, d), 8.28(2H, d), 8.18~8.04(5H, m), 7.94~7.25(27H, m) |
| 4-63 | δ = 9.15(1H, s), 8.93(2H, d), 8.28(2H, d), 8.18~8.12(3H, m), 8.04(1H, d), 7.88~7.31(24H, m), 1.72(6H, s) |
| 4-68 | δ = 9.15(1H, s), 8.93(2H, d), 8.28(2H, d), 8.18~8.12(3H, m), 8.04(1H, d), 7.95~7.41(28H, m), 7.25(2H, d) |
| 4-74 | δ = 9.15(1H, s), 8.93(2H, d), 8.28(4H, d), 8.18~8.04(4H, m), 7.95~7.75(10H, m), 7.64(2H, s), 7.51~7.41(6H, m), 7.25(2H, d) |
| 5-5 | δ = 9.15(1H, s), 9.35(2H, d), 8.28(4H, d), 8.12~8.04(9H, m), 7.88~7.82(5H, m), 7.51-7.41(6H, m) |
| 5-20 | δ = 8.28(4H, d), 8.18~8.00(8H, m), 7.82~7.77(2H, m), 7.63~7.41 (13H, m) |
| 5-31 | δ = 9.15(1H, s), 8.93(2H, d), 8.28(4H, d), 8.18~8.05(9H, m), 7.88~7.82(5H, m), 7.70(2H, s), 7.57~7.41(12H, m) |

TABLE 7

| Compound | FD-MS | Compound | FD-MS |
|---|---|---|---|
| 1-1 | m/z = 475.17 (C$_{33}$H$_{21}$N$_3$O = 475.55) | 1-3 | m/z = 525.18 (C$_{37}$H$_{23}$N$_3$O = 525.61) |
| 1-5 | m/z = 625.22 (C$_{45}$H$_{27}$N$_3$O = 625.73) | 1-6 | m/z = 581.16 (C$_{39}$H$_{23}$N$_3$OS = 581.69) |
| 1-10 | m/z = 565.18 (C$_{39}$H$_{23}$N$_3$O$_2$ = 565.63) | 1-15 | m/z = 591.23 (C$_{42}$H$_{29}$N$_3$O = 591.71) |
| 1-20 | m/z = 640.23 (C$_{45}$H$_{28}$N$_4$O = 640.75) | 1-26 | m/z = 551.20 (C$_{39}$H$_{25}$N$_3$O = 551.65) |
| 1-29 | m/z = 777.28 (C$_{57}$H$_{35}$N$_3$O = 777.93) | 1-30 | m/z = 701.25 (C$_{51}$H$_{31}$N$_3$O = 701.83) |
| 1-31 | m/z = 777.28 (C$_{57}$H$_{35}$N$_3$O = 777.93) | 1-42 | m/z = 716.26 (C$_{51}$H$_{32}$N$_4$O = 716.84) |
| 1-50 | m/z = 715.23 (C$_{51}$H$_{29}$N$_3$O$_2$ = 715.81) | 1-55 | m/z = 807.23 (C$_{57}$H$_{33}$N$_3$OS = 807.97) |
| 1-59 | m/z = 866.30 (C$_{63}$H$_{38}$N$_4$O = 867.02) | 1-63 | m/z = 817.31 (C$_{60}$H$_{39}$N$_3$O = 817.99) |
| 1-68 | m/z = 853.31 (C$_{63}$H$_{39}$N$_3$O = 854.02) | 1-74 | m/z = 701.25 (C$_{51}$H$_{31}$N$_3$O = 701.83) |
| 2-5 | m/z = 641.19 (C$_{45}$H$_{27}$N$_3$S = 641.79) | 2-20 | m/z = 656.20 (C$_{45}$H$_{28}$N$_4$S = 656.81) |
| 2-31 | m/z = 793.26 (C$_{57}$H$_{35}$N$_3$O = 793.99) | 3-3 | m/z = 560.23 (C$_{42}$H$_{28}$N$_2$ = 560.70) |
| 3-4 | m/z = 560.23 (C$_{42}$H$_{28}$N$_2$ = 560.70) | 3-7 | m/z = 636.26 (C$_{48}$H$_{32}$N$_2$ = 636.80) |
| 3-31 | m/z = 636.26 (C$_{48}$H$_{32}$N$_2$ = 636.80) | 3-32 | m/z = 636.26 (C$_{48}$H$_{32}$N$_2$ = 636.80) |

TABLE 7-continued

| Compound | FD-MS | Compound | FD-MS |
|---|---|---|---|
| 4-1 | m/z = 475.17 ($C_{33}H_{21}N_3O$ = 475.55) | 4-3 | m/z = 525.18 ($C_{37}H_{23}N_3O$ = 525.61) |
| 4-5 | m/z = 625.22 ($C_{45}H_{27}N_3O$ = 625.73) | 4-6 | m/z = 581.16 ($C_{39}H_{23}N_3OS$ = 581.69) |
| 4-10 | m/z = 565.18 ($C_{39}H_{23}N_3O_2$ = 565.63) | 4-15 | m/z = 591.23 ($C_{42}H_{29}N_3O$ = 591.71) |
| 4-20 | m/z = 640.23 ($C_{45}H_{28}N_4O$ = 640.75) | 4-26 | m/z = 551.20 ($C_{39}H_{25}N_3O$ = 551.65) |
| 4-29 | m/z = 777.28 ($C_{57}H_{35}N_3O$ = 777.93) | 4-30 | m/z = 701.25 ($C_{51}H_{31}N_3O$ = 701.83) |
| 4-31 | m/z = 777.28 ($C_{57}H_{35}N_3O$ = 777.93) | 4-42 | m/z = 716.26 ($C_{51}H_{32}N_4O$ = 716.84) |
| 4-50 | m/z = 715.23 ($C_{51}H_{29}N_3O_2$ = 715.81) | 4-55 | m/z = 807.23 ($C_{57}H_{33}N_3OS$ = 807.97) |
| 4-59 | m/z = 866.30 ($C_{63}H_{38}N_4O$ = 867.02) | 4-63 | m/z = 817.31 ($C_{60}H_{39}N_3O$ = 817.99) |
| 4-68 | m/z = 853.31 ($C_{63}H_{39}N_3O$ = 854.02) | 4-74 | m/z = 701.25 ($C_{51}H_{31}N_3O$ = 701.83) |
| 5-5 | m/z = 641.19 ($C_{45}H_{27}N_3S$ = 641.79) | 5-20 | m/z = 656.20 ($C_{45}H_{28}N_4S$ = 656.81) |
| 5-31 | m/z = 793.26 ($C_{57}H_{35}N_3O$ = 793.99) | | |

<Experimental Example 1>—Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), a hole injection layer 4,4',4"-tris[2-naphthyl(phenyl)amino]triphenylamine (2-TNATA) and a hole transfer layer N,N'-di(1-naphthyl)-N,N'-diphenyl-(1,1'-biphenyl)-4,4'-diamine (NPB), which are common layers, were formed□ㅏ.

A light emitting layer was thermal vacuum deposited thereon as follows. The light emitting layer was deposited to 400 Å using a compound described in the following [Table 8] as a host, tris(2-phenylpyridine)iridium (Ir(ppy)$_3$) as a green phosphorescent dopant, and doping Ir(ppy)$_3$ to the host by 7% of the deposited thickness of the light emitting layer. After that, BCP was deposited to 60 Å as a hole blocking layer, and Alq$_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Electroluminescent Device For the organic electroluminescent devices manufactured as above, electroluminescent light emission (EL) properties were measured using M7000 manufactured by McScience Inc., and with the measurement results, 190 when standard luminance was 6,000 cd/m$^2$ was measured using a lifetime test system (M6000) manufactured by McScience Inc. The organic electroluminescent device according to one embodiment of the present disclosure has properties as in Table 8.

TABLE 8

| | Light Emitting Layer Compound | Driving Voltage (V) | Efficiency (cd/A) | Color Coordinate (x, y) | Lifetime ($T_{90}$) |
|---|---|---|---|---|---|
| Example 1 | 1-1 | 4.71 | 57.2 | (0.243, 0.714) | 152 |
| Example 2 | 1-3 | 4.32 | 68.3 | (0.241, 0.711) | 131 |
| Example 3 | 1-5 | 4.33 | 74.2 | (0.241, 0.714) | 221 |
| Example 4 | 1-6 | 4.66 | 71.1 | (0.241, 0.715) | 175 |
| Example 5 | 1-10 | 4.69 | 69.2 | (0.231, 0.712) | 179 |
| Example 6 | 1-15 | 4.66 | 71.2 | (0.251, 0.714) | 187 |
| Example 7 | 1-20 | 4.38 | 76.4 | (0.241, 0.711) | 200 |
| Example 8 | 1-26 | 4.67 | 71.2 | (0.251, 0.714) | 201 |
| Example 9 | 1-29 | 4.48 | 70.2 | (0.241, 0.714) | 206 |
| Example 10 | 1-30 | 4.36 | 78.9 | (0.242, 0.713) | 239 |
| Example 11 | 1-31 | 4.35 | 79.2 | (0.241, 0.714) | 261 |
| Example 12 | 1-42 | 4.45 | 72.8 | (0.251, 0.714) | 189 |
| Example 13 | 1-50 | 4.42 | 75.7 | (0.251, 0.714) | 221 |
| Example 14 | 1-55 | 4.33 | 75.2 | (0.247, 0.727) | 227 |
| Example 15 | 1-59 | 4.11 | 72.2 | (0.231, 0.711) | 211 |
| Example 16 | 1-63 | 4.31 | 79.2 | (0.246, 0.717) | 243 |
| Example 17 | 1-68 | 4.41 | 75.8 | (0.231, 0.711) | 249 |
| Example 18 | 1-74 | 4.66 | 71.1 | (0.248, 0.711) | 196 |
| Example 19 | 2-5 | 4.41 | 68.4 | (0.246, 0.717) | 176 |
| Example 20 | 2-20 | 4.33 | 69.1 | (0.233, 0.701) | 140 |
| Example 21 | 2-31 | 4.32 | 71.5 | (0.251, 0.713) | 199 |
| Example 22 | 3-3 | 4.75 | 51.2 | (0.254, 0.724) | 119 |
| Example 23 | 3-4 | 4.83 | 50.9 | (0.233, 0.703) | 101 |
| Example 24 | 3-7 | 4.73 | 52.2 | (0.234, 0.714) | 111 |
| Example 25 | 3-31 | 4.81 | 49.9 | (0.243, 0.693) | 112 |
| Example 26 | 3-32 | 4.74 | 55.2 | (0.251, 0.724) | 103 |
| Example 27 | 4-1 | 4.63 | 59.4 | (0.242, 0.713) | 142 |
| Example 28 | 4-3 | 4.21 | 67.4 | (0.243, 0.712) | 135 |
| Example 29 | 4-5 | 4.35 | 75.6 | (0.242, 0.716) | 189 |
| Example 30 | 4-6 | 4.53 | 76.4 | (0.241, 0.713) | 170 |
| Example 31 | 4-10 | 4.70 | 71.6 | (0.236, 0.715) | 181 |
| Example 32 | 4-15 | 4.47 | 77.2 | (0.247, 0.712) | 166 |
| Example 33 | 4-20 | 4.42 | 75.1 | (0.243, 0.712) | 210 |
| Example 34 | 4-26 | 4.54 | 70.1 | (0.249, 0.711) | 197 |

TABLE 8-continued

| | Light Emitting Layer Compound | Driving Voltage (V) | Efficiency (cd/A) | Color Coordinate (x, y) | Lifetime ($T_{90}$) |
|---|---|---|---|---|---|
| Example 35 | 4-29 | 4.12 | 69.8 | (0.242, 0.713) | 211 |
| Example 36 | 4-30 | 4.42 | 75.4 | (0.243, 0.718) | 224 |
| Example 37 | 4-31 | 4.30 | 80.3 | (0.242, 0.715) | 247 |
| Example 38 | 4-42 | 4.32 | 71.0 | (0.245, 0.717) | 199 |
| Example 39 | 4-50 | 4.39 | 74.7 | (0.249, 0.713) | 230 |
| Example 40 | 4-55 | 4.41 | 78.2 | (0.246, 0.725) | 219 |
| Example 41 | 4-59 | 4.18 | 74.4 | (0.239, 0.712) | 209 |
| Example 42 | 4-63 | 4.24 | 77.8 | (0.242, 0.716) | 238 |
| Example 43 | 4-68 | 4.31 | 78.6 | (0.233, 0.715) | 240 |
| Example 44 | 4-74 | 4.29 | 76.3 | (0.239, 0.712) | 211 |
| Example 45 | 5-5 | 4.21 | 69.8 | (0.245, 0.716) | 166 |
| Example 46 | 5-20 | 4.34 | 72.1 | (0.242, 0.711) | 162 |
| Example 47 | 5-31 | 4.22 | 70.8 | (0.249, 0.714) | 177 |
| Comparative Example 1 | Ref.1 | 5.14 | 48.9 | (0.246, 0.717) | 40 |
| Comparative Example 2 | Ref.2 | 5.26 | 47.6 | (0.255, 0.698) | 31 |
| Comparative Example 3 | Ref.3 | 5.13 | 50.5 | (0.254, 0.697) | 30 |
| Comparative Example 4 | Ref.4 | 5.64 | 43.9 | (0.236, 0.696) | 20 |
| Comparative Example 5 | Ref.5 | 5.54 | 45.9 | (0.246, 0.686) | 26 |
| Comparative Example 6 | Ref.6 | 5.67 | 47.0 | (0.251, 0.683) | 24 |
| Comparative Example 7 | Ref.7 | 5.30 | 45.0 | (0.246, 0.725) | 50 |
| Comparative Example 8 | Ref.8 | 5.23 | 43.1 | (0.239, 0.712) | 41 |
| Comparative Example 9 | Ref.9 | 5.62 | 46.0 | (0.243, 0.690) | 70 |
| Comparative Example 10 | Ref.10 | 5.33 | 48.1 | (0.230, 0.719) | 61 |

<Experimental Example 2>—Manufacture of Organic Light Emitting Device

A glass substrate on which ITO was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and UVO treatment was carried out for 5 minutes in a UV cleaner using UV. After that, the substrate was transferred to a plasma cleaner (PT), and plasma treatment was carried out under vacuum for ITO work function and remaining film removal, and the substrate was transferred to a thermal deposition apparatus for organic deposition.

On the transparent ITO electrode (anode), a hole injection layer 4,4',4''-tris[2-naphthyl(phenyl)amino]triphenylamine (2-TNATA) and a hole transfer layer N,N'-di(1-naphthyl)-N,N'-diphenyl-(1,1'-biphenyl)-4,4'-diamine (NPB), which are common layers, were formed.

A light emitting layer was thermal vacuum deposited thereon as follows. As for the light emitting layer, one type of compound described in Chemical Formula 1 and one type of compound described in Chemical Formula 25 were premixed, and then deposited to 400 Å in one source of supply as a host, and a green phosphorescent dopant was deposited by doping Ir(ppy)$_3$ by 7% of the light emitting layer deposition thickness. After that, BCP was deposited to 60 Å as a hole blocking layer, and Alq$_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å to manufacture an organic electroluminescent device.

Meanwhile, all the organic compounds required to manufacture the OLED were vacuum sublimation purified under $10^{-6}$ torr to $10^{-8}$ torr by each material to be used in the OLED manufacture.

2) Driving Voltage and Light Emission Efficiency of Organic Electroluminescent Device For the organic electroluminescent devices manufactured as above, electroluminescent light emission (EL) properties were measured using M7000 manufactured by McScience Inc., and with the measurement results, $T_{90}$ when standard luminance was 6,000 cd/m$^2$ was measured using a lifetime test system (M6000) manufactured by McScience Inc. The organic electroluminescent device according to one embodiment of the present disclosure has properties as in Table 9.

TABLE 9

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 48 | 1-31: 3-3 | 1:8 | 4.73 | 54.2 | (0.233, 0.714) | 289 |
| Example 49 | | 1:5 | 4.71 | 57.2 | (0.243, 0.714) | 283 |
| Example 50 | | 1:2 | 4.35 | 79.2 | (0.241, 0.714) | 402 |
| Example 51 | | 1:1 | 4.41 | 75.8 | (0.231, 0.711) | 388 |
| Example 52 | | 2:1 | 4.67 | 71.2 | (0.251, 0.714) | 342 |
| Example 53 | | 5:1 | 4.32 | 68.3 | (0.241, 0.711) | 273 |
| Example 54 | | 8:1 | 4.21 | 67.0 | (0.247, 0.727) | 261 |
| Example 55 | 1-68: 3-4 | 1:2 | 4.33 | 74.2 | (0.241, 0.714) | 360 |
| Example 56 | | 1:1 | 4.42 | 72.2 | (0.231, 0.711) | 350 |
| Example 57 | | 2:1 | 4.66 | 71.2 | (0.251, 0.714) | 328 |
| Example 58 | 1-20: 3-7 | 1:2 | 4.38 | 76.4 | (0.241, 0.714) | 349 |
| Example 59 | | 1:1 | 4.45 | 72.8 | (0.251, 0.714) | 328 |
| Example 60 | | 2:1 | 4.66 | 71.1 | (0.241, 0.711) | 305 |
| Example 61 | 1-30: 3-31 | 1:2 | 4.33 | 75.2 | (0.247, 0.727) | 365 |
| Example 62 | | 1:1 | 4.48 | 70.2 | (0.241, 0.714) | 343 |
| Example 63 | | 2:1 | 4.69 | 69.2 | (0.231, 0.711) | 316 |

TABLE 9-continued

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 64 | 2-31: 3-32 | 1:2 | 4.31 | 79.2 | (0.246, 0.717) | 387 |
| Example 65 | | 1:1 | 4.42 | 75.7 | (0.251, 0.714) | 363 |
| Example 66 | | 2:1 | 4.66 | 71.1 | (0.241, 0.711) | 332 |
| Example 67 | 4-31: 3-3 | 1:8 | 4.77 | 56.4 | (0.232, 0.714) | 280 |
| Example 68 | | 1:5 | 4.69 | 57.9 | (0.241, 0.712) | 279 |
| Example 69 | | 1:2 | 4.44 | 81.3 | (0.243, 0.714) | 399 |
| Example 70 | | 1:1 | 4.31 | 79.9 | (0.240, 0.713) | 391 |
| Example 71 | | 2:1 | 4.69 | 81.8 | (0.249, 0.713) | 335 |
| Example 72 | | 5:1 | 4.31 | 67.8 | (0.243, 0.712) | 284 |
| Example 73 | | 8:1 | 4.42 | 66.3 | (0.248, 0.725) | 267 |
| Example 74 | 4-68: 3-4 | 1:2 | 4.23 | 77.4 | (0.242, 0.714) | 359 |
| Example 75 | | 1:1 | 4.33 | 79.1 | (0.241, 0.713) | 362 |
| Example 76 | | 2:1 | 4.42 | 77.7 | (0.249, 0.713) | 330 |
| Example 77 | 4-20: 3-7 | 1:2 | 4.23 | 79.2 | (0.242, 0.715) | 355 |
| Example 78 | | 1:1 | 4.33 | 74.6 | (0.245, 0.712) | 323 |
| Example 79 | | 2:1 | 4.42 | 77.1 | (0.241, 0.714) | 311 |
| Example 80 | 4-30: 3-31 | 1:2 | 4.33 | 79.3 | (0.245, 0.725) | 355 |
| Example 81 | | 1:1 | 4.48 | 78.9 | (0.239, 0.712) | 342 |
| Example 82 | | 2:1 | 4.69 | 72.4 | (0.241, 0.714) | 300 |
| Example 83 | 5-31: 3-32 | 1:2 | 4.31 | 74.2 | (0.244, 0.714) | 372 |
| Example 84 | | 1:1 | 4.42 | 80.4 | (0.241, 0.713) | 370 |
| Example 85 | | 2:1 | 4.66 | 72.4 | (0.243, 0.712) | 342 |

Comparative Example 1

(Ref. 1)

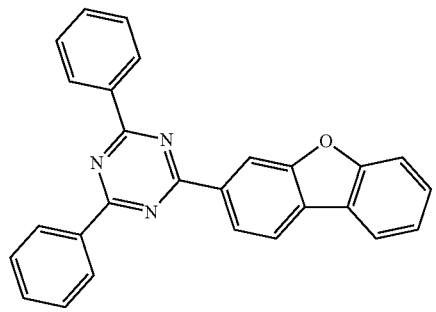

Comparative Example 2

(Ref. 2)

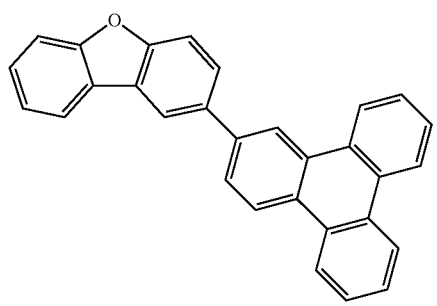

Comparative Example 3

(Ref. 3)

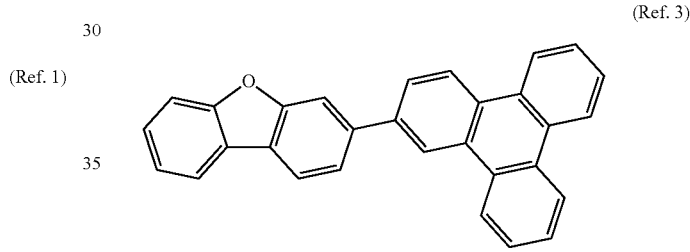

Comparative Example 4

(Ref. 4)

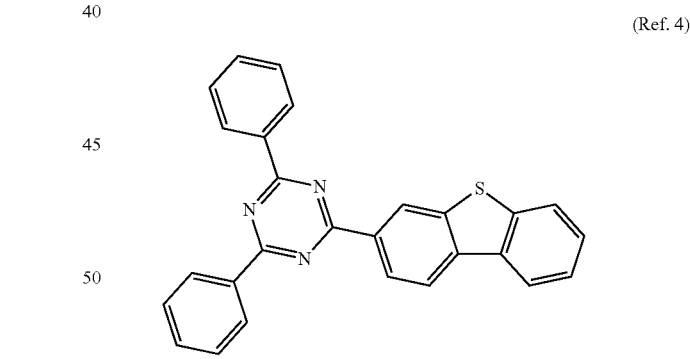

Comparative Example 5

(Ref. 5)

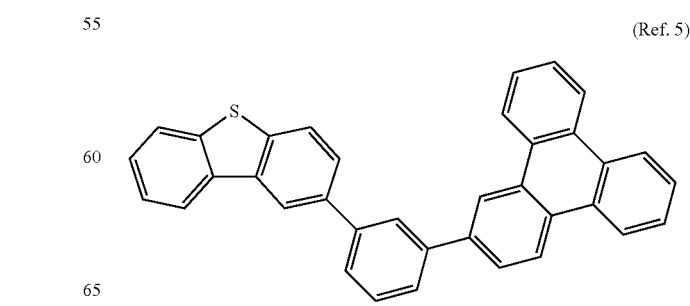

Comparative Example 6

(Ref. 6)

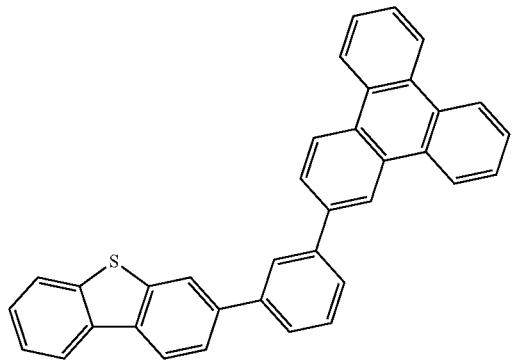

Comparative Example 7

(Ref. 7)

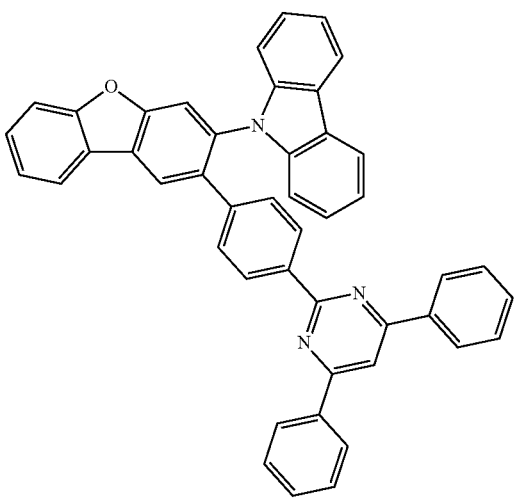

Comparative Example 8

(Ref. 8)

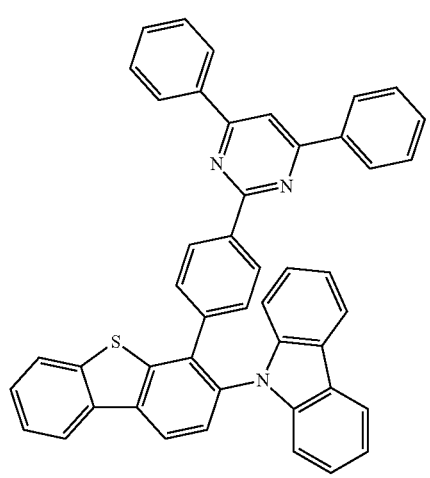

Comparative Example 9

(Ref. 9)

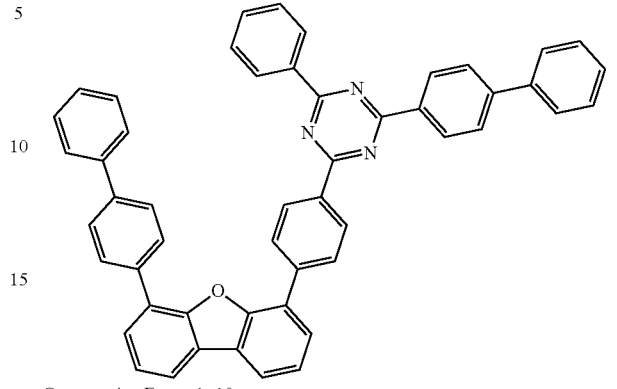

Comparative Example 10

(Ref.10)

Based on the device evaluation results, it was identified that the heterocyclic compound of the present disclosure had excellent efficiency, particularly, lifetime properties. For commercialization of a material, a long lifetime is a most important factor. Particularly, a device lifetime may decrease by an increase in the electron instability in the LUMO site due to strong electron donor properties of the oxygen of dibenzofuran or the sulfur of dibenzothiophene, and the influence is particularly bigger when a carbon position of the dibenzofuran or the dibenzothiophene is substituted with an electron transferring group due to ortho and para directivity. However, the compound according to the present disclosure may improve a device lifetime by having an N-containing ring positioned on the number 3 carbon.

As can be seen from the results of Table 8, the organic electroluminescent device using the organic electroluminescent device light emitting layer material of the present disclosure had a significantly improved lifetime as well as having a lower driving voltage and enhanced light emission efficiency compared to Comparative Examples 1 to 10.

Based on the results of Table 9, more superior efficiency and lifetime effects were obtained when comprising the compound of Chemical Formula 1 and the compound of Chemical Formula 2 at the same time in the organic material layer of the organic light emitting device. Such results may lead to a forecast that an exciplex phenomenon occurred when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with lifetime enhancement. In the disclosure of the present application, it was identified that excellent device properties were obtained when, as a light emitting layer host, using the compound of Chemical Formula 25 for a donor role and the compound of Chemical Formula 1 for an acceptor role.

Meanwhile, as can be seen from FIG. 4, the HOMO orbital of Compound 1-25 was delocalized to the aryl group of the dibenzofuran. However, it was identified that, when there were no substituents as in Comparative Examples 1 or 4, the HOMO was localized in the dibenzofuran and the dibenzothiophene failing to effectively stabilize holes and reducing a lifetime.

In addition, when there were no triazine group in the dibenzofuran or the dibenzothiophene group as in the compounds of Comparative Examples 2, 3, 5 and 6, electron mobility decreased breaking a balance between holes and electrons in the light emitting layer, and a lifetime was reduced.

When comparing the compounds of the present disclosure and the compounds of Comparative Examples 7 to 10, the constitution of the dibenzofuran and the dibenzothiophene substituted with a specific substituent (heteroaryl group or aryl group) and a triazine group is the same, however, the substituent position is different. Particularly, it was identified that, when bonding to an ortho position in the dibenzofuran and the dibenzothiophene as in Comparative Examples 7 and 8, the compound became structurally unstable due to steric hindrance between substituents reducing a lifetime.

When number 4 or number 2 of the dibenzofuran or the dibenzothiophene is substituted with a triazine group as in Comparative Examples 9 and 10, the triazine group needs to pull electrons injected into the light emitting layer to stabilize the electrons, however, it is considered that, with the influence of oxygen or sulfur of the electron-donating dibenzofuran or dibenzothiophene, a device lifetime is reduced due to instability of the injected electrons.

The invention claimed is:
1. A heterocyclic compound represented by the following Chemical Formula 1

[Chemical Formula 1]

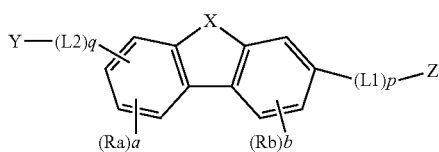

wherein, in Chemical Formula 1,
X is O or S;
Y is a hole transferring group or a substituted or unsubstituted aryl group;
Z is an electron transferring group;
L1 and L2 are the same as or different from each other, and each independently a direct bond, a substituted or unsubstituted arylene group; or a substituted or unsubstituted heteroarylene group, p and q are each an integer of 0 to 3, and, when p is 2 or greater, L1s are the same as or different from each other, and when q is 2 or greater, L2s are the same as or different from each other; and Ra and Rb are the same as or different from each other, and each independently selected from the group consisting of hydrogen; deuterium; halogen: a cyano group; a substituted or unsubstituted alkyl group; a substituted or unsubstituted alkenyl group; a substituted or unsubstituted alkynyl group; a substituted or unsubstituted alkoxy group: a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine, oxide group; and a substituted or unsubstituted amine group, or t or more groups adjacent to each other bond to each other to form a substituted or unsubstituted aliphatic or aromatic hydrocarbon ring or heteroring, a and b are each an integer of 1 to 3, and when a is 2 or greater, Ras are the same as or different from each other, and when b is 2 or greater, Rbs are the same as or different from each other.

2. The heterocyclic compound of claim 1, wherein Chemical Formula 1 is represented by the following Chemical Formula 2:

[Chemical Formula 2]

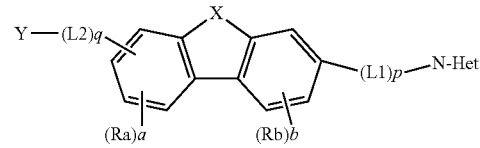

in chemical Formula 2,
N-Het is a substituted or unsubstituted monocyclic or polycyclic heteroarylene group comprising one or more Ns; and
the remaining substituents have the same definitions as in Chemical Formula 1.

3. The heterocyclic compound of claim 1, wherein Chemical Formula 1 is represented by one of the following Chemical Formula 3 to 5:

[Chemical Formula 3]

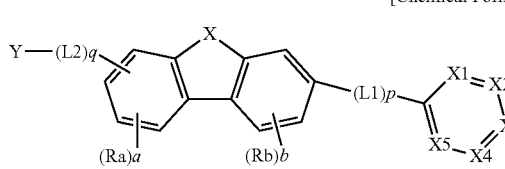

[Chemical Formula 4]

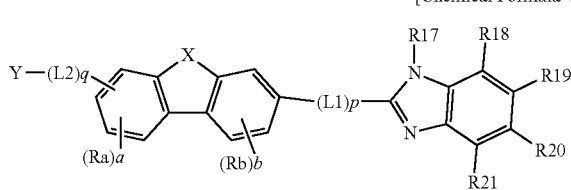

-continued

[Chemical Formula 5]

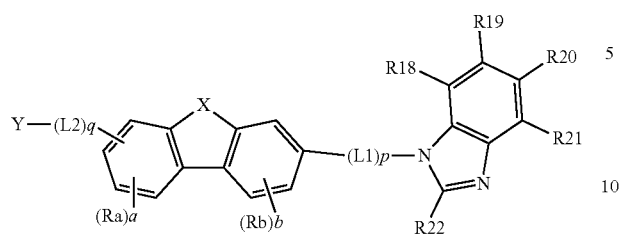

in Chemical Formula 3 to 5, 1X1 is CR11 or N, X2 is CR12 or N, X3 is CR13 or N, X4 is CR14 or N, and X5 is CR15 or N, R11 to R15 and R17 to R22 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or substituted aryl group; a substituted or substituted heteroaryl group: a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring and the remaining substituents have the same definitions as in Chemical Formula 1.

4. The heterocyclic compound of claim 1, wherein Chemical Formula 1 is represented by one of the following Chemical Formula 6 to 8:

[Chemical Formula 6]

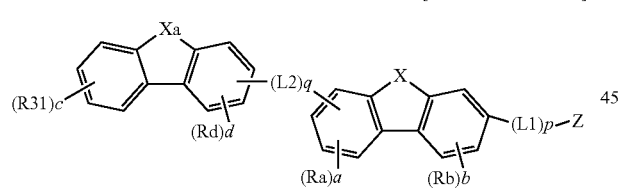

[Chemical Formula 7]

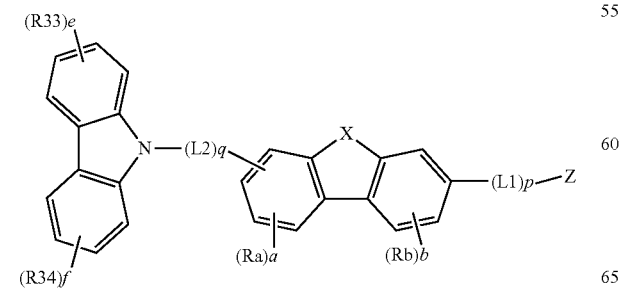

[Chemical Formula 8]

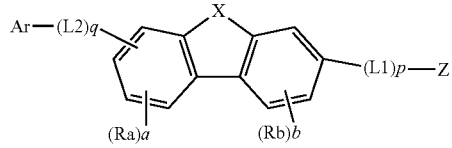

in Chemical Formula 6 to 8,

X is S, O, CReRd or NRe;

R31 t 3 R34, Re, Rd and R e same as or different from each other, and each independently selected from the group consisting of hydrogen deuterium; halogen; a cyano group; a substituted or unsubstituted alkyl group: a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or a substituted aryl group; a substituted or unsubstituted, heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring, or heteroring, c, e and f are each an integer of 0 to 4, d is an integer of 0 to 3, and when c is 2 or greater, R31 is are the same as or different from each other, when d is 2 or greater, R32s are the same as or different from each other, when c is 2 or greater, R33s are the same as or different from each other, and when f is 2 or greater, R34s are the same as or different from each other;

Ar is a substituted or unsubstituted aryl group; or a substituted or unsubstituted silyl group; and the remaining substituents have the same definitions as in Chemical Formula 1.

5. The heterocyclic compound of claim 3, wherein

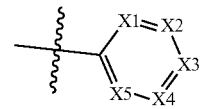

is represented by one of the following Chemical Formula 9 to 11:

[Chemical Formula 9]

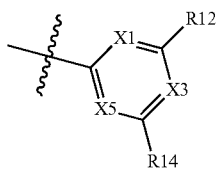

-continued

[Chemical Formula 10]

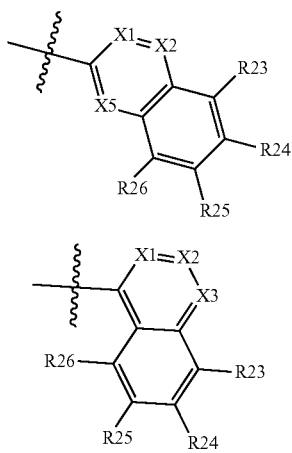

[Chemical Formula 11]

in Chemical Formula 9, one or more of X1, X3 and X5 are N, and the same definitions as in Chemical Formula 3;

in Chemical Formula 10, one or more of X1, X2 and X5 are N, and the rest have the same definitions as in Chemical Formula 3;

in Chemical Formula 11, one or more of X1 to X3 are N, and the rest to N3 are definitions as in Chemical Formula 3; and R12, R14 and R23 to R26 are the same as or different from each other, and each independently selected from the group consisting of hydrogen; deuterium; halogen; a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

6. The heterocyclic compound of claim 5, wherein Chemical Formula 9 is selected from among the following structural formula:

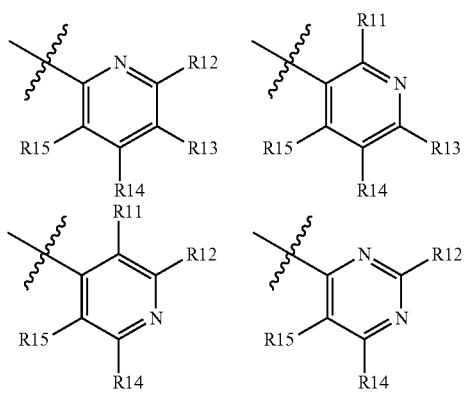

-continued

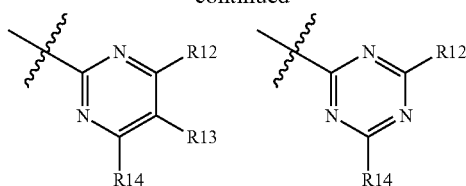

in the structural formula,

R11 to R15 are the same as or different from each other, and each, independently selected from the group consisting of hydrogen; deuterium; halogen: a cyano group; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group: a substituted or unsubstituted heterocycloalkyl group; a substituted or unsubstituted aryl group; a substituted or unsubstituted heteroaryl group; a substituted or unsubstituted phosphine oxide group; and a substituted or unsubstituted amine group, or two or more groups adjacent to each other bond to each other to form a substituted or unsubstituted aliphatic or aromatic hydrocarbon ring or heteroring.

7. The heterocyclic compound of claim 1, wherein Chemical Formula 1 is represented by the following Chemical Formula 15:

[Chemical Formula 15]

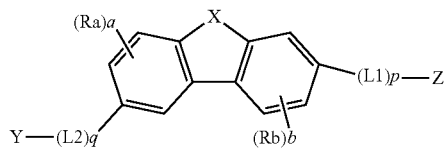

in Chemical Formula 15, substituents have the same definitions as in Chemical Formula 1.

8. The heterocyclic compound of claim 1, wherein Chemical Formula 1 is represented, by the following Chemical Formula 19:

[Chemical Formula 19]

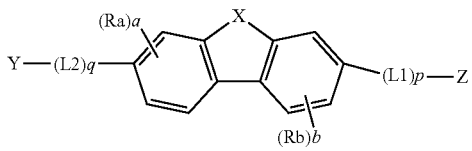

in Chemical Formula 19, substituents have the same definitions as in Chemical Formula 1.

9. The heterocyclic compound of claim 1, wherein Chemical Formula 1 is represented by any one of the following compounds:

281 282
1-1
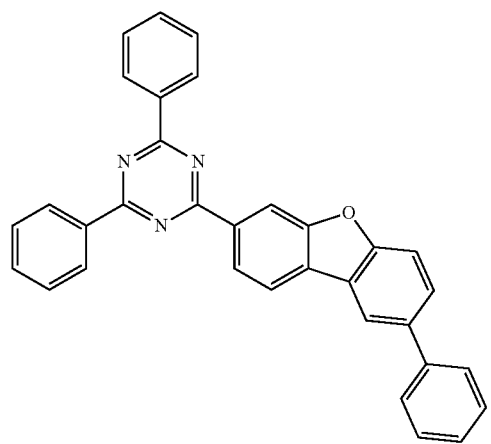
1-2
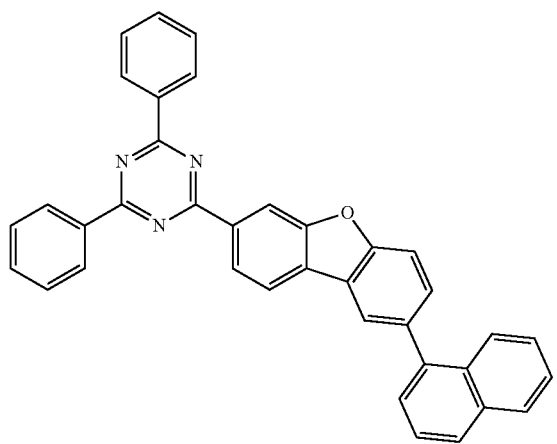
1-3
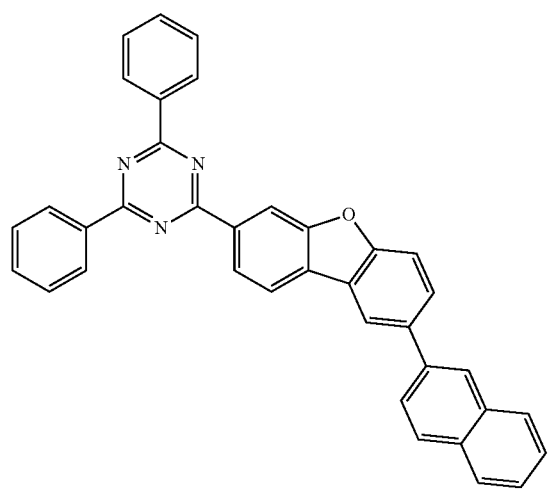
1-4
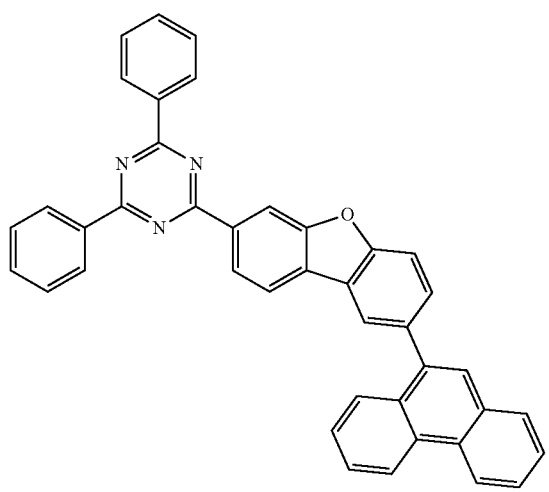
1-5
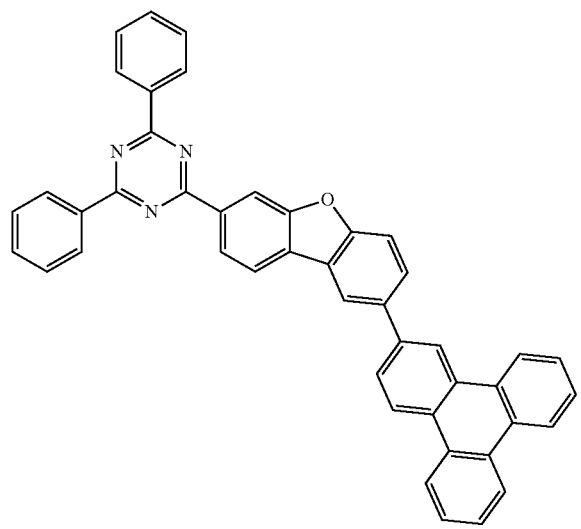
1-6
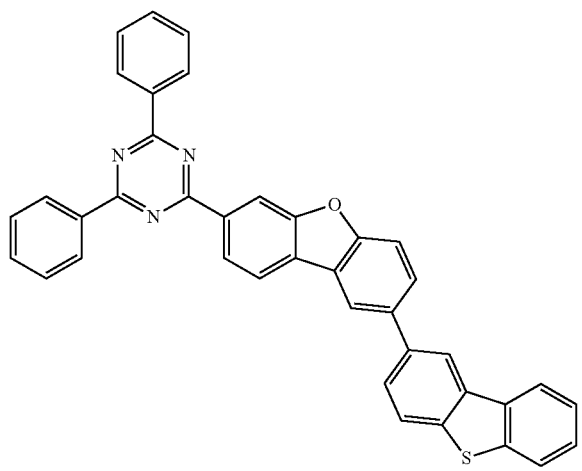

1-7
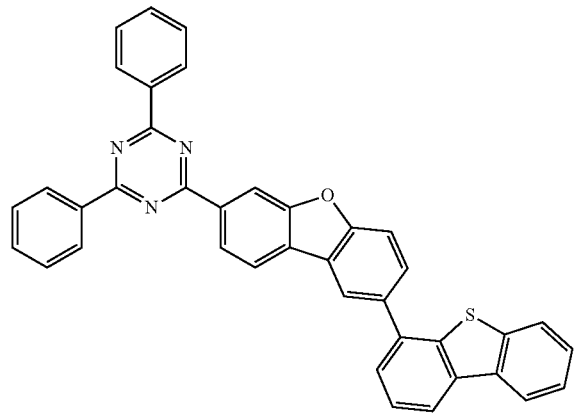
1-8
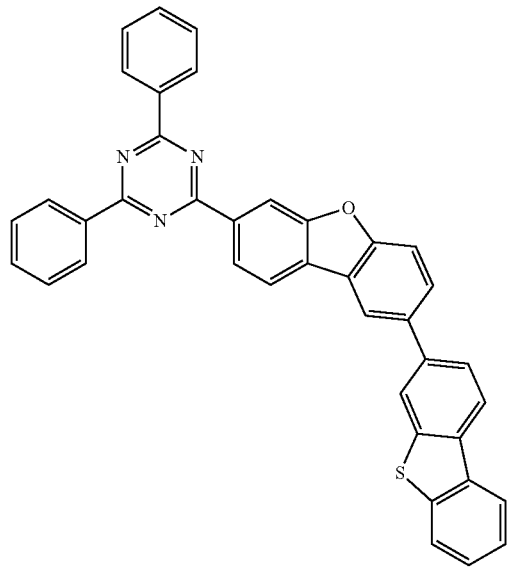
1-9
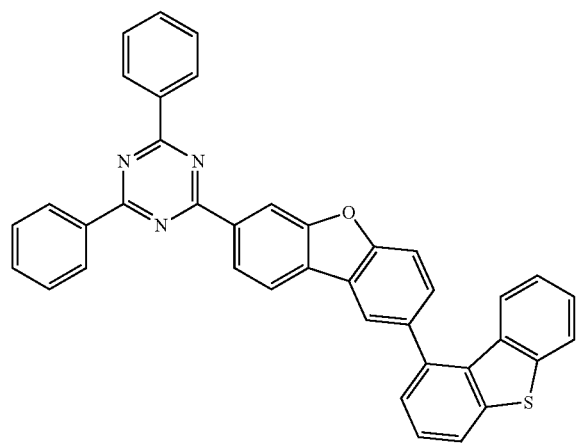
1-10
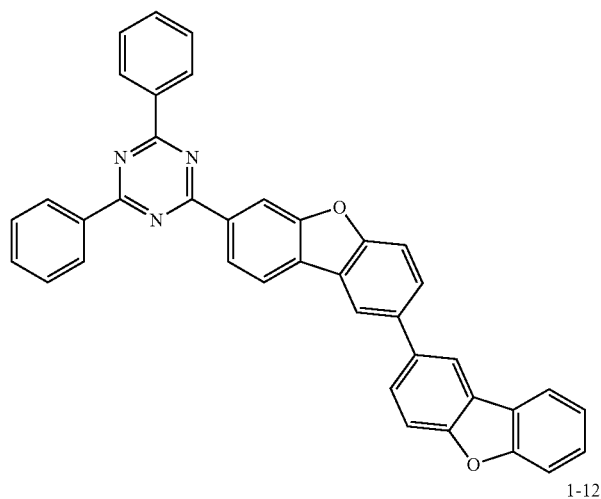
1-11
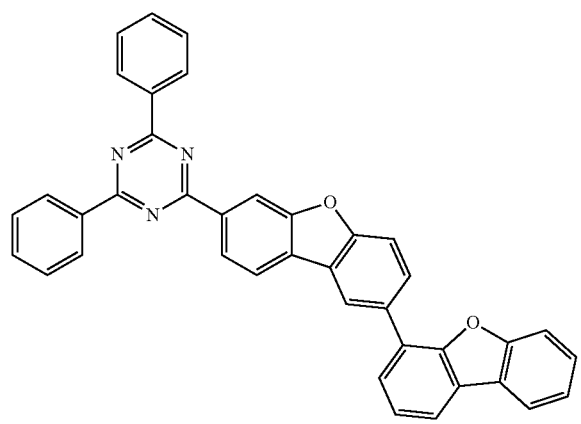
1-12
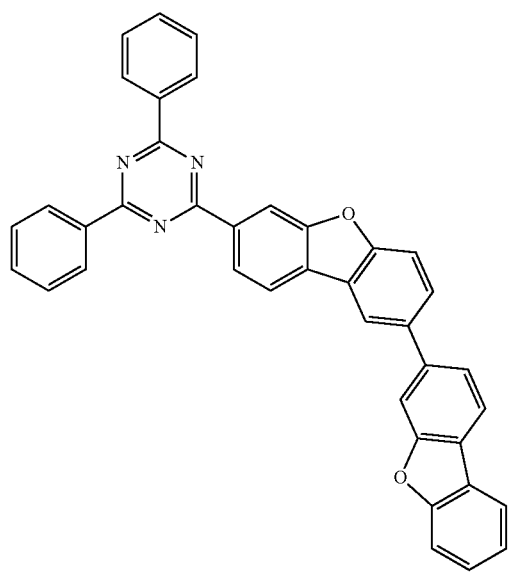

1-13
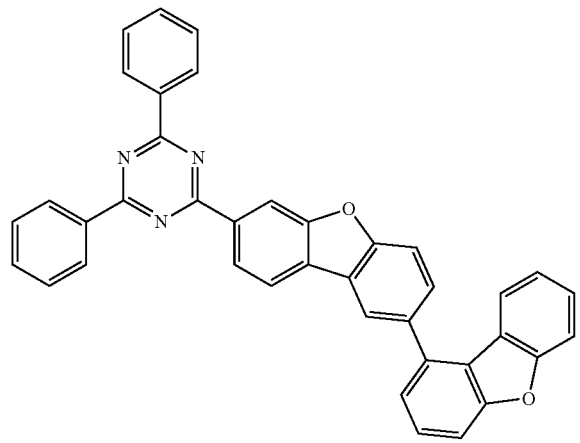
1-14
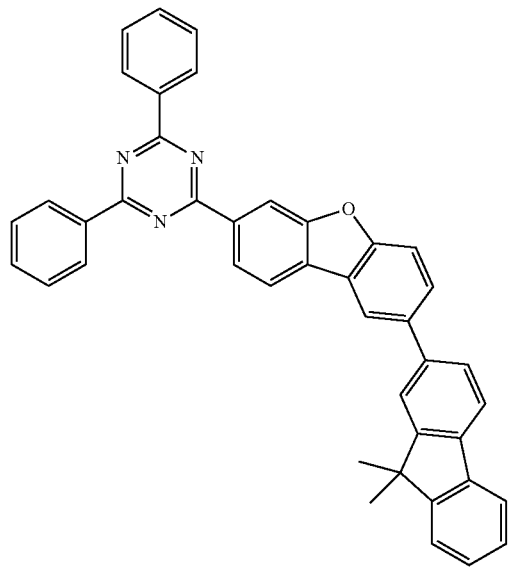
1-15
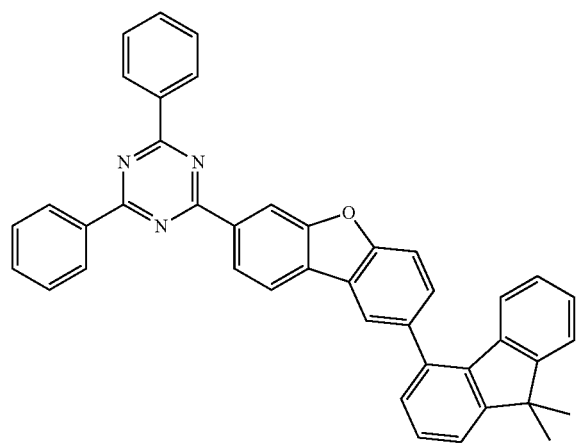
1-16
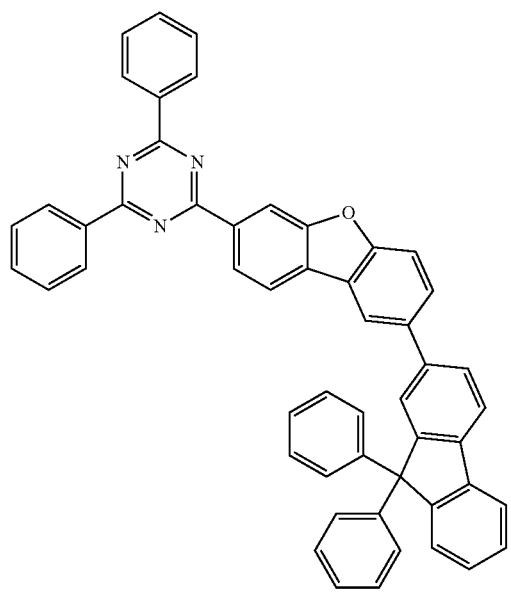

-continued
1-17
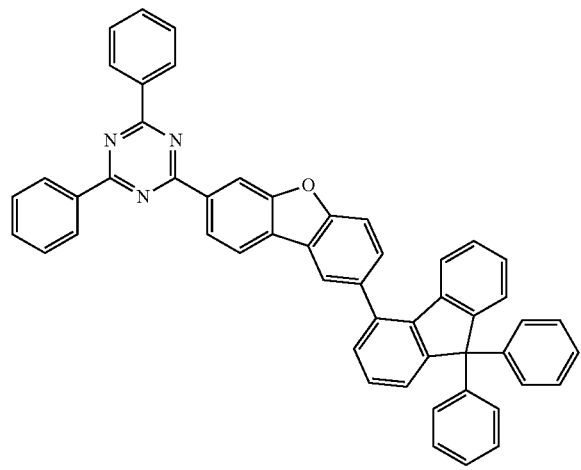
1-18
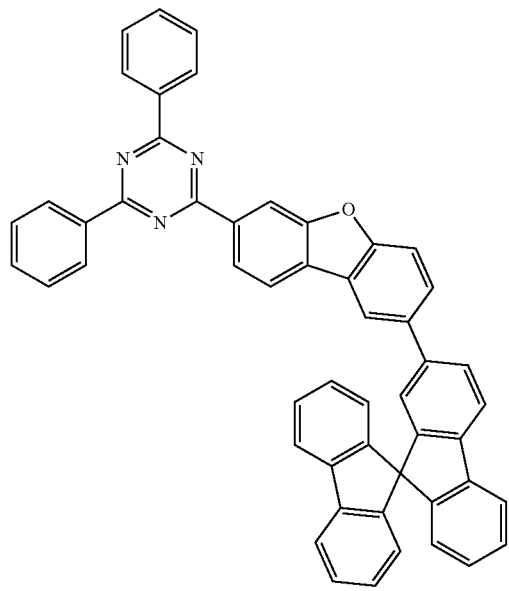
1-19
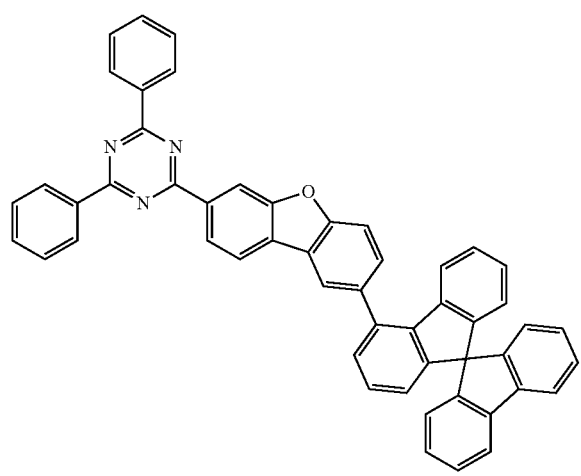
1-20
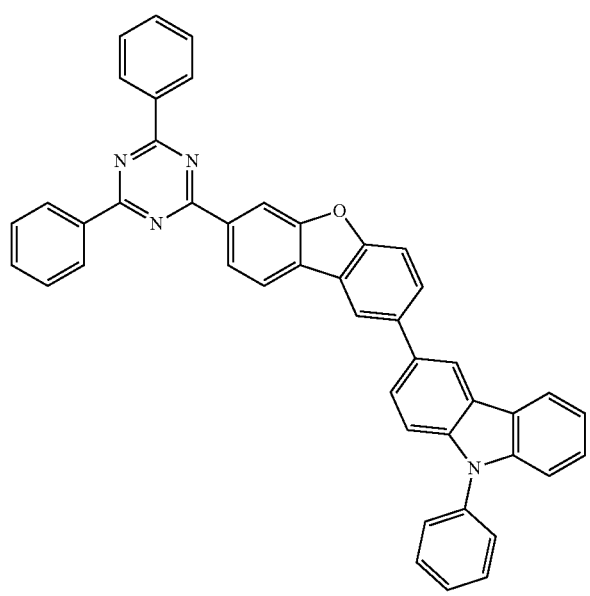

-continued
1-21
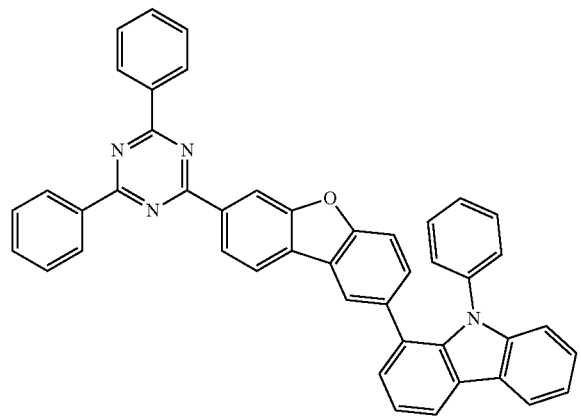
1-22
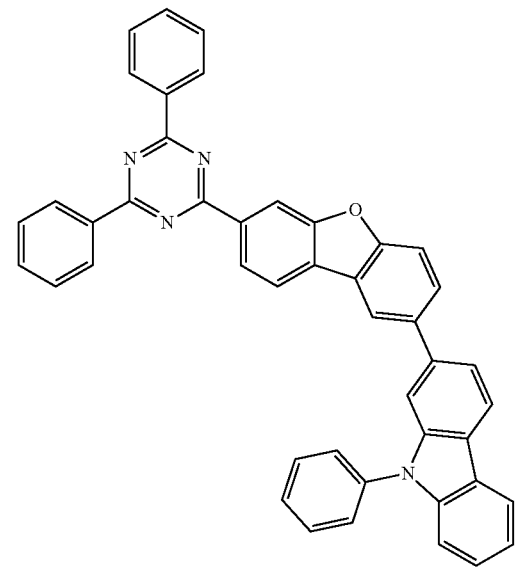
1-23
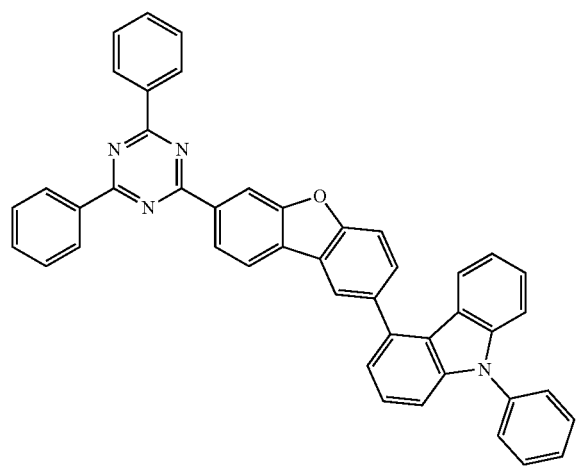
1-24
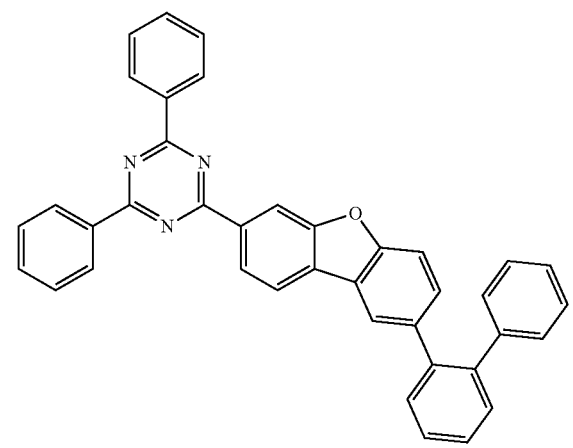
1-25
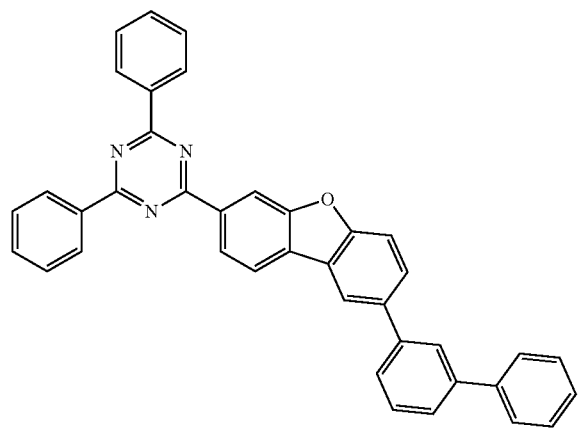
1-26
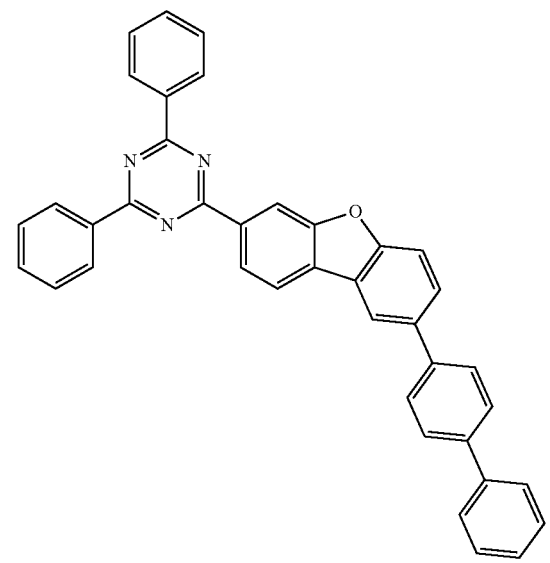

1-27
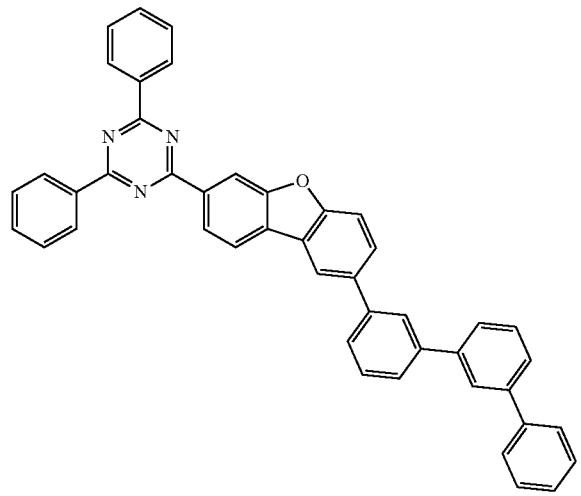
1-28
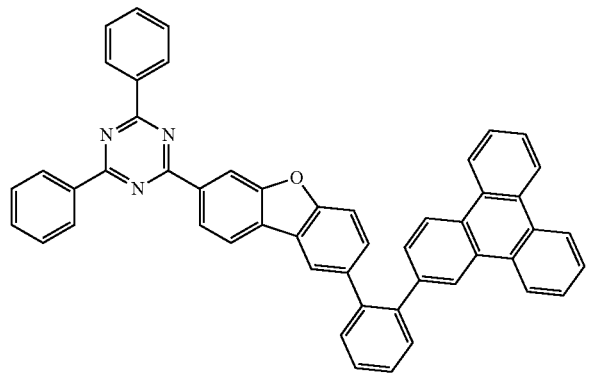
1-29
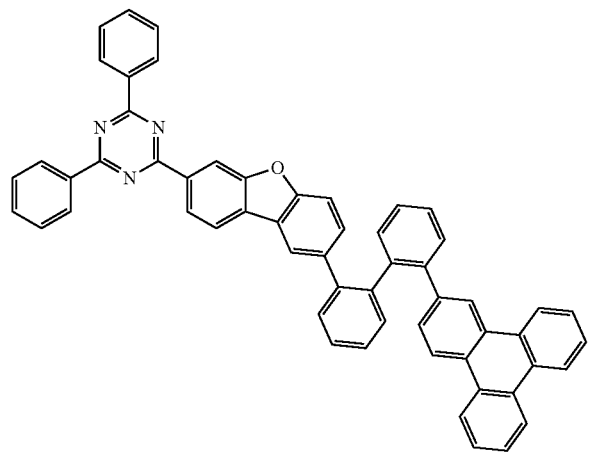
1-30
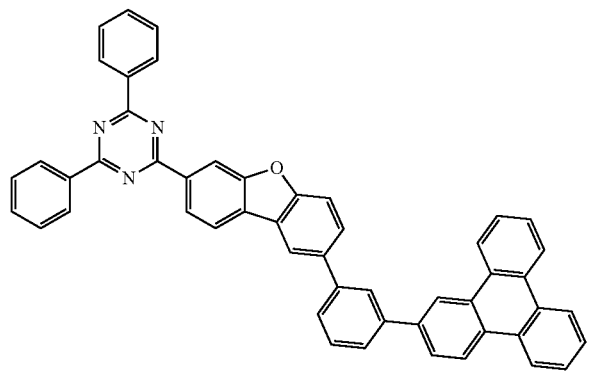
1-31
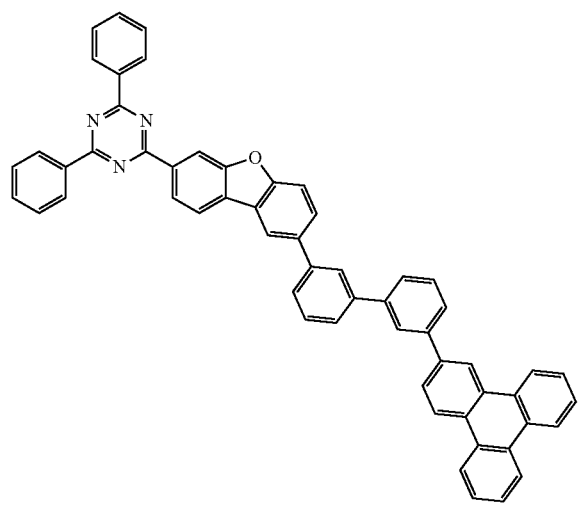
1-32
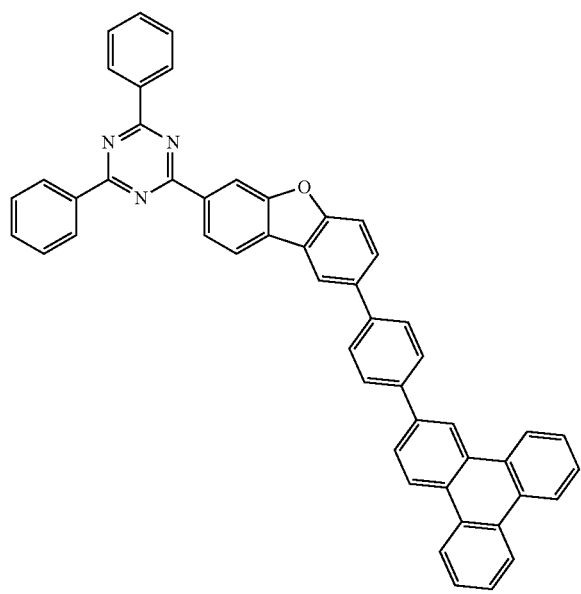

-continued
1-33
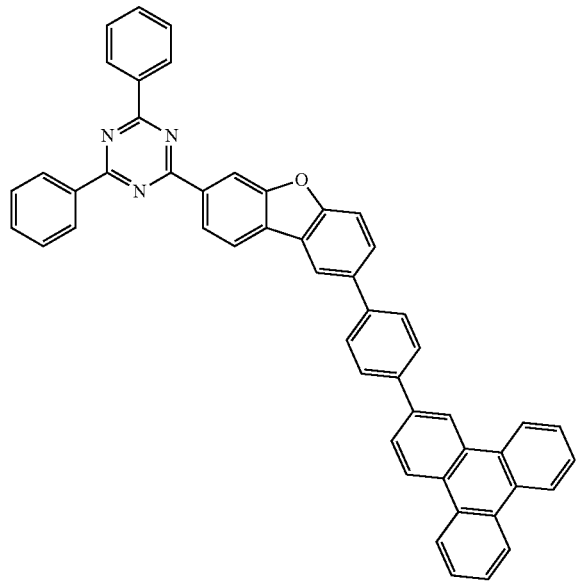
1-34
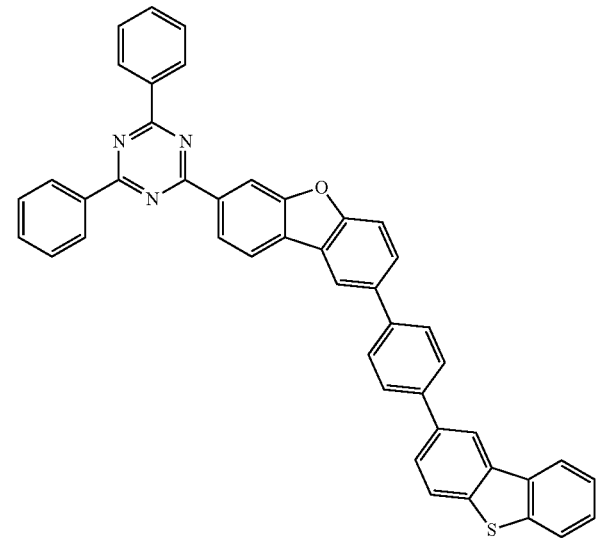
1-35
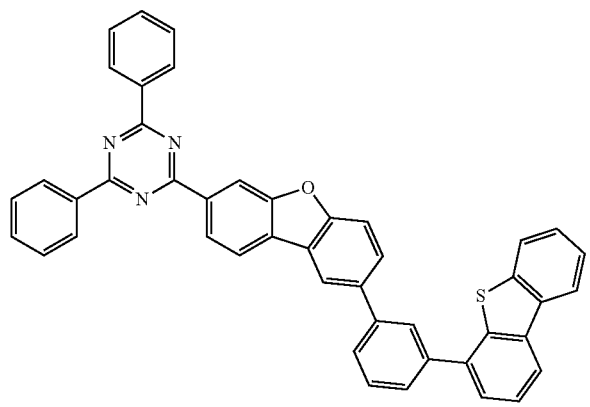
1-36
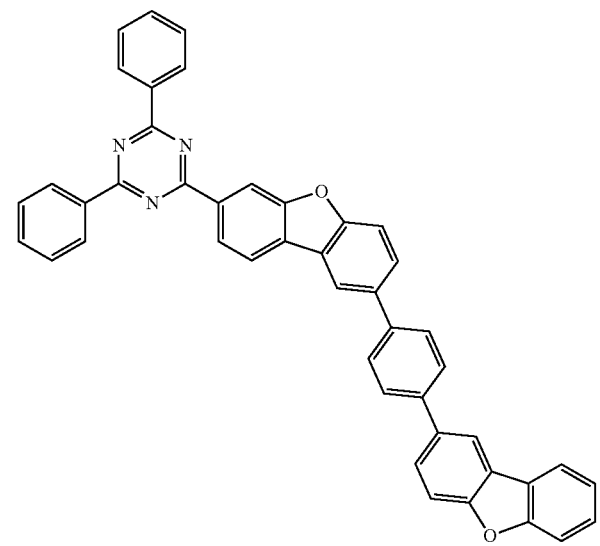
1-37
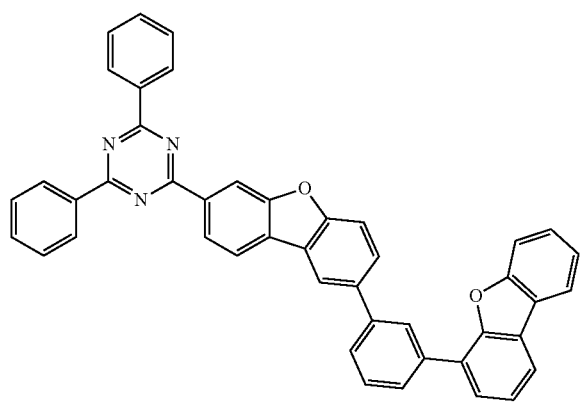
1-38
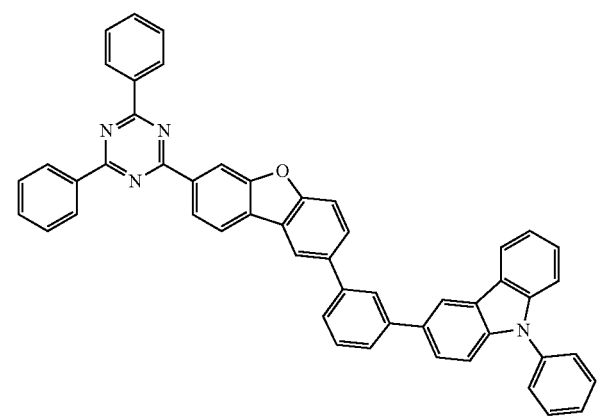

1-39
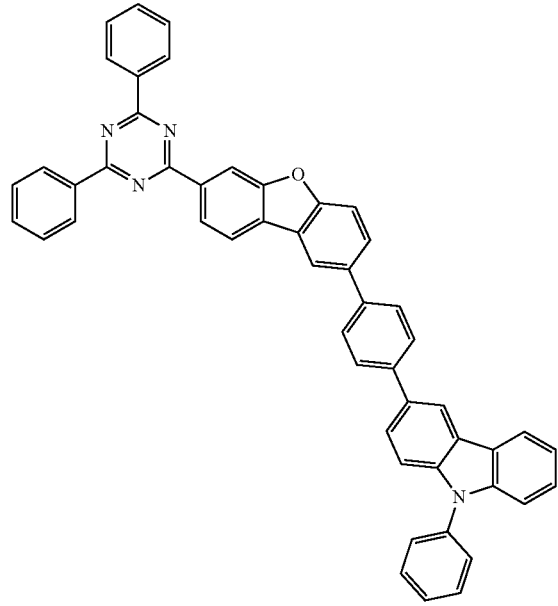
1-40
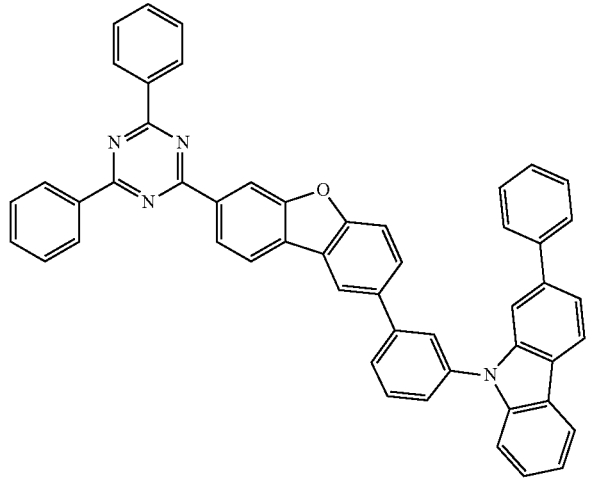
1-41
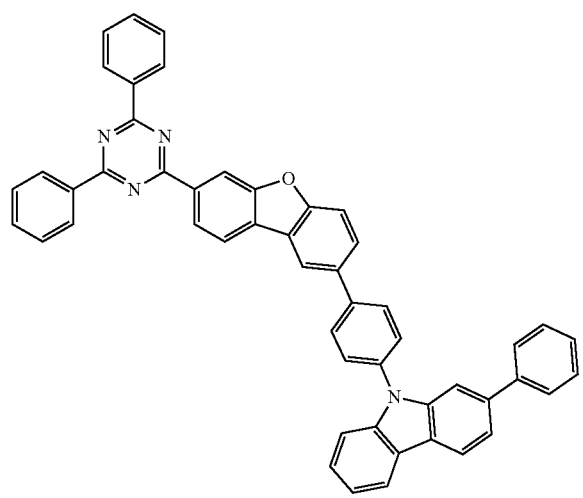
1-42
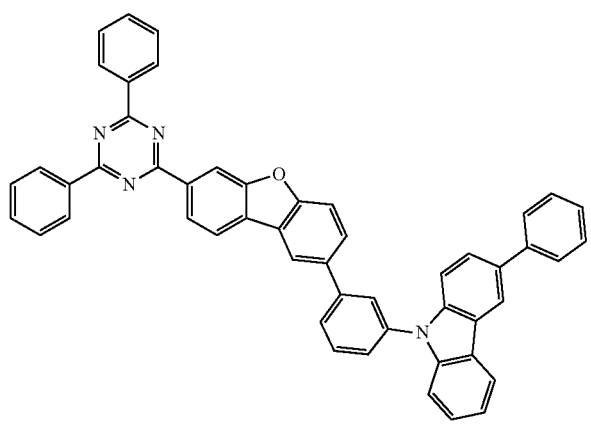

-continued
1-43
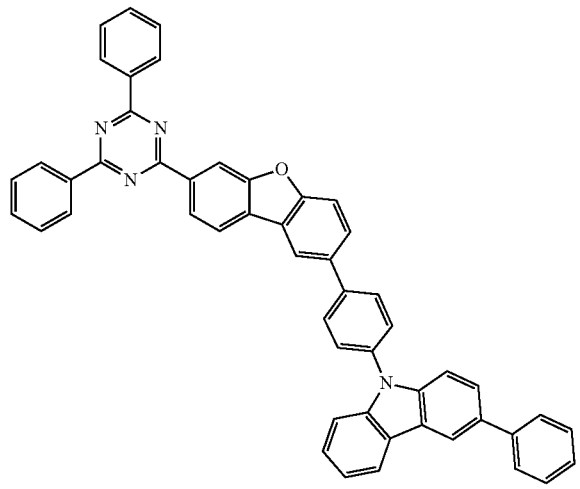
1-44
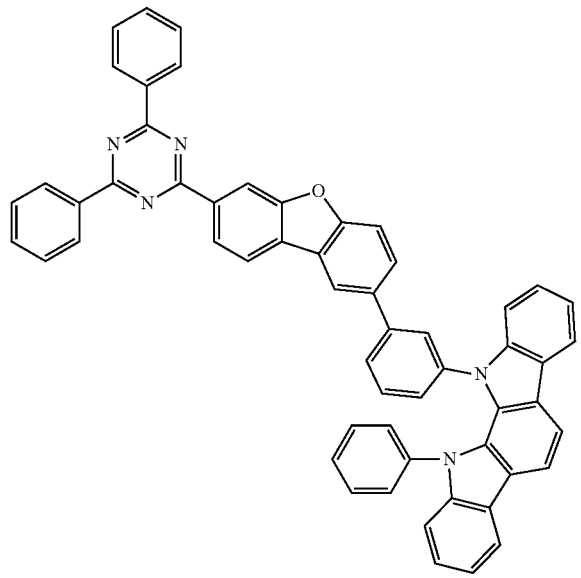
1-45
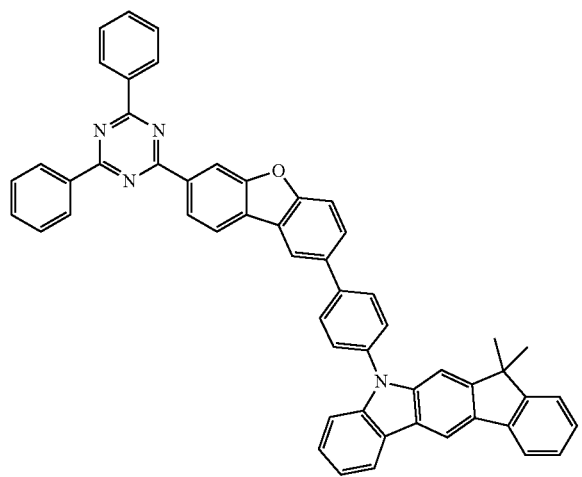
1-46
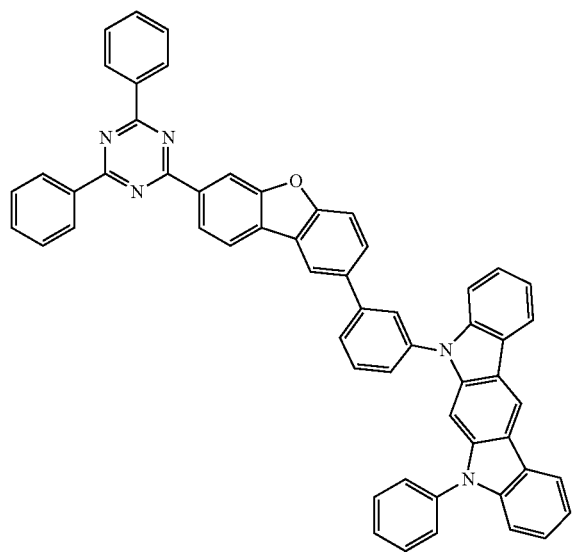

1-47
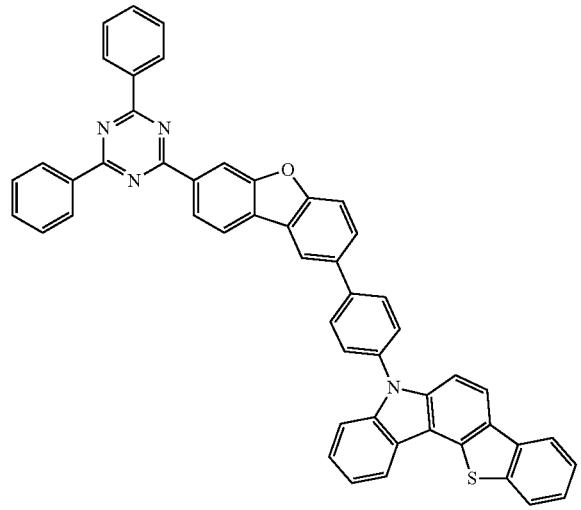
1-48
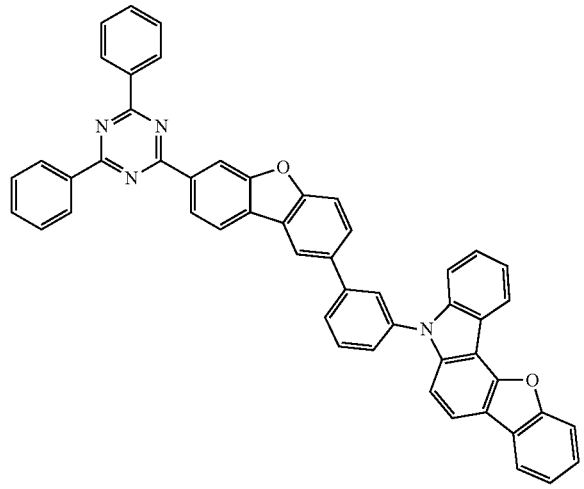
1-49
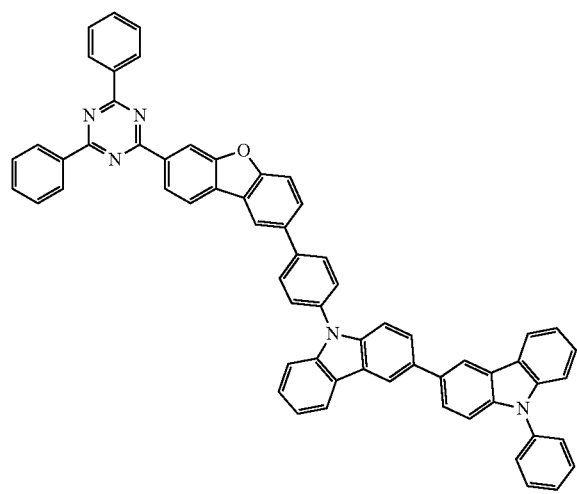
1-50
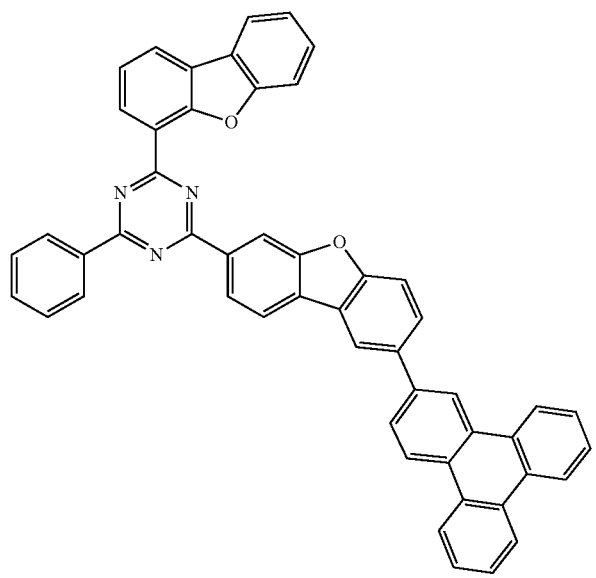

-continued
1-51
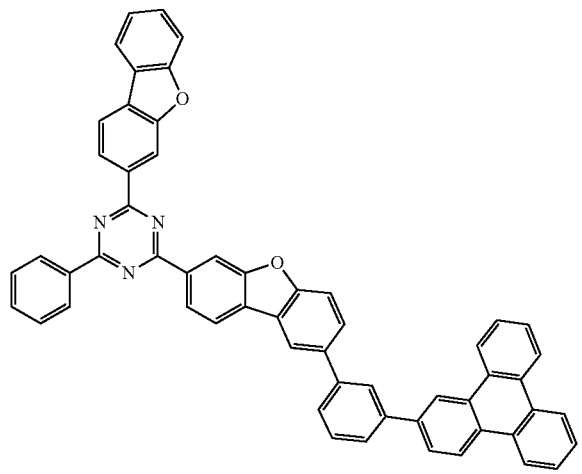
1-52
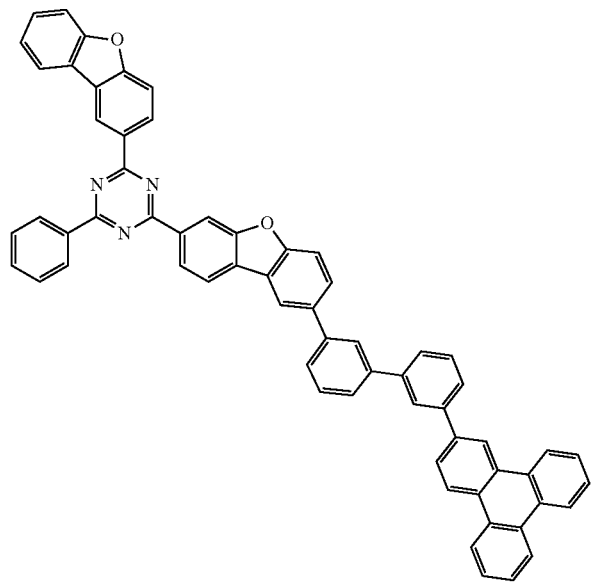
1-53
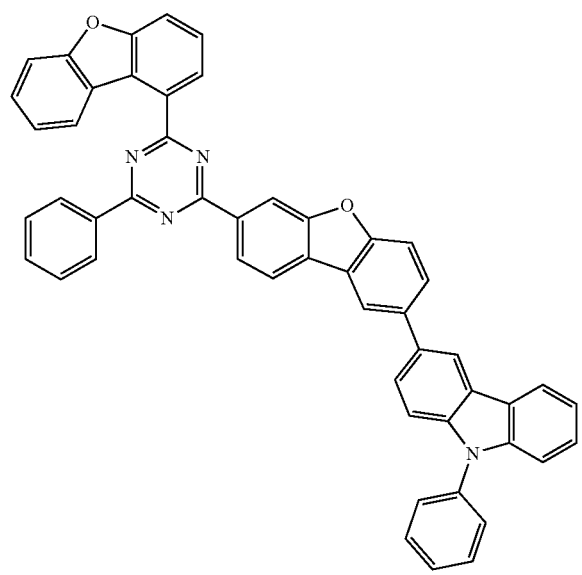
1-54
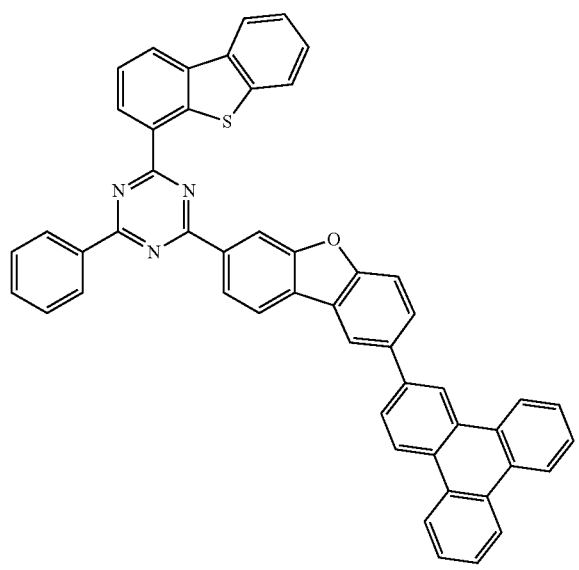

1-55
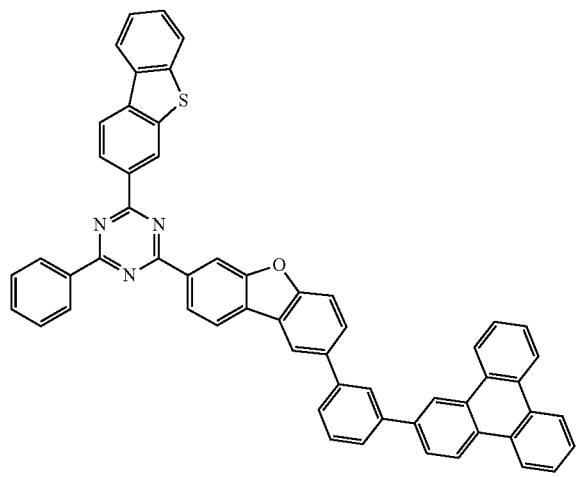
1-56
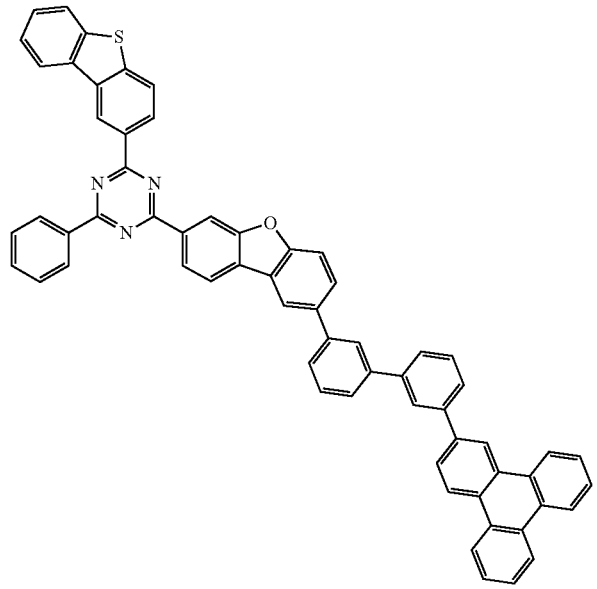
1-57
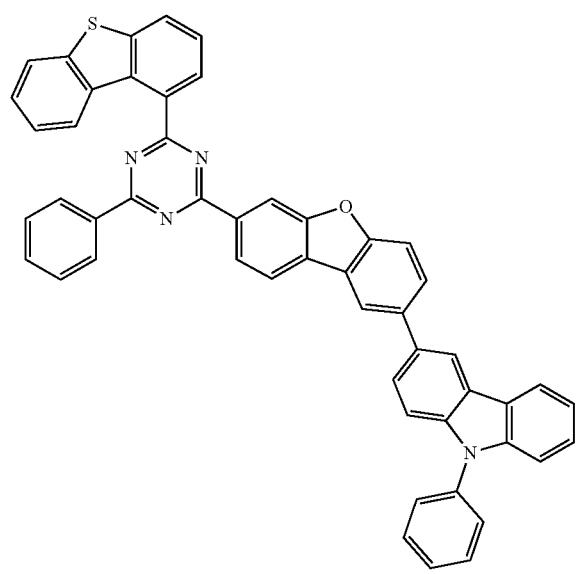
1-58
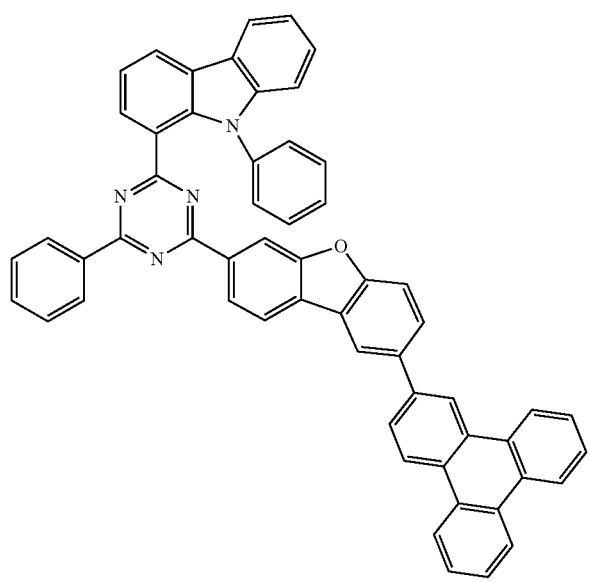

-continued
1-59
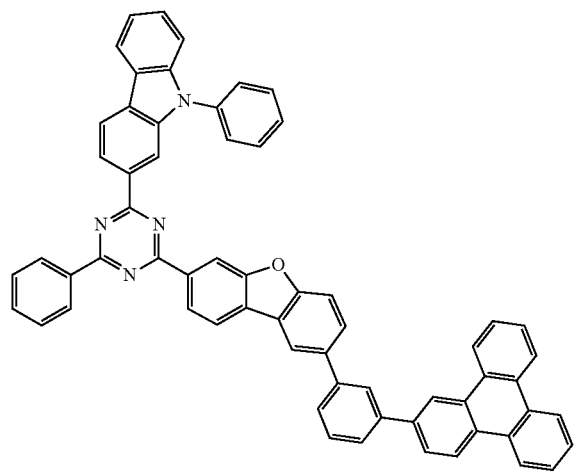
1-60
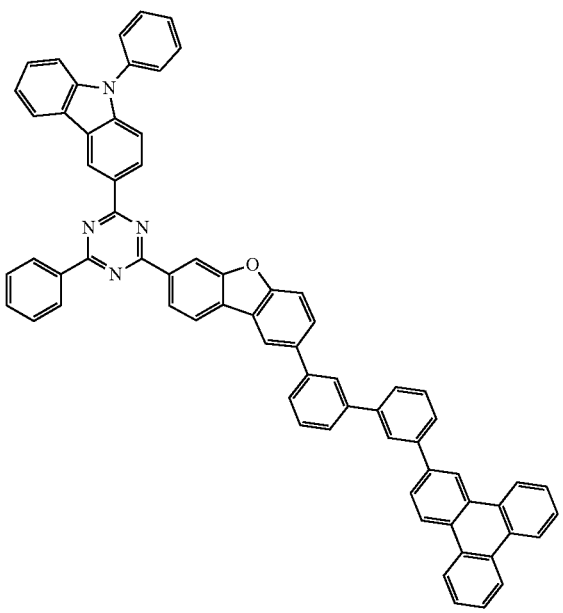
1-61
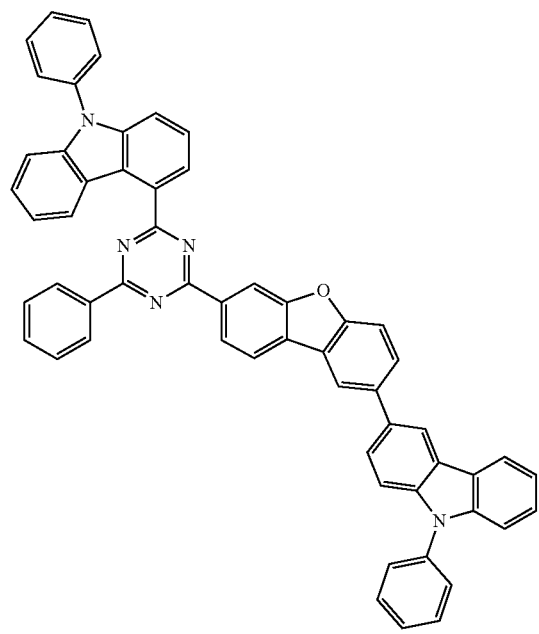
1-62
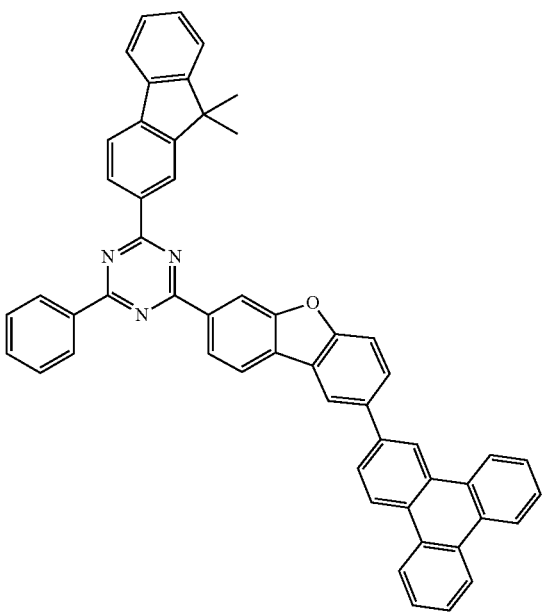

-continued
1-63
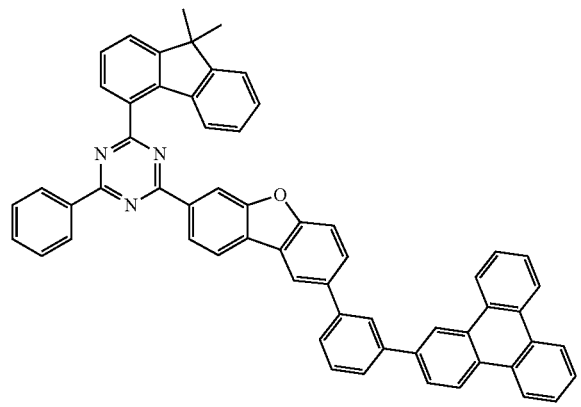
1-64
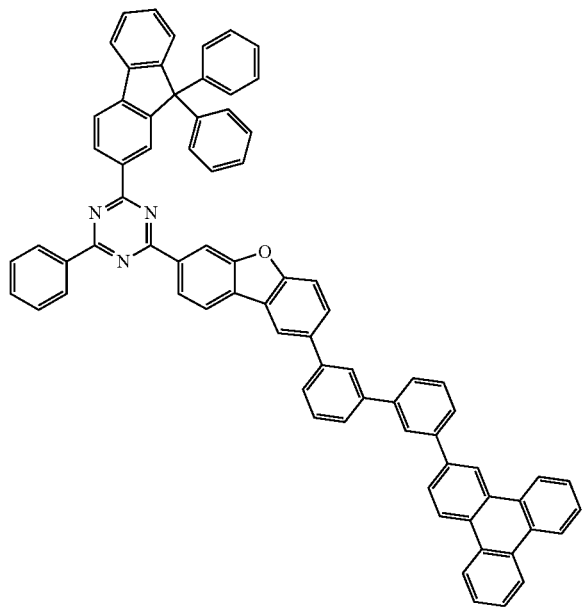
1-65
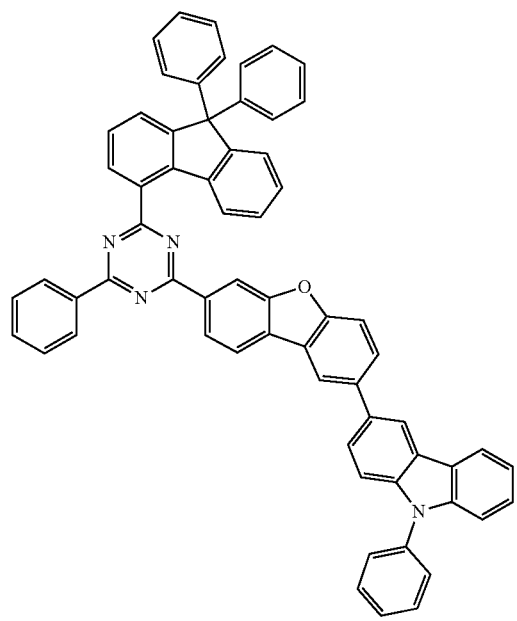
1-66
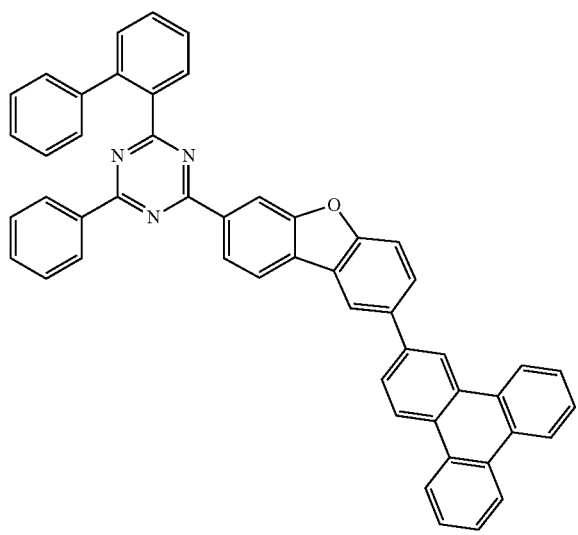

1-67
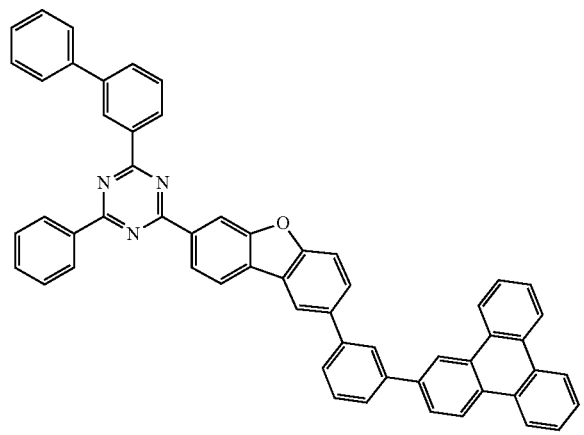
1-68
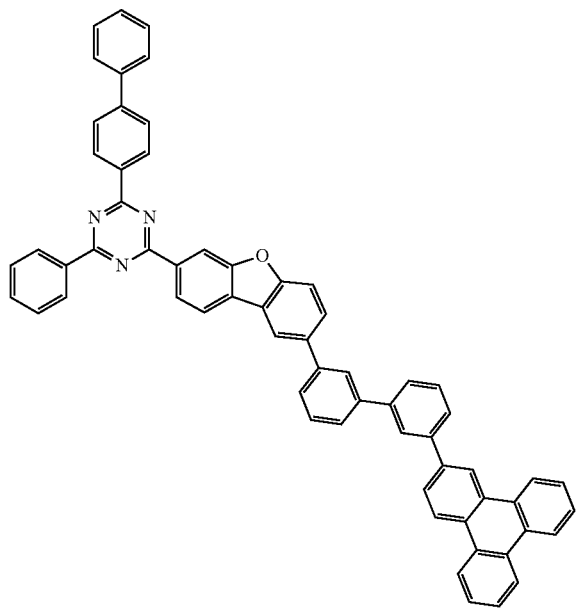
1-69
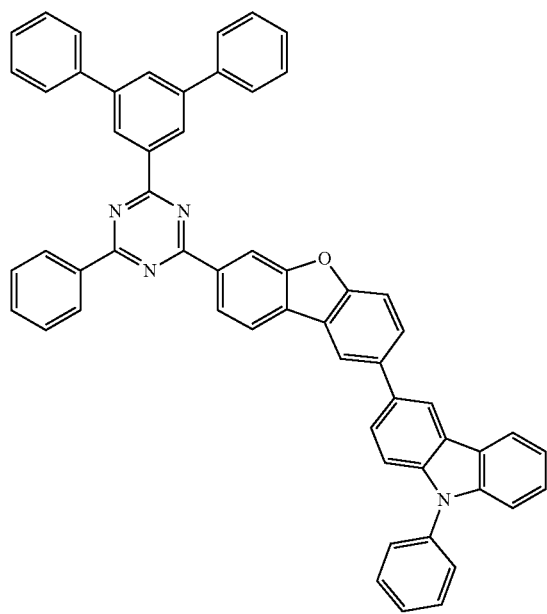
1-70
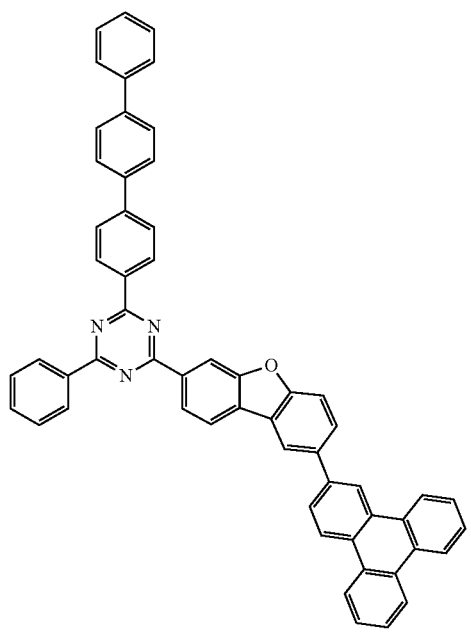

-continued
1-71
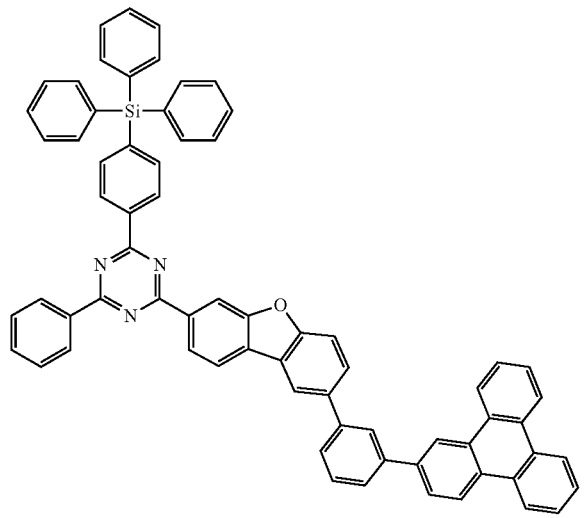
1-72
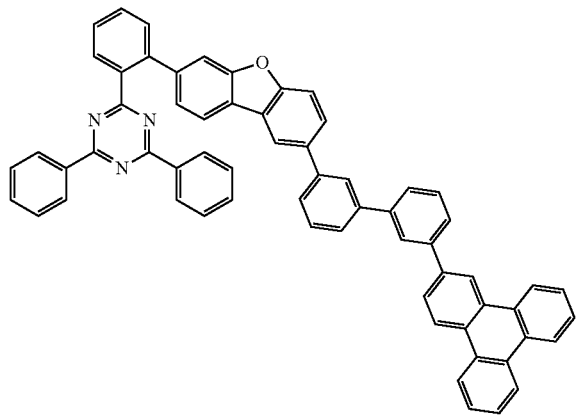
1-73
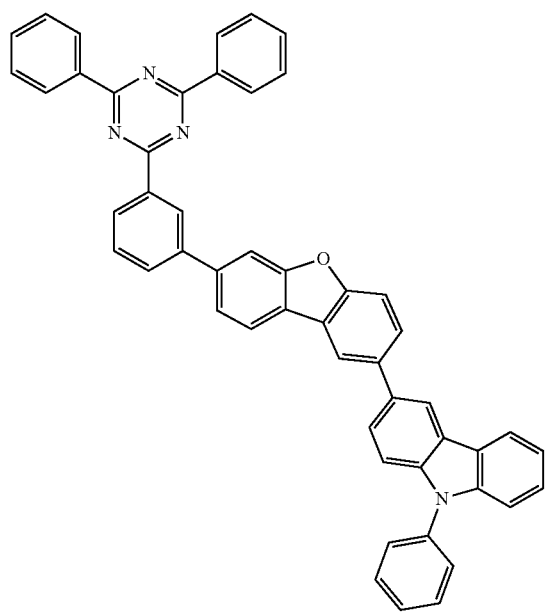
1-74
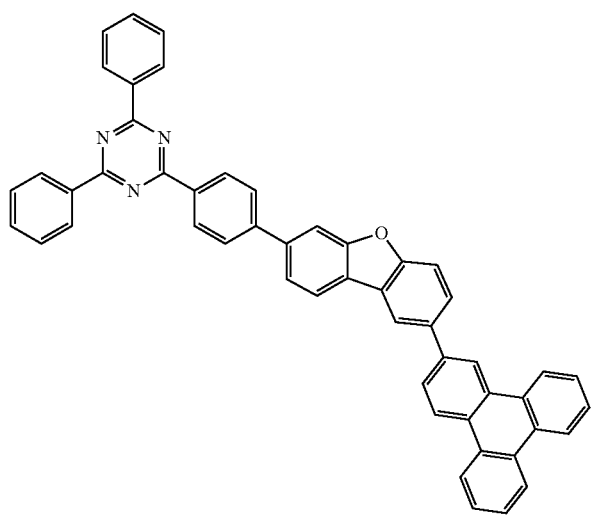

1-75
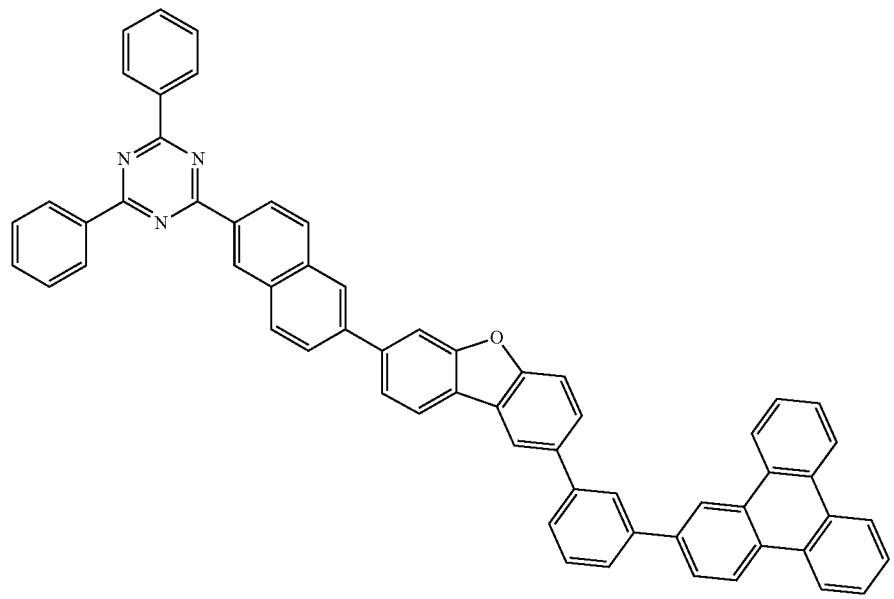
1-76
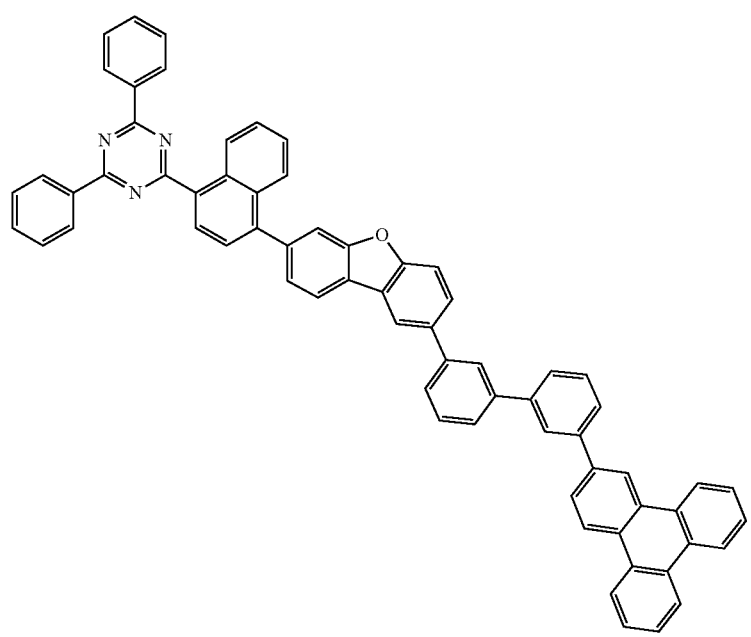

-continued
1-77
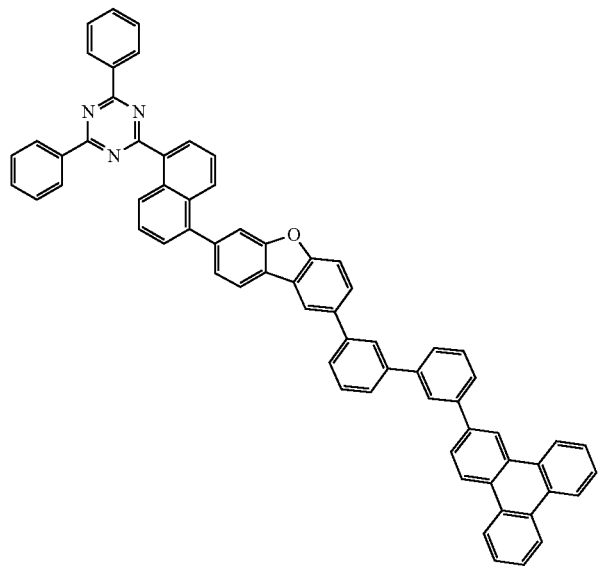
1-78
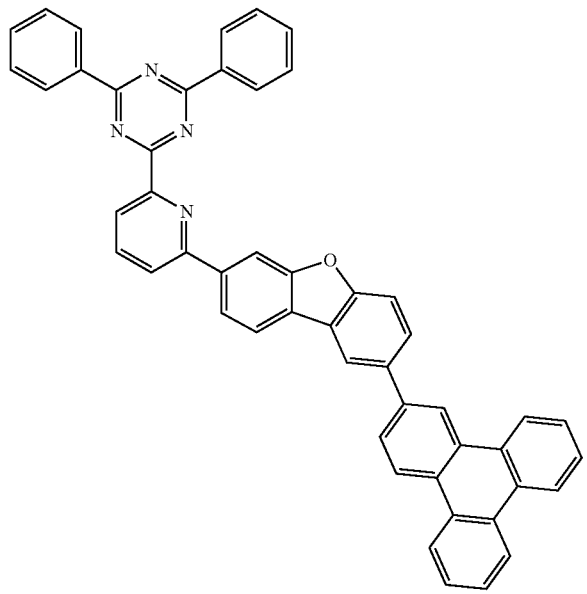
1-79
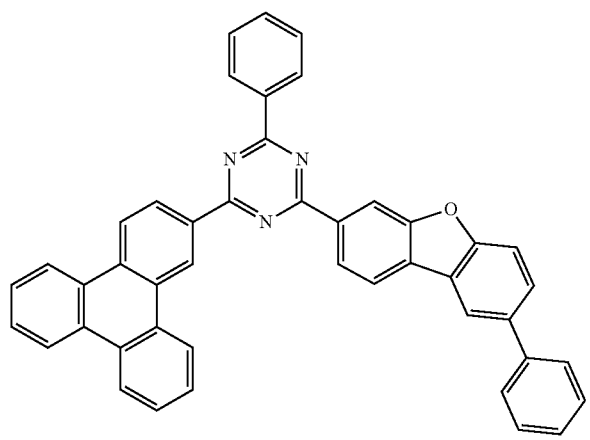
1-80
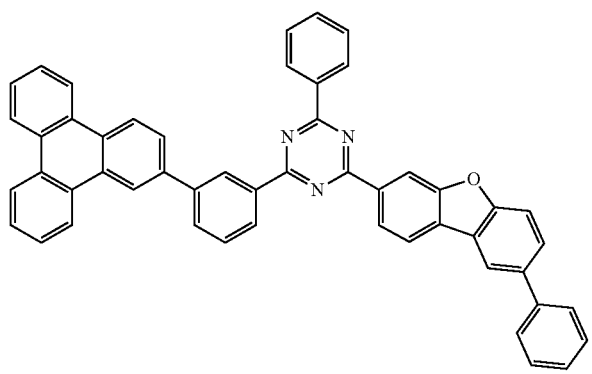
1-81
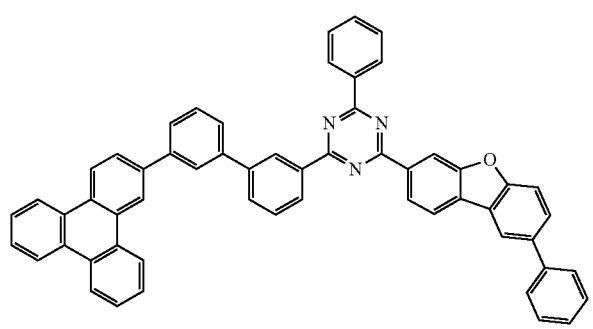
1-82
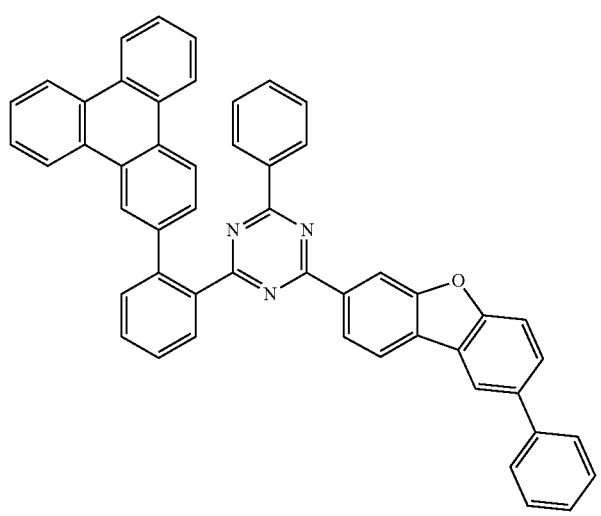

-continued
1-83
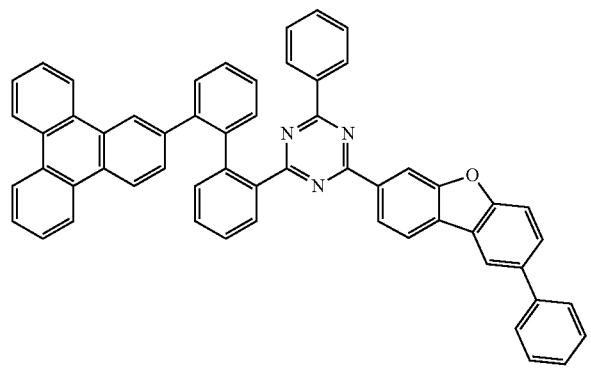
1-84
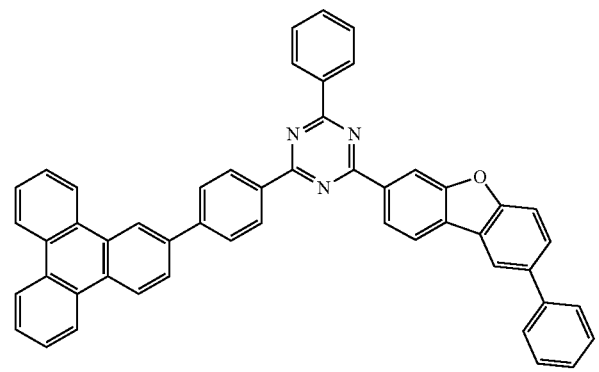
1-85
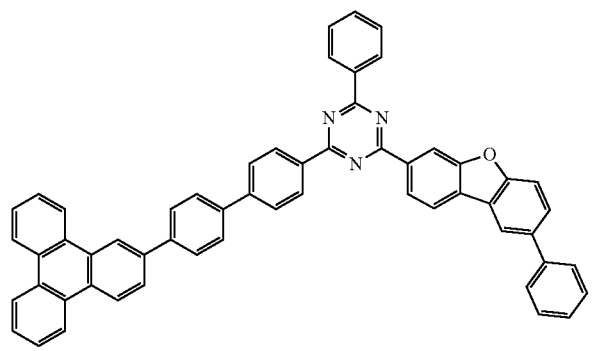
1-86
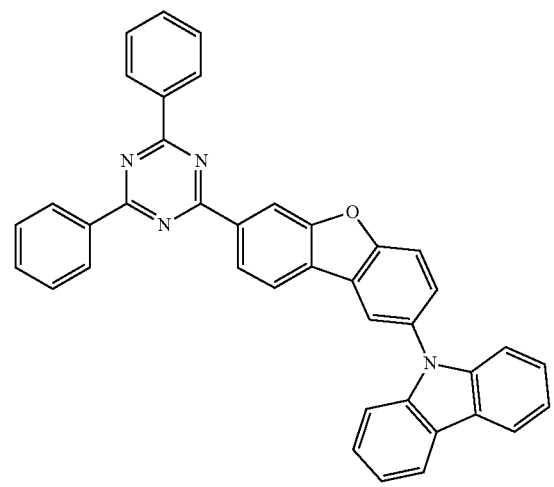
1-87
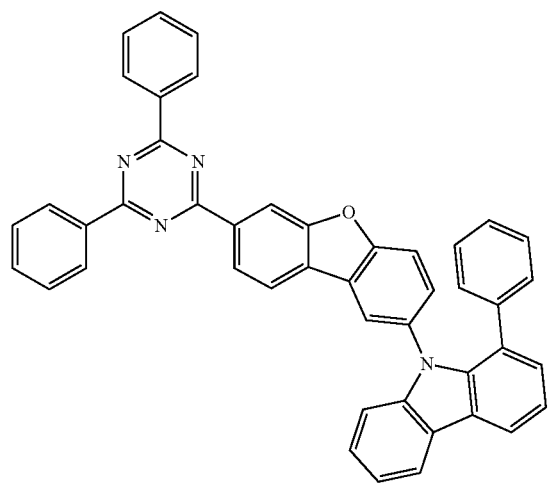
1-88
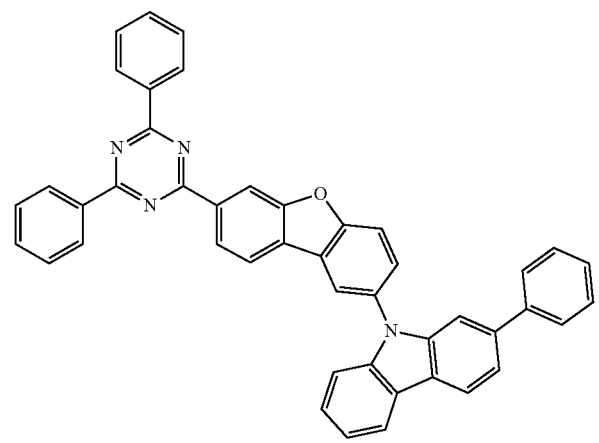

1-89
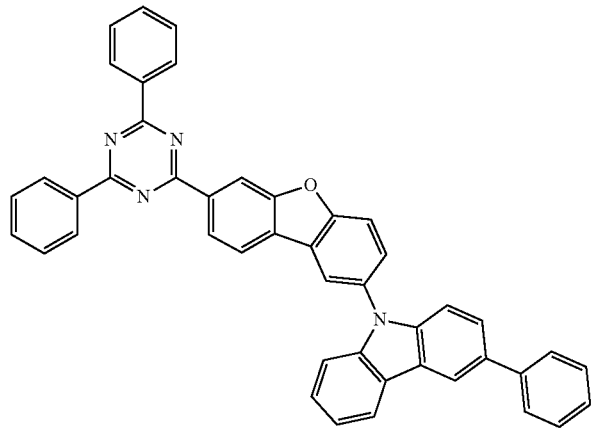
1-90
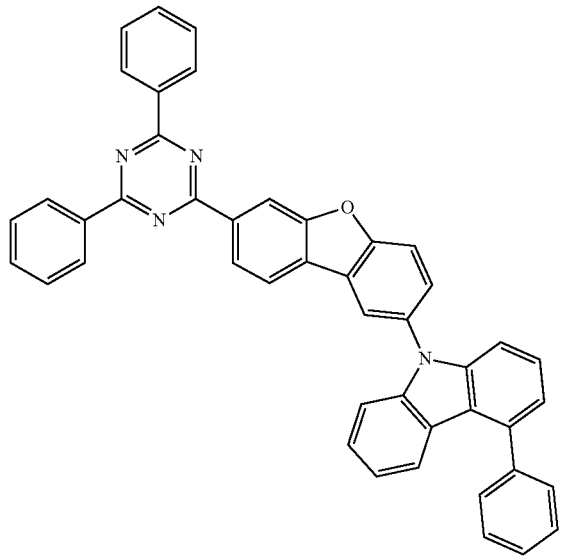
1-91
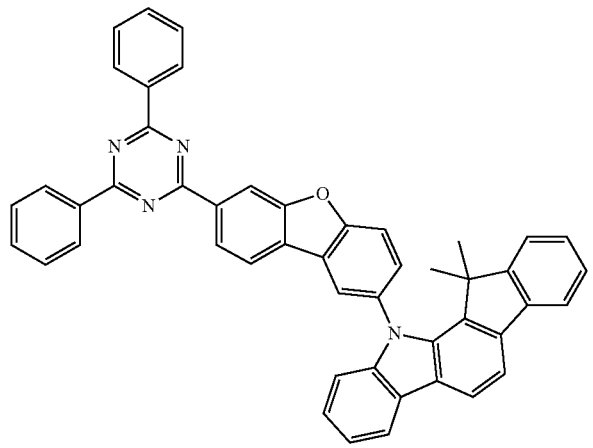
1-92
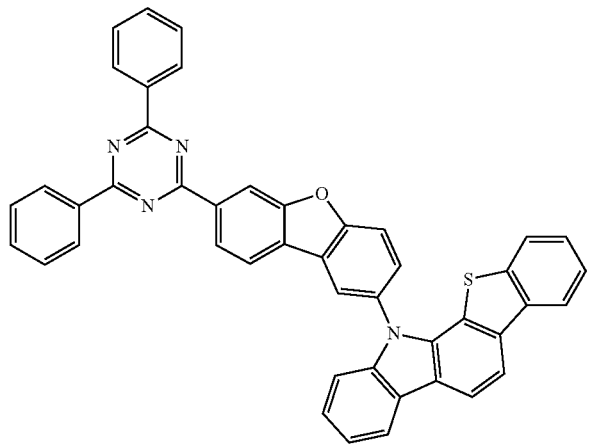
1-93
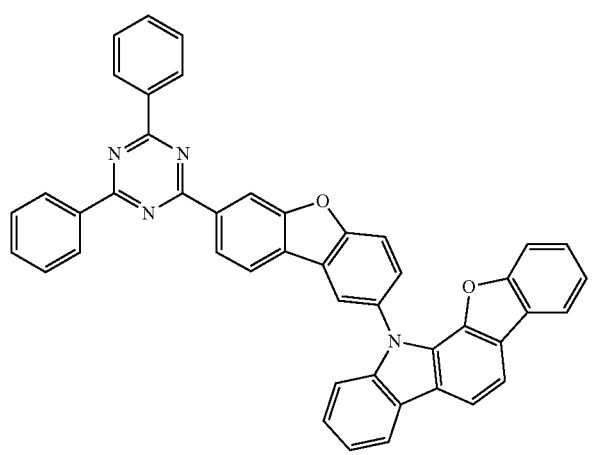
1-94
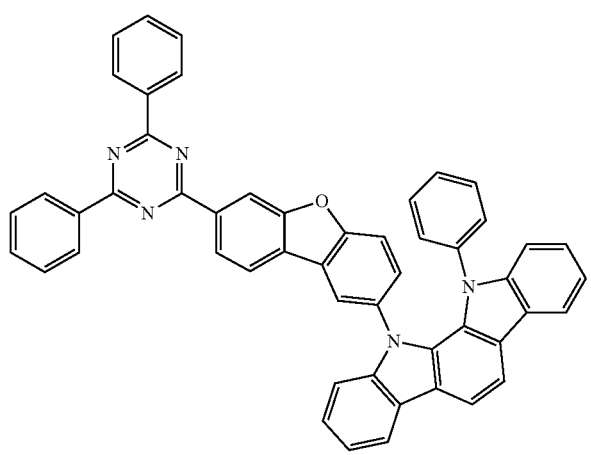

1-95
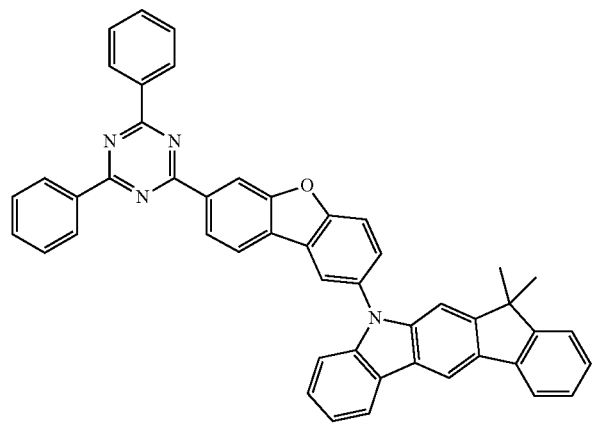
1-96
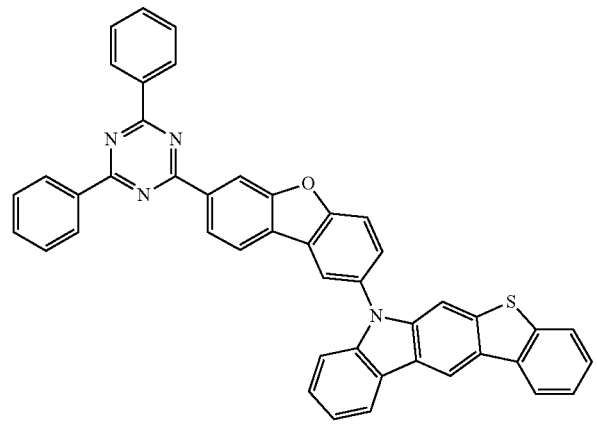
1-97
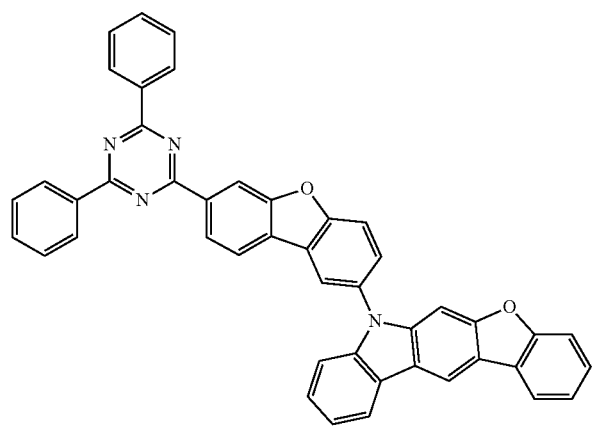
1-98
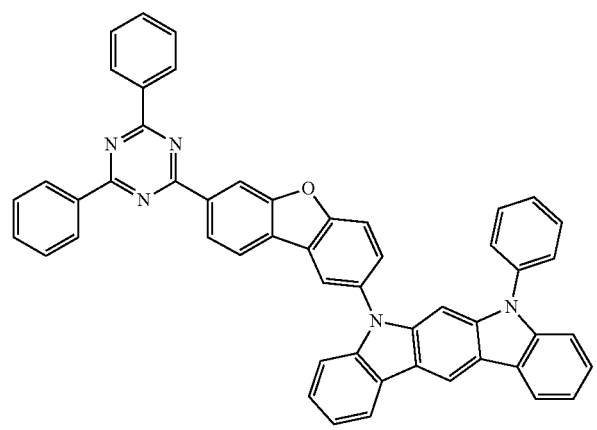
1-99
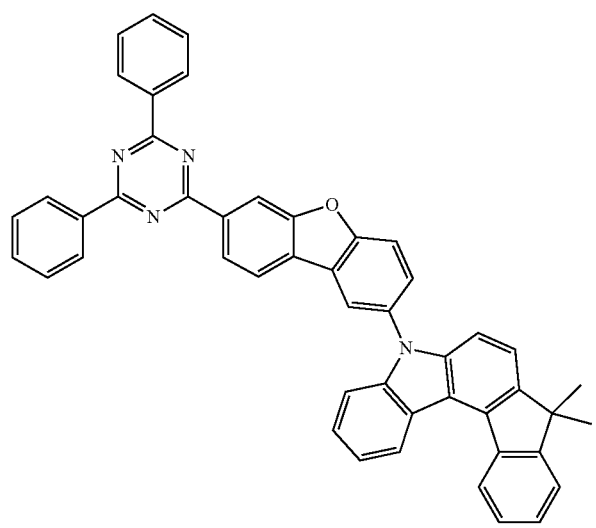
1-100
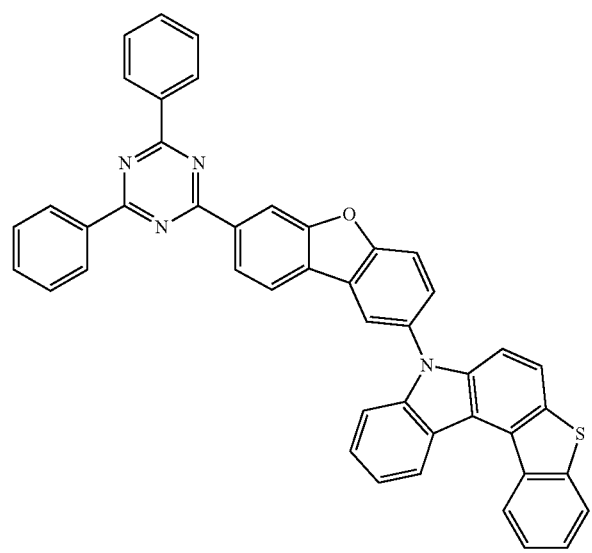

-continued
2-1
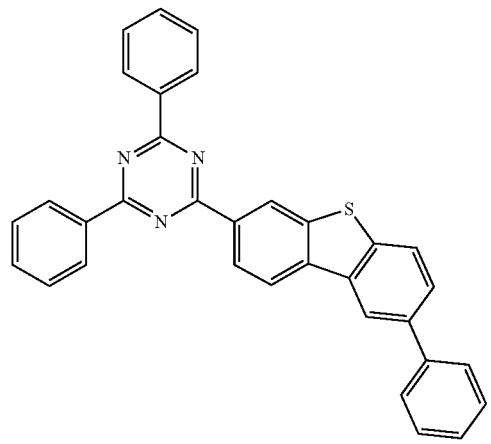
2-2
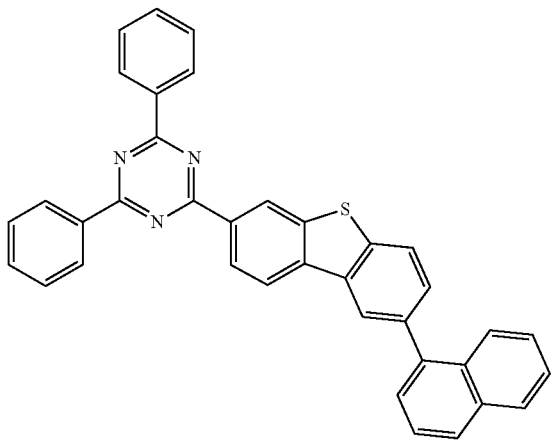
2-3
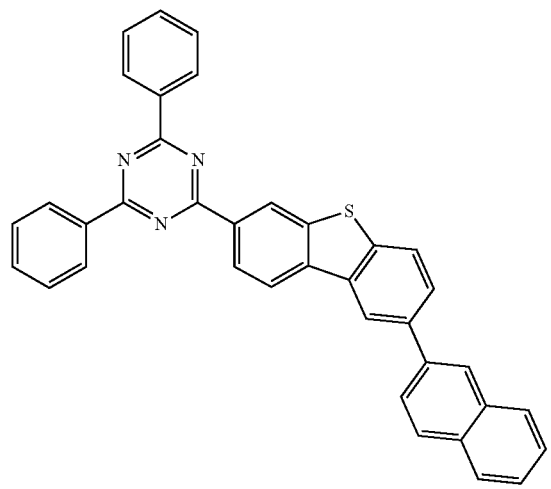
2-4
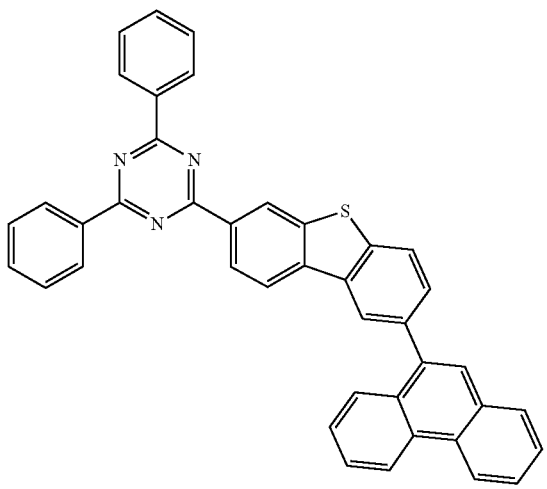
2-5
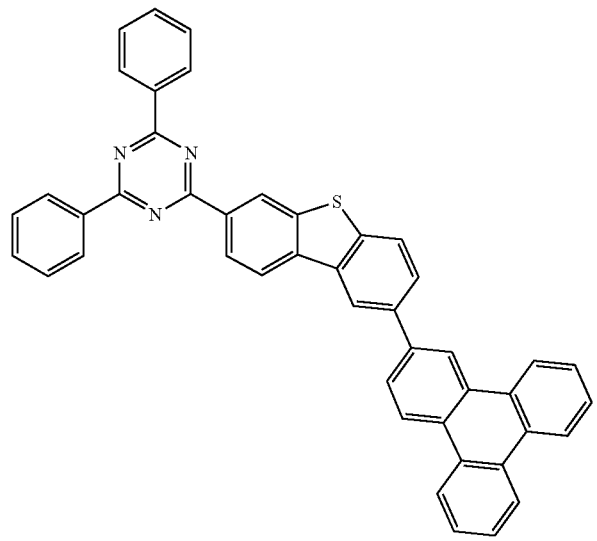
2-6
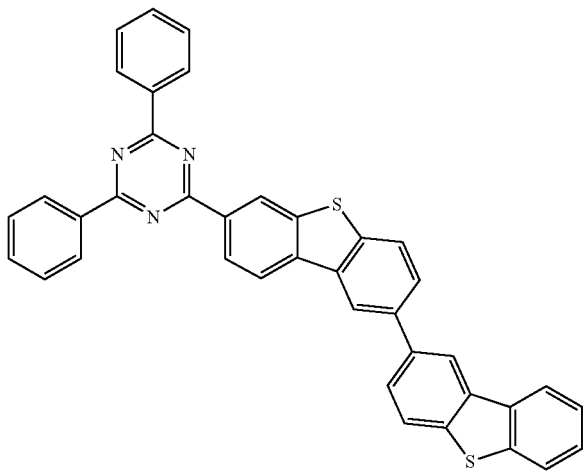

2-7
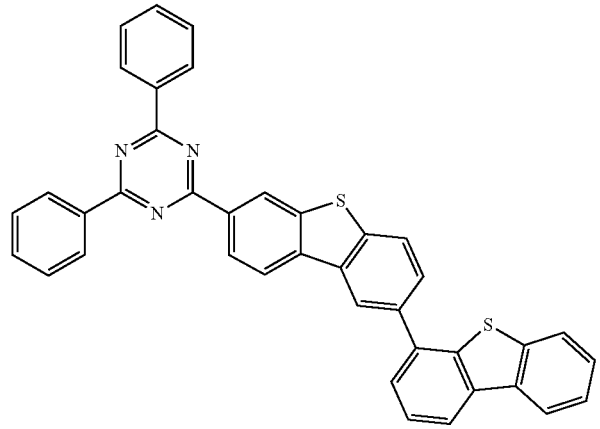
2-8
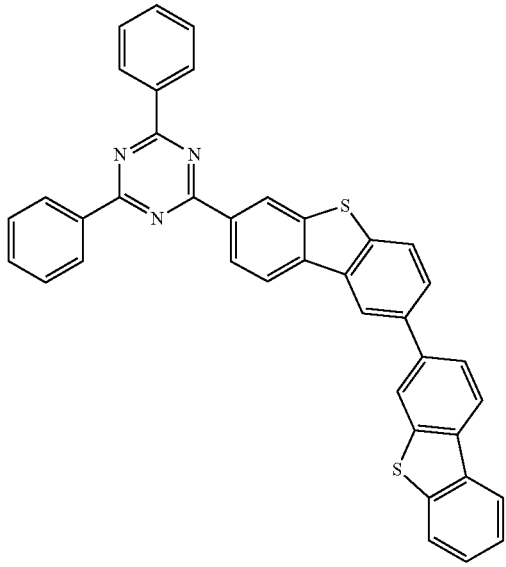
2-9
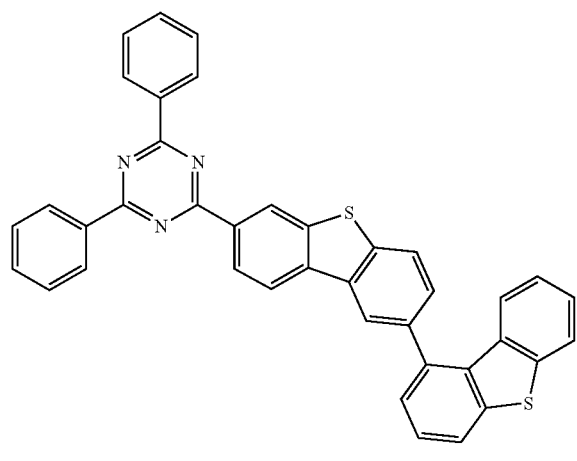
2-10
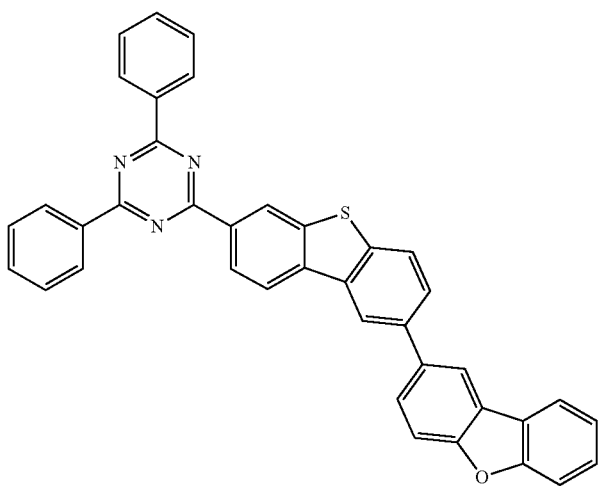

-continued
2-11
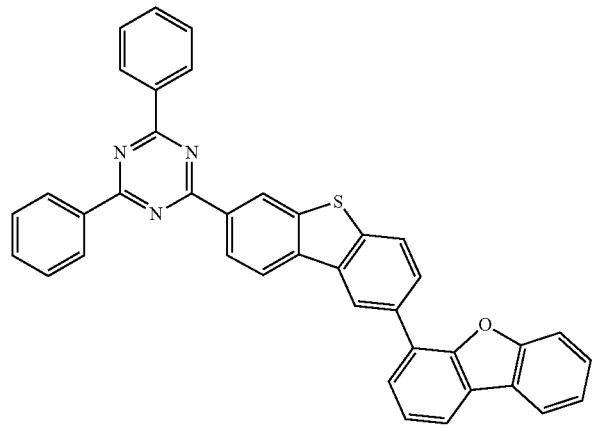
2-12
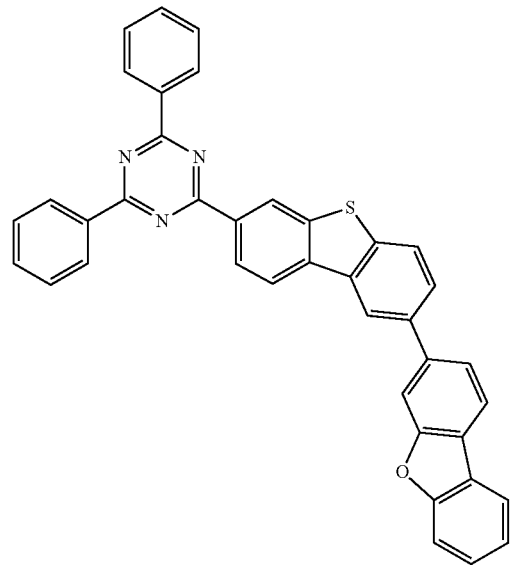
2-13
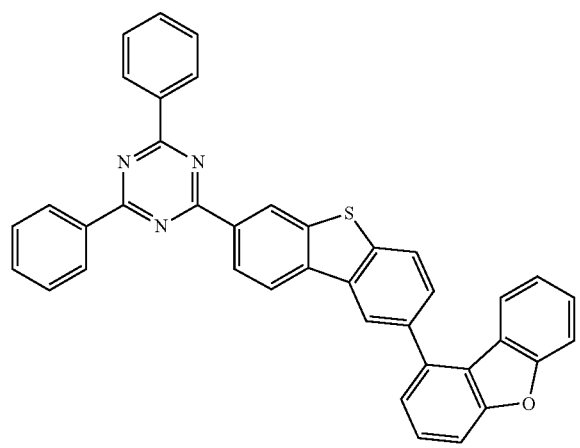
2-14
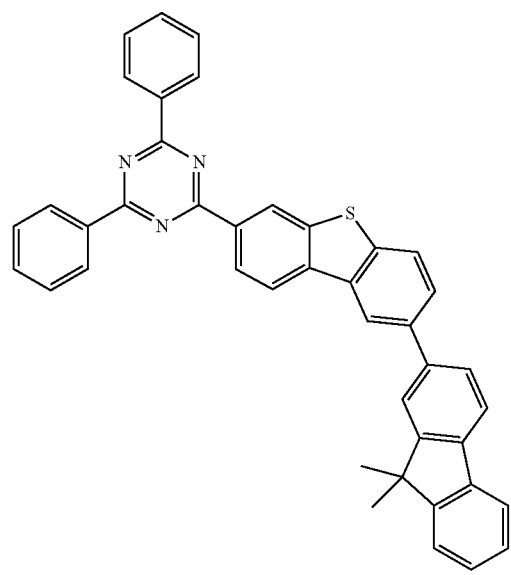

2-15
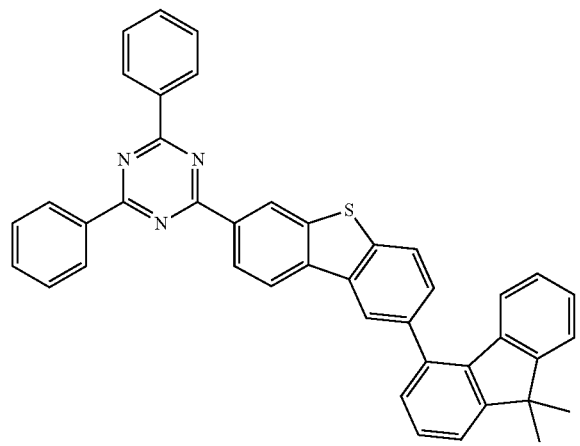
2-16
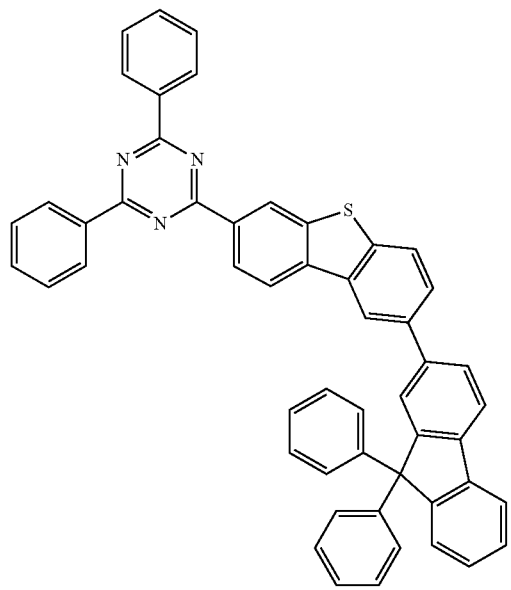
2-17
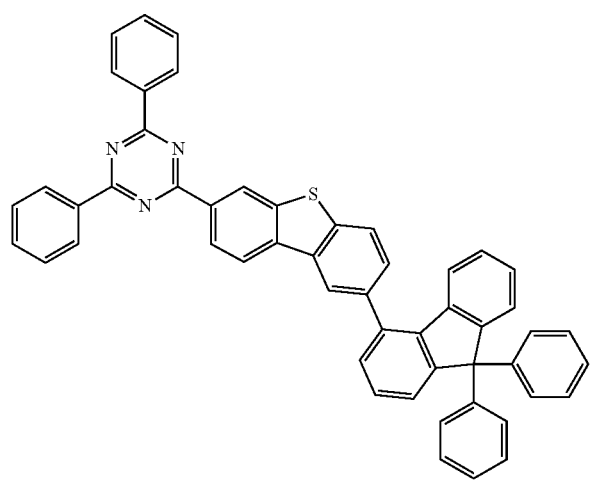
2-18
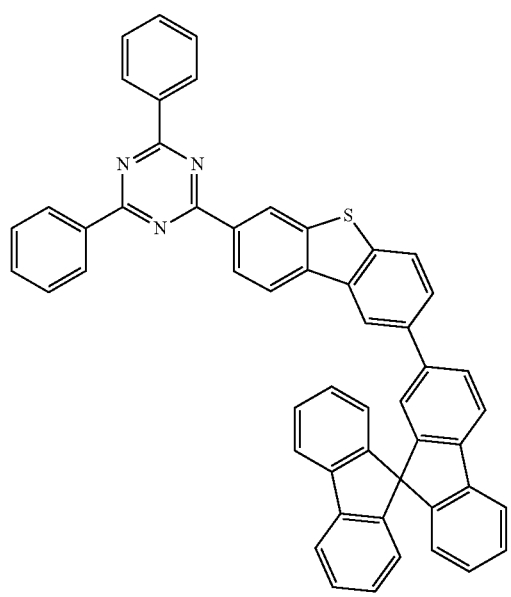

2-19
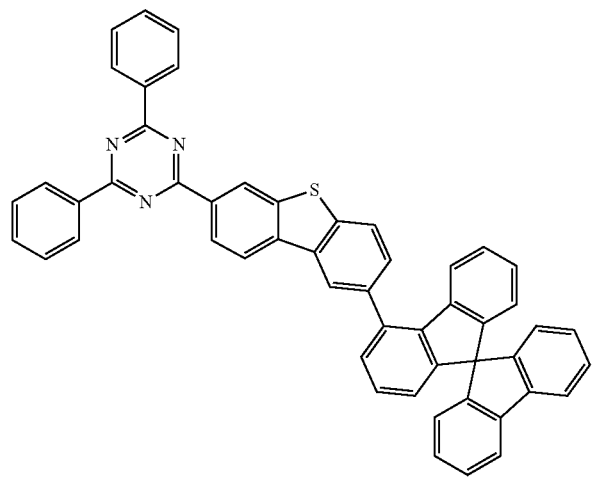
2-20
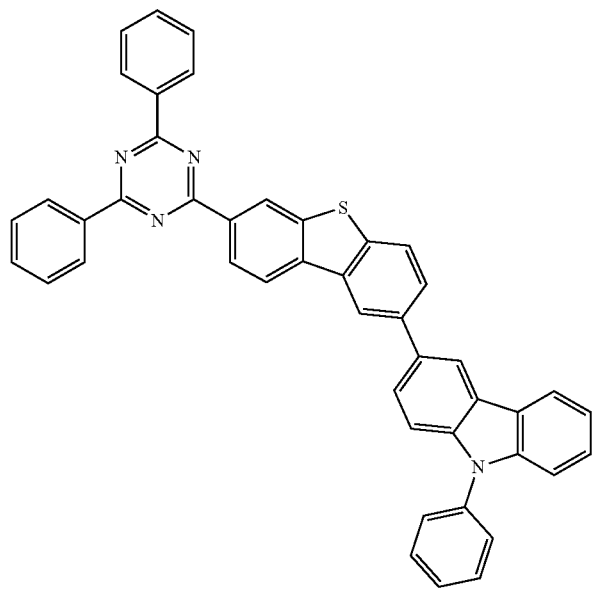
2-21
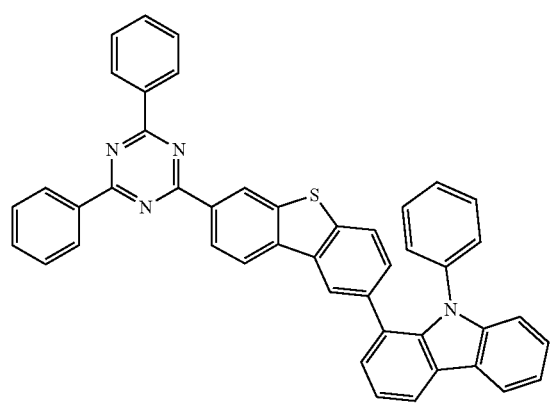
2-22
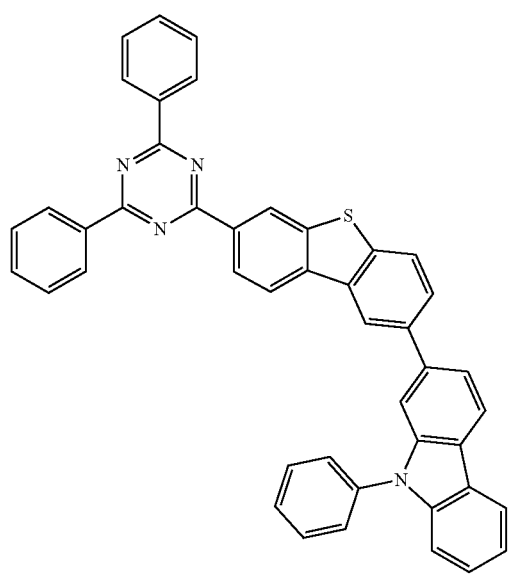

-continued
2-23
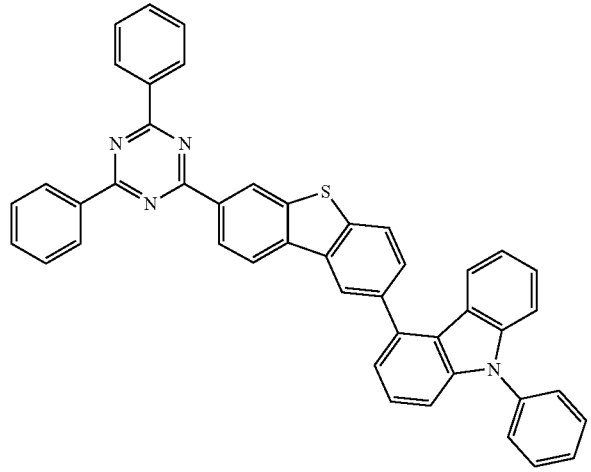
2-24
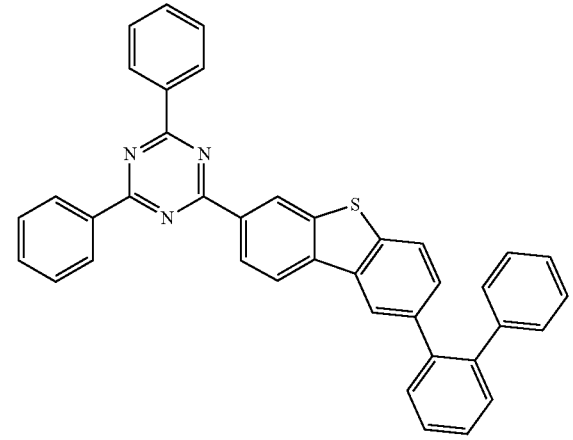
2-25
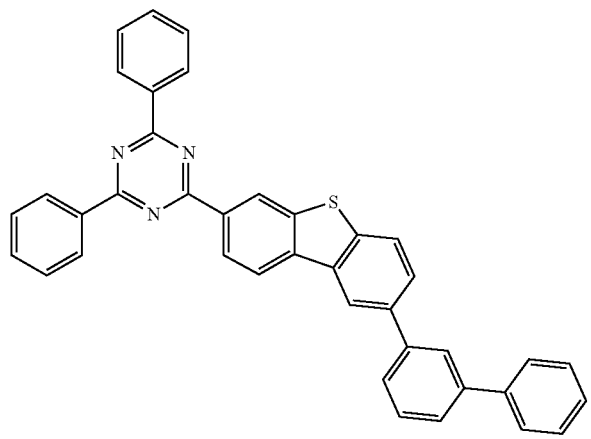
2-26
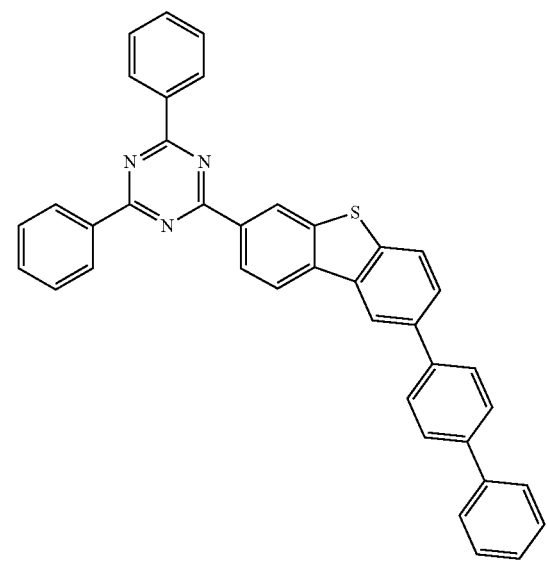
2-27
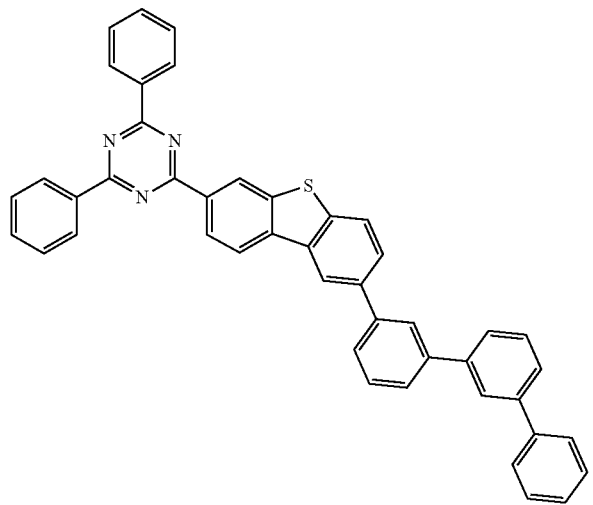
2-28
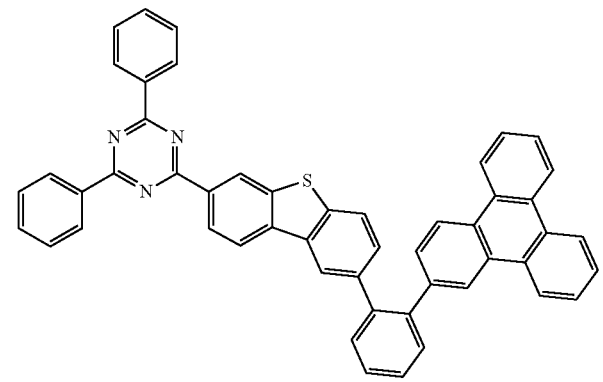

2-29
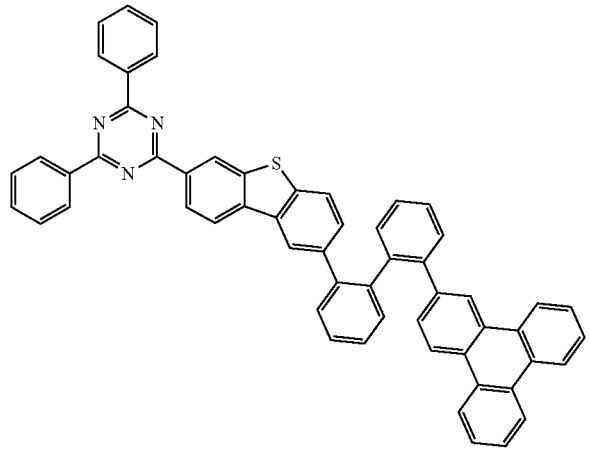
2-30
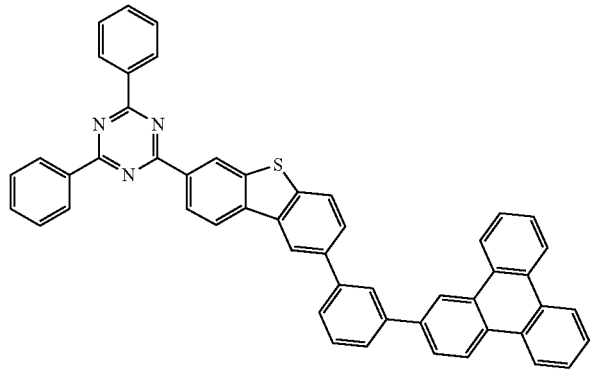
2-31
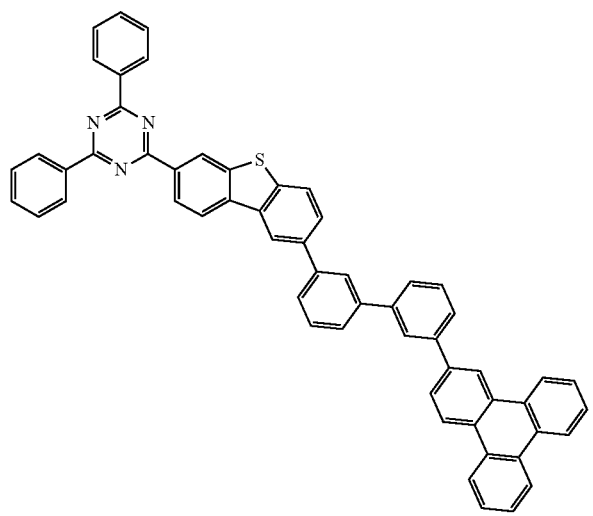
2-32
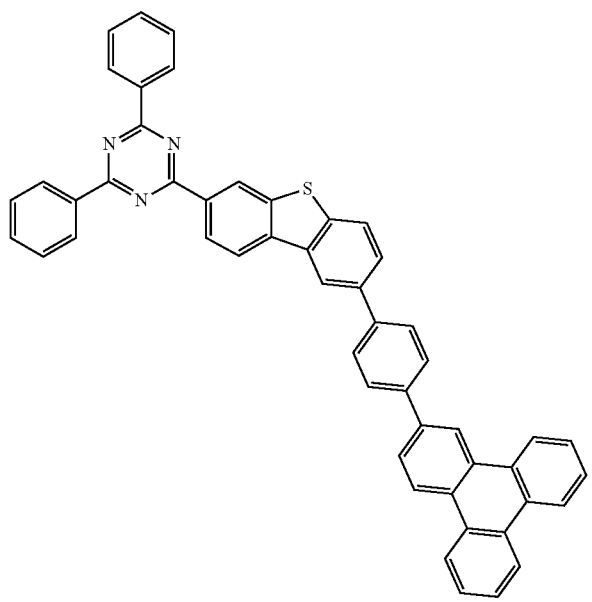

-continued
2-33
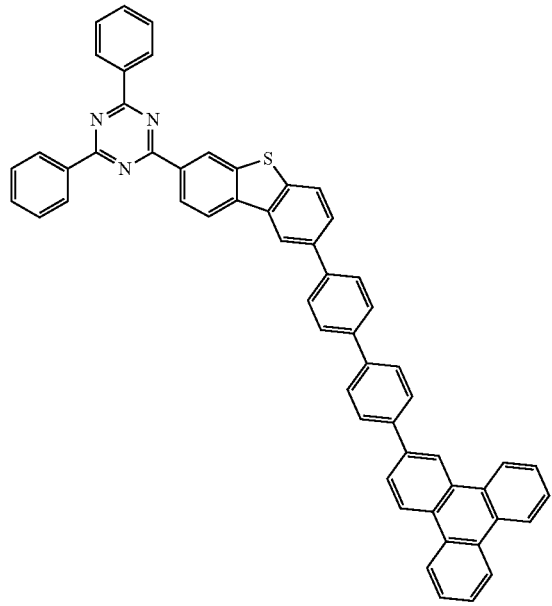
2-34
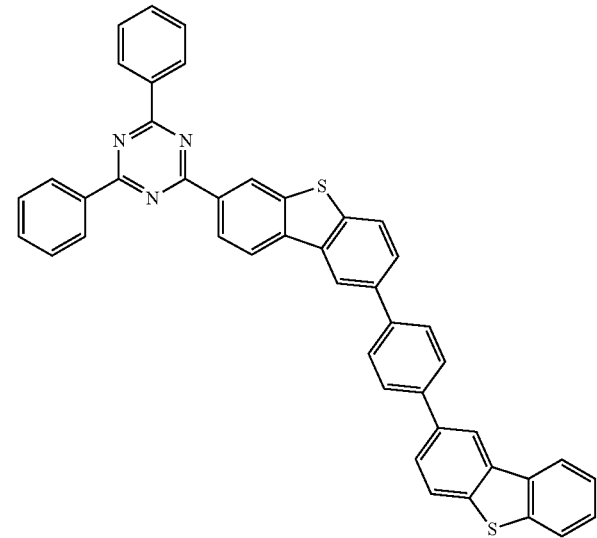
2-35
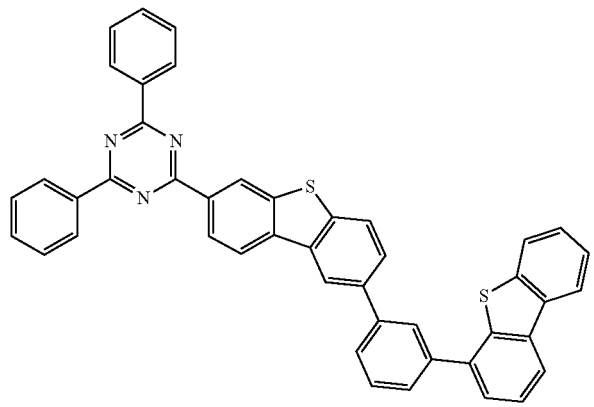
2-36
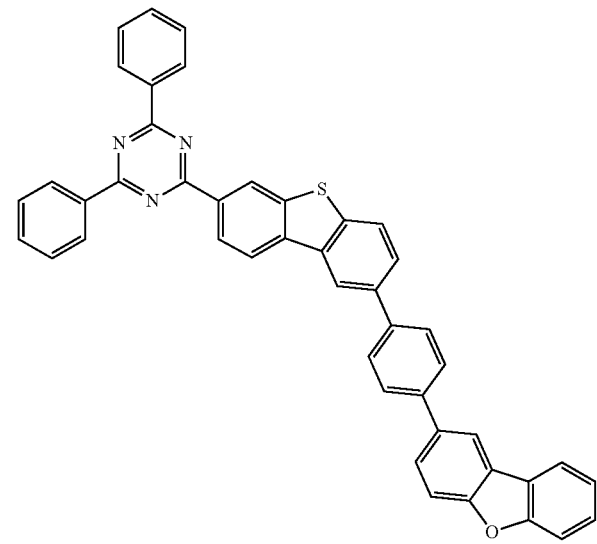
2-37
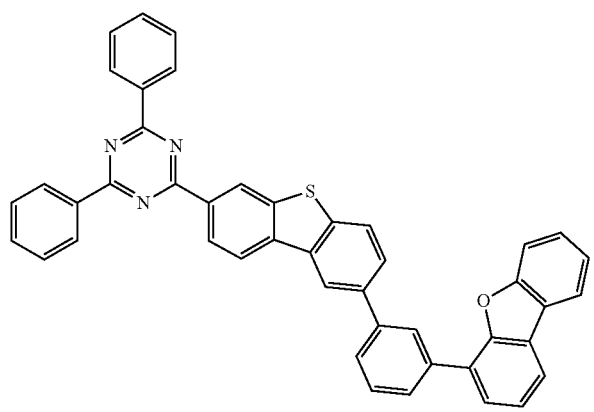
2-38
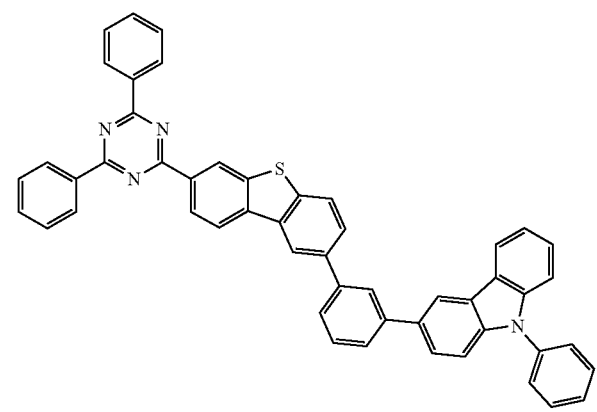

2-39
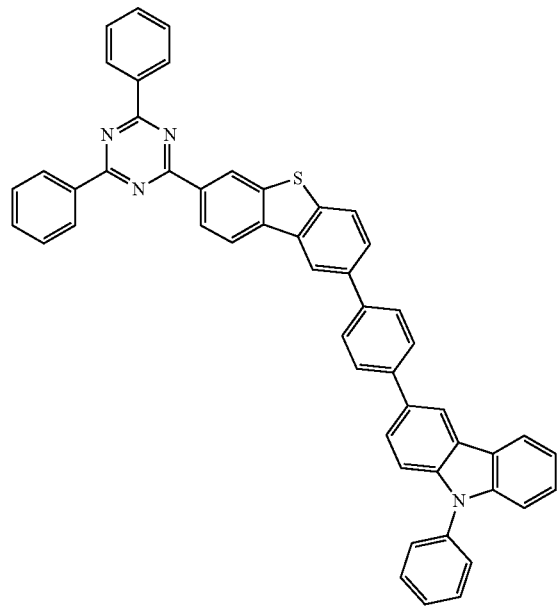
2-40
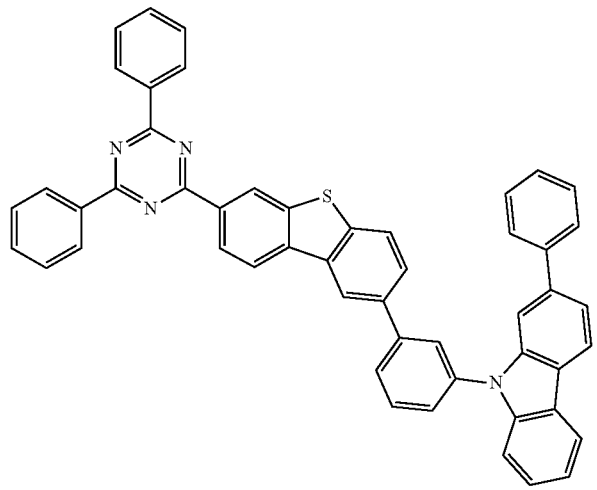
2-41
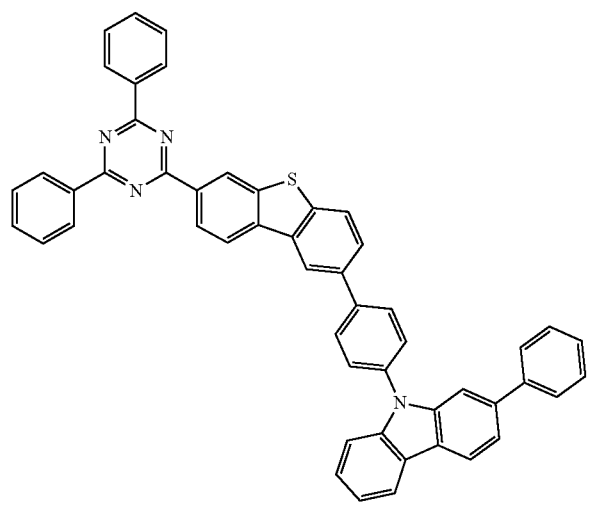
2-42
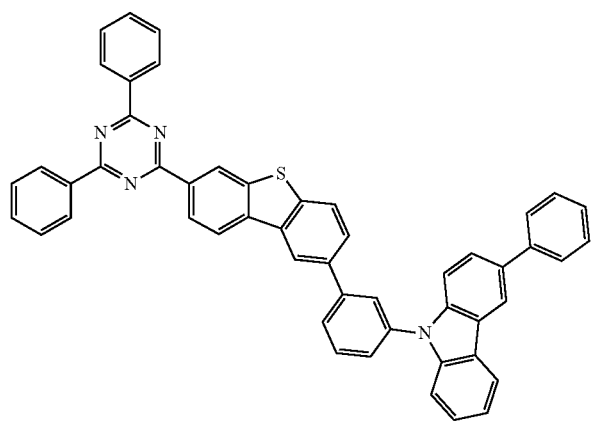

-continued
2-43
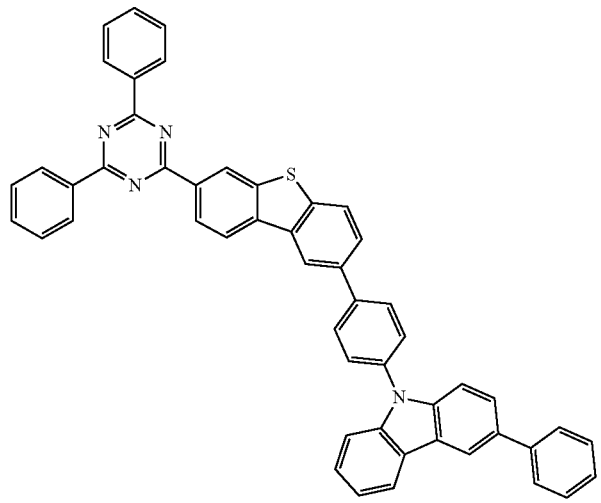
2-44
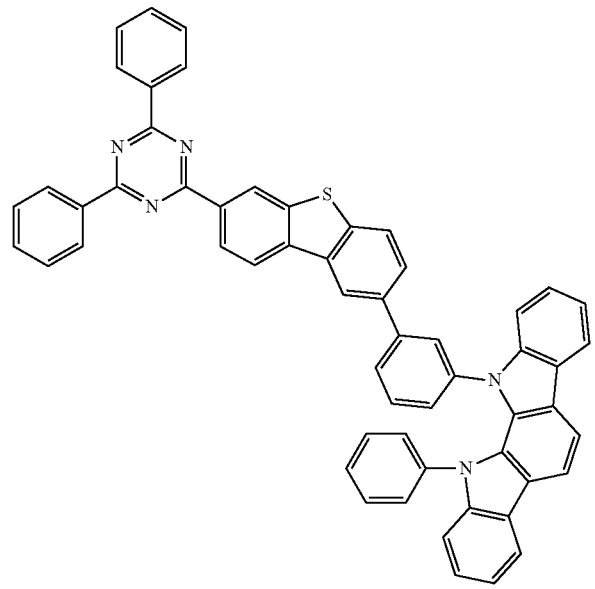
2-45
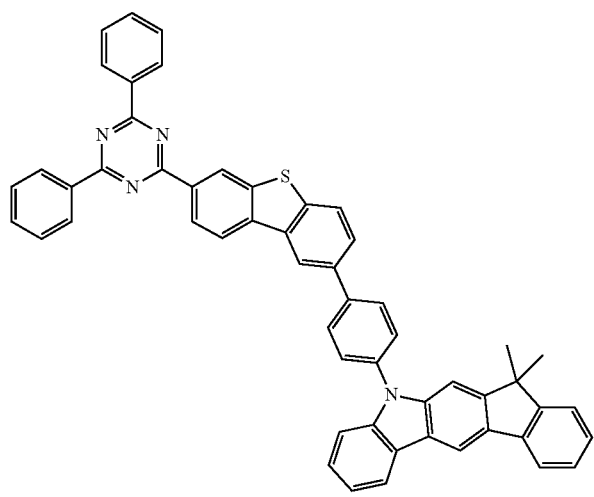
2-46
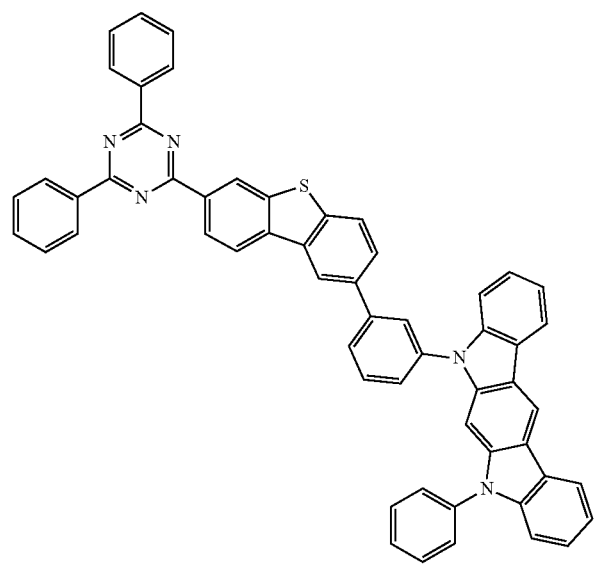

2-47
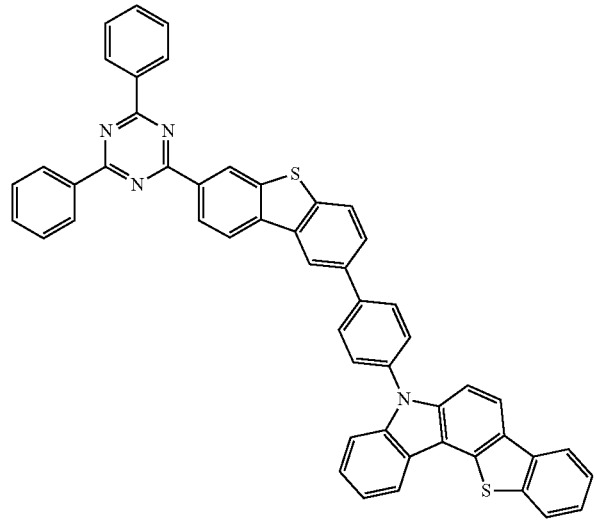
2-48
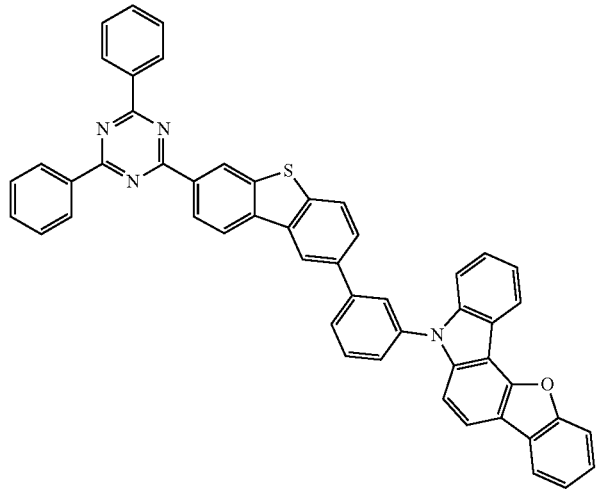
2-49
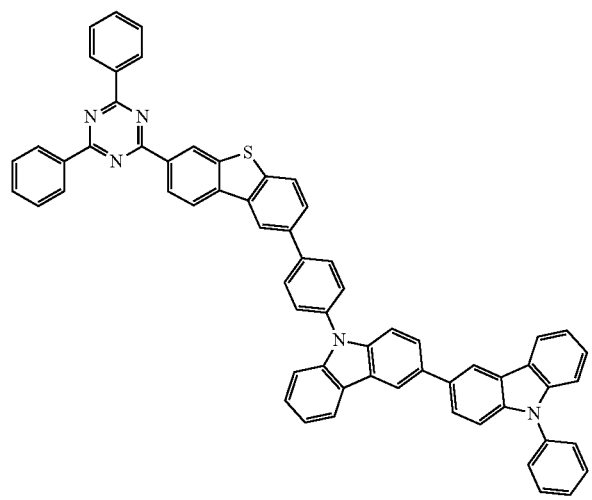
2-50
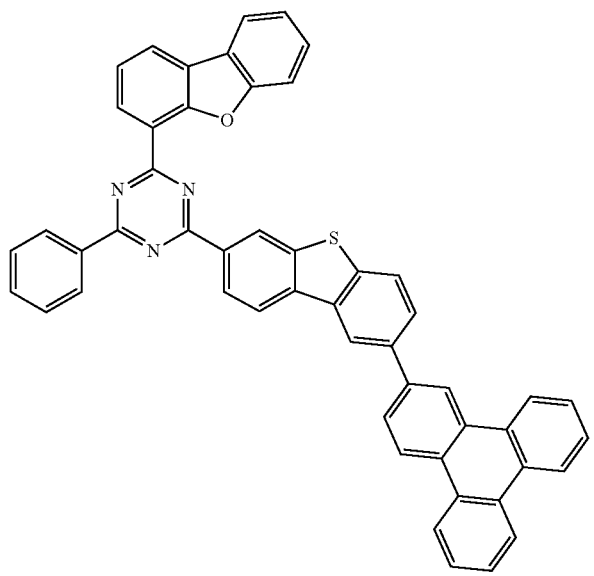

-continued
2-51
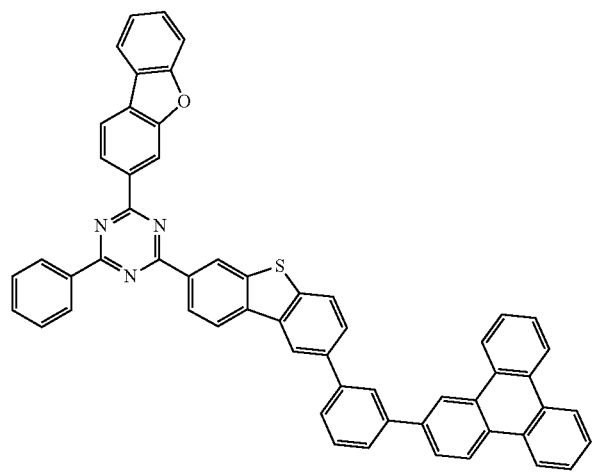
2-52
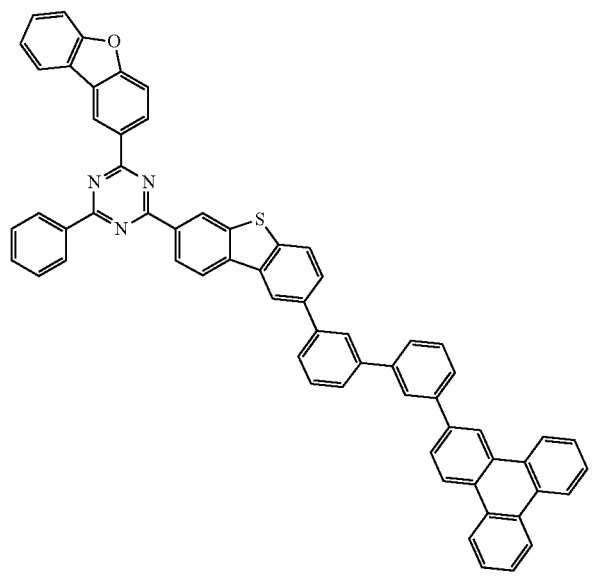
2-53
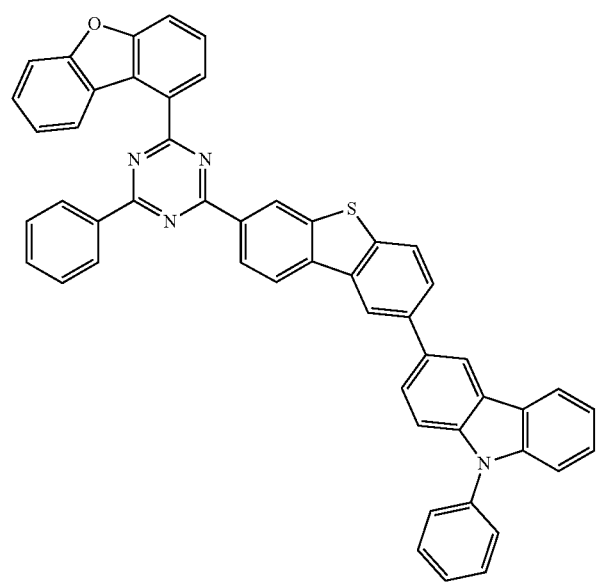
2-54
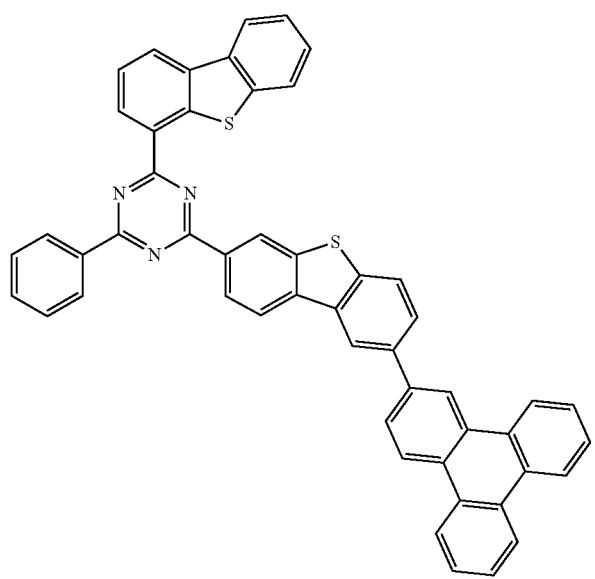

-continued
2-55
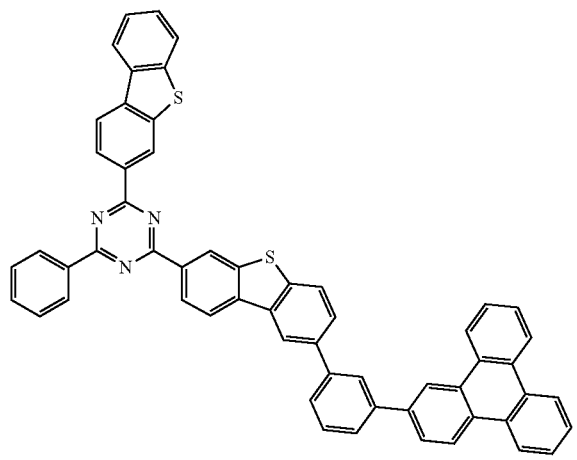
2-56
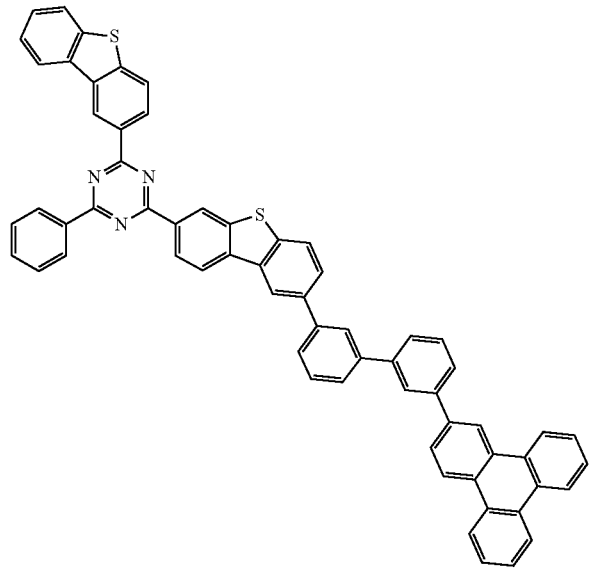
2-57
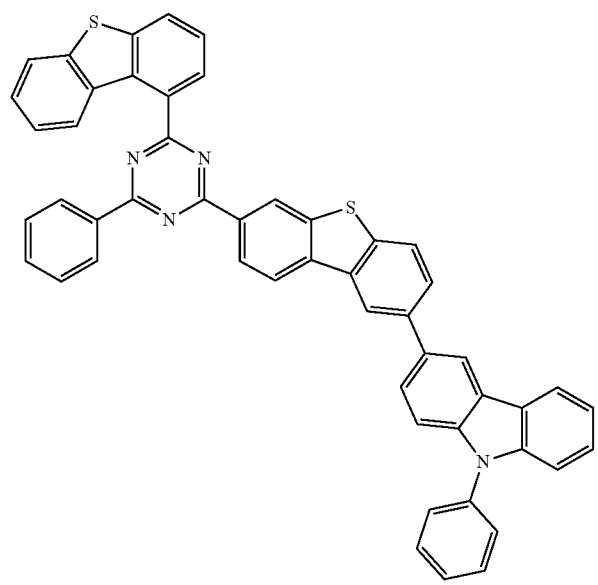
2-58
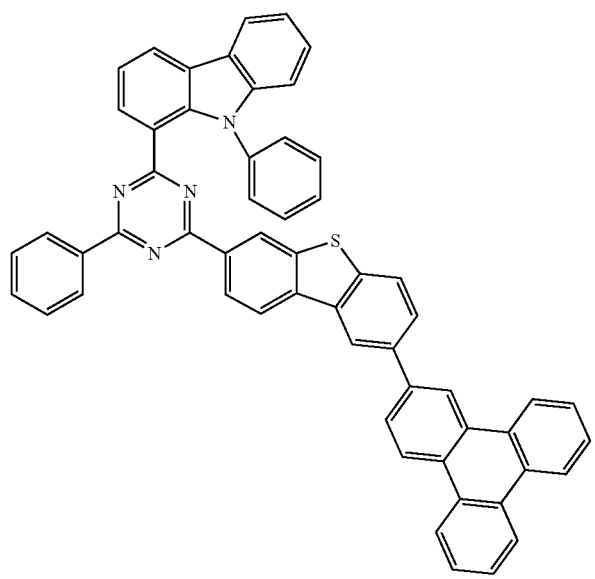

-continued
2-59
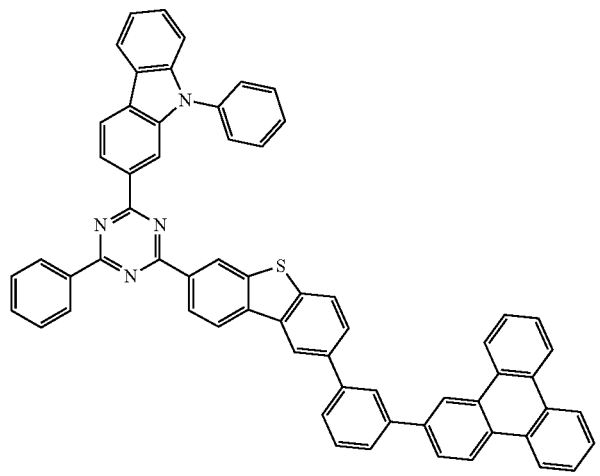
2-60
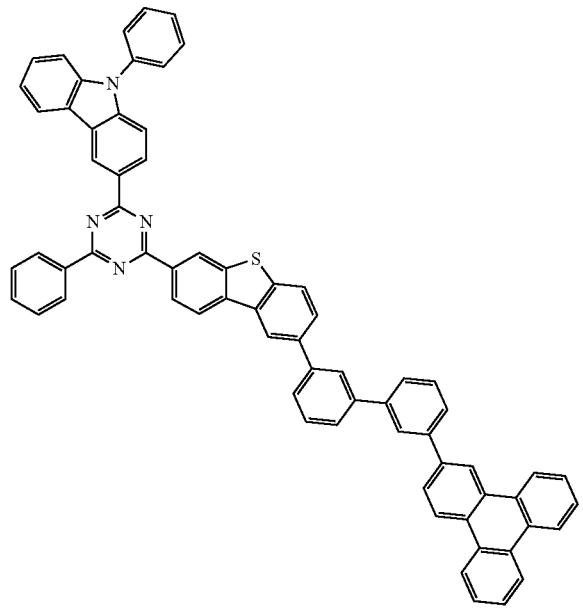
2-61
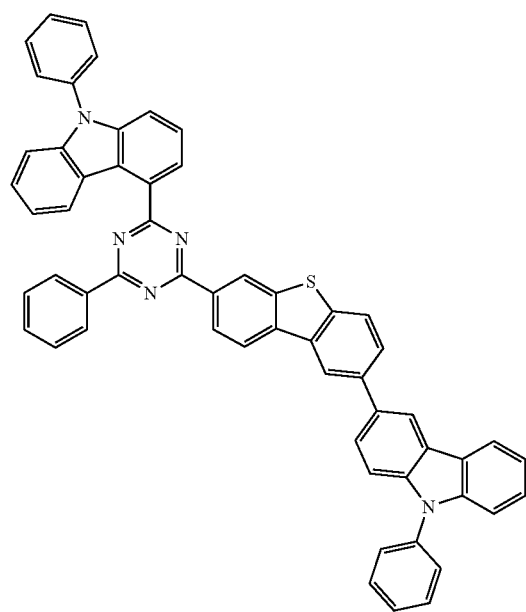
2-62
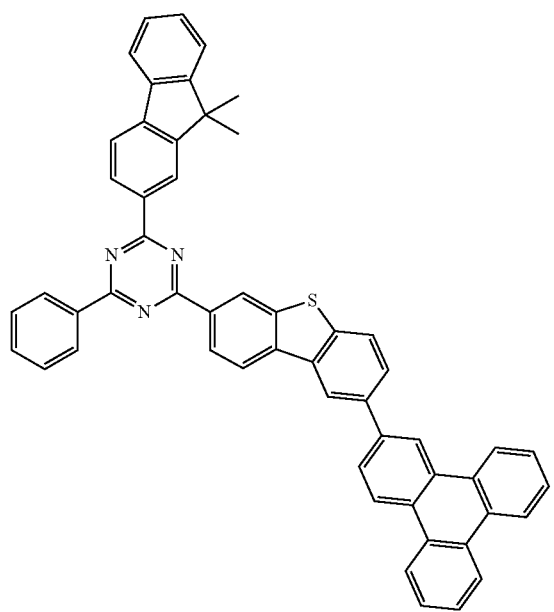

2-63
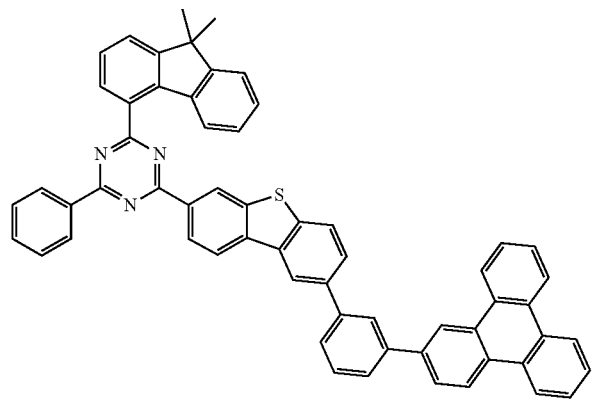
2-64
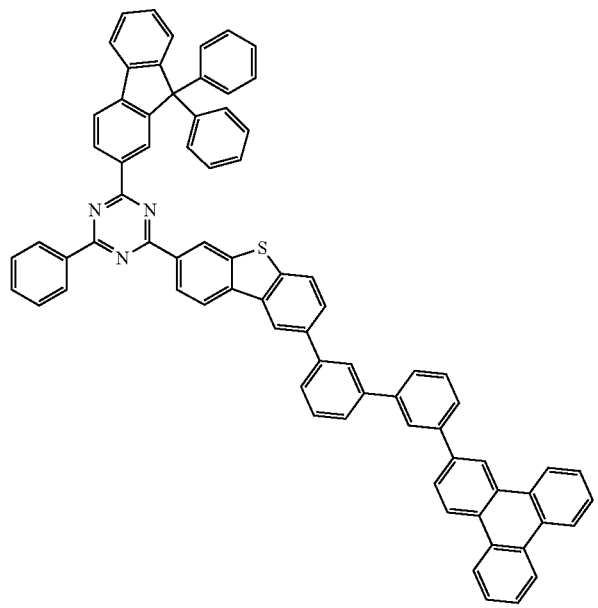
2-65
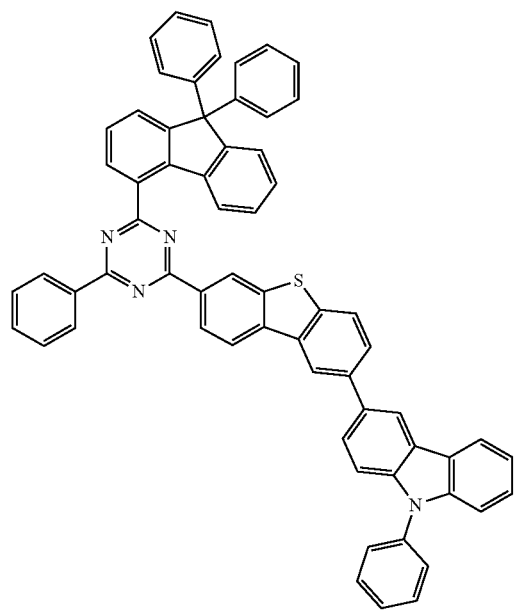
2-66
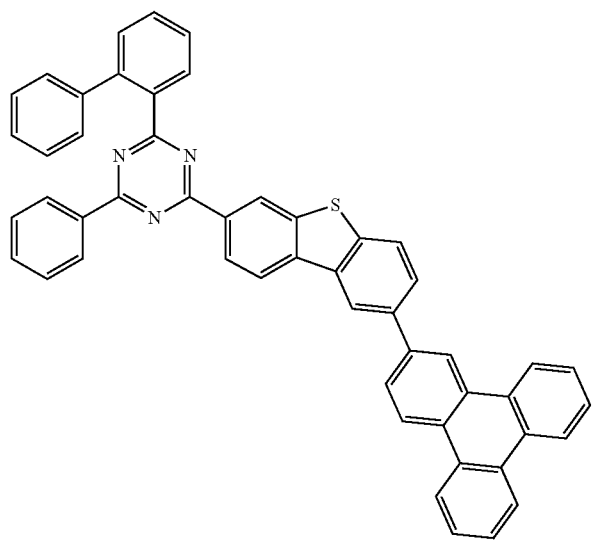

2-67
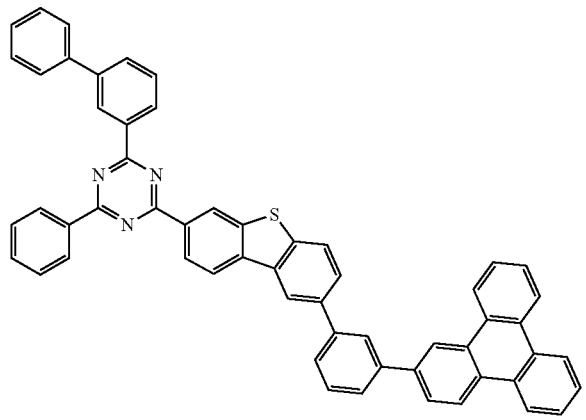
2-68
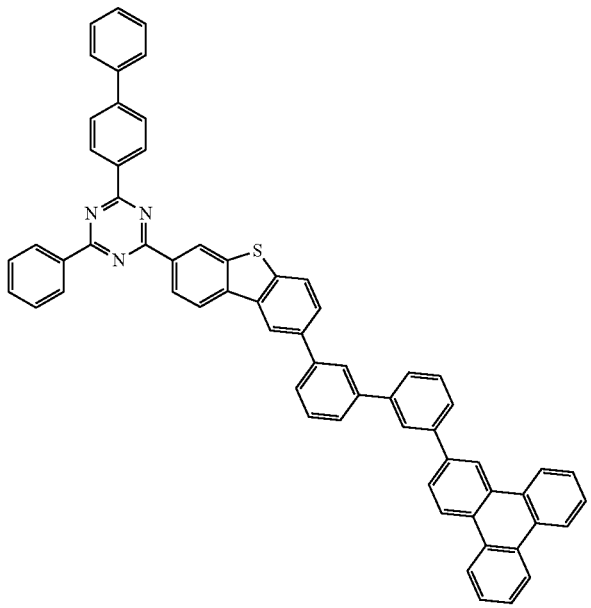
2-69
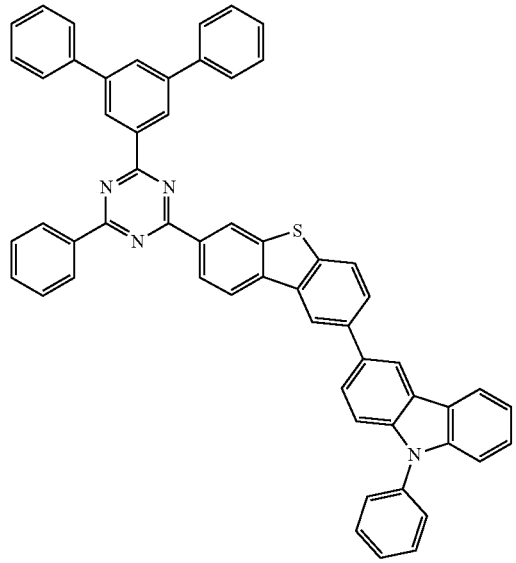
2-70
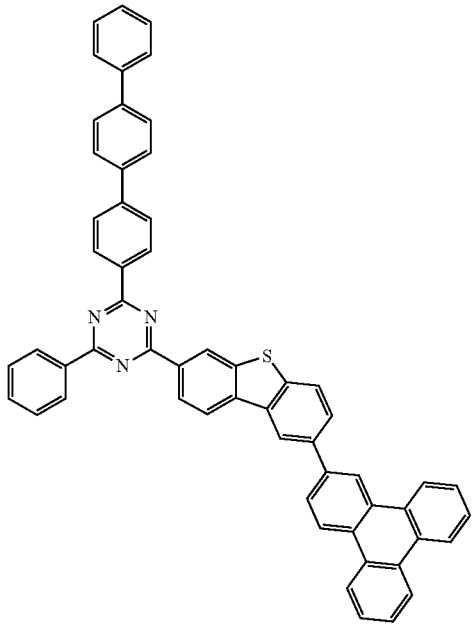

-continued
2-71
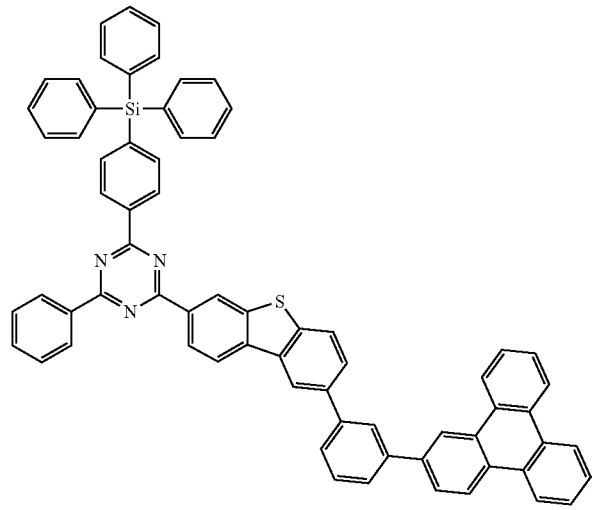
2-72
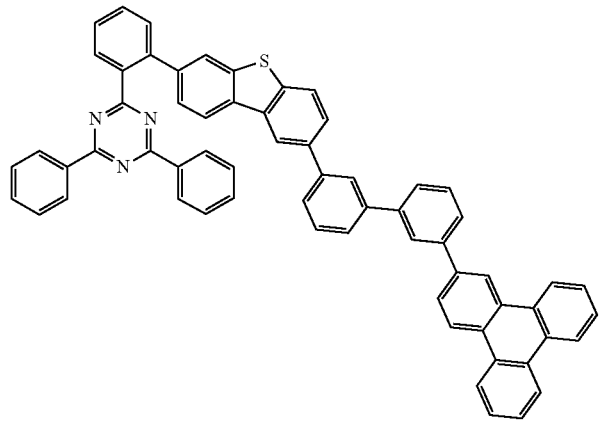
2-73
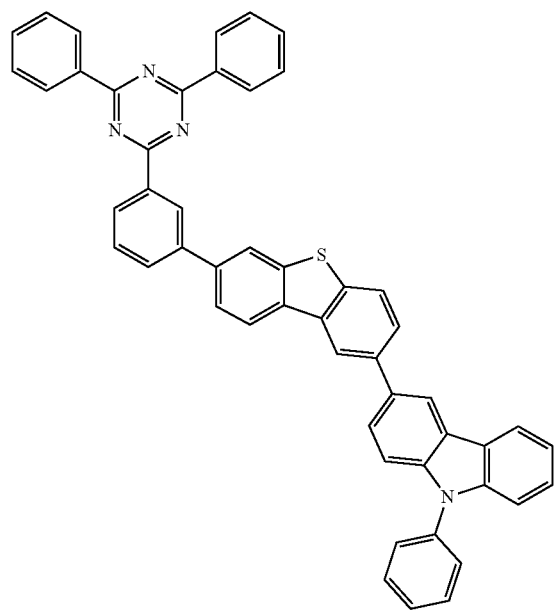
2-74
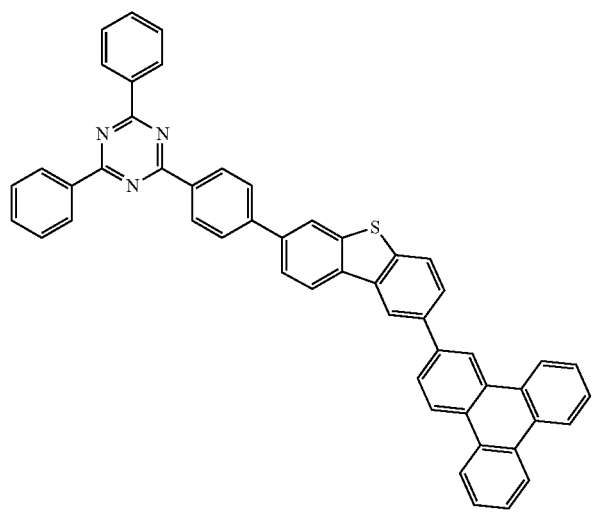

2-75
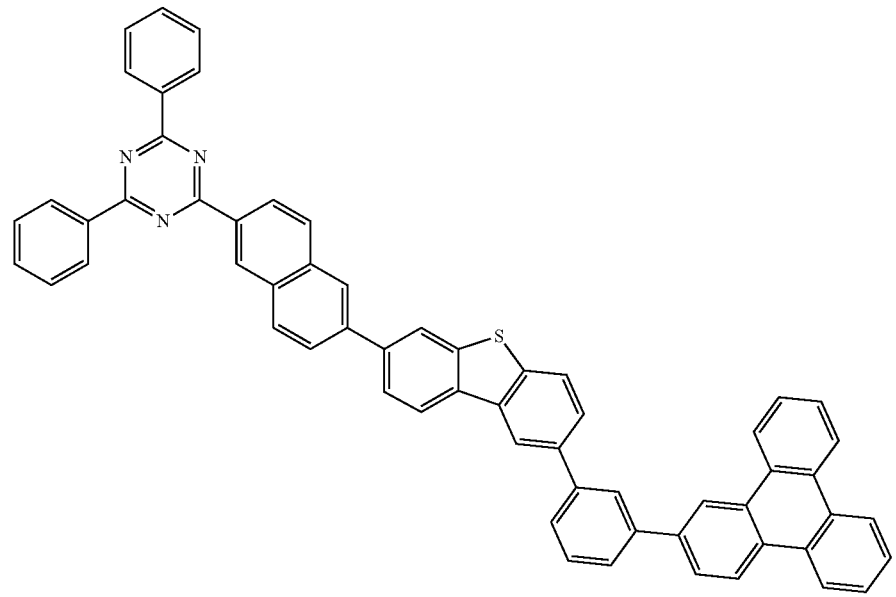
2-76
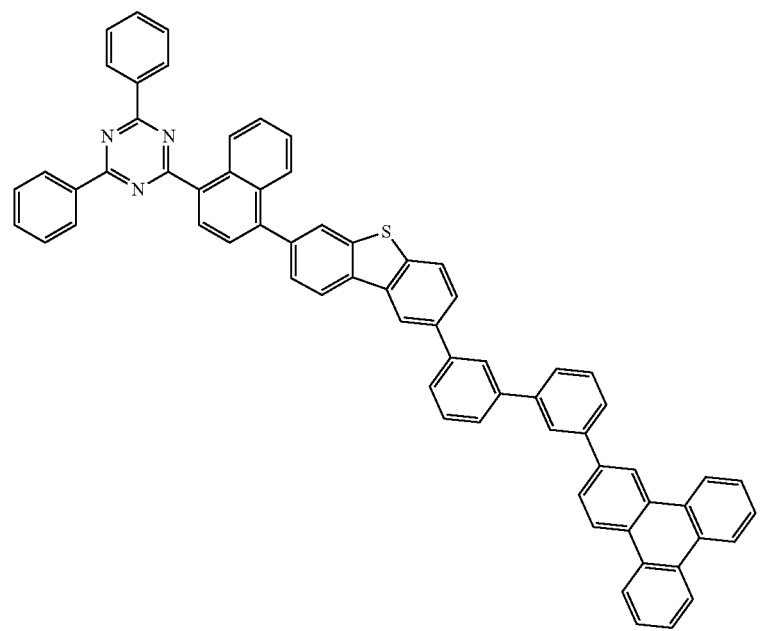

2-77
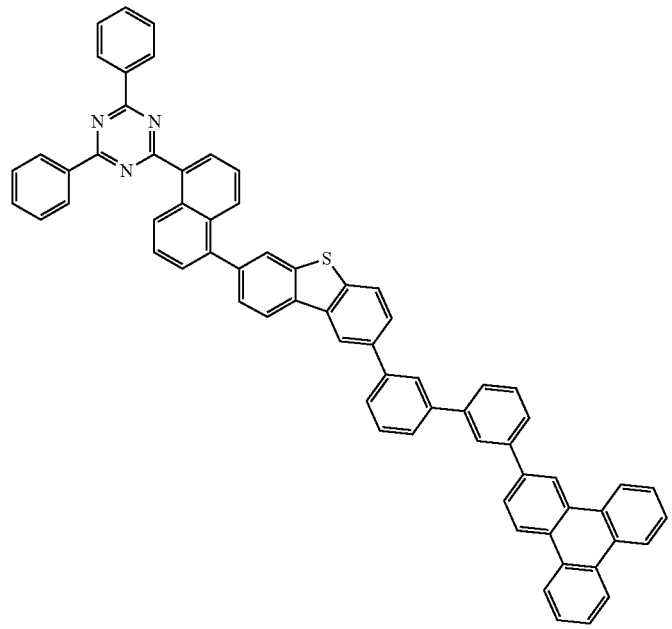
2-78
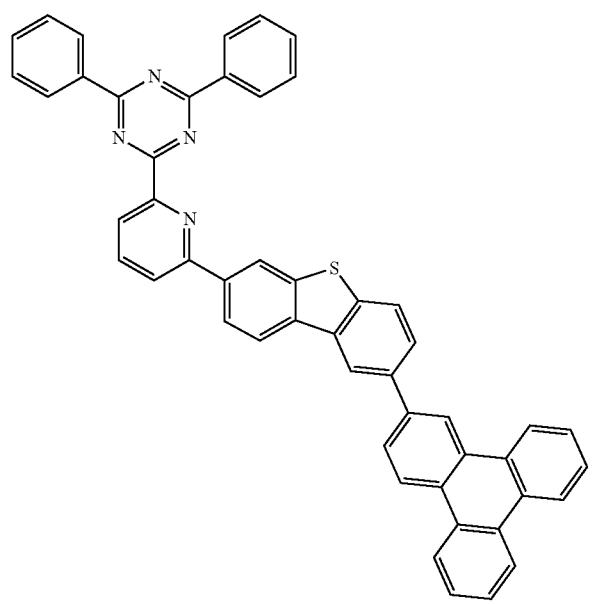
2-79
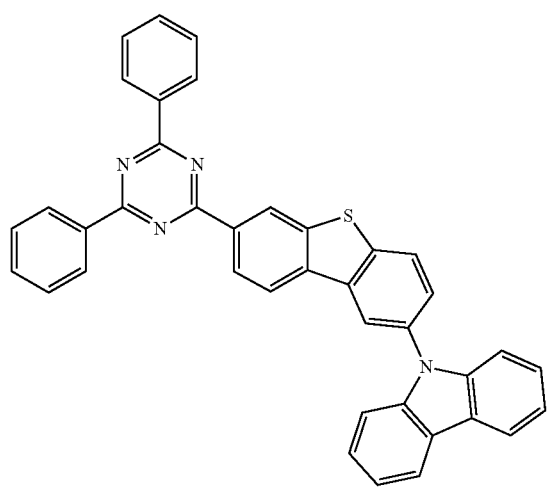

-continued
2-80
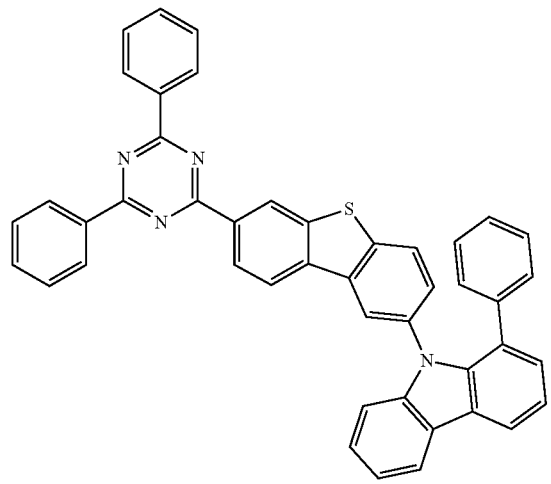
2-81
2-82
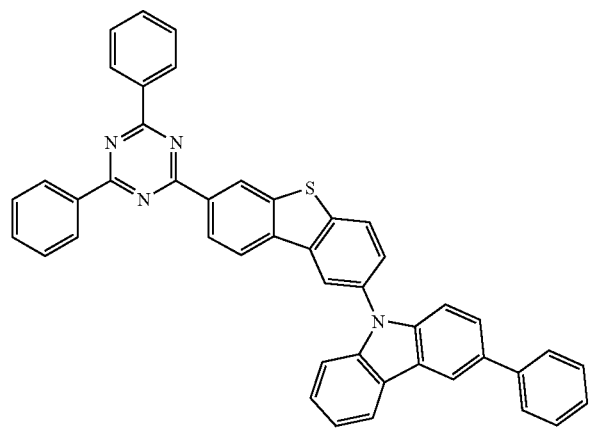
2-83
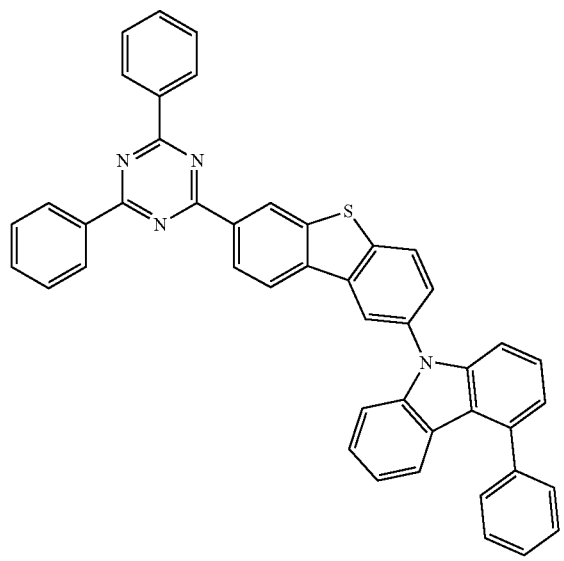
2-84
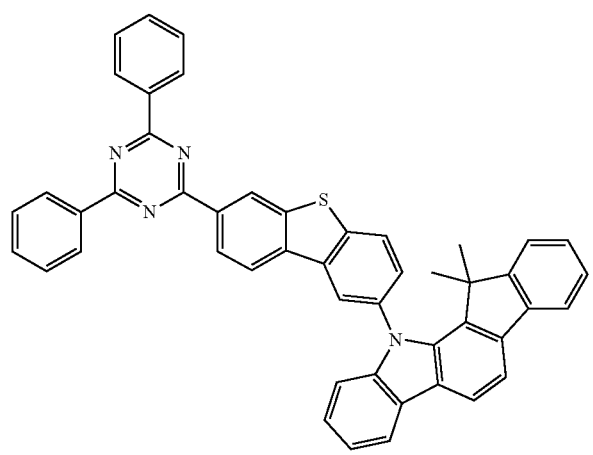
2-85
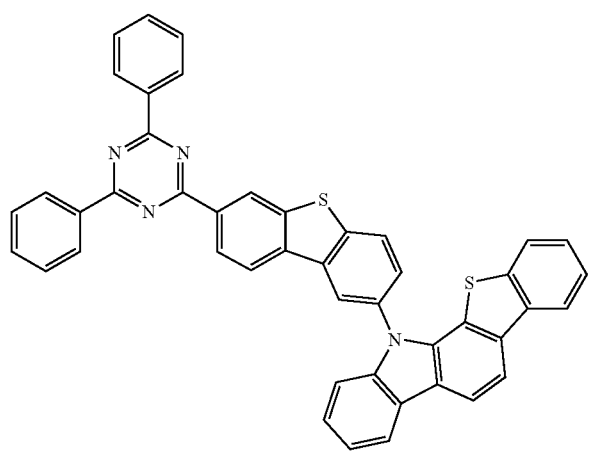

-continued
2-86
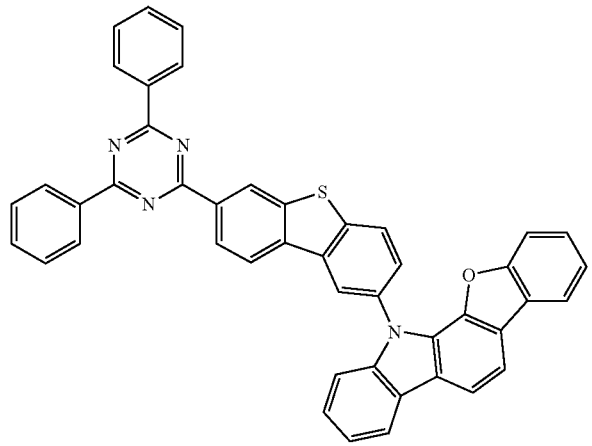
2-87
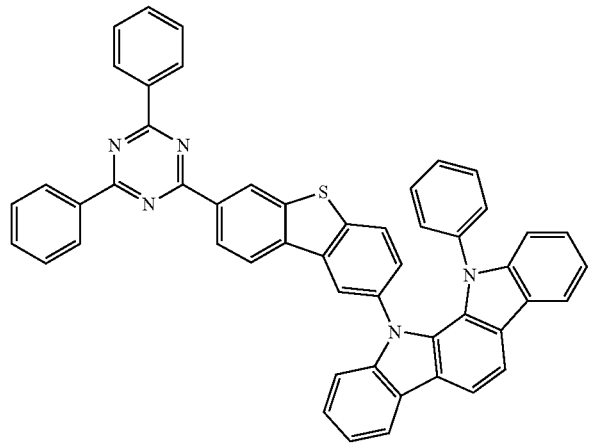
2-88
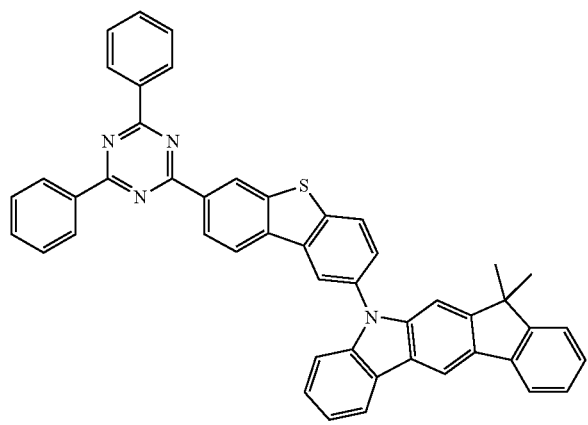
2-89
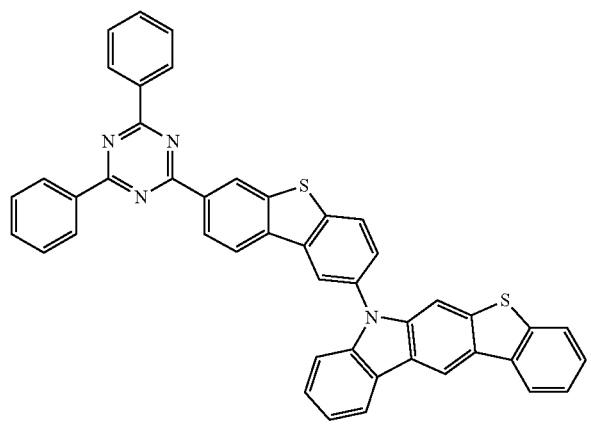
2-90
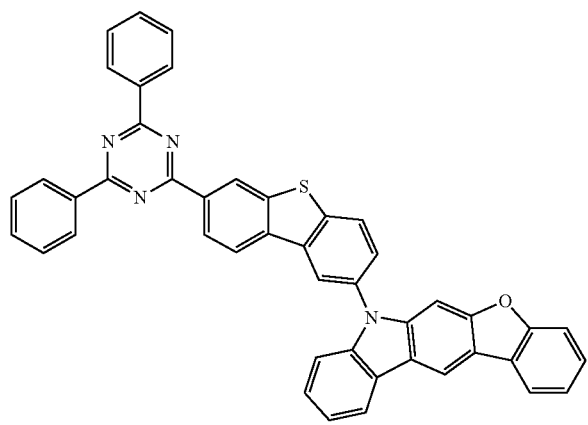
2-91
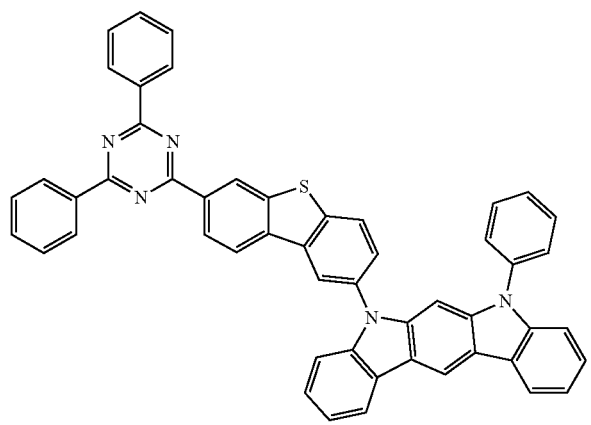

-continued
2-92
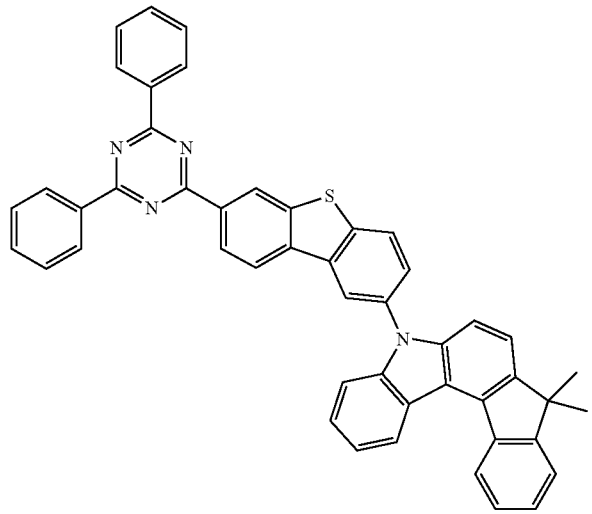
2-93
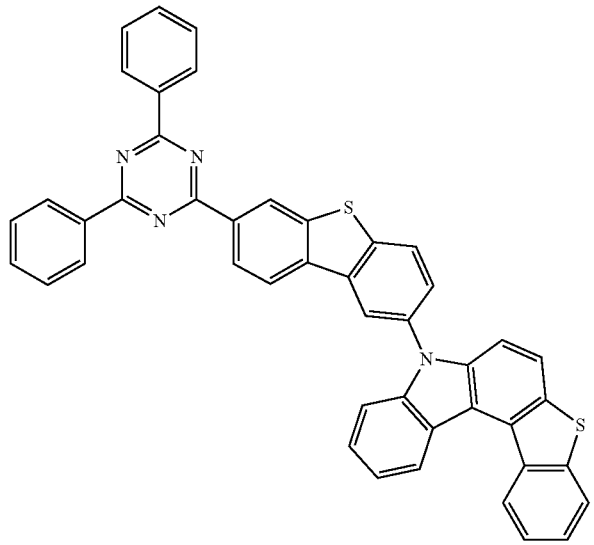
2-94
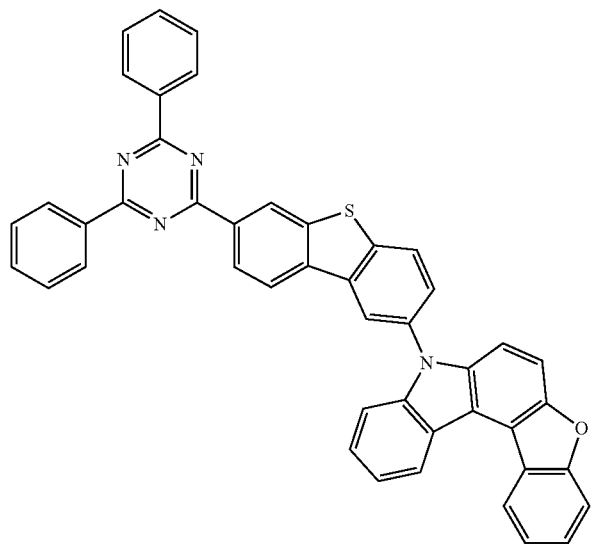
2-95
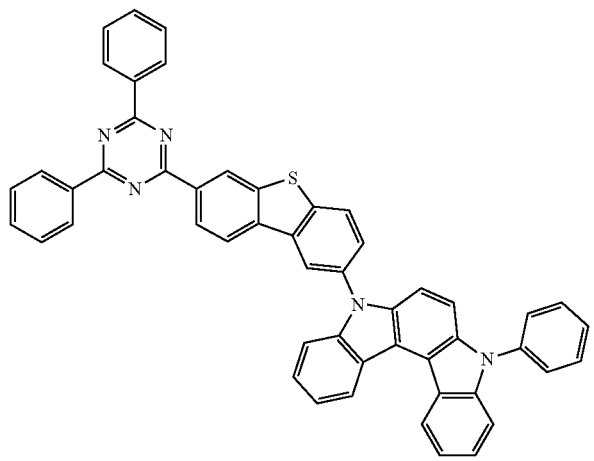
2-96
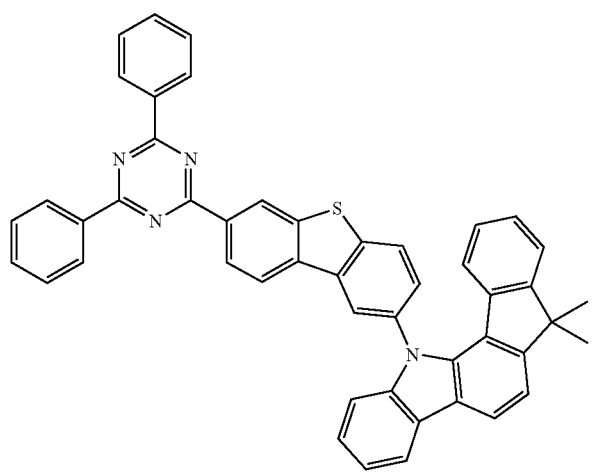
2-97
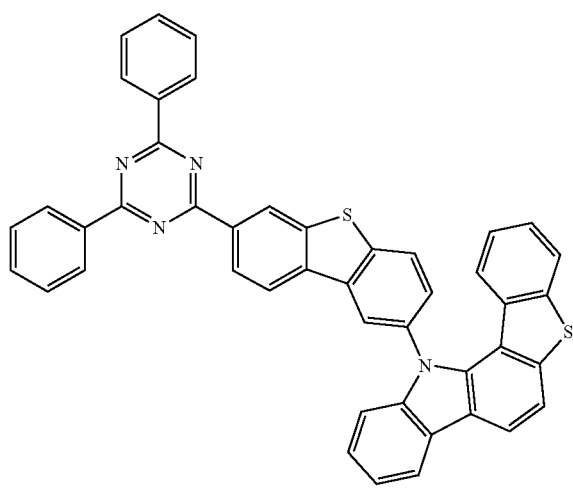

2-98
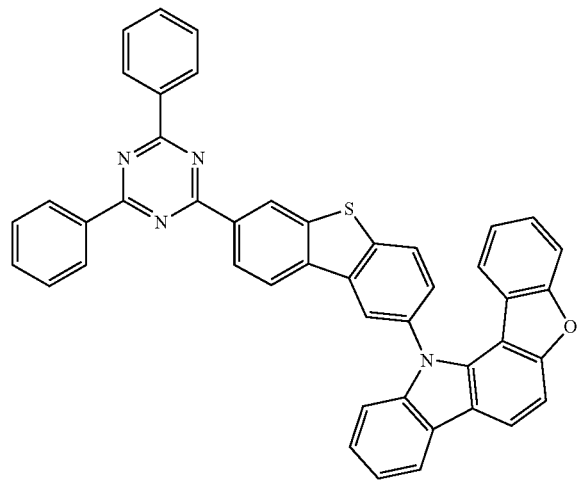
2-99
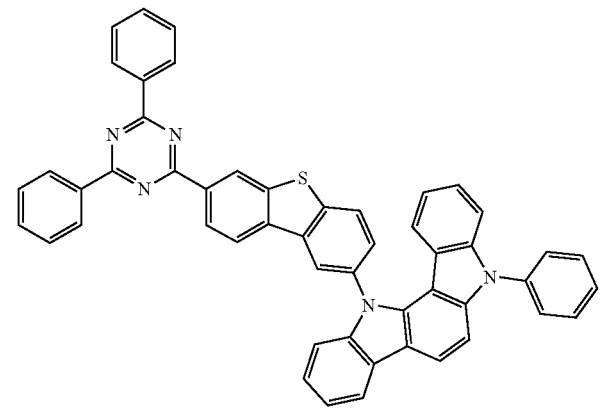
2-100
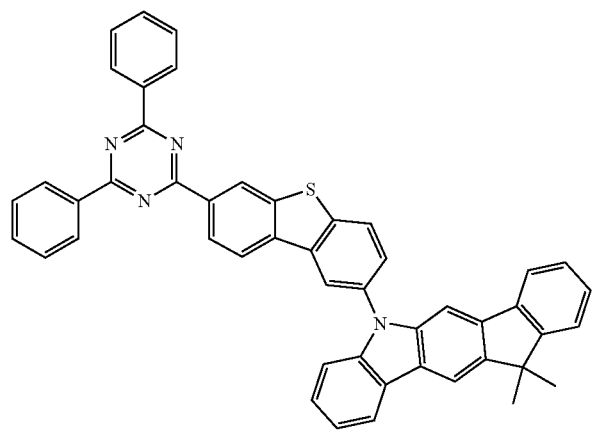
2-101
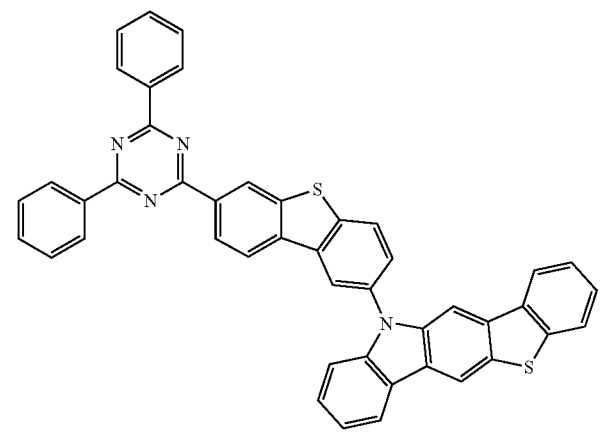
2-102
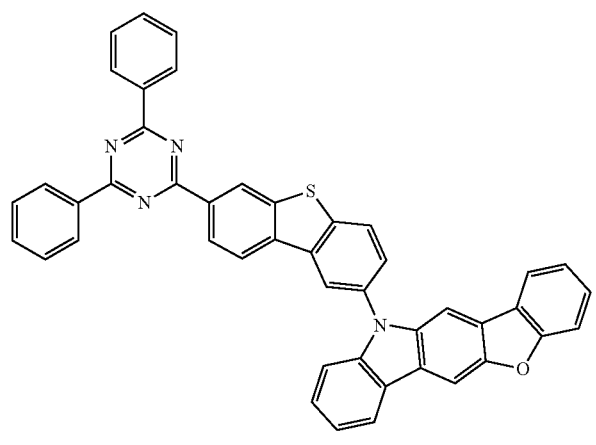
2-103
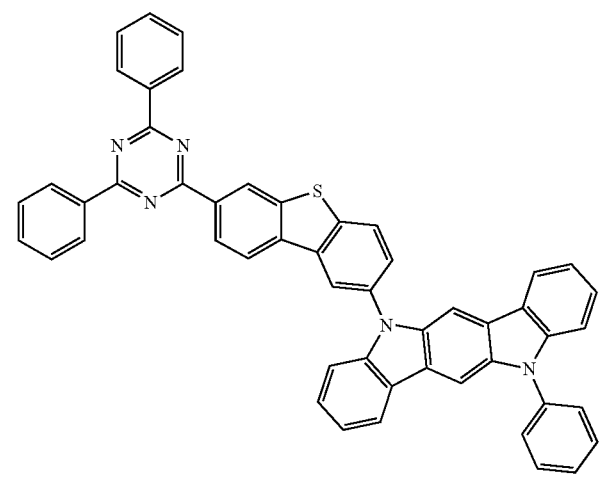

-continued
2-104
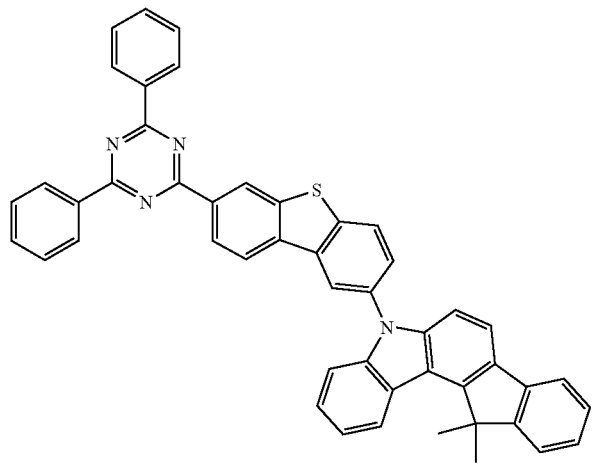
2-105
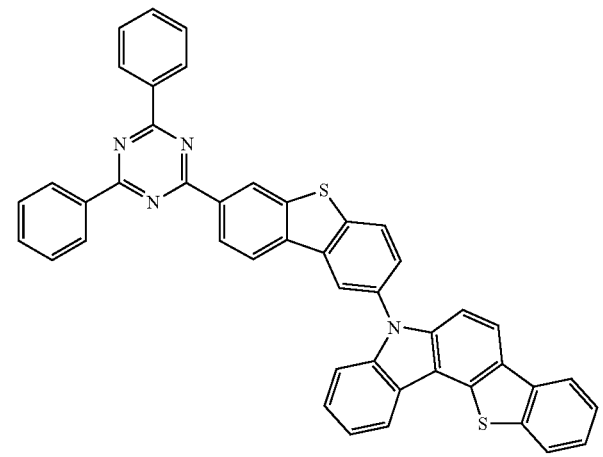
2-106
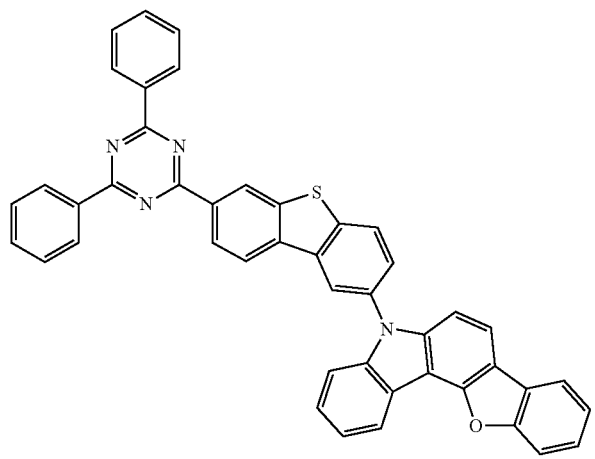
2-107
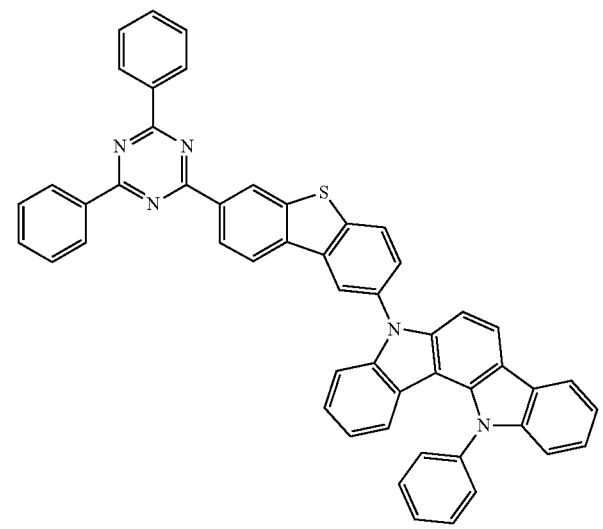
2-108
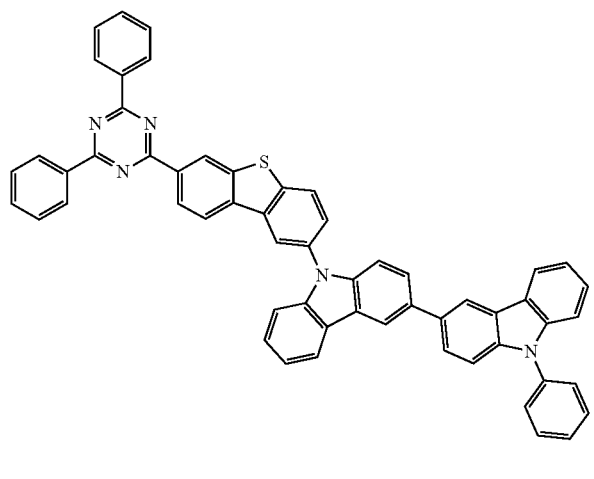
2-109
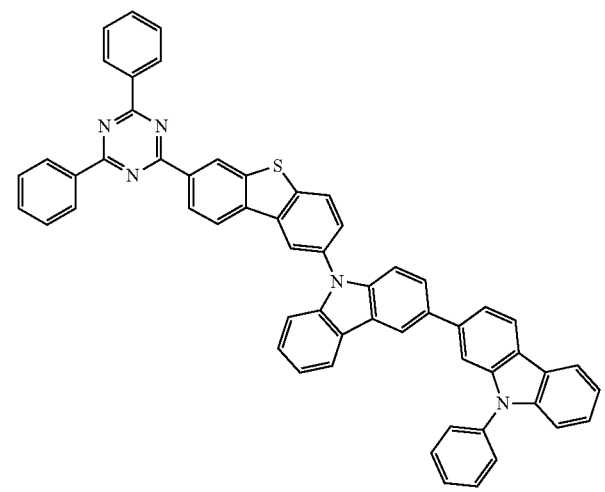

-continued
2-110
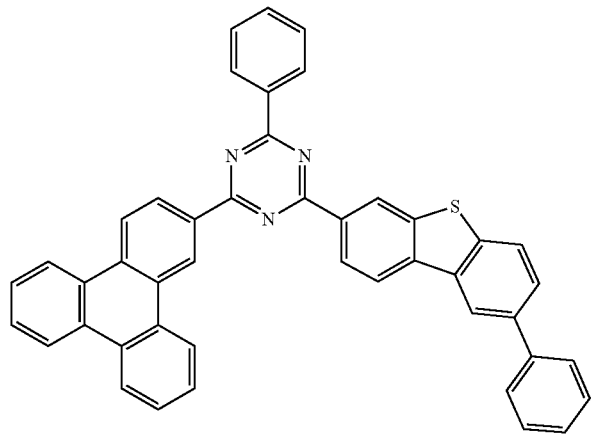
2-111
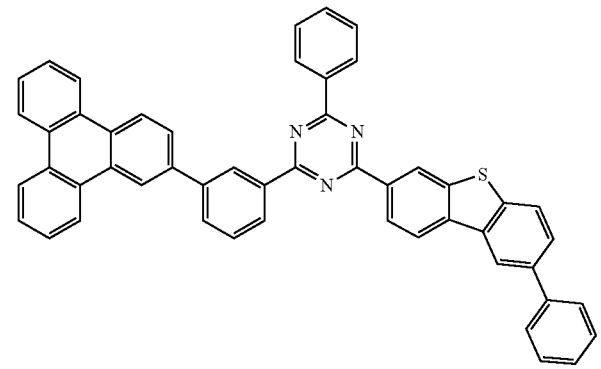
2-112
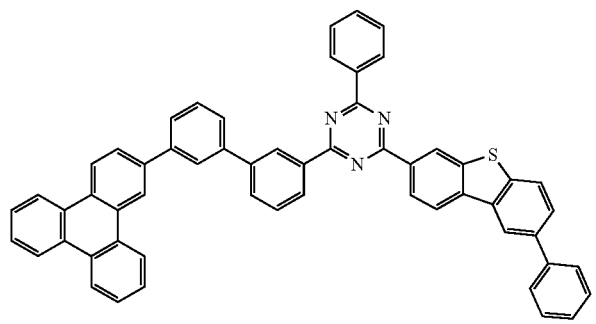
2-113
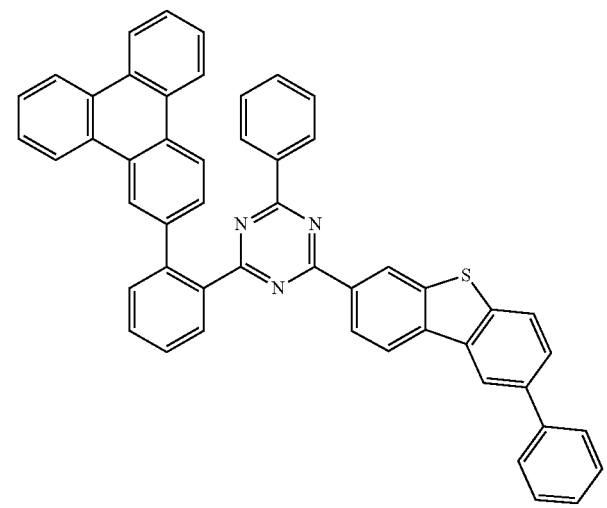
2-114
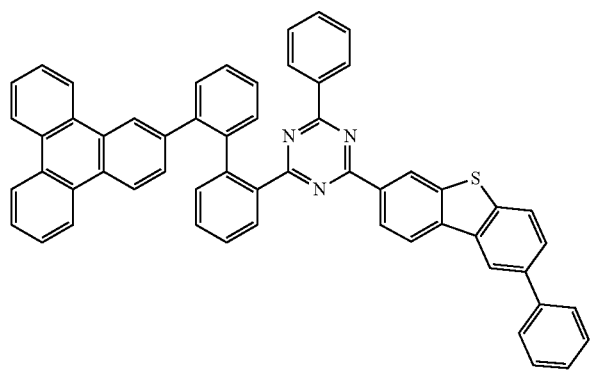
2-115
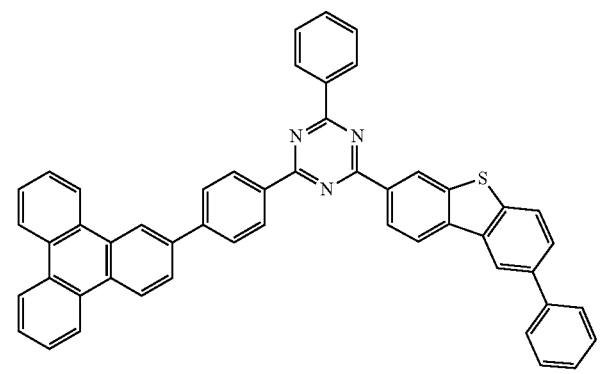

2-116 2-117
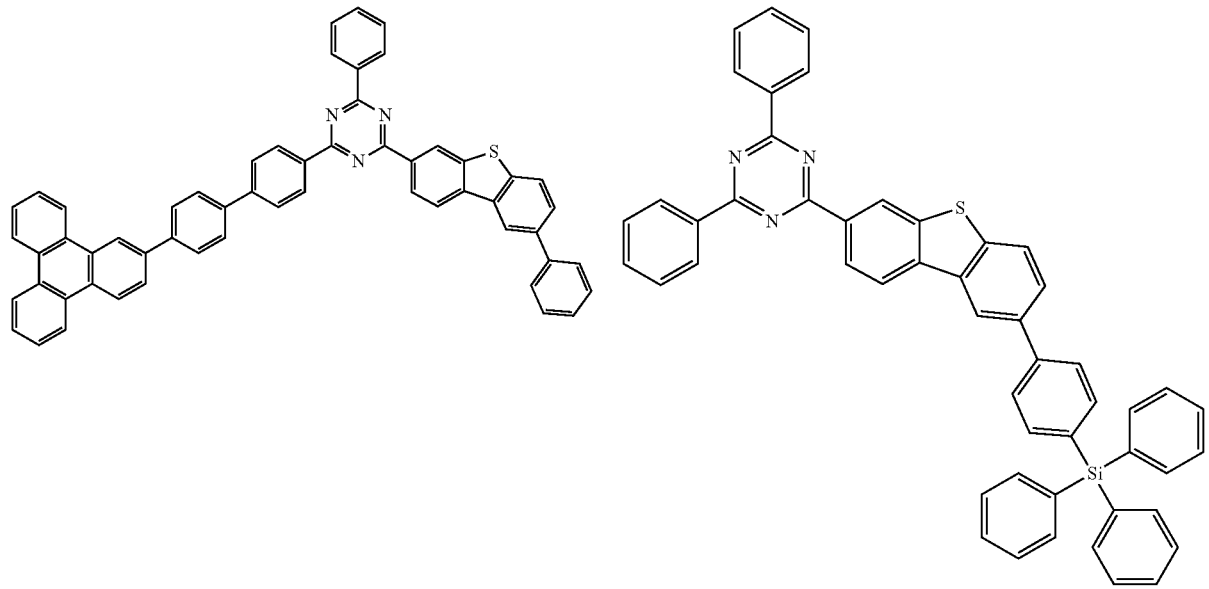
2-118 2-119
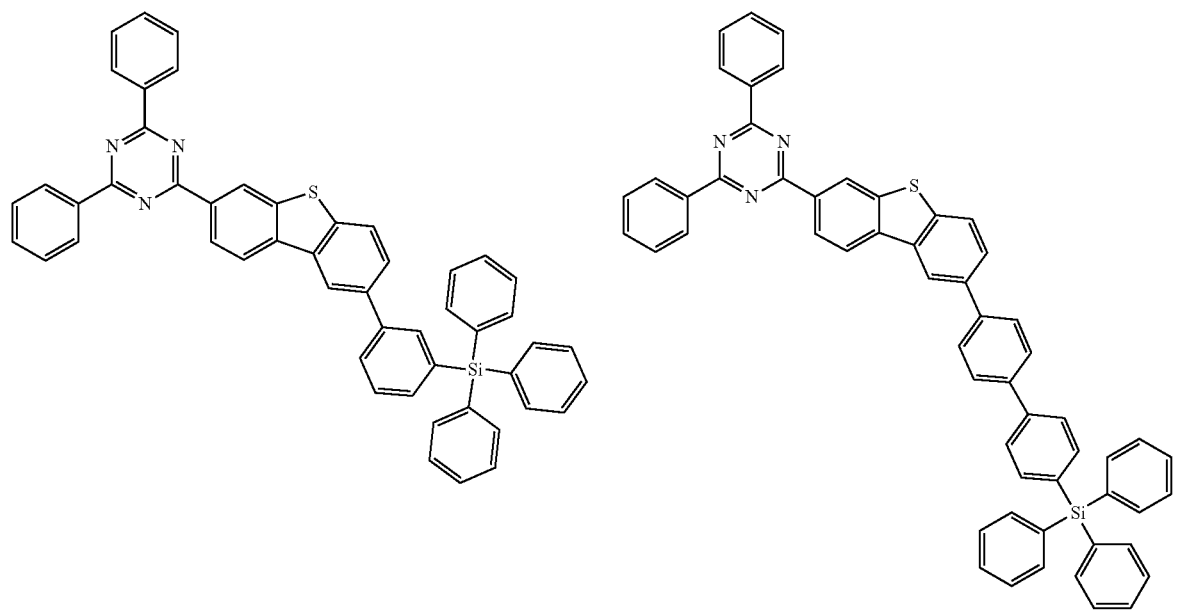

-continued
2-120
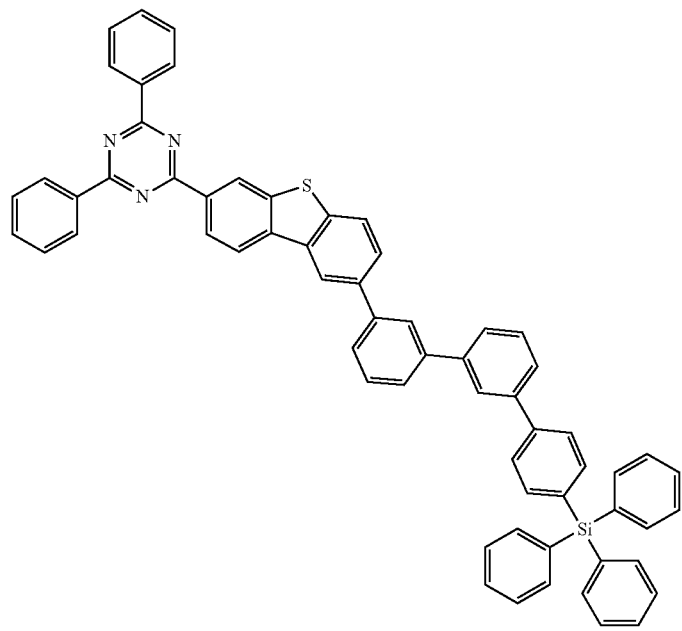
4-1
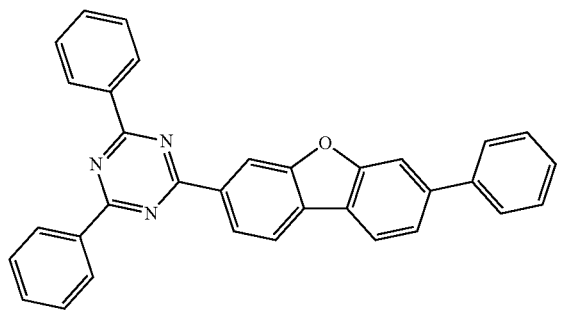
4-2
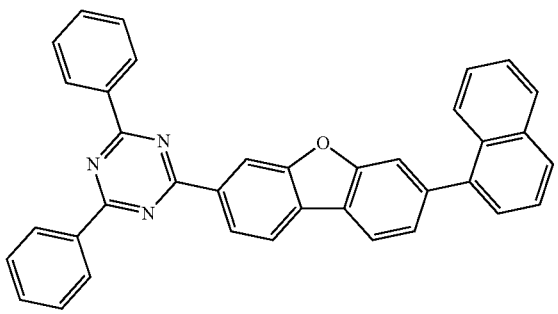
4-3
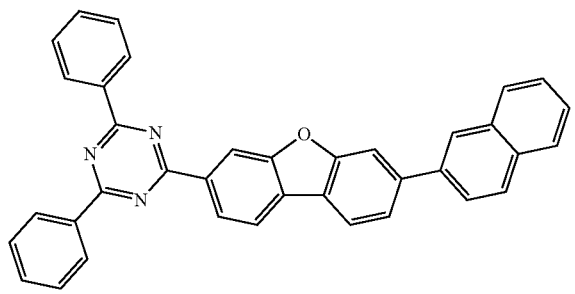
4-4
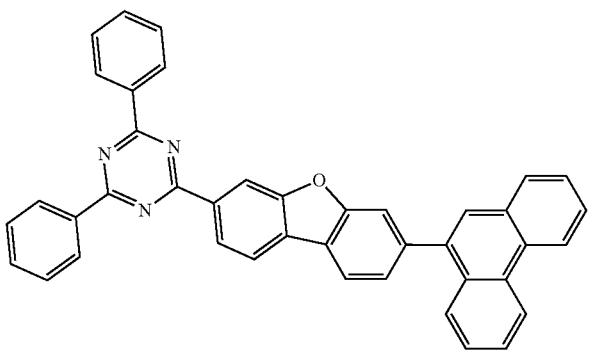

-continued
4-5
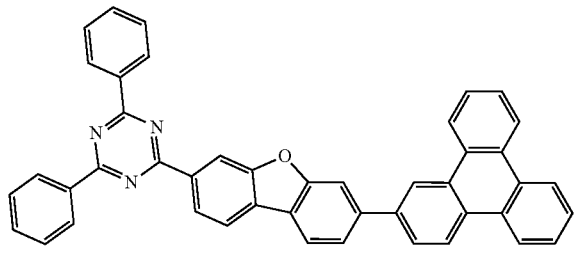
4-6
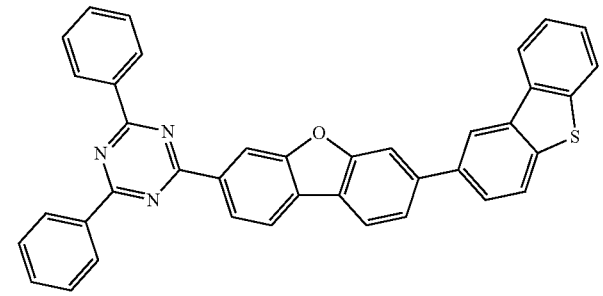
4-7
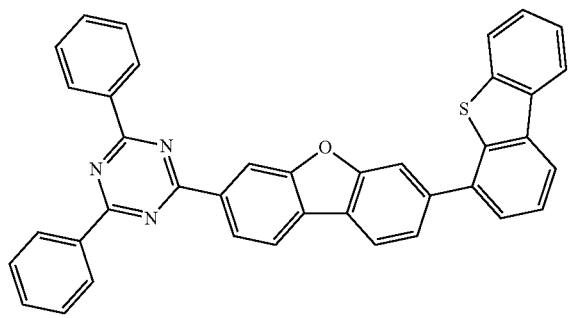
4-8
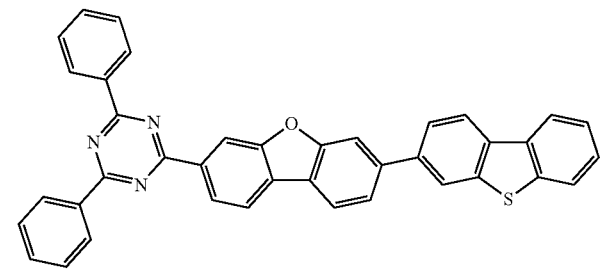
4-9
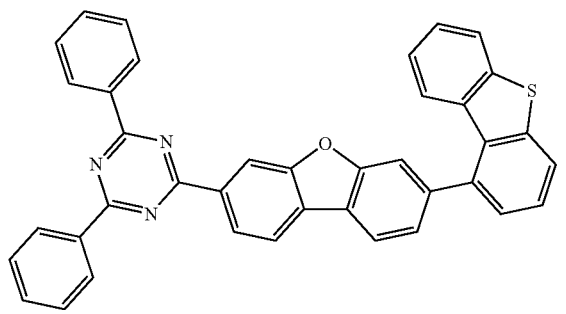
4-10
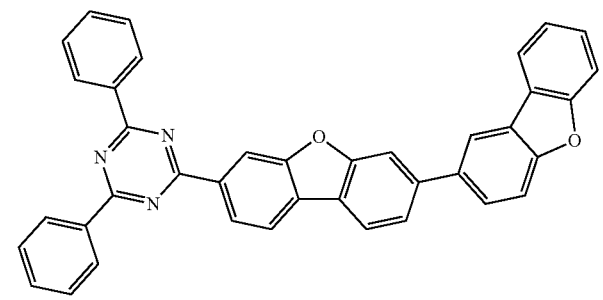
4-11
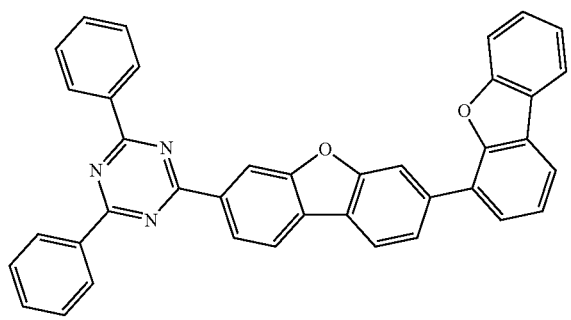
4-12
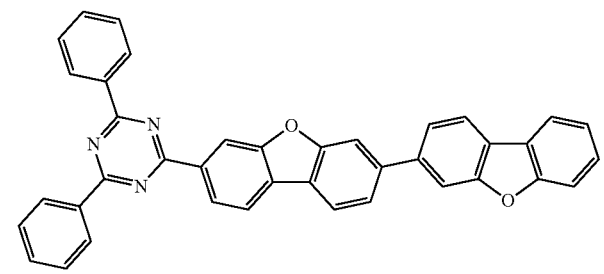

-continued
4-13
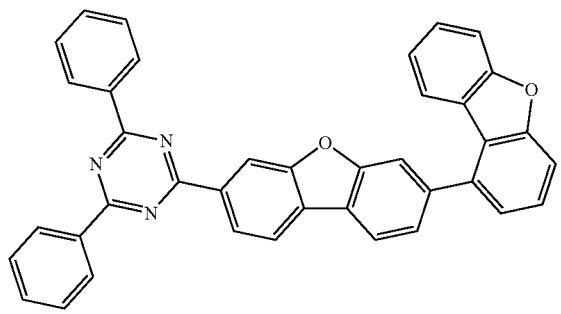
4-14
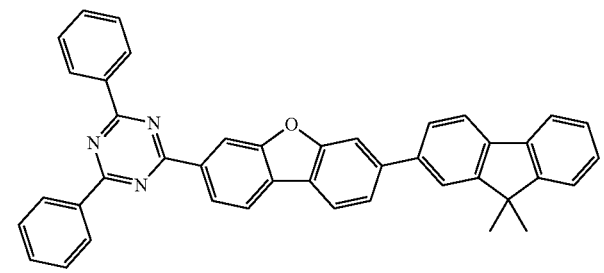
4-15
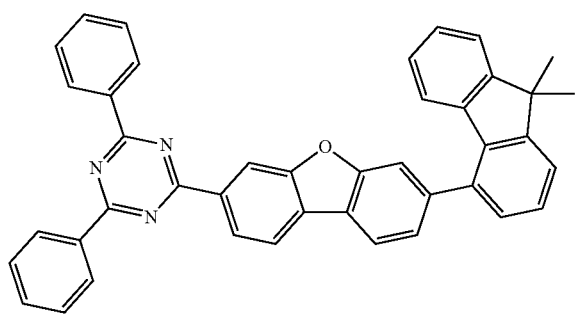
4-16
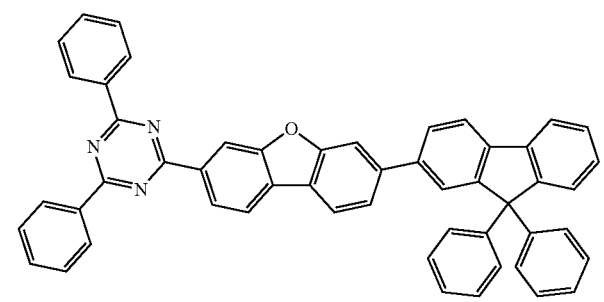
4-17
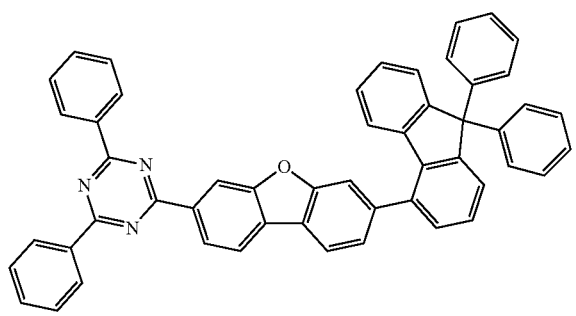
4-18
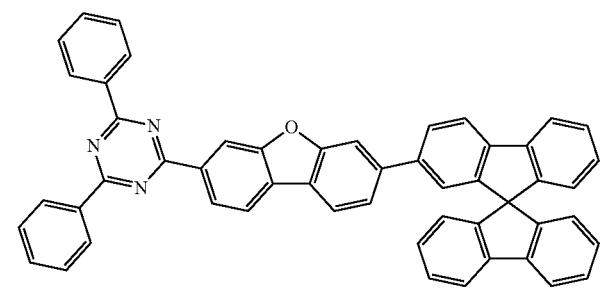
4-19
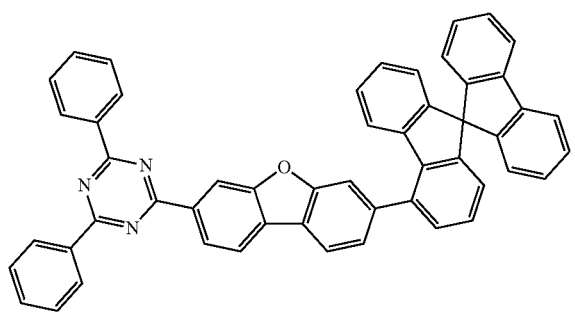
4-20
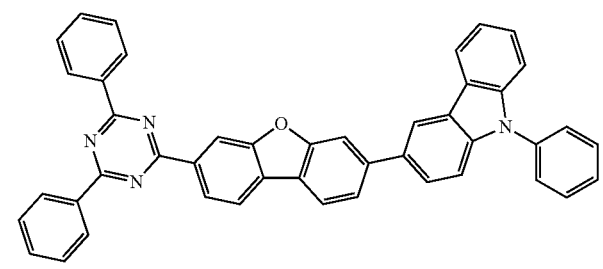

-continued
4-21
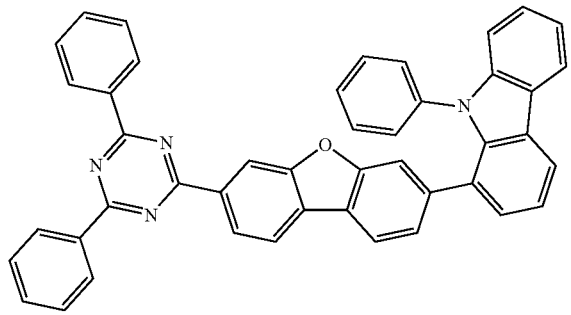
4-22
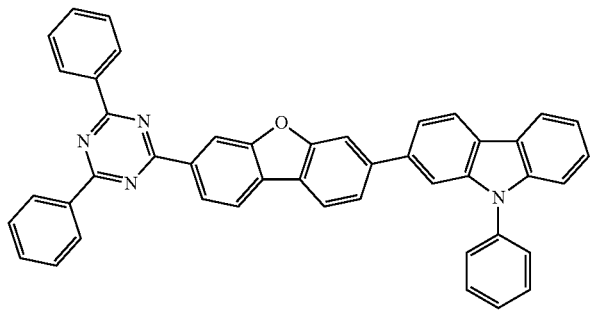
4-23
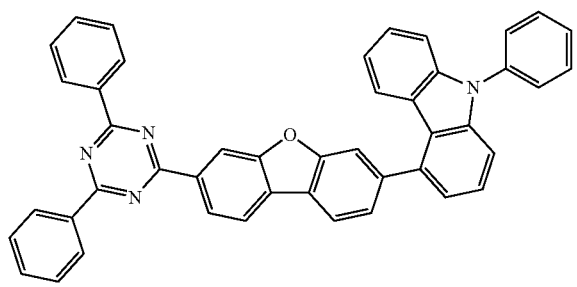
4-24
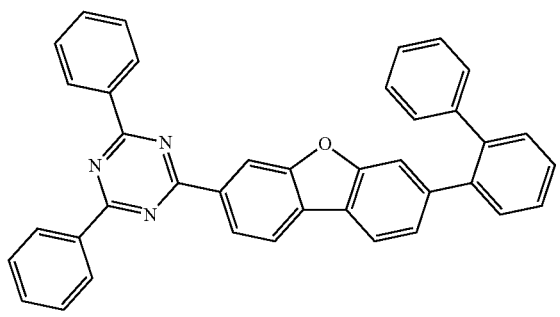
4-25
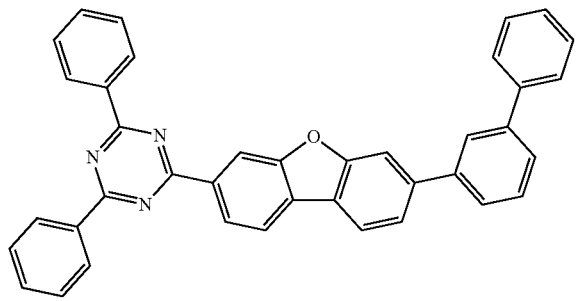
4-26
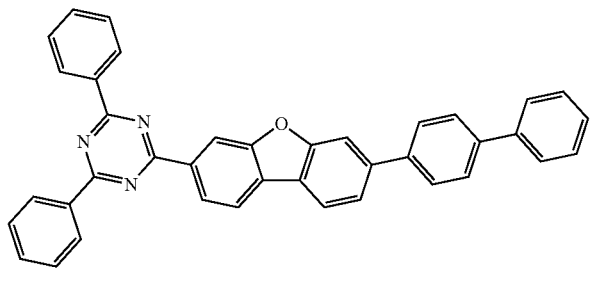
4-27
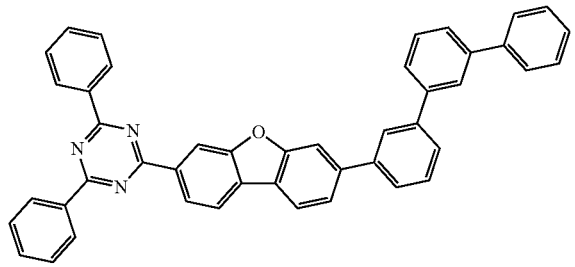
4-28
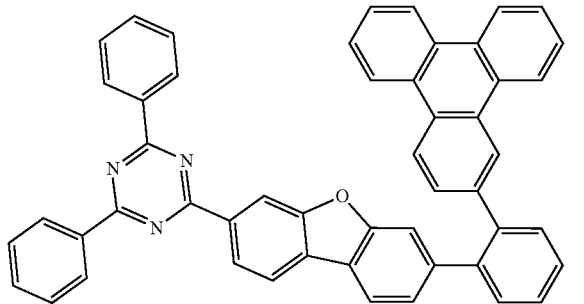
4-29
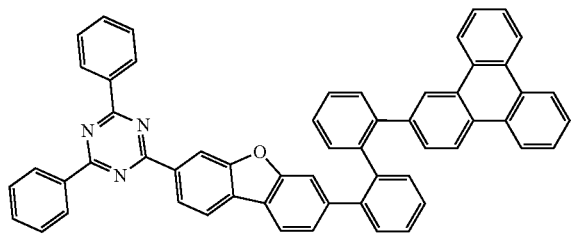
4-30
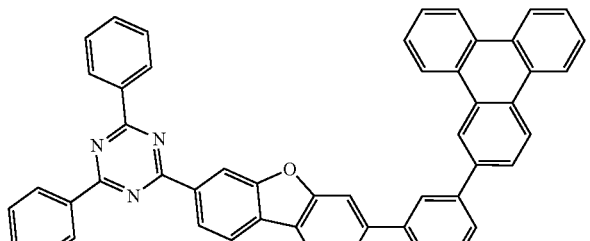

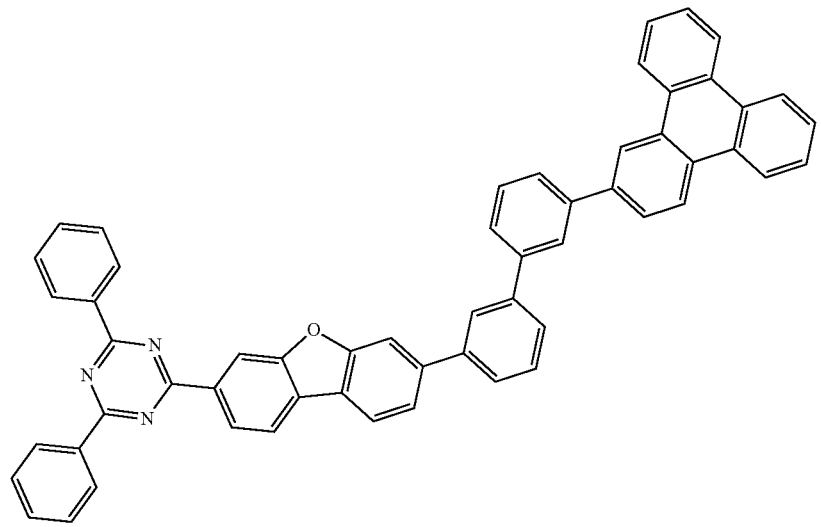
4-31
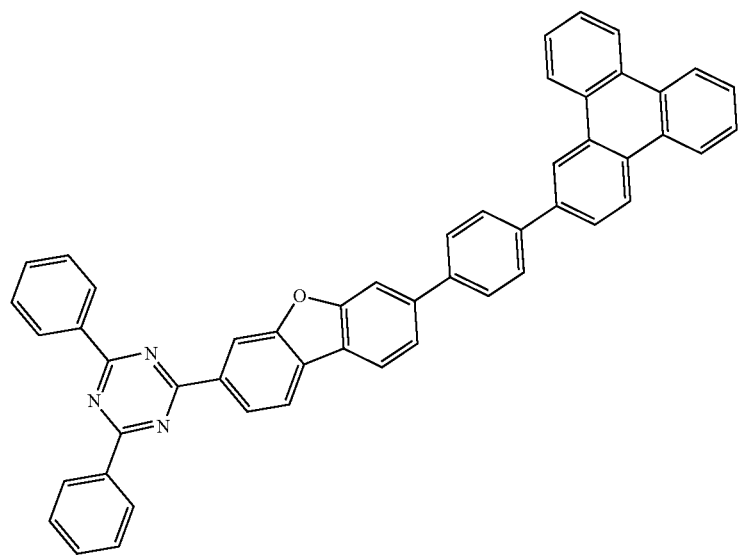
4-32

4-33
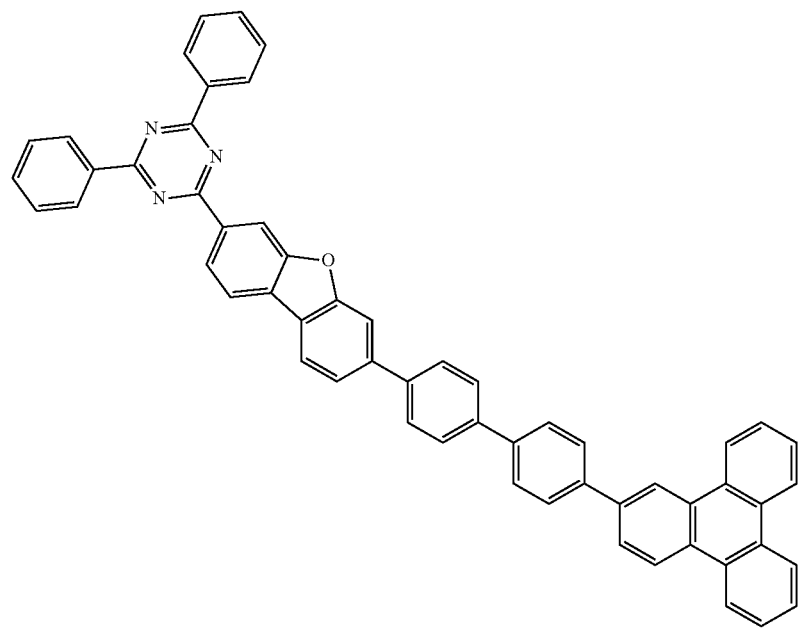
4-34
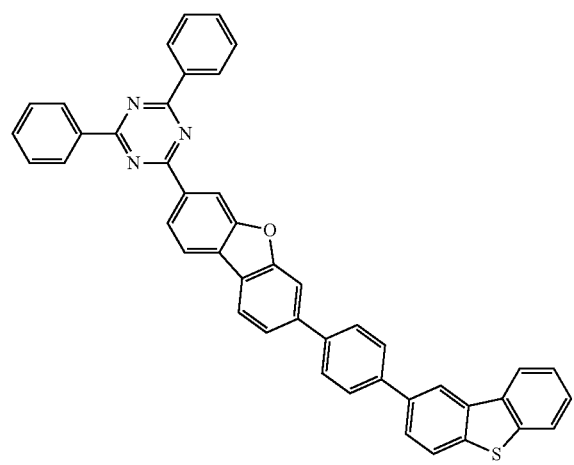
4-35
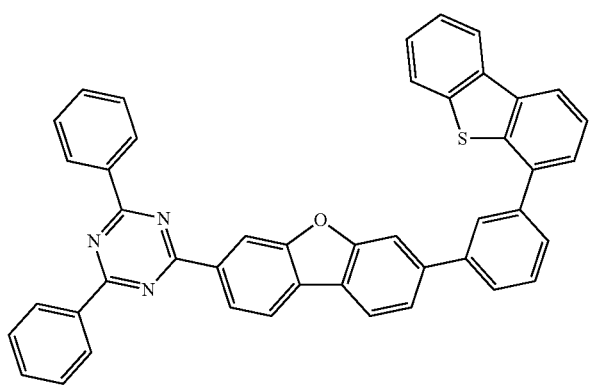
4-36
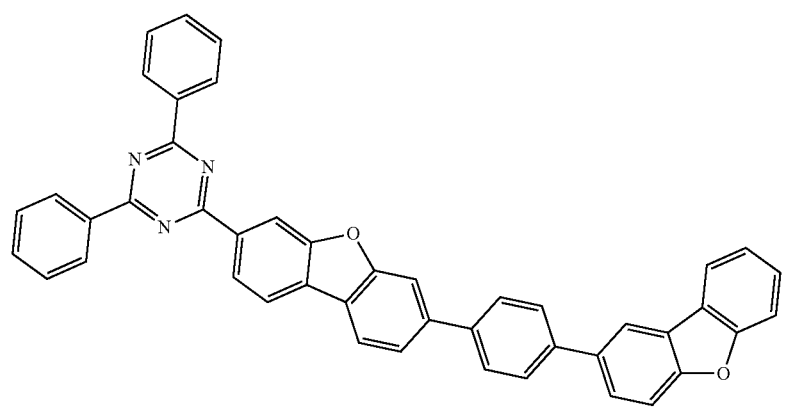

-continued
4-37
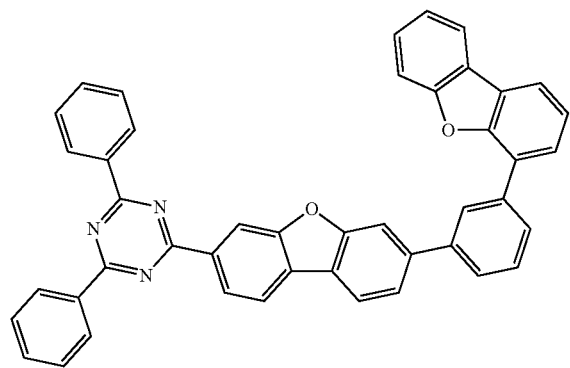
4-38
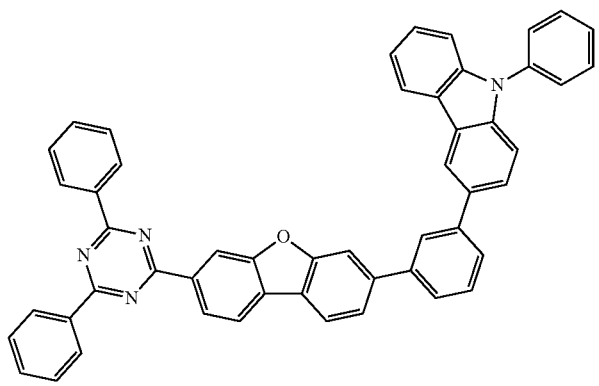
4-39
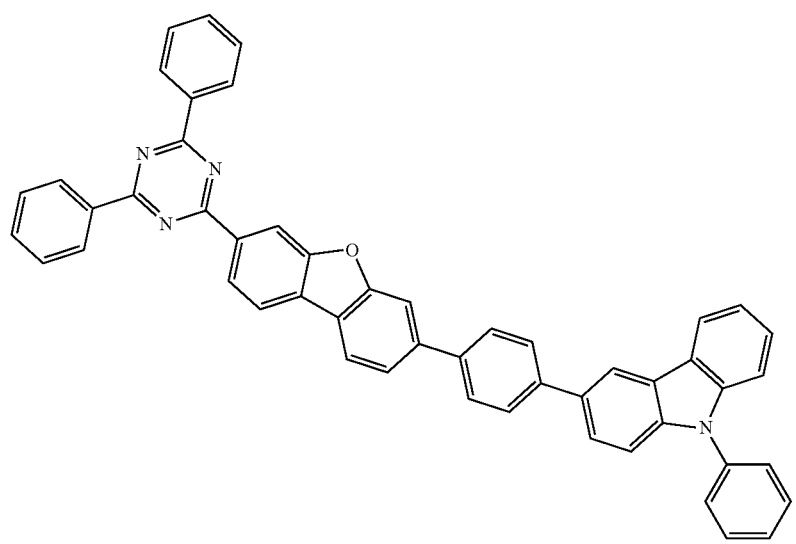
4-40
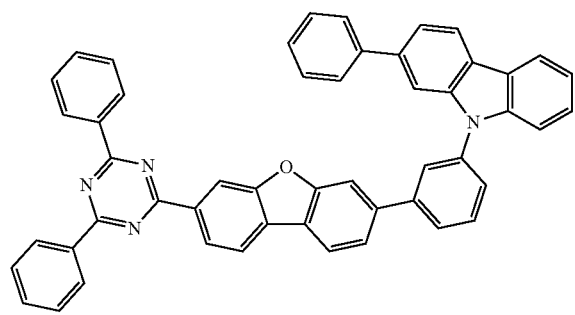
4-41
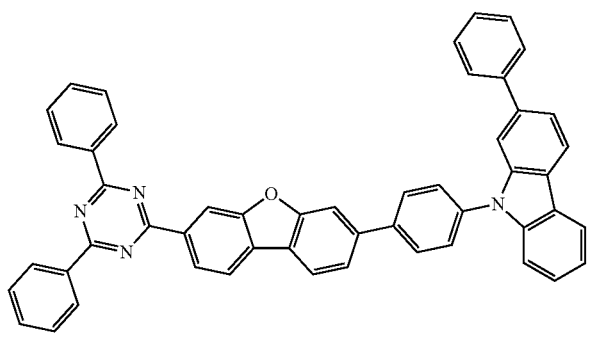

-continued
4-42
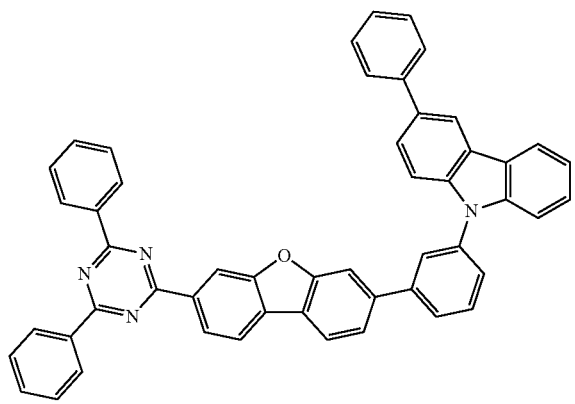
4-43
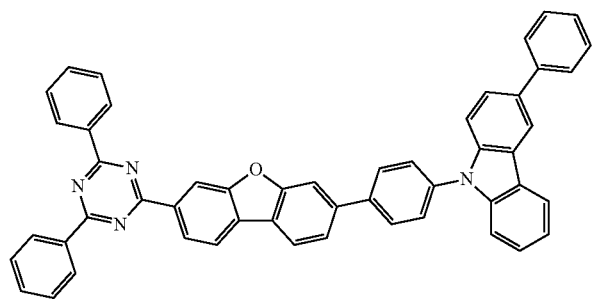
4-44
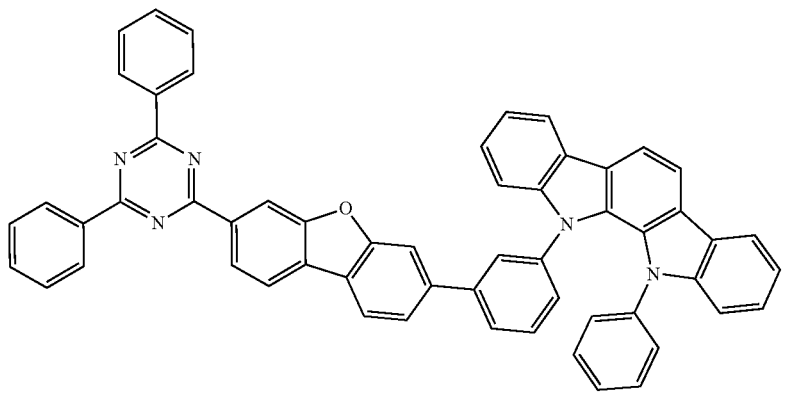
4-45
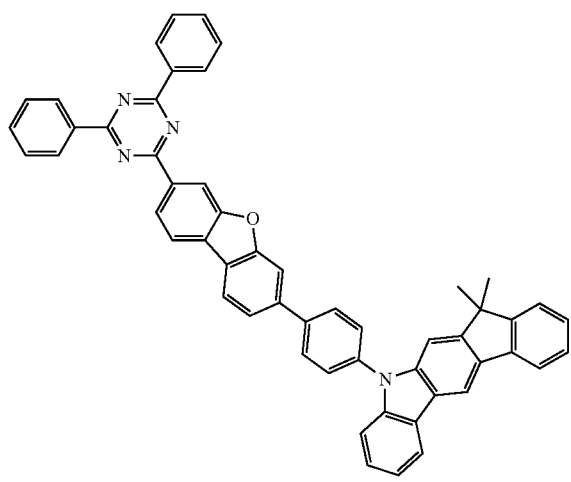
4-46
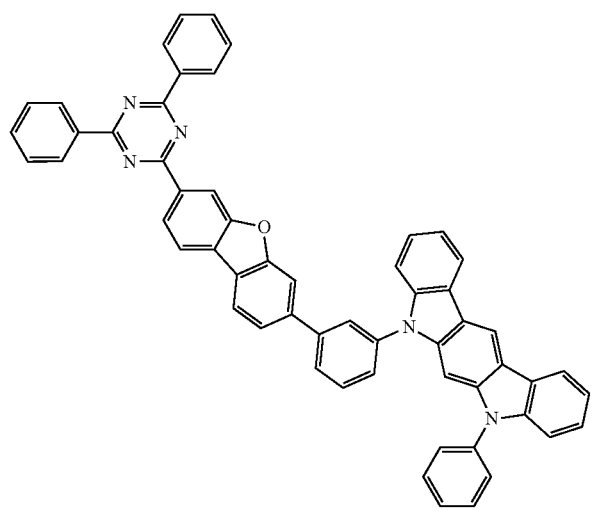

-continued
4-47
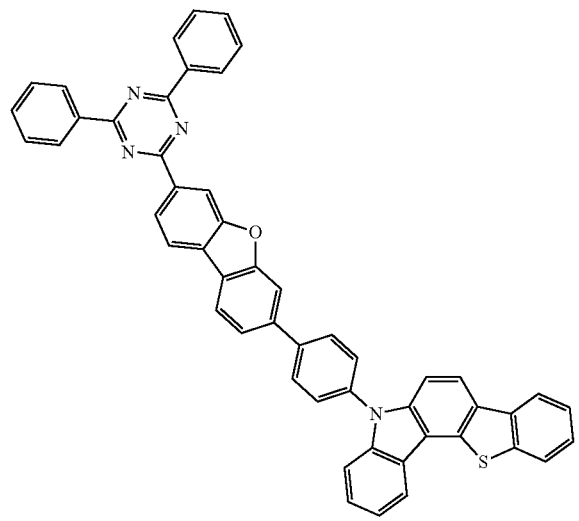
4-48
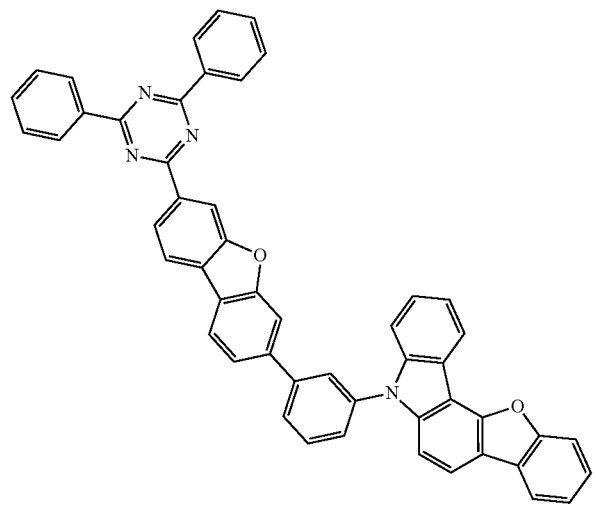
4-49
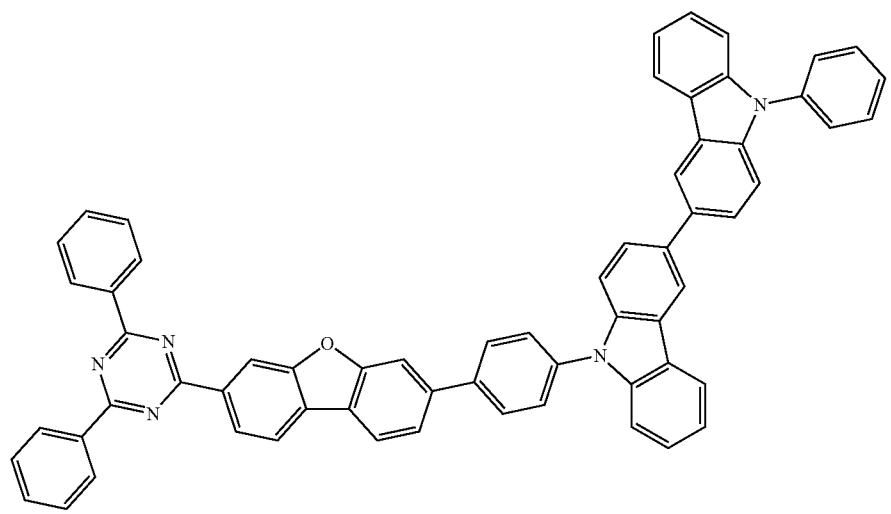
4-50
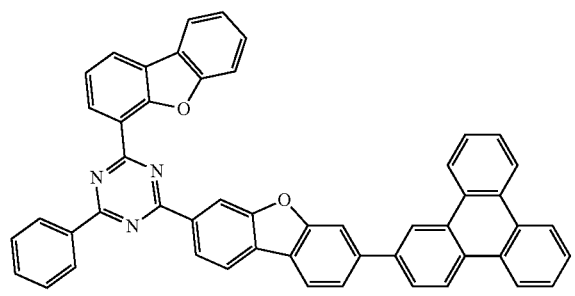
4-51
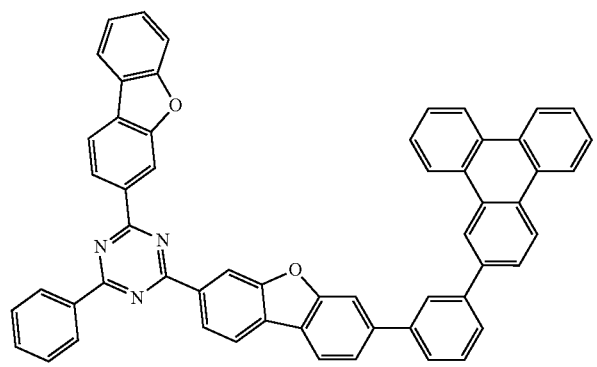

4-52
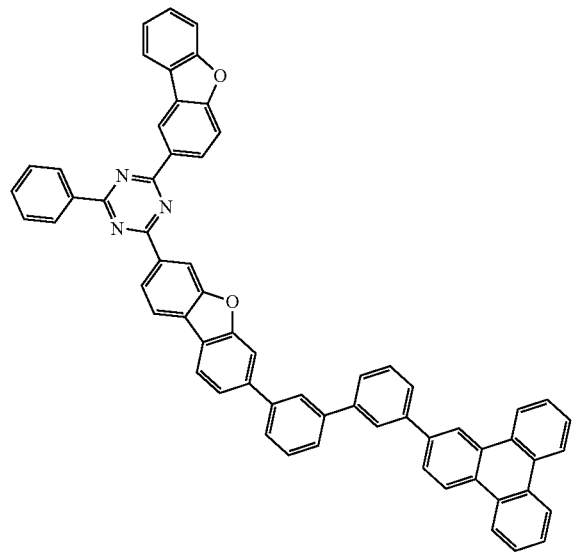
4-53
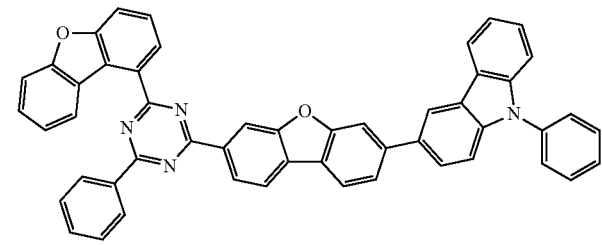
4-54
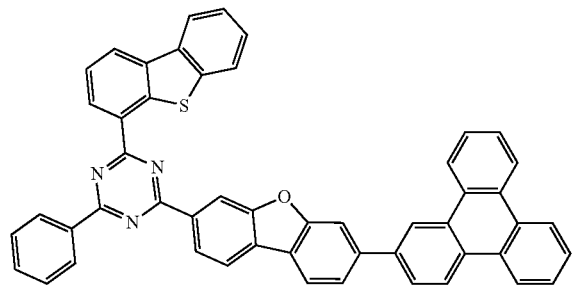
4-55
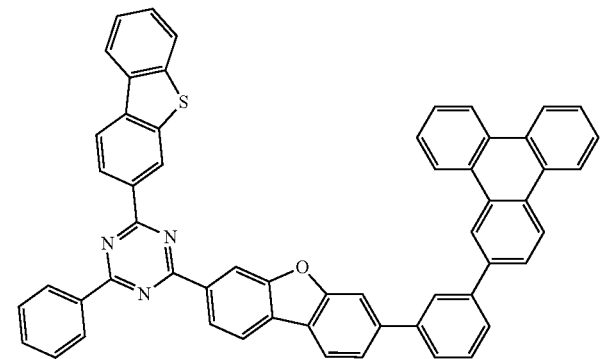
4-56
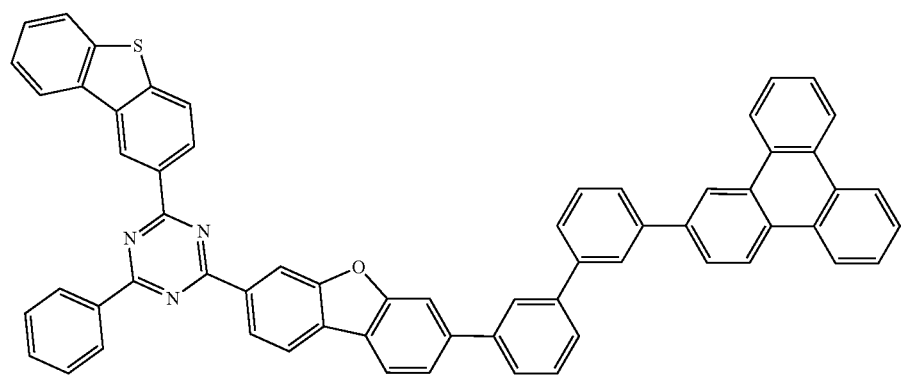

-continued
4-57
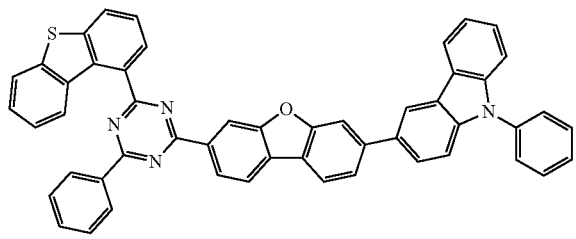
4-58
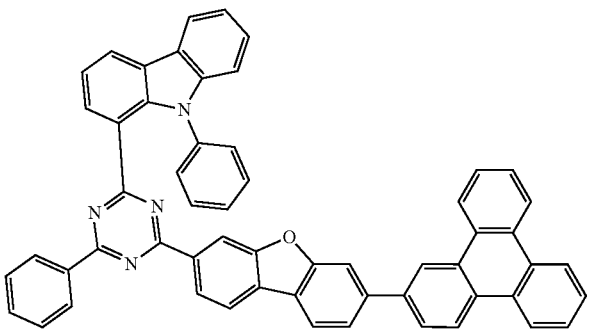
4-59
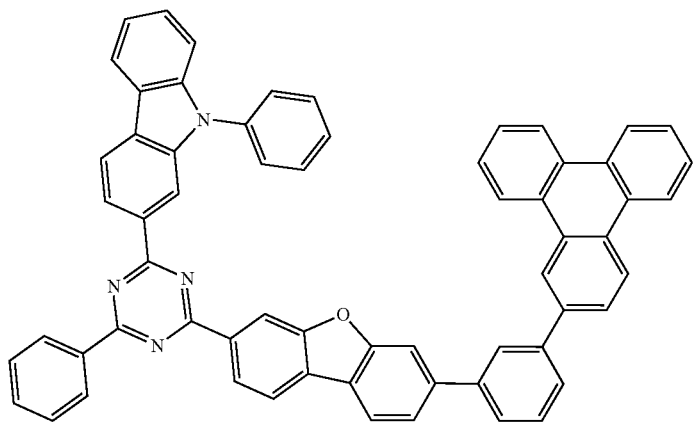
4-60
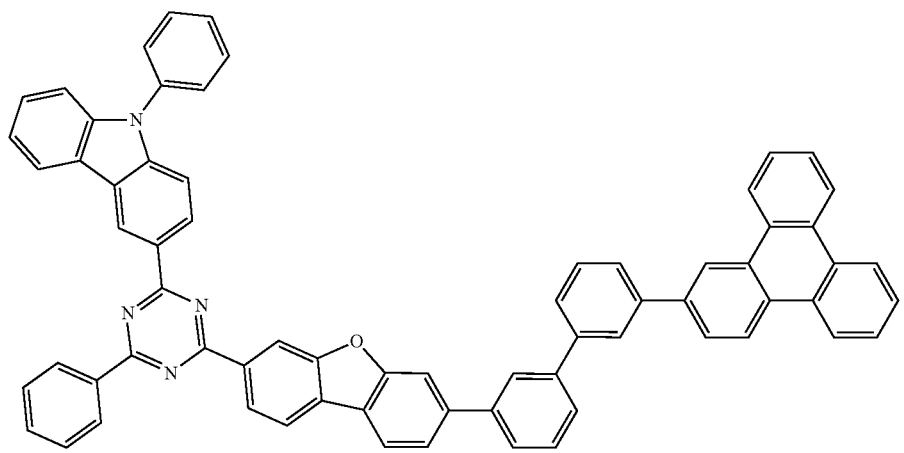
4-61
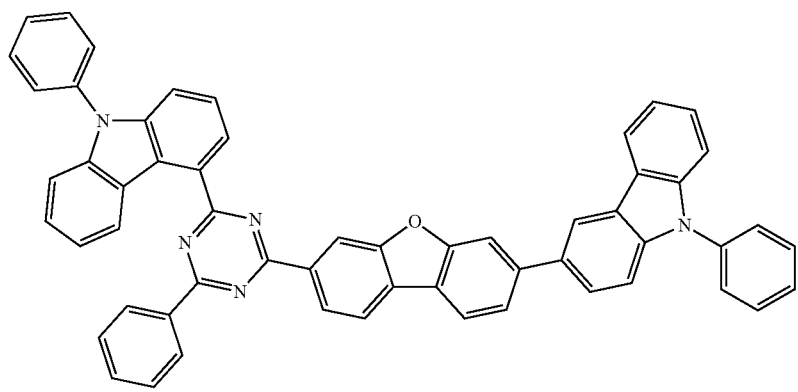

-continued
4-62
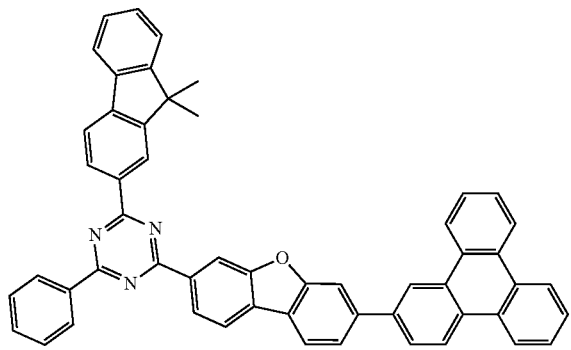
4-63
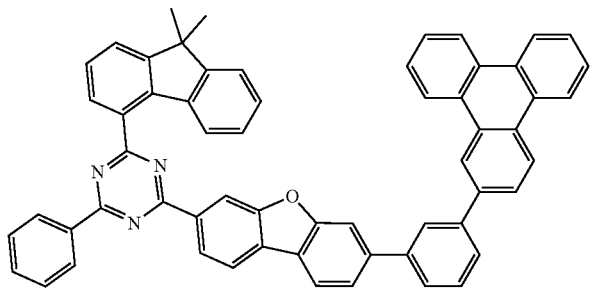
4-64
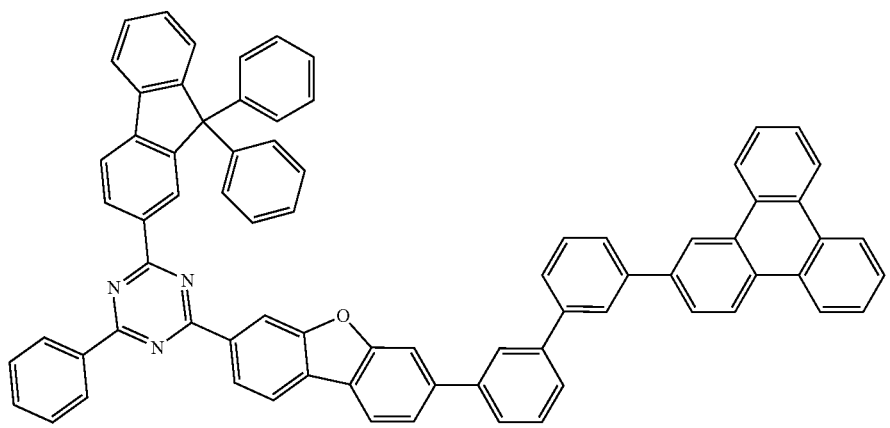
4-65
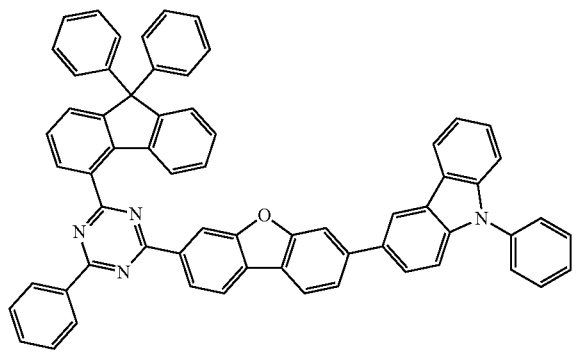
4-66
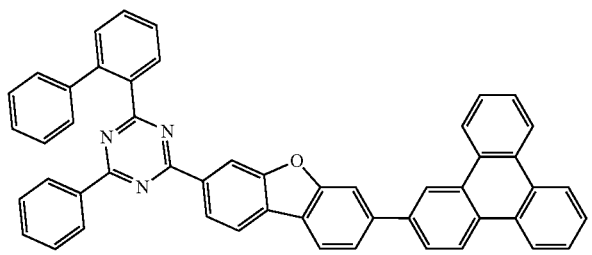
4-67
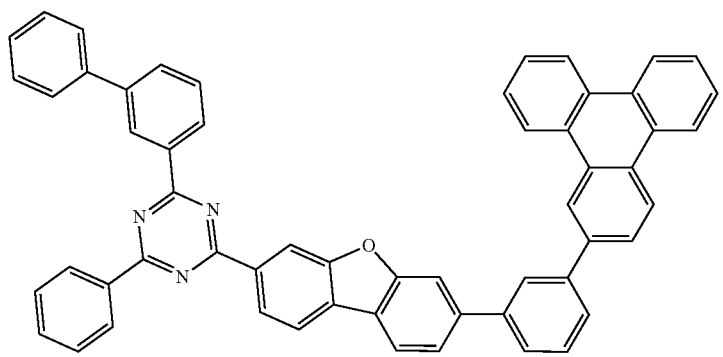

4-68
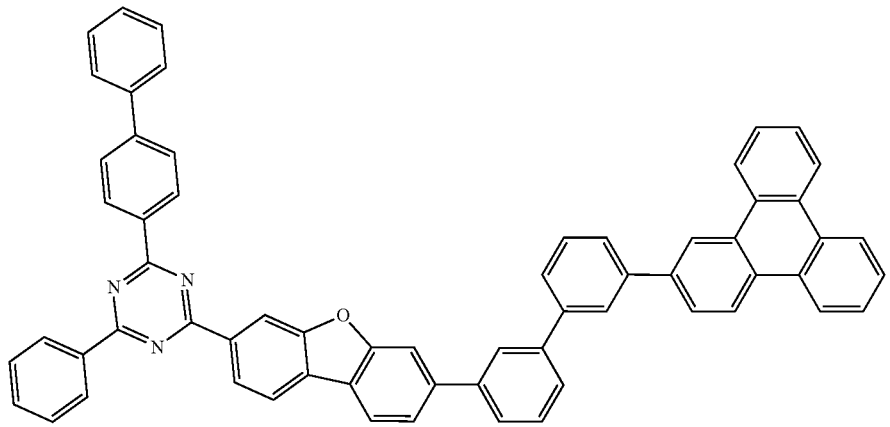
4-69
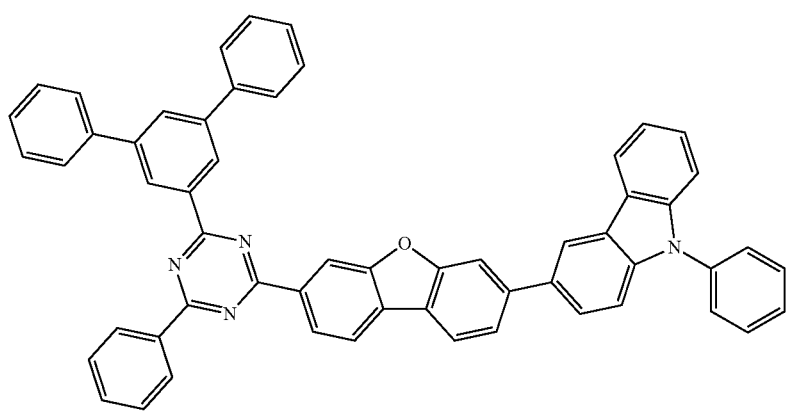
4-70
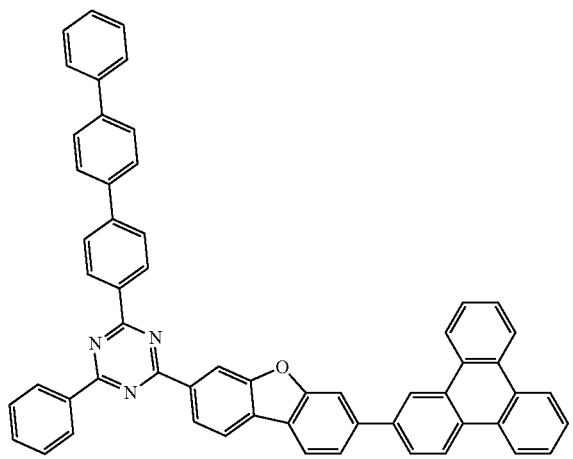
4-71
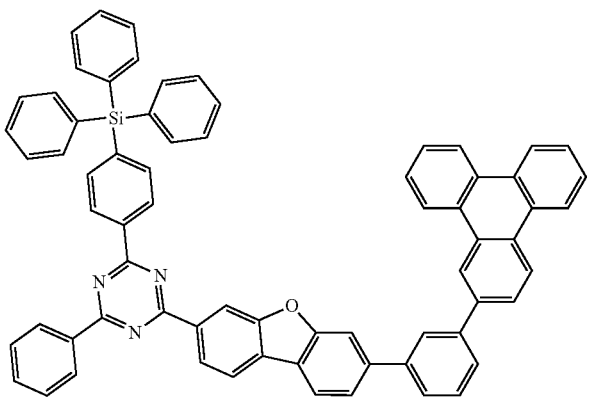

-continued
4-72
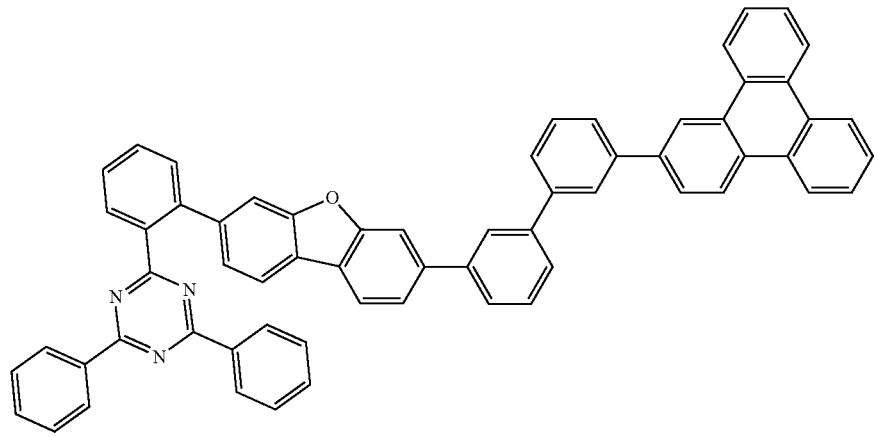
4-73
4-74
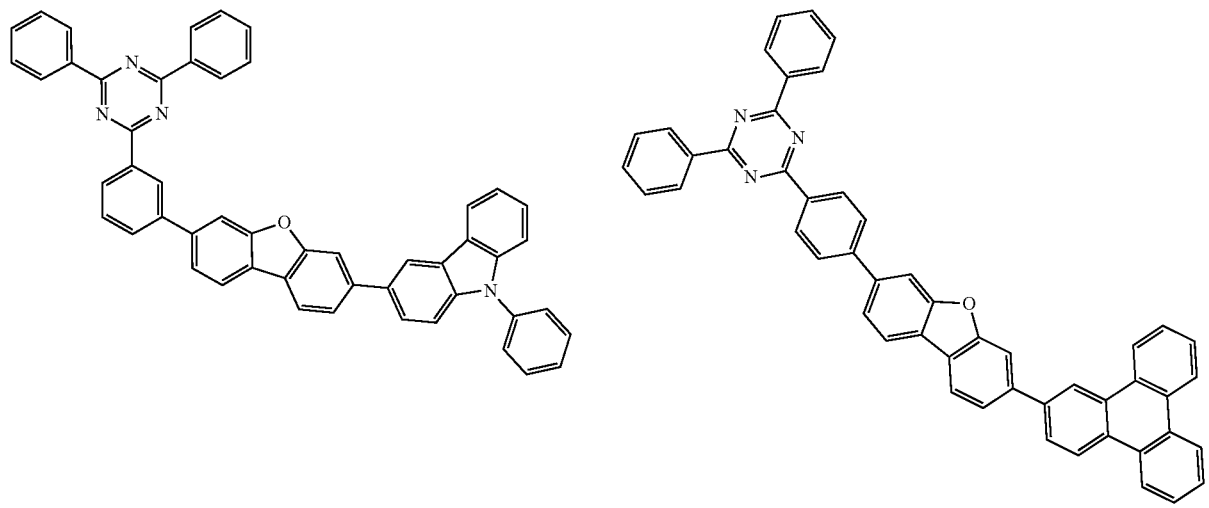
4-75
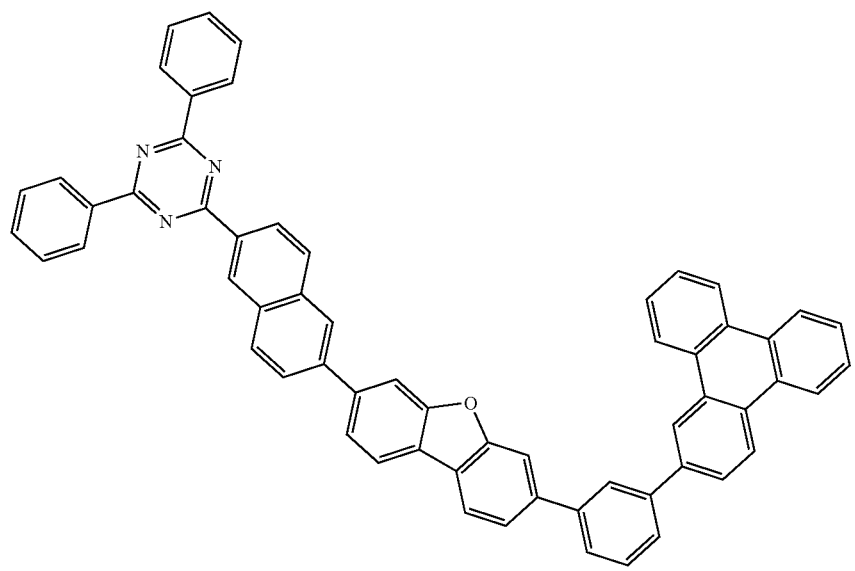

-continued
4-76
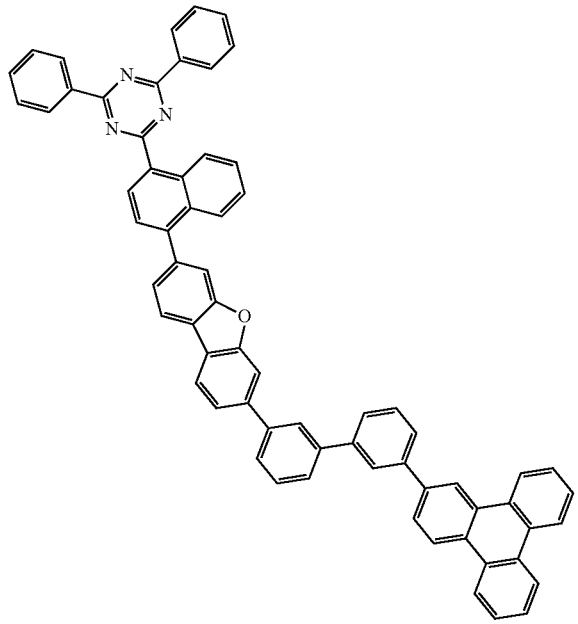
4-77
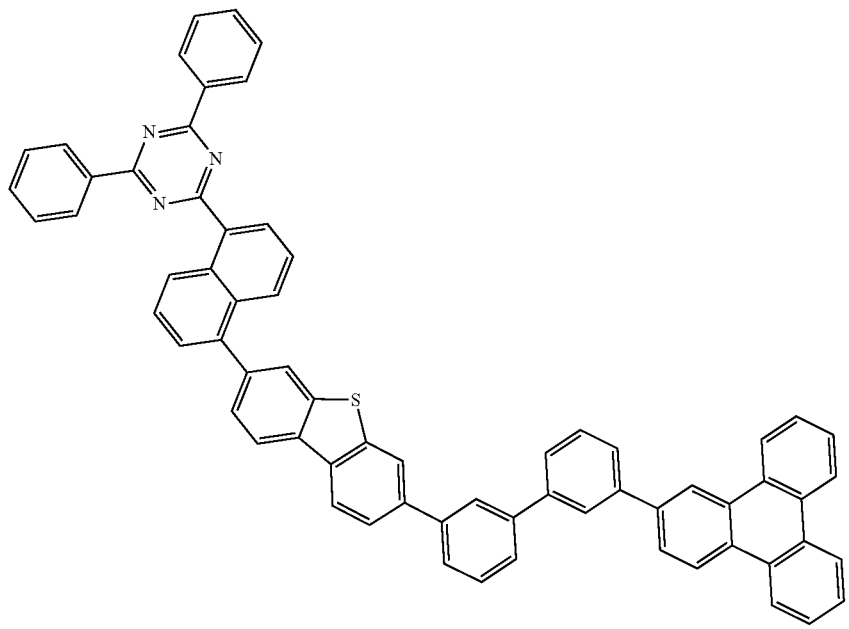
4-78
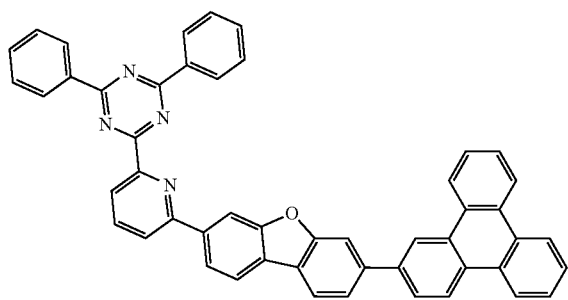
4-79
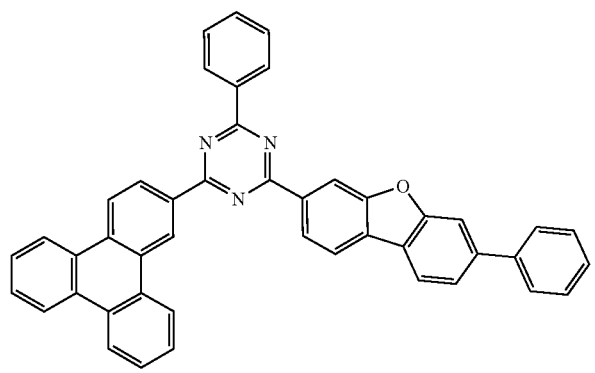

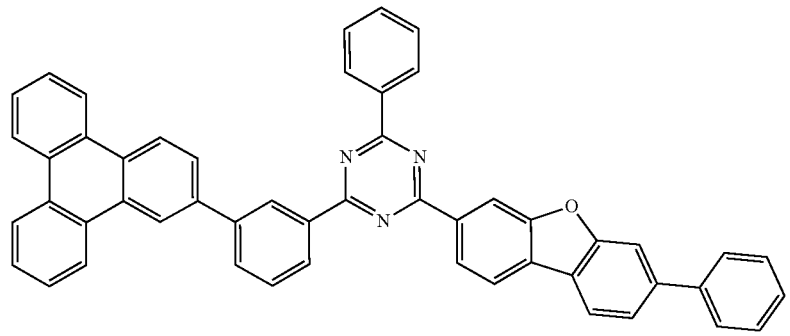
4-80
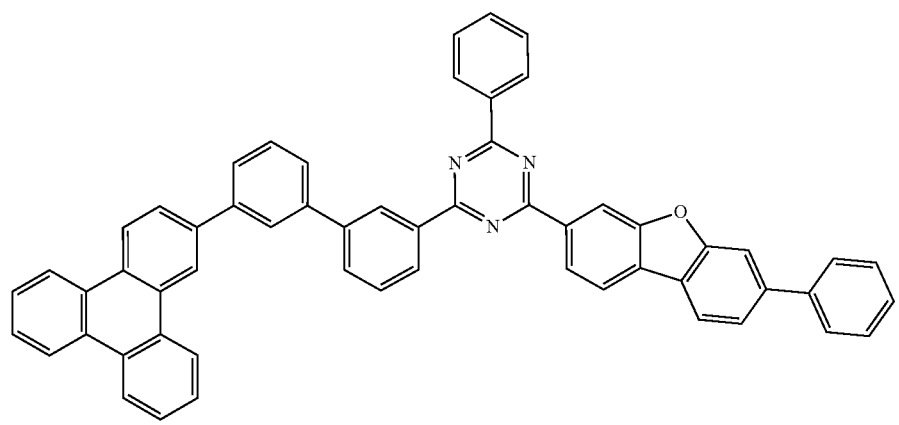
4-81
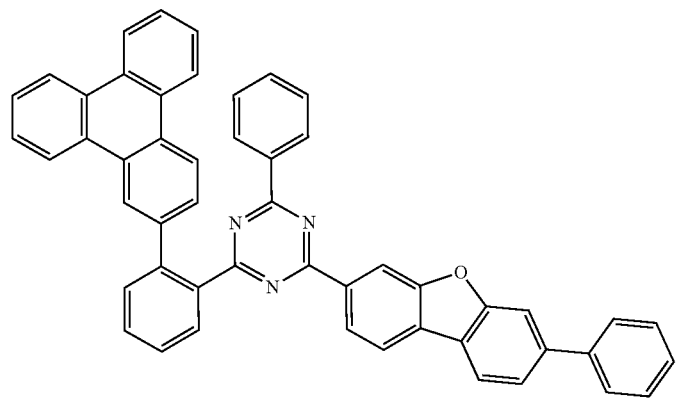
4-82
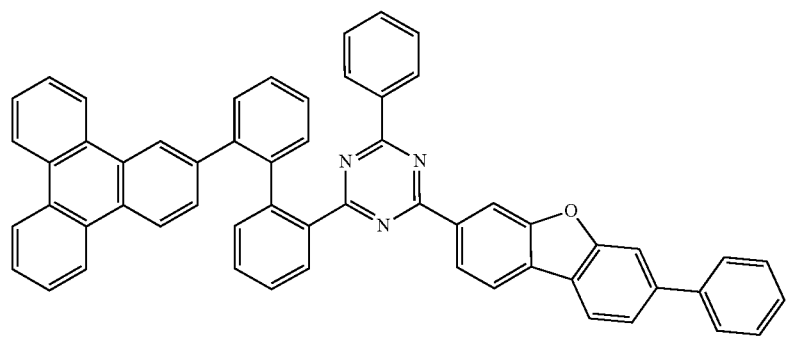
4-83

4-84
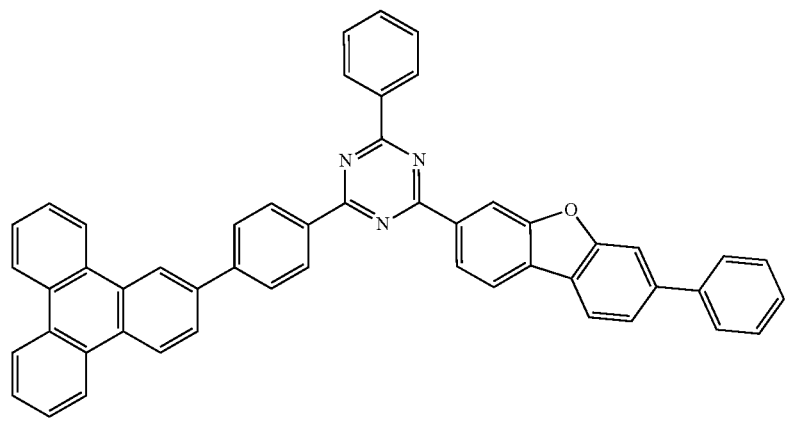
4-85
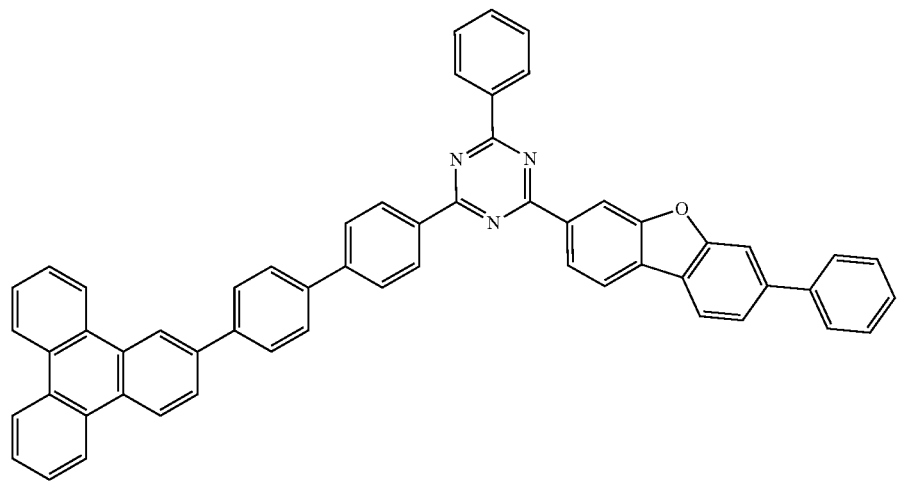
4-86
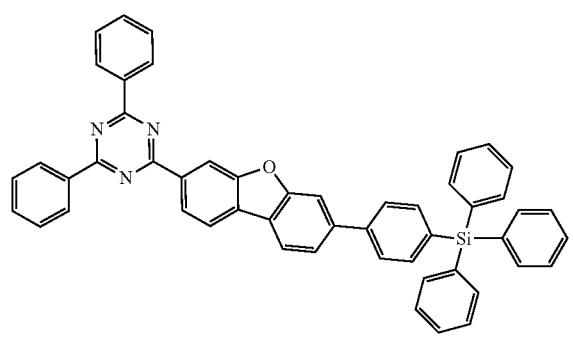
4-87
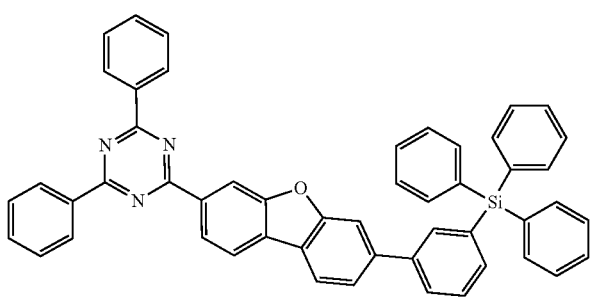
4-88
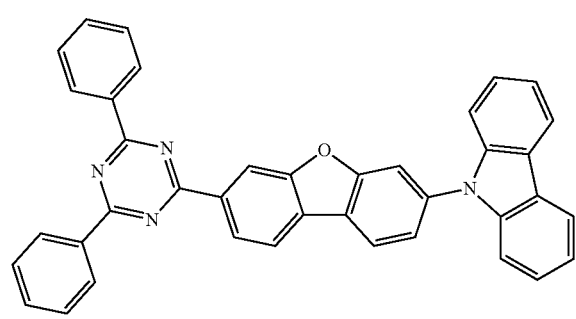
4-89
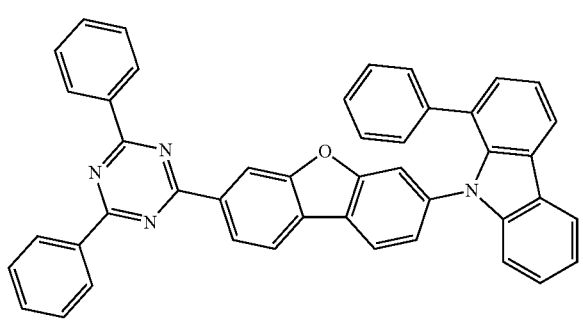

4-90
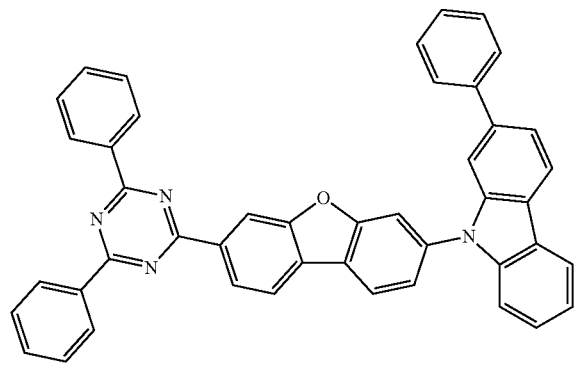
4-91
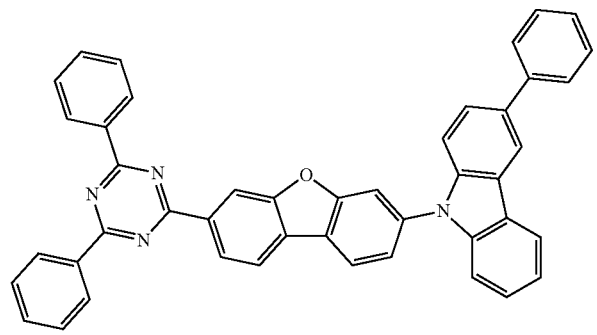
4-92
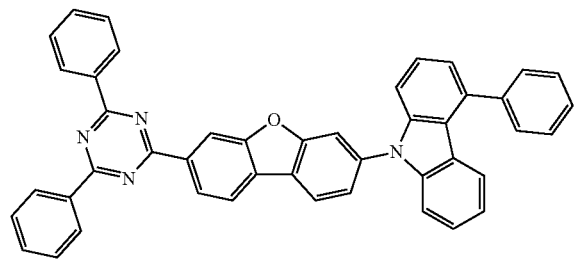
4-93
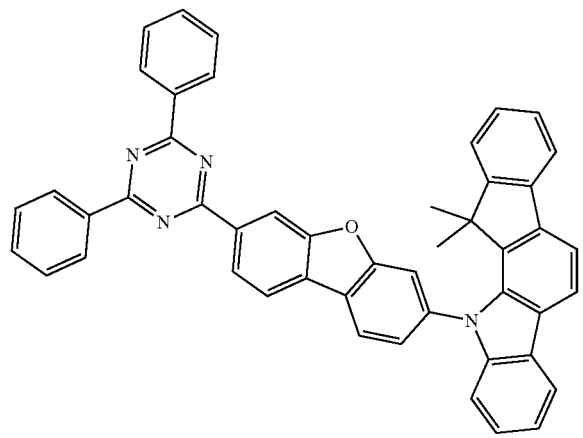
4-94
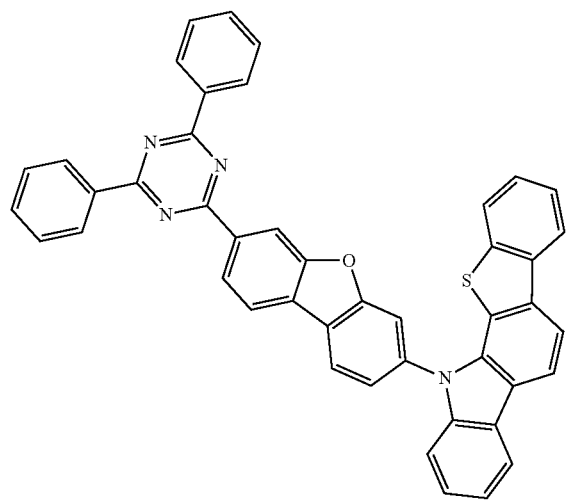
4-95
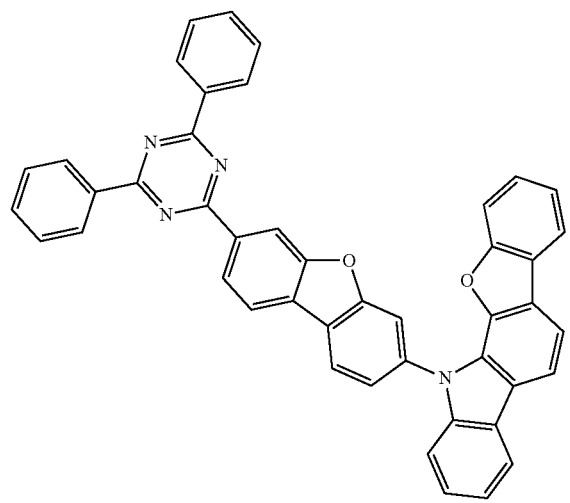

-continued
4-96
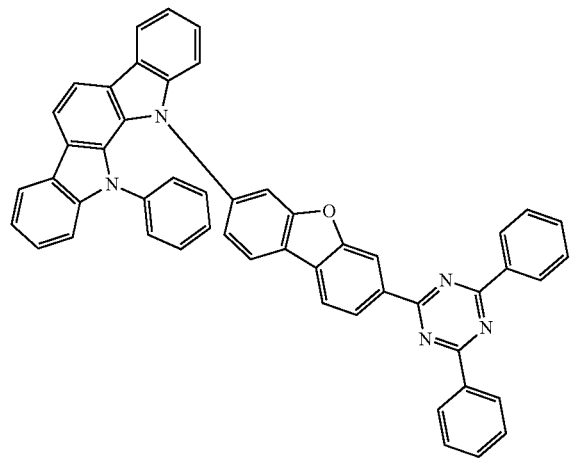
4-97
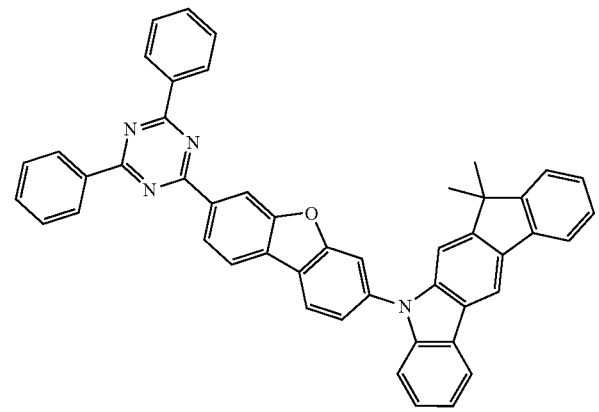
4-98
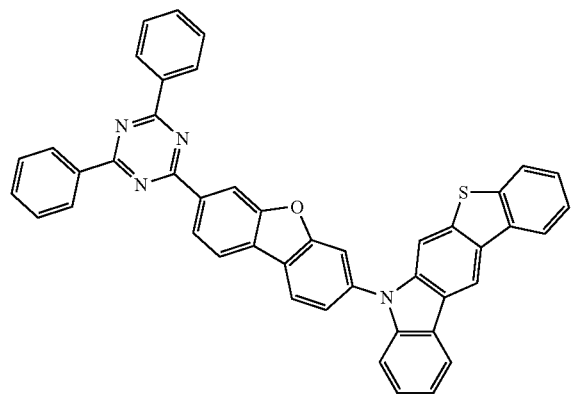
4-99
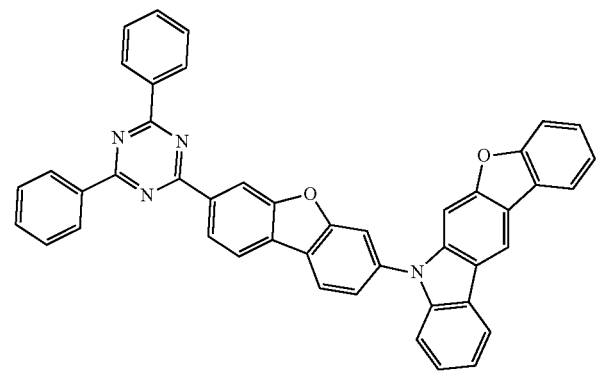
4-100
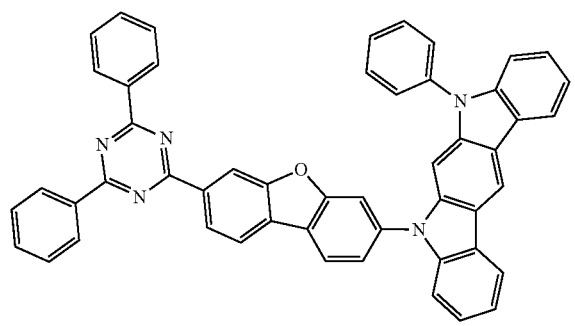
4-101
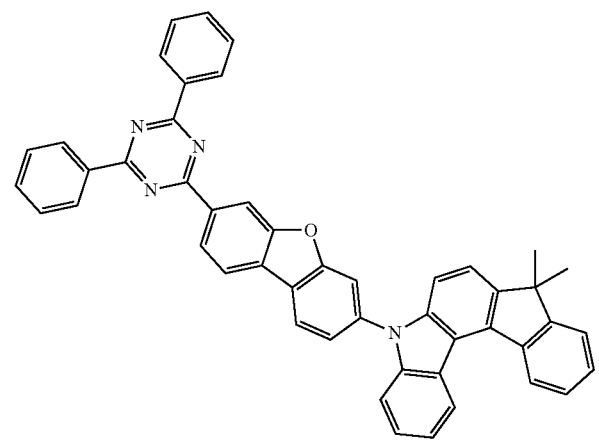

-continued
4-102
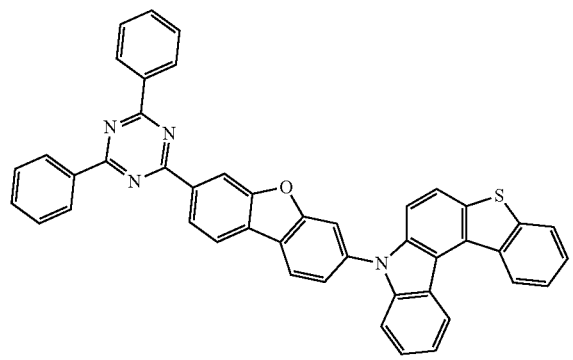
4-103
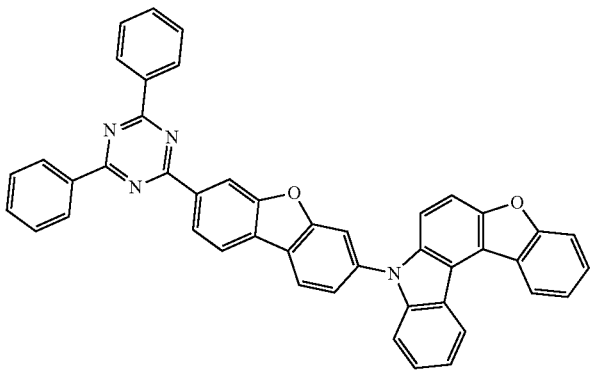
4-104
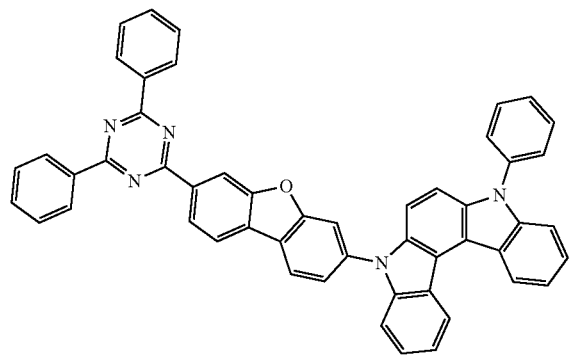
4-105
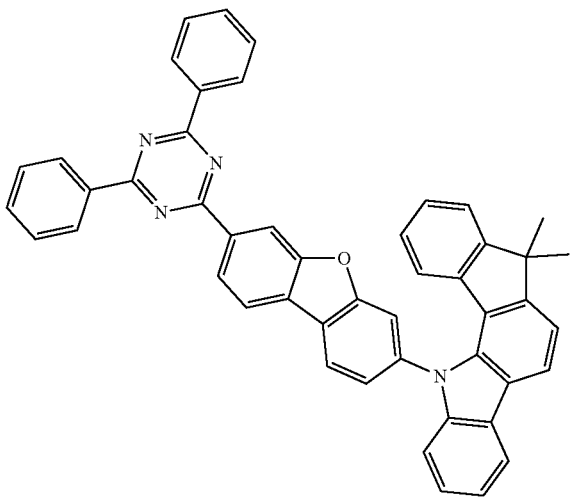
4-106
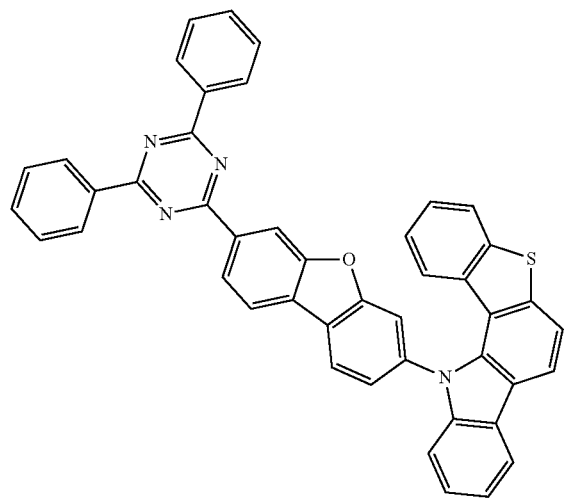
4-107
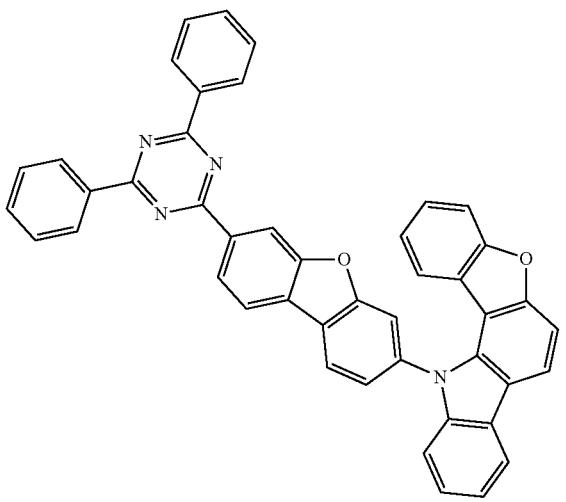

-continued
4-108
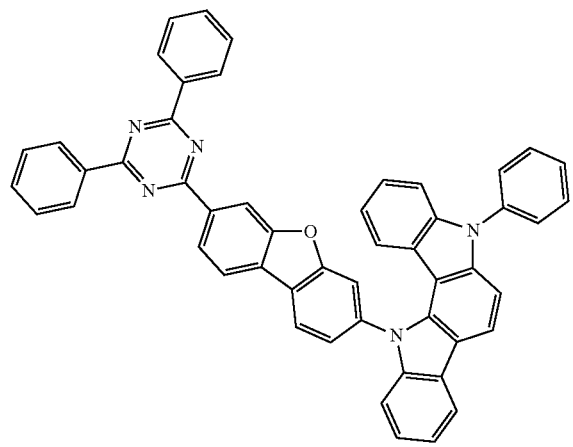
4-109
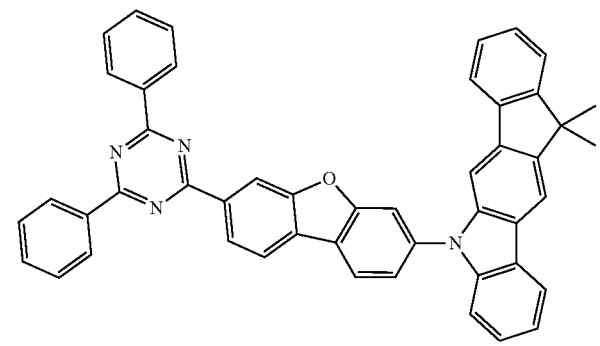
4-110
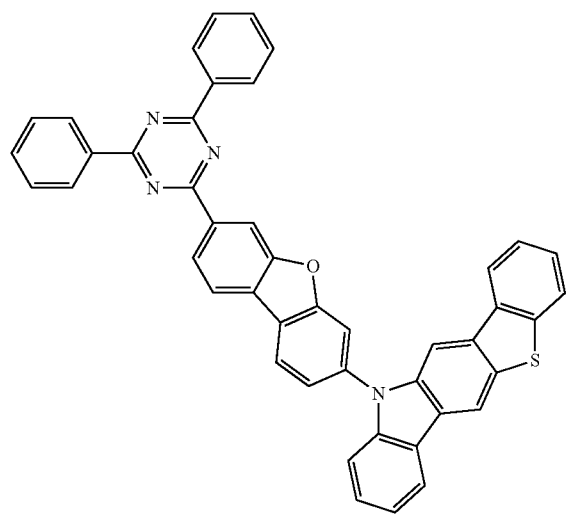
4-111
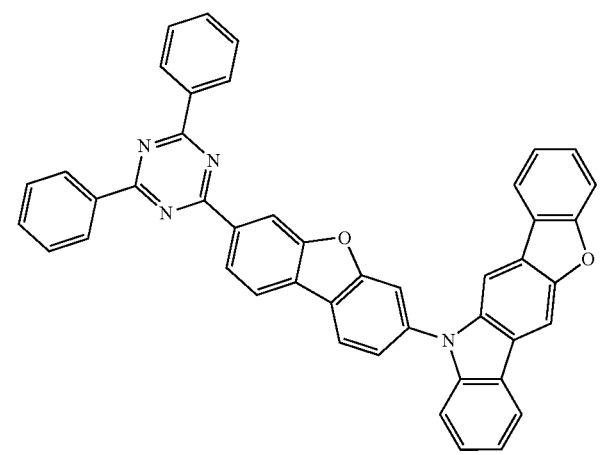
4-112
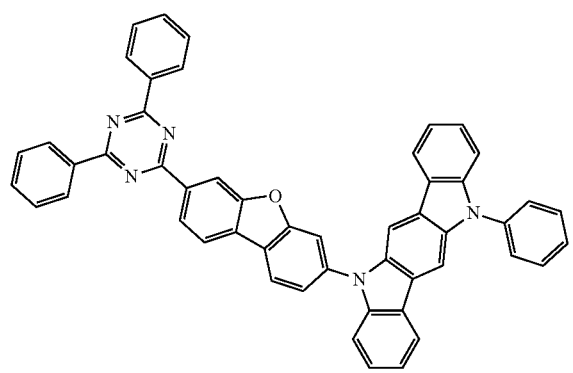
4-113
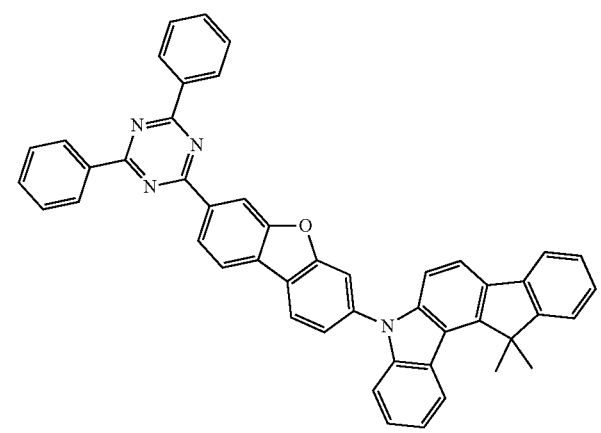

-continued
4-114
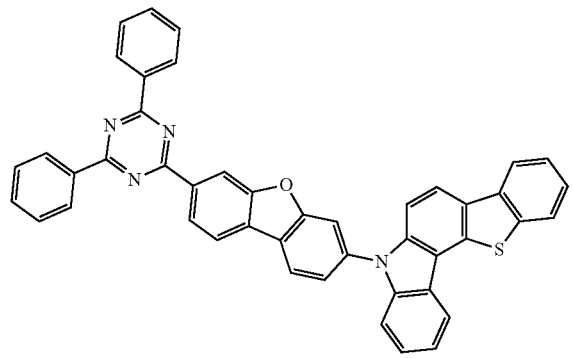
4-115
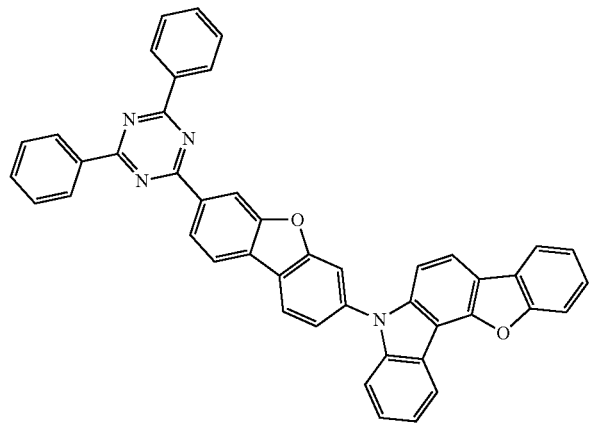
4-116
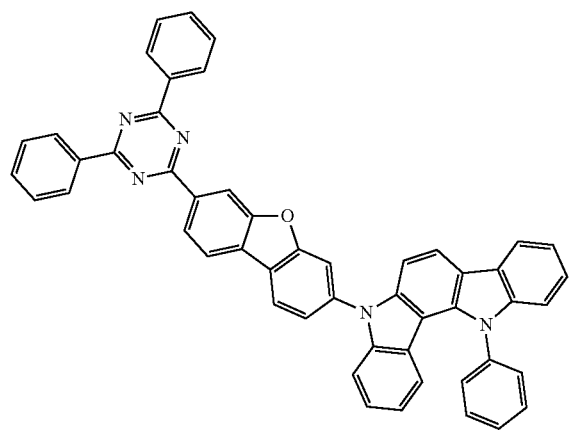
4-117
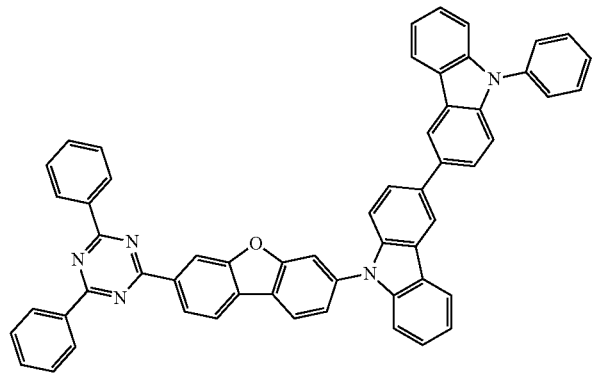
4-118
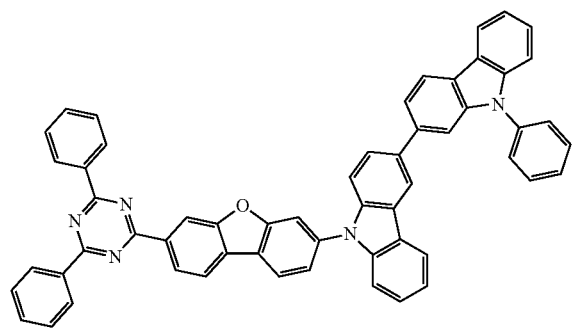
4-119
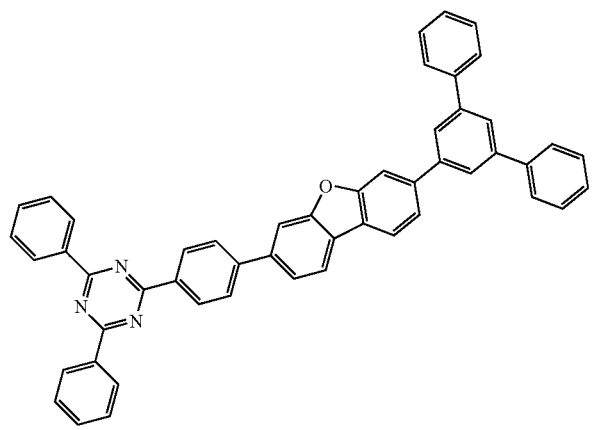

-continued
4-120
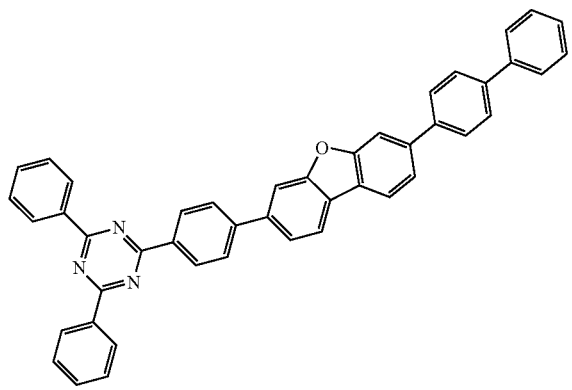
4-121
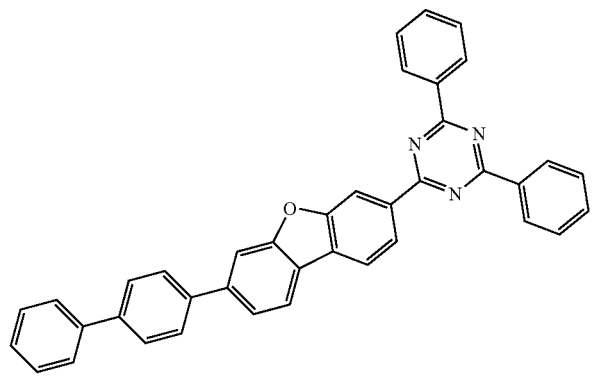
4-122
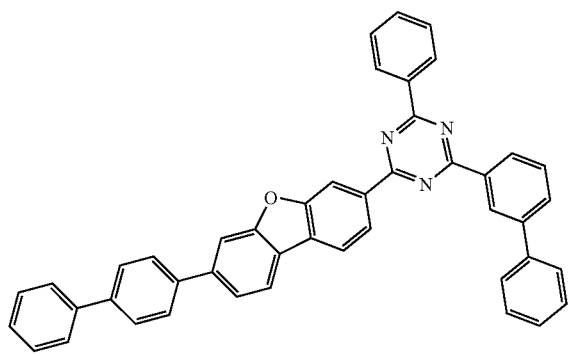
4-123
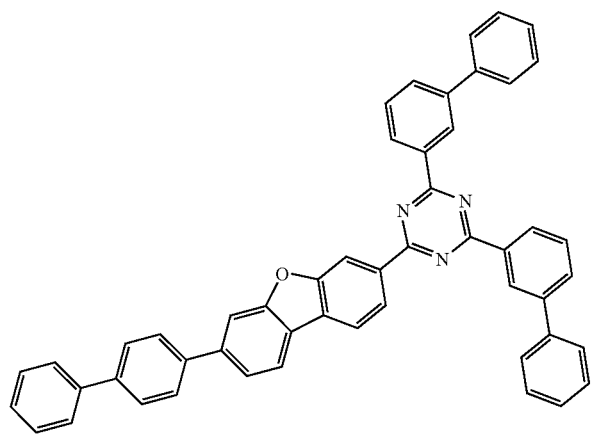
4-124
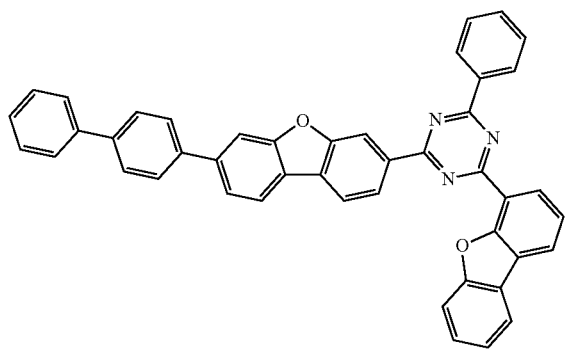
4-125
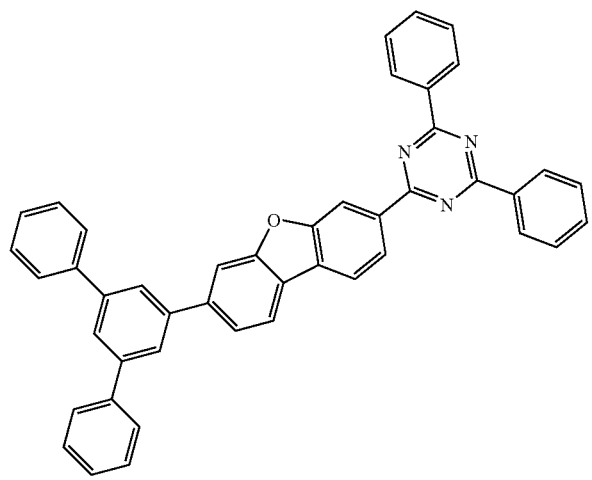

-continued
4-126
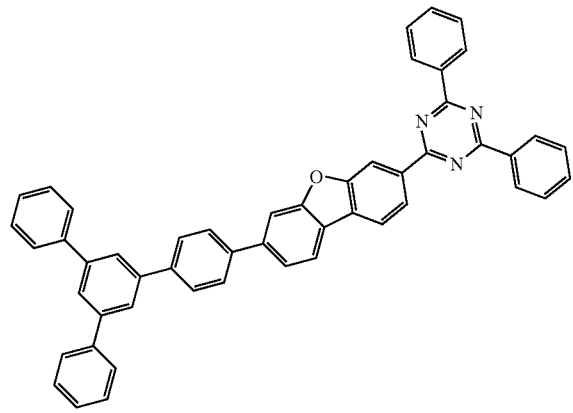
4-127
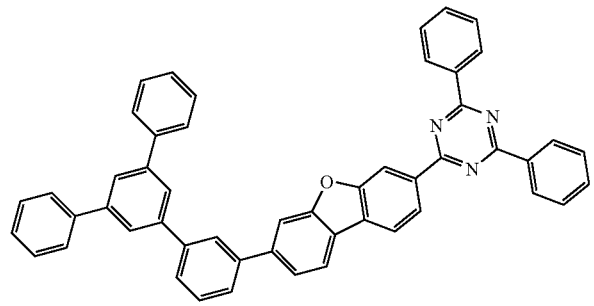
4-128
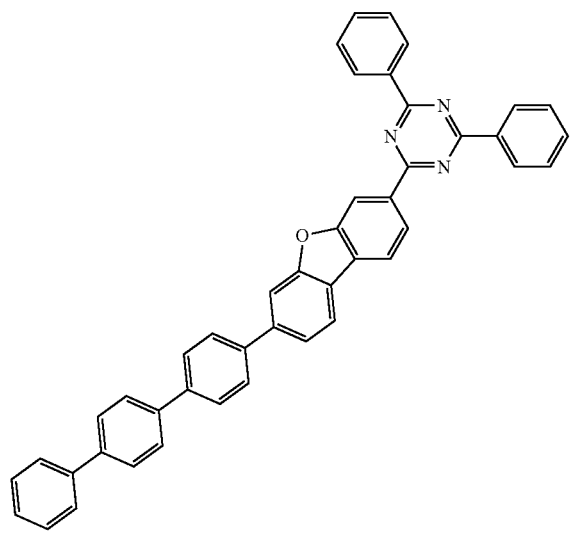
4-129
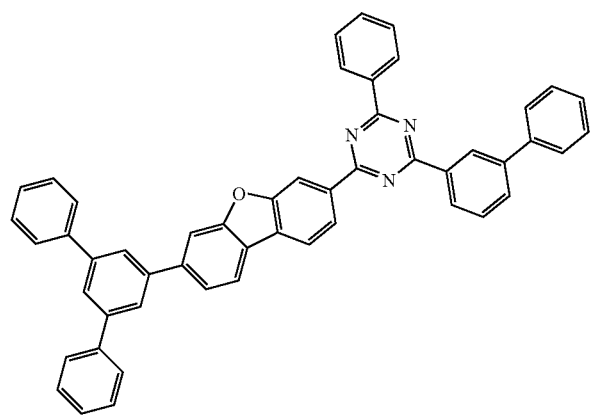
4-130
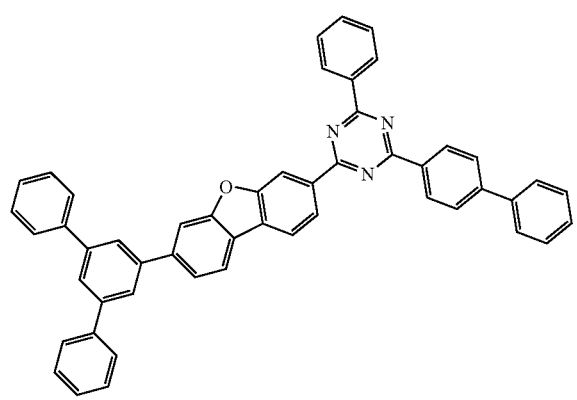
4-131
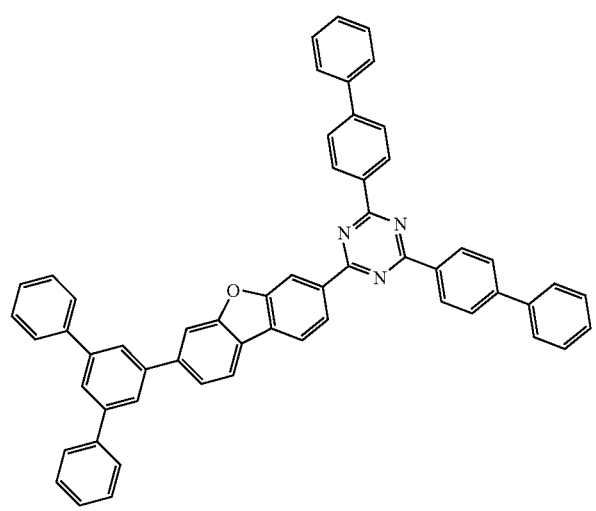

-continued
4-132
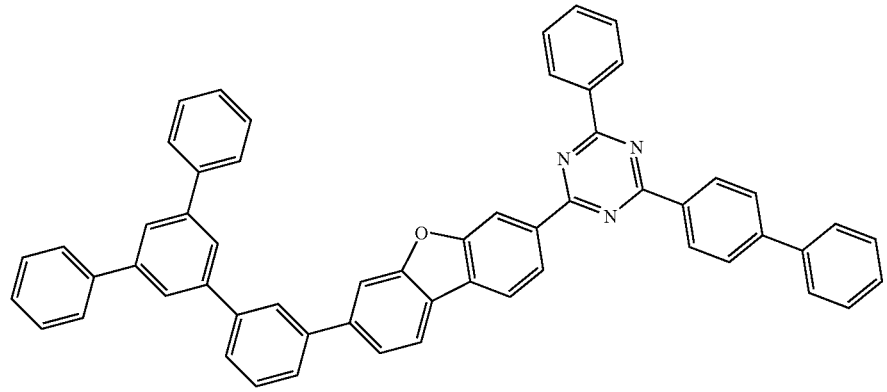
4-133
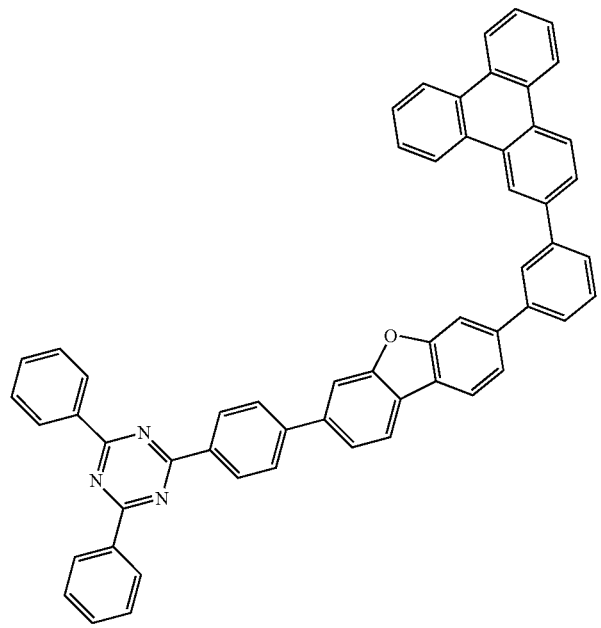
5-1
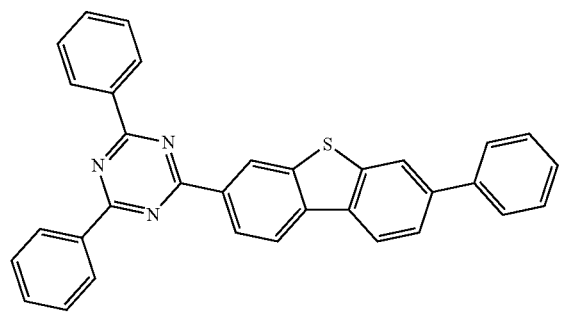
5-2
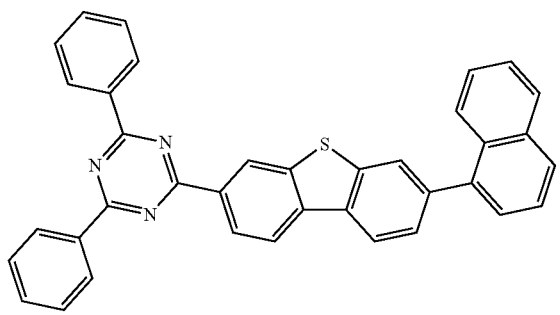

-continued
5-3
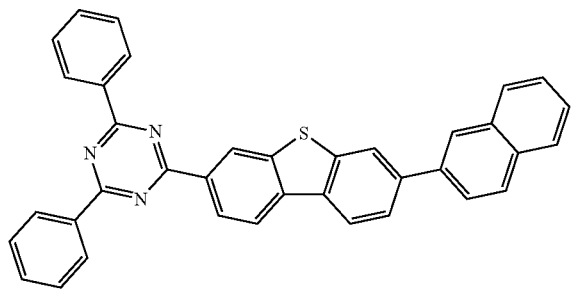
5-4
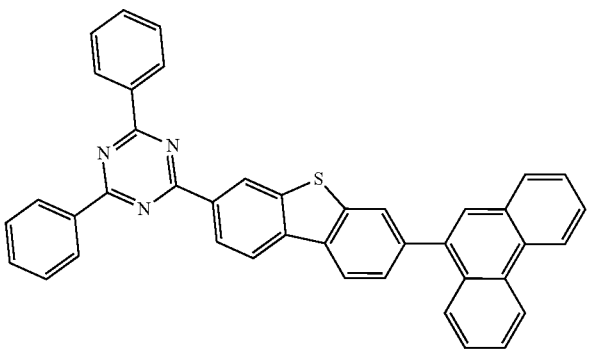
5-5
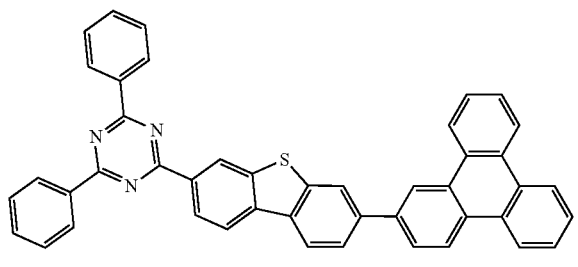
5-6
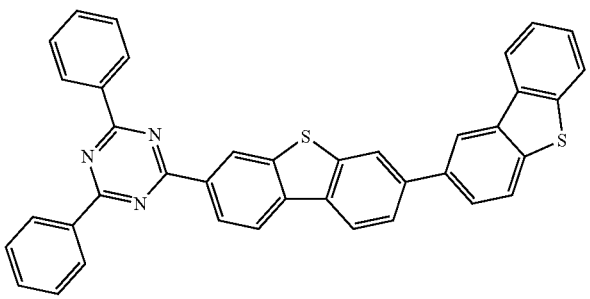
5-7
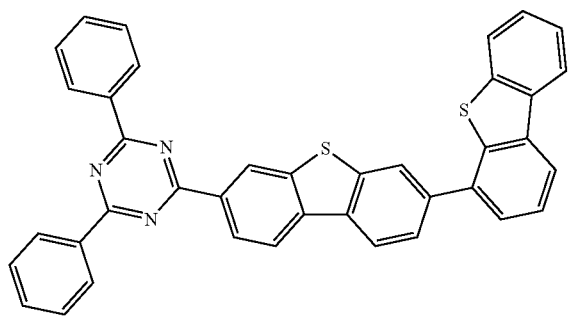
5-8
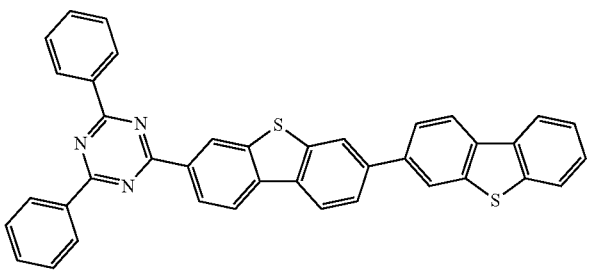
5-9
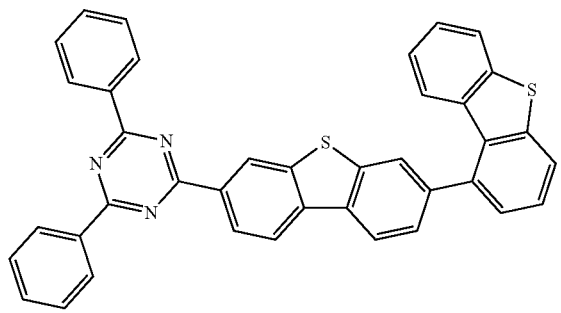
5-10
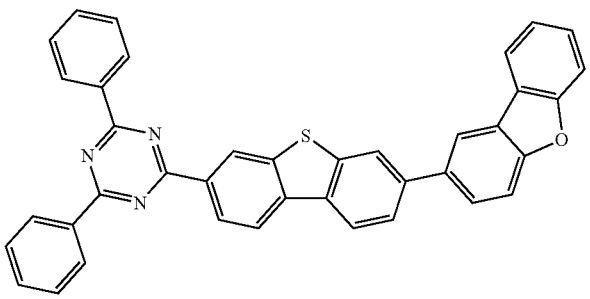

-continued
| 5-11 | 5-12 |
|---|---|
| 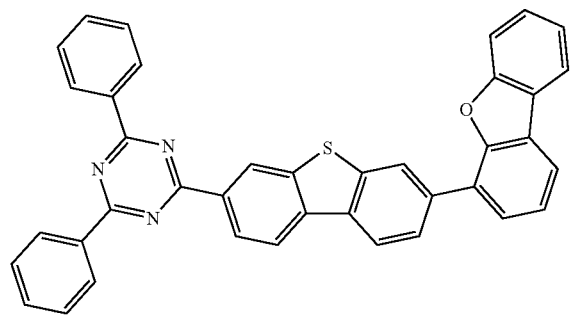 | 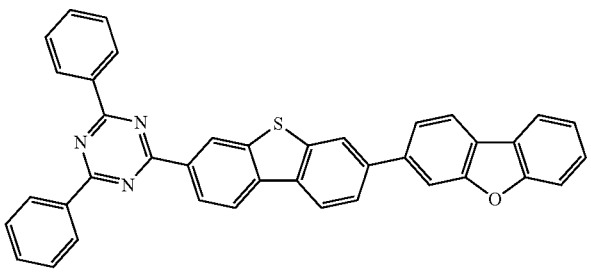 |
| 5-13 | 5-14 |
| 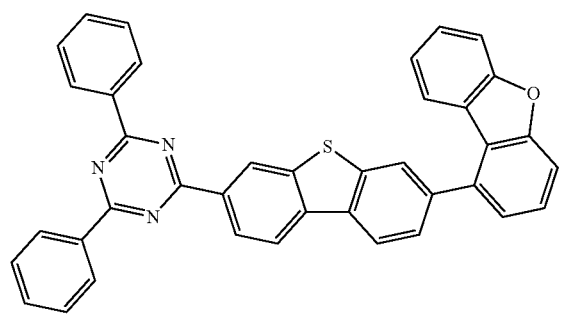 | 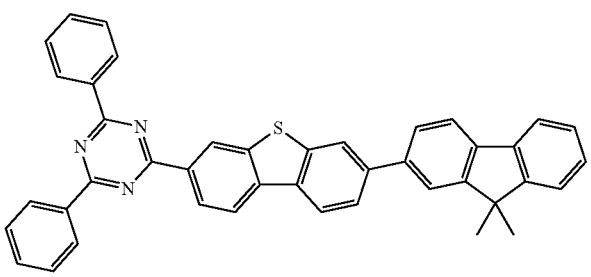 |
| 5-15 | 5-16 |
| 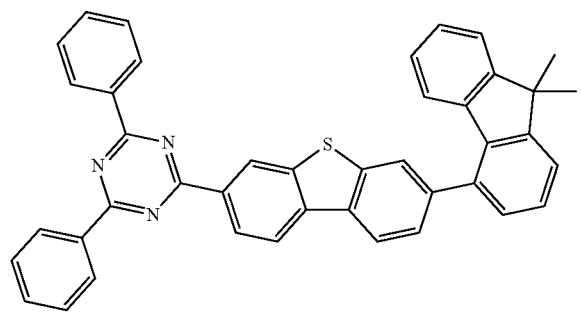 | 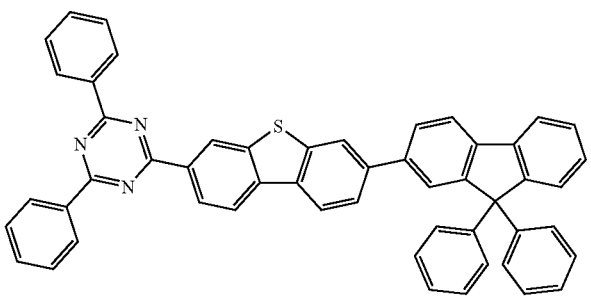 |
| 5-17 | 5-18 |
| 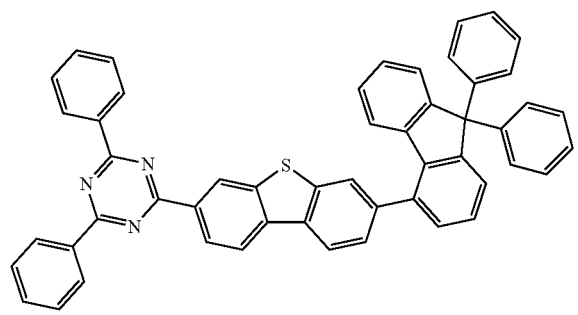 | 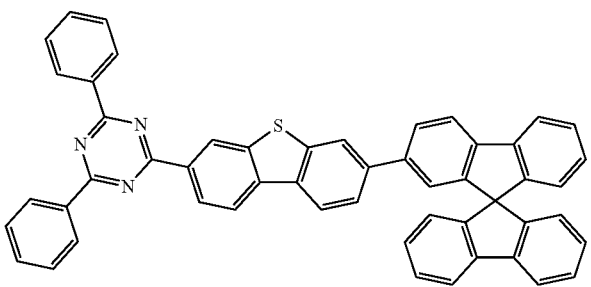 |

-continued
5-19
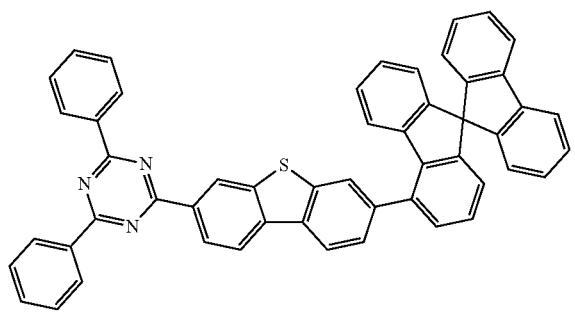
5-20
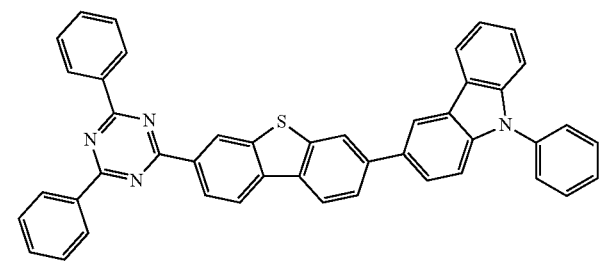
5-21
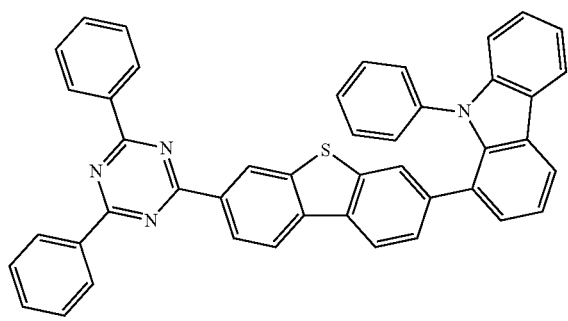
5-22
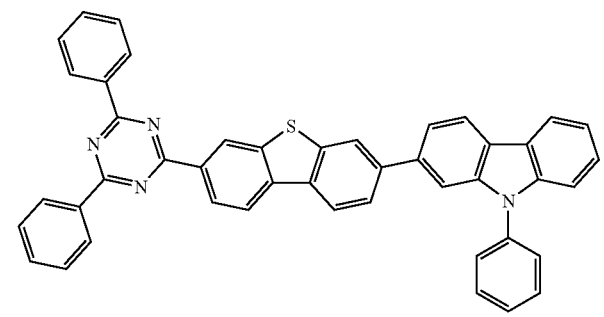
5-23
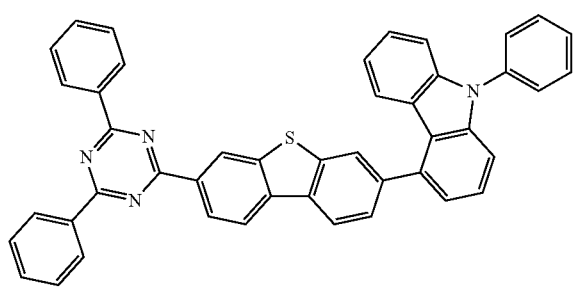
5-24
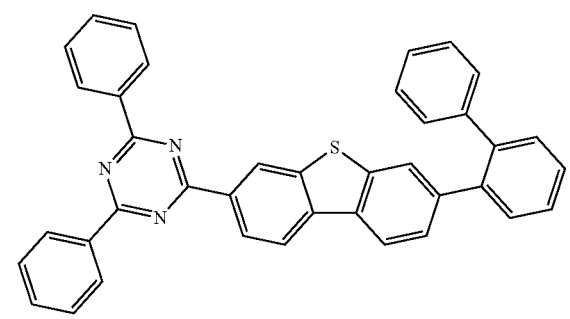
5-25
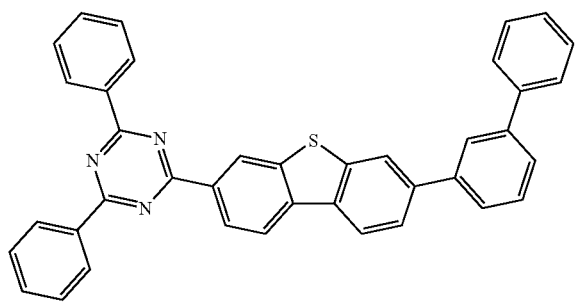
5-26
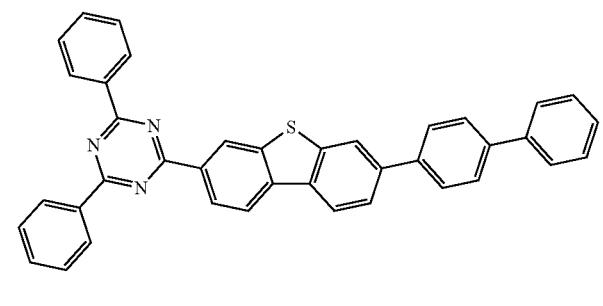

-continued
5-27
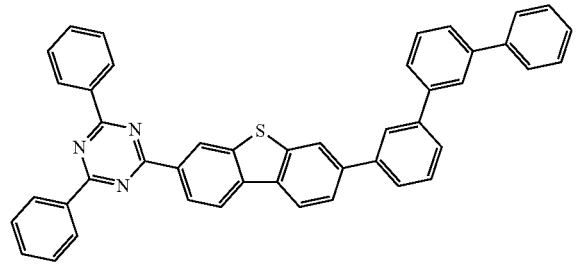
5-28
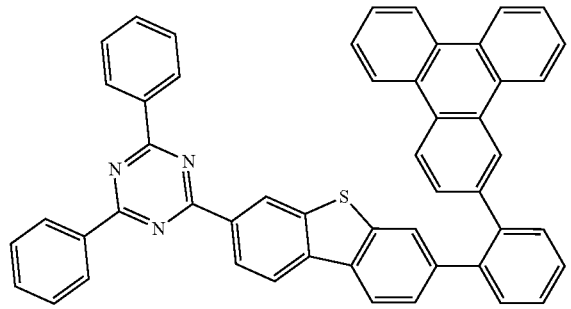
5-29
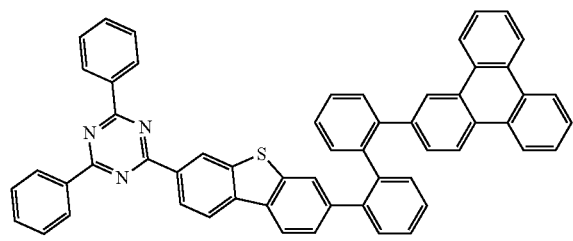
5-30
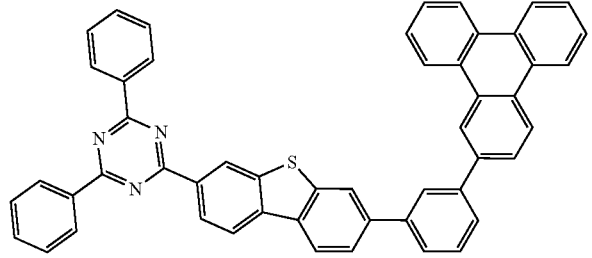
5-31
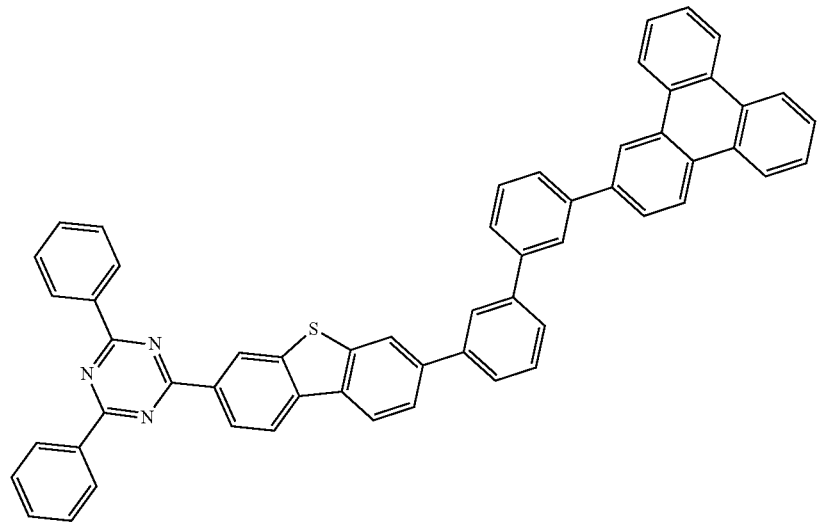

5-32
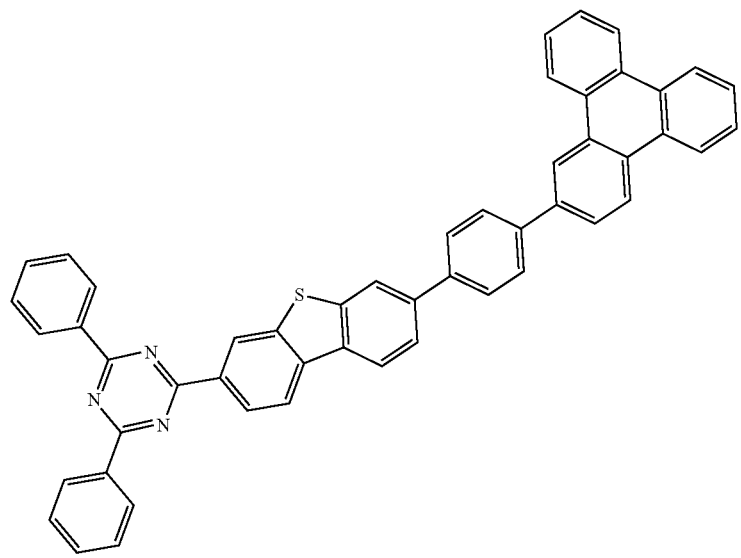
5-33
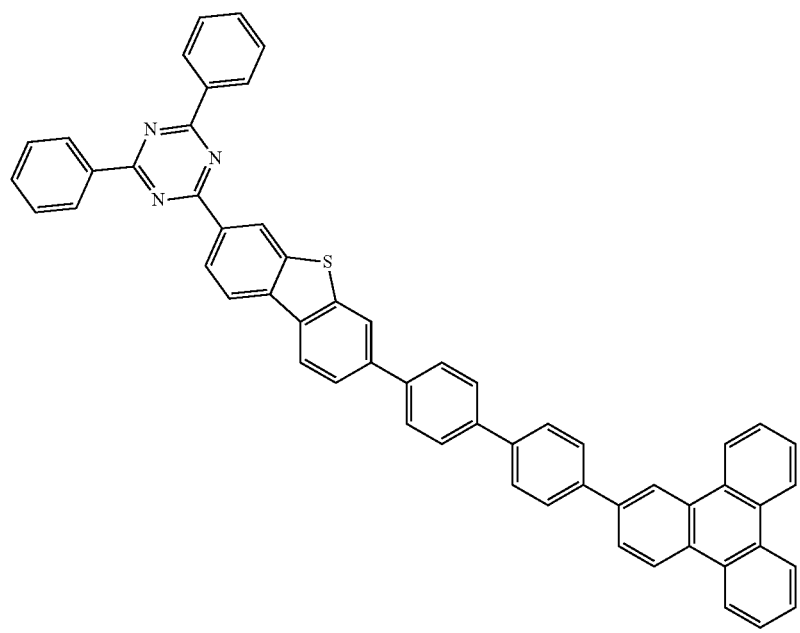
5-34
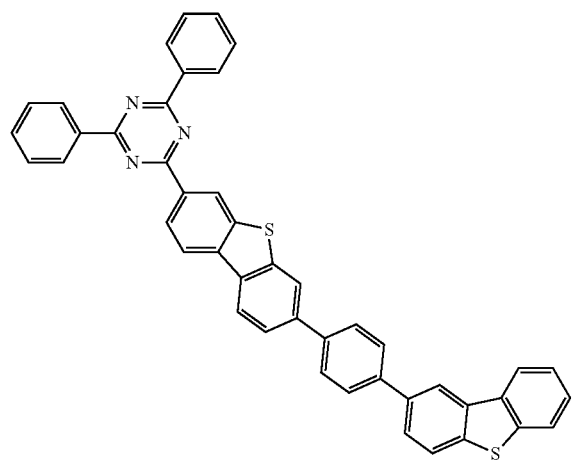
5-35
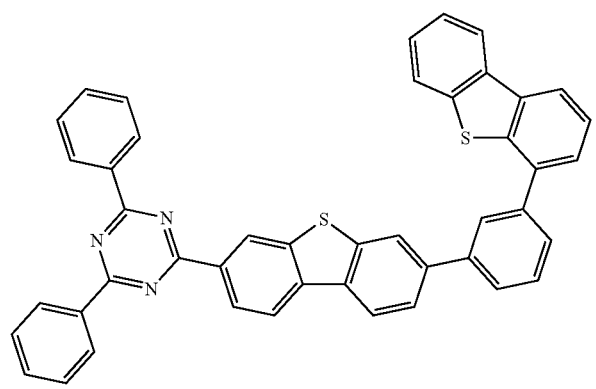

-continued
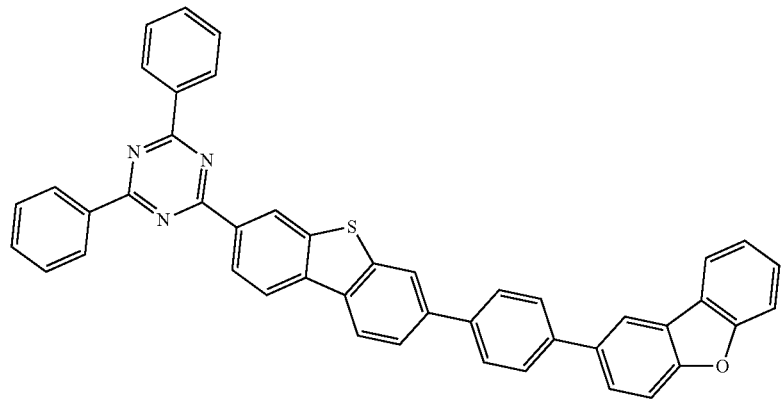
5-36
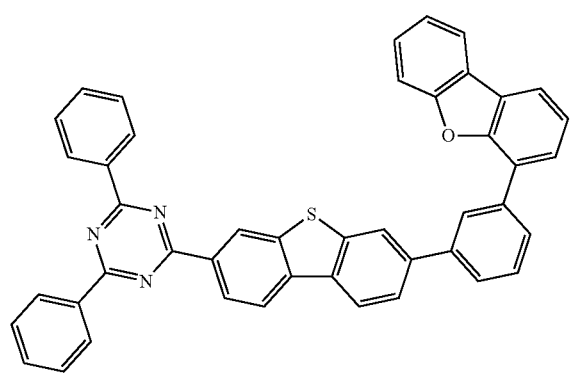
5-37
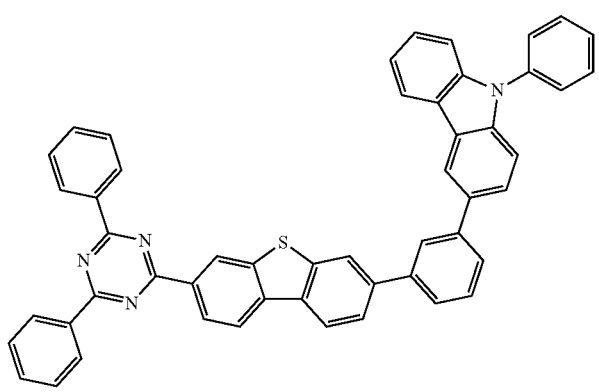
5-38
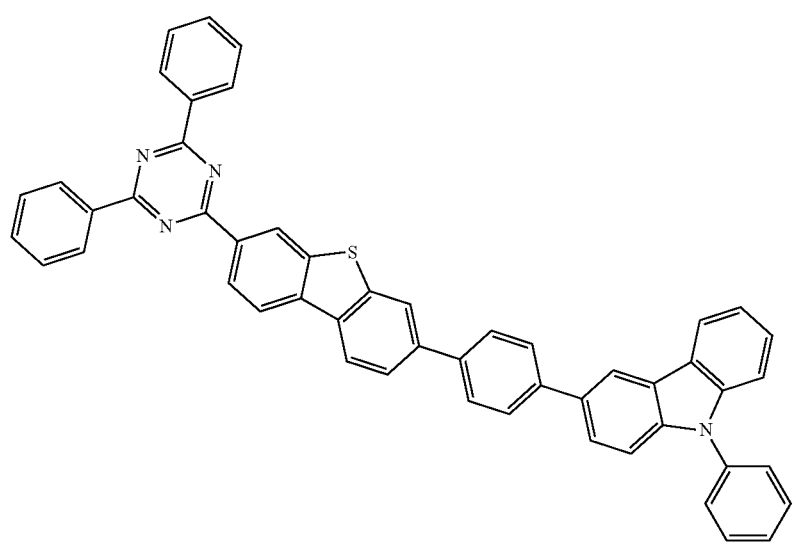
5-39

-continued
5-40
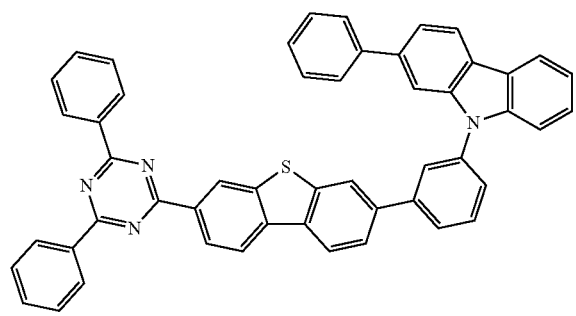
5-41
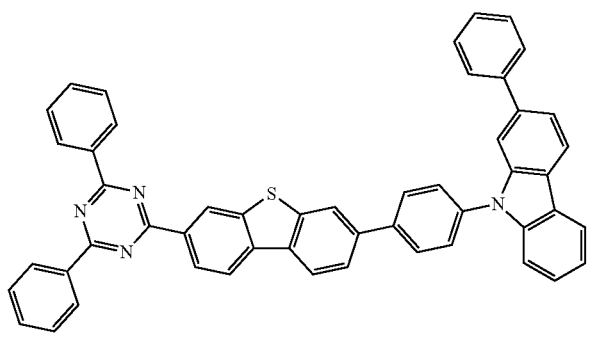
5-42
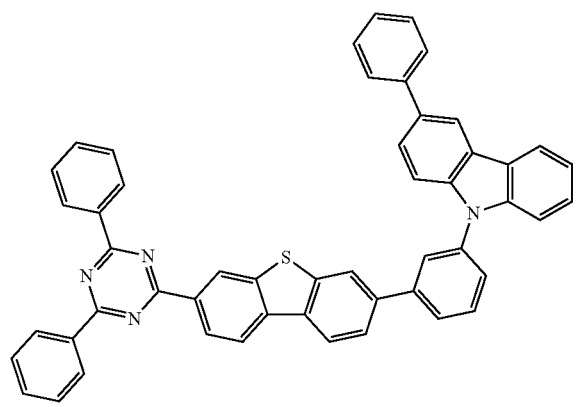
5-43
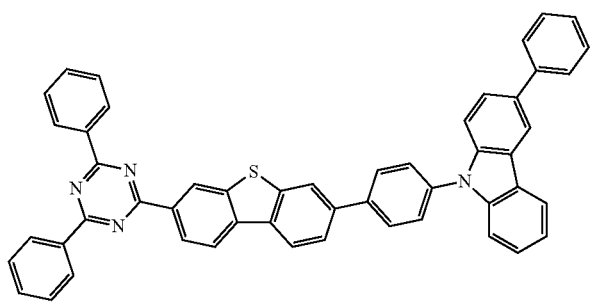
5-44
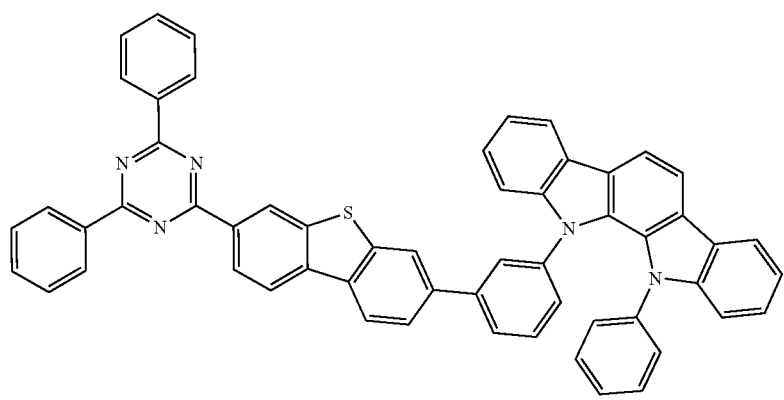

5-45
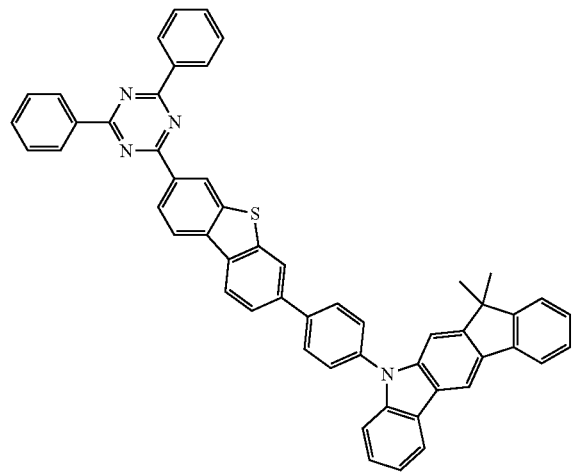
5-46
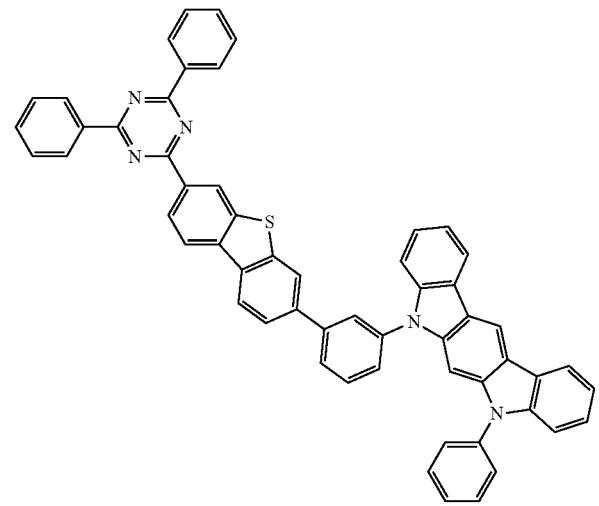
5-47
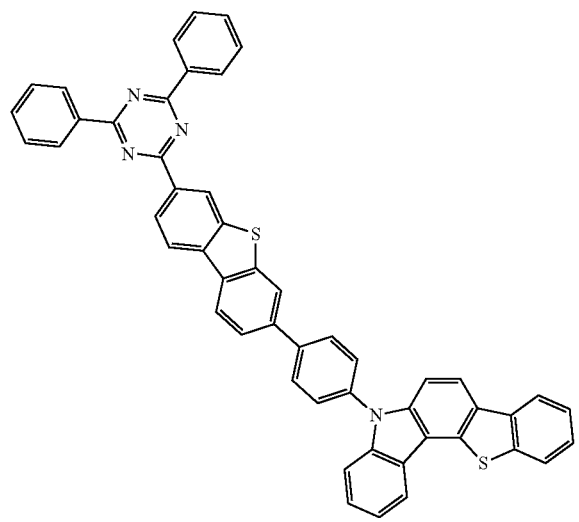
5-48
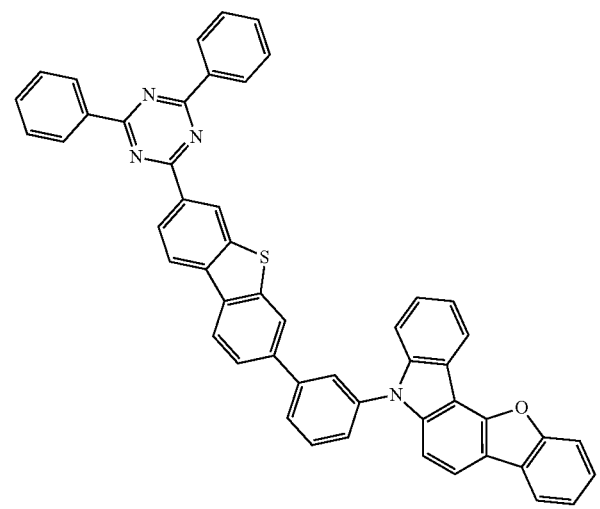
5-49
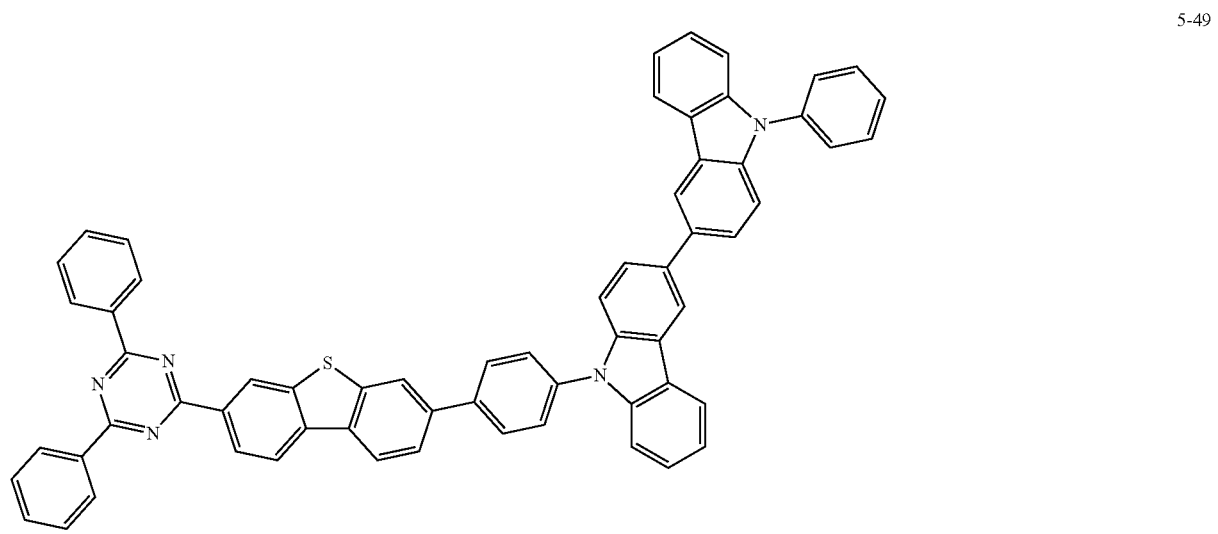

-continued
5-50
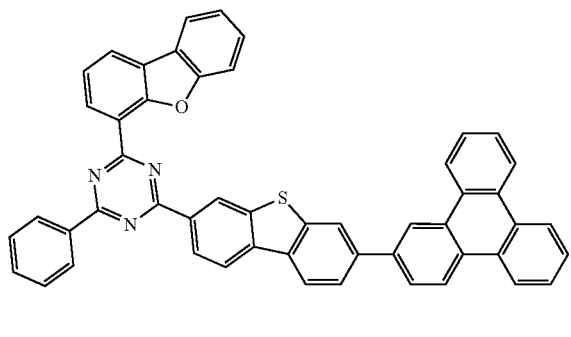
5-51
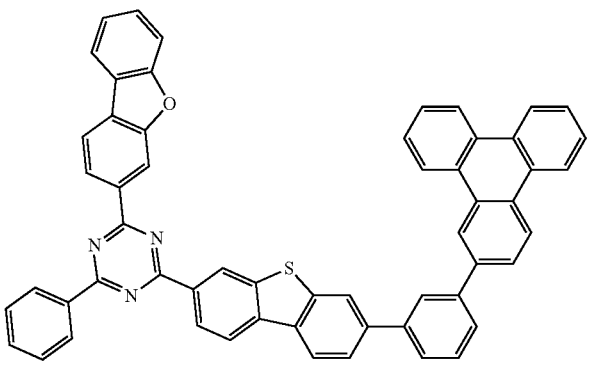
5-52
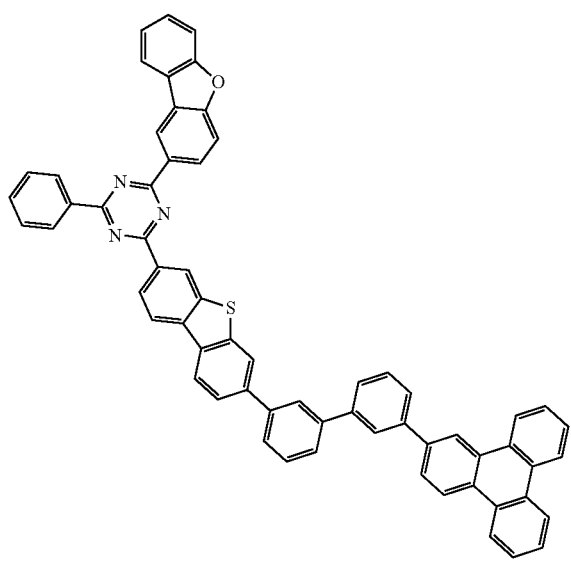
5-53
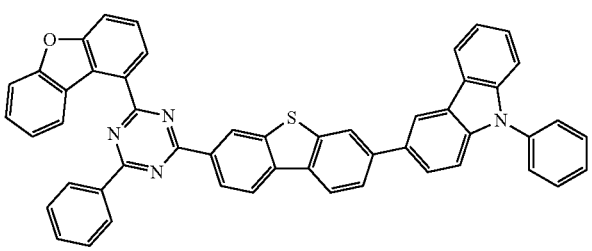
5-54
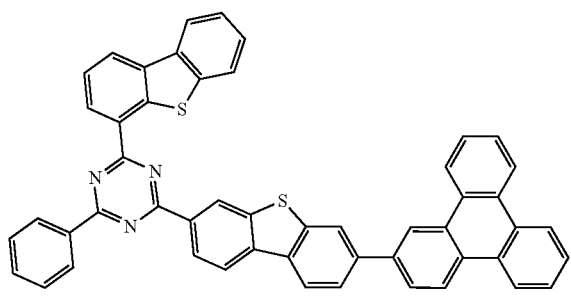
5-55
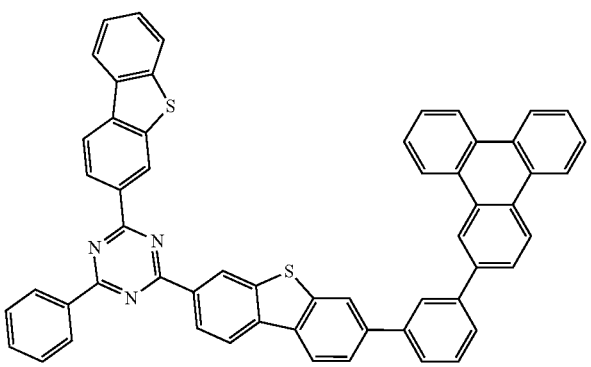

-continued
5-56
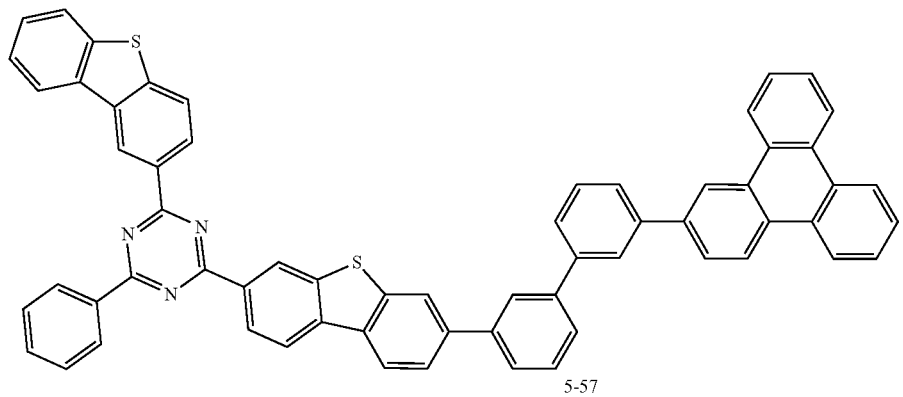
5-57
5-58
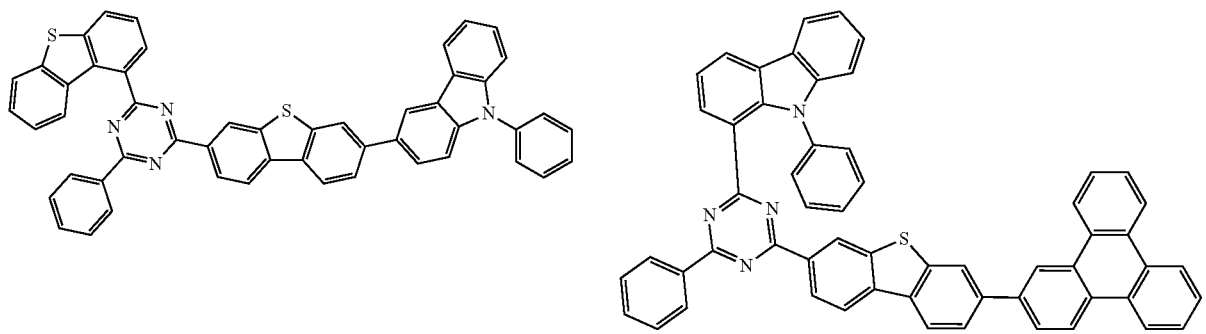
5-59
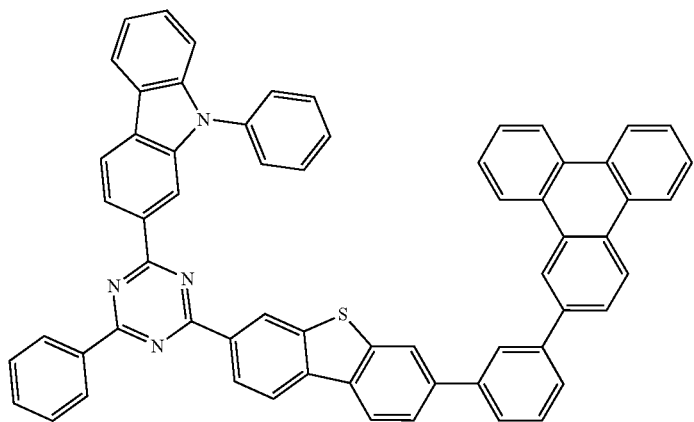
5-60
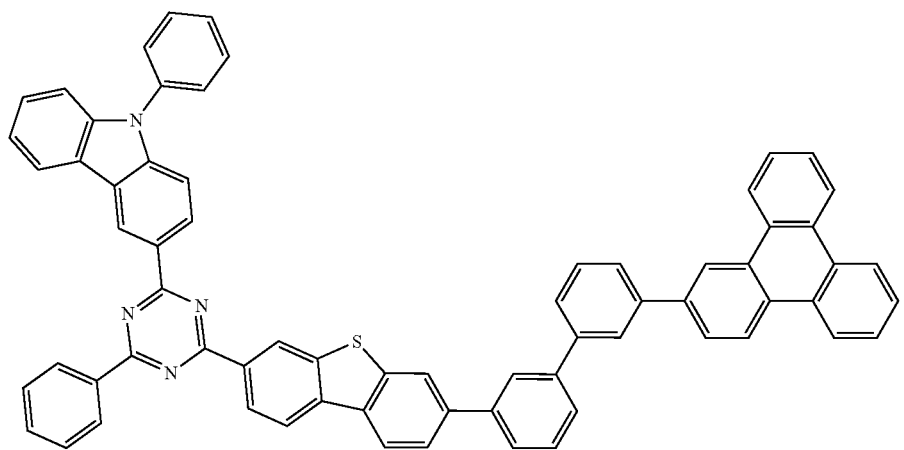

-continued
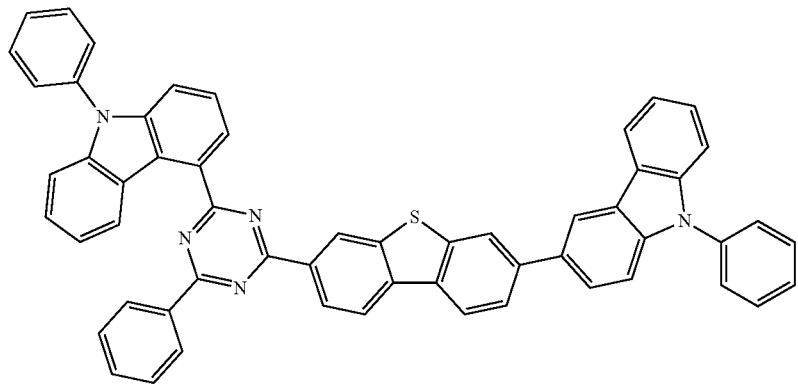
5-61
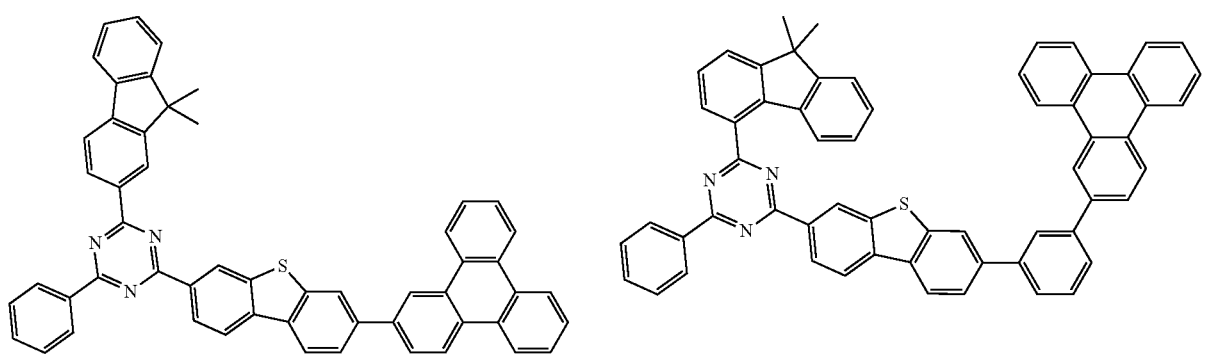
5-62
5-63
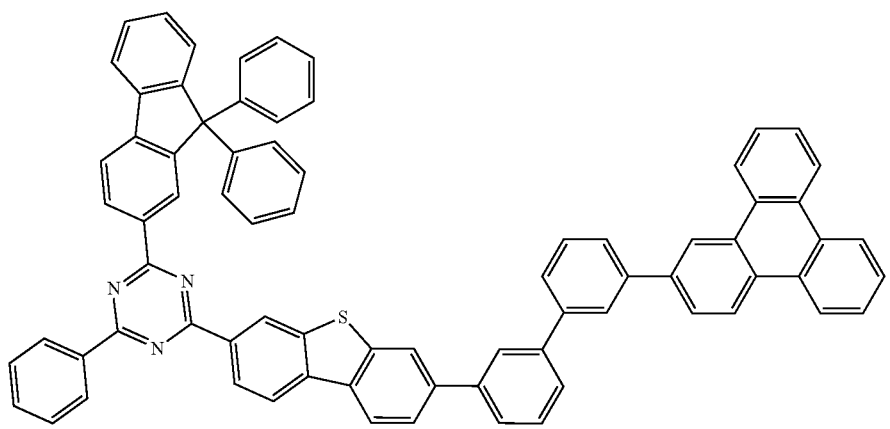
5-64
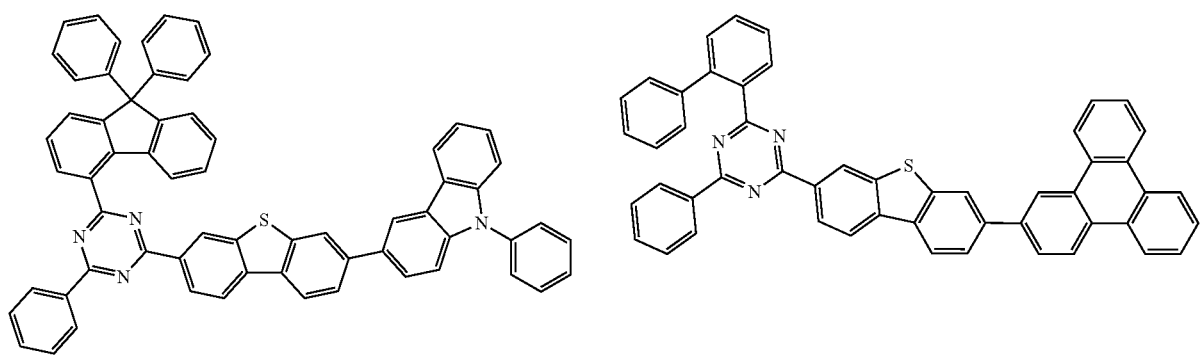
5-65
5-66

5-67
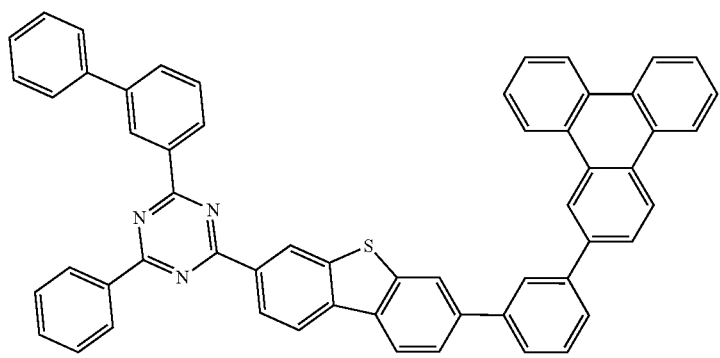
5-68
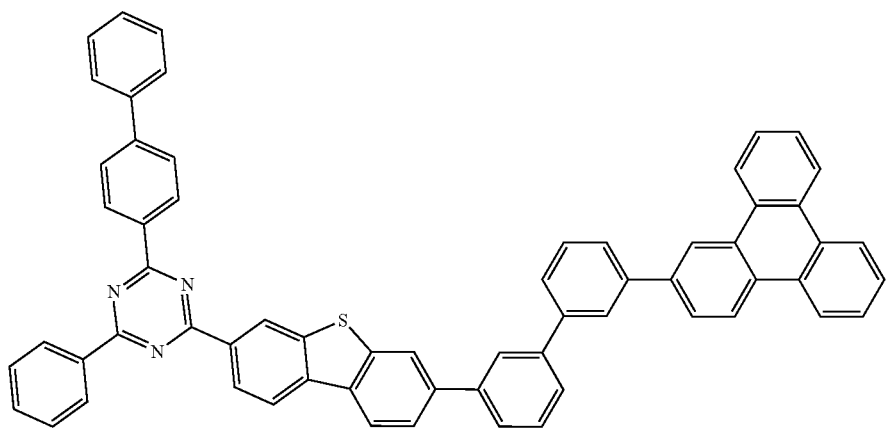
5-69
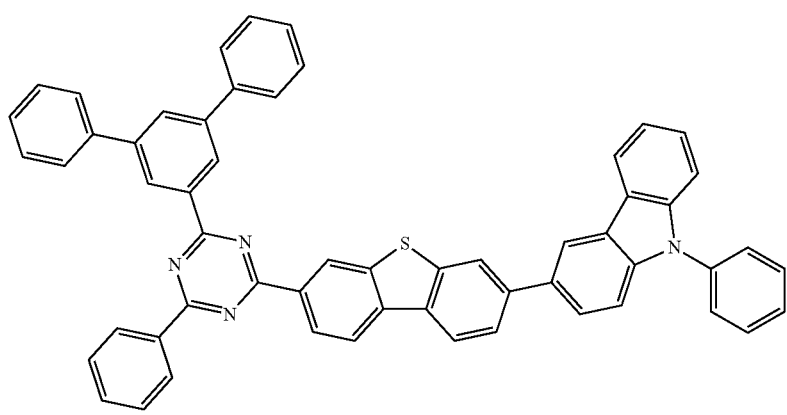

-continued
5-70
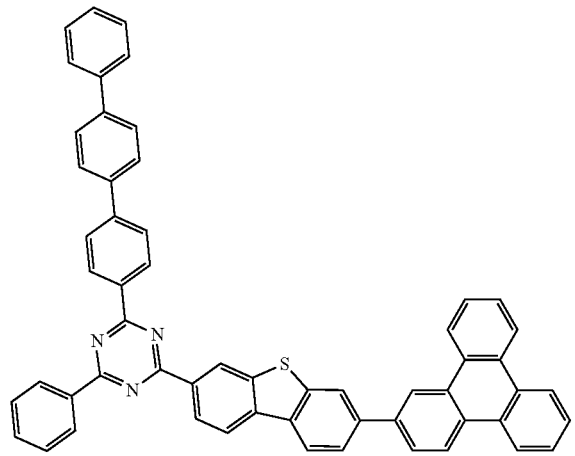
5-71
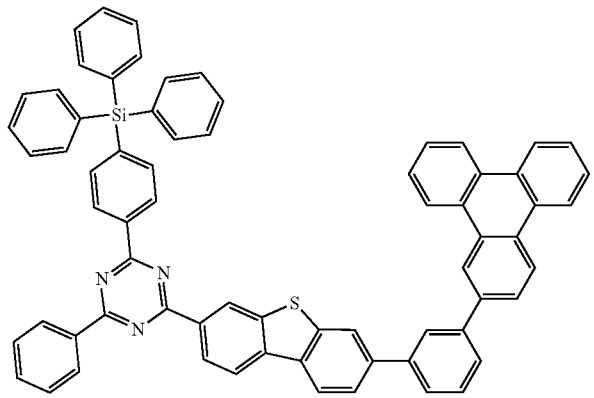
5-72
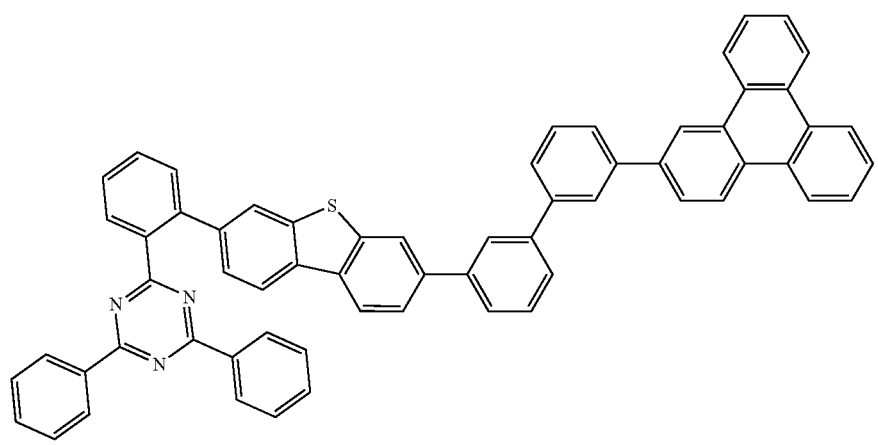
5-73
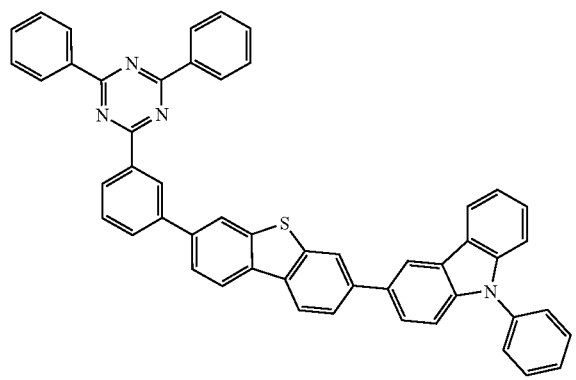
5-74
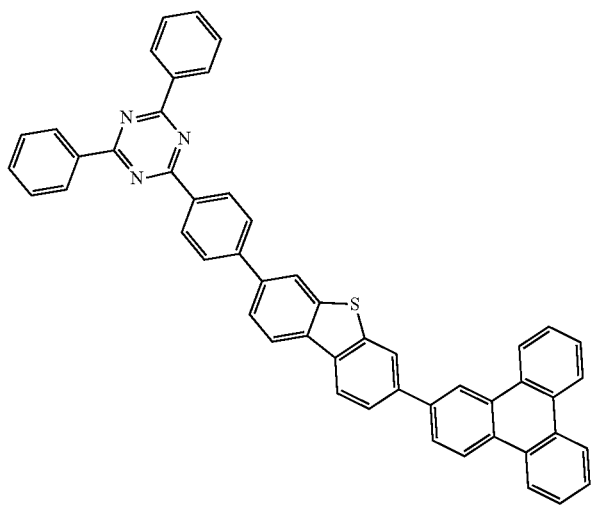

5-75
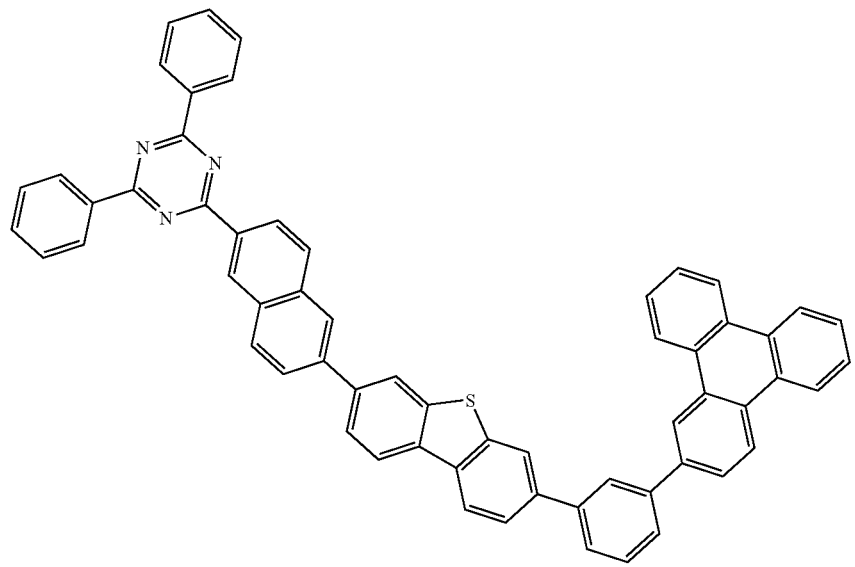
5-76
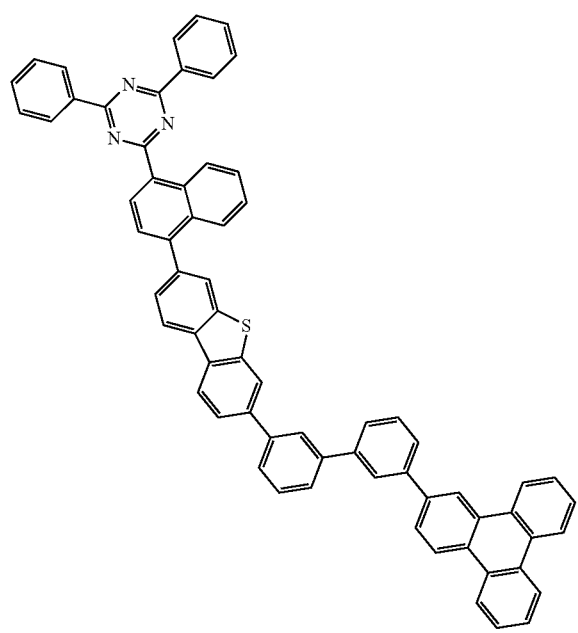

-continued
5-77
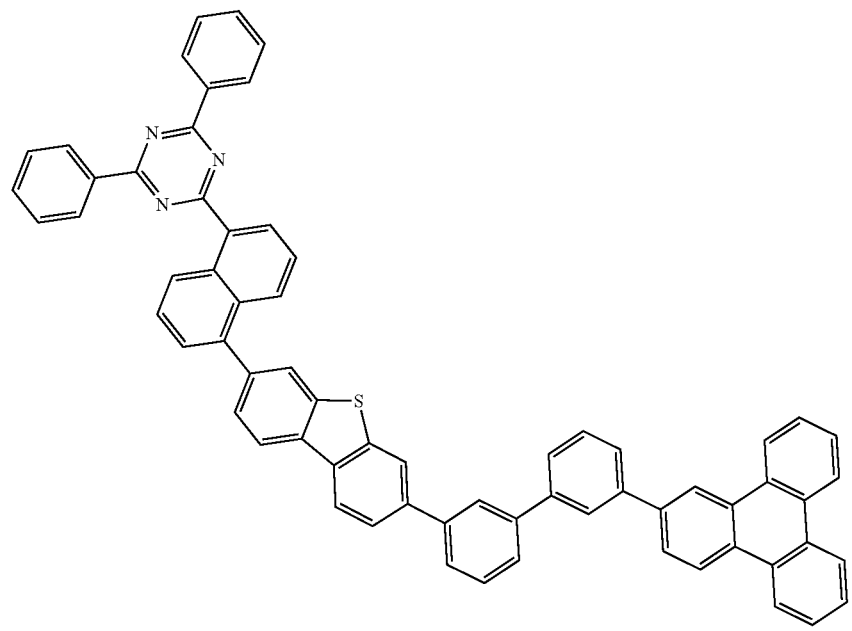
5-78
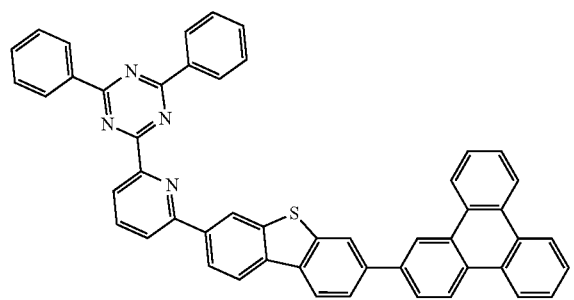
5-79
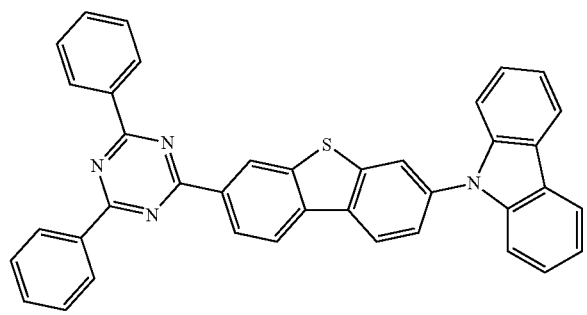
5-80
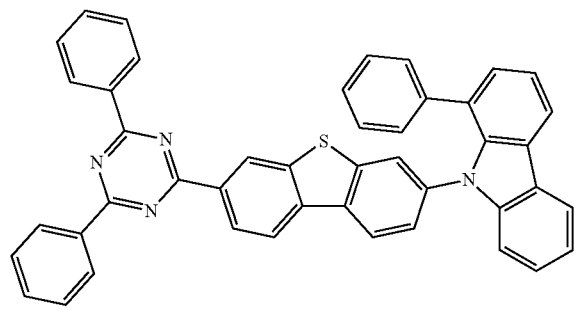
5-81
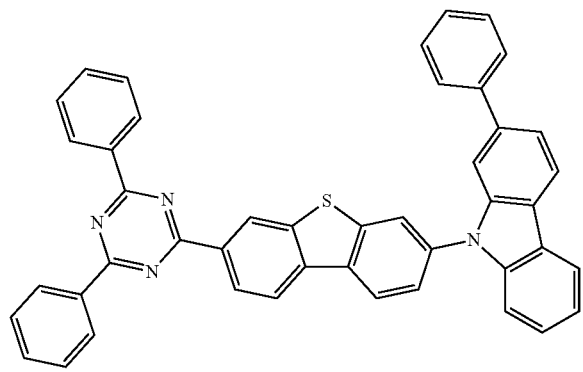

-continued
5-82
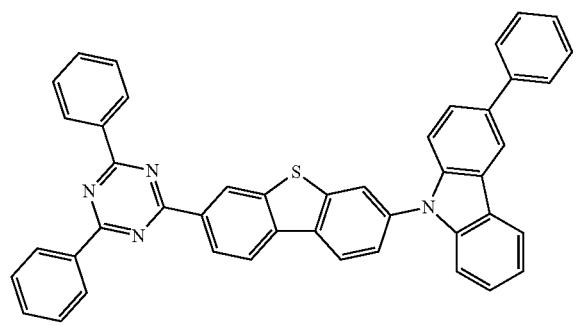
5-83
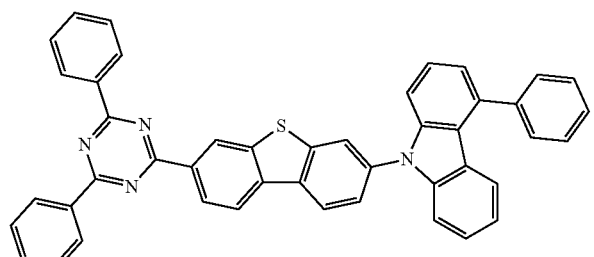
5-84
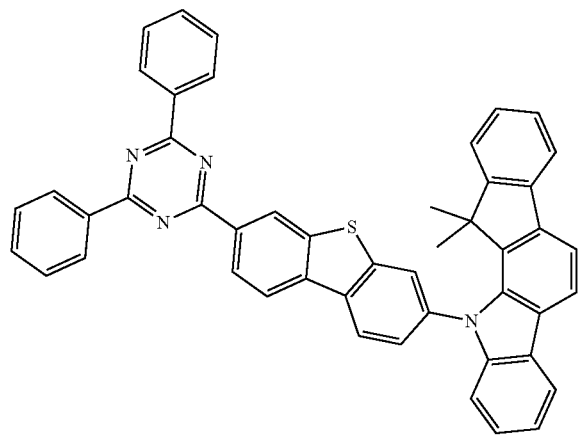
5-85
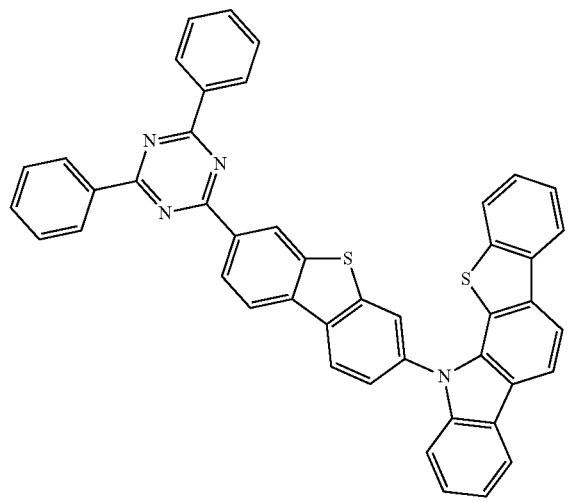
5-86
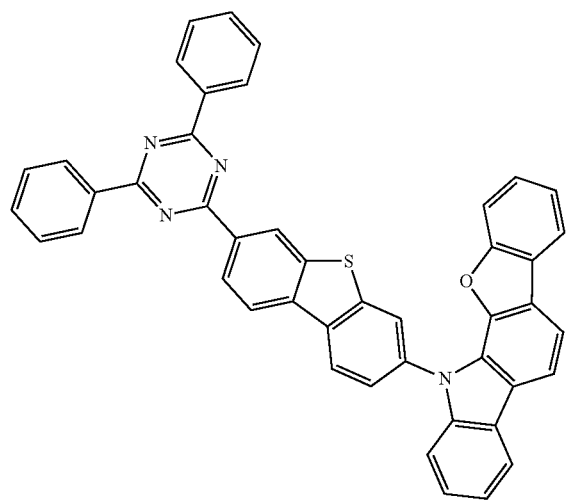
5-87
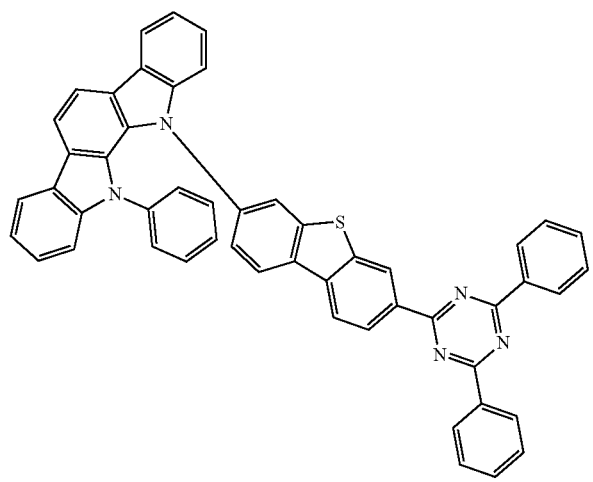

-continued
5-88
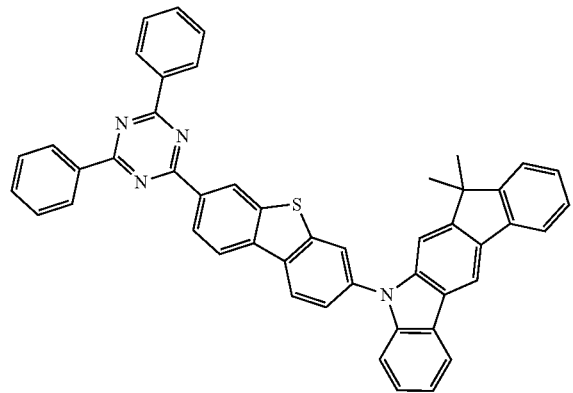
5-89
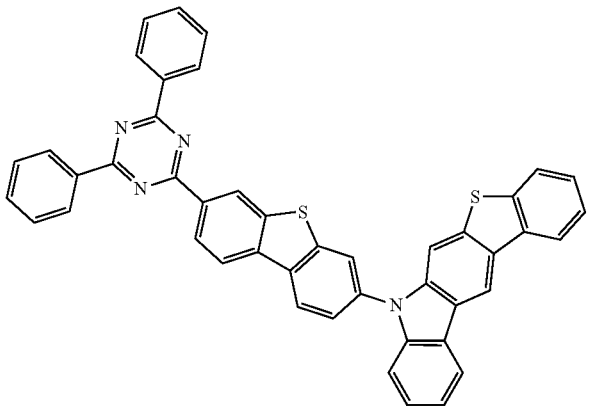
5-90
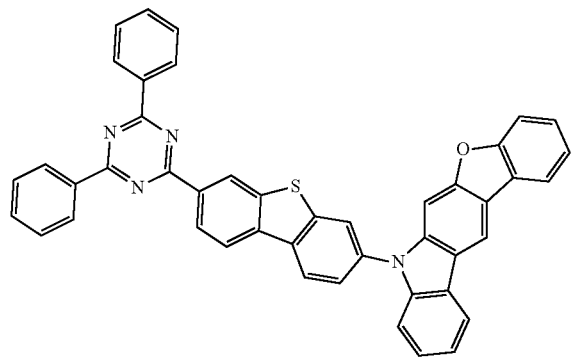
5-91
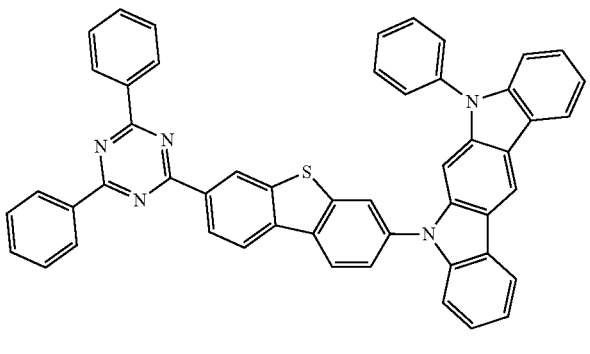
5-92
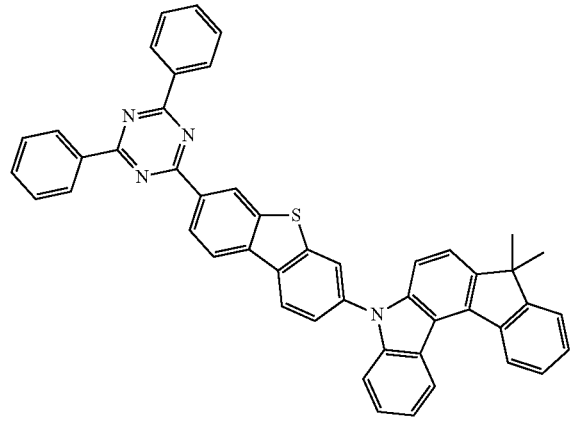
5-93
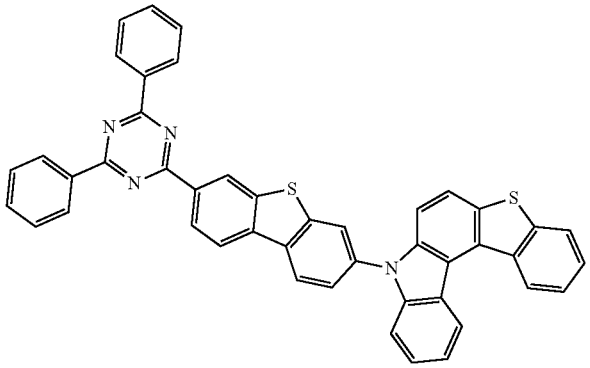
5-94
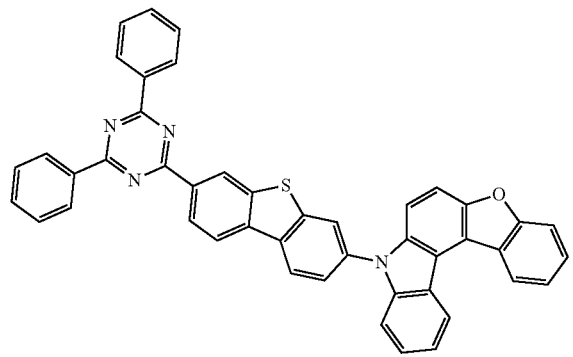
5-95
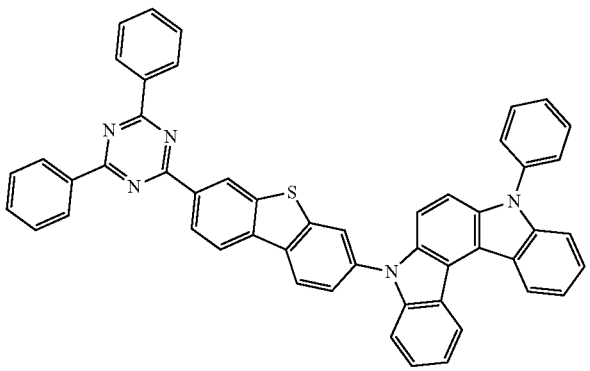

-continued
5-96
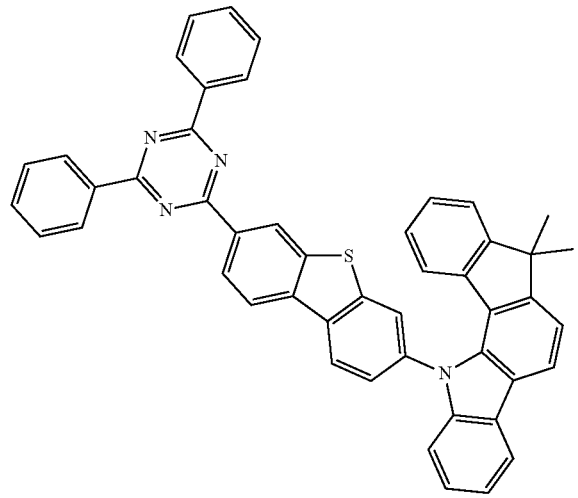
5-97
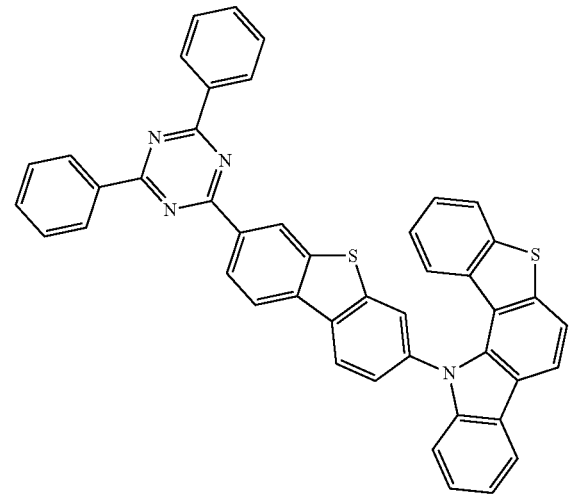
5-98
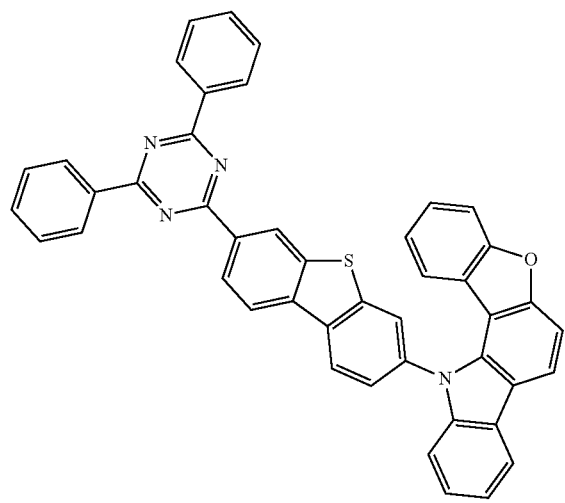
5-99
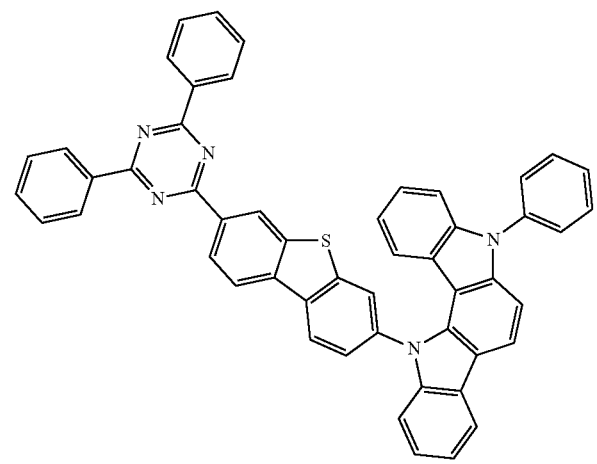
5-100
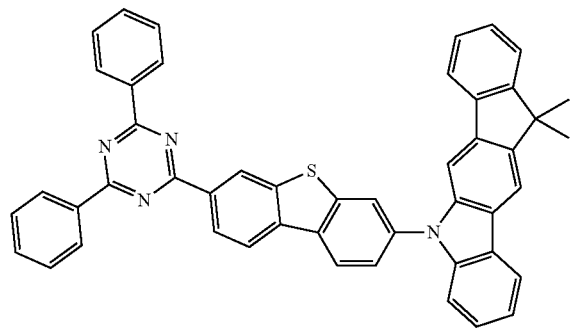
5-101
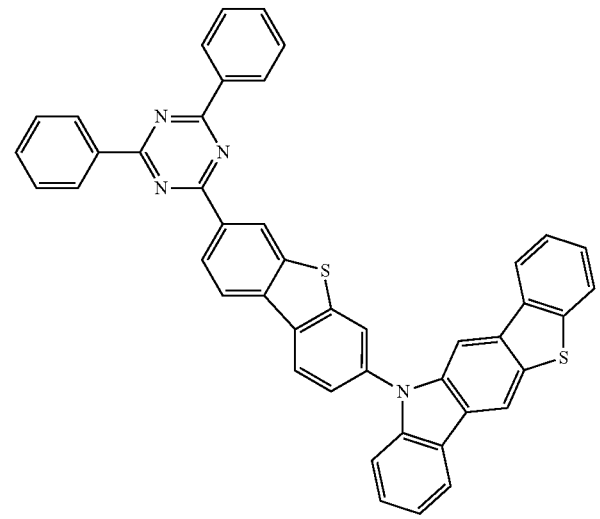

-continued
5-102
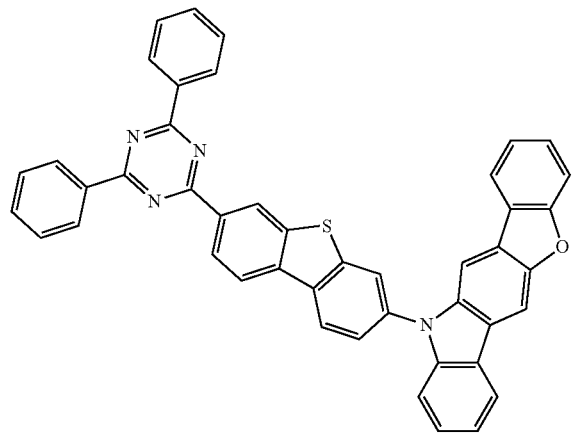
5-103
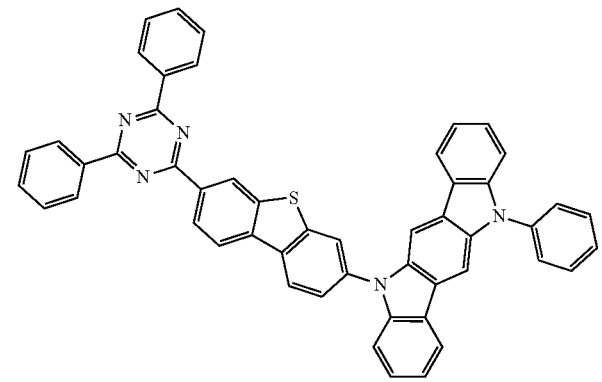
5-104
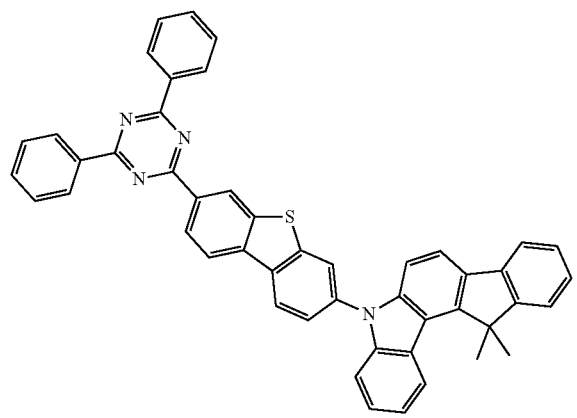
5-105
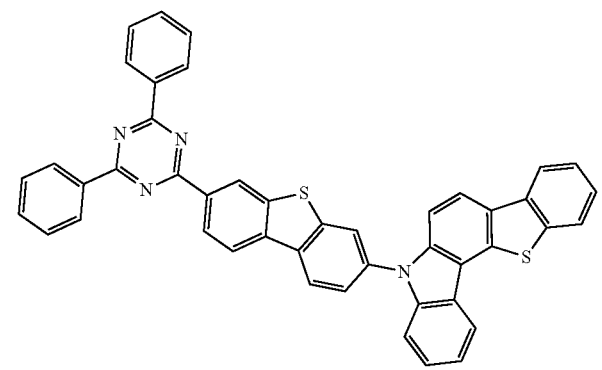
5-106
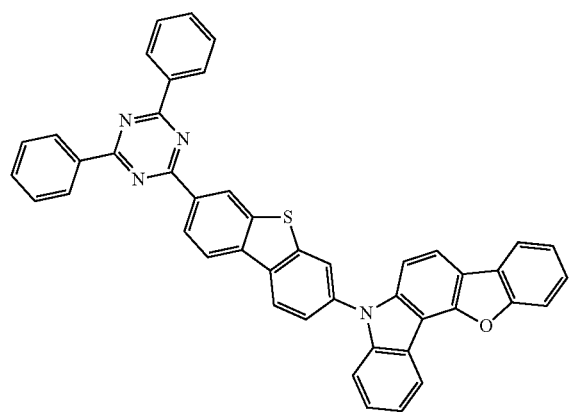
5-107
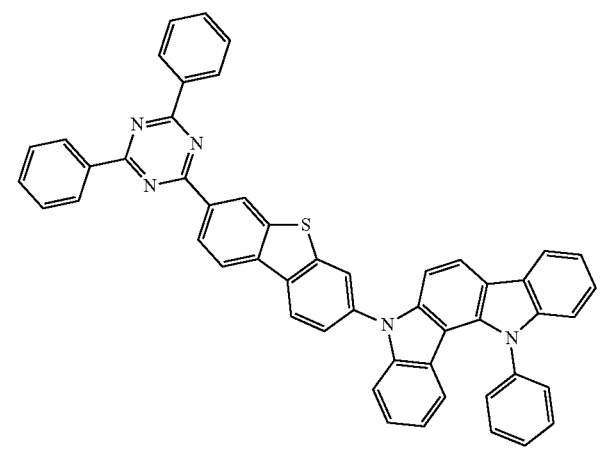

-continued
5-108
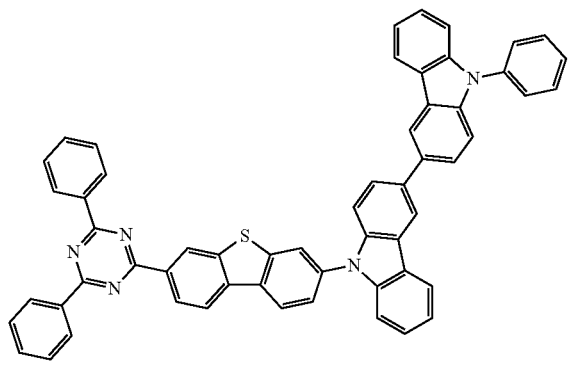
5-109
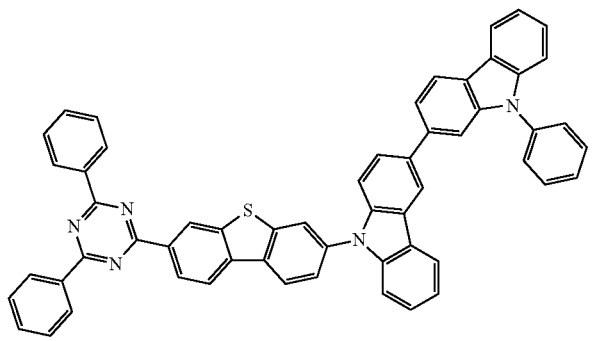
5-110
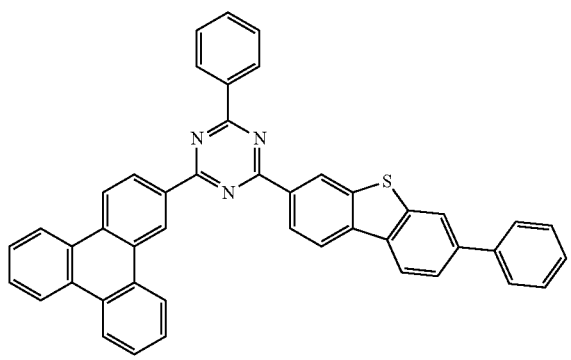
5-111
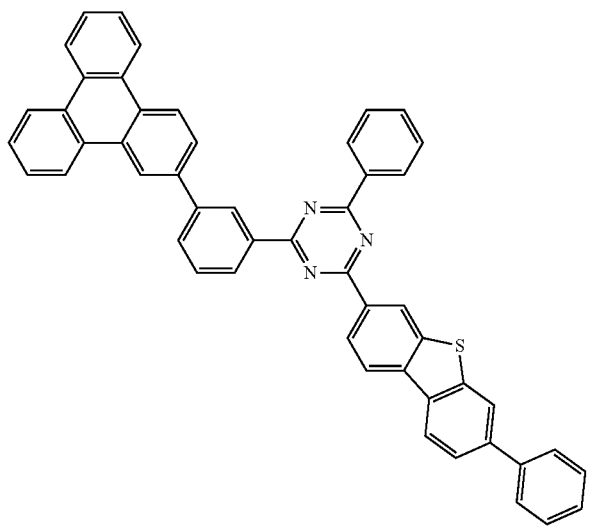
5-112
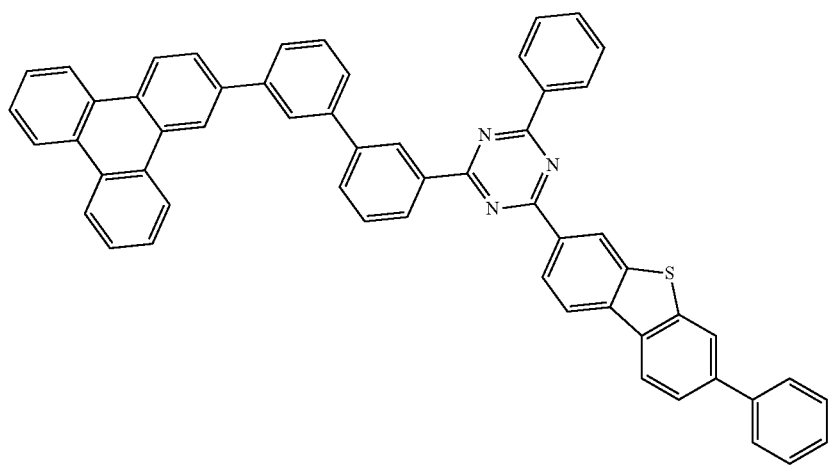

5-113
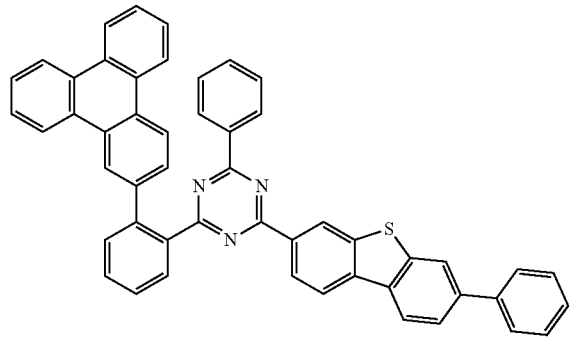
5-114
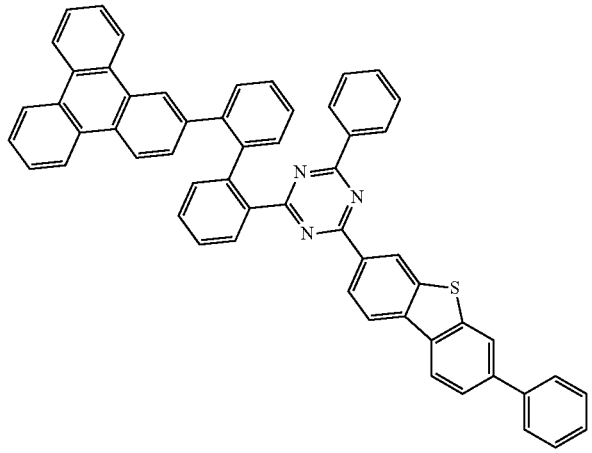
5-115
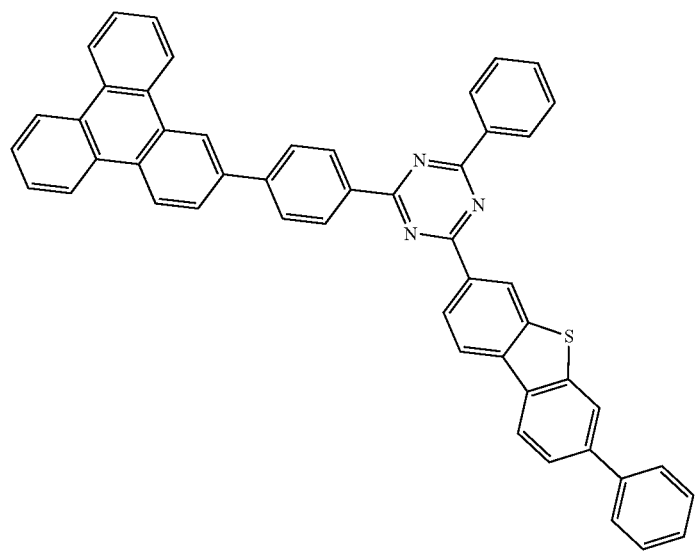
5-116
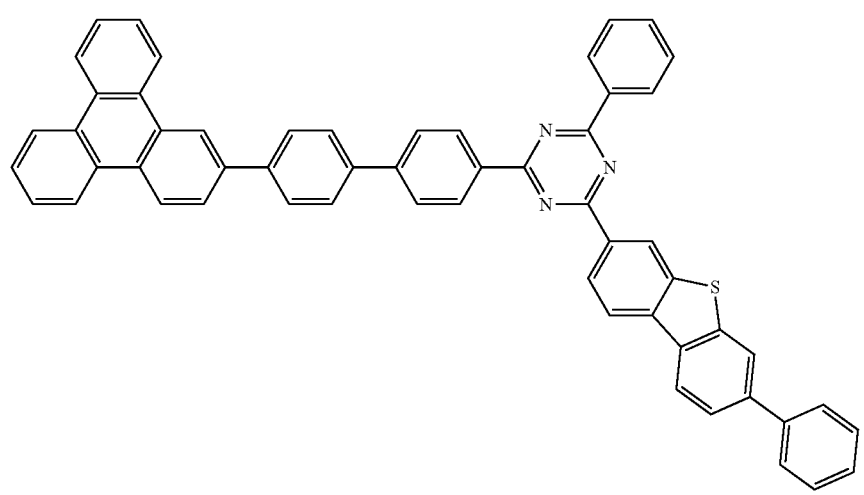

5-117

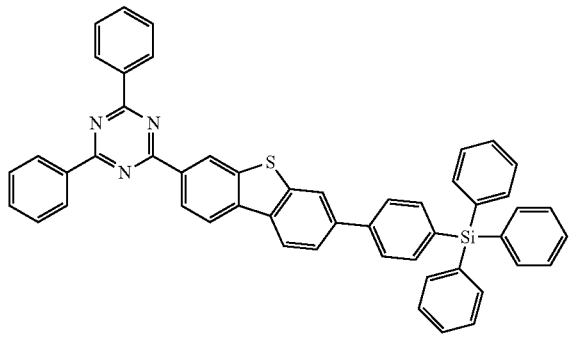

5-118

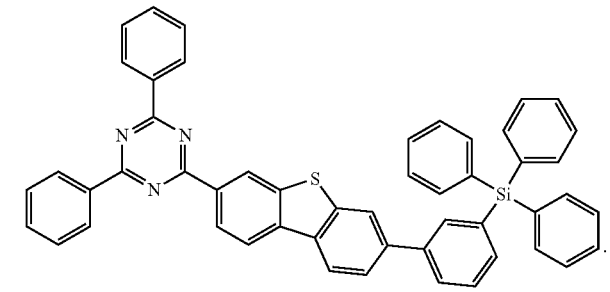

10. An organic light emitting device as an organic electronic comprising:
a first electrode;
a second electrode provided opposite to the first electrode; and
one or more organic material layers provided between the first electrode and the second electrode,
wherein one or more layers of the organic material layers comprise the heterocyclic compound of claim 1.

11. The organic light emitting device of claim 10, wherein the organic material layer comprises a light emitting layer, and the light emitting layer comprises the heterocyclic compound.

12. The organic light emitting device of claim 10, wherein the organic material layer comprises a light emitting layer, the light emitting layer comprises a host material, and the host material comprises the heterocyclic compound.

13. The organic light emitting device of claim 10, wherein the organic material layer comprises an electron injection layer or an electron transfer layer, and the electron transfer layer or the electron injection layer comprises the heterocyclic compound.

14. The organic light emitting device of claim 10, wherein the organic material layer comprises an electron blocking layer or a hole blocking layer, and the electron blocking layer or the hole blocking layer comprises the heterocyclic compound.

15. The organic light emitting device of claim 10, further comprising one, two or more layers selected from the group consisting of a light emitting layer, a hole injection layer, a hole transfer layer, an electron injection layer, an electron transfer layer, an electron blocking layer and a hole blocking layer.

16. The organic light emitting device of claim 12, wherein the light emitting layer further comprises a compound of the following Chemical Formula 25:

[Chemical Formula 25]

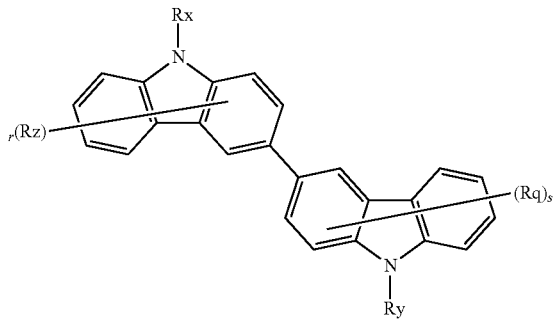

in Chemical Formula 25,
Rz and Rq are the same as or different from each other, and each independently selected from the group consisting of hydrogen; deuterium; a halogen group: —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R''; —P(=O)RR'; and an amine group unsubstituted or substituted with a substituted or unsubstituted alkyl group, a substituted or unsubstituted aryl group, or a substituted or unsubstituted heteroaryl group, or two or more groups adjacent to each other bond to each other to form a substituted or unsubstituted aliphatic or aromatic hydrocarbon ring;
R, R' and R'' are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group:
Rx and Ry are the same as or different from each other, and each independently a substituted or unsubstituted aryl group; or a substituted or unsubstituted heteroaryl group; and
r and s are an integer of 0 to 7.

17. The organic light emitting device of claim 16, wherein Chemical Formula 25 is represented by any one of the following compounds:

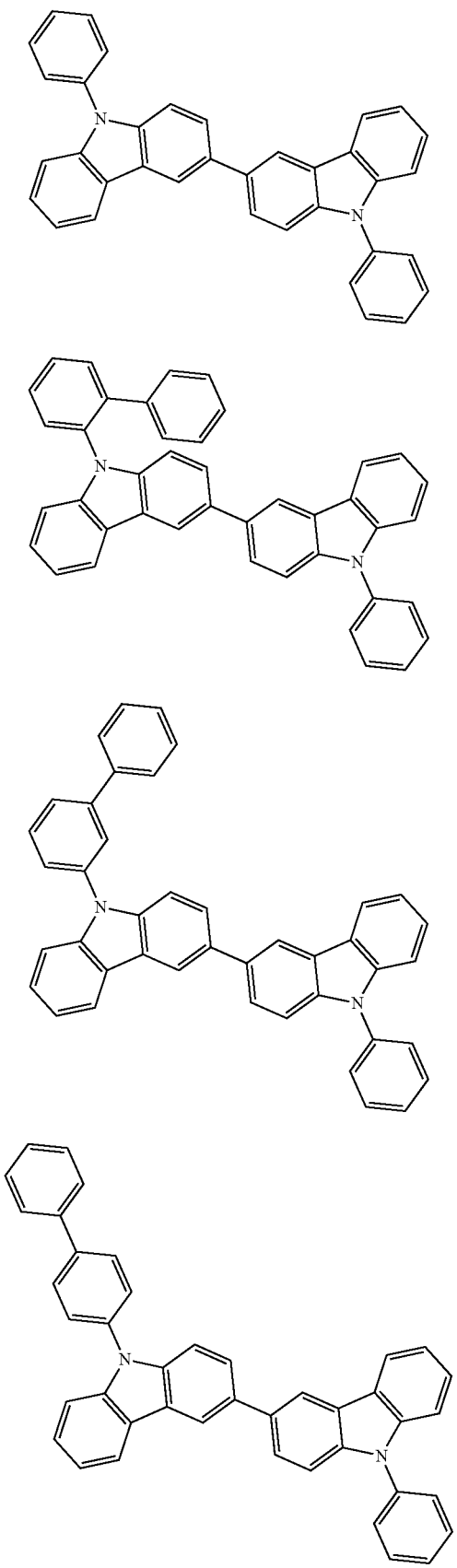
3-1
3-2
3-3
3-4
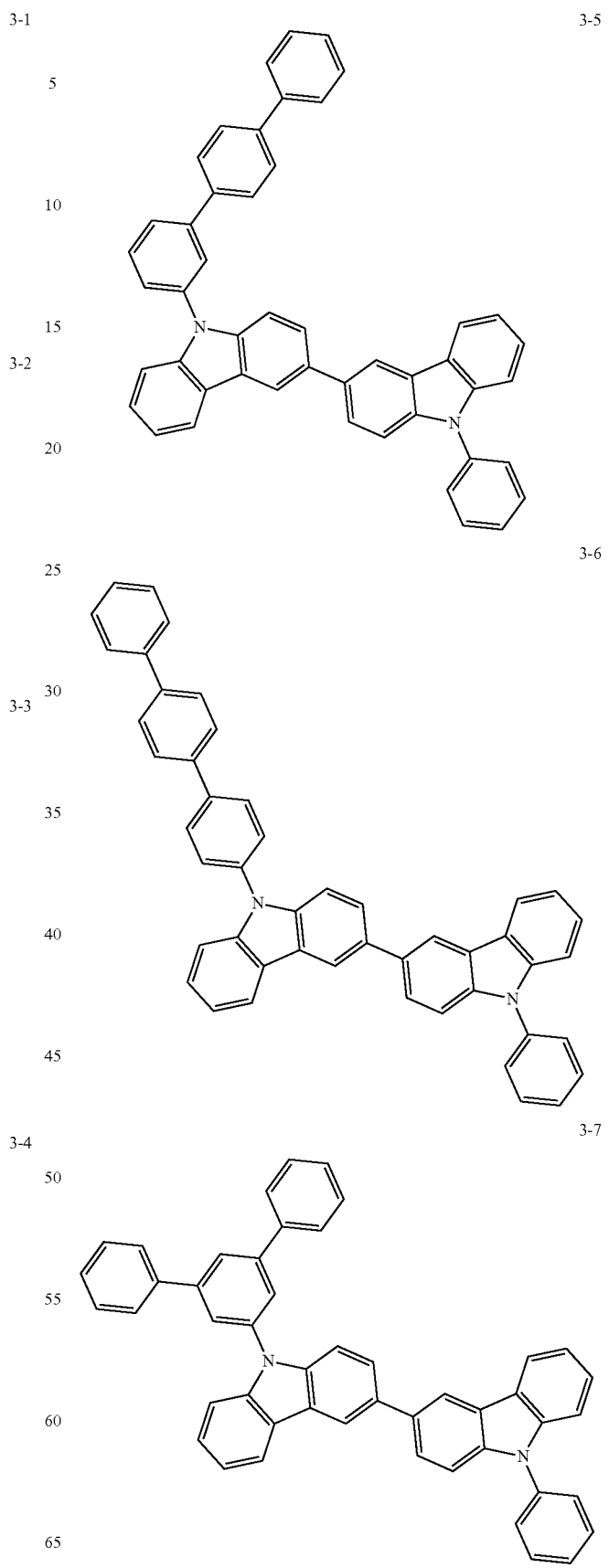
3-5
3-6
3-7

-continued
3-8
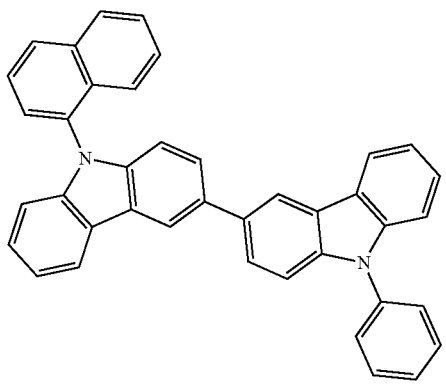
3-9
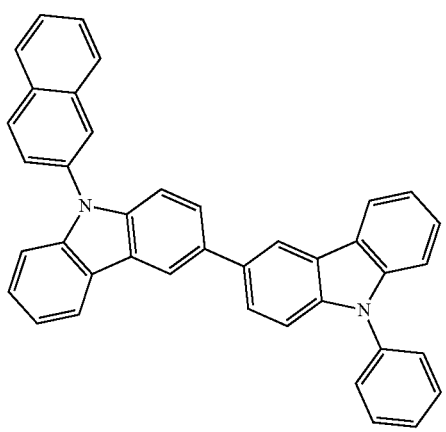
3-10
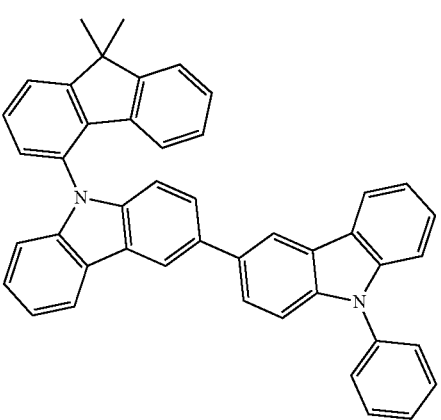
-continued
3-11
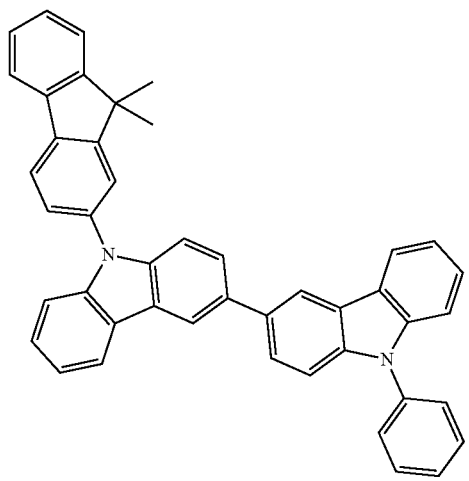
3-12
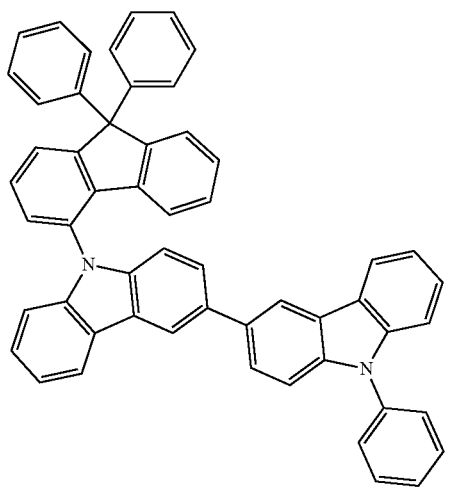
3-13
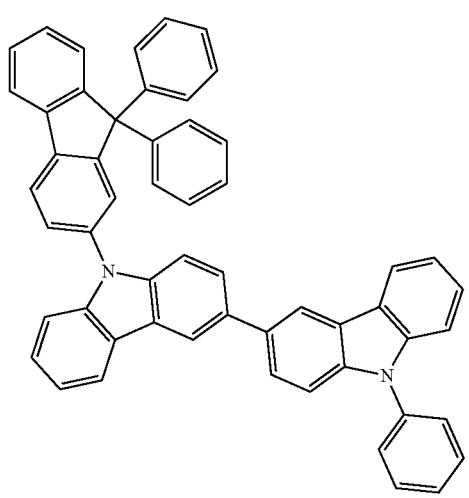

3-14
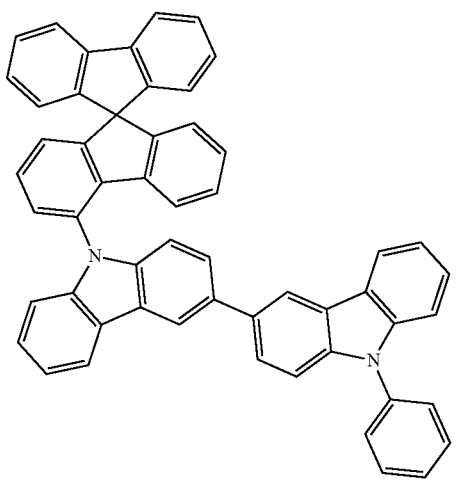
3-17
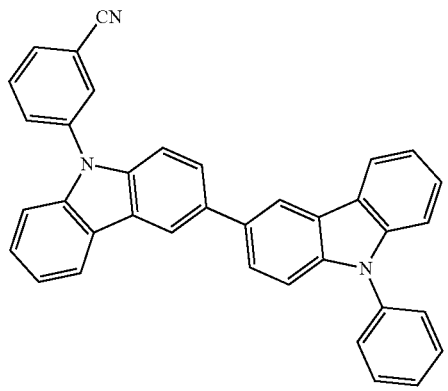
3-15
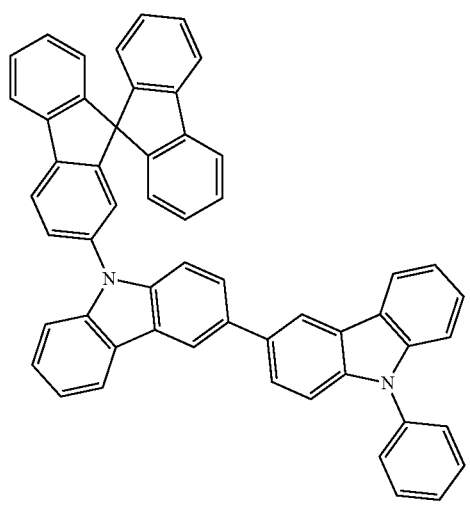
3-18
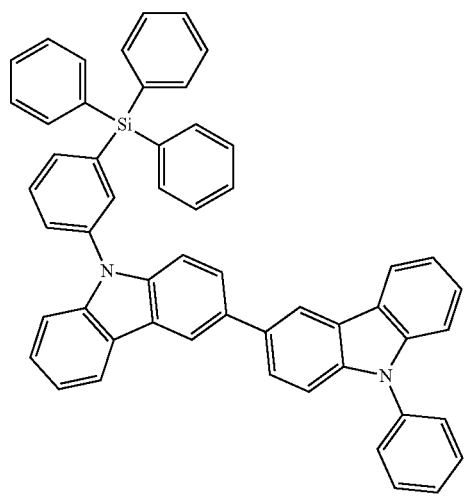
3-16
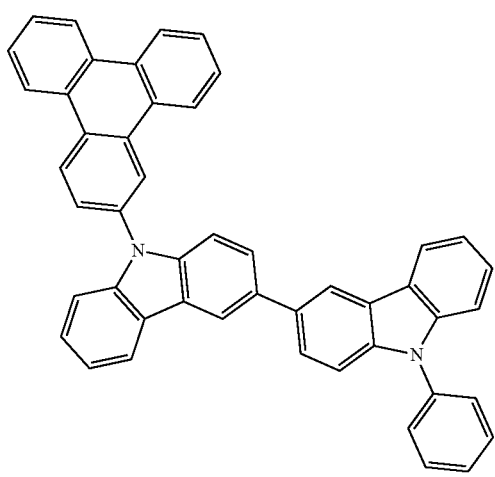
3-19
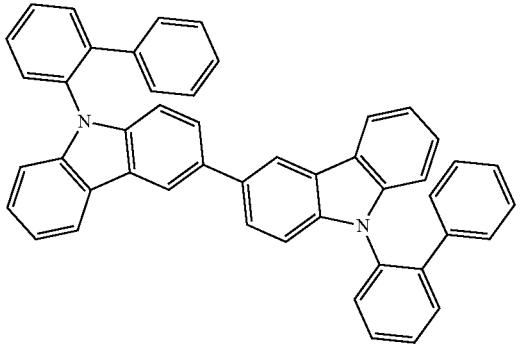

-continued
3-20
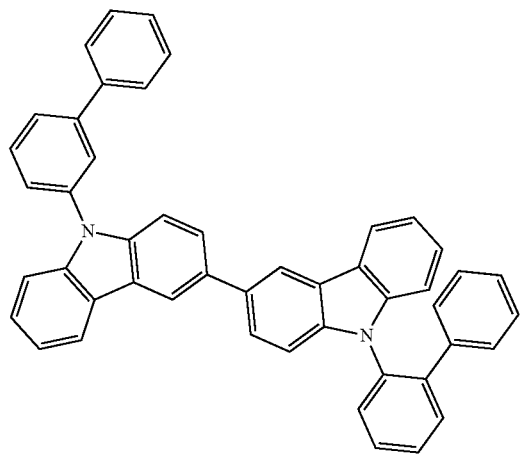
3-21
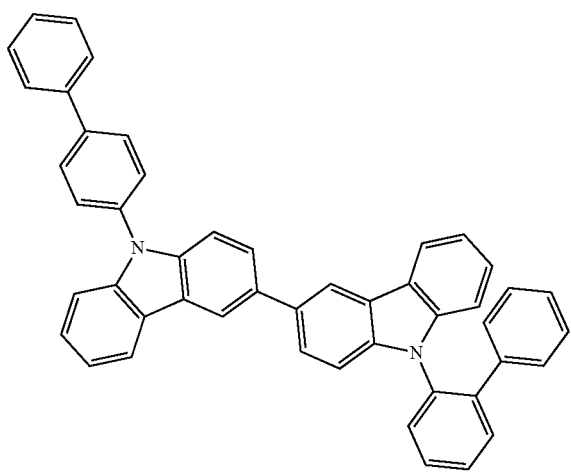
3-22
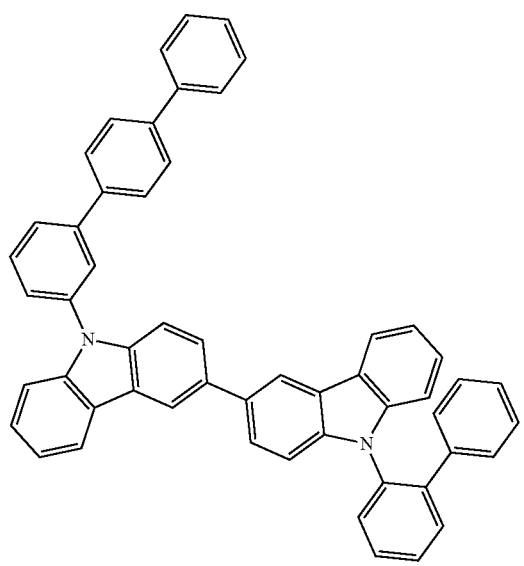
-continued
3-23
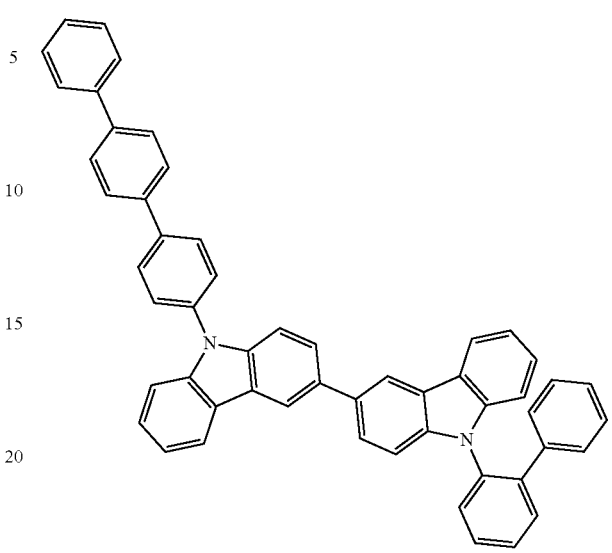
3-24
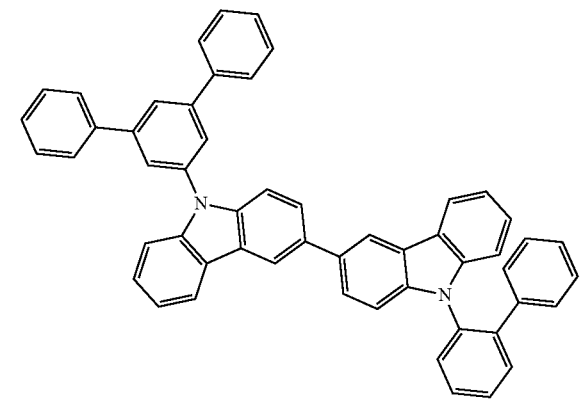
3-25
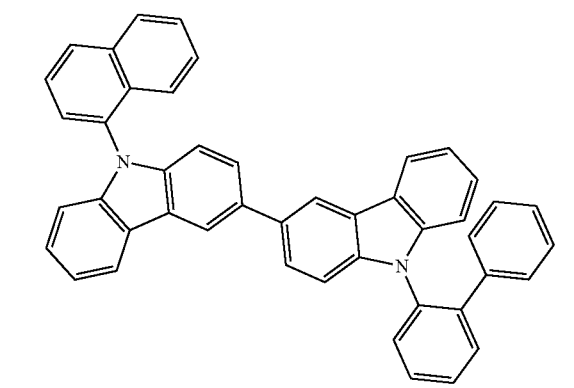

-continued
3-26
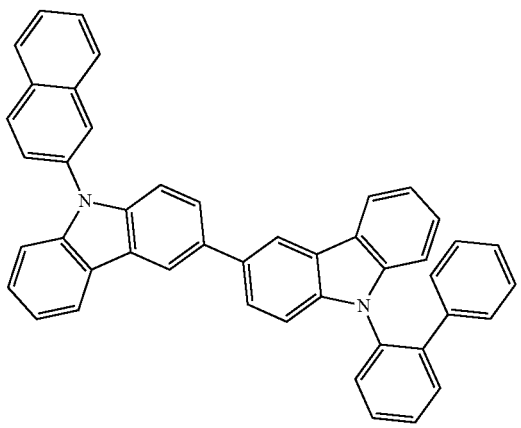
3-27
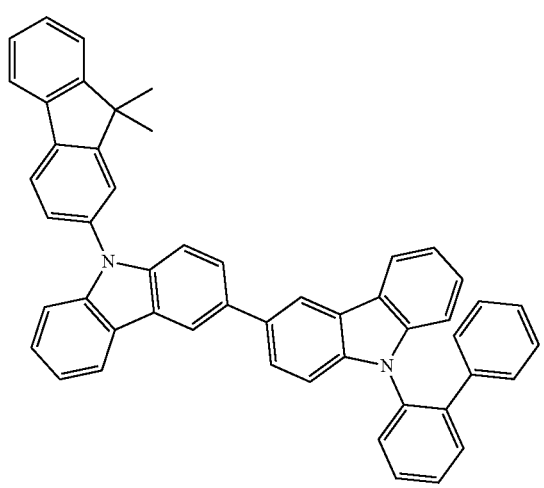
3-28
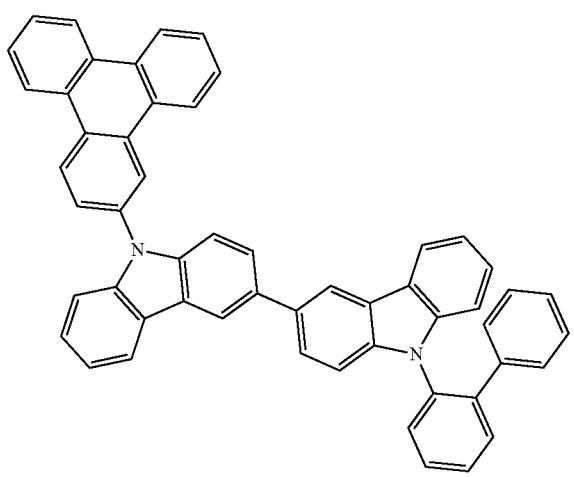
3-29
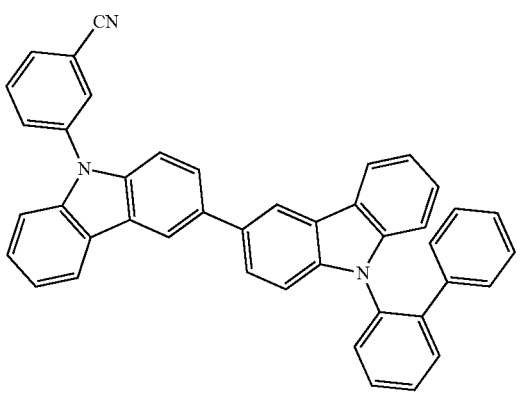
3-30
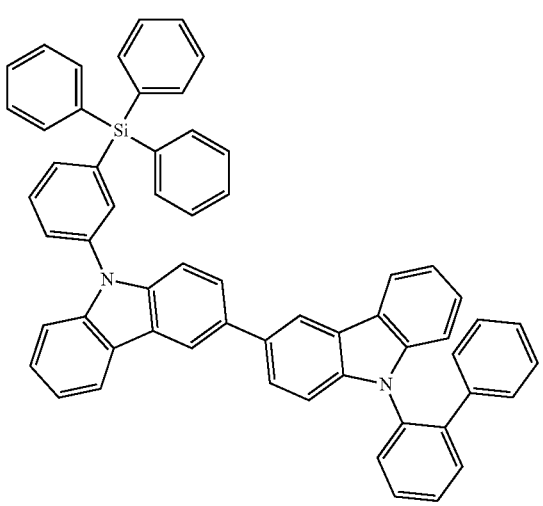
3-31
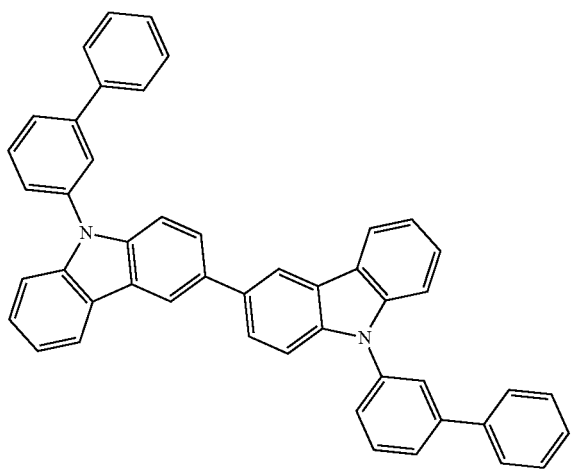

3-32
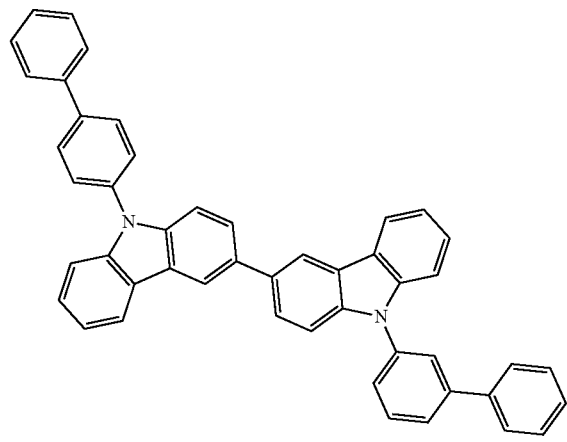
3-35
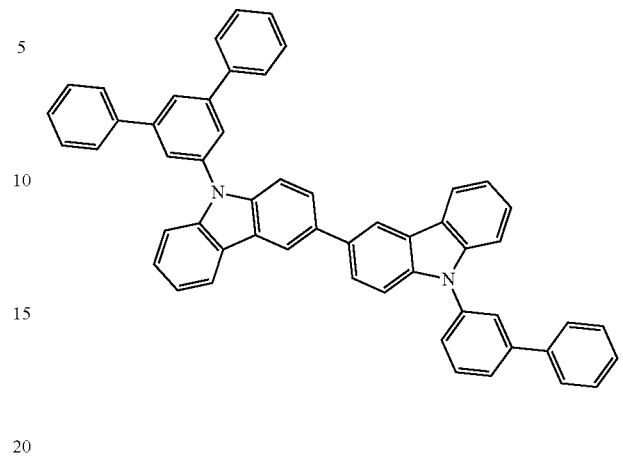
3-33
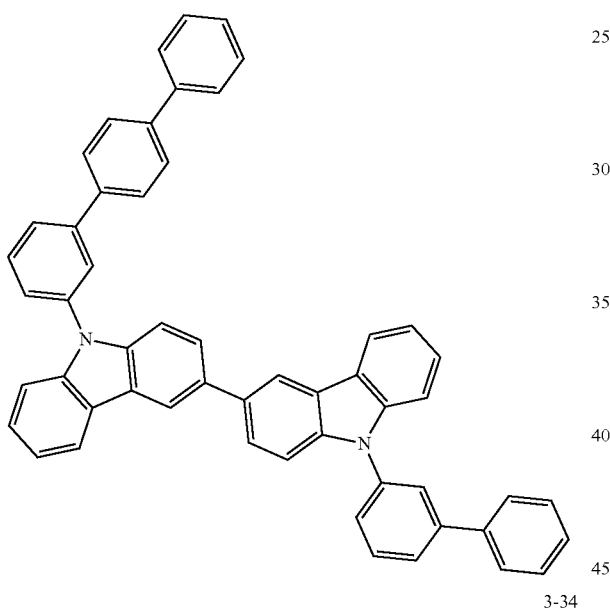
3-36
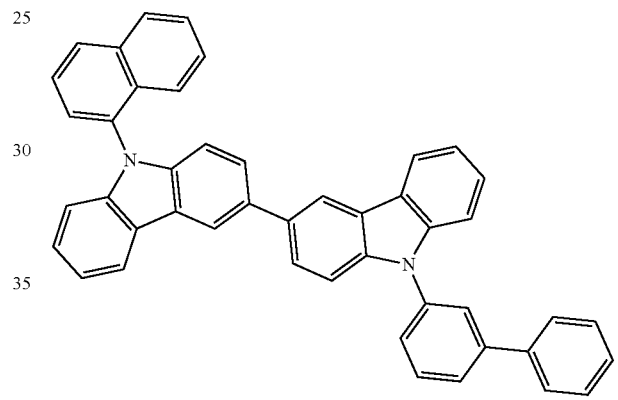
3-34
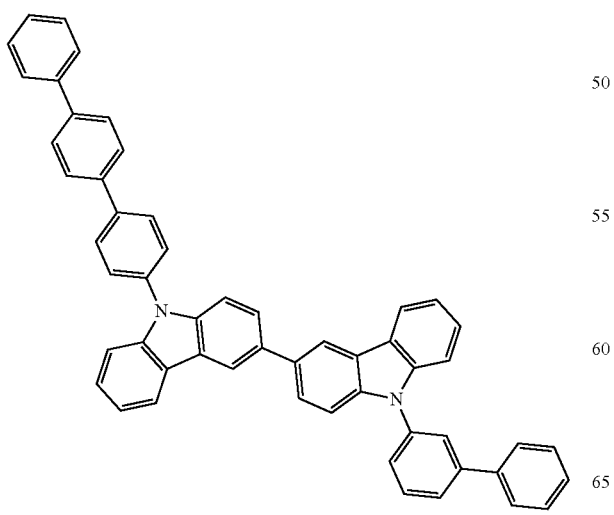
3-37
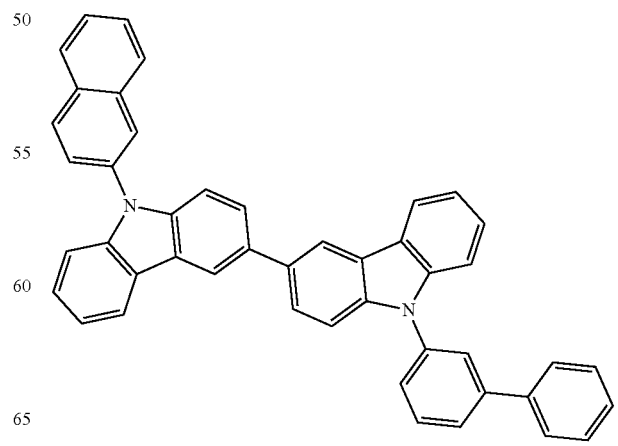

3-38
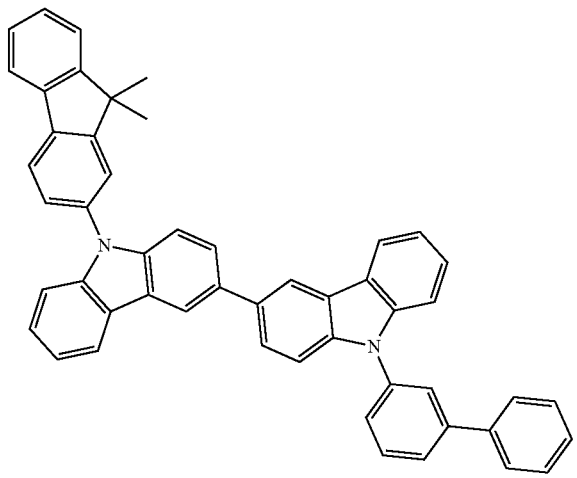
3-39
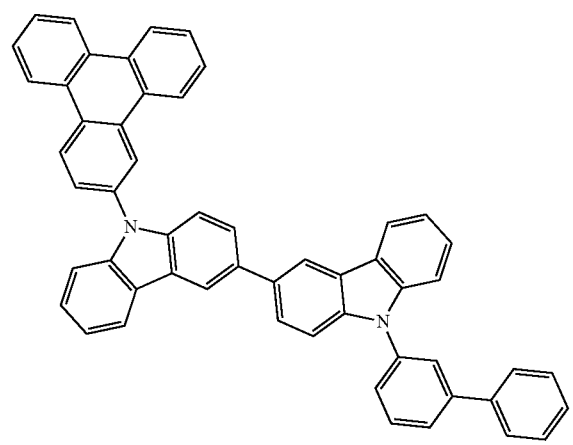
3-40
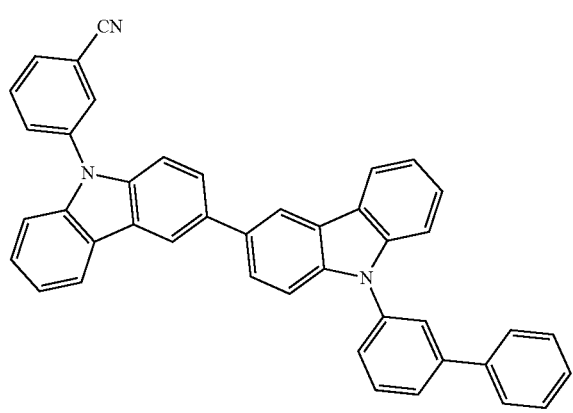
3-41
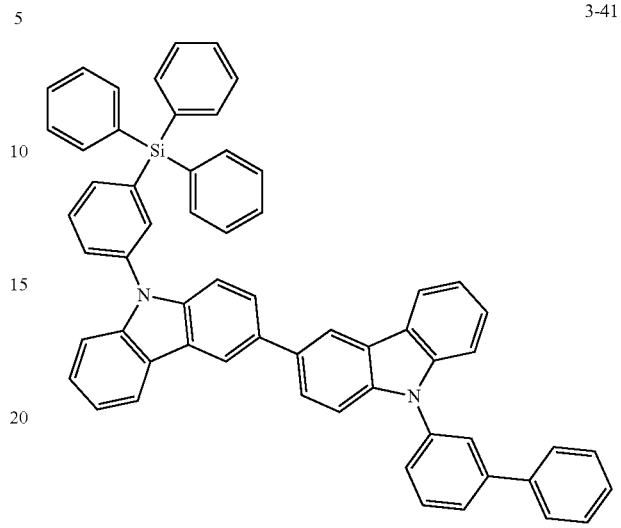
3-42
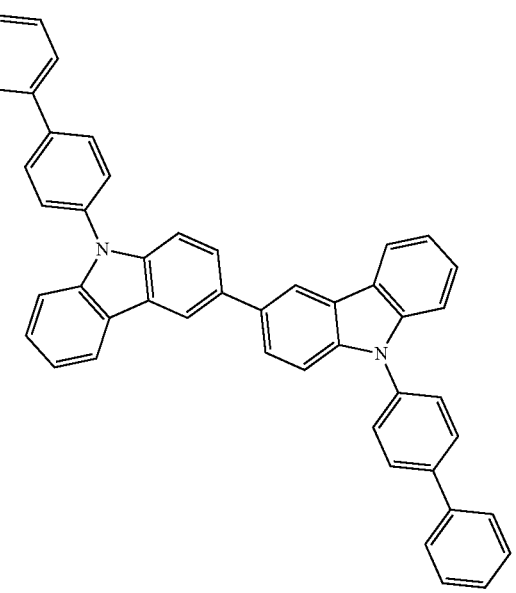

3-43
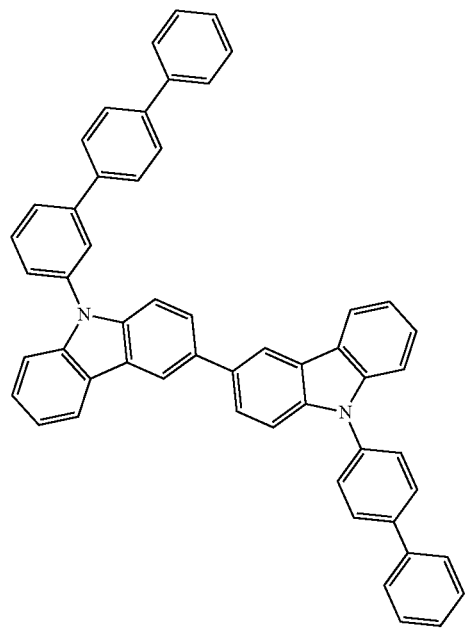
3-44
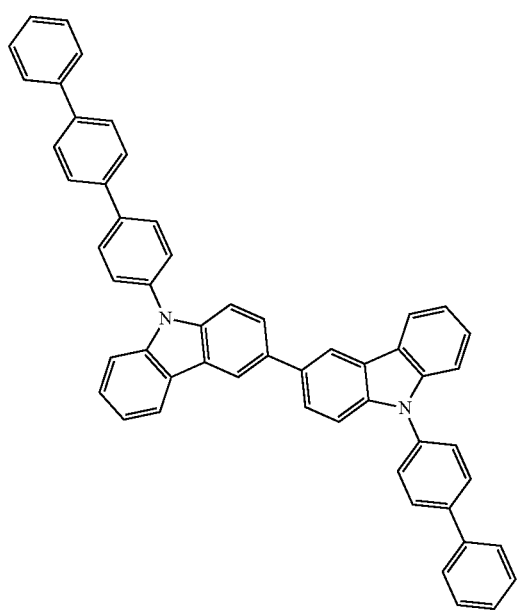
3-45
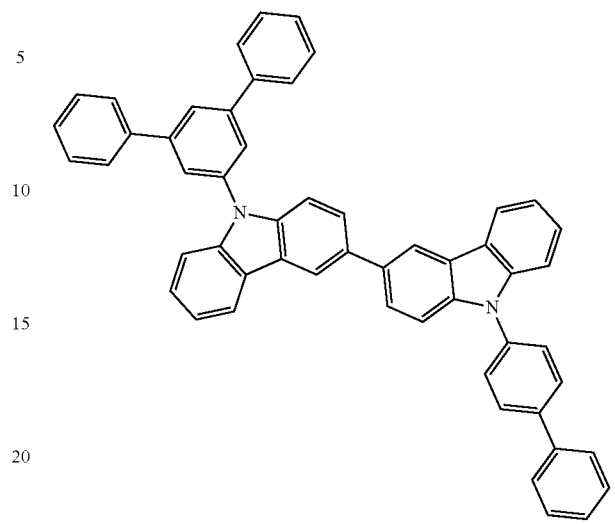
3-46
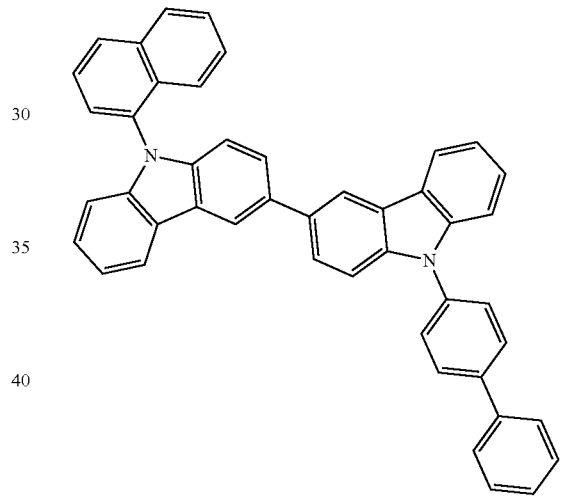
3-47

3-48
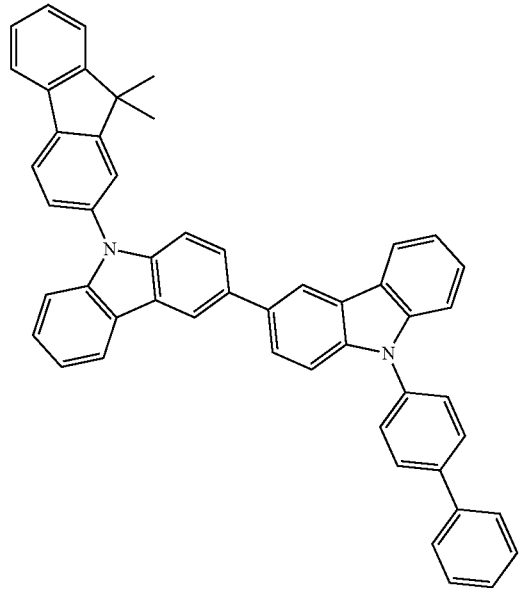
3-49
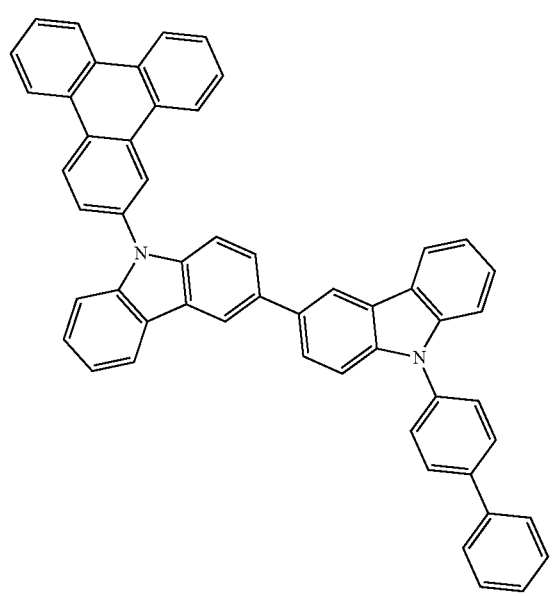
3-50
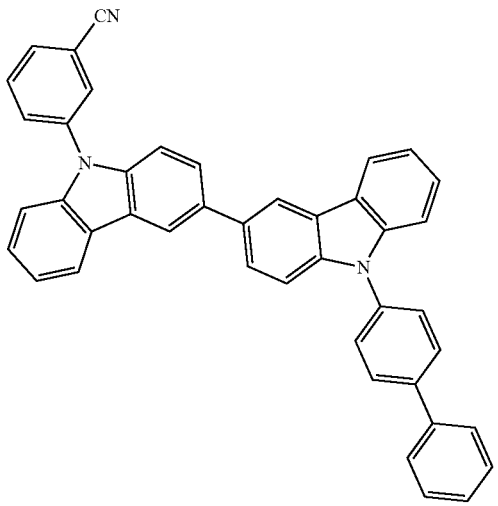
3-51
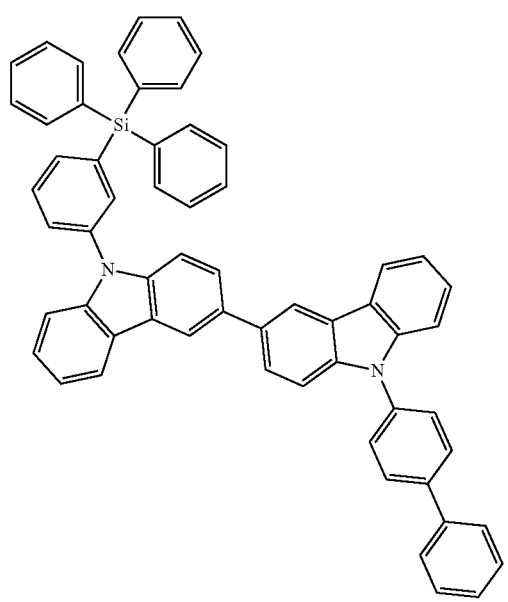
3-52
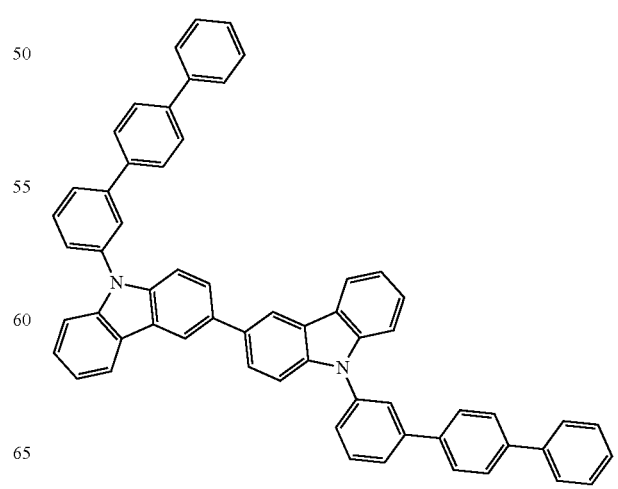

3-53
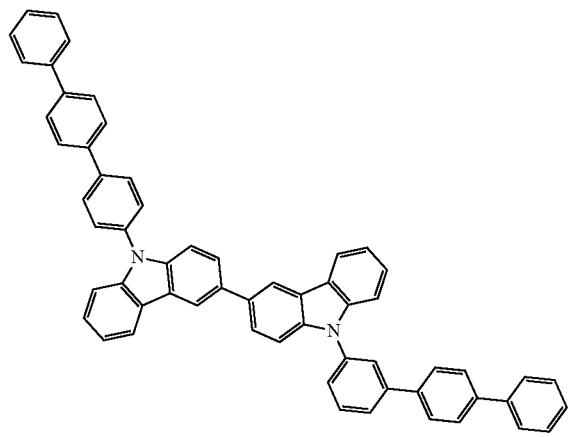
3-57
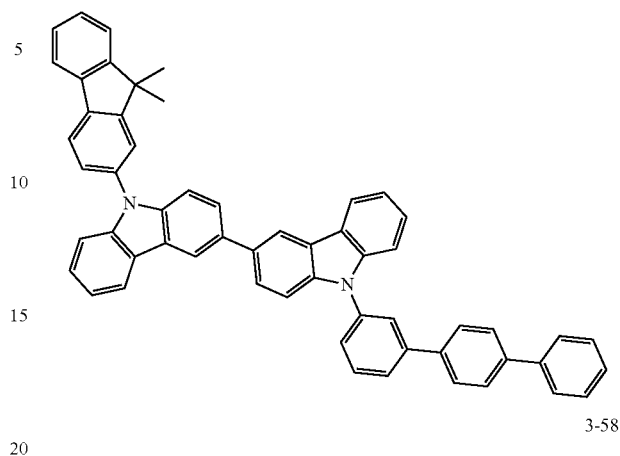
3-54
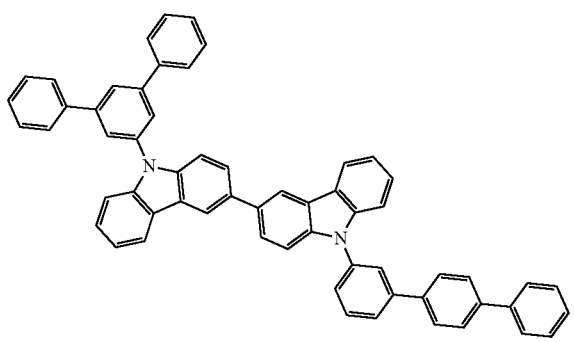
3-58
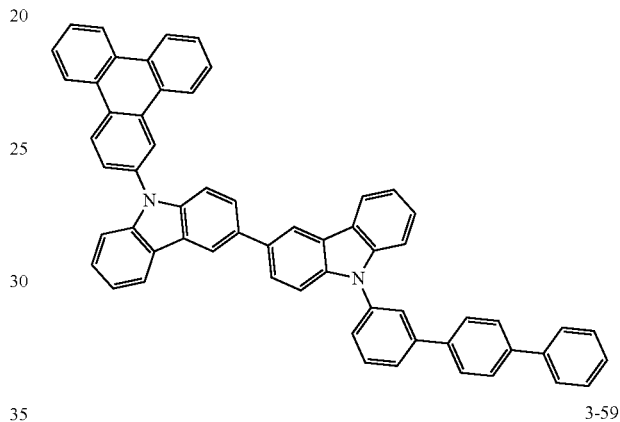
3-55
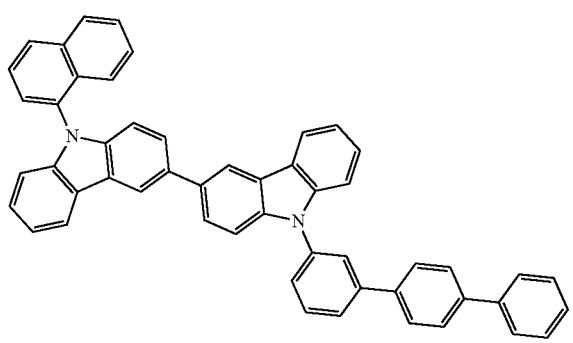
3-59
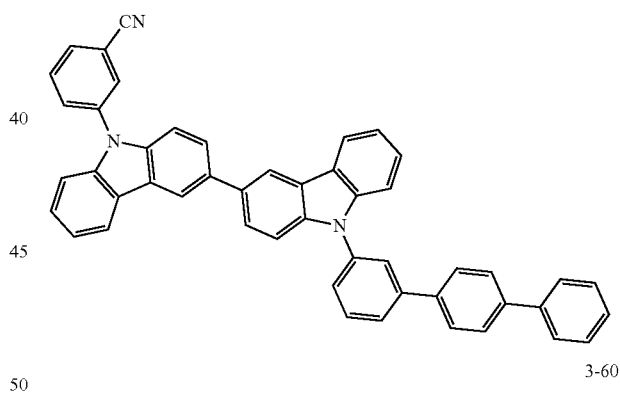
3-56
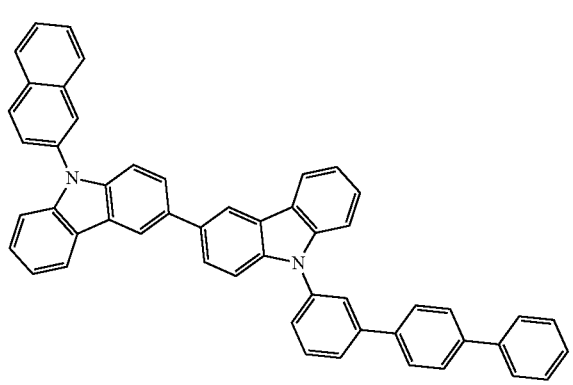
3-60
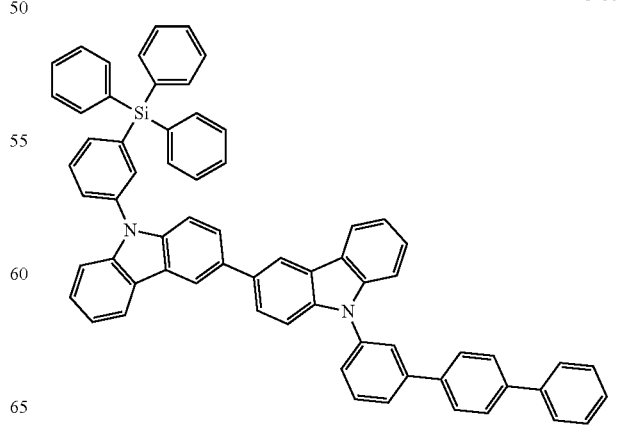

3-61
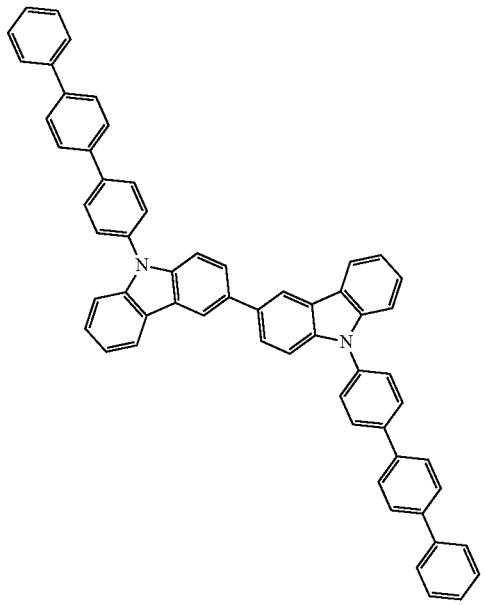
3-62
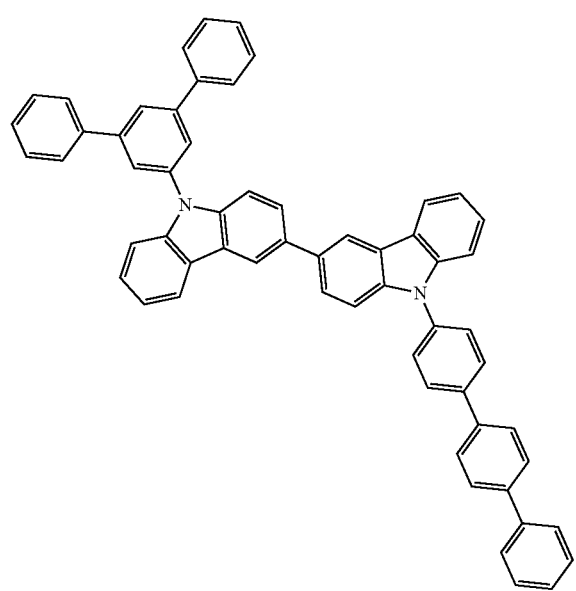
3-63
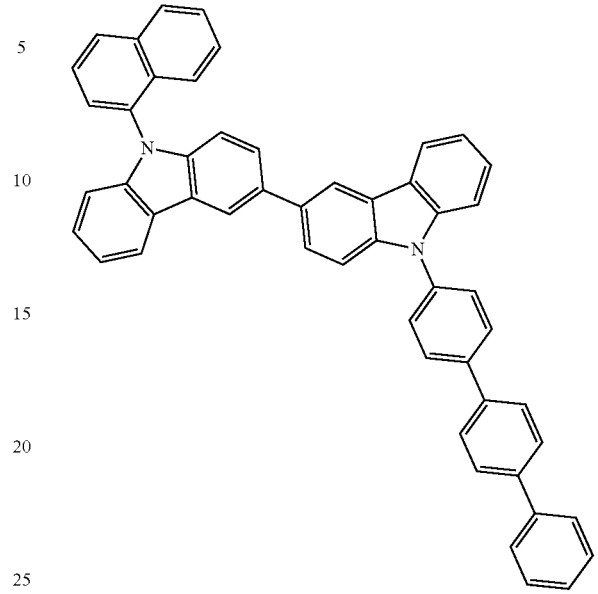
3-64
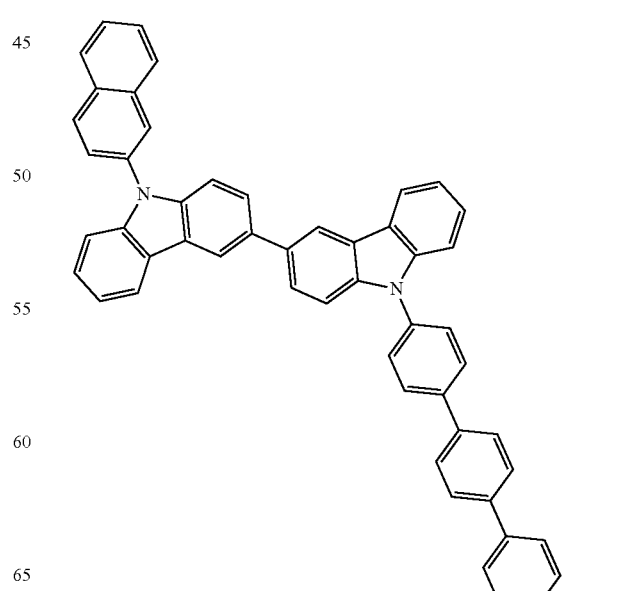

491
-continued
3-65
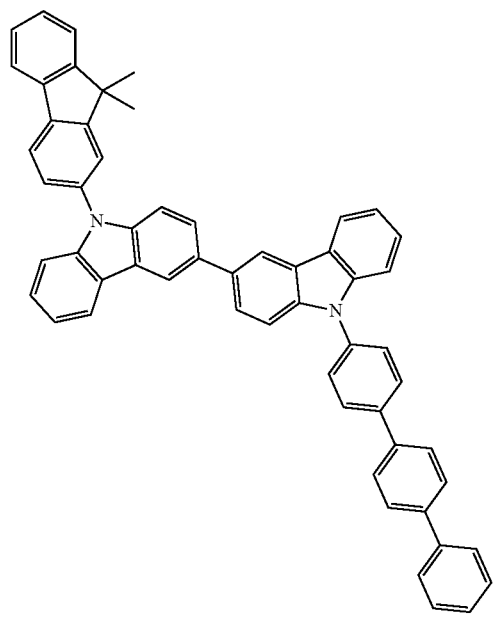
492
-continued
3-67
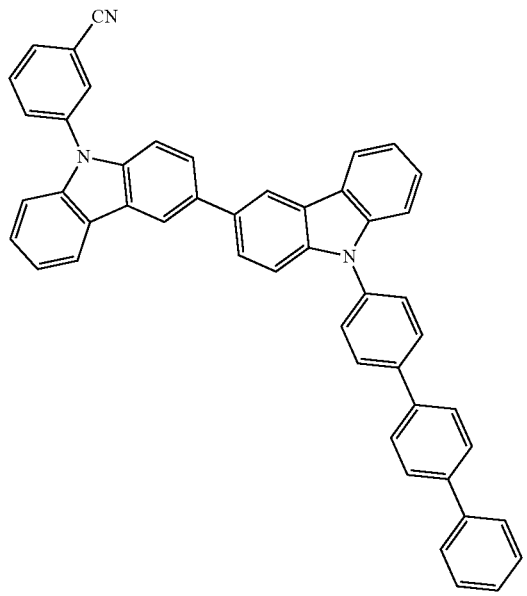
3-66
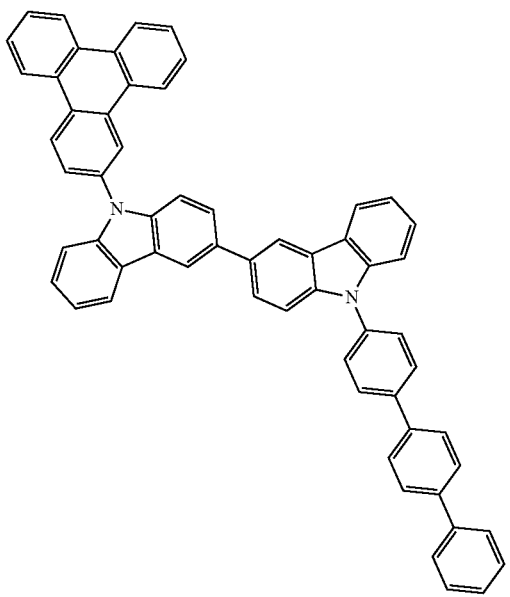
3-68
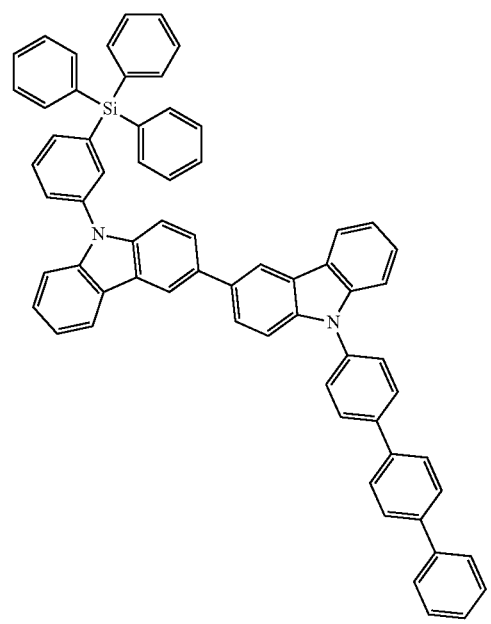

3-69
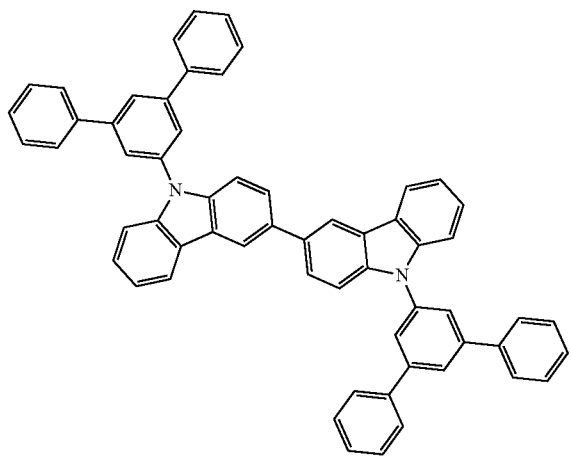
3-70
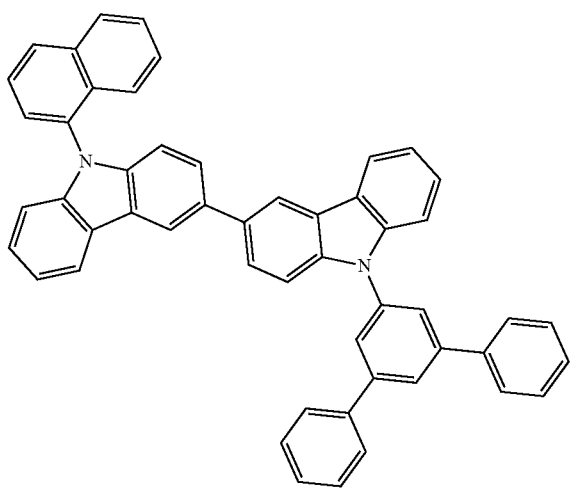
3-71
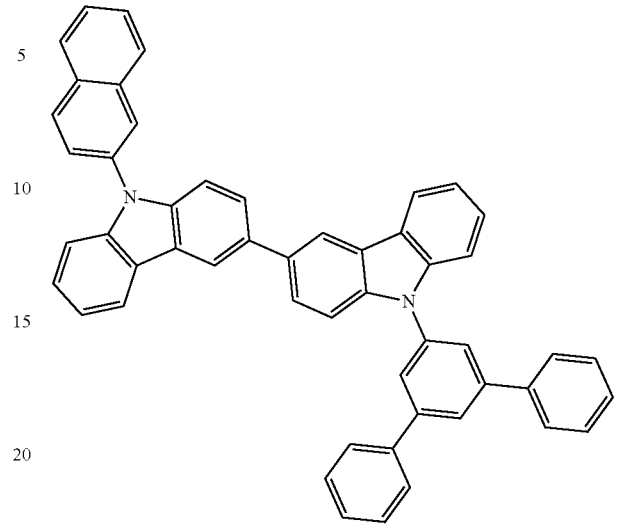
3-72
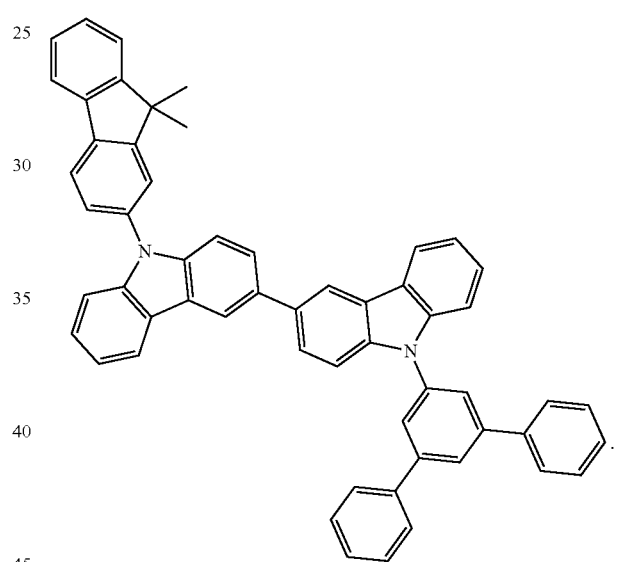
* * * * *